US006723547B2

(12) United States Patent
Beasley et al.

(10) Patent No.: US 6,723,547 B2
(45) Date of Patent: Apr. 20, 2004

(54) ISOLATED HUMAN PHOSPHATASE PROTEINS, NUCLEIC ACID MOLECULES ENCODING HUMAN PHOSPHATASE PROTEINS, AND USES THEREOF

(75) Inventors: Ellen M. Beasley, Rockville, MD (US); Marion Webster, Rockville, MD (US); Valentina Di Francesco, Rockville, MD (US); Ming-Hui Wei, Rockville, MD (US)

(73) Assignee: Applera Corporation, Norwalk, CT (US)

( * ) Notice: Subject to any disclaimer, the term of this patent is extended or adjusted under 35 U.S.C. 154(b) by 472 days.

(21) Appl. No.: 09/822,871

(22) Filed: Apr. 2, 2001

(65) Prior Publication Data

US 2003/0099942 A1 May 29, 2003

(51) Int. Cl.[7] ........................ C12N 9/16; C12N 15/55

(52) U.S. Cl. .................. 435/196; 435/325; 435/252.3; 435/320.1; 536/23.2

(58) Field of Search ........................ 536/23.2; 435/196, 435/252.3, 325, 320.1

(56) References Cited

U.S. PATENT DOCUMENTS 5,585,233 A * 12/1996 Moller et al. .................. 435/6

OTHER PUBLICATIONS

M.B. Wright et al. "Proliferating and Migrating Mesangial Cells Responding to Injury Express a Novel Receptor Protein–tyrosine Phosphatase in Experimental Mesangial Proliferative Glomerulonephritis", J. Biol. Chem. 273(37): 23929–23937. (Sep. 1998).*

Results of BLAST search of SEQ ID NO:2 against Derwent (FastAlert and GeneSeqP) and NCBI (pataa) protein patent databases on Sep. 29, 2003.

* cited by examiner

*Primary Examiner*—Rebecca E. Prouty
(74) *Attorney, Agent, or Firm*—Celera Genomics; Lin Sun-Hoffman

(57) ABSTRACT

The present invention provides amino acid sequences of peptides that are encoded by genes within the human genome, the phosphatase peptides of the present invention. The present invention specifically provides isolated peptide and nucleic acid molecules, methods of identifying orthologs and paralogs of the phosphatase peptides, and methods of identifying modulators of the phosphatase peptides.

19 Claims, 97 Drawing Sheets

```
   1 TAATTGTGTA CTTGCCAGAA GGATCTGTCT TTAAATCATT AATGCAGGCA
  51 ACATTTCTCT CTAGAGCCAT CAATGTGATT CTACTGGCTG AAAAATGTAA
 101 TAAAGATGGA TTTTCTTATC ATTTTTCTTT TACTTTTTAT TGGGACTTCA
 151 GAGACACAGG TTGATGTTTC CAATGTCGTT CCTGGTACTA GGTACGATAT
 201 AACCATCTCT TCAATTTCTA CAACATACAC CTCACCTGTT ACTAGAATAG
 251 TGACACCAAA TGTAACAAAA CCAGGGCCTC CAGTCTTCCT AGCCGGGGAA
 301 AGAGTCGGAT CTGCTGGGAT TCTTCTGTCT TGGAATACAC CACCTAATCC
 351 AAATGGAAGG ATTATATCTT ACATTGTCAA ATATAAGGAA GTTTGTCCGT
 401 GGATGCAAAC AGTATATACA CAAGTCAGAT CAAAGCCAGA CAGTCTGGAA
 451 GTTCTTCTTA CTAATCTTAA TCCTGGAACA ACATATGAAA TTAAGGTTGC
 501 TGCTGAAAAC AGTGCTGGCA TTGGAGTGTT TAGTGATCCA TTTCTCTTCC
 551 AAACTGCAGA AAGTGCTCCA GGAAAAGTGG TGAATCTCAC AGTTGAGGCC
 601 TACAACGCTT CAGCAGTTAA GCTGATTTGG TATTTACCTC GGCAACCAAA
 651 TGGCAAAATT ACCAGCTTCA AGATTAGTGT CAAACATGCC AGAAGTGGGA
 701 TAGTAGTGAA AGATGTCTCA ATCAGAGTAG AGGACATTTT GACTGGGAAA
 751 TTGCCAGAAT GCAATGAGAA TAGTGAATCT TTTTTATGGA GTACAGCCAG
 801 CCCTTCTCCA ACCCTTGGTA GAGTTACACC TCCATCGCGT ACCACACATT
 851 CATCAAGCAC GTTGACACAG AATGAGATCA GCTCTGTGTG GAAAGAGCCT
 901 ATCAGTTTTG TAGTGACACA CTTGAGACCT TATACAACAT ATCTTTTTGA
 951 AGTTTCAGCT GCTACAACTG AAGCAGGTTA TATTGATAGT ACGATTGTCA
1001 GAACACCAGA ATCAGTGCCT GAAGGACCAC CACAAAACTG CGTAACAGGC
1051 AACATCACAG GAAAGTCCTT TTCAATTTTA TGGGACCCAC CAACTATAGT
1101 AACAGGGAAA TTTAGTTATA GAGTTGAATT ATATGGACCA TCAGGTCGCA
1151 TTTTGGATAA CAGCACAAAA GACCTCAAGT TTGCATTCAC TAACCTAACA
1201 CCATTTACAA TGTATGATGT CTATATTGCG GCTGAAACCA GTGCAGGGAC
1251 TGGGCCCAAG TCAAATATTT CAGTATTCAC TCCACCAGAT GTTCCAGGGG
1301 CAGTGTTTGA TTTACAACTT GCAGAGGTAG AATCCACGCA AGTAAGAATT
1351 ACTTGGAAGA AACCACGACA ACCAAATGGA ATTATTAACC AATACCGAGT
1401 GAAAGTGCTA GTTCCAGAGA CAGGAATAAT TTTGGAAAAT ACTTTGCTCA
1451 CTGGAAATAA TGAGTATATA AATGACCCCA TGGCTCCAGA AATTGTGAAC
1501 ATAGTAGAGC CAATGGTAGG ATTATATGAG GGTTCAGCAG AGATGTCGTC
1551 TGACCTTCAC TCACTTGCTA CATTTATATA TAACAGCCAT CCAGATAAAA
1601 ACTTTCCTGC AAGGAATAGA GCTGAAGACC AGACTTCACC AGTTGTAACT
1651 ACAAGGAATC AGTATATTAC TGACATTGCA GCTGAACAGC TGTCTTATGT
1701 TATCAGGAGA CTTGTACCTT TCACTGAGCA CATGATTAGT GTATCTGCTT
1751 TCACCATCAT GGGAGAAGGA CCACCAACAG TTCTCAGTGT TAGGACACGT
1801 CAGCAAGTGC CAAGCTCCAT TAAAATTATA AACTATAAAA ATATTAGTTC
1851 TTCATCTATT TTGTTATATT GGGATCCTCC AGAATATCCC AATGGAAAAA
1901 TAACTCACTA TACGATTTAT GCAATGGAAT TGGATACAAA CAGAGCATTC
1951 CAGATAACTA CCATAGATAA CAGCTTTCTC ATAACAGGGT TAAAGAAATA
2001 CACAAAATAC AAAATGAGAG TGGCAGCCTC AACCCACGAT GGAGAAAGTT
2051 CTTTGTCTGA AGAAAATGAC ATCTTTGTGA GAACTTCAGA AGATGAACCG
2101 GAATCATCAC CTCAAGATGT CGAAGTAATT GATGTTACCG CAGATGAAAT
2151 AAGGTTGAAG TGGTCACCAC CCGAAAAGCC CAATGGGATC ATTATTGCTT
2201 ATGAAGTGCT ATATAAAAAT ATAGATACTT TATATATGAA GAACACATCA
2251 ACAACAGACA TAATATTAAG GAACTTAAGA CCTCACACCC TCTATAACAT
2301 TTCTGTAAGG TCTTACACCA GATTTGGTCA TGGCAATCAG GTATCTTCTT
2351 TACTCTCTGT AAGGACTTCG GAGACTGTCC CTGATAGTGC ACCAGAAAAT
2401 ATCACTTACA AAAATATTTC TTCTGGAGAG ATTGAGCTAT CATTCCTTCC
2451 CCCAAGTAGT CCCAATGGAA TCATAAAAAA ATATACAATT TATCTCAAGA
2501 GAAGTAATGG AAATGAGGAA AGAACTATAA ATACAACCTC TTTAACCCAA
2551 AACATTAAAG TACTGAAGAA ATATACCCAA TATATCATTG AGGTGTCTGC
2601 TAGTACACTG AAAGGTGAAG GAGTTCGGAG TGCTCCCATA AGTATACTGA
2651 CGGAGGAAGA TGCTCCTGAT TCTCCCCCTC AAGACTTCTC TGTAAAACAG
2701 TTGTCTGGTG TCACGGTGAA GTTGTCATGG CAACCACCCC TGGAGCCAAA
2751 TGGAATTATC CTTTATTACA CAGTTTATGT CTGGAATAGA TCATCATTAA
2801 AAACTATTAA TGTCACTGAA ACATCATTGG AGTTATCAGA TTTGGATTAT
2851 AATGTTGAAT ACAGTGCTTA TGTAACAGCT AGCACCAGAT TTGGTGATGG
2901 GAAAACAGGA AGCAATATCA TTAGCTTTCA AACACCAGAG GGAGCACCAA
2951 GCGATCCTCC CAAAGATGTT TATTATGCAA ACCTCAGTTC TTCATCAATA
3001 ATTCTTTTCT GGACACCTCC TTCAAAACCT AATGGGATTA TACAATATTA
3051 CTCTGTTTAT TACAGAAATA CTTCAGGTAC TTTTATGCAG AATTTTACAC
3101 TCCATGAACT AACCAATGAC TTTGACAATA TGACTGTATC CACAATTATA
3151 GATAAACTGA CAATATTCAG CTACTATACA TTTTGGTTAA CAGCAAGTAC
3201 TTCAGTTGGA AATGGGAATA AAAGCAGTGA CATCATTGAA GTATACACAG
3251 ATCAAGACAT ACCTGAAGGG TTTGTTGGAA ACCTGACTTA CGAATCCATT
3301 TCGTCAACTG CAATAAATGT AAGCTGGGTC CCACCGGCTC AACCAAACGG
3351 TCTAGTCTTC TACTATGTTT CACTGATCTT ACAGCAGACT CCTCGCCATG
3401 TGAGACCACC TCTTGTTACA TATGAGAGAA GCATATATTT TGATAATCTG
```

FIGURE 1, page 1 of 3

```
3451  GAAAAATACA CTGATTATAT ATTAAAAATT ACTCCATCAA CAGAAAAGGG
3501  ATTCTCTGAT ACCTATACTG CCCAGCTATA CATCAAGACT GAAGAAGATG
3551  TCCCAGAAAC TTCACCAATA ATCAACACTT TTAAAAACCT TTCCTCTACC
3601  TCAGTTCTCT TATCATGGGA TCCCCCAGTA AAGCCAAATG GTGCAATAAT
3651  AAGTTATGAT TTAACTTTAC AAGGACCAAA TGAAAATTAT TCTTTCATTA
3701  CTTCTGATAA TTACATAATA TTGGAAGAGC TTTCACCATT TACATTATAT
3751  AGCTTTTTTG CTGCCGCAAG AACTAGAAAA GGACTTGGTC CTTCCAGTAT
3801  TCTTTTCTTT TACACAGATG AGTCAGTGCC GTTAGCACCT CCACAAAATT
3851  TGACTTTAAT CAACTGTACT TCAGACTTTG TATGGCTGAA ATGGAGCCCA
3901  AGTCCTCTTC CAGGTGGTAT TGTTAAAGTA TATAGTTTTA AAATTCATGA
3951  ACATGAAACT GACACTATAT ATTATAAGAA TATATCAGGA TTTAAAACTG
4001  AAGCCAAACT TGTTGGACTG GAACCAGTCA GCACCTACTC TATCCGTGTA
4051  TCTGCGTTCA CCAAAGTTGG AAATGGCAAT CAATTTAGTA ATGTAGTAAA
4101  ATTCACAACC CAAGAATCAG TTCCAGATGT CGTGCAGAAT ATGCAGTGCA
4151  TGGCAACTAG CTGGCAGTCA GTTTTAGTGA AATGGGATCC ACCCAAAAAG
4201  GCAAATGGAA TAATAACGCA GTATATGGTA ACAGTTGAAA GGAATTCTAC
4251  AAAAGTTTCT CCCCAAGATC ACATGTACAC TTTCATAAAG CTTCTTGCCA
4301  ATACCTCATA TGTCTTTAAA GTAAGAGCTT CAACCTCAGC TGGTGAAGGT
4351  GATGAAAGCA CATGCCATGT CAGCACACTA CCTGAAACAG TTCCCAGTGT
4401  TCCCACAAAT ATTGCTTTTT CTGATGTTCA GTCAACTAGT GCAACATTGA
4451  CATGGATAAG ACCTGACACT ATCCTTGGCT ACTTTCAAAA TTACAAAATT
4501  ACCACTCAAC TTCGTGCTCA AAAATGCAAA GAATGGGAAT CCGAAGAATG
4551  TGTTGAATAT CAAAAAATTC AATACCTCTA TGAAGCTCAC TTAACTGAAG
4601  AGACAGTATA TGGATTAAAG AAATTTAGAT GGTATAGATT CCAAGTGGCT
4651  GCCAGCACCA ATGCTGGCTA TGGCAATGCT TCAAACTGGA TTTCTACAAA
4701  AACTCTGCCT GGCCCTCCAG ATGGTCCTCC TGAAAATGTT CATGTAGTAG
4751  CAACATCACC TTTTAGCATC AGCATAAGCT GGAGTGAACC TGCTGTCATT
4801  ACTGGACCAA CATGTTATCT GATTGATGTC AAATCGGTAG ATAATGATGA
4851  ATTTAATATA TCCTTCATCA AGTCAAATGA AGAAAATAAA ACCATAGAAA
4901  TTAAAGATTT AGAAATATTC ACAAGGTATT CTGTAGTGAT CACTGCATTT
4951  ACTGGGAACA TTAGTGCTGC ATATGTAGAA GGGAAGTCAA GTGCTGAAAT
5001  GATTGTTACT ACTTTAGAAT CAGCCCCAAA GGACCCACCT AACAACATGA
5051  CATTTCAGAA GATACCAGAT GAAGTTACAA AATTTCAATT AACGTTCCTT
5101  CCTCCTTCTC AACCTAATGG AAATATCCAA GTATATCAAG CTCTGGTTTA
5151  CCGAGAAGAT GATCCTACTG CTGTCCAGAT TCACAACCTC AGTATTATAC
5201  AGAAAACCAA CACATTCGTC ATTGCAATGC TAGAAGGACT AAAAGGTGGA
5251  CATACATACA ATATCAGTGT TTACGCAGTC AATAGTGCTG GTGCAGGTCC
5301  AAAGGTTCCG ATGAGAATAA CCATGGATAT CAAAGCTCCA GCACGACCAA
5351  AAACCAAACC AACCCCTATT TATGATGCCA CAGGAAAACT GCTTGTGACT
5401  TCAACAACAA TTACAATCAG AATGCCAATA TGTTACTACA GTGATGATCA
5451  TGGACCAATA AAAAATGTAC AAGTGCTTGC GACAGAAACA GGAGCTCAGC
5501  ATGATGGAAA TGTAACAAAG TGGTATGATG CATATTTTAA TAAAGCAAGG
5551  CCATATTTTA CAAATGAAGG CTTTCCTAAC CCTCCATGTA CAGAAGGAAA
5601  GACAAAGTTT AGTGGCAATG AAGAAATCTA CATCATAGGT GCTGATAATG
5651  CATGCATGAT TCCTGGCAAT GAAGACAAAA TTTGCAATGG ACCACTGAAA
5701  CCAAAAAAGC AATACTTATT TAAATTTAGA GCTACAAATA TTATGGGACA
5751  ATTTACTGAC TCTGATTATT CTGACCCTGT TAAGACTTTA GGGGAAGGAC
5801  TTTCAGAAAG AACCGTAGAG ATCATTCTTT CCGTCACTTT GTGTATCCTT
5851  TCAATAATTC TCCTTGGAAC AGCTATTTTT GCATTTGCAA GAATTCGACA
5901  GAAGCAGAAA GAAGGTGGCA CATACTCTCC TCAGGATGCA GAAATTATTG
5951  ACACTAAATT GAAGCTGGAT CAGCTCATCA CAGTGGCAGA CCTGGAACTG
6001  AAGGACGAGA GATTAACGCG GCCAATAAGC AAGAAATCCT TCCTGCAACA
6051  TGTTGAAGAG CTTTGCACAA ACAACAACCT AAAGTTTCAA GAAGAATTTT
6101  CGGAATTACC AAAATTTCTT CAGGATCTTT CTTCAACTGA TGCTGATCTG
6151  CCTTGGAATA GAGCAAAAAA CCGTTTCCCA AACATAAAAC CATATAATAA
6201  TAATAACAGA GTAAAGCTGA TAGCTGACGC TAGTGTTCCA GGTTCGGATT
6251  ATATTAATGC CAGCTATATT TCTGGTTATT TATGTCCAAA TGAATTTATT
6301  GCTACTCAAG GTCCACTACC AGGAACAGTT GGAGATTTTT GGAGAATGGT
6351  GTGGGAAACC AGGGCAAAAA CATTAGTAAT GCTAACACAG TGTTTTGAAA
6401  AAGGACGGAT CAGATGCCAT CAGTATTGGC CAGAGGACAA CAAGCCAGTT
6451  ACTGTCTTTG GAGATATAGT GATTACAAAG CTAATGGAGG ATGTTCAAAT
6501  AGATTGGACT ATCAGGGATC TGAAAATTGA AAGGCATGGG GATTGCATGA
6551  CTGTTCGACA GTGTAACTTT ACTGCCTGGC CAGAGCATGG GGTTCCTGAG
6601  AACAGCGCCC CTCTAATTCA CTTTGTGAAG TTGGTTCGAG CAAGCAGGGC
6651  ACATGACACC ACACCTATGA TTGTTCACTG CAGTGCTGGA GTTGGAAGAA
6701  CTGGAGTTTT TATTGCTCTG GACCATTTAA CACAACATAT AAATGACCAT
6751  GATTTTGTGG ATATATATGG ACTAGTAGCT GAACTGAGAA GTGAAAGAAT
6801  GTGCATGGTG CAGAATCTGG CACAGTATAT CTTTTTACAC CAGTGCATTC
6851  TGGATCTCTT ATCAAATAAG GGAAGTAATC AGCCCATCTG TTTTGTTAAC
6901  TATTCAGCAC TTCAGAAGAT GGACTCTTTG GACGCCATGG AAGGTGATGT
6951  TGAGCTTGAA TGGGAAGAAA CCACTATGTA AATATTCAGA CCAAAGGATA
```

FIGURE 1, page 2 of 3

```
7001  CAATTGGAAG AGATTTTTAA ATCCCAGGGG CCAAAGTTAC CCCCTCATTC
7051  TTCCGAATTG AAATGTGCAA CCTTAAAGAA ATATCTATGC TTCTCTCACT
7101  GTGCCTTT
 (SEQ ID NO: 1)
```

FEATURES:
5'UTR: 1-105
Start Codon: 106
Stop Codon 6979
3' UTR 6982

Homologous proteins:
Top 10 BLAST Hits

| Sequences producing significant alignments: | Score (bits) | E Value |
|---|---|---|
| CRA\|148000053730152 /altid=gi\|12621078 /def=ref\|NP_075214.1\| pr... | 2375 | 0.0 |
| CRA\|89000000193395 /altid=gi\|7290546 /def=gb\|AAF45998.1\| (AE003... | 363 | 2e-98 |
| CRA\|18000004876831 /altid=gi\|158645 /def=gb\|AAA28952.1\| (M80538... | 363 | 2e-98 |
| CRA\|18000004876357 /altid=gi\|157296 /def=gb\|AAA28484.1\| (M80465... | 363 | 2e-98 |
| CRA\|89000000195290 /altid=gi\|7292674 /def=gb\|AAF48072.1\| (AE003... | 360 | 1e-97 |
| CRA\|18000004876735 /altid=gi\|433182 /def=gb\|AAA76834.1\| (L20894... | 359 | 2e-97 |
| CRA\|18000004952843 /altid=gi\|548624 /def=sp\|P35992\|PTP1_DROME P... | 359 | 3e-97 |
| CRA\|18000004996351 /altid=gi\|103342 /def=pir\|\|D41214 protein-ty... | 359 | 3e-97 |
| CRA\|18000005034127 /altid=gi\|1362625 /def=pir\|\|A49502 protein-t... | 358 | 5e-97 |
| CRA\|18000005034128 /altid=gi\|1362626 /def=pir\|\|B49502 protein-t... | 358 | 5e-97 |

EST:

| Sequences producing significant alignments: | Score (bits) | E Value |
|---|---|---|
| gi\|6036191 /dataset=dbest /taxon=9606 ... | 454 | e-124 |

EXPRESSION INFORMATION FOR MODULATORY USE:
gi|6036191 colon adenocarcinoma

Tissue expression:
Placenta

FIGURE 1, page 3 of 3

```
   1 MDFLIIFLLL FIGTSETQVD VSNVVPGTRY DITISSISTT YTSPVTRIVT
  51 PNVTKPGPPV FLAGERVGSA GILLSWNTPP NPNGRIISYI VKYKEVCPWM
 101 QTVYTQVRSK PDSLEVLLTN LNPGTTYEIK VAAENSAGIG VFSDPFLFQT
 151 AESAPGKVVN LTVEAYNASA VKLIWYLPRQ PNGKITSFKI SVKHARSGIV
 201 VKDVSIRVED ILTGKLPECN ENSESFLWST ASPSPTLGRV TPPSRTTHSS
 251 STLTQNEISS VWKEPISFVV THLRPYTTYL FEVSAATTEA GYIDSTIVRT
 301 PESVPEGPPQ NCVTGNITGK SFSILWDPPT IVTGKFSYRV ELYGPSGRIL
 351 DNSTKDLKFA FTNLTPFTMY DVYIAAETSA GTGPKSNISV FTPPDVPGAV
 401 FDLQLAEVES TQVRITWKKP RQPNGIINQY RVKVLVPETG IILENTLLTG
 451 NNEYINDPMA PEIVNIVEPM VGLYEGSAEM SSDLHSLATF IYNSHPDKNF
 501 PARNRAEDQT SPVVTTRNQY ITDIAAEQLS YVIRRLVPFT EHMISVSAFT
 551 IMGEGPPTVL SVRTRQQVPS SIKIINYKNI SSSSILLYWD PPEYPNGKIT
 601 HYTIYAMELD TNRAFQITTI DNSFLITGLK KYTKYKMRVA ASTHDGESSL
 651 SEENDIFVRT SEDEPESSPQ DVEVIDVTAD EIRLKWSPPE KPNGIIIAYE
 701 VLYKNIDTLY MKNTSTTDII LRNLRPHTLY NISVRSYTRF GHGNQVSSLL
 751 SVRTSETVPD SAPENITYKN ISSGEIELSF LPPSSPNGII KKYTIYLKRS
 801 NGNEERTINT TSLTQNIKVL KKYTQYIIEV SASTLKGEGV RSAPISILTE
 851 EDAPDSPPQD FSVKQLSGVT VKLSWQPPLE PNGIILYYTV YVWNRSSLKT
 901 INVTETSLEL SDLDYNVEYS AYVTASTRFG DGKTGSNIIS FQTPEGAPSD
 951 PPKDVYYANL SSSSIILFWT PPSKPNGIIQ YYSVYYRNTS GTFMQNFTLH
1001 ELTNDFDNMT VSTIIDKLTI FSYYTFWLTA STSVGNGNKS SDIIEVYTDQ
1051 DIPEGFVGNL TYESISSTAI NVSWVPPAQP NGLVFYYVSL ILQQTPRHVR
1101 PPLVTYERSI YFDNLEKYTD YILKITPSTE KGFSDTYTAQ LYIKTEEDVP
1151 ETSPIINTFK NLSSTSVLLS WDPPVKPNGA IISYDLTLQG PNENYSFITS
1201 DNYIILEELS PFTLYSFFAA ARTRKGLGPS SILFFYTDES VPLAPPQNLT
1251 LINCTSDFVW LKWSPSPLPG GIVKVYSFKI HEHETDTIYY KNISGFKTEA
1301 KLVGLEPVST YSIRVSAFTK VGNGNQFSNV VKFTTQESVP DVVQNMQCMA
1351 TSWQSVLVKW DPPKKANGII TQYMVTVERN STKVSPQDHM YTFIKLLANT
1401 SYVFKVRAST SAGEGDESTC HVSTLPETVP SVPTNIAFSD VQSTSATLTW
1451 IRPDTILGYF QNYKITTQLR AQKCKEWESE ECVEYQKIQY LYEAHLTEET
1501 VYGLKKFRWY RFQVAASTNA GYGNASNWIS TKTLPGPPDG PPENVHVVAT
1551 SPFSISISWS EPAVITGPTC YLIDVKSVDN DEFNISFIKS NEENKTIEIK
1601 DLEIFTRYSV VITAFTGNIS AAYVEGKSSA EMIVTTLESA PKDPPNNMTF
1651 QKIPDEVTKF QLTFLPPSQP NGNIQVYQAL VYREDDPTAV QIHNLSIIQK
1701 TNTFVIAMLE GLKGGHTYNI SVYAVNSAGA GPKVPMRITM DIKAPARPKT
1751 KPTPIYDATG KLLVTSTTIT IRMPICYYSD DHGPIKNVQV LATETGAQHD
1801 GNVTKWYDAY FNKARPYFTN EGFPNPPCTE GKTKFSGNEE IYIIGADNAC
1851 MIPGNEDKIC NGPLKPKKQY LFKFRATNIM GQFTDSDYSD PVKTLGEGLS
1901 ERTVEIILSV TLCILSIILL GTAIFAFARI RQKQKEGGTY SPQDAEIIDT
1951 KLKLDQLITV ADLELKDERL TRPISKKSFL QHVEELCTNN NLKFQEEFSE
2001 LPKFLQDLSS TDADLPWNRA KNRFPNIKPY NNNNRVKLIA DASVPGSDYI
2051 NASYISGYLC PNEFIATQGP LPGTVGDFWR MVWETRAKTL VMLTQCFEKG
2101 RIRCHQYWPE DNKPVTVFGD IVITKLMEDV QIDWTIRDLK IERHGDCMTV
2151 RQCNFTAWPE HGVPENSAPL IHFVKLVRAS RAHDTTPMIV HCSAGVGRTG
2201 VFIALDHLTQ HINDHDFVDI YGLVAELRSE RMCMVQNLAQ YIFLHQCILD
2251 LLSNKGSNQP ICFVNYSALQ KMDSLDAMEG DVELEWEETT M
  (SEQ ID NO: 2)
```

FEATURES:
Functional domains and key regions:
[1] PDOC00001 PS00001 ASN_GLYCOSYLATION
N-glycosylation site

```
Number of matches: 39
      1       52-55 NVTK
      2   1802-1805 NVTK
      3     160-163 NLTV
      4     167-170 NASA
      5     316-319 NITG
      6     352-355 NSTK
      7   1380-1383 NSTK
      8     387-390 NISV
      9     731-734 NISV
     10   1719-1722 NISV
     11     579-582 NISS
     12     770-773 NISS
     13     713-716 NTST
     14     387-390 NISV
     15     731-734 NISV
     16   1719-1722 NISV
```

FIGURE 2, page 1 of 7

```
     17   765-768 NITY
     18   579-582 NISS
     19   770-773 NISS
     20   809-812 NTTS
     21   894-897 NRSS
     22   902-905 NVTE
     23   959-962 NLSS
     24 1161-1164 NLSS
     25   988-991 NTSG
     26   996-999 NFTL
     27 1008-1011 NMTV
     28 1038-1041 NKSS
     29 1059-1062 NLTY
     30 1071-1074 NVSW
     31   959-962 NLSS
     32 1161-1164 NLSS
     33 1194-1197 NYSF
     34 1248-1251 NLTL
     35 1253-1256 NCTS
     36 1292-1295 NISG
     37   352-355 NSTK
     38 1380-1383 NSTK
     39 1399-1402 NTSY
-----------------------------------------------------------------
[2] PDOC00004 PS00004 CAMP_PHOSPHO_SITE
cAMP- and cGMP-dependent protein kinase phosphorylation site

Number of matches: 3
      1   630-633 KKYT
      2   791-794 KKYT
      3   821-824 KKYT
-------------------------------------------------------------------
[3] PDOC00005 PS00005 PKC_PHOSPHO_SITE
Protein kinase C phosphorylation site

Number of matches: 38
      1   187-189 SFK
      2 1277-1279 SFK
      3   191-193 SVK
      4   862-864 SVK
      5   205-207 SIR
      6 1312-1314 SIR
      7   213-215 TGK
      8   318-320 TGK
      9   333-335 TGK
     10 1759-1761 TGK
     11   213-215 TGK
     12   318-320 TGK
     13   333-335 TGK
     14 1759-1761 TGK
     15   213-215 TGK
     16   318-320 TGK
     17   333-335 TGK
     18 1759-1761 TGK
     19   337-339 SYR
     20   346-348 SGR
     21   353-355 STK
     22 1381-1383 STK
     23 1530-1532 STK
     24   416-418 TWK
     25   515-517 TTR
     26   561-563 SVR
     27   733-735 SVR
     28   751-753 SVR
     29   571-573 SIK
     30   611-613 TNR
     31   561-563 SVR
     32   733-735 SVR
     33   751-753 SVR
     34   561-563 SVR
     35   733-735 SVR
```

FIGURE 2, page 2 of 7

```
     36    751-753 SVR
     37    767-769 TYK
     38    834-836 TLK
-------------------------------------------------------------
[4] PDOC00006 PS00006 CK2_PHOSPHO_SITE
Casein kinase II phosphorylation site

Number of matches: 47
      1      17-20 TQVD
      2      28-31 TRYD
      3    109-112 SKPD
      4    125-128 TTYE
      5    254-257 TQNE
      6    303-306 SVPE
      7    353-356 STKD
      8    368-371 TMYD
      9    392-395 TPPD
     10    494-497 SHPD
     11    618-621 TTID
     12    642-645 STHD
     13    649-652 SLSE
     14    660-663 TSED
     15    661-664 SEDE
     16    668-671 SPQD
     17  1385-1388 SPQD
     18  1941-1944 SPQD
     19    678-681 TADE
     20    687-690 SPPE
     21    715-718 STTD
     22    757-760 TVPD
     23    761-764 SAPE
     24    772-775 SSGE
     25    849-852 TEED
     26  1145-1148 TEED
     27    906-909 TSLE
     28    911-914 SDLD
     29   998-1001 TLHE
     30  1013-1016 TIID
     31  1048-1051 TDQD
     32    849-852 TEED
     33  1145-1148 TEED
     34  1334-1337 TTQE
     35  1338-1341 SVPD
     36    668-671 SPQD
     37  1385-1388 SPQD
     38  1941-1944 SPQD
     39  1411-1414 SAGE
     40  1424-1427 TLPE
     41  1558-1561 SWSE
     42  1590-1593 SNEE
     43  1628-1631 SSAE
     44  1635-1638 TTLE
     45  1836-1839 SGNE
     46  1884-1887 TDSD
     47  1894-1897 TLGE
-------------------------------------------------------------
[5] PDOC00007 PS00007 TYR_PHOSPHO_SITE
Tyrosine kinase phosphorylation site

Number of matches: 2
      1    704-710 KNIDTLY
      2  1933-1940 KQKEGGTY
-----------------------------------------------------------------
```

FIGURE 2, page 3 of 7

```
[6] PDOC00008 PS00008 MYRISTYL
N-myristoylation site

Number of matches: 17
      1      13-18 GTSETQ
      2      71-76 GILLSW
      3    315-320 GNITGK
      4    472-477 GLYEGS
      5    694-699 GIIIAY
      6    743-748 GNQVSS
      7  1037-1042 GNKSSD
      8  1179-1184 GAIISY
      9  1226-1231 GLGPSS
     10  1324-1329 GNQFSN
     11  1523-1528 GNASNW
     12  1617-1622 GNISAA
     13  1711-1716 GLKGGH
     14  1845-1850 GADNAC
     15  2162-2167 GVPENS
     16  2195-2200 GVGRTG
     17  2200-2205 GVFIAL
----------------------------------------------------------------------
[7] PDOC00017 PS00017 ATP_GTP_A
ATP/GTP-binding site motif A (P-loop)

         1621-1628 AAYVEGKS
----------------------------------------------------------------------
[8] PDOC00323 PS00383 TYR_PHOSPHATASE_1
Tyrosine specific protein phosphatases active site

         2190-2202 VHCSAGVGRTGVF

Membrane spanning structure and domains:
Candidate membrane-spanning segments:
 Helix Begin   End   Score Certainity
     1     3    23   0.743 Putative
     2   542   562   1.032 Certain
     3   955   975   0.971 Putative
     4  1017  1037   1.332 Certain
     5  1073  1093   0.694 Putative
     6  1544  1564   0.948 Putative
     7  1606  1626   0.852 Putative
     8  1908  1928   2.284 Certain
     9  2185  2205   0.677 Putative
```

FIGURE 2, page 4 of 7

BLAST Alignment to Top Hit:

```
CRA|148000053730152 /altid=gi|12621078 /def=ref|NP_075214.1| protein
            tyrosine phosphatase, receptor type, Q [Rattus
            norvegicus] /org=Rattus norvegicus /taxon=10116
            /dataset=nraa /length=2302
          Length = 2302

 Score = 4104 bits (10526), Expect = 0.0
 Identities = 1977/2302 (85%), Positives = 2139/2302 (92%), Gaps = 11/2302 (0%)
 Frame = +1

Query: 1    MDFLIIFLLLFIGTSETQVDVSNVVPGTRYDITISSIS-TTYTSPVTRIVTPNVTKPGPP 177
            MDF   FL L IGTSE+QVDVS+   GT YDIT+SS+S TTY+SPV+R +  NVTKPGPP
Sbjct: 2    MDFHFSFLFLLIGTSESQVDVSSSFDGTGYDITLSSVSATTYSSPVSRTLATNVTKPGPP 61

Query: 178  VFLAGERVGSAGILLSWNTPPNPNGRIISYIVKYKEVCPWMQTVYTQVRSKPDSLEVLLT 357
            VFLAGERVGSAGILLSWNTPPNPNGRIISY+VKYKEVCPWMQT YT+ R+KPDSLEVLLT
Sbjct: 62   VFLAGERVGSAGILLSWNTPPNPNGRIISYVVKYKEVCPWMQTAYTRARAKPDSLEVLLT 121

Query: 358  NLNPGTTYEIKVAAENSAGIGVFSDPFLFQTAESAPGKVVNLTVEAYNASAVKLIWYLPR 537
            NLNPGTTYEIKVAAEN+AGIGVFSDPFLFQTAESAPGKVVNLTVEA N SAV LIWYLPR
Sbjct: 122  NLNPGTTYEIKVAAENNAGIGVFSDPFLFQTAESAPGKVVNLTVEALNYSAVNLIWYLPR 181

Query: 538  QPNGKITSFKISVKHARSGIVVKDVSIRVEDILTGKLPECNENSESFLWSTASPSPTLGR 717
            QPNGKITSFKISVKHARSGIVVKDVS+RVEDIL+GKLPECNENSESFLWST SPSPTLGR
Sbjct: 182  QPNGKITSFKISVKHARSGIVVKDVSLRVEDILSGKLPECNENSESFLWSTTSPSPTLGR 241

Query: 718  VTPPSRTTHSSSTLTQNEISSVWKEPISFVVTHLRPYTTYLFEVSAATTEAGYIDSTIVR 897
            VTP  RTT SSST  +++ISSVWKEPISFVVTHLRPYTTYLFEVSA TTEAGYIDSTIVR
Sbjct: 242  VTPTVRTTQSSSTAARSKISSVWKEPISFVVTHLRPYTTYLFEVSAVTTEAGYIDSTIVR 301

Query: 898  TPESVPEGPPQNCVTGNITGKSFSILWDPPTIVTGKFSYRVELYGPSGRILDNSTKDLKF 1077
            TPESVPEGPPQNC+ GN+TGK+FSI WDPPTIVTGKFSYRVELYGPSGRILDNSTKDL+F
Sbjct: 302  TPESVPEGPPQNCIMGNVTGKAFSISWDPPTIVTGKFSYRVELYGPSGRILDNSTKDLRF 361

Query: 1078 AFTNLTPFTMYDVYIAAETSAGTGPKSNISVFTPPDVPGAVFDLQLAEVESTQVRITWKK 1257
            AFT+LTPFTMYDVY+AAETSAG GPKSN+SVFTPPDVPGAVFDLQ+AEVE+T++RITW+K
Sbjct: 362  AFTHLTPFTMYDVYVAAETSAGVGPKSNLSVFTPPDVPGAVFDLQIAEVEATEIRITWRK 421

Query: 1258 PRQPNGIINQYRVKVLVPETGIILENTLLTGNNEYINDPMAPEIVNIVEPMVGLYEGSAE 1437
            PRQPNGII+QYRVKV V ETG++LENTLLTG +E I++PM+PEI+N+V+PM+G YEGS E
Sbjct: 422  PRQPNGIISQYRVKVSVLETGVVLENTLLTGQDESISNPMSPEIMNLVDPMIGFYEGSGE 481

Query: 1438 MSSDLHSLATFIYNSHPDKNFPARNRAEDQTSPVVTTRNQYITDIAAEQLSYVIRRLVPF 1617
            MSSDLHS A+FIYNSHP  +FPA  RAE+Q+SPVVTTRNQY+TDI AEQLSYV+RRLVPF
Sbjct: 482  MSSDLHSPASFIYNSHPHNDFPASTRAEEQSSPVVTTRNQYMTDITAEQLSYVVRRLVPF 541

Query: 1618 TEHMISVSAFTIMGEGPPTVLSVRTRQQVPSSIKIINYKNISSSSILLYWDPPEYPNGKI 1797
            TEH ISVSAFTIMGEGPPTVL+VRTR+QVPSSI+IINYKNISSSSILLYWDPPEYPNGKI
Sbjct: 542  TEHTISVSAFTIMGEGPPTVLTVRTREQVPSSIQIINYKNISSSSILLYWDPPEYPNGKI 601

Query: 1798 THYTIYAMELDTNRAFQITTIDNSFLITGLKKYTKYKMRVAASTHDGESSLSEENDIFVR 1977
            THYTIYA ELDTNRAFQ+TT+DNSFLITGLKKYT+YKMRVAASTH GESSLSEENDIFVR
Sbjct: 602  THYTIYATELDTNRAFQMTTVDNSFLITGLKKYTRYKMRVAASTHVGESSLSEENDIFVR 661

Query: 1978 TSEDEPESSPQDVEVIDVTADEIRLKWSPPEKPNGIIIAYEVLYKNIDTLYMKNTSTTDI 2157
            T EDEPESSPQDV+V  V+  E+RLKWSPPEKPNGIIIAYEVLY+N DTL++KNTSTTDI
Sbjct: 662  TPEDEPESSPQDVQVTGVSPSELRLKWSPPEKPNGIIIAYEVLYQNADTLFVKNTSTTDI 721

Query: 2158 ILRNLRPHTLYNISVRSYTRFGHGNQVSSLLSVRTSETVPDSAPENITYKNISSGEIELS 2337
            I+ +L+P+TLYNIS+RSYTR GHGNQ SSLLSVRTSETVPDSAPENITYKNISSGEIE+S
Sbjct: 722  IISDLKPYTLYNISIRSYTRLGHGNQSSSLLSVRTSETVPDSAPENITYKNISSGEIEIS 781

Query: 2338 FLPPSSPNGIIKKYTIYLKRSNGNEERTINTTSLTQNIKVLKKYTQYIIEVSASTLKGEG 2517
            FLPP SPNGII+KYTIYLKRSN +E RTINTTSLTQ I  LKKYT Y+IEVSASTLKGEG
Sbjct: 782  FLPPRSPNGIIQKYTIYLKRSNSHEARTINTTSLTQTIGGLKKYTHYVIEVSASTLKGEG 841

Query: 2518 VRSAPISILTEEDAPDSPPQDFSVKQLSGVTVKLSWQPPLEPNGIILYYTVYVWNRSSLK 2697
            +RS PISILTEEDAPDSPPQ+FSVKQLSGVTV LSWQPPLEPNGIILYYTVYVW++SSL+
Sbjct: 842  IRSRPISILTEEDAPDSPPQNFSVKQLSGVTVMLSWQPPLEPNGIILYYTVYVWDKSSLR 901
```

FIGURE 2, page 5 of 7

```
Query: 2698 TINVTETSLELSDLDYNVEYSAYVTASTRFGDGKTGSNIISFQTPEGAPSDPPKDVYYAN 2877
             IN TE SL LSDLDYNV+Y A VTASTRFGDG   S+II+F+TPEG PSDPP DV+Y N
Sbjct: 902  AINATEASLVLSDLDYNVDYGACVTASTRFGDGNARSSIINFRTPEGEPSDPPNDVHYVN 961

Query: 2878 LSSSSIILFWTPPSKPNGIIQYYSVYYRNTSGTFMQNFTLHELTNDFDNMTVSTIIDKLT 3057
            LSSSSIILFWTPP KPNGIIQYYSVYY+NTSGTF+QNFTL ++T + DN+TVS  I +L
Sbjct: 962  LSSSSIILFWTPPVKPNGIIQYYSVYYQNTSGTFVQNFTLLQVTKESDNVTVSARIYRLA 1021

Query: 3058 IFSYYTFWLTASTSVGNGNKSSDIIEVYTDQDIPEGFVGNLTYESISSTAINVSWVPPAQ 3237
            IFSYYTFWLTASTSVGNGNKSSDII VYTDQDIPEG VGNLT+ESISSTAI+VSW PP+Q
Sbjct: 1022 IFSYYTFWLTASTSVGNGNKSSDIIHVYTDQDIPEGPVGNLTFESISSTAIHVSWEPPSQ 1081

Query: 3238 PNGLVFYYVSLILQQT-PRHVRPPLVTYERSIYFDNLEKYTDYILKITPSTEKGFSDTYT 3414
            PNGLVFYY+SL LQQ+ PRH+ PPLVTYE SI FD+LEKYTDYI KITPSTEKGFS+TYT
Sbjct: 1082 PNGLVFYYLSLNLQQSPPRHMIPPLVTYENSIDFDDLEKYTDYIFKITPSTEKGFSETYT 1141

Query: 3415 AQLYIKTEEDVPETSPIINTFKNLSSTSVLLSWDPPVKPNGAIISYDLTLQGPNENYSFI 3594
             QL+IKTEEDVP+T PIINTFKNLSSTS+LLSWDPP+KPNGAI+ Y LTLQGP+ N++F+
Sbjct: 1142 TQLHIKTEEDVPDTPPIINTFKNLSSTSILLSWDPPLKPNGAILGYHLTLQGPHANHTFV 1201

Query: 3595 TSDNYIILEELSPFTLYSFFAAARTRKGLGPSSILFFYTDESVPLAPPQNLTLINCTSDF 3774
            TS N+I+LEELSPFTLYSFFAAART KGLGPSSILFFYTDES PLAPPQNLTLIN TSDF
Sbjct: 1202 TSGNHIVLEELSPFTLYSFFAAARTMKGLGPSSILFFYTDESAPLAPPQNLTLINYTSDF 1261

Query: 3775 VWLKWSPSPLPGGIVKVYSFKIHEHETDTIYYKNISGFKTEAKLVGLEPVSTYSIRVSAF 3954
            VWL WSPSPLPGGIVKVYSFKIHEHETDT++YKNISG +T+AKL GLEPVSTYS+ VSAF
Sbjct: 1262 VWLTWSPSPLPGGIVKVYSFKIHEHETDTVFYKNISGLQTDAKLEGLEPVSTYSVSVSAF 1321

Query: 3955 TKVGNGNQFSNVVKFTTQESVPDVVQNMQCMATSWQSVLVKWDPPKKANGIITQYMVTVE 4134
            TKVGNGNQ+SNVV+FTTQESVP+ V+N++C+A  WQSV V+WDPP+K NGII  YM+TV
Sbjct: 1322 TKVGNGNQYSNVVEFTTQESVPEAVRNIECVARDWQSVSVRWDPPRKTNGIIIHYMITVG 1381

Query: 4135 RNSTKVSPQDHMYTFIKLLANTSYVFKVRASTSAGEGDESTCHVSTLPETVPSVPTNIAF 4314
             NSTKVSP+D  YTF KLL NTSYVF+VRASTSAGEG+ES C +STLPETVPS PTN+AF
Sbjct: 1382 GNSTKVSPRDPTYTFTKLLPNTSYVFEVRASTSAGEGNESRCDISTLPETVPSAPTNVAF 1441

Query: 4315 SDVQSTSATLTWIRPDTILGYFQNYKITTQLRAQKCKEWESEECVEYQKIQYLYEAHLTE 4494
            S+VQSTSATLTW +PDTI GYFQNYKITTQLRAQKC+EWE EEC+E+QK QYLYEA+ TE
Sbjct: 1442 SNVQSTSATLTWTKPDTIFGYFQNYKITTQLRAQKCREWEPEECIEHQKDQYLYEANQTE 1501

Query: 4495 ETVYGLKKFRWYRFQVAASTNAGYGNASNWISTKTLPGPPDGPPENVHVVATSPFSISIS 4674
            ETV+GLKKFRWYRFQVAASTN GY NAS WIST+TLPGPPDGPPENVHVVATSPF I+IS
Sbjct: 1502 ETVHGLKKFRWYRFQVAASTNVGYSNASEWISTQTLPGPPDGPPENVHVVATSPFGINIS 1561

Query: 4675 WSEPAVITGPTCYLIDVKSVDNDEFNISFIKSNEENKTIEIKDLEIFTRYSVVITAFTGN 4854
            WSEPAVITGPT YLIDVKSVD+D+FNISF+KSNEENKT EI +LE+FTRYSVVITAF GN
Sbjct: 1562 WSEPAVITGPTFYLIDVKSVDDDDFNISFLKSNEENKTTEINNLEVFTRYSVVITAFVGN 1621

Query: 4855 ISAAYVEGKSSAEMIVTTLESAPKDPPNNMTFQKIPDEVTKFQLTFLPPSQPNGNIQVYQ 5034
            +S AY +GKSSAE+I+TTLES PKDPPNNMTFQKIPDEVTKFQLTFLPPSQPNGNI+VYQ
Sbjct: 1622 VSRAYTDGKSSAEVIITTLESVPKDPPNNMTFQKIPDEVTKFQLTFLPPSQPNGNIRVYQ 1681

Query: 5035 ALVYREDDPTAVQIHNLSIIQKTNTFVIAMLEGLKGGHTYNISVYAVNSAGAGPKVPMRI 5214
            ALVYREDDPTAVQIHN SIIQKT+T +IAMLEGLKGGHTYNISVYA+NSAGAGPKV MRI
Sbjct: 1682 ALVYREDDPTAVQIHNFSIIQKTDTSIIAMLEGLKGGHTYNISVYAINSAGAGPKVQMRI 1741

Query: 5215 TMDIKAPARPKTKPTPIYDATGKLLVTSTTITIRMPICYYSDDHGPIKNVQVLATETGAQ 5394
            TMDIKAPARPK+KP PI DATGKLLVTSTTITIRMPICYY+DDHGPI+NVQVL  ETGAQ
Sbjct: 1742 TMDIKAPARPKSKPIPIRDATGKLLVTSTTITIRMPICYYNDDHGPIRNVQVLVAETGAQ 1801

Query: 5395 HDGNVTKWYDAYFNKARPYFTNEGFPNPPCTEGKTKFSGNEEIYIIGADNACMIPGNEDK 5574
             DGNVTKWYDAYFNKARPYFTNEGFPNPPC EGKTKFSGNEEIY+IGADNACMIPGNE+K
Sbjct: 1802 QDGNVTKWYDAYFNKARPYFTNEGFPNPPCIEGKTKFSGNEEIYVIGADNACMIPGNEEK 1861

Query: 5575 ICNGPLKPKKQYLFKFRATNIMGQFTDSDYSDPVKTLGEGLSERTVEIILSVTLCILSII 5754
            ICNGPLKPKKQYLFKFRATN+MGQFTDS+YSDP+KTLGEGLSERTVEIILSVTLCILSII
Sbjct: 1862 ICNGPLKPKKQYLFKFRATNVMGQFTDSEYSDPIKTLGEGLSERTVEIILSVTLCILSII 1921

Query: 5755 LLGTAIFAFARIRQKQKEGGTYSPQDAEIIDTKLKLDQLITVADLELKDERLTR------ 5916
            LLGTAIFAF RIRQKQKEGGTYSP+DAEIIDTK KLDQLITVADLELKDERLTR
Sbjct: 1922 LLGTAIFAFVRIRQKQKEGGTYSPRDAEIIDTKFKLDQLITVADLELKDERLTRLLSYRK 1981
```

FIGURE 2, page 6 of 7

```
Query: 5917 ---PISKKSFLQHVEELCTNNNLKFQEEFSELPKFLQDLSSTDADLPWNRAKNRFPNIKP 6087
               PISKKSFLQHVEELCTN+NLKFQEEFSELPKFLQDLSSTDADLPWNRAKNRFPNIKP
Sbjct: 1982 SIKPISKKSFLQHVEELCTNSNLKFQEEFSELPKFLQDLSSTDADLPWNRAKNRFPNIKP 2041

Query: 6088 YNNNNRVKLIADASVPGSDYINASYISGYLCPNEFIATQGPLPGTVGDFWRMVWETRAKT 6267
            Y NNNRVKLIAD S+PGSDYINASY+SGYLCPNEFIATQGPLPGTVGDFWRMVWETR KT
Sbjct: 2042 Y-NNNRVKLIADVSLPGSDYINASYVSGYLCPNEFIATQGPLPGTVGDFWRMVWETRTKT 2100

Query: 6268 LVMLTQCFEKGRIRCHQYWPEDNKPVTVFGDIVITKLMEDVQIDWTIRDLKIERHGDCMT 6447
            LVMLTQCFEKGRIRCHQYWPEDNKPVTVFGDIVITKLMED+QIDWTIRDLKIERHGDCMT
Sbjct: 2101 LVMLTQCFEKGRIRCHQYWPEDNKPVTVFGDIVITKLMEDIQIDWTIRDLKIERHGDCMT 2160

Query: 6448 VRQCNFTAWPEHGVPENSAPLIHFVKLVRASRAHDTTPMIVHCSAGVGRTGVFIALDHLT 6627
            VRQCNFT WPEHGVPEN+ PLIHFVKLVR SRAHDTTPM+VHCSAGVGRTGVFIALDHLT
Sbjct: 2161 VRQCNFTGWPEHGVPENTTPLIHFVKLVRTSRAHDTTPMVVHCSAGVGRTGVFIALDHLT 2220

Query: 6628 QHINDHDFVDIYGLVAELRSERMCMVQNLAQYIFLHQCILDLLSNKGSNQPICFVNYSAL 6807
            QHIN+HDFVDIYGLVAELRSERMCMVQNLAQYIFLHQCILDLLSNKG +QP+CFVNYS L
Sbjct: 2221 QHINNHDFVDIYGLVAELRSERMCMVQNLAQYIFLHQCILDLLSNKGGHQPVCFVNYSTL 2280

Query: 6808 QKMDSLDAMEGDVELEWEETTM 6873
            QKMDSLDAMEGDVELEWEETTM
Sbjct: 2281 QKMDSLDAMEGDVELEWEETTM 2302 (SEQ ID NO: 4)
```

Hmmer search results (Pfam):

Scores for sequence family classification (score includes all domains):

| Model | Description | Score | E-value | N |
|---|---|---|---|---|
| PF00041 | Fibronectin type III domain | 595.2 | 3.9e-175 | 21 |
| PF00102 | Protein-tyrosine phosphatase | 369.0 | 5.1e-107 | 1 |
| CE00202 | CE00202 EPHRIN_TYPE_A_RECEPTOR | 31.5 | 3.5e-08 | 5 |
| CE00527 | E00527 CDC14_PHOSPHATASE | 7.7 | 0.13 | 1 |
| PF00541 | Adenoviral fiber protein (knob domain). | 2.7 | 1.4 | 1 |
| PF00150 | Cellulase (glycosyl hydrolase family 5) | 2.2 | 9.8 | 1 |

Parsed for domains:

| Model | Domain | seq-f | seq-t | | hmm-f | hmm-t | | score | E-value |
|---|---|---|---|---|---|---|---|---|---|
| PF00041 | 1/21 | 15 | 43 | .. | 54 | 84 | .] | 7.8 | 0.86 |
| PF00041 | 2/21 | 56 | 143 | .. | 1 | 84 | [] | 59.8 | 8.4e-16 |
| CE00202 | 1/5 | 74 | 158 | .. | 462 | 544 | .. | 23.6 | 5.4e-06 |
| PF00041 | 3/21 | 155 | 198 | .. | 1 | 44 | [. | 13.7 | 0.017 |
| PF00541 | 1/1 | 227 | 235 | .. | 1 | 10 | [. | 2.7 | 1.4 |
| PF00041 | 4/21 | 267 | 291 | .. | 57 | 84 | .] | 10.1 | 0.18 |
| PF00041 | 5/21 | 305 | 386 | .. | 1 | 84 | [] | 30.3 | 2.7e-07 |
| CE00202 | 2/5 | 403 | 435 | .. | 450 | 483 | .. | 1.9 | 5.7 |
| PF00041 | 6/21 | 397 | 440 | .. | 1 | 44 | [. | 28.1 | 1.2e-06 |
| PF00041 | 7/21 | 530 | 558 | .. | 57 | 84 | .] | 7.8 | 0.86 |
| PF00041 | 8/21 | 569 | 651 | .. | 1 | 84 | [] | 53.4 | 5.9e-14 |
| CE00202 | 3/5 | 682 | 703 | .. | 460 | 482 | .. | 4.3 | 1.2 |
| PF00041 | 9/21 | 665 | 743 | .. | 1 | 81 | [. | 59.6 | 9.6e-16 |
| PF00041 | 10/21 | 759 | 842 | .. | 1 | 84 | [] | 42.3 | 9.4e-11 |
| CE00202 | 4/5 | 871 | 888 | .. | 460 | 478 | .. | 1.6 | 6.5 |
| PF00041 | 11/21 | 854 | 935 | .. | 1 | 84 | [] | 54.2 | 3.5e-14 |
| PF00041 | 12/21 | 948 | 1040 | .. | 1 | 84 | [] | 34.5 | 1.7e-08 |
| PF00041 | 13/21 | 1053 | 1134 | .. | 1 | 84 | [] | 15.5 | 0.005 |
| PF00041 | 14/21 | 1158 | 1231 | .. | 8 | 84 | .] | 44.7 | 2e-11 |
| PF00041 | 15/21 | 1243 | 1328 | .. | 1 | 84 | [] | 40.7 | 2.7e-10 |
| CE00202 | 5/5 | 1400 | 1416 | .. | 511 | 527 | .. | 4.2 | 1.3 |
| PF00041 | 16/21 | 1340 | 1418 | .. | 1 | 84 | [] | 47.9 | 2.3e-12 |
| PF00041 | 17/21 | 1430 | 1468 | .. | 1 | 39 | [. | 27.3 | 2e-06 |
| PF00041 | 18/21 | 1500 | 1526 | .. | 59 | 84 | .] | 14.5 | 0.0099 |
| PF00041 | 19/21 | 1538 | 1620 | .. | 1 | 84 | [] | 36.1 | 5.7e-09 |
| PF00041 | 20/21 | 1641 | 1734 | .. | 1 | 84 | [] | 30.5 | 2.4e-07 |
| PF00150 | 1/1 | 1786 | 1815 | .. | 307 | 340 | .. | 2.2 | 9.8 |
| PF00041 | 21/21 | 1864 | 1889 | .. | 63 | 84 | .] | 1.1 | 74 |
| CE00527 | 1/1 | 2190 | 2204 | .. | 313 | 327 | .. | 7.7 | 0.13 |
| PF00102 | 1/1 | 2018 | 2250 | .. | 1 | 264 | [] | 369.0 | 5.1e-107 |

FIGURE 2, page 7 of 7

```
   1 CATTATCTAT GGAACATAAT CTGAGGCTTT TTTTTTACAG TTGGTAGATA
  51 CTTATGTACA AGATTTTGCT GTGAAAATCA GGGCAAGAAG GTAGTGATGC
 101 AAGGTAGCAG ATAACATTGA AATACATTTT TGAAAATAAT TTTTAAAATT
 151 GATGTAATGC AATTAGATTA CTTGAGCTAA TAGCATAGCT TTATTTTATT
 201 TTATTTATTT TATTTTATTT ATTTTTTTGA GACACAGTCT TGCTCTGTTG
 251 CCCAGGCTGG AGTGCAGTTG CCGATATTGG CTCACTTCAG CCTCCGCCTC
 301 CTGAGCTCAA GCAATTCTCG TGCCTCAGCC TCCTGAAAGC TGGGACCACA
 351 GGTCTGCCCA CCACGCAGGG CTAATTTTTT TATTTTTAGT GGAGACAGGG
 401 TTTTGCCATG TTGCCCAGGC TGACCTTAAA CTCCTGGTCT CAAGTGATCC
 451 AACCGCCTTG GTCTCCCGAA GTGCCGGCAT TACAGGTGTG AGCCACCACA
 501 CTCGTCTTAA TTGCATAGTT TTAGAGATCC ATGTTGGATT AGCTCTTCTG
 551 TAGTGTCCTG ATGACCTGTG ACCAATGATA AGAGTATGGA ATTAGGTAGT
 601 TTCTATGAAA AGGCATCTTT TCTGGCGACT AATAGCCACA GTATCAAGAG
 651 TTTTAAAAGC CCCTCTCCTC TGGTCTCAAT GGAGTCAAAG AAAACTCTCC
 701 CGACTGCTCC TGAAAAAGGA TGTCAAATGA AACTGTTTCA AATTGCTGAA
 751 TAGCCTGGCT AATCCTGCCT GTCTCCAATC ACATACTCCG AATCCATATT
 801 TTTCTCACTG TGGTAAGCTT TCCAACTATT TTTCAGAAAA CAAAACTTAT
 851 ATTTGGAATA ACTTGGTGCT TCTGTGGCAG TAAAACCATG ACTGAAATGT
 901 ATCTCTGTGG AAACCCTTAC TTCATTTAAA ATTTATTATT CCTCCTAATG
 951 ATTCAAGGCT TCAAATATTT CAATGGTAAA GAAAGAGCTT TTTCTATTCA
1001 GAGGGAATAT TCATTTACTT CTTCAGTGCT TTGTGTGTCT AAAGTAGAAA
1051 AATATGAGAT TACATGAGAC ATATACTTTT TCAGTGTTAC TGATCATATT
1101 CCCTTATCTA AATTCTTTAA TAACTAACTT TATTATTCCT AAAATATAAA
1151 TAAAAAATAA TGCACATTTT TCAGCATCAC TATACACATG TTCATTTTTT
1201 GGTTTTAGAT ATTAATCTAT ACCCAGTTCA AACTGTGGAA ACTGAACTAA
1251 CATGACTGAA ATAAAATAGT GTTATATTTT GTTCTTTAGA CTCTTTTTTC
1301 CCTTCCTGAG ATTTTGATAT GTATTTGGAG AGTTTTGAGT CAATATTTAT
1351 TTGATTTGTT TTCTTTTCTG GAGTGATATT GTAAATACTT TAAAGATTTT
1401 GATTGAGTGA GAGGTGTGAG CTATATTTTC TTCTTTCCTG TATGATATAC
1451 ATACATTGTT TCCAATCTAA TTTCTATTAA ATAACTATAG GAGAGCCCAC
1501 AGCCTTGTTA TTTTACATAT CACTATTTAG ATATTTGTTA TTTATTTATT
1551 TGTGTTGGCC TGAAGTAAAT GTTACTTTTG TACGATATTT GAAGGATAGA
1601 TTTATTTTAT AAATTAATAG TTTAAATAAG ATTTTGCCAG CATTTGAAAT
1651 GAACAAATGT TTGGACAATG AAAACATCAG TATGAAAGGG AATACTGTAA
1701 TTACTTTAGT ACATAGTATT CCTTAATATC CATTAAAATT GGTCCAAGCA
1751 AACTCTAATT ATGAACATCA TATTAACATT TGATCTAATT ACTGAATATA
1801 ATTAAAAGCA AAATAAGTTA ATTTACTAAA GAATTCTGAA ATTTACTATT
1851 TTCAGTATTT CAGGATAACC AACATCTTTT TTCTATTAAT CTAGAATAAA
1901 TTTCCATATA TTAATGTTGT TTACTTTTAA TGTTAGTGTG CTCAAAAAGT
1951 ATTGTTAACT TTTAAAATTC AATTCTACAG ATAATATTCT TTTTATCTCA
2001 GGAATAGATC ATCATTAAAA ACTATTAATG TCACTGAAAC ATCATTGGAG
2051 TTATCAGATT TGGATTATAA TGTTGAATAC AGTGCTTATG TAACAGCTAG
2101 CACCAGATTT GGTGATGGGA AAACAAGAAG CAATATCATT AGCTTTCAAA
2151 CACCAGAGGG AGGTGAGTTA AGGATGTATG CCAATTAAAA GAATGTTCTT
2201 TTTCTTTAAA AAAAAAATCC TGCCCAGAAA AATATTCAAA TATCAAAATG
2251 TATGATGAAG CCTAATATTC ATCATCAGTT TGATGAAAAA TTGCATTTTG
2301 ATCACTTTTT AGCTGTGTGA TGTTGGGAAA ATTAATCTCT GTGTGCCTCA
2351 ATTTCCCATT GGTAATGTGG AAACAGTATC ATTCTACTTC ACAGGGTTCT
2401 TATGAAGATT ACATAAGTTT ATATTTTTAA AAGCACTTAG TACAGAAGTT
2451 ACTTGGACAA ATAGAATTTT ATGTGTTTAT TAAACGAAAC AACATAAAAT
2501 GCATGAATCA TTTGTCTATG ACTTTTATTA TTCAATATAA AAATTCTAAG
2551 TTATATTAGA ATTTCAAATT ATGTATTTTG TATTGGAAAC CTGTTATAAT
2601 ATTGTTCTCA TATCCAGAGC AGTGGACAGG TTTTAGAACG GAGATAGTAT
2651 TTTATGGGTA AGAAATCTAT CTGTCTTCAG CTTGAATATG CCTATAATAA
2701 AGTATTAGAG GGGTGACCCA ATGTGTTTTA TGGATTTCAT TTCTGACATT
2751 TCTAATTCAA GCTTTTTTGA AAAACATTTT TTATCACTTT AATTTATAAA
2801 CTGTAGGTAA AATTCAGGCC ATTTCAGACA TTACTTGTAA ACACAAATAC
2851 AGTAATTTGT TCAATTATTT GTTTTATAGC ACCAAGCGAT CCTCCCAAAG
2901 ATGTTTATTA TGCAAACCTC AGTTCTTCAT CAATAATTCT TTTCTGGACA
2951 CCTCCTTCAA AACCTAATGG GATTATACAA TATTACTCTG TTTATTACAG
3001 AAATACTTCA GGTACTTTTA TGCAGGTAAG AACTGAATTT TCTTCTAGTT
3051 CTTTATTAAC ATCCTTAAGT TTTATTAATA ATACAGACTT GTCACAGTAA
3101 AAGAAATTGT TTACCTTACA TTGATAATTA GGCACAGATG TATTTTATAA
3151 AACTCCCATT GACATAGAAA AATGCGGTGT AGAAATGTCA GATACATTTA
3201 ATCTCTCTTT ACAGACACAC ACACACACAC ATACAACTTC TATATAAGCT
3251 TCACATGTAT TAAAAATAGT GAATCTGCCA CCTACTGAAA ATTCTGTTTA
3301 TAAAGATGGC CCTCAATTAC ACTTCCTCCA ATAAGTGTTC TCTAAAGTGC
3351 TGATGGTATC ATTTATCCTC AAAGTTATTT ATTAGCTAAA TTTTTTTTCA
3401 TTTGTTTGTA TATGATATAA ATAGTTCTAG TGTTTGGATG TGTTTGTTTT
3451 TCTTTAATTA AAAAAAGTTT TTGATAGCAG GAAGGGTTAT TATAATAATA
```

FIGURE 3, page 1 of 87

```
3501 GTATATTAGT AGTTAATGTT TAATGTCAGA TGAAATGAAG ACCACTCGGA
3551 ATGTGTTTAA TTAATTTGTC ATAGATAAGA TTCTAGGCTT GCACAGTTTG
3601 TAGATGGGCA CTCTCTAGGA TGTGAATGAT GATGGCTATG AAAATAGCTA
3651 ACATGCATTT ACTTTGAAAA AATATTTTCA ATTTTCAACA GAATTATATT
3701 ATTTCTTCAA ATTAGATGTT TCACAGAACT CTAACATATA AAAAGGATAA
3751 TTGGAATGAT TATGATTGAA TCAAAGATGC AGAGAGCTGG AATATAATTA
3801 GAAAAACACG GCCGGGCGTG GTGGCTCACG CCTGTAATCC CAGCACTTTG
3851 GGAGGCCGAG GCGGGCGGAT CACAAGGTCA GGAGATCGAG ATCATCCTGG
3901 CTAACACGGT GAAACCCCGT CTCTACTAAA AATACAAAAA ATTAGCCAGG
3951 CGTCGTGGCA GGCGCCTGTA GTCCCAGCTA CTGGGGAGGC TGAGGCAGGA
4001 GAATGGCGTC AACCCGGGAG GCGGAGCTTG CAGTGAGCTG AGATCCCGCC
4051 ACTGCACTCC AGCCTGGGCG AGAGAGCGAG ACTCCATCTC AAAAGAAAAA
4101 GAAAAACACG AATTTAGAAG AAATGCTGCA ATGTACAGAA TACATCCCTT
4151 AGTGGTAGAA ATTATTGACC ACATGTTTGT GTCTTAGGTG ATTCTTAATT
4201 ATTTCTATCC TTTTAAGTAA AAGAAGAAGA AAGATAAGTC TTACAAATTC
4251 TGAGTTACCT AATCCCATTT GTGACTGACA GCCCAAGTTT AGTCACTAGT
4301 TAGCTCTACT GAGTAACAGC CTCTGTAATT AAGACTTTAG TGCAGCTATA
4351 GTGCAATGTA GGCTAATGAA GAGGGCAAGA GCAGAACTTG CAAGCTATCT
4401 CAGGACTAAC CTAGCAGGGA GAAAGACAAA GTCCAGAAGG TGGTTTAGTG
4451 TTTATATTCT GTTCTATAAG AGTAGGGTTG TATAAGTCTG TCTATTTAAA
4501 ACTTGATGCA AAGAGAAAAC TACTTTATAA AAGACATGTA GATATAATTA
4551 TAGCTGTAAT GAAAGACATG TAGATATAGT TACAGATGTA ATCGTAAATC
4601 AACATTTTTG AACAAATGCC TTAAGAGCAG AAGGAGAAAG GAAGGTCTAG
4651 TTTTCTACTC TCTATGTCAC GCAGTTTTTG CTTTTTGTTT TGTTCTCTGT
4701 AGGGAAGAGA AATGGGGCCT AGAGAGGCAA TTTATTTTTT AACCAAAATG
4751 TTGTTTACAA TTGTAACAAT ATGTCATTAT ACCCATAGAA GATATGCAAA
4801 TTGGAGATTT TCCTTCTTTT ATGCATTTAA AAAACATTGC ACAATTGTTC
4851 CAGTAGTTCT AAATTTTAGC AATCATTTTG TCTCTGTACA ATTTACTTAT
4901 GGCTTCTATG TGATTTATAT TTTGGTTCTC TTTATCCATA TCTAAATAAT
4951 ATAGCATAAG TATCAAACTA TGGTTCCAAC GTGATCTTCT AAACCTACTT
5001 ATTCACACCT GGGTGTGTAA TATGATCTAA TTTGCAATTC ATCTGCCTTA
5051 GAACATGTTA TCTTTTATTA AATAATCTTA AGAATGCTTT TAAGTGTGAC
5101 AGCTGCAAGA GGGCACAGGC TAATGATGTT AAAATATTTC AGAAGTATAG
5151 TCTCATATTG CTTGAAGTTT ATCCGTGCTT TAACTTATTC CTAAAGTTAA
5201 TGTTAAAAAT AGCATCAATA CCTTCACTAC CTAATTTTCT ATTTTGAATT
5251 AGTGGAAGAA AGCCTCAAAA TGAAAATTAT GTAGCAGAAT AAGTGTATAC
5301 CTTTTTATTT GTTCCTTATC ATCTTTCCCC TTCCTACAGA ACTTTGTAGA
5351 ATATGTCATG CGTGGCATAT CATGTTCTGC CTCCTATTAC CGATAACTGT
5401 TGCTTCTCTT AGTTCCCTTA TGCCATGACA AGCATCTTGT AGAAAAAGAA
5451 TTGTGTAATA TTTATTTTTT CATCTCCAAA AGTCTTCTGC AACTATGTCA
5501 GACATAGGTT TAATGCTCAA TACATATTTT AATTGAAAGA TTTAAAAAAT
5551 ATTATAGTAG ACCAACATCA CTTTTAGTAC ATAGTCATAA TTTTGGAGCC
5601 CTTGAGTATG TAGCAAAGCC ATCTTTCCTT TTTCTTATCT TGGAGAATTT
5651 AACCTCTTTG CTACTACTTG GCAATCCATA TTGTTCTTCC TTCAGTTGTT
5701 GCACATTGTA TTTTGTACAG CATATTAACT TTTCTACTTT TTAAGTTTTA
5751 CCCACTTATG TTTCCTTAGT GTGCCTGGCA TAATGTCTTC TATTTTAAAA
5801 AGTGTTAAAT GGGCCGGGTG TGGTGGCTCA CGCCTGTAAT CCCAGCACTT
5851 TGGGAGGCTG AAGCAGGTGG ATCACGAGGT CAGGAGATCG AGACCATCCT
5901 GGCTAACAAG GTGAAACCCT GTCTCTACTA AAAATACAAA AAATTAGCCG
5951 GGCATGGTGG CAGGCTCCTG TAGTCCCAGG TACTCAGGAG GCTGAGGCAG
6001 GAGAATGGTG TGAACCTGGG AGGTGGAGGT TGCAGTGAGC CGAGATCGTG
6051 CCACTGCCCT CTAGCCTGGG CAACAGAGTG AGACTCTGTT TTAAAGAAAA
6101 AAAAAGTGTT AAATGAATAT TAGTTGGTTG GTCAAATTTG AAAAAGTTTT
6151 ACTAAATACC TTCTGACTAT ATTTATATAA ACAAAAGAAT AAGCCTTACT
6201 TAGATAATTT GTGCCAAAAG ACATTTTGTT TTTGCAAAAA TAAACAGCTG
6251 AATAAAATAA TCATCTGGAT AATTGATTTA ATGTTACAAA TTTGTTACAT
6301 GCCTATGCAC ATTAAGTCAC ACAGTCAGCA GGAATGACTT CTGGGTGATT
6351 CAGATAATTT GTTATGTATT AGCCATCAAG GTCATAGGTA ATCAGAATAA
6401 ATTCTATAAC AAAAATTAAA ATTTACATCA AAAAGCTATG TTAATACTTT
6451 TAAGTGGTGC TTTATATAAG CCAGTTGTTC CATGTGTAAA GTAGATGTAT
6501 TGGAAGGTAT TAAAGTTCAT GGATCATATT TTGTGTGAGA TTGCTATATT
6551 ACTTTAACTT GTCTATTTCT ATGTAAATCA CCACAAAATT GTAGTAAATC
6601 TTTTATTGCA CTATATTTTT CCCTGAATAC TGGCAAAAGA ACCATAAAAT
6651 TTTGCTAATT TAATTTGTTG ATAAATTTCA GAACCATTCT TACTATAAAT
6701 TTGGTAAATT TGCTTATCCT ATGTTATTCA TTTAAATGAA ACTAATTACT
6751 GTTTTTTTTT AATTGTGTGC TAGACATGGT ATTAATGGCT TTTTGTGCTT
6801 CATGTCATCT AATCCTCACA AGTTGTCTGT GAAGTGGAGA TGATTATTTC
6851 CATTTTACAG TTGAAGGAAG AAAAGCTTTG AGATTAAATG ATTTATCCAG
6901 GATACCCTGA CAGAATTTGA ATGCAGGTCT ATAGGACTTA AATGGCTTCA
6951 TGTGGATTGG AATGATTCAG GTTACTCTGC AGATGGAAAT TATAAAATTA
7001 TTCATACTGA TTAGCTATGT GTTTAAGTCT CCTTTTATTT TAGAATTAAT
```

FIGURE 3, page 2 of 87

7051 TTTATTTGGC TATATGTTTT ATTTTTAAAA TTTGATAGGA AAGAAAATGA
7101 TTACATACAT ACCCTAATAC TTTTTTTTAA GCCTTGGGGA AAAATGCAAC
7151 TGGGAGTCAG TCAAGAGAAT TTAAAACTTT CTCTTACTCT ACACATCAGA
7201 GAGTACATCA GTCTGCTATC CCTTTGCTAC AACTGTGAGA AGTAAAGTCT
7251 GAAAAGAAAT GTGAAAGTCT GAAAGCCCAC TAAATGTGAA TAATAATAGC
7301 GATTTGAGTT CATAGAAACA GGCAAACACA TTCGAAATTC CTTCATCACA
7351 AATGGAAAGA AACACAATTA AAAGTTTTCT AATACTCCCA AACTTGTTTA
7401 AAATTAGCTG ATGCTTTGAA AATTACTTGA ATGTTTTTAT AAGGAAAGTG
7451 ATGCTGATCA GCACAGTTGT AGCATTTCCA TTTGGCCACT TGACATTCTT
7501 CATTGTTGGC TTGGAGTTTT TATTCTTTGC TATTTTTTTG TATTGGCTTT
7551 GCAATAAAAA CCACCATCTA TTTCTCTTTT AGTACAAACA TATTTCCAGT
7601 TTAATTGTTG CAATAAAAAA TGTTCTATGT CGATTTTCCT AAAACAACAT
7651 ATTAAAATAA TGATAAATAA TAAAATCGAT CCATTGATAA CAATTAGTTT
7701 GAAGTGTTCA TGCATACTAA AAAAATACAT TCTGAACAAT GAATGTGTTT
7751 ATTTTTCAGA ATTTTACACT CCATGAAGTA ACCAATGACT TTGACAATAT
7801 GACTGTATCC ACAATTATAG ATAAACTGAC AATATTCAGC TACTATACAT
7851 TTTGGTTAAC AGCAAGTACT TCAGTTGGAA ATGGGAATAA AAGCAGTGAC
7901 ATCATTGAAG TATACACAGA TCAAGACAGT ATGTAAACAA AAAACACTAA
7951 TCTTTAATAT GATTAATTTA AAACTTATTA TTTTAGGAAA TTTTACTATT
8001 TGTTTGAATT TGTAATAACA TCTTTTATTT AGACACGTTC ATTATAGGAG
8051 TTTGAAAATG CAATTAATAT ACTTACAAAA CTATTGCAGT AATAGCCTCT
8101 TCTGTTCAAG AAAACTGCTA ACATCCATTC ATGAAAATTC TGTTCTTTTT
8151 ATTGCTTCAA AAGATGTCGT GGCCATCCAG TTATGGGCAC AAAAAGTACT
8201 GCATACATGG ATGAATTTTC CAGTAGTTAA TTTATTTATT CATTTTCCTT
8251 AAGGACTTAA AAAATCTCTA GCAACTTGTT TTCTTTTCAG ACTTTGAATC
8301 TACACAGGAC TCTGCAGCAC ATCTCTTCTC ACTGTGTTTG TGACTAATAT
8351 ATCCAGAGTA TTTTCCTTAA CTCCAGAAGT TTCTCGTATG CATCTTCTGA
8401 AGAATCCTAT TTATCCCGAG TATTCAGAAA ACTATAATGA TTGAAGATCT
8451 TGATGTTTTT TATGTTTCAA TTTTCAGAAT ACAGTGATAA GTGGATCATT
8501 GCCTATTTTT CTTGTAGTTG TTTCTGTCAT CCATTTGCTT ATTTTCAAAG
8551 ATTAATCCCT TATTGAGAAG TGGCAGTGAC CTAAACTTCT GGAGTAAAAC
8601 TCCATGTTTA TTATCTGAAA GCCATAAATT GACAGATTCC TTAAGCATGA
8651 GAAGTGAATG CTTGATTTGT TGTTGGAACA GTCTTTTGAA TTGTTGACAA
8701 GTTGGTCAAC ATAAAAATAA ATGATAAATG TGGGGAAATA TGTATTTGGG
8751 GAGTCTTTAG CAAAAATGTT ATATTGTAAT ATATGATCAA TACCATTTCA
8801 GGTATTCTTT AAATGCAGAT CTCTCCCAGG ATTTTTGCCA ACCTATGACA
8851 TTTTATCACT TATAATTTCC ACACCATGGA TAATAAGCAC TTACTATGCA
8901 CTACTCCAGG TGGATGTCAA ATTTACGTTA ATAGAGTTTA ATATCACAAT
8951 ACAACTTATA TCTGAGAATT GGAACTTGTG TGTAAGTAGA GTAACTTTGT
9001 AATGTACAAA TGTGAGTTGG TAGTCTGGTG ACTGGAGAGA TTTTGAGACT
9051 AGATCTTGGG AAAGCTTTTA GTATTGATTC TTCTGGCTAC CCACATGACC
9101 TTGGAGAAGT AACTTAATGG CTGAGCTTTA GTTTCCTCAT ATGTACAACA
9151 AGGGTAATAT TTAGAAGAAA TAAGCTAAAA AGATGGTTTA AATAACATAA
9201 ATTATCAAAA TATTTAAATA AGGCAGTATA CATACACATA TTATGCACAC
9251 ACACGCACAC ACACACAATC TCCACATAGT AGGAAAGAAG AGTCAAGAGA
9301 ATATTATAGA AACAATTCCC ATACATATTA AAGATGACAG AGTTTATTTT
9351 GAATGATTTT TAAAATAATT ATTTAGAAGA TATTTTATAA TAGGTGAATG
9401 TTTGCCACAT CTGCATTTAA ATAATTTAAG AGCTGATGAT GTAATAGTTG
9451 CCATTTCAAC AATTATACTC AGTTTGTGAA TTTAGATTCT GTTTAGGGTA
9501 ACTGTTGATT TTTGTATTTT GCCCATTACC TATCATAGTA CCTGAAGGGT
9551 TTGTTGGAAA CCTGACTTAC GAATCCATTT CGTCAACTGC AATAAATGTA
9601 AGCTGGGTCC CACCGGCTCA ACCAAACGGT CTAGTCTTCT ACTATGTTTC
9651 ACTGATCTTA CAGCAGACTC CTCGCCATGT GAGACCACCT CTTGTTACAT
9701 ATGAGAGAAG CATATATTTT GATAATCTGG AAAAATACAC TGATTATATA
9751 TTAAAAATTA CTCCATCAAC AGAAAAGGGA TTCTCTGATA CCTATACTGC
9801 CCAGCTATAC ATCAAGACTG AAGAAGATGG TAGGCTAGAC CCTTTTATTG
9851 TCTGTTAAGC AGATTGTTGT TCTTTTCATT TACATTGCTT TCTGATAGGA
9901 AATAGTCTTC AATTATATTG ATTCTGTTTG ATCTCAAGTA ATTAGCCTTT
9951 CAATAAACAC AGTGTTTCTT AAAATAATCT GCTAAGAAAA TCAAATCCCA
10001 TTATGATTGA ATCCTCTTTT TTTAATGCTG ATTCACTTTT GTTTCATTTA
10051 ATATTCTCTT TTTCTTTTAT AGTCCCAGAA ACTTCACCAA TAATCAACAC
10101 TTTTAAAAAC CTTTCCTCTA CCTCAGTTCT CTTATCATGG GATCCCCCAG
10151 TAAAGCCAAA TGGTGCAATA ATAAGTTATG ATTTAACTTT ACAAGGACCA
10201 AATGAAAATT ATTCTTTCAT TACTTCTGAT AATTACATAA TATTGGAAGA
10251 GCTTTCACCA TTTACATTAT ATAGCTTTTT TGCTGCCGCA AGAACTAGAA
10301 AAGGACTTGG TCCTTCCAGT ATTCTTTTCT TTTACACAGA TGAGTCAGGT
10351 AAGCCAGAAT CCACATTTCT TCAAACAATT TCACTGTTGC AGCGCCTGCT
10401 CTCTCTTTTT AAGGAACAGC ATGGAATATG AAAGGATATC TGATTGTCTA
10451 TTTGTAACAG CCTTACCATT ATATTTACTT TGTTGATTTT TTTTTTGCAA
10501 TTTGAGCTTC AGAATTTCCT GTTCTGTTTA AAGCTACTTT GGAACTACTC
10551 TGTCCAAATA CAAATTATAA TTAATTATGA TATTTGTTTC TGAAATTTAA

FIGURE 3, page 3 of 87

```
10601 ATATGATCAT TTTATAAATC TTTTTAAACT AGTGTCTTCA AGAAAGTAAG
10651 TCACGGTGCT ATTTTTATGT TAAAAGTTTT ATGAATGTAA GTTTCTTCAT
10701 GTGTTTTCCT ACAGTGCCGT TAGCACCTCC ACAAAATTTG ACTTTAATCA
10751 ACTGTACTTC AGACTTTGTA TGGCTGAAAT GGAGCCCAAG TCCTCTTCCA
10801 GGTGGTATTG TTAAAGTATA TAGTTTTAAA ATTCATGAAC ATGAAACTGA
10851 CACTATATAT TATAAGGTAG GTTGATTATA ACAGTATATG TTTATTTTTA
10901 AAAATCAGAA ATTGAATTAA AATCTTTTGA CATATAGGAG GAAAATGGAC
10951 TACTAAATTA AACAATGACT ATTTTTTTAA ACTTCTTTAT TTCCTACAAT
11001 TTAAGGATGC TTATGGAAAA CACAAGCAAG CGTTTGACAG GTATATAAGC
11051 TGAATACTTC ATAGAGCAAT GTACTTAGAT TTGTAACTTC CAGATATCTA
11101 CAATTTAAGA AACAGTTGCA TCATTTTGTT AATGCTGGAA AGTGTATAGT
11151 ACTTTTTTCC TGACTTACAA ATATAAAATG TATTTCTATC TATTGTTAAC
11201 AGCAGCACCA AGGGAATCTT TTTAACCTTT TAGAAAGGTA TTCATCTTTA
11251 TTCTGGACTT CTGGTCATCT TTCCAGATAG CATATGATCC TACACTAATT
11301 GGTCTTTTAC GATATATCCT TATTTTTTTT TTTATTTTCA AGAGTAATTC
11351 ATTTGCAACA CTAACCACAT TTTCCCTCCT CCATTTTTGG AATTCAGAAT
11401 TAGTGAAAAA TATCCACAGA ACTGATGCAA CAAAGAGTCT CAAATATATG
11451 TCTGTGATTT CTAGCATTTA ATTGCCAAAA TGTAATTAAC AAGCATTTAT
11501 TTAAGAAAAG TTTCTTATTT TTTTCCCCAA AGGCAAATGA AGTCCTGGAA
11551 TGTTCTTATT TAGTTTACAG CAAGAAGAGT GCAAAAAATC TGCAGTAAAT
11601 ATTTTACTCA ATATTATGAG TATTACAATT TATGACTATG GTAAATCATT
11651 GTTATAGCAT ATGTAGTTTA CAAATTGAAT AGTAAAAGTC AAAAGCAGGC
11701 ATTAACTTTA TGTCATCGGG AACAATGACT TTCTTTCTGG AAACCAAGAT
11751 ATTACTTTAA AACTTGATAG TCTGAGTATA ATTTGAATCC TATTACTCCA
11801 TAAATGTGAA ATTTGTTTCC CAGAGGTGTG AAATAACATT AAATGACATG
11851 AAGCCTCTTG CCCTTTAATA TCTATCCCTG GTTTAATCTT AACATTATTC
11901 CATTTTTTAT TTGCTTTGTC TGTATGGGTC ACTGGGAGAT AGATATCAAA
11951 AGGAAAAAAG AATCATTTTC TCAGAGTAAT CGCATTCCTA GGATAATTGT
12001 GTACGTGTGT TAGAGTGTGG TTGTCTATAT ATGGATCTTG TCTCCTCAGA
12051 ATGGTGATCT GTAACATAGG CTCTCTTAGC ATAGCGGTGA AGCAAGGGCT
12101 CTGACTCCAA ATTACCTGGC TCAGATTCTG CCTTTGAGAC TTACTGTGCT
12151 TCAGTAGGGA CATTGCTTAC CTCTTAATGC AAAATGGGAG TTACAAAGAT
12201 GTGTACATTC GAAATTGAGG ATTAAAAAGG AAAGTCTCCA TAGAGCATTT
12251 TGAACAATTC CAAGCATGTG ATAAATATGT TAGCTATTGT TGCTGTAATT
12301 GTACACAGTT TTTAAAAGAA CAAAAAAACT GTCCAACATT GTAATAGCAC
12351 TAAGCATGAA ATGACAATAT GCCATTATGT GAACATGAGA ATAACTTGTA
12401 TTCTAAGATT TGTAAACAGG TTTTCTCAAT AGAAGCACAT CTTTAATATT
12451 TCAGAAGTAG CAAAAATACC ATCTTTATAC CATTAAGTAT TCAATACATC
12501 ATTTGGGATG GGCAGTAGTT TTGTGTTTTA AAATCTACTG CGTCATGTTA
12551 CTCCTTTTTA CATCTATTTT CTCTTTCATC AATTTTCATA ATCTTATTTG
12601 CTTTCAAATT CCTTTAAATG TACTCTCATG CCATCTTTTT CCCTGTCTTG
12651 GCATCTAGTT ACTATATCTG CTTTCCTTTT TCTATTTCGC TTTCTCTCCT
12701 AGTGTGTTCT ATTTTCCTTT CTCTTTCATC TACCCTGATA TCCTGACAGT
12751 ATCAATTTAT ATTATTTTCT CTGTTTTTCT ATTCTTTTTC TTCTTTTAAA
12801 TTATGTGTGC ATTTGTGGAG GTAGAATAAT GCTTGAACCA CTTCAAATGT
12851 TACTGCTATC CCAGTCAATC CACTGTGGTC CACAGATAAT AAAATCAATA
12901 GGTGACTTAG GTCACTCACA CATACTGAAA GAAATTATTT ATTTAGTACA
12951 AAGTTCTATT AAAATATGTT TGTAAGTATT CATCACTCAT GTTTCTCTTT
13001 TTGACAACAT ATTCTTGTGT AAATCTGTTC ACTATCCCAT AAACTATTCT
13051 CTTATTATTA TGCCCTCTTG GGTTCAGTTG TTTCTCTGGT TTTTAGCCCT
13101 TCCTAACCAA AATCATAATT TGCTTGTTTT GTGTTTAATT TTTTCTCATT
13151 CAGAAATTGT AGATTTCTCT AGTTAATATA AAAATTCCTT GATGGCAGGG
13201 ACCATGCCTT ACATGTGTCT ATAATCTCCA GATTATCTAA TGGCATGTTT
13251 TGTAAATAGT AAGCAGGAAA GAATGACTGA AATAAAGAGA TTCAGTAAGC
13301 CCCTAAATTC AGTGAATTTC TAGAGATTAT TTTAAAATAG GATTCTAATT
13351 GTAAATTCCC CAAGAATTAA TATTCTTGTT AAAATTTCTG TTACTGTGAT
13401 GTTTGATAAA TGATCAACAT GGTTTATATT TTGTCAGATA TAATGTAAGA
13451 TTCCTACATT TATATCACAT AGGAGATTAT CTTCTCTTTC CATGAGGATA
13501 GCTGATTAAT CTTAGCTGCT TTCTTGGTTA GGACAATTAT CTTTGAATGA
13551 AAACTTTGTA CTTAATGATA ATTTTTTTCT ATGAGAAAGC ATATTCCTCC
13601 TTGGGCAACT ATGATACTCT TTTGTTCCTT TTCTCATATC TCTAAAAACA
13651 GTGTCAAATT AGAAATAGAG GAATCGGCTG GGAAAACTCC CAATTTAAGC
13701 TTCATGGAAG CAGATATTTT AAAATTATTA TTTTAAAATA ATAATAATTT
13751 ATTATTATTA TATATAATAA TGTTATTATT ATTTATTACT GTTTTGCCAG
13801 TGTCTACATA CAGTAGCTGA AGAATAAATA AATTTACACA GGAATGCTGT
13851 GGGTATTAAA AATGAATTTA GATAAGTTCA GAAAACTCAA GTATCTCTGA
13901 CCATGCACAA GTTGGATTTA AATTGCAGAC TGTAATTATG CAAATTAAAA
13951 AAAATGAGTA TATAATTCCA AGTGAAAATC ATGAAAATAA AACACTCTAG
14001 TTTTTTAAAA AGGCAATTAT ACGCCAGGTG CAGTGGCTCA CGCCTGTAAT
14051 CCCAGCACTT TGGGAGGCCG AGGTGGGCAG ATCACCTCAG GTCAGGAGTT
14101 CAAGACCAGC CTGGCCAACA TGGCTAAACT CTGTCTCTAC TAAAAACTAC
```

FIGURE 3, page 4 of 87

14151 AAATATTAGC TGGGTGTGGT GGCACATGCC TGTAATCCCA GCTACTTGGG
14201 AGGCTGAGGC AGGGAGAATG GCTTGAACCT GGGAGTCCAC CTCCCACTGC
14251 ACTCCAACCT GGGCAACAAA ATGAGACTCT GTCAAGAAAA AAAAAAAGTC
14301 TAAAAAAGGC AATTATGAGG TTCTTCAGGG AAAAGAAGGT GCCCAATTCA
14351 TCCTTGTATC ATAAACTGAG CACACTCTAT GGCACAAAAT AAATGCTAAT
14401 ATTTGTTTTA TTATAATTTA AAATATCCAT GCTTATTAAA CTATAGGTTA
14451 AATATAAAAG GAATAACTTC AATGAAAATA TTCCATTGAT GAACAATTTT
14501 TTGACAGTGC ATTAACTAAT AACTTTTTTT CTGTTTTTCA GAATATATCA
14551 GGATTTAAAA CTGAAGCCAA ACTTGTTGGA CTGGAACCAG TCAGCACCTA
14601 CTCTATCCGT GTATCTGCGT TCACCAAAGT TGGAAATGGC AATCAATTTA
14651 GTAATGTAGT AAAATTCACA ACCCAAGAAT CAGGTTAGAT ACAGTTTTTG
14701 AGCCTAAAAT GTTTCTTTTT ATATTTAACA CCTTTCTTTT CCTTTTCTTA
14751 GTTTATATGA TAAAGTATCA TTACTTAAGA GTCTACTCAA AGGGAAATTG
14801 CATTTCAGTG CTTTACGTTT AGTCTTGGTC TTGTGTGAAA TCATATGCTG
14851 TATGTGTGTT TATACATATA TTTTCACACA TGGTTTTTCC TTTTGAACAG
14901 AGGAAGTTGA AATAAAATAG TAGTTTGGGA ACAAAATAGC CTTCTAGATA
14951 TCTGTGAAAA TTACCTAATT CTTAGAACTC TTTGAGACAG CTGGGGAAAA
15001 AGGGGGAAAT GAACTAGCAG TCACTTTTAA CGGGCTGATT TATATTTTTA
15051 ATGAAACAAT ATCTATAATT TTCTTTTAAG AAGATTAGTT GTGACATTTG
15101 GAGAGCATGA GTCATTGCAT AAGCCCCCTA TGTTCCCATC ATCCCATCTT
15151 TACCATGTGG CGGACACTGA AATATCATTG GTCTAATTCA TCAACAGCTT
15201 ACCTGCTGTG TCACACATGT AGTATACATG ACATATCTTG CCTTTGTGTG
15251 CACACTGAAT AGTTTTTATT TAGGACCTAT TTAATGATGG CTTAGAAATG
15301 TACTTTTCCT TTTCTCAACT GCACCATACC TTTAAAAGCA CCTCTTCTTA
15351 ATTTTTTTTT TGTTTACTTC TGTCAATGTT TATTGAATGA GCAAAAGATC
15401 CCGTTCTAGT CATTTCTTCT TATCAGCTCT GGATGCACTT CCTGGTATGT
15451 TAGTGAATCT TTAAATCGAG ATTGTAGACC ACTGACTACT AAATTAATCA
15501 TTTCTGCATA AATTTATGGC TACCTGACAC TGTTTTTCGT GCATTTCTGT
15551 AACAAATGCA AAATAAATAG CATTTATAAT GGATAAAAGT ACATGCTGTG
15601 AAGTCATTTT CTGGATTTGA ATTTGAGCCC CATGACCTAC TAGTTGTATA
15651 ATCTTGGCAA AGGCTCATGA CTCTGTGAGC CTCTGTAACC TTAACTGAAA
15701 AGAAGCACAT ATTAGCAGTA GCCATCTCAT AATGTTGTTG TCAAAAATAT
15751 TTGGAAAGAT CCACATAAAG CACTTTATAG AGTGTTGTAC ACACAGTAAA
15801 TGCCCACTTC ATAGAGTGTT GGACACACAG TAAATGACCC CTGAATATTA
15851 CTGTTGCCCC CATTCCCATG TTACAGATGA AGAAGCCATG ATTGAGCTAG
15901 ATTAGATGAA AAGGACCTTG AAAAAATTAG TGAAGAACCT AACTAGAACA
15951 TTGGCCTTCT GACTTCTAGT GAAGAGTGGA CATGACTGCA GGAAATGCAT
16001 GTTGTGAATG AGTGATAGAA TATAAAAATG TTCAACCCAT AAATAAAAAA
16051 ATATTTTAAT AATATTTGTA CATGAGGACA ATAAGAATCA GGGCTAATCT
16101 TGTAGAAAGT GCTCTGTAAA CCCATAAATA TTTTTTATCA GTAAGATAAA
16151 ATTGTACCCC AACATTCTAT ACTCTGATTA TTTAAATAAA TAAAATTTTC
16201 ACCTTTAAGT GTTTTAATAT CAATGGTTAA TTTTTTTTTG AGGTTCAAAA
16251 AATCAGGAAA ATGGATATTC ACAAAATCTG GATTTAGAAA CTAAAGTTCA
16301 GCAAATTGTC AACTATCTTA TGTTAACTTA TTTTATAAAA ATGTTCTTAT
16351 ATGATTCTGA AAACAAGGAA GTGAATAGTT AATAGCATTT AATTGCCAGA
16401 TCCCTTGATC AGCCAGAAAT TATCTTTAAA AAATTTTTTA ATGCCACATA
16451 TTCCCTAAAT ATTCTCCTTT AGTACTGGTG TCTTTATCTT ACAGAGGAAG
16501 AAAAGTTTAT AACAGCTCAG TTTAGACCCA GGTAGAGCGG TGTAGGCAGA
16551 TCAGGGATCA CCTGAGTATT CTTTAAAGCA CTATGTTTTG CATAATGGCA
16601 GCAAGTTATT TTCTTTCAAT TTTCATTGTT TGTAATCCAC AAATTGACTG
16651 TGTCCCAATT TTTCTTCTAC CATTATCTTT TACTGTGACC AGAAAAGTTA
16701 TTCTACTAAT GCCACCATTA GGGGACATTG GCTAATTGGA CATTTCTGTG
16751 GGAAGTAACC AGTTTCTCTA ATGTGCAGTC ACTTTGGTGG GCTAGGATAT
16801 TGTTCTTTGA CCAGGCCTAC CAGATATAGA GGACCTCTGA GAAGCTGGGT
16851 TAGTTTCAAG TAAATTCAGA GAAGCTCTAG AAAATAAGAC TGAGACTCCT
16901 TAAATCTTCC TTCCAATGAT GTCTACAAAA GGTACTTAAA AATGAAATCC
16951 TCAAGATTCT TCCAAAGAAG CCATCCCGGT AAAAACCAGT ACCTTTAAAT
17001 TAGTTAGGGG TTTCCAAGTA CTGTGAAGCC CAGATTTGTC ACAACAGGGA
17051 GGCACCTGCA TACTATGTTT TGCATAAAAA TGTTCCATAA TAAAGTATTG
17101 CTAAGATTTT TCCTTTCCAA TTAAGAGAGC AGTTATCAAA CACTGCCTGG
17151 GNNNNNNNNN NNNNNNNNNN NNNNNNNNNN NNNNNNNNNN NNNNNNNNNN
17201 NTAAGAGAGC AGTTATCAAA CACTGCCTGG GCCTGGGCTT GAGGCTACAC
17251 ATTTGCTTCT GAGCTTTTGA GGATGTGATT GGTGCTTCGA ACTGGAAGAT
17301 ATTTAGTGAC TGGTTCAATA CTGTAATGAT TAATACAATA GCATAAAAAG
17351 CAAGTCAACA GCCTTTTGAT TCTGTCTATG TTAATGACTT TTTAAGCACA
17401 CATTGAAAAT TTGATATATT AAATATTTTT CTAGTTCTAA ACACAGATGT
17451 ATCTAGTGAT CACGTAATTC AATCAATTAT CTACTTACAT ATGTATACAC
17501 TTTAACTTTG GGCATATGTT TATCTCTTAA GTTCCAGATG TCGTGCAGAA
17551 TATGCAGTGC ATGGCAACTA GCTGGCAGTC AGTTTTAGTG AAATGGGATC
17601 CACCCAAAAA GGCAAATGGA ATAATAACGC AGTATATGGT AACAGTTGAA
17651 AGGAATTCTA CAAAAGTTTC TCCCCAAGAT CACATGTACA CTTTCATAAA

FIGURE 3, page 5 of 87

17701 GCTTCTTGCC AATACCTCAT ATGTCTTTAA AGTAAGAGCT TCAACCTCAG
17751 CTGGTGAAGG TGATGAAAGC ACATGCCATG TCAGCACACT ACCTGAAACA
17801 GGTAACTAAC GTGAAACAGG TAACTAACAT GAAACCTTTA ACTATTTGGG
17851 GATTGTGTCA ATACCACCTG CAATCTTTAT AGCATACTTA TCTAAACATA
17901 CAAAGCACAT ATTAAAAAAT ACAACACAGG CTTTTTATCC CACGTGTTGC
17951 TTGAGTGCCA GCTGTGTACT ACATTGACCC TTCTCCAAAA CATTGGGAGA
18001 TTGAAGGGAG GAAAAAAAGA GAGATGATCC TCTTTACTGT ATTTCCACAA
18051 ATATAAAACC CCCACCTAAT GAATTATGCT TTATTGTGAT TTAAAAGAAG
18101 AAATAAACAT GTAAACCTTT CATGTATATC TCTTTTTAGT CTTACTTGTT
18151 TTTATGGAAT TCTAGATGTT TTCCTGAACT ATATGGTTGC AGTATCAGAC
18201 TCATTTTCAT CTATTTTCTC CCCTTTATAC CAGCCTTTAT CTTTCATGTT
18251 ATTTGAATAA AATATCCGGG TCGTTAAGCT TTAGTCCACA AGACGAAATT
18301 CTCACCTTCC CTAGCAGTGC TCTGTCCTGT ATCATAATAT CCTTCATCCT
18351 ATTTTCTTCC ATATTCTACC TGCTTATATA AATTAAAACC TGTTTCTTTC
18401 CTGATAACAC CACTTCACTG TAGATATTGG CAATAATTGT TAACTTCTGG
18451 CACATCCAGA CCCTTTATCT TGGAAACGTC TTTCAAGCTG TCTTGAGGCT
18501 GTAAACCTAG AACATCAAGA CATAGTCTGC CTTCTCTCTG ATTTCAGCAT
18551 CTAACTCCAC ATCCTTTCCT TCTCATTCTT CCAGTGCAAC ATTTTTTCAG
18601 ACTACGGTGT TTCCCTTTCC AGGATGGAAT AGTTACATTT CAACAACACC
18651 ATCTCTTTGC TCCTTAGATC TCATACCATG TCATTGTGAC TTACCCTCCA
18701 GGAAGCTTCC TCACTCTGAG AAGGCCCCAT TATTTGTTTT TTCCAAGATG
18751 CTGACTGGTA AATATTTCTA GGAAAAAATA GAAATGATTC TACTTTGTTT
18801 GTCTATAAAT TCATCGTCCT TAATTGTCCC AGCTGCTCCA AAATTTTCTA
18851 TGTATCCCTT GTTTATTCTT CATAGGAAAT ATGTTCATAG GAATACTCTC
18901 TATTCCATAT GAAAATTGTT CTCTTTCTGA ACCTAGTCTG TTCCCCCATC
18951 ATCCATATTT ATTGTTATTT TACTAATAAT ATCAAATATA TTGATAGGCC
19001 CTCCTTCCAT CAAAATTTAT CCATGTCTTT ATTTATGCCC TCCAGATATC
19051 TTCTCTTAGG AAGTCCTTGC CTTCCTCTTT CAGGGATCTA GCTGTTCATT
19101 TTCATTTTAA TCTTATGTCT TCTCTAGGAT ATTACCCCAT CAATTTATTC
19151 TAATATCTCC TGCATTTATC CTCTTTCTCT TTTTCTTGCA CATTCACCCA
19201 AATTGTTGAA AAATCCCAAC TGAAGACCTA GTTGGAGTAT CAACTCCAAA
19251 TATATATGAA ATGGAATTTG TGTTACATGA AATCACTGTC TTTTTCTTAG
19301 TTTTCTATGC CTGTTCTTGA CAATCCATTG GACCCCAAGC CTCATAGTTT
19351 TATACAATTC CTTACTCCAT CTCTTCTACA TACAATCAGG TCTTATCAAT
19401 TCAATTTCCA TCAGGGCTCT GCAATTTGCC CCTTCTCCAC CTTGGCCACC
19451 ACCATTGTAT ATTAGAGGGA CCTTGTTGCT TCCTGTAATA ACATCTTAAC
19501 TAGCCTTATC ACCCACACTA CTTTAGCCTA CCCATAAGTC TCATCTTTCC
19551 TCCTACTCAC TTAATTGAAT TGGTTCTAAC ATACAATTAG ACCATTTATA
19601 CATTGGCAGG TGAAATGTAA TATCTGAACA ATAAAGTTTA GACGTGTCAA
19651 GTTGGGTACC TGAAGCACAG AAGTAATAAT GAAAGGCACC ATGTGTAGGA
19701 GATGGGTTAA AATACTCCAA ATATTTTGCT CATTCTCATT GTCTAGAAAA
19751 TATCCCAGAA TCCATCGCTA ATTAGAATTT GGCTTCTCTC TAGCTTTTTA
19801 TTCTTATATC CTTTTATTGT ATCTTCTCAT ATAGCTGATG TCTCCAGCCA
19851 AACTTCATTT ATTTAGCATG CTATTTCACT ATTTCAGTAT TTTAACTCAG
19901 AAAACATTTA TTAAACATCT AGTATGAACT AATAATTGAC TAGATTCTCT
19951 TCTTTAAACA TATCCAACCA TTTTTCATCA TCAGATTGCT TTGCTTCCTT
20001 TAACTGTATT ATTATTTTCC CTTTCTATGA CACATAAAAT TTTATTCATT
20051 TTTAAAAGCC CAGCTTAAAT GTGCCTTCTT TATTAAAGCC TTTAATGGCA
20101 TTTCTGGACT TCATCCCAGA CTTGCTGACT CATAGCCTCA ATGAGTGAAG
20151 CTTAAGAATC CATGCACTTA AGAATCTCTC TAGGTAATTC CGATATTCTG
20201 TATGTATTGG AGAGTACTGG AGTAGATTAC CAGGAACTTT TGAGGACAGG
20251 CAAAGAGTGT CAGAAAGGTC CATCAAGGGG TGACAGGTGT TTTCCCAGTG
20301 GGTGGCCAGC ACATCATTGC TATGTGGAGT CTGTGGGAAG AAAAAATGTC
20351 AAAATGTCAA AATCCAGGTA GGTGGTCTGC ATCAGGGTGG TCTAGCACCA
20401 GGTATAATGG TCTTGATCAT TGGGCAGGAG CTGAGTCTTT GAGAACTGGC
20451 AAATAAAATT ACAGGACAAC ATATCTGAAA TAAATGAGAG ATTCAGGAAC
20501 AAGGCAGGAG ATACTAGGTT GGTGCAAAAG TAACTGNNNN NNNNNNNNNN
20551 NNNNNNNNNN NNNNNNNNNN NNNNNNNNNN NNNNNNNNNN NNNNNNNNNN
20601 NNNNNNNNNN NNNNNNNNNN NNNNNNNNNN NNNNNNNNNN NNNNNNNNNN
20651 NNNNNNNNNN NNNNNNNNNN NNNNNNNNNN NNNNNNNNNN NNNNNNNNNN
20701 NNNNNNNNNN NNNNNNNNNN NNNNNNNNNN NNNNNNNNNN NNNNNNNNNN
20751 NNNNNNNNNN NNNNNNNNNN NNNNNNNNNN NNNNNNNNNN NNNNNNNNNN
20801 NNNNNNNNNN NNNNNNNNNN NNNNNNNNNN NNNNNNNNNN NNNNNNNNNN
20851 NNNNNNNNNN NNNNNNNNNN NNNNNNNNNN NNNNNNNNNN NNNNNNNNNN
20901 NNNNNNNNNN NNNNNNNNNN NNNNNNNNNN NNNNNNNNNN NNNNNNNNNN
20951 NNNNNNNNNN NNNNNNNNNN NNNNNNNNNN NNNNNNNNNN NNNNNNNNNN
21001 NNNNNNNNNN NNNNNNNNNN NNNNNNNNNN NNNNNNNNNN NNNNNNNNNN
21051 NNNNNNNNNN NNNNNNNNNN NNNNNNNNNN NNNNNNNNNN NNNNNNNNNN
21101 NNNNNNNNNN NNNNNNNNNN NNNNNNNNNN NNNNNNNNNN NNNNNNNNNN
21151 NNNNNNNNNN NNNNNNNNNN NNNNNNNNNN NNNNNNNNNN NNNNNNNNNN
21201 NNNNNNNNNN NNNNNNNNNN NNNNNNNNNN NNNNNNNNNN NNNNNNNNNN

FIGURE 3, page 6 of 87

```
21251 NNNNNNNNNN NNNNNNNNNN NNNNNNNNNN NNNNNNNNNN NNNNNNNNNN
21301 NNNNNNNNNN NNNNNNNNNN NNNNNNNNNN NNNNNNNNNN NNNNNNNNNN
21351 NNNNNNNNNN NNNNNNNNNN NNNNNNNNNN NNNNNNNNNN NNNNNNNNNN
21401 NNNNNNNNNN NNNNNNNNNN NNNNNNNNNN NNNNNNNNNN NNNNNNNNNN
21451 NNNNNNNNNN NNNNNNNNNN NNNNNNNNNN NNNNNNNNNN NNNNNNNNNN
21501 NNNNNNNNNN NNNNNNNNNN NNNNNNNNNN NNNNNNNNNN NNNNNNNNNN
21551 NNNNNNNNNN NNNNNNNNNN NNNNNNNNNN NNNNNNNNNN NNNNNNNNNN
21601 NNNNNNNNNN NNNNNNNNNN NNNNNNNNNN NNNNNNNNNN NNNNNNNNNN
21651 NNNNNNNNNN NNNNNNNNNN NNNNNNNNNN NNNNNNNNNN NNNNNNNNNN
21701 NNNNNNNNNN NNNNNNNNNN NNNNNNNNNN NNNNNNNNNN NNNNNNNNNN
21751 NNNNNNNNNN NNNNNNNNNN NNNNNNNNNN NNNNNNNNNN NNNNNNNNNN
21801 NNNNNNNNNN NNNNNNNNNN NNNNNNNNNN NNNNNNNNNN NNNNNNNNNN
21851 NNNNNNNNNN NNNNNNNNNN NNNNNNNNNN NNNNNNNNNN NNNNNNNNNN
21901 NNNNNNNNNN NNNNNNNNNN NNNNNNNNNN NNNNNNNNNN NNNNNNNNNN
21951 NNNNNNNNNN NNNNNNNNNN NNNNNNNNNN NNNNNNNNNN NNNNNNNNNN
22001 NNNNNNNNNN NNNNNNNNNN NNNNNNNNNN NNNNNNNNNN NNNNNNNNNN
22051 NNNNNNNNNN NNNNNNNNNN NNNNNNNNNN NNNNNNNNNN NNNNNNNNNN
22101 NNNNNNNNNN NNNNNNNNNN NNNNNNNNNN NNNNNNNNNN NNNNNNNNNN
22151 NNNNNNNNNN NNNNNNNNNN NNNNNNNNNN NNNNNNNNNN NNNNNNNNNN
22201 NNNNNNNNNN NNNNNNNNNN NNNNNNNNNN NNNNNNNNNN NNNNNNNNNN
22251 NNNNNNNNNN NNNNNNNNNN NNNNNNNNNN NNNNNNNNNN NNNNNNNNNN
22301 NNNNNNNNNN NNNNNNNNNN NNNNNNNNNN NNNNNNNNNN NNNNNNNNNN
22351 NNNNNNNNNN NNNNNNNNNN NNNNNNNNNN NNNNNNNNNN NNNNNNNNNN
22401 NNNNNNNNNN NNNNNNNNNN NNNNNNNNNN NNNNNNNNNN NNNNNNNNNN
22451 NNNNNNNNNN NNNNNNNNNN NNNNNNNNNN NNNNNNNNNA TTTGGTTTTA
22501 AAAACTTGGT CTTTTGTGGA AGATAATTTT ATAATTTGGG TTTATCCAGA
22551 GCTCTTCCAA GCTCCATAAT TTAGAATCAA AAGAGAAAAA TAAGGTACTT
22601 CCCTCAGATG CAAAAATTTA ATTTAGGGAA AGTAAAATGT GTATTTCTGG
22651 TTTTTAGGGG TGTTCTTTTC TGCAGTGATT TCTTTATTAG CTTTTTGTCC
22701 AGTGGAAGAT ATCAGGCATA TGCAGTGATC CACTGGAAAT CCACTGAGCT
22751 TGCAAATATA TTAATGCTAC AATATGATTG ACTTGGCATG TATTCAATTT
22801 AATTATCATC ATCATCATCA TCATCATTTT AGAGACAATA TCGCACTATG
22851 TCACCGAGGC TGGAGTGCAG TGGCTTTATC TCAGCTCACT GTAGCCTTAA
22901 CCTCCTGGGC TCAAGTGATC CTTCTACCTC AGCCTCCTGA GTAGCTAGGA
22951 CTACATGTTT GCACCACCAT GACCAGCTTA TTTTTTGTTT GTTTGTTTGT
23001 TTGAGACAGG GTCTCATTCT CTTGCCCAGG CTGGAGTGAA GTGGCGCTAT
23051 CTTGACTCAC TGCAGCCTCC ACCTCTCAGG TTCAAGCAAT TCTCGTGCCT
23101 CAGGACTCCC AAGTAGCTGA GATCATAGGT GTGCACCACC ACACCTGGCT
23151 AATTTTTGTA TTTTTAGTAG AGACAGGGTT TCACCATGTG GGCCAGTCTG
23201 GGTATCGAAC TCCTGACTTC ATGTGATCTA CCTGCCTCGG CCTCCCAAAA
23251 TGCTGGTATT ACAGGCGTGA GCCACCGCTC CCAGCCTGCC CAGCTAATTT
23301 TTTATTTATT TTTGTAGAGA TAGTCTCACT ATGTTGCCCA GGCTGGTCTC
23351 AAACTCCTGG TTCAAGCAAT CCTTCTGCTT CAGCCTCCCA AAGTGTTGGG
23401 ATTACAGGCA TGAGCCACAC ACCCAATCTA GCTTATTTGT TAAATACATT
23451 ACTTATATAT TTTATAAGAA TTTATAAAAT TCTTATATAC CATTTAATAG
23501 ATTGAATGTG GGCAGTAAAA CTGCTGCCCT TCTATGGCTA CAAATTAGTG
23551 CACTAAATCA AAAGTTCACT TTTCCTTTGT ATCCTACTTA CATAGCTTTC
23601 CTCATCCATC TCCTGAATTA AGATTTGAAA TAAAGGATGT AGGAAAGTTG
23651 CATGATTCTG ATTGCTCTCA AGCAAGTGAA TAAAAACATT CAACTTACCG
23701 GTGGGTAATC ACTAGAAGCA CAAAAGACAT TATAGTTGCC TATCATAAAT
23751 CAGAGGGAAA TAACTATTAG TATATCTAAT TGAAATTCAG GTGTTTTATA
23801 CAGTATCTTT TATATAGACT TAATTATTAA ATATAATATT TTTCTTCAGT
23851 GTGAACATCA GGTGAGGAAT CTCTTTTTAC ACTTCTTGTA GTGCAGTGGA
23901 CAGTTGACCA ATATATACTT ATTTACTGCT TGCTATGTTC AGGTTCTAGG
23951 TGTGGGGTTC AAGACCCAAG TTTGAGTGCC AGGTGGCATT GGGGATCTTT
24001 GCCCTGCACA TCCAAATAAC TCCATTATTA TAATAAAAAC ATATTTAATA
24051 TGTATAAAAC AAACACAAAC CTACATAATA TGTTGGTCAA TTNNNNNNNN
24101 NNNNNNNNNN NNNNNNNNNN NNNNNNNNNN NNNNNNNNNN NNNNNNNNNN
24151 NNNNNNNNNN NNNNNNNNNN NNNNNNNNNN NNNNNNNNNN NNNNNNNNNN
24201 NNNNNNNNNN NNNNNNNNNN NNNNNNNNNN NNNNNNNNNN NNNNNNNNNN
24251 NNNNNNNNNN NNNNNNNNNN NNNNNNNNNN NNNNNNNNNN NNNNNNNNNN
24301 NNNNNNNNNN NNNNNNNNNN NNNNNNNNNN NNNNNNNNNN NNNNNNNNNN
24351 NNNNNNNNNN NNNNNNNNNN NNNNNNNNNN NNNNNNNNNN NNNNNNNNNN
24401 NNNNNNNNNN NNNNNNNNNN NNNNNNNNNN NNNNNNNNNN NNNNNNNNNN
24451 NNNNNNNNNN NNNNNNNNNN NNNNNNNNNN NNNNNNNNNN NNNNNNNNNN
24501 NNNNNNNNNN NNNNNNNNNN NNNNNNNNNN NNNNNNNNNN NNNNNNNNNN
24551 NNNNNNNNNN NNNNNNNNNN NNNNNNNNNN NNNNNNNNNN NNNNNNNNNN
24601 NNNNNNNNNT TTATCAGTAT GCTATGAGAA AAATGGCAAT TGTACATATC
24651 AAAGAACATT TCCTCTTTTA TTGGAAATAT TCTTGGATGG TTAGGTTGAG
24701 ATCAGAAGAG ATTATGGGTT GACTAAAGCA CTCATGGTAA GCTGCCCTCC
24751 GACACCCTCA CTATTCATGA AAATAGTGAG AATAGTAGTT AGAGGAGAAT
```

FIGURE 3, page 7 of 87

```
24801 AAATAGGAAT TTCAAGATAC AGCAAGAGAA AACACATAGT GGAGAAAGGA
24851 ATGCAGTACA AGGGGTCAGG CTGAGACCAA AGCTTGACTA CAGAGGAGGG
24901 TATTTTATTA GAAGGAGTGT AAGCAGGAAG GTTGAATAAC TGAAGTGGAC
24951 CCCTACTTAC TCTGCTCTTA GTTTGATGTG ACTGTCCCAG AAGTTTGAAT
25001 CTGTTATAAT AGAAAATCAG GAACTTGTGC TAAATTTAGA GAAGGAAACA
25051 ACATAAGTAA TTCTAAAAAC AGTGATTGTT TTTGGCCATT TTCCTGAACA
25101 CTGCAGAAAT CTCTTTAGAT GGAGGATTTG TTCATTACAT ATTTACTGAG
25151 CCTCCTAAGT AATACAGAAT AAAATCTCCA GTCATTTCAA TGGCCCATAA
25201 AGCCCTTCTT CTCAATCCAG TTATCTGTCA CTTCCCTTAT CTTGAAATTT
25251 ATGCTCAAAT GCTACCTCTT CAAAAAGGAT TTCTGACTAA TTTGCCCTTG
25301 AACGTCCTTC CTCCCAGCTA GAATTTTCCA TACTCCTTTC CTGCTTTACT
25351 TTTCTCTTTT GGATATATTA TATGTACCAT TATCTGTGGG TCTGTTCTCA
25401 CATGCTGCAT GGGGACAGAG ATTTTTCTTG GTTCAAACCT ATTTCCAATG
25451 TCCAGAAAAG TATCTGGCAT ACGTGATAAT AAGTATATTA TAAATGAATG
25501 AATCAATCAA TGCACAGGCC AAGAAGAGTG ATAGGCATAG AGCAAACACC
25551 AAGTATGCAT ATGCTGGGTG TCTTAAGTAG AAACTTGCAG TCACAAAACA
25601 ATTTTTAAAC AGTTATGTAT TAAAACATAT GAGAAAGGCA TGTCTTGATG
25651 AATNNNNNNN NNNNNNNNNN NNNNNNNNNN NNNNNNNNNN NNNNNNNNNN
25701 NNNNNNNNNN NNNNNNNNNN NNNNNNNNNN NNNNNNNNNN NNNGTTTCAC
25751 CATGTTGGCC AGGCTGGTCT TGAACTCCTG AGCTCAGGCA ATGTGCCCAC
25801 CTCGGCCTCC CAAGTGCTGG GATTACAGAC ATGAGCCACT GCACCTGGCC
25851 TTTTTTTTTT TTTTTTTTTT CTTTTTGGTA TGGATGTACC ACAGTTCCCT
25901 TAACCATTCA CTAGTTGAAG GACATGTGAG TTGTGTCCAT TTTGTGGCTA
25951 TTAGAAATAA AGCTTCTATA AACACACGTG CACAATTTTT GTAGGAACAT
26001 AAATTTTCCT ATGTCTAGGA TATGCACTGA GGAGCACATT GCTGAGTCAT
26051 ATGGTAGTTG CATGTTAAGT TTTTTTAAGA AACTGACAAA CTGTTTTCCA
26101 AAGGAATTGT ACCCCTTTAA ATTCACACCA ACAATGTATG AGCCATCCAG
26151 GTTCACACAT AGGTGTATAA TGATGTATCA TTCTGGTTTT GTGTTTCCCT
26201 GATGGCTAAC GTTCAATAGC TAATTGAATA TATTTTTTAT GTACTTATGT
26251 ACCATCTGTA TATCCTCTTC TATGAAATGG CTGTTCATTA CTTTTGCCCA
26301 TTTCCTCATT GGATTGTTTT GTTTTATTGT TGAGTTTGGG GACATTTTTA
26351 ATACATTCTA GCTACTTGTT TTTGTTAGAT ATATGGTTTG CAAATGATTT
26401 TTGCCAGGCT GTAGCTTGTC TTTTCTTTTC TTTCTTTTCT TTTTTTGAGA
26451 CGGAGTCTCG CTCTGTCGCC CGGGGTGGAG TGCAGTGGCG CAATCTCAGC
26501 TCACCGGAAC CTCCGCCTCC CGGGTTCAAG CAATTCTCCT GCCCCAGCCT
26551 CCCGAGTAGC TGGGACTACA GACGCGTGCC ACCATGCCCG GCTAATTTTT
26601 TGTATTTTTA GTAGAGGCAG AGCTTCGCAG TGTTACCCAG GATGGTCTCA
26651 ATCTCCTGAT TTCGTGATCC GCCCACCTCG GCCTCCCAAA GTGCTGGGAT
26701 TACAGGCGTC AGCCATCGCG CCCGGCCTGT AGTGTGCCTT TTCATCCTGT
26751 TAGTAGGGTC TTTTACAAAG CAAAACTTTT TAATTTTGAT GAAGTCCTAT
26801 TTATCAATTT TTTCTTTTAT GGATTGTGTC TATGGATGTC TAATTGCTCT
26851 AGCACCACTT GATGAAAGAG CTGTCTCTCC TCCATTGAAT TGCTTTTTCT
26901 TTTGAAGCTT AGTATGTTGC TTGAAACTAT GCTTGTTAAT ACTGTATACT
26951 GAAAACGTAC AAAGAATAAT GTTCCAATTT AAGTTAGATT TAAGTTAATG
27001 ATGTTCATTA ATAAGGACTC TTCAGATATA AATATTCCAG AATTTCTCTT
27051 AGCTTTCTAA TCAAAACAAC CATCAGTGAA TATTACCTTA CTTTGGAAGG
27101 TATAGATATA CATTTGAATT AAATTTAGTT TTTCCAAATA ACCCCTAATT
27151 TGAGAAATAT ATTCTATCTT GAAACTAAAA TAATTTAATA CAACTTTATT
27201 TTCTTCCCTC CCCTCCCCTC TCCTGTCCAC ATTTTGTAAA ATCTGGTCCT
27251 GAATAAGTCA CAATATAAAA ATAAATGTAC ACTTAACTTC CACTTCCTCC
27301 AACCACAGGC TACTTTCTGT TCCTCAACCT TGGGAACAAG GTGAAAAACA
27351 GTAAGCAATT TGGGCAGGGC ATTGCCAAAA CAAGATTCAA GCAGCCACAT
27401 GTGGACACCT CTTAAAAGAA TTTGGGGAAA CGAGACCAAA GAAGTCAGGT
27451 TTGATTTTTA GTGACAATAA CAAACATGAA GTGACTCTTC CCAAGTAAGA
27501 GTGCCACTGG GATGTGGCCT GGCCACATGC TTACCTATGC TATACTTCCC
27551 AGGAAACCCT GATGCTCTGC TCCAGGAGAG ACCTTTATCC TTTGGAGGTT
27601 CAGTGTCTTG GGAGCTCTTT GATTTTGTCA AAGAGATGAG CAGAGATTCC
27651 CTGTGGGTAT TTTAAGGCTT GGTGTCAAGG TATTTTTCTG ACACTGCTGA
27701 GCAAAGTCCA TGTATCAAAT GATCTGTTTC TAGTTTGTTT AAATTCTTCA
27751 CATCACTTGT AGACCTAACA TGGCAAAGCT TCATTATTTA ATCATAATAA
27801 CACCTACTAC CCATACTAAC TTATGATTTA TTTTCTGTGC CTGGAAATAG
27851 TCTCTGTGTT TAACAATAAT ACCTGGATGC AAAACAATCC ACTGTTATAT
27901 GGCCACAAAA TATTAATGAT CTTCTGAAGG CCAAGAAAAC ATTTTAACTA
27951 TAGTTCTTGC ACAGAAATTC ACACCCAGAA TCCCCAAAAT TAAAAAAAAT
28001 TTGGACAACA CAAATAATAG TTTAAGATAC ACATACATAC AACACAGATA
28051 CTCTTACACA TAACATCTTT TACGGAAATG TGTTTAGTGA AACTGTTCAT
28101 TTGTTGACAG CCACAGAAGT CATATTTTGC TAAATAGCTG CTCCAGCTGT
28151 TTTTTTCTTT GGAAAATGTA TCACTATAGG ATACCCTGTT TATTGCATAA
28201 GATAAAAGAA AAATATGTTG TGATAACCAA AAAGTTTTAA GGGCTTTCAA
28251 GTTATGTAAA AATGGACCTA TGGACATGGT TAATTGTCCT CAGGATGCAA
28301 AATTGGAGCT GAAATAGTAT ATCAAACAAT TGCAAAAAGT GTACTGCAGC
```

FIGURE 3, page 8 of 87

28351 TATCTCTTGG GTCAAATCTG GTACCCAGAA ATGGAGAAAA GCCTCAAGAA
28401 ACATTGCTGG TTGGCCCTCT GCCACTTGAC TGTATGATCT GATCACATGT
28451 AAGTTTCACA AACGATTCAT ATTTCTCTGC TAGTTTGACG TTGAGAATTT
28501 GCTCATAAAC CTCCCTAATT TTATCTTCTT GGTCCTTTGA GAAACACATA
28551 GTATCCCAAC TTGTCAGAGA GGAAATTTGA GCTGGTCCTT CTTTATCCAG
28601 GAGAGACCTG AAAAATTAGG TGGTGTGAGT ACTGCAGAGT GAGGCTGATT
28651 TTCCAAAGCA CTAACTTTGT TCTGATTAAG AACAATTTAC AATGGTCTCC
28701 ACTGCTGGTA ATGATTATCT TCTTTTACGT TCTGAAAAAT CTGCTCTGGC
28751 TGGGAAGGTG CTGCTCACTG CCAGGTGGGA TGGGNTGCCA TACCTTTGGA
28801 AAACCATGGC TTAGCAGTGC CACCTCCATC TCCATGGTTC ACTCCAGGGT
28851 CACCCACCGG TCATGCCATG CTGTTGAGGG GCAGAGACCT GGAGCAGACA
28901 CTGATATGAC TGCCTGCACA GCCACTGGCT TCTCGGTGGT ATTCAAACGC
28951 CAAGCCATTT TCCCATACTC TTTGAGTTTG AGGAACTTTT TGGAGATTGC
29001 TTGAGATTCT CTGCGTAGAA AATCATGCCA TTTGTAAAAA GGGTCAGTTT
29051 TGCTTCTTCC TTTCTCATCT GTATGCCTTT TGTTTTTTCT GTCTTACTGC
29101 ACTGACTAGA AATTTAGCTC TATGTTGAAT AAGAGCAATG AAAGAGGACA
29151 CCCTTGCCTT GTTCCTGATC TTGAGAGAAA GCATTCAATT CTTTTACCAT
29201 TGTTTGTGAT GTTAGCTGTA GGTTCCTCTT TATCGAGTTG AGGAAATTAC
29251 CCTTTACTTG TATTTTTCTG AGAATTTTTA TCTTAAATGG GGGTTAAATT
29301 TTGTCAAATG CTTTTTTTTG CATTGATTGA TAGTATTCTT GCAATTTTTC
29351 ATCTTTGCTT GTTAATAAGG TGGATTATGT TGATTGATCT TCTAATATTG
29401 AACCAGCCTT GGGATTCTTA CACTGCTTGG CCATGATATG CATATTCCTA
29451 CCCCACTTGG CATTGATGTA TGTGTATATA TAACTGATTT CTATTTGATG
29501 ATATTTTGTT AAGGATTTTT GCATCTATAT TTATGAAAAA TACTGGTCAG
29551 TAGTTTGCTT TTTTGCACTG CCTTTATCTA GTTACTGTAT AAGAGTAATA
29601 CTAGCTGTGT GAAATGAATC TCTTCTAATT TCTAAAACAG ATTGTGTGGA
29651 AATGGTATTC ATTTATCTTT AAACAATTGG GAGAGTTCTC CAGTGAAACT
29701 ATCTGAACTT AGAGATGTCT TTTTGGAGAA TTTTAAAATT ACATTTTTAT
29751 GCTCTCAGGA TGCAAAGTTT GAGCTGAAAT ATACTATCAA ACAAGTTAGA
29801 AAAAGCAACA CTTCTCGATA ATTCATAGAT TGCAAAGGAA ATCTTAAGAT
29851 AATTTTTAAA ATACATCAAA CTGAATATGC TAAAATATAT TGAATTGAAA
29901 TGAAAATTCA ACATATCAAA ATTTGTGAGA CTCAGTGAAA AGAAAGAAAT
29951 TTGTAGCACT AAGTGAATAT ATTTAAAAAG AGAAAATAGA CCAATAATCT
30001 AAATTCCCTC CACAAAAGAA AGCCTAGAGA TAGAAAAGGC AGAGAATCCA
30051 AACCATGCAG AAGGCAGGGA ATAATAAAAT GCAGAAATCA ATGAAATTGA
30101 AAACAGAAAA ACAGTAGGAA AAATCAATGA AATGAAAAGC TTGTTCTTTG
30151 AAAAAATAAA TAAAATTGAC AAATCTCTAG CAAGCCTGAC AAAGAAAAAA
30201 AGAGAAAATT CAAGAATGAA ACAAGTGCAG ACACTGCAGA CATAAAAAAA
30251 AAATAAGAGA ATACTACAAA CAGCTCTCAC AGTTAAATTT TATATATGAG
30301 ATGAAATGTA CTGATTCTTC AGGAAACACA CCTACTACAC TATACTCCCT
30351 AATATGAAAT AGGTAATTTG AATATTTTGA ACAGTTGAAT AAAATTAATA
30401 CTATAAGTAT TAAAGACATT AAGTGTATAA TGGTTTCTTT GTTTGGGCTG
30451 CTATAATACC AGAAACTGGA TGACCGATAA ACAACAAAAC TTTATTTCTT
30501 ACAGTCTGGA AGCTGGAAAG TCCAACATCA GGGCACCAGC AGATTCAGTG
30551 CTTGGTGAGG GCCCATTTTC GTGTTCATAG ATGGTTCCTT CTTGTTGTGT
30601 CCTCATATGG TGAAAGGGAT GAGGCAGCAC TCTGCAGCCT AATCCCACTC
30651 GTGATTACTG CCCTAATCCC ACTCGTGAGG GCAGAGCCCT CATGAGCTAA
30701 TCCCACTCAT AAGGGCCCTA ATCCCACTCG TGAGGGCAGA GCCCTCATGA
30751 GCTAATCACC TCCCAAAGGC CTTATATCCT AATGTCATCA CACTGCTGTT
30801 TAGGTTTCAA CATATGAATT TTGGGGTGAT GCAAATATTC AGACCAAAGC
30851 AGTTTTCTTT TATACCACTC TAGTAGAGAA AGGGAGGAGT ACGTCTGTTA
30901 TTGCCAGGTA GGGGTAGAAA TCCGGGTTTC CAACTTGGGC TTTGTTATAC
30951 CCAAGGAGAG GATTTCTCCT TGCTCCTGGG TTAGCTTGGG ATTTTTGGCT
31001 CCCTACTAAG TCTCCACTGG GATCACCCTG GTTGGGAGGA GTAGTGATAC
31051 CTTTTCACTG ATGTCCACAT GTTTTCCATT GACATTATGG TGGAAGGGTC
31101 TTATTACTAN NNNNNNNNNN NNNNNNNNNN NNNNNNNNNN NNNNNNNNNN
31151 NNNNNNNNNN NNNNNNNNNN NNNNNNNNNN NNNNNNNNNN NNNNNNNNNN
31201 NNNNNNNNNN NNNNNNNNNN NNNNNNNNNN NNNNNNNNNN NNNNNNNNNN
31251 NNNNNNNNNN NNNNNNNNNN NNNNNNNNNN NNNNNNNNNN NNNNNNNNNN
31301 NNNNNNNNNN NNNNNNNNNN NNNNNNNNNN NNNNNNNNNN NNNNNNNNNN
31351 NNNNNNNNNN NNNNNNNNNN NNNNNNNNNN NNNNNNNNNN NNNNNNNNNN
31401 NNNNNNNNNN NNNNNNNNNN NNNNNNNNNN NNNNNNNNNN NNNNNNNNNN
31451 NNNNNNNNNN NNNNNNNNNN NNNNNNNNNN NNNNNNNNNN NNNNNNNNNN
31501 NNNNNNNNNN NNNNNNNNNN NNNNNNNNNN NNNNNNNNNN NNNNNNNNNN
31551 NNNNNNNNNN NNNNNNNNNN NNNNNNNNNN NNNNNNNNNN NNNNNNNNNN
31601 NNNNNNNNNN NNNNNNNNNN NNNNNNNNNN NNNNNNNNNN NNNNNNNCAT
31651 CCATGGGTAT ATTTTGAATA TCAAGCAGGG ATACTTTTTA TCCATCTATT
31701 CAAGATCAAG TTATTAAACA CATATTAAGT GCTGTGGTAG AAAGTATTGG
31751 GATGACTGTA ATGAAATGAA TATATTTCTT GTGCTATTAA AGTTTAGAAT
31801 TATATAATTT TAGATCTTCA TTGAATCTCA TAGATAACTT CATTTAGTCA
31851 TTTCATTTTG CAGACATAGG AAATGAAGCA CACAACTGAA GTGTTTGTTG

FIGURE 3, page 9 of 87

31901 AGTTTTCTAC AATTAATTAT TTGCAAAACT ATTACTAGTC CAGAATTCTT
31951 TCTACTATAT TGTCTCCCCT ACCTTAGAAA TTCAATACAT CATTGTGTTC
32001 ATTGGAATTA CAGGAGTTTT CTTCCATTAT TTCACAATGT CTAAGTACAG
32051 ACATTATGAA GTAGGGAAAT TTACTTTCAT TATAAAACTT TCTTCATTAA
32101 CATGTATAGA TACATTTATA ATGTGAGTAT ATACATACTT TTGTCCAAAG
32151 TGGATTTAAA ATTCAAAAAA AACTAAATTT CTATGATCAA ATCCATGCTT
32201 AGTCTATAAA ACTAAAAATA TTGTGAGTTA ACGTAATAAG ATCTGTAAAA
32251 TACTGAGGCC ATTATGGGAA ATGTTTAAAG TTCCTACATT CATATCACAT
32301 TTTTTATCTT GGATCAGTTC CAAAAGTGTA ATGTTTGCTA TTTTGAAATT
32351 ATCTTAGGTA TCAAATTCCA ACTTATAAAT TTAAAAGTTC TTTAAATGTA
32401 ATTCCTTTTA TAAAAAGTGA ATTTGGGTTA CTCTGCATAA TTCTCCTTGA
32451 CCCCACTGAT GCTTTAATAT CTCTCATTAA GTGGACTCCA GGCAGCCACT
32501 CTTTGCTTTA TCCAAGCTCC AGCTAAGGCC AGCTGTTCTT TGAGCAGTGT
32551 TTTTATTAAC TTATTTAGGA ACTGGTGCAT ATCTTATTAC CCTATTTTCC
32601 ATTCCTGTCC TATGCAGCTG TAGTTGATAC TTTTCATAAC AGCCTTTACA
32651 TATCAACCTC CTCCCCTATT TTTTTTCTTA TTCTCTTTTA CTTCCCTTTT
32701 TAAGTAAATT AAGCATGTGT GTGCATGCAA AAGCCCTCTT CTTTCTTTCT
32751 GGTAACCATA TGACGTGAAA GCTTCAGGAA TGTGCCTGTT GTTTGTCTGA
32801 GATTATAAAC GTCATGGAAA AACTTTTACT AATGATGTAA ACATTCAGAA
32851 ATGTAGAATA CATGAATTTT AATAATAGCA AAATTTCTTC AATGTTGCAT
32901 TTAAGAAATT AATTTAGACC TAATTTAAAA TCAATGCAAT GTAAATACAA
32951 AGAAAAGGAT TTGAACAGAT AGAAGACTGT ACAAAATACT ACTAACCTCA
33001 GCTTACTGAA TTTCAAATAT TACAAGTTTC ATGGCATATG AAAATACAAG
33051 TTTGAGGAGG GAGCTATTTT ATAAATGTAA GACACGCATA AGTTGCAGCC
33101 ACTATGAGAT TAAACACATT CAAAATTCAA ATAAGGTAAA AGTAGCATTT
33151 TTTAGTATAT TAATAAGTTA TCATTGCAAT TTGAATTTTC ACTACCTACT
33201 CACTACAACC TTGAATAAAT CACCCATTGC TTCTATGTCT AGATACCTTT
33251 TTATGCAGAA TTACTATTTT AAAAGCAACT TATATTAGAA ATATAATAAA
33301 TATTATTCCA TATGAATTGC AATAATGAAA TCTATACTTA TTAAAAGATA
33351 CATTAAAAAT TAATAGCCCA AGCCAGGCAT GGTGGCTCAT GCCTGTAATC
33401 CCAGCACTTT GGGGAGGCCG AGGCAAGGTG GATCACTTGA AGTCAGGAGT
33451 TCGAGATCAG CCTGGCCAGC ATGGCAAAAC CCCGTCTCTA CTAAAAATAC
33501 AAAAGTTANN NNNNNNNNNN NNNNNNNNNN NNNNNNNNNN NNNNNNNNNN
33551 NNNNNNNNNN NNNNNNNNNN NNNNNNNNNN NNNNNNNNNN NNNNNNNNNN
33601 NNNNNNNNNN NNNNNNNNNN NNNNNNNNNN NNNNNNNNNN NNNNNNNNNN
33651 NNNNNNNNNN NNNNNNNNNN NNNNNNNNNN NNNNNNNNNN NNNNNNNNNN
33701 NNNNNNNNNN NNNNNNNNNN NNNNNNNNNN NNNNNNNNNN NNNNNNNNNN
33751 NNNNNNNNNN NNNNNNNNNG ATCTCACTCT GTCACACAGG CTGGATATGC
33801 AGTGGCACCA TCACAGCTCA CTGCAGCTTT AACCTTTTGG GCTCAAGCGA
33851 TCATCCTGCC TCAGTCTCCC GAGTAGCTGG GACTACAGGC ACATGCCACC
33901 ACACCTGGCT AATTTTTAAA ATTTTTATTG AGACAAGATC TCACTATGTT
33951 GCCTAGGCTG GTCTCAAACC ACTGAACTCA ATCAATCCTC CTGCCTTGGC
34001 CTCACAAAAT GCTGCGATTA CAGGCATGAG ACACTGTGAC TGGCCTACTT
34051 TAATATTTTT TAAAAATCAA GATCACATTT TGTAATTTTT AAACACACTA
34101 CATTAATGAT ATTTGTTGTG CATGAGAGGT CTAGCATTTT TAAACTTTGG
34151 ACTTGAAATT TAAAGCAAAA TTTGTATTTA GGTTGTTATC AAAGAAATGG
34201 TTAACTGTGT AAAACATGTT AAAAGTTGTG TGTGCACCTT AAAAGCTAAA
34251 TAGGATGCCA TACTCAGAAG CACTATTAGG AACTTTGACT GCAGATTAAA
34301 CAGGTACCAA ACAATAGTTG AAAGTAGTTG GTGACATACT TGGGCTAATC
34351 ATTGCTAAGG CTTCCTTTCT AATATGGATG TATGAGAAAT ATAGTAAAGC
34401 CCATGATTGT TTTTCTATTA AAAATCTACA TTTACAAAAT ATTATCTAGA
34451 AAGTATGAGT GTCTAGTACT TTTAATTTCT ATATACATGC ATAACCTGTG
34501 ACTTGTTTTG AGTATTATTT GTACATTTTT ATGGGAAAGC TTTTTCATGC
34551 TTTTAATATT TTCTACTTAT GGGAAATGTA TATGCAGTGA CATGTACAGA
34601 ACTTGTGTAC AATTCAATGA GTTTTGACAA GGGCATACAC CCATGGAACC
34651 ACCATTCATN NNNNNNNNNN NNNNNNNNNN NNNNNNNNNN NNNNNNNNNN
34701 NNNNNNNNNA TATATTTTAT TGTAACTTTA ATTCACATTT TTCTGATGAT
34751 TCATTATGTT GGATACTTTC ATATGATTAT TGGCCATTCA TATACAGGCA
34801 GTCTTTGCTT TACATAGTAG TATAGGACTA AAAAATGATT ATAGAAACTG
34851 AATTTGTGCA AAGTAATCCT AATAATCAAT GTAGAAAATT ATGATTGTTC
34901 TGTGACCTTC AAAAATTTTG TTACAATATT CAAAACTTCA AGTGTCAATT
34951 ATAAATGTAT GTGAAAACAA AAAATTATTT AGTATACTAA TTTAAAACAT
35001 TAGAAACATA GAGATTTTTT TGTATAAAAA CTTATCAAGA ATTTTTTTTC
35051 TCATTGTTCA GCTTATGTTA CAGAGAGGGC CTCTTTTCTA TGTTTCAGTT
35101 AATTGTTATA CACTTTCAAA GTTTAGATCA GTTTTCAATA TTTTATCCTT
35151 TGCACTTTCA ATATTGTCAA ATATCAGCAA GAGTTCTCTT GGTGTGAAAT
35201 TTTTGTTTTG CTGTTTTTTA CTTCCTTCAA GACATCATCC TTCATTGAAT
35251 TCATCAGAAC CACTTGCTTT AATTTCTGTC CATATTTGTC TTCAGTAAGT
35301 TGTCTTGGCT GCATATGTAA AGTTTCTTGA ACAGCAGTGT TAACATTCCC
35351 ATGGTCAGCT CTTTGTTCTG AAACTCCGTT TATGTTATAT TCAAATTTCA
35401 TTTCCAGCAC TCTCACTTTT GTTGCTCTGC TACCATCTTT GTTAGCCAAT

35451 ATGTGTCACA CGAGTTCATT GCTGTGAGAC AAGGAGGCAA CATAACTACA
35501 CAATTTTCTC CCTGTGCATA AACTGAAGAA CAAATGCACA ATGACCAATC
35551 AATGACAGAT TTTGAACAAA GTGATGTCAC TGATTATAAT GTGCATCTGT
35601 TATTTATGTA ATGATTTTAT GGATGAAAGA GCTAGAAGCA AAGTTTTCAT
35651 ATTATAAAAT TTTTCATACC CAATATATGA TAGTAACAAA TTCAAACTCT
35701 GTTTTGAGAA GACAGGTGTT ACTTAACTAA ACCATAGTAA CAAAAATTCA
35751 AGCACATTGG AATGTGCAAA GGACTGACTT ATCTCCTTTA GGGAAGTTTC
35801 TGTTCAAGTC ATTACTGCAT TTTTCTCCTG AATTGTCTGT CTTTTTAGTA
35851 CTGAGTTATA GGAGTTCTTT ATACATTTTG GATACAATTN NNNNNNNNNN
35901 NNNNNNNNNN NNNNNNNNNN NNNNNNNNNN NNNNNNNNNN NNNNNNNNNN
35951 NNNNNNNNNN NNNNNNNNNN NNNNNNNNNN NNNNNNNNNN NNNNNNNNNN
36001 NNNNNNNNNN NNNNNNNNNN NNNNNNNNNN NNNNNNNNNN NNNNNNNNNN
36051 NNNNNNNNNN NNNNNNNNNN NNNNNNNNNN NNNNNNNNNN NNNNNNNNNN
36101 NNNNNNNNNN NNNNNNNNNN NNNNNNNNNN NNNNNNNNNN NNNNNNNNNN
36151 NNNNNNNNNN NNNNNNNNNN NNNNNNNNNN NNNNNNNNNN NNNNNNNNNN
36201 NNNNNNNNNN NNNNNNNNNN NNNNNNNNNN NNNNNNNNNN NNNNNNNNNN
36251 NNNNNNNNNN NNNNNNNNNN NNNNNNNNNN NNNNNNNNNN NNNNNNNNNN
36301 NNNNNNNNNN NNNNNNNNNN NNNNNNNNNN NNNNNNNNNN NNNNNNNNNN
36351 NNNNNNNNNN NNNNNNNNNN NNNNNNNNNN NNNNNNNNNN NNNNNNNNNN
36401 NNNNNNNNNN NNNNNNNNNN NNNNNNNNNN NNNNNNNNNN NNNNNNNNNN
36451 NNNNNNNNNN NNNNNNNNNN NNNNNNNNNN NNNNNNNNNN NNNNNNNNNN
36501 NNNNNNNNNN NNNNNNNNNN NNNNNNNNNN NNNNNNNNNN NNNNNNNNNN
36551 NNNNNNNNNN NNNNNNNNNN NNNNNNNNNN NNNNNNNNNN NNNNNNNNNN
36601 NNNNNNNNNN NNNNNNNNNN NNNNNNNNNN NNNNNNNNNN NNNNNNNNNN
36651 NNNNNNNNNN NNNNNNNNNN NNNNNNNNNN NNNNNNNNNN NNNNNNNNNN
36701 NNNNNNNNNN NNNNNNNNNN NNNNNNNNNN NNNNNNNNNN NNNNNNNNNN
36751 NNNNNNNNNN NNNNNNNNNN NNNNNNNNNN NNNNNNNNNN NNNNNNNNNN
36801 NNNNNNNNNN NNNNNNNNNN NNNNNNNNNN NNNNNNNNNN NNNNNNNNNN
36851 NNNNNNNNNN NNNNNNNNNN NNNNNNNNNN NNNNNNNNNN NNNNNNNNNN
36901 NNNNNNNNNN NNNNNNNNNN NNNNNNNNNN NNNNNNNNNN NNNNNNNNNN
36951 NNNNNNNNNN NNNNNNNNNN NNNNNNNNNN NNNNNNNNNN NNNNNNNNNN
37001 NNNNNNNNNN NNNNNNNNNN NNNNNNNNNN NNNNNNNNNN NNNNNNNNNN
37051 NNNNNNNNNN NNNNNNNNNN NNNNNNNNNN NNNNNNNNNN NNNNNNNNNN
37101 NNNNNNNNNN NNNNNNNNNN NNNNNNNNNN NNNNNNNNNN NNNNNNNNNN
37151 NNNNNNNNNN NNNNNNNNNN NNNNNNNNNN NNNNNNNNNN NNNNNNNNNN
37201 NNNNNNNNNN NNNNNNNNNN NNNNNNNNNN NNNNNNNNNN NNNNNNNNNN
37251 NNNNNNNNNN NNNNNNNNNN NNNNNNNNNN NNNNNNNNNN NNNNNNNNNN
37301 NNNNNNNNNN NNNNNNNNNN NNNNNNNNNN NNNNNNNNNN NNNNNNNNNN
37351 NNNNNNNNNN NNNNNNNNNN NNNNNNNNNN NNNNNNNNNN NNNNNNNNNN
37401 NNNNNNNNNN NNNNNNNNNN NNNNNNNNNN NNNNNNNNNN NNNNNNNNNN
37451 NNNNNNNNNN NNNNNNNNNN NNNNNNNNNN NNNNNNNNNN NNNNNNNNNN
37501 NNNNNNNNNN NNNNNNNNNN NNNNNNNNNN NNNNNNNNNN NNNNNNNNNN
37551 NNNNNNNNNN NNNNNNNNNN NNNNNNNNNN NNNNNNNNNN NNNNNNNNNN
37601 NNNNNNNNNN NNNNNNNNNN NNNNNNNNNN NNNNNNNNNN NNNNNNNNNN
37651 NNNNNNNNNN NNNNNNNNNN NNNNNNNNNN NNNNNNNNNN NNNNNNNNNN
37701 NNNNNNNNNN NNNNNNNNNN NNNNNNNNNN NNNNNNNNNN NNNNNNNNNN
37751 NNNNNNNNNN NNNNNNNNNN NNNNNNNNNN NNNNNNNNNN NNNNNNNNNN
37801 NNNNNNNNNN NNNNNNNNNN NNNNNNNNNN NNNNNNNNNN NNNNNNNNNN
37851 NNNNNNNNNN NNNNNNNNNN NNNNNNNNNN NNNNNNNNNN NNNNNNNNNN
37901 NNNNNNNNNN NNNNNNNNNN NNNNNNNNNN NNNNNNNNNN NNNNNNNNNT
37951 GTATAAGGTG TAAGGAAGGG GTCCAGTTTC AGTTTTCTGC ATATGGCTAG
38001 CCAGTTTTCC CAACACCATT TATTAAATAG GGAATCATTT CCCCATTGCT
38051 TGTTTCTGTC ATTTTTGTCA AAGATCAGAT GGTTTTAGAT GTGTGGCTTT
38101 ATTTCTGAGG CCTCTGTTCT GTTCCATTGG TCTATATATC TGTTTGGTAC
38151 CAGTACCATG CTGTTTTGGT TACTGTAGCC TTGTAATATA GTTTGAAGCC
38201 AGGTACCATG ATGCCTCCAG CTTTGTTCTT TTTGCTAAGG ATTGTCTTTG
38251 CTATGTGCTC TTTTTTGGTT CCATATGAAA TTTAAAGTGG TTTTTTTCTA
38301 ATTCTGTGAA GAAAGTCAAT GGTAGCTTCA AGGGGGATAG CACTGAATCT
38351 ATAAATTATG GAGTCTCACT CTGTCACCCA GGCTGGGGTG CAATGGCATG
38401 ATCTTGGCTC ACTGCAACCT CTGCCTCCCG GGTTCAAGTG ATTCTCCTGC
38451 CTCAGCCTCC TGAGTAGCTG GGATTACAGG CATGTGCCAC CTGGCTAATT
38501 TTTATATTTT TAGTAGAGAC AGGGTTTCAC CCTGTTGGTC AGGCTGGTCT
38551 CGAACTGCTG ACCTCATGAT CTACCAGCCT TGGACTCCCA AAGTACCTGG
38601 ATTACAGGTG TGAGCCACCA CACCCAGCCT ACAATTCTTT ATTAGAGATA
38651 TGTATAACAA ATATTATGTT CCAGTCAATA GCTTGACTTT CTGTTTTCTT
38701 AATGGCACCT GTGCATAATC AGACGAGTTT AATTTTGATG AAATCTAAAT
38751 TAGCAACTTT TAATCTCATG TCAGTACATT TTGTGTCCTA ATTAAATATT
38801 GTGAAAATAA TATCCTGGGT TTTATTCTAG AAATGTTATA GTTTTAACTT
38851 ATACATTTAT ATTTTTGATT CATCTTGAAT TTTGGGTGTG TAGTATGAGA
38901 AGTGATTCAA AGTTTTTTTT TGTACATTTA TCAAAACATT TAATAACTAT
38951 TTTAAAGATA CTTTTATTTA TAATAAATAA ACATAGGTCA TAATAAATTG

FIGURE 3, page 11 of 87

39001 ATATAGGTCA ATCACTTGAC CCTATGTGCT TGAATTTATT TCTGGAATAT
39051 ATTTTATTCC ATTGATTTAT TTATCTGTTA TTGTAATAAA ACCACACTGT
39101 GTTGATAACT GTAGCTTTAT TATAAGTCTT GAAATCAGTT TGTGTAAGTT
39151 CTACAAATGT GTTCTTTTTT CAAAATTCTT CTGGCTATTT TTGGTCTTTG
39201 CATGTCCATA TAAACTTTTA AATTATAATG ATCTTATTAA TTTTTACAAA
39251 AATGCCCATG GCATTTTCAT TGGGATTGCA TCAGATCTAT ATACATGCAT
39301 GTATACATCT ATACATGGGG AGAATTGACA TCTCAGCAAT GAGTTACTAA
39351 TGAATATGTT ATTATTTCTC CATTTTTAAA ATTATTTATT TCAGTAATGT
39401 TTTGTGGTTT TAAGTAAATG GATTTTGCAT ATCTTTTGTT AAAATTATTT
39451 GCATGTATTT AATTTTTTAA TGTTATTCTA AATAGAATTG ATTTTAGTCA
39501 TTAGTTTGAT GCAAAATACA GAAACACAAT CAATTTTTAT ATTGACATTG
39551 TATCCTATGA CATTGTTAAA TTTACTTCTT AGTTCTGGAA TGTTAAAAAA
39601 ATTTAAATAA TATTCTATAT TAAAATTATT GTGTCTTCTA AAATTAAAAG
39651 TATTTTTCTC TCTTTCTTTC TTTCTTAACT CCATGACTTT ATTGTTTGTT
39701 TGTTTTGCCT TATAGCACTG GCTTGACTCT CCAGTACAGT GTTAAACAGA
39751 GGTGATAAAA GCCAATATCC TTGTGTTGTT CCCAATTTCA GGGAGAAGGA
39801 TTAGTTTTTC ATCATTTTAT ATGATATTGG CTGTAGACTT TCTGTAGATA
39851 CCCCTTATTA AATTGAAGAA GATTCTTTCA TTTATAGTTT GCTATGAGTA
39901 TTTATTGTGA ATGGATGTTA AATTTTGCCA CTTGATTCTG AATTTAAGGC
39951 AATAATTTGC TTTTTCTCTT TTATTCTCTT GCTGTGATAA GTTACATGGT
40001 TTATTTTTGA ATGTTAAATT ATATTTACAT TCCTGGGATA AAACACACTT
40051 GATCAGATGT GTTATTCTAC TATATATTGC TGGATTTGAT TTAGTAACAT
40101 TTTGCTTAAG ATTGTTGTAT TTTTGTTCAG GATAGGTATT GGTCTATAAT
40151 TTTCTTTTAT TATAACATTT TTTCTCAGAT ATTTACATCA AAGTTATACT
40201 ACCCTAATAT CAGTAGTTGG GGAATGTTCT TTCCTCCTTT ATTTTCACAG
40251 TTATTATTTC ATCCTAAACT ATTTGATAGA ATTCACTAGT GAAACCATCT
40301 GAACCTGGAG TTTTCTATTG TGGCAGATTT TGTATTACTT TGACTTCTTT
40351 AATAAATATA GAACTACTCA TACTTTCTTT TTAAAAAATT TTACTTTAGG
40401 GCCGGGCGCG GTGGCTCACG CCTGTAATCC CAGCTCTTTG GGAGGCCAAG
40451 GCAGGCGGAT CACGAGGTCA GTAGATCGAG ACCTTCCTGG CTAACACAGT
40501 GAAACCCCGT CTCTACTAAA AATAGAAAAA ATTAGCCGGG CATGGTGGCG
40551 GGCGCCTGTA GTCCCAGCTA CTCGGGAGGC TGAGGCAGGA GAATGGCGTG
40601 AACCCGGGAG GTGGAGCTTG CAGTGAGCCG AGATCATGCC ACTGCACTCC
40651 AGCCTGGGCC ACAGAGTGAG ACTCCGTCTT AAAAAAAAAA AAAATTATTT
40701 TAAGTTCTGG GATACATGTA CAGAATGTGC AGGTTTGTTA CACAGGTATA
40751 CATGTGCCAT GGTGGTTTGC TGTACCTATT AACCCATCAG AATTTCTATA
40801 TCATTTTATA TGTTATGTTT CCAAGAAACT TGACCATTTT ATTTAAAATG
40851 TTGAAAATAT TGGCTCAAGG TTTTTTGTAA TCTGCAGTGA TATTCCTGAT
40901 TTTATTCATG ATGTGAATTG TGTTTACTTT CTTTTTATAC ATCTTAATAA
40951 GTGTTTATGA AATTTATAAA TTTTTCCAAA TAACCAACTT TTATATTAAT
41001 TAATGTTCTC TATTGTTTTT GTGCTTTCCA TTACATCGAT TTCTGATCAT
41051 TATGATTTTC TTGCTTCTAA ATATTTTGCC ATAAGGTTCT ATGTATTAGT
41101 TCCATGTGGT TAATAGTGTT TTGCAAAATG TCTGTATCAT TATCACTTTT
41151 CCGCCTAATC GTTCTAACAG TTATTGAGAA GGAAATGATA AAATATTTAA
41201 CTACGATTGT GGGTTTTTTT CTTTCAGTTC TGTCCAGGTT TGCTTCATGT
41251 AGTTTCAGTT AAAAAAAAAG TTTTTACCAA AAACATGCGT ATTGTGATTG
41301 TTATATTTTC CTAATTAACT GATCCTTTGA TCATTATAAA CTATCCCTTT
41351 TATCTTTGGG GACACTTCTT GTATTAAGGC TTTTTTGTCT GTTATTAATA
41401 TAACACATGT TCTTTTATTC GTGGTTTGCA TCATATATCT TTTTCTATTC
41451 TTACTTGTGA ATTATTTGTA TTGTATTTAA ACTGTGGCTG GTGGACAACA
41501 AAGTACGTCT CTTGTGAACA ACCTATAATC AGGTCTTTAA TCTTGTCTGA
41551 CAACCTCTGA CTTTTAAATG GAGTATTTAC TTCATTTAGA TTTAAACTTA
41601 GTATTAATTT ACTTGACTTT GGATGTACTA TTTTTTCTTT GTTTTCTATA
41651 TGTCCTATCT CATTTTTAGT TCCTCTGTTC TTGCTTTCTT TCTTGCCTTC
41701 TACTGGGTTA ACTATATATT TTTAGCATTA TATTTTAATT CTTCTATTTG
41751 ACTTTTAGCT ATGTTTCTTT GTATTATTAT TTTTCGTGGC TTCTCAAGGG
41801 ACTGCAATAT GAATACTTGA CTTATATCTA CTTAATTTAT GTAACTGGAA
41851 ATAAAATACA TGAATTTTGC AGAAGTATTC CCATGTACTT CCCTGTAGTT
41901 TCTGCTGTTA TTGTTATATT TTTTGTACTT ACTTTTATAG ATGTCAGGTT
41951 GTTATACGTG TCAGCTATAT ATATTAATAT ACGTGTGTAT GTGTGCATGC
42001 ACACTCGGTT TTTCAGCTGT CTTTCTACTG AGCTCCTTGG ATTCTCCGTC
42051 ATGTACATAT AATTAAAATA TTAGGCAAGG ATTTAAGGGG AGTTTAGTCC
42101 CAAACTTTGG ATCTAACTCC TCTGTTTCCA ACTACTTTAG CAGCCTCATA
42151 CTTTATTCTC TGACACCTCA AGCCAATAGC TGCGTTTTTT TTCCTTTTCC
42201 AAGTTCATAC ATGTTATCTG CAGAATAGTT TGATATAAGT TATCACCAGA
42251 TCAGAGTTCC TCAAGTTGGA ATATTTTGTT TTAAATTCTT AGCTGCTTTT
42301 GCAAAATTTT TGCCCAAAAT ATGAATCTGA GCTCCTTTCA AGGTTTTTAT
42351 TAAAATATCT AGTCACACTG AACACTTTAG TGTATAATAG CCTTAATGTC
42401 ACTTGGTGAT GGGTAGATAG AAGAGGAGTT TACATTGCAA TAATATATAT
42451 GGCTTTAAAT TGATTATTAG ACATTTTTGT TCTAAAAATC TTTTGATCCA
42501 AGTGTGGTGG CTCACACCTG TAATCACAGA GCTTTGGAAG GCTGAGGTGG

FIGURE 3, page 12 of 87

42551 GAGGATCTTT TGAGCCTAGG AGTTTGAGAA CAGCCTTGGC AATGTAGCGA
42601 GATCCCGTTA GTACAAAAAA AAAAATTAGC CTAGAGTGGT GGTGTGTGCC
42651 TGTAGTTCCA CCTACTCAGG AGGCTGAGGT GGAGGATTGC TTAAGCCCAG
42701 ATGTTTAAGG TTACACTGAG CTATGAAGGT ACCACTGCAC TCCAGCCTGG
42751 GCAACAAAAT GGCACCCTCA TCCCTGTAAT CCCAGCACTT TGGGAGGCCA
42801 GGGTGGGCAG ATCTCCAGGT CAGGATTTCG AGACCAGCCT GGCCAACATG
42851 GTGAAACCCT GTCTCTACTA AAAATACAAA ATTAGTCAGG TGTGGTGGCA
42901 CATGCCTGTA ATCCCAGCTG CTCAGGAGGG TGAGGTGGGA CAATTGGTTG
42951 AAATCAGGAG GCAGAGGTTG CAGTGAGCCA AGATCATGCC ATTGCACTCC
43001 AGCCTGGGCA ACAAGAGCGA AACCCCATCT CAAAAAAAAA AAAAAAAAAG
43051 AAAAAAGAAA AAGAAAAAGA AAAGAAAATC TTTTGGCAAT CAGAGAGTTT
43101 TCTGTTGGTT GCTTTATACC ACTGAGGCCC ATGTCCCCAA CCTCACACCA
43151 TCCTTTGAGC CTTTGTTCTC ATTGTTTCTC CTTCCATCTC TTCCTTCTCT
43201 CTCGCTTTCT CATATGGGCT CCTGAACAAT CCCAATTCTT TCTTTATTCT
43251 TTCTTATGGA TATTTTCCCA AAGCTTACAG TCAGAACTCC TTGTGTATAT
43301 TTTAATCAAT AAAGTTTNNN NNNNNNNNNN NNNNNNNNNN NNNNNNNNNN
43351 NNNNNNNNNN NNNNNNNNNN NNNNNNNNNN NNNNNNNNNN NNNNNNNNNN
43401 NNNNNNNNNN NNNNNNNNNN NNNNNNNNNN NNNNNNNNNN NNNNNNNNNN
43451 NNNNNNNNNN NNNNNNNNNN NNNNNNNNNN NNNNNNNNNN NNNNNNNNNN
43501 NNNNNNNNNN NNNNNNNNNN NNTATTTTTG AAATCTGTCC ATCCATCCAT
43551 TCATCTATCC GTCTGTTGAT TTGTTCACTG ATTCACATTT TTGCTAAGCA
43601 AGTACTTATT AAATATCAAT GTGTGCCAGG CATTATATGC TTATCTGTTT
43651 CTTCTGACCT TTTTTTTTTT CCTATTCTAC TTCACTGTAC ATTAACTATT
43701 GATATAGACT CAATTCTTCA TCTCTGGTGT TTTGATAATA TGAGTACTCC
43751 TTTCAAATGT TCATTTACTC TCATGATTTC AATTACTTAT AGATACAGGA
43801 ATTCTCCCAA ATTCCTTTAC GTGACCCATT ATGCTAACAC AAACCTCTCC
43851 TGTGATAACT CTGTTTATCC TGCTAACAAG ATATGAAGCT AACATTTTAT
43901 TTCCTCATAC TCATTCTTGG GTAAATCTCC ACAAGCCAGT ATGTCTTTCT
43951 AATTTCTTCG TCACTCTCAA TGGTTCAATT TAGTCTCCAG GTGTTATAGG
44001 AGTGGTCTCA ATAGATAATT AAGTTGGCTT TCTAATTAGT CTTCTAAGAA
44051 CTGTTTCAGA TAAACTATGT AAAATCAAAG TTGTCATTTT TGATAAATAT
44101 TCTCATGAGA TGACTTACTG CATGCAGCTG TCAAAACTAA TGAATTTATA
44151 AATCAAGCCA GCTCATTTTG CCTTTGTATT AGTCTGTTCT CACACTGCTA
44201 TGAAGAAATA GCTAAGACTG GGCAATTTAT AATGGAAAGA AGTTTAAGTG
44251 ACTCACAGTT CAGCATGACT GGGGAGGCCT CAGGAAACTT ACAGTCATGG
44301 CAAAAAGGGA ACCAAACACC TCCTTCTTCA CATGGCAGCA GCAAGGAAAA
44351 GTATGAGTGC CCATTGAAGG GGCGAGCCCC TTATAAAACT ATCAGATCTT
44401 GTGAGACCTA ACTCACTATC ATGAGAACAG GATGGGGGAA ACCACACCCA
44451 TGATTCAATT ATCTCTTCCT GGTCCCTCCC ATGACATATG GGGATTATGG
44501 GAACTACAAT TCAAGATGAG ATTTGGGTGG GGACACAGCC AAACCATATT
44551 GGCCTCCAAA CAGAATATGT ATAACTATAT GTATAACTAG CTTTCCTTGT
44601 AACGATCCCT AAAAAATGAC TTTTTCTTTG GAAGTTTTAT TGAGAAATTT
44651 TTTAAAGGTA AGTGTTTCAC AGTATGTAAT TTTAAGACTA AAATTATAGC
44701 CATGGTTTAT ATTTGGGGCC CCAATTGTCC AACTATACAT GCATGGGAAC
44751 AGATACAAAA CAATTTTAAA ATATCTTACT CCTATTTCAT GCACATTGAA
44801 TACATTTATA AGACTAATTT GGCACATTAG TATGAATGGG TCAGTCCATA
44851 TTCTCAGCTT TGTAGTAGCA CTCAAAATCC TGTTTGTGTT TCATAACTTG
44901 ATAAATACTC CAAAATTTCT CTGGATTAAG CCAGGCTACC AGAGAGAGTT
44951 GCACATGAAC GGTATACTTA CAATCTCTGA AGACATAGTT TTAATAAAAC
45001 ATATTTGAGA ATTATTCCAC CTACGTACTC AGAGTGACGT TGTAAGAATG
45051 GGAAATTTTT TTTTTTGGAT TTTTTTAATT TTTATTTTTT ATTATACTTT
45101 AAGTTTTAGG GTACATGTGC ACAACGTGCA GGTTTGTTAC ATATGTATAC
45151 ATGTGCCATG TTGGTGTGCT GCACCCATTA ACTTGTCATT TAGCATTAGG
45201 TATATCTCCT AATGCTATCC CTCCCCCCTC CCCCCACCCC ACAACAGGCC
45251 CCGGTGTGTG ACGTTCCGCT TCCTGTGTCC ATGTGTTCTC ATTGTTCAGT
45301 TCCCACCTAT GAGTGAGAAC ATGGGGTGTT TGGTTTTTAA AATAAATTTT
45351 TTTTCCCATC CCAAAAAAATC AGAATGGGAA AAAATTTTTA TTTTTATTTA
45401 TTTATTTATT TTTTATGAGA TGGAGTCTCA CTCTGTCGCC CGGGCTGGAG
45451 TGCAGTGGCG CGATCTGGGC TCACTGCAAG CTCCGCCTCC CGGGTTCATG
45501 CCATTCTCCT GCCTCAGCCT CCTGAGTAGC TGGGGCTGCA GGCGCCTGCC
45551 ACTACGCCCG GCTAATTTTT TGTTGTATTT TTAGTAGAGA CGAGGTTCCA
45601 CCGTGTTAGC CAGGATGGTC TGGATCTCGT GACCTCGTGA TCCGCCCGCC
45651 TTGGCCTCCC AAAGTGCTGG GATTACAGGC CTGAGCCACC GCACCCGGCC
45701 AAGAATGGGA AAAATTAAAC ATACTTAGTA TTTACTGTGT ATGGATGTTG
45751 TCGAGGACAT TGCTTATTAA ATTATGGTAC CCTCTTTATG GGTTTTTTCA
45801 GAAGAAATGT ATCTTTGGTT TCAGTATCAG AGATTATTGT ATTTTTGTTC
45851 ATTTAATTTA TCTTTATTTG CGATAACAAA GATTTACTAT CTTGCTTTTC
45901 CCTTTATTTT ATTTATTTGT TATAAAGAGC CAAATTTATA ATTTACTTCT
45951 AGGAAGTCTA CAGTGTGTAT TTTGTCAGTT AATCTAATTC CTGGGTTCAT
46001 TCCATTTGTT TTACCCCTAT TTTCTCTGTG CTCAATATAC CATCACATCC
46051 TGTCAATATT TCTTTACATT TTTCTTTAGC TCTACTCCTA ATTATTTTTA

FIGURE 3, page 13 of 87

46101 ACCTACCAGA TCATTGTAAT CTATGTTGTG CTTTATATGT AAAATATCGA
46151 ACAAGTTTTT ATCAAACTTG CCTATTCCTA ATAACAAGTG ATATGAAGGC
46201 TCAGACTTTT AAGTTTATAT GTCACTAATT AATCTCTGTC TGTTGTTTCT
46251 CTGTCACCTA CTGTAGTCAC CTAAACTGCT TTCAAACTTT CACTGCCTTT
46301 CAATAACACC AAACCTGATA ATCCCCCACA CTTTTTTCTT ATGACTGCCT
46351 TACACTATTT TCCTTCAGCC TAAGATTTTT CCCAGCCCTT GACAAACATT
46401 TTGTTGCCAC TTATGTATCT CTCCCCGTAC TCAACCCACT GAATCCTTTT
46451 TCTTTCACAT CTTTACTAAT CCTCAGTTGT TCCTTCAAAT TAGAGCTCCC
46501 AGATCTTCTT CTCTGTCCTG TTGCATTTAC CTCTTTGTAG TTATTTCTAT
46551 TAACTAAAAT ATTTTTCATC TATGTATGAA AAGGTTCTTA TACATTGACT
46601 TGTATCCTGC CCACATCATT CAATGTGAAT GTTCAATAAA TGCTATTGAT
46651 TAAATTCAAG CTAGTGCAAA ATTTGTAGCT GGTATGCTGA AATATGCTTT
46701 GAACTTAACT TTGAAGGTAT TTCCATTTTT GTATTGATCC ATACTATATT
46751 AATGTTAGCA AATTTTACTT TGTGTATGTT TAAATTATCT ATCTGTATGT
46801 TGTGTTTCTA AAAGGATAGT AGATTATTTA AAATTTCTAG AGACAAAAAT
46851 ATTCTTAAAC TTGGGAAGAT TGGGTTGATA ATTTTGTATG TTTTATAAAT
46901 ATAATTCACA AATATAACTT TTCAGACATC TGTTTTGCTT AAAAGAGAGT
46951 ACATCTGTTC CTGAAAAATA AAAATATATA GTCATAAATA AACAATTTAA
47001 ACTTGGTCAT CCAACTTAGT GTACTTATCC AGGTCAATGA GAAGTCAATA
47051 CAAAACTACC TTCACAATCC TATCAGGAGA GTTTGGCAAT TTCTAATAAC
47101 TGATATTCAG AAGTTTATAG AATAATTACA TTTTATACAT GTATTCATCT
47151 TCTAAGTAGA ATTTACTGGT CAGTAAAAAC TCTCATGCAT TTAAACCTAT
47201 AACAAATTCT TGCTTATTTA GATCTACAGA CCCTAATTTC AACCATGATG
47251 AAAGTATTTT AGTGATAAGA ATAATTTATG AATAAAAATG TAATTTAGTG
47301 AATACCTTGG CAGTTAATGT TGATCGCTTC ATCACAGTTC AGTCATGTTT
47351 AGAAAATCTA AGCAAGCTGT GTGATTACTC CAGGAAGCAT GGAATGATGT
47401 GTTCAAATTA GTACCATCTG TGGATAGAAA AAGTTTGAGG TTTTTAGTCA
47451 TTCTTAAAGA ATGGAAATCT GATTCTCCAT GCTGAAATGA GTGTAATCCT
47501 TTTTCTATCT GTAATTCAAT AGGGCAGTTG CCTTGAAATA GTCTAGTTCA
47551 GCACACAGTT CATCAAAGAG AAGATACTGG ATATAAATGA GGGTTACTGC
47601 TGGTCACTTA TGAATACTTC TGAGGTAGCC TTGTTTAAAA AATTGTCTAC
47651 AAGTTATACC ATATATTTCA CCTCAGATCA GATTCATTTT TGGTTTATCT
47701 TTCTAAATAC ATTTGAGTGA AAATGTGGAC TAGATTTTGT ACCACATGAA
47751 AACAAAAGGC TGTTTCAATG AACCATCATT TATTTCCACA GTCAACAAAC
47801 ACTTATGAGT GCCAGTATGT TCCAGTGTCC CATCACTGTG CCTGTCACAT
47851 AATAGGAGGC TGAAATTGTC ATTATGTTTC CTATAGCCAG GTTACAAATA
47901 ACTCTTGCCT GGATTTAGTG GTTTTTCTTT TTAAGACCTT TTCTTCTCTG
47951 AAAGCTTAAT TGGAGAATAC TAGAGTCTGT GAACGAATAT TGATCTGCTG
48001 AAAATTTTTA CTGTGTAGCA AAATTTGCTA GTAACAAACA CCAGCTATCC
48051 TAAAATCTGA ACATTGGAGG AAAAAATAGT TGATCATAGA GGCATGGGCA
48101 TCTAGTCATC CCTCCAGATG GGATTAGCAA AGGGCAGCCT CTTCTGCCTT
48151 CTCTAGTTCA TTAGCTAGTG AATATTTCCC TCTCATTTCC AGTGGTTTAG
48201 CAAACTCTAG GGAGAGAAAA TTGAAACATG GGAAAGGTAA CTGGTAGTAG
48251 ATCTAAAAAA GAATAAATAA AAGAAGGAAA GCATTTGTAC ACTGATTCTT
48301 ATGAGGAAAG AGTAGAGTGT AAGATTTTAA TGAAAACAAA AGTCAATATA
48351 AAAATTTTCA AGGCCAGGTG CCATGGCGCA TGCTTGTGAT CCTAGCACTT
48401 TGGGAGGCTG AGGTGGGCAG ATCAGTTGAG CCCAGGAGTT CAAGACCAGC
48451 CTGGGTAACA TGGCGCAACT CCATCTCTAC AAAAAGTACG AAATTAGTTG
48501 GGTGTGATGG CACACGCCTG TGATTCCAGC TACCCGAGAG ACTGGGTTGG
48551 GAGGGTCATA TGAGCCTGGG AGGTTGAGGC TGCAATGAGC CATGATTGTG
48601 CCACTGCATT CCAGCCTCAG CAACAGAGTA AGACTCTGTC TCAAGAAAAA
48651 AAAAGTAAAA ATTTCCACAT AATAAAAACG ATCATCAGCA AAATAAAAAG
48701 ACAAATAACA GATTTGGAAA ATATATCTTC ATCAAGGATC ACAAAAAGGT
48751 TATATTAAAG GCTTAAATAA ATAAATAGCA AAGCCATACA CCCAATAGAA
48801 AAAAAAGTAG AAAAAATACA AATGATAGTT TATGAAAAAG GAAATTAAAG
48851 AGAGAGAAGT GCAATAAGCT TCACACTGAA ACAGAATTTT TTCCCTCTGA
48901 AACTTTTATT GCATACTCTG TTGGCTTGGG GAACAGGCAT TCTCATGCAT
48951 GTTGACAGGA GTAGGTATTG GTAAAACCTT TCTGGAGTGT GATTTAGCAA
49001 TGTCTACCAA TGCTACAAAT ATGCATATGT TTTACCTAGC AACGATTATC
49051 CTACAGATTT ACTCACACAT ATGTGTGGAA TATGAAAGCA TAGGCTTGTA
49101 CATTACAGCT TGTTTACTGC AAATATTGGA CACAGCTTAA TATCATTTCA
49151 TAGAGGCTGG TAAAATCAAA TTCGATATAT CCATTTCAAT GTGCTTACTC
49201 CATACAACTC CAAACACTGA AGAAAAAGGC AAAATATATC CAAAGCATAT
49251 ATATAGTGAC CCTAAATCCC AGTTTCCAGG GCAGTCTGGG TTTATGCTTG
49301 CTGTGCTGGC ATTTCATCCA ATAGACATTG CCTTTTACTC TCAAAAGTGA
49351 CCTGTCTGTA TAACAAATAA TTTGCTGCAA TGGAGTGAAT GTTTATTTCC
49401 CCCCTAGAAT CATATGTTGT AGTCCTAACT CCCTGTGTGA TGCTATTAGA
49451 AGGTGAGGCC TTTCAGAGGT AATTAGGTCA TTAGGGTAGA ACCCTCCATG
49501 AATGGGATTA ATGCCCTTAT AAAAAGAATG CAGAGAGCTC TTTTGCCCTC
49551 TTTCTGCTAT ACAAGGACAC AATAAGAAGC CAGCAGTCTG GAACCAGGAG
49601 GCTGGTTCTC ACCAGAAACC TGCCATGCTG GCACCCTCAT CTGACTTTCA

FIGURE 3, page 14 of 87

49651 GTTCCAGAAC GTTGAGAAAT AAATTTCTGT TGTTTGTAAA TCACTCAGTC
49701 TATAGTAACT TGCTACAGCA GCCAAACTAA GACAGTCACT CTAGATATAT
49751 TCTTTGGAAG TGAGAGAAGG GACTGGGAGG AAGAAGAGAG TCGGATATGA
49801 GGTTAGATGA AAAGAAAGGG AAGGCTGCAC TCCAGCCTGT GCAACAGAGT
49851 GAGACCTTGT CAAAACAAAA CAAAAACAAA AACAAAAACA AAACAAAAAA
49901 AACTTTTCAA GTATATCACT GTGCTTCAGA TAAAGCTAAA AGTCATATAT
49951 TTGGTTTAAG GACTCAGTTT AATGTGATTC CACTTACATT GCCTACTTCG
50001 CCCCTTCCCA TTCATCTCCT TGTAGACCCA GCAGCCTTCA TTAAGTGTTT
50051 TCAATGTGTG ACACTCTTCT TCTTCAGGGT CTTAACACCT TCACACATCC
50101 TGATATTTTT TATCTGTGAA GCTTCTTCTT ATCCTTCAGG TCTCTAATTA
50151 AATTATCCTT CACCAGGAAA GCCAAATAAA GTCCCCTGTT ATACCCTCGA
50201 TTCATTTGCT CACACATTCA AAAAACATTT ATTGAATCAC CATTTTGTTT
50251 CATTCAGTAG TCTAGACTCT GAGAGAGAAA ATCTGTTATG TACATTGACA
50301 TTTTATGTGT TTATAACCTA CAAATAAACA TCTATTTTTG AGTGATTTTT
50351 TTCAATATTT TTATTGAGAT GGATGCGGAA GCAAAATCTT TTTGAATCTT
50401 TTATATATAA TGTTGGGGTG ATGTGGAGGT GAAAGTAGAT TAGGCCTCTT
50451 TGGAGTGGGT TTTCAGTGCA GAGCTGAGAT TTATAGGAAA GTAAATATCA
50501 GTTCAAAATA ATGCAGGCTA TACAAACTAA TAGAGCTATC TGAAAATGAA
50551 TTTTAAAATA AACTACCCTT GAGATGTTGA GTTTCCCTTG CTCTATGTAT
50601 GTAAGCAGAG GCTGGGTAAG TAGTGATTGC TCATTTTGTA GGGGGAGGTT
50651 TGTATTGGTC TTCTATTGCT GTGTAACAAA TTATCACAAA CTTAGTGGCT
50701 TAAAACAATA CCCATTTATT AGCTCATAGT TCTATAGGTC AGAAGTCCAG
50751 GCGTGTTGTG CCTAGGTTTT CTACTTATTC TCACAAGCTG AAGTCAACTT
50801 GTCAGTCAAC ATTTTCTTGT GTAACTCAGG GTCCTCTTTC AGGTTCACGT
50851 GGTTGTGGTA GAATTTAGTT CCTTGCAGTC ACAGGATTGA GAGCCCCTTC
50901 CCTGGCTGGC TTTTAGCTAA GGGCTTCTCT CAGCTCCCAA AGATGTTCTG
50951 TGTTCCTTAT CATGCAGCTC CCTCCTTCTT GAGAGCCAAC AATAGAGAAA
51001 TTTTTGTACG TTGAATCCAT CTCTTTAAAG CTTTGACTTC CTTTTCTGAA
51051 AACGGCCAAA AATACTATCC TCCTTTTAGA GGGCTCAGGT TATAAGGTCA
51101 GGTCCACTGG ATAGCTCTCT ATTTTAAAGT AAACTGATTA AGATTCTTAG
51151 TTACAGCAGC AACATAGCTT TCCATCTGTA CCTAGATCAG TGTTTGGTTG
51201 AGTAAGTGGA AGAATCTGTT TTTGTACAGG GACCGGGAAT CTTGAGGGAT
51251 ATCTGCAGAC ACAAAGGTCA GACAAAGAGA CAAGATGACC AAGATGATCT
51301 CTCAATTTCA AATTCTGAGA TTACGTGATT TTTCTCATTT ATTTGCCTGT
51351 TCTTATGGAT TCAGTCGCCA AAATATATCT TAAAAACTGA CTTCTGTACT
51401 GTTGCTATCA CCTAATTTCG TCTTTCCTGG ACAAATCAAG TAGTCTCTGA
51451 ATTTCTCCCT TTTCCTGTTT TGCAATTACC AGACTGTAGT TGATAAAATG
51501 TACCTCTGGA CATACTGTGA CATTTTTTAT AGCTTTCAAT TGCCTGACAA
51551 GCTATCTATA GTTTCCTCTG ACACAGTAAG TCCCCAAGCT ATTGTGCAGT
51601 CTTGCTGTTT GTTATTGCCG ACATGAATTA CAAGCTGCAA TTAAACTTGT
51651 CTTAGCTCAC ATCACCCTCT CTTCCATGAT CTCCACTTTT ACAATCAGTG
51701 AAATTCCATC TCATGTGCCA TCTCTTCTCT AAAAACATTT TCTGAACACC
51751 CACGTCAATC AAATACATCT GATTTATATT AGAATATTTT GAAAATGTAT
51801 CTTATGTTCA GATGATCTGA GTTCAAATTT AGTGACTGAG GCATTTGAAA
51851 AAATTATGAA AATTCTAAAA CTTCTTCCTC TATAAATTTA CATTTTTTTT
51901 CCCTAAAGAT AGTGTTTTCT CTAATTGCTT TTCTTCATGA TAGGTAAAGA
51951 TAAAACAGAA TGTGTTGTAA ATAGTGTGCC AGTTTTGGTA AATATATATA
52001 TATATATAGT AAATAAGCAA TAGATCTGTA AATAATTCGA TAAAAATTTA
52051 AGATGAAATC CAAAATTTTA ACTGAAGTCC AGACCTCTCT CTACAGAATC
52101 CAGACTCAAG CTTCTATCTA GTATTTGATT TCTCCTTCTG GGTGTCTGAG
52151 AGGAATTTCA AAGTTAACCT ACTCAAAAGA AATTGTTAAT CTTCCTCCCC
52201 AAAGCTTACC CCTCTTACGG TCACCCACAT CTTGATTAAT AGTGACTTCA
52251 TCTTTTTATT TGCTCAATCC ATAAACCTTA GGGCATTTTT TATTCCTCTC
52301 TTTCTCTGAT ATTTCACATA CCACACATCA GCAAACCCTG CCAGCTCTCC
52351 TTCACATTAT ATTCAGGAGC TGAATGTTTC TCTTCACTTC TGCCACTACC
52401 ACCTTGGACC AGGCCACTGT GATCTCTTGT GTTGACATTG CAGTTGCCTG
52451 CTAATTACTC TCCAGCCTTG TTACCCTTTA GTCTGTTCTC AACACAGTAG
52501 CTAGAGTGAT TCTGTGAAAG AGAGAGCCTG CCACTTCTCT GCTCAAATGA
52551 AAGCCATGAC AATGTCCTCT AGTGTCATGT ACTGGTAGCT TGTACCAGTC
52601 ACTCAGTCCT TCTTGTTATT CTCCAAATAT ACCAGGCATG CCTCCAACTA
52651 TACAGTTTCC TCTGCTTCAA ATTTCTCTTT CTGAAATATT GACATGGCTA
52701 GGTCCCCTAC CTACATATGG AATTTAGTAT CTTCTTTTTC TTTTTTTTTT
52751 TATTATTATA CTTTAAGTTT TAGGGTACAT GTGCACATTG TGCAGGTTAG
52801 TTACATATGT ATACATGTGC CATGCTGGTG CGCTGCACCC ACTAACTCGT
52851 CATCTAGCAT TAGGTATATC TCCCAATGCT ATCCCTCCCC CCTCCCCCCA
52901 CCCCACAACA GTCCCCAGAG TGTGATGTTC CCCTTCCTGT GTCCATGTGA
52951 TCTCATTGTT CAATTCCCAC CTATGAGTGA GAATATGTGG TGTTTGGTTT
53001 TTTTGTTCTT GCGATAGTTT ACTGAGAATG ATGATTTCCA ATTTCACCCA
53051 TGTCCCTACA AAGGACATGA ACTCATCATT TTTTATGGAT GCATAGTATT
53101 CCATGGTGTA TATGTGCCAC ATTTTCTTAA TCCAGTCTAT CATTGTTGGA
53151 CATTTGGGTT GGTTCCAAGT CTTTGCTATC GTGAATAATG CCGCAATAAA

FIGURE 3, page 15 of 87

```
53201 CACACAAGAA AAAAACAAAC AACCCCCATC AAAAAGTGGG CGAAGGACAT
53251 GAACAGACAC TTCTCAAAAG AAGACATTTA TGCAGCCAAA AGACACATGA
53301 AAAAATGCTC ATCATCACTG GCCATCAGAG AAATGCAAAT CAAAACCACA
53351 ATGAGATACC ATCTCACACC AGTTAGAATG GCAATCATTA AAAAGTCAGG
53401 AAACAACAGG TGCTGGAGAG GATGTGGAGA AATAGGAACA CTTTTACACT
53451 GTTGGTGGGA CTGTAAACTA GTTCAACCAT TGTGGAAGTC AGTGTGGCGA
53501 TTCCTCAGGG ATCTAGAACT GGAAATACCA TTTGACCCAG CCATCCCATT
53551 ACTGGGTATA TACCCAAAGG ACTATAAATC ATGCTGCTAT AAAGGAATTT
53601 AGTATCTTCT AATCCCTTCT CTGATTACCT AATTTAAATT TTCAATATCC
53651 CTGAAACTCT CCTTCTTCTC ATTCTTCTTT TTCTCCGCAA CTCTGATCAT
53701 CATCCAAAAC ACTACAGTTG GCCCTCCAAA TCCATGTGTT CTGCATCCGT
53751 GGATTCAATC AACTACAGCT GGAAAATATA CAAAACCAAA ATGTGTCTGT
53801 ACCCCACATG CCCAGACTTT TATTTCTTGG CATTAATCTC TAAACAGTAC
53851 AACAGCTATT TATAGAGCAT TTACATTGTG TTAGGTATTG TAAATAACCT
53901 AGAGATTATT TGAATTATAT GAGAAGATGT GTGTAGTTTA TATGCAGATA
53951 CTACACCATT TTATATAAGG AATTTGAACG TCTTCTGATT TTGTTCTCCG
54001 TGGAAGGTCT GGGAGCCAGT ACCCTGTGGA TACAAAAGGT GACTATGTAC
54051 AATACTTATT GATACTTTTA TTGTTTACAG CTCCCCTGAA TGTAAATTTT
54101 CAGGGGCAGG AATTTTTGTC TGTTTTGTTC ATTGTATTTT CAGCACCTAT
54151 AATCCTACCT GTACATATTA GATGCTCTTA GATATTTATT GAATGTTGAA
54201 TTAATATATC TTTAGAGATC AATGAGCTTT CTAAATATTT ATTAATTTTC
54251 TTATTTTAAA ATGTGAATAT TAATATACAG TTCGCATTAT GTAATTTTCA
54301 CATGTCATCA TTTTGATTCT CTTTATCTCC ATCTTCTTAA CAAAGGCCGT
54351 TGAAGATATA CAAAGAAAGG CATGGTTAAG AAGAGTTCCA ATATCACTTA
54401 ATTGATTGCT CTTTCTTATT TCTAACCATA ACATGTGTAT ATTACTTGCC
54451 CAATAAACTG TCTCTTGAAA ACAGGACATG AGCTTTATTG TATCCTGAAT
54501 CCCTAACACC AGGCTCAGAG CCTGACACAT GGTATGCATT TGGCAAACCT
54551 GTAGTTAGTG TGGAAGCAAA TAAATGACTC CAAGCAGGAC TACATGTTAA
54601 TTCTAAATAT ACATGAGATA AAATAAAAAA AAATAGATGA ATTATATACA
54651 TTAAAACTGT CAGTAATATT GTTTATTTAA AATTGTTTTA TAATCAACAT
54701 TTANNNNNNN NNNNNNNNNN NNNNNNNNNN NNNNNNNNNN NNNNNNNNNN
54751 NNNTAATGCC CTTGACCCAG GCCCACATTT TTCCTTCATA TTTAGAGGTT
54801 CTGTTGCTTT TAAGCCCAAC TTTACAACCT TTTCAGTGAC TTCAAACTTA
54851 CACACACACA CGTGTGACCA CAATAACCCT GATTGATCTG TCTGCAAGTC
54901 GTTTTTCAGC TTGTGTTTTT CAACTGCACA AAATTCTGAG GCAAAGAAAT
54951 ATCAAGCATT CAACTCCCAG CTTGAGATGG GAAGAAGAAA ATACAGAGAA
55001 GAAACACAAA TACTTGAAAT TGTTTTGCCA TCTATACATC TTTCAGGACT
55051 TTAAGTGCTT TTCCATACAA ACCACTAAAT GTATAGGTAA AGATTGCTCT
55101 TGCAACTTAG GTTTTATGTT TATAGCTAAC TGGTTGCCCT GCTTGCTTGG
55151 AGAATATCAT TAACCATAAT TAAGTAAAAA ATGTATATTC CTTATCCTGA
55201 ACTCTGTTTA CATAGAATTG TGATGGTTAC TATGCAACAT AAATAAGTTG
55251 CAAATCAAGT CCTGCAAGCC AGAGCTCTGG GAAATGGCTG CATTCTCTGA
55301 AATGCCATTT CTGCCCCAGC CCTCCAGAGC AAATTTCAGG TTTGCCAGGC
55351 CACCCATCCC ATATAAATCC TTCAGATATA GGCCTTATGT TATCATCTTC
55401 CTATCTTGAC TGAGACTCTT TAAAGGGGAT TCCTTTCAAA TCCAAATTAC
55451 ATATTCTTAA ACATTTTTGA TACTTATTAG TATAGTAACA TACCTACACA
55501 CACACACATA GATTTTCAGT GACAAATACC ATGTTAGTAC TTATAGATAG
55551 TGAAATACAC TTTGATCTAG AGGGCTTTAT TTTCTAGGCC ACCAATTGTG
55601 TCTCCTGTTA CAATTTCCCA GAGTATCTGG CATAATGTCT GTAATAGTAA
55651 ATGTTCAATA AATGTTTGTT AATATAATTT GACATTTGAG GTAGAATCCT
55701 GACAACTCAG ACTTTGACAC AATTGTCCAA CCTTTTCTCT TTCTGGCACT
55751 TTGACACTTG GTTTCTGTAA GATCTACCCT TCTGTTTTTT CTCCTACCTT
55801 CCTGGTAGCT CCGTCTCCGT CCTCTTTGCT GAATTATTCT CAGCAAATAA
55851 TTGTTTTTTA ACTGTAAGCA TTGGAGAGAT GAGAGAGCTG TACTTGGCCC
55901 TTTTCTCTTC TTTATCAGCA CACAACCNNN NNNNNNNNNN NNNNNNNNNN
55951 NNNNNNNNNN NNNNNNNNNN NNNNNNNNNN NNNNNNNNNN NNNNNNNNNN
56001 NNNNNNNNNN NNNNNNNNNN NNNNNNNNNN NNNNNNNNNN NNNNNNNNNN
56051 NNNNNNNNNN NNNNNNNNNN NNNNNNNNNN NNNNNNNNNN NNNNNNNNNN
56101 NNNNNNNNNN NNNNNNNNNN NNNNNNNNNN NNNNNNNNNN NNNNNNNNNN
56151 NNNNNNNNNN NNNNNNNNNN NNNNNNNNNN NNNNNNNNNN NNNNNNNNNN
56201 NNNNNNNNNN NNNNNNNNNN NNNNNNNNNN NNNNNNNNNN NNNNNNNNNN
56251 NNNNNNNNNN NNNNNNNNNN NNNNNNNNNN NNNNNNNNNN NNNNNNNNNN
56301 NNNNNNNNNN NNNNNNNNNN NNNNNNNNNN NNNNNNNNNN NNNNNNNNNN
56351 NNNNNNNNNN NNNNNNNNNN NNNNNNNNNN NNNNNNNNNN NNNNNNNNNN
56401 NNNNNNNNNN NNNNNNNNNN NNNNNNNNNN NNNNNNNNNN NNNNNNNNNN
56451 NNNNNNNNNN NNNNNNNNNN NNNNNNNNNN NNNNNNNNNN NNNNNNNNNN
56501 NNNNNNNNNN NNNNNNNNNN NNNNNNNNNN NNNNNNNNNN NNNNNNNNNN
56551 NNNNNNNNNN NNNNNNNNNN NNNNNNNNNN NNNNNNNNNN NNNNNNNNNN
56601 NNNNNNNNNN NNNNNNNNNN NNNNNNNNNN NNNNNNNNNN NNNNNNNNNN
56651 NNNNNNNNNN NNNNNNNNNN NNNNNNNNNN NNNNNNNNNN NNNNNNNNNN
56701 NNNNNNNNNN NNNNNNNNNN NNNNNNNNNN NNNNNNNNNN NNNNNNNNNN
```

FIGURE 3, page 16 of 87

56751 NNNNNNNNNN NNNNNNNNNN NNNNNNNNNN NNNNNNNNNN NNNNNNNNNN
56801 NNNNNNNNNN NNNNNNNNNN NNNNNNNNNN NNNNNNNNNN NNNNNNNNNN
56851 NNNNNNNNNN NNNNNNNNNN NNNNNNNNNN NNNNNNNNNN NNNNNNNNNN
56901 NNNNNNNNNN NNNNNNNNNN NNNNNNNNNN NNNNNNNNNN NNNNNNNNNN
56951 NNNNNNNNNN NNNNNNNNNN NNNNNNNNNN NNNNNNNNNN NNNNNNNNNN
57001 NNNNNNNNNN NNNNNNNNNN NNNNNNNNNN NNNNNNNNNN NNNNNNNNNN
57051 NNNNNNNNNN NNNNNNNNNN NNNNNNNNNN NNNNNNNNNN NNNNNNNNNN
57101 NNNNNNNNNN NNNNNNNNNN NNNNNNNNNN NNNNNNNNNN NNNNNNNNNN
57151 NNNNNNNNNN NNNNNNNNNN NNNNNNNNNN NNNNNNNNNN NNNNNNNNNN
57201 NNNNNNNNNN NNNNNNNNNN NNNNNNNNNN NNNNNNNNNN NNNNNNNNNN
57251 NNNNNNNNNN NNNNNNNNNN NNNNNNNNNN NNNNNNNNNN NNNNNNNNNN
57301 NNNNNNNNNN NNNNNNNNNN NNNNNNNNNN NNNNNNNNNN NNNNNNNNNN
57351 NNNNNNNNNN NNNNNNNNNN NNNNNNNNNN NNNNNNNNNN NNNNNNNNNN
57401 NNNNNNNNNN NNNNNNNNNN NNNNNNNNNN NNNNNNNNNN NNNNNNNNNN
57451 NNNNNNNNNN NNNNNNNNNN NNNNNNNNNN NNNNNNNNNN NNNNNNNNNN
57501 NNNNNNNNNN NNNNNNNNNN NNNNNNNNNN NNNNNNNNNN NNNNNNNNNN
57551 NNNNNNNNNN NNNNNNNNNN NNNNNNNNNN NNNNNNNNNN NNNNNNNNNN
57601 NNNNNNNNNN NNNNNNNNNN NNNNNNNNNN NNNNNNNNNN NNNNNNNNNN
57651 NNNNNNNNNN NNNNNNNNNN NNNNNNNNNN NNNNNNNNNN NNNNNNNNNN
57701 NNNNNNNNNN NNNNNNNNNN NNNNNNNNNN NNNNNNNNNN NNNNNNNNNN
57751 NNNNNNNNNN NNNNNNNNNN NNNNNNNNNN NNNNNNNNNN NNNNNNNNNN
57801 NNNNNNNNNN NNNNNNNNNN NNNNNNNNNN NNNNNNNNNN NNNNNNNNNN
57851 NNNNNNNNNN NNNNNNNNNN NNNNNNNNNN NNNNNNNNNN NNNNNNNNNN
57901 NNNNNNNNNN NNNNNNNNNN NNNNNNNNNN NNNNNNNNNN NNNNNNNNNN
57951 NNNNNNNNNN NNNNNNNNNN NNNNNNNNNN NNNNNNNNNN NNNNNNNNNN
58001 NNNNNNNNNN NNNNNNNNNN NNNNNNNNNN NNNNNNNNNN NNNNNNNNNN
58051 NNNNNNNNNN NNNNNNNNNN NNNNNNNNNN NNNNNNNNNN NNNNNNNNNN
58101 TGCCGTGGCC TCCCACAGTG CTGAGATTTC GGGCATGAGC TACCATCCCA
58151 CGCATATTTT CTTATTGTCT AGAATAGTTC CCAGTACCAG TAGATACTCT
58201 ATAAATATTC CCTGAATGAC AGAAATTTGA TTCATTAAGT TCTAGTGGGT
58251 AGGACAAAAC AGATTGTTTT CCAGTGCAGG TGATGATAAG GATGACGATA
58301 CTATAACAAA GATAGCAAAA ATATAGAAAA AATTCAGTTT ACTTTGGGGT
58351 TAGTCAGTAG GTATGGTTAT TTTGAACCTG CTGATTTTGT CAAGAAATAG
58401 CTATTCTAAT ATAACTAGAA AACAGAAATA AATAAATGCC CAGAGAACAA
58451 AACCAAATAC ATCAGTAGCC TAGATCTGGC TTGTGGACAG CTGATTTGTA
58501 ACCTTTGGTT AAATTATGCC TGTGCCTTTG TGCCTGCTGC CACTAAGAGT
58551 TCCTATTCTG AGTATCTCAC TTGGGGAGTA CCTGCTTCTA ATTGCCACAC
58601 TGAGCCAGGA AGTGAACTTT TTAAATGCAC AGTCTCTTGC AAGCACACTT
58651 GACACTATTA TACAAGATGT TTAATTAGCA TAAAACAACA TATAACATGA
58701 TCAGTTCAGA AGTTGGTAAA TGAAACTGAA AAGTTGGATT TCTAAATAAT
58751 CCTACATTCT CAAGTCTTTC CACTTGAATA TCATTCTTTC CACCCTATTT
58801 CCTCCACTTC TTACCCCCTT TTAAGTTCTA TGGCCATATT TTATTTCCAG
58851 GAGACACAGG GGAAATGGTC TTTCTACCAC TGTGATTAGG AGAGAAAGAT
58901 GAAAAGATTT ATATTTTTCA ACTTCGTGAT AACAAACATA TGATTGCATT
58951 CTCAAAACTC ATAGCTTTTC AACTAAGTAG TCATAAGTGG TTGAGGATAA
59001 TTCTTTAAAT TTTGACGATG AGTTGGTTAC TCGTCTTTTA GTTTCAAGAA
59051 TGGAGGAAAT TTTTGCTTCC AATGGAATAG AAGACATTTT TCTAATGATA
59101 AATATTGTAC AATTGAATTT CCAAATTTCA TAATTTATAC ATCAAAATAA
59151 AAGTTCTATT TATTATATTA AGTCAGGAAG AGATAATTTG AGATTATATG
59201 GGGAACTGCA TATATTATTG CAACATAATA TATATGGTGA AATAACATAA
59251 GAATAAAAGA AATTATAACA GTTAAGTAAC GGAAGTCTTG AAGAGCAATA
59301 ATCCTTTTAA TATTAAAAAT AAGGCATTCA TAGATGTTGC TTCTGCATAC
59351 CAAAGATGAA AATATAATGG CCATGTTGCA AACTCAAAAA ATAATTTGGA
59401 TGAAGAATAT TAATAAGTTT TGTATTATGT ATAATTCACT TAAAAATGTG
59451 GCATGAGTCA TGTGGTGGCT CATGCCTGTA ATCCCAGCAC TTTGGGAGGC
59501 TGATGCGGGC GGATCATTTG AGGTCAGGAA TTTGAAATCA GCCTTTCCAA
59551 CATGGTGAAA CCCTGTCTCT TCTAAAAATA CAAAAAATTA TCCGAACATG
59601 GTGGTGGGCA CCTGTAATCC CAACTCCTTG GGAGGCTGAG GGAGGAGAAT
59651 TGCTTGGACC CGGGAGGTGG AGCTTGCAAT GAGCCAAGAT TGTGCCACTG
59701 CACTCTAGCC TGGGTTACAA AGCCAGACTC CATCTCAAAA ATAAAATAAA
59751 AATGCAATAT GTTGTTTCAT GATATAAAAT AAAATAATAA CTCTTTCTCT
59801 GAATTAGAGA AAAGACTAAA CAACAATATA AAATAGTACA AAATAACTAT
59851 CTCAGAGAAC TGCATTTTAT CCTAATGACA TAAAGTTGTA CTCAAGCACT
59901 TACTAATATA ACATCTTGTC AAAACCTGGA TCTTCTCTAT AAAGAGTTAT
59951 TGATTAATGG GTAGTTTGAA ATCAAATTGT TTAAAATTTG AGTAACTCCA
60001 ATAAAAGACC ACCTAGTTTT AATAATAAAT ATTATAAAAG TTTCTACAAT
60051 GGATTATATA ATCAGAAAAC ATGTTATCAT TAACTATCTG AGCCCATAAC
60101 AAAGAGCATC AAAATTGAAG ATCAGGAAGA AAAGTCAGAA TGCAAGCTGA
60151 GATTTAAATT GGATTACCCT GTGAATCTGA GTGTACACCT GTAAAACAGA
60201 ATAAATAAGG GAAACAATAT TCAACCAACT CAAGCTAACC ATTCTTTCTC
60251 TCACATGCTC TCACCTAGAT CATTGAAGCC AAATTGCTTT TGTTCTCAAC

FIGURE 3, page 17 of 87

60301 TAATCCGTAT AATAGCCATA ATCCTACTGC ATGCTGAGAG TGTATAGATA
60351 CAAATATAAG CATAAAAATT TTAAAAAATG GCAGAAATAT TTACCTTGAA
60401 ACATTACAGT CATGCAAATT ATTTTACTCA TCTATTTTTC TGATTATCCT
60451 TAAAGTCAAA AGCAGTTTGA GTGGTGTGTG TATATATGTG GTGGTGATGT
60501 AAAGTCACAA GCTGTTAAAT GTTTCTGTGG TGCACAATAG ATACTTATGC
60551 TGAGGAAATG TACAACTTTA AAGGAGTGTG GGTGTGAAAT TAGTATGAAA
60601 TGGAATGGGA CTCTCATAAT GTGCGTCTCC TATAGACCAC CAAGACTGGA
60651 AGACAGCAAG AAAGGAAAAT TCCTGGGGTA ACACTTAGGT TGGGAAAACC
60701 ACAGGATACC ATACTCATGA GGAATTTTAA CTACCCAAAC ATCTGTTAGG
60751 TTAAAAAAAA TTCAACAAAA CATGCCTCAT CAAAGAAGTT TCTAAGGAAT
60801 GCAACTTTAT GATCTAAAAA GAAGAAAACC AAATAGAGGG CAAAGTACAC
60851 TTTAACATTA TTTAAAATTA AAAATTGTCA ATGTGTTACT AAATATCAGT
60901 TGTTTTCCTT AGTTTTTTCT AAACTGTGTA ATACACTTAT GTGATAAGTG
60951 TTATAGTAAC AGAGGTAGAA ATTATCCTTT TTATAAAGAA GCAATTATAT
61001 AATGGTAAGA AGTGATTTTA GCCATAAGTA AATAGGAGTC TATAATTCAA
61051 GACATTTAGA AGTTCATTTG GTGGCAGTGC AGTATTAGGA TGGGCTCCAT
61101 CTTGCTGCCA CTAGAGAAAA TAAATATCAT TTATTCTAGA CATGATGGTT
61151 GCACTTCTGC AAAATTAGTT AGATGCTGTT GAAAATCTTC TAAATTAGTT
61201 ACACAGGACT CCCTAATGGG TAATTCAAGA CAACATTTCT GTCCTCTAGG
61251 CCCGAATATT GAAGTTATTG GTATAACCAC TTAGGTTCCC ATAGACATCT
61301 CAAACTCCAT ATTGCCACCT TCCCTTGCAA GTCTTTTCCT TTCTGTGTGT
61351 TCCGTGTCTC AGTTTACTGC ACCACTATTC ATCTAGTTGT TCAAACTAGT
61401 TATCTAGAAA TCATTGTTAG TTCTTTTTAC CTACTCTCAT CCCCCACGAG
61451 GCAAAACCTG AGTCCTATTG TATTTACCTT CTAAATATCT CTTGTATTTG
61501 TTTATTTTTC TTTTCAAGTG TCTCTAAATC CAGACTTTTA CATTTATCTC
61551 TTAGATAATT ACAAAAGAGA TCTAAATGGT CTTTCTGCTC TCATTTTCTA
61601 CCATTCACCT GAACTCAGCA TTTCAATACA CCTGCCTGAC CATGAATTTC
61651 CTCTGCTGAA AATCTTTGAT CATTTTCTAC ATGCCTGCAT GTTAAAACTA
61701 TGCCCATTAG TAAGTTCTAC AAGGTCACTT ATGATTTGGT TTATATTTCT
61751 CACACATGCA CTGTTCTTTC TCCTTTATGA TCCAGAATCT TTGCTATTCT
61801 TTCTTATTGT CCTTTCTTTC CTCCTCTTCT GGTGACCAGC TTTGTTTTCG
61851 CTATGTTTTT AAGTATCTCT TTTGAGAAAC CTTTCAGAAA TCCTTATTTC
61901 CAGTCCCACC TCCCAAAATT TGTTTCTCAA CAAGTGAGCA TATTACATCA
61951 TAGTTATTTC TCTCTCTTTC TTTAGTGGGG CTTTGAGTTC CTTAAAAGCA
62001 TAAATAGCCA GCCGCGCATG TCTTATGTAC CTTTCTGTCC CCTGTGCCTA
62051 CTTTTAATCT AAGATTTGTT ATGAATATGG AAGAAAGGCA TTTGACTTTA
62101 ATGTTAAAGT GTTACAGTGT CAAAATTCTC CATATTTTAA AATAGTTCAT
62151 GCTGATATTT TTTAATTTTT TTGGTCTAAT GCTTGTCTTT CAAATGCTTG
62201 CATTGTTATT GCCAAAATTA AAATTCTCTT GGCCAGTAGC TTTTCATGTT
62251 TGATATATTC AGCTTCTTTT ATTTCACAAA ACCAGTATAT ATTTATTATT
62301 ATTATTATAC TTTAAGTTTT AGGGTACATG TGCACAATGT GCAGGTTAGT
62351 TACATATGTA TACATGTGCC ATGCTGGTGT GCTGCACCCA TTAACTCATC
62401 ATTAGCATTA GGTATATNNN NNNNNNNNNN NNNNNNNNNN NNNNNNNNNN
62451 NNNNNNNNNN NNNNNNNCCC CCATCCCACA ACAGTCCCCA GAGTGTGATG
62501 TTCCCCTTCC TGTGTCCATG TGTTCGCATT GTTCAATTCC TACCTATGAG
62551 AGAGAATATG CGGTGTTTGA AAACCAGTAT ATTTTATATT GTTGATCATT
62601 TTGTGATTTT CCTTTTCATT AATTAACATA AGAAATATAA ATTATTGCAT
62651 ATAGGAAATA TTTGTATTGC ATGTAAGAAA TATGAATTAT TGCATATAGA
62701 AAGGAAATAA TTATTGCATT TAGAAATATT TCAAACAGTG AAGGAAAATA
62751 ATAAATGTCC ATTTCAGAAT AGATTGGAGA AGCATTAAAA ATATCTAAAT
62801 GATTAACTGA GATAATTAGC TGGTAATAAG TATGTATAGT GAGACAGAGT
62851 TATAATAGAT TGATGGTCCA TGAAAGAACA AAGGGGAAGA ACAATGTTTA
62901 AATTTAGAGT GCTAAGTGTG ATTACAAAGA GGAGATATAT GGGTGAAATC
62951 ATAATTTAAA GGAAATGATA GAAAGCATAT AACATTAAAG TATCTAATAA
63001 AGTATTCAAC TATATATTTA ATGTCAAAAG ACCTTATGCT AGATTATGAT
63051 GCAAATATTC TAGAATTTAA ATAAAAATAC TTGTTTTTGA AATCCTATTT
63101 ACATAAGCAA GTAGAAAGTT GTAGCAAAAT CACTAAAAAT CAAACAAAGA
63151 AAAGTGTAAA GATTATCACT GTTTTTTTTT AAATCATCAA TATTTTAGAA
63201 AGTCTGATTT TCATAAAGGA AAAAGGGGAG GAAATTTTCT CCCCATTAAT
63251 AGCTTAGCTG TATTTTATCT TTTTAAACTT CAAATGAATT CTCCTATTTT
63301 CTCTGAGATC TCAGACTAAA TTTCACATTG AATTGAATTA ACTTTTACTC
63351 TTCTGAGAAT CTTCTTTCTG TCCATTCAAC AAGAAGTGTA AAGTAGGTGT
63401 AATACATTGT GAATTTTTGT CTTTAACCTC AGTTCTAAGT TCTAGCTCAG
63451 CATTAGGCCC TAGGTCAGCA AAATTTCAGC TCCTATTTCT TCTGCATTTA
63501 CCAAGAAAGA ATTCTGATTT AACTATGAAA ATTCCAAACT ATAGAAAAAT
63551 CCTGGGATTA CTATGTATGG TGTCTTGGTC ACTTTTTGTT CATGCCTAGT
63601 AAATCAATTG AGATCCATAG GCTGCACAGT TAAGAATATT AGCAATGACT
63651 TACCTTACTG TGTGTTTGCT ATGTGCTGGT ACTATTCTAA GTACTTAAAA
63701 CATTGATTCA TTCATAAGTC TTTATTTCTA GCACAGAGTC TACACTCTTA
63751 GATCTTGACT AGGACTTGAG CAAAGCCTCA GGGTGGTAGA AAAGTACCAA
63801 GAGATGGAGA GGTACTAACT GATATGACAT AGAGAAGCTA TCCAACTGTC

FIGURE 3, page 18 of 87

```
63851 CAATCATCTC CCAAAACAAA TTGAGTGAGA ATTTTGACAT GCACCTCAAA
63901 ATTATACTTT TGAGGTTTCT GATACCCTTG ATTTTCATTT TTCTTTAATG
63951 ATATCCTAGA TATTTTTTAC CCCAATTATG CCTGCATACA AATGAACAGG
64001 AGAAGAAAAT AGCAAGATTT ATCCTGGCCC TAAGACTCCA GTATGACGAT
64051 GGCCTTACCT GAATTATTCC AGTTTGTTCC AATGCAGAGC TTCATGGTAG
64101 CATGAAAATG GTGATATTTT ATGCTCTAAT GGAACACGCT GACCTGTTGT
64151 TCTAAAAACT TTGGGAATTG GAGGAAGTGA GTAGGGAGAA CCCTCTTCAT
64201 AGTTTATCCA GAATTAAAAT AGAATGAAAG ATAGGAGACC AGTCTGTGGA
64251 ATATTTGATG GCTTGATACA TGTTTCCATG TTGATTACCA GCTCCCAAAC
64301 TTCCTTTACA TCTACTTCCC TAGTCTTCAC AGAAGGAGTA ATTCAATCCC
64351 CTTTTCCAAT CCACTCATTT CTAAGAGTTG TAATCATTGG TCATCTAATC
64401 TGAAGAGCAG TGTCACTATT TTTTCAAATG GCATGTCGAC GTTATAGAGC
64451 AGTGATTCTT AAACTTGAAC TACAGTCATT ACAACCACCT GGAGGACTGT
64501 TAATTACTAA GCCCCACACT CACGGTTTTT GATTCAGTAA GTCTGGGGTA
64551 GTGCCTCAGA AACTGCTTTT CTATGGCTTC CCCAGTGATG TTGATGCTGC
64601 TGGCCTGGAG ACACATTTTG AGGACCACTG TTGTAGAAAG TTGTTTTATA
64651 AACATGATGC TATTCTCAGA AAATATGTAT TCTCTGATTC CAAAGTAATA
64701 GTAGTAATTA GAATATTTTC ATTCTTACCT GGCATGTCCA GTATTGAAAC
64751 TGAGAGGTTT TCTTTCTATT TTGTATTTTT TTTCTAGCTT AAGCCAGTCT
64801 GAAATTAGTC AGGAAATAAC TCATTTAAGC ATCAAATAAG ATGATCATAC
64851 AGTGAGGTCT AATACTATGA ACATCCATGA ATCATTCTTA GTATTCATGA
64901 ATCTAATCTG ACAAATTCTT AGGCTTACTG TATTTGTAAC ACTATTGTGC
64951 TATACCCTCT GCAGCACCAC CTTGCGGTTA GGAAATCTAA TTAGAAAACA
65001 CACTTAACAT CTCATAAAAT GATAGGAAAT ATTTCCTACA CTGACAGTGG
65051 TGATGCGTTT TGGTCAGCGA AATCACTGGG CTCTAGGAAA ACATCCAAAC
65101 TACAAAAGGA TAGCCAGTTA TCAAAGTGTT TTAACCAGTG GACAGGAATA
65151 TGTCCTGAGA TACTCTTGCT GTGTGGAAAT AAGATGAATC CAATTGCAGA
65201 GCTTCTTCAG GGCCCTTGAT GCCCTGAATT GCTTAAGACA CAGGAATCCA
65251 CCAGCGAGTT GGATTTCTTC TAGTCCTGAG AGACATCTAA CAGTCAGTGC
65301 TAATTTGTCC AGGTGTGCTG AGTCAAAGTC GACTTGTAGT CCTTGAAGTT
65351 GTTAATATTT GTATAGCTGA GAAAGGACAG AGCCCTTCAC TTAGTGATGA
65401 CAGTCACTAG AAATCTGGTG GCCTAGTGCA CCAAATTCTG AAACTAAAAC
65451 ACCCTGAGTG GTAGGCCCTT TTAATAAACT TTATACTGAA CTTAAATTCA
65501 AATAATTGTG CAGACAATTT AAATTGAAGG TATATAGAGC TGAAGTTTTC
65551 TGTTTTGTAA GTTGATGTTA AACCATATAT TCATTTATGT TTATTCTTTT
65601 AGGAAAGTGA TCATAACGAG GTACACTAAA AACCATAGAG TATTTTCTAG
65651 AATATTTTCC ACTATTAAGT TAGACTTACA GGGATCTGCA GATGGCAAAG
65701 TTACAAATAA GTCTTTGAAT GTGCTTATTT TAAAAGTATA GTATCAGGCA
65751 CAACAAAACT TGTTGATTCT TAAACAAAGT GGCATGGATG GGGGCATTCA
65801 AATTTTTATA TGGACTAGGC AAAATGATGG TCTATCCAGA CTCACCTTTG
65851 AGCTAACACA CTCAGCATCA AGACACAGAT GGATGGGAAA GATGACCCTG
65901 ACCCACATAA GACCCACATT CCTGTGCAAG GATAGAAGCA TGATAATCAG
65951 GAAATGATGG TTGTTAGTTA CAGAAAATGC ATTATGGTGA AAACCAGGGG
66001 GAAAGTGCTT ATGAGAGGAA GTGATTGGAT TATGGGGAAT GAGAGAATAA
66051 GGATAGATCA TTCCTACTGA GTAAATTGCT GTGATTTATA AGAGAAAGGG
66101 TATAGTGATA TCTTGGCCCA TTACTGACTA GATTCATTTC ACAAACAATC
66151 CTAAATCAGA ATGTGACAGT TTATGGGGAG ACAAACAAAG CTCCCAAAGA
66201 TGCTTATAAG TTACTAAGCT TTTAAACTGG CATATTTTCA ACTCCTCATA
66251 CTTTTGCCAC CATCAGCTCC ATTTATTTTT GTAGCTGACA TTCATAAATG
66301 TAATTCTGTA GCCACCCTTA TGTGACACTA GTAATAGTTT ACTATATGCT
66351 GTGATAAAAG GGAAAATGCT GGATATATTT TATTATATGT TTTGGGATTT
66401 TGTTAAATTT CATAAGAAAG ATACCTAAAA TAATTTTATA TGTATTTAAG
66451 TATATTATAA TACTCTACAA TACTAAAATA ATTAAGTGCT GTTTTATAAT
66501 AGATGGGCAT TTTGGTGTTC TAAATATTTC TCTTAAATTA CCTATGAATT
66551 AATCAAACAG TTACCTTTCA TTGCTCCAGA CAGGTGAAAC ACATATTGTT
66601 ATATATTATA TATTAATATA TATTCAGTTA TATAAGTTTA CTTTTATTTT
66651 TCAGTTTGGA TTTAGGAGCT CTAATCCTTC AAGAATACAA GTTGACAAAA
66701 TACATTCTGA AGGAAATTTT TGGCAAAGGA TTCAACACAG AAAACTTGTG
66751 TAACAAGACA GGCAATTTTA TCAAGAACTT TACTGAAAAT GCAAACATTG
66801 TTTACAGTGA TTGTTTCTTT TAAAAAATGA AGAAAGAAGG GAAAACGATT
66851 TTTGGAAAAG TTCAAGAAAT GGCATTAAAG CATAGCTCAG CAAGGGGCTA
66901 AATACCTTGC TTTTTTATAA TGATTGATCA GTGCAAGGAA ATTAAAATAT
66951 TTAGTAGTAT AGGTGATTAT ATGTGTTGTC ATGAATGATC TTTGAATGTC
67001 ATTTTTCTCT TACCTCTGCT TGGGGTCACA CACTCCCTGA TGAGAGATTT
67051 GATTGCTAGT ATTAAAGGAA TGATTGCAGG GTTGACATTT TATTGTGAAA
67101 GAAGAGAAGT TGAAAGCAAA GCGCTATATT TCTTTCTGAG CTGGCATACA
67151 GACACACTCA CAAGCCAGAG TTTTCCTTGG GAAAACTTTG CACTTTGTCC
67201 TCAAATGAGA CCCGAAGAAG CCATTATAGA GCAGAGATAC AGAAATTTTT
67251 CCAGATACAA GCTACCGCAG AAAAATCTCA CAACTTTCTT AGCCGCAGAA
67301 AATTCTCAAT ACATTTTTCA TGATGTCTGG GCAACGATAA TGTGCCACTC
67351 TACTTGCTTG CTAGAATGAG TTAGGTTGAA AAGTATAGTC CCAACAGCAT
```

```
67401 CGAGTAGTAT ATGTTACAGA GGTACATGAA TCAAATAGAT GTTGGAGATG
67451 ATCTTTCCTT TTTGACGTAA TTAATTTTAG CCCATCTTTC TGGTATGAGT
67501 TAGATACCAA GGATCACAGT CTATCACAGC CCCTTCTACT TCATGGCGTT
67551 TGTCTTTTTG TTCACAATAG CCATCCTAAC AAAAGAAGAC ATTAACGCTG
67601 GTCTTAACGG CCTTACATTT TCTGGCCCCC ATTTCCTCTC GGATTCTCTC
67651 ATTCCAACTC AACTGGGCTT CAGCTTCACT GTGGTCCTTG TTATTCTTAG
67701 GACATACCAG GCGAAATCCT GCCTCAGGGT CTTCACGCTG GCCATTCTCC
67751 TCCTGGACAC TCTTTCTCCA AACAGCCAAA CAGTATTCCC TTACCTCCTT
67801 CAAATATTTG TTTAAATGTT ATCTGCTTAG TGAGGCATGA GCTGACCACT
67851 ATATTTAAAA TAGTAACGCC CTAAGCATCT TCATGCCCAT GACCTTGTCT
67901 CATTTTTCAC CATGGTACAT AATACTTCCT AACATGGTAT ATAATTTACT
67951 TGTGTATTAT ATATTCATTT ATTTATATTT TTCTAATATA TATTATTTGT
68001 CTCTCTCCAT TAAAATGGAA GTTCCATGGT CTTTGTCTCT TTGGTTCTCT
68051 TCTATATTTC CAGCACTTCC AAAGTGCCTG GCATGCCATA GGTGTTCAGT
68101 AAACTGTTGC TAAATGAAAA GGGTTAAACA GTAGAAGCTT TATGGATGGA
68151 TCCAAAGCTA CCTTGATCAC CTGTATGAGC TTTTTGTCCT CTTAGTGCCT
68201 AGCACATAGT AAGCACTTAA TAAATATTTA TTCATTCAAT GAATGCATAA
68251 ATTTATTCTC AAGGCCAACT AAACATTTGG TTATAATAAA GACAAGGGGA
68301 CTCTAAAATA TTTTCCTGTT TTATACCACT TGAAATGTGT GGCCGATCAG
68351 AAAATTGTTT CTGTCCACAC TGGTTCTTAC AGAGCTGGAA GTCAAATTTT
68401 TCAAATAACA TTAATAATAA GGGAGCCTTA ATACATTTAT ACAGAGGTCA
68451 TATCCCATCC CCTTTTATAG AGTCAGAGGC AGAAGAGAGG CCATTGAAAC
68501 CCACAAAGCA TCTTATATTT ATATTTTTCA AGGCAATTAA TTATGCTGAT
68551 GGCAGGAGAC CTCTTATAGC TCTCATCTGT TATGTATAAT TACCTAAATG
68601 AATTAGGCTA CAATTTGAGG CAGTTTTCCT AGGACCATAA AGCTAGCAGT
68651 AAAAAGAATG AAAATGTCTG TTTATGCAGG GTATGTGTAT GATTCCTTGA
68701 TACCTTAGTT GTTGCAGAAA CTGTGTACCC AATTCTGTCT TCATCATTAG
68751 CATCTCTTAG CTCATCAAAT CGAATCCTGG AGCATTCTTT CTTTACCCTC
68801 TCCCCTGGAT GTTTTCTTGG CAATGTAAAA CTGGATCTTT GAGTACGGGG
68851 TGTCAATGTT CAGATTATTG TACAGTTTTC AGAAGTACAA ATAGGAAGAG
68901 TATCTTTGTC ACTCCAAAGG TATTTGTTCA CTGAAAGTTC CTGAAATGTA
68951 TTTTCTAGAT TCCTGTATAG TTATATTCAA GTACTATTAT TAAAATATGT
69001 CAATGCTATT ATTAAAATAT TTTTGGATTG AGTTGTGCAC CTAAATTCCA
69051 TAGACATAAT GTTATATGCC TAAGAAATAT ATTCTAAATA TCAATTACTT
69101 ATTCACAGTT TAAAGATTGT CACCACTATT AATCTCTTAG TCTGTTTTGT
69151 GTTGCTATAA GAAAGTATCA GAGACTTGGT AATTTGTAAG AATAGACATT
69201 TGTTTTCTTA TAGTTCTGGA AGCTGGGAGG TCCAAGATGA AGGTGCAGAC
69251 AGATTTGCTT ATCTGGTGAG GGTTGCACCC TCTGGAGGGG AGGAACGCGT
69301 GTCCTCACAC AGTGGAAAGC AGAAGAGCAA GCTATCCAAA TGCTTAGTGA
69351 AGCCTGTCTT ATAAGGACCT TAATCCCATT CACCATGGGA GGTATTCTCA
69401 TGACGTAATC ACCTCTTATA GGCCCCCACCT CTTCATACCA TCACATTGGC
69451 CATTGTATTT CAACATCTAA ATTTTGGAGG GGACATGTTC AAATGATAGT
69501 AACATCTTAT AGCTCTCTAG TATTGAAATA AACCTTTTGA CTCTCTTCAG
69551 AGCATGTGAT TCACTTGAAC CAGATATACT GCCCATATTT ATACCATCCC
69601 AACTTGCAAG AAATTATCTG CAATTTAAAA ACAAAGACAG AAACTTTCTC
69651 CATTCTGATC CTATTTGCCT CATTCCAAGC TCATCTTTCC ATTTGCCAGA
69701 TAGGCCTCTC AGACTTCTGG AGGTTCTCAA ACTCAATGAA TATGAATCCA
69751 AATTTGTCAT CTCCTACCAT AGTCTTACCC CACCAAAATC AGTGTATGTT
69801 CCTGAATGTG CTGTTGTGAA CTGCCAAAAT TCACTAATAT TAATGCATGA
69851 GTTAGCTTTT ACTANNNNNN NNNNNNNNNN NNNNNNNNNN NNNNNNNNNN
69901 NNNNNNNNNN NNNNAATTTG CACCCACATC AAATTATTCC GAGTTCTTTT
69951 TATTAATCTT TCTATAGTGA CTCTAGGTTT CATCTCCTTC TATCTATCCC
70001 TTCTGTCACT ATTCTTATTT AGGATCTCAT GTTTTACTTG GCCTTTTGGA
70051 AAGAGCTTAT CTACACTCAG TGTTTTTCAA ATAACTTAAC TTTTTCATAG
70101 TTACCTGAGT TGTCTTCCTA AATCAATGGA AAAATAATTC TTTTCTCAAA
70151 AACCTCAGCG GAATCCCACT ATTTAAAGAA TAAACTCCAA ATTCTTTAAC
70201 GTAACAATCA GGTACTCTCT AGCTTAATTC CTAAATTACT ACTTGGGCTT
70251 GTACATTTTT ATTCCTCCAT AAATACTGGT CTCTCTGTGA TAGTTCTGTT
70301 TCTTGGATTT AGGGATTCTG AATCTTTTTT TGTACCATGA ATCCCTTTGG
70351 AAATCTGGTG AAGTTTATTG ACTCCTTCCT AGAGTAATTT ATTTTTTACT
70401 TGTAAAATAA TAACATTACC AAGATAAGCA ATTCTACAGC AATACAACTC
70451 TATCTGTCTG TGGGTCCTGT TGTTTATGTC TTTGTGGCTT TTCTATGATC
70501 CTCCCCTTAT CACAGAAGTG CCCCTAACCC TGCTCTATCC TTCTCATCTA
70551 TCAAAGACTA GTGCAATTCC CACCTTCACT GTGCATCTTT ACCTTGCAAC
70601 CCTGCCCCAT CTGTATCATC ACTTTGCTCT CTCATTGTAG ATTATATGTT
70651 ATTTATTTCT ATTTATCCCT TATCTTTATC TTTTATGATA CCTTGGTAAT
70701 TGACAACAAT GTGGCAAATA CTGAACTAGC CACTTTTACA TACTTTGTTT
70751 TCATAATTTC TTTTAAAGCA CTATAAAATA TTCATATGAT GGGGAAACTG
70801 AGGTCCAAAC ATTTTGGTGT TTCACCAAGA TCATACAACT TGTATTCTTG
70851 CTAGATTATG AGTTATTTGA GGAAAGGAAT ATTTCATCTT CCTGATTATA
70901 TCTTCTCCGG ATCTGTGGGA TAGTACTTTT TCAATAATGT TTGCCCATAT
```

FIGURE 3, page 20 of 87

70951 GTATTTAAAA ATTGAAAATA TTGGGAAATA CTTATCTCTC AATATTTAAT
71001 ATCATTAGAA TTGACTAGGG GCCCCAGGAG GACAGAGGTG TGTGCAGCAG
71051 TGTTCTTAGG TTAATGTCTG TGTGAAATTA ACTGTGGCTA AATCTTTCCC
71101 TGCATACTAT TATCTCTCCT AATTCCCAGT GGCTTCACAA ATTGAAATTG
71151 TACACATAAG GATTTTAAAC AGAAACATTT TTAAGATATT GTCTCTTGTT
71201 TTGCGTTACT GAAAAAATAA CAAAGTAGGA CAAATTAAGA AAGTAGAACA
71251 AATTAAAGAA TTTAATTGGA GTCATAAGGA ATTCAAGAAA TATTTGAAGA
71301 TTGCATTTCT AATAATAGAT CAGAACAATT GAATAACCAT TTCATATTCT
71351 CCACCCTCAG TGAAAACAAT AAAATCAACT CAATTTACAT TTGTAAAACA
71401 ATATATGTAT ACTTTCATTA TACCAGTTTT AATTTTCAGC TGTGCTTCTC
71451 TATCTCTCTG TAGTCAAATA CTACGTTTCT GCAAGGGTTT TCTTAAAACA
71501 GCATTGCTAG GTTAACTGTT TTAAAATAAA AATATTTGCT TAAAAAGGTT
71551 TACTTTAGCA ATAGTAATGC TTTCCTTTCA AAATATTATT TCAAGTTTTA
71601 AAATAATGAA CTTATGATTT TAATTAATTA AGTTTTCATG TGGAAGTTGT
71651 TCATCTAGAG TAACTAATTT TAAAGAATTG GATCTTTTTA TTTGGTAATG
71701 CCTTTAGCAC TCTGTGAAAT ATAAATTAAT GTAAAATTAA AATTAATTTA
71751 TTATGACTAT CCATTTTTCA TGGTCTTTTC TATTATTGTG CTGTAGCAAG
71801 TACTAATTCT AATGTAGCTA GATAATTAAT TTTCTATTGT CATAGCTCCA
71851 GATGGTCCTC CTGAAAATGT TCATGTAGTA GCAACATCAC CTTTTAGCAT
71901 CAGCATAAGC TGGAGTGAAC CTGCTGTCAT TACTGGACCA ACATGTTATC
71951 TGATTGATGT CAAATCGGTA AGGCATGTCT TACCTTCTGT AAAAAGCCAG
72001 TATAAAATGG TTAATAATAC AAGATTTGGA ACCAGACTAT TTGAATTTGA
72051 ATTTTGGCTC TGTTAGACAG TAGGAAAATT ACTTTACTTG TTTGTGTTTC
72101 AATGTCTACA TCTGTAAAGA TTAATAATAG TAAACAGGGT ATGAGGACTG
72151 AATCAGTTAA CATGCATAAA GAACTTGGAA CATTCCCTGA GATATGGTAA
72201 ATGCTCAATA AATATAAGAT ATTAGTAACA TTATTATAAT ATGTTTTATC
72251 AGTGTATAGA ATGTGTATAT ATATGTATGT ATATATACAC ACATACAAGT
72301 GGTTAAATTG GTAGTAATAC AAATATCTGG TTTACAGTAC GGTAGAAAGT
72351 AATTCATAAT ACAAAATGAG AAGAGAGAAG GCATTAGGAG AAATATCTTC
72401 CAGATAAAAT AACATCAGAG CTAAGTCTTG AAAAATAAGT GAAGCAGAAC
72451 ATAAAAGGTA AATGGGAATA GGGGTGTAAA AAAGTAAGCC TCATTCAAGA
72501 AAAATCAAGT CTTTTGGCAA TCCCAGGCTA TAGCATTAAA AAAAATAAGT
72551 TCTAAGAGAT GAGGCTAGAT CCAGAGGCTG ACTATACAAC AAGTTACAGA
72601 GTTAGGGTTT TATGTTAAGG GCAGTGGGGT GCCAGTTGGT GATACAGATT
72651 TCTACTGTAT AACATAGGCA TGGTTGCAGT GTAGAGGATA GATTGAGAGC
72701 AGTATGGGGG GTGTAAAATC AGGCAAGGAG ACAGGAAACT ATAAAAGGGC
72751 AAGGAAAAAG AACAGAGGAA ATGTAGCAAG AGAACGAATG AAAAATAATC
72801 TAAACCTATA GAATTTGGTG AAAAATCAAC TAACTCATGA TGGTGAGTGA
72851 GTAGGATAAT TAAGGATGAT TGTAAGTTAT ATGACAGAAG ATTATGAGGA
72901 GGAACAGATC TGTAGAGGAA AGGAATGAGT TCAGTATTAG ACACACTGAG
72951 TTTGAAATAT GTGGCAGTCC TCCAGGTCAA TACACCCATT GGCAGTATTA
73001 AATATGGATC TGGAGCTCAG GAGAGAAATT CTGGATTTCC AGATTTGGGT
73051 AATGTTAGTA TTTAGAAGAT AGTCAAAATT ATAAGAGTGA ATGAGATTCA
73101 CTATGGAATG TGCAAAGTAA GATGACAACC TAAGGACAGC ACCCTGGGGA
73151 CTATCAACAC TTAAATAAGA GGCCATTGAA GAGACTGAAT GGGAGTAGAT
73201 AGCCATTTGG ATGGAAATCC AGGTATGAAA GTCAAACCCT TCATATAAGA
73251 TAGGATGCTC AATGATGTCA ATAATGCAGA ACTGTTAGCC AGAATAAAGA
73301 CTGGAAGTAT TTCCTTTGCA CCCTGCTTGG GTTTTGCTGG GCCTGATGAA
73351 CACAGTTTTC TAATAGCATC TTATGCATTA AATTGTATAG CATAGTGATT
73401 TCTCCTCCTT TCTCTCTGTC TCTTGACCAA CTTTATAATT TTATTATGTC
73451 TTTGTAGTAT TCCTTAAATG GAGATATAAT GCTTCTATCT CAAAAGACCT
73501 GTCATCATTA AAATAAAATT GAAAGAATTG TTGATGTATT TGTTCTCCAA
73551 TTCAGTCTCT ATTTTCTGTT CCTTTTGTAG AGCATATTTG TGAAGATTTT
73601 AGTATGTAAT TAGCCAAAAA TAATTAGCAC GAATGATGAA TGCCCTGGGA
73651 ATATGCATTA AAAACAAATT ATAAAATGAT AAAGCTTTAC TCTGTCAAAT
73701 GAAAGGCACT TTATTAATGA AAATAGTTCT CCCTTGGAAA TTCTGCTTAA
73751 AGGAACAAAA AAAATAAAAC ATATTAAGAA GTGATTTTGT AATCTCATTC
73801 TTGTAGCCTT CTTGCTGAGT TTCAAAGTGA GCAAGGGAAA GAGGGTAGAA
73851 TGGGAAGATA ACAAATATTT TAATTGCTTA TTTTCTACAA GTTACATGTT
73901 CATCTCTTCC TATTCATTAT CTTATTATAT GTTATCCAGC AATATTTTCA
73951 TATAAACATT ATTACCTTCA TTTTGCATAA AAGAAATCTA AGGAACAGAG
74001 ACGGTGAATA ACTTCTCACA GAGCTAAGAC TTGGCTAAAA CTAACAGATC
74051 AACAATGGTT TGACAGGAGA AAGGGAAGGT CATTAAATAA CAAATAAAAT
74101 TCGCCAACAT AAATATAGCC TCACCAAAAC TCCTTTAGAT CAACAATAGC
74151 AAGAACAGAT TCAGATAGAA CCTAGTAATT CACAGTTTCT TTAGGATTCT
74201 TGGAATTAAG TAGAGGTATT TCCTTCCTTC CTTCCTTCCT TCCTTCCTTC
74251 CTCCCTCCCA CCCTCCCTCC TTCCCTTACT TCCTTCCTTC CTTCCTCACA
74301 CATTTTAAAA TACTTCCAAT GTACCAGAAC TGTGCTAGGT GCTGGATATG
74351 TAGAAGTGAA CAACTCTGAT AAAGCACTTC TGCAGCTCAT TTCATTAATA
74401 TGTAATTATC AACATTCAAG AATCACTGGT TCCCAGACTA AGGAAGAATA
74451 CATAGCATTG CACTTGGGAC TTATTGTGCA GCCTGTCTTC TACAAAATAC

FIGURE 3, page 21 of 87

```
74501 TAGCCACACC GATAAAACTC TTAACTTTAA AAGTGTAAAC AAAAATTGTC
74551 AATCTTAATA AAATGTAAAT ATCATCCTAG ATGATTCTGC TGGAAATTAA
74601 TGCATTTAGG ATCATTTTCA TTGTTCCTTT TACTCTTTGA CTGAACAAAT
74651 TGTTATGAGT AGCTTCTGTG CATCAAGACA AGGATGAAAA ACATAAAGCT
74701 CTGCTGTCAG GTAGCTCACA CCCTAGTGGT ACACACTGGA ATAGAAACAG
74751 CTAATTATAG AGTTTGAGGT ATGAAGTTTT GTGGGGAATA TAAGGTAACA
74801 AAATAATTAA AGTTCCTGTT ATGGGAGGAA TAGAAGATAA AGGAGACTTC
74851 ATAGAGCAGG TTAAATATAT TCTAGGACTT GACGAATGAA TAGGGGTACA
74901 CAAGATGGGA AAGGGTGGAG GCGGGGTAGG AAGAGAAAAA AAATAGGAAG
74951 TGGGGCAGGA AGAGGAGAAC CAGAGTCTAA TTGCTGATAA TGAATATAAA
75001 GTAACACTTC AAAAATGATG AAAGACATTT TATAACAATA GATTATCAAG
75051 TACAATATGA GCAAACAAAC TTGGAATTGA TTGAAGGAAA ATGAGTCAGA
75101 AAGATGTGAT TTCAGTCCTG GGTAAGTGGA CAAGTAATAG CTAACAACAA
75151 CAAAGGTGTA GTAGGTTTAA TAAAGAAAGG TAATGATGAT CTTTTGTACT
75201 GCCAGATTTG AGGACCGAGA ATTCCTTTCA AATTTTGTTA AATACTTTTA
75251 AAGATATAAT ATATGCGTGC CATGTCATAT TTTGCGACTT GATATTTGTT
75301 ATCTATTGTT TTAATGGAAG GCATTGGAAG AGTATAATTT ATAAATTATA
75351 CTTATAAATT ATAAATTTAT AATTTATAAA TTATAAATAG TTAAATTTAT
75401 AAGATCAAAC CCAGTGACCT TGTGGAAGTG TAGAATTCTA TGGACTCTTG
75451 AAAGACCTGG GCTCAAATCC TTCCTCTGCT ACTAAGTAAC ACTGAGGAAG
75501 TCACCTTACC TCTATAAAAT CAGAATTCAA ATAGCTATAA AAGACAAGTG
75551 ACATGAACCA GTAGTCAAAG TGAAGCCAAT TGAGTGGGGC TCCAATGAAT
75601 GGGACCCAGG CCCCTTTACA GAGGTCAATA GTTACCCATC TCTGCACCTC
75651 TCAATAATAT TTTTTCAGCA TGAAATTAAG CCTAGTCTTA AGGAAAATTA
75701 CAAAAAGCAT ATTTTATGT GATATTCAAA TGTTAACAAC TAGTTAAATA
75751 CACATTTTCT GCCAGTGGCA TATATTCCTG ATCAATAGGA TTTCTACGCT
75801 GATTTGTTTT TCTTCCATTT TCGAGAAGTG GGGCATTTCT GTCCACTGCT
75851 CTGTCTTAAG GTGGGAATGA TCTATTTGAC TGTATGCAAC GATAGTATTA
75901 TTTATATCAT CCTTTTACTA TGTTTCTTTT TTTTCTTTTT TTATAGCAAC
75951 ATCTTTTTTT TAAAAAAAAA TTGAGTTAAT TTTATTTACA TTACCTCAGC
76001 AAACATCTCT ATAAATGAGT TTCCAGGACA ACATTTACAA TATAGTTATA
76051 CCATATGCAA ATCAATGTGT GTTTCGCCAT ATTATCAATA AAATATGTTC
76101 TTAGCAAAGA GCATTAAAAG AATACATTGA ACCAACCAAC CAAACAAAAA
76151 ATATTTCAAA GTTATAAGGG AAGGTCAAGT TGAAAATGGA CTTAATAGTG
76201 TTCACTGTGT ATAAAACCTG GTTTTAAGTG TTTCAATTAA GATACCTGAA
76251 AGTAGTATGT ATGATAGGAT TTTGAATTTT CTCATGGTTA TCTTGGGAAA
76301 AGCCCTTCTA CTTAGTGCTA GCAAGTTTAG TTATGTTTAA TATCTGGAGT
76351 GAATAGGCCA GAACCTCCAT AAAGGACAGA CTATGTTTGA ACAAATCATA
76401 TAGCTACATT TCATATGCCT AAAGACACTC ATTTATGCAC ATTAATAATT
76451 ATGACATCCA CAATTAATTA CTATCCAGTG CTACACATAG TACTAAATCA
76501 GAGTTTTTCA AACTGCAGCC ATCATCAGAA TTTTTAAATG AGGTGGAATA
76551 AAGTTAAAAA GAGCAGAAAA TATCAAAGTG TACTTCAGAA AGATGGTGTA
76601 TTTCTGAAAA ATGTGTTACA GTCATAAGAT ACGTATATAT TTTATATCTA
76651 TCAGTCTTAT CTTCTGAATT ATGTTACAAA GAGTGTTTCC TTTTGTGGGT
76701 AATGGTGAAA AAATATTGAA ATCTATGTGC CAACTACTTT AGATTTGTCC
76751 TTTCTAAATC TCAGTGAAAC ACTGTAAATA GTTGTTATTA GCCCAATTTT
76801 ACATGCATTG AAAGACTAGA CTGTGTAGGT GGTTTCTCAA ATACTACAGG
76851 AGCTATAAGT GGCCAATTTG GGATTTGAGG CCTGTGTGAT TAGGTACCAA
76901 AACCTCTATG CTTTCTTCTA CAAAATATTG GAGTCAAAAG TAGAGTTTCA
76951 TTGACTGCAA AGATGATTTT TGCTTATTTA TTTAATGGGT TGGTTAATCA
77001 CGGTTGGCTG GTTTGTCTTT TTTCTTTTAC TTTCAACTAT TAAAATAATT
77051 AATAATTAGT AAGCTGTTAT AATAGCACTT TAGATTTCCC AGAGCAATCT
77101 GATTGTAAAA TAAATAAATA CAAATTTGGC TAGATAAATA CATCTCACGT
77151 AGCTTTGTAT TATTATGTTT TGGTGACTCA GATTTCAAGT GCTGCTTCCT
77201 TAATTTTTAC TTATATTTTC CTATAGGTAG ATAATGATGA ATTTAATATA
77251 TCCTTCATCA AGTCAAATGA AGAAAATAAA ACCATAGAAA TTAAAGATTT
77301 AGAAATATTC ACAAGGTATT CTGTAGTGAT CACTGCATTT ACTGGGAACA
77351 TTAGTGCTGC ATATGTAGAA GGGAAGTCAA GTGCTGAAAT GATTGTTACT
77401 ACTTTAGAAT CAGGTAAGGA GAATTTCTCA ACCTTGCTAA AAATTGACTG
77451 AGATTTAGCT GGCTTTCTTA CAGTTCATCA TACTCCACCA AAAAAGGATA
77501 TGTGTTATGA GAAGTTTTTA AAGCATATAA ACAAAAAAAT TAGTGACTCT
77551 CTGCAACTGA CAAAAAGGAA GATTTCTATT TATATTTTTG AGGTAAAGAG
77601 GAGTTATGTA GAATATTCAA TCCTTGTAAA TACAGCAACA ATTAAAGGTA
77651 TCCGCTGTAT TTCTTTGCAC TTATTTAATC TGCTAGTTGT TTCAGAAATT
77701 AAGTAAGCTT GCCTAAGAGA TAATATTTCC AACTGTCTAT ATCCAATAAC
77751 ACTTCAACTA AAATTCTATT TCAATTATTT CTGTCCCATT ATTTGAATGA
77801 ATATTAAACT TGTAATACTC TGTGAGTATT AAATAATCTG GAATTCGAAA
77851 GTAGAATCCA GCTCACATTT ATCACAGCTG TTGTCTTCCC TTAGTCAAGT
77901 AATATATGTC TTATTATATA ACTCTTTGAT AAATGTCAGA ATACATACAG
77951 ATTTCCTCAA GTTCTTATGA ACAGGGTCTG AATGAATAAT AAGATTGTAA
78001 CCAATAAGAA ATAAATTTGG AAATCAACAT CCCAGAACTT GCTTGCCCCA
```

FIGURE 3, page 22 of 87

```
78051 TCCTCCTTCA GACTCCTGAT GTTCTTTGCC ACCAGATATA TCATTGGAAA
78101 AAGCAGATGA AGGGATATGT TGCTATAGTT TATTTGTTGC TATCTGTAAG
78151 GTAAGTATAG GAAGTAAAAT TTTTTTACAG CTAGTTTTTT TCGTTACATT
78201 ATATTCTCTA TGCATTTTGT CTGTAAAGTT ATGGTTCTAA ATTAAAAGGT
78251 AAATTTTATT ATCAGCATCC TAAAATTCCA TTTGTTCCTA TTCGTCTGCC
78301 AAGTATCACA GGTATCTATT TTCTGATTAT GCTTTTTACT TCTCAATCCC
78351 TCCTACCTGT GAGGAAAGAT ATGATGAATG TACTCACATT TATACCATAA
78401 AGCATTGTTT GTCAAATCTT AATGTGCTAT CTGTTTCAAG GATATCACAA
78451 TTTAATACAT TTTTACTAAA TCTCTAAGAG TAGAATTTTA TGTGTATAAC
78501 CAAAAATCTG GGTACTAGGA AATTTTTTAC AACATTGAGA GAATTCCTTG
78551 GTTTATCTGA CTTAAAATCA CATCCTAAAT TTAGAGAAAC ATCTCATAAG
78601 AAAATATATT TATGACACAG CATAAAAACG TGTAGTAACA AATGCAAAAA
78651 TATCTCTCTT GAACCAACTT AACCTTTATT TTAGCTTTGC ATTTTTCCAT
78701 TTAAAATGAA ATATTTGACA CAATAGTACG TTTATCTGCT TCTCTCTCTT
78751 TTATTCTTTG CTGTTAATTT ATTTACATTT TTTGCAAGAT AATGAAGCTT
78801 GAATATCTGA ACTGTTGACA GCCAAATATT ACATTTCTTC ATGGAAATTC
78851 TTTACTTAGT ATGGAAGGAT ATAACTATTT CAAGTTGAAC AAAATAGATA
78901 TAGTCATTCA ATCAGTCACT TATATAAAGA ACACTAATTA TGTTATGCAT
78951 CAAGAAGTAG CTCCTTTATT CATAAAATAA CTTTTATCCT CATACATATT
79001 TTAATAATGT ATTGGTGCTT AGCTTGTCAT ATGTTAAGCT GTTATTTATC
79051 TAAAATAAAC TAAAATATTT ATACTATATA AAGAACTCTT AAAACCCAGC
79101 AATTTAAAAA AATCCAATTA GAAAATTGGC AGAAGACATG AACAGACATT
79151 TCACCACAAA GGAGACATTG TTGGTAAAAC AAACAAACAA ACAAAAAATG
79201 ACAACATAAG TTTTCAATAC CATTAGCCAT TCGGAAAATG CAAATTAAAG
79251 CCACAATAAG GTATTATTGT CTATGTACTA GAACAGATAA GATAATAATT
79301 TAAAATATGG CGATGATACC CAATGCTGGC AAGGGATGCA GAAAGACTGG
79351 ACCTCTCATA CATTGCTAGT AGGAATGTAA AATGGAATAG CCACAATGGA
79401 AAATAATTTT GCAGCCACTT ATAAAACTAA ACATGAAATT ACTGTGTGAC
79451 CCAGTAGTCA CACTCTTGGG CACTGATCAC AGAGAATTGA AAAATTATGC
79501 TCACACAAAC ATCTGTCACC AAGATTGATT GCAGTTTTAT TAGTAATAAT
79551 GAAAACTGGA AACAACCCAA ATGTTTTTCC ATGATTAAAC AAACTCTGCT
79601 ACATCCACAA AATGGAACAC TACTCGGCAA TAAAAAGAAG AATGTACTAT
79651 TAATACATGT AGTATCCACC TTGATGGACC TCAAGGCCAT TGTGCTATTG
79701 TCATTTTCAA AATGACAAAA CTATACAGAG GAAGAGTTAT TAGTGTTGTG
79751 AAGAAGCATA TACTGCAAAT AAAAGAGGAT ACTAGGAGAG AGTTTCTTTA
79801 GGGTGATGTA ATAGTTTTAT ATCTTGTTTA CGGTGGTGGT TAAAGGAATC
79851 TATACAGAAG ACAAAATTGC ATAAAAGTAT AACAAAACAT GGAAAGGGGT
79901 GAAATTGGGA TAAAGTCTGT AGCATTAACA GTATTGTACC AATATCAGTT
79951 TCCTGGTTTC ATATAAACTC CAGTTACATA AGATATTACC AATGGGGAAA
80001 ACTGGGAGAA AGTTAAATGG TATGTCCTGT TTTTGCCACT TCTTTTGACT
80051 CTAAATTGTC ATGCCATTGC ACTCCAGTCA GGGTGACAAA GGGAGACCCT
80101 GTCTCGAAAA CAAACAAAAG ATTAAAATGT CATAGAAACA CATTCTGTGT
80151 AAAAATAAGT GCATATAAAA CAAACAAACT GGATCACCAT TATGGTTGCT
80201 GTGAATTACA GATGTCAATG ATTCTATAAT GCGTCAGTCA TTTTGCTAGT
80251 TTTTGCAGTT TATATGGTTT AATTTGTGGA ATACTCTTTA AAAACAGAAG
80301 TTCAAAGCAA ATAAATTTAT GTGGAGATAA AAAGGAATAC AATATTTTTA
80351 AAAATTAATT GTTAAATATT TTATTTTAGC CCCAAAGGAC CCACCTAACA
80401 ACATGACATT TCAGAAGATA CCAGATGAAG TTACAAAATT TCAATTAACG
80451 TTCCTTCCTC CTTCTCAACC TAATGGAAAT ATCCAAGTAT ATCAAGCTCT
80501 GGTTTACCGA GAAGATGATC CTACTGCTGT CCAGATTCAC AACCTCAGTA
80551 TTATACAGAA AACCAACACA TTCGTCATTG CAATGCTAGA AGGACTAAAA
80601 GGTGGACATA CATACAATAT CAGTGTAAGA ATCCGTAGCT TCAGTTAATT
80651 ACCCAAATGA CAATGTCAGT TTATGAACTT GGCATTTAAA AATATTGCAG
80701 TTTGTGTACA CATGACATTT CCCATATCTT TTTGTGAGAT TGTTTGACAT
80751 CTCAACAAAA ATAAATTTTG AGAACTGAAA TTACCTATTT TCTGCTATAA
80801 TACAAGTACT ATTAAATTAA AATATGTAAA TAACCAAGAA GTTTGCACAA
80851 TAATAGTAGA AACTCAGACA TAAAAGAGAA AGAAAATGCA CATTAAAAGT
80901 AAAAGAACAG TGATATATAA AGAGATAACT CTGCCTAAAA AAAAGCTATA
80951 TGATTATGAA TTTAAAATGG AAAAGCAAAT TTTAAGGACA AAAGACAGAA
81001 ATAATTGTTT ACCTGTTTAA AATTCTCATG CATTTTAACC AAGTATTACT
81051 AAAAGCTAAT AGCATTTTAT GTCTTAATTC TAAATTCCCT ATATTTGGAC
81101 AGAAATGTAT GCATGAGTTC ATATACATAC ACAGAGACAT ATACAGACAC
81151 AATTTGTTTT ATTCCTTGCC TACTTTTAGA TCATCTTGAA ATTTTCAAAT
81201 AAAATTATAT GGTTCAGAGA AATCATCTTC TAAGAAACAG AATTTACTCT
81251 AAATCTTCAA GTAGTTTAGT AATCTGCCTA CCAACTCTTG ATTAATATCA
81301 ATGTAATTAT CAGGTCATTG ATAATAATTT GTATATGTAT ATGTGTATAA
81351 AATGAATATA TTTACTACTT CTCTCAGTCA CTTTGACTTT ATATCTTTAT
81401 AAAATAAATC TTTTGGGGAT TCTTTTTGCA TGTCCCATTA AGTGGACCAC
81451 CATTGTGAAA GATCGATTAG AGGGAAGACG GTGACTAAGA GAATAAAGTA
81501 ACCTGGGTTC AAATACTGGC GTCTGTGCCA GGGCAGCTTT ATCAAATCTG
81551 AGCCCAGTTT TCTTATGTGA AAAATTGGTA ATAGGAATAA TAACTTCTTT
```

FIGURE 3, page 23 of 87

```
81601 ATAGGATATT TGTGAGGATT AAATATTCAT AGTTATGGTA GGTAGTGAAT
81651 GGTACATATA TTTTGGCTAT TGGAAGAGAG AAAATAGGAA CCAAAAATGT
81701 GCAACTAATT AATAATTTTT AAAAATCCTG TTTGCAGACT GCAATTTGCA
81751 GTATCCTTAA AACCTTGAAG TTTGTTAGGA TGTATAACTT TAGCACCTGT
81801 ATTGACCTAC TGAATCAAAA TCTGCATATT TGCATTTAAC AAGGTGTGCG
81851 AATGACTTCT TTGCACACTG CAATTTCAGA GGCAGTGCCC AAATTTTCAC
81901 TTATTATTTC ACTTAAATGT TAGATTCTAC CATAAAGAAA TAAAAATAAT
81951 GGACCATACT ATAACATACG TTTTTTATTT TTAATACTTT TTTTTTGAAT
82001 TTACAAACTC AAATATTTTC TCTAGGCATT TTCAAGCCAC ATTTTATGGT
82051 CTTGGTTTAT TTATCATATC TACCACATGT ATATTGTAAT ATTAACTCAA
82101 TAAAAACATT TTAAAAGTAT CTAGAGTGTG GGAGGGTGGG CCACTAATAT
82151 ATAAAACAAA TTAAGTAATT CCAATAAACA TTTCGTATAC TGAATTGGGT
82201 TTATCGAGTA CAATGAAATA AGCCAAGAAT ATAGTCTCTG TTTAATATAG
82251 CAAGATAAAG TGAAGAAAAG AAGATTCTCT GTCTACAGCT TCCTTAGCAC
82301 AAAGTTAATT GAAAGGATTC ACGTTTGTGT AAATCACCCT CTGTGTATAC
82351 AAACAGAAAT GTTTTATGTG TATATGCTGC ATTATGCAGG TTATAGCGTC
82401 AGATACTTTG GGGCAGGGGT GAAGAAGGGC ATAAAGGCCA TCTTTCAGGG
82451 GAATGATTTA ATACAGGAAA ACTGGGAGGC TGAAGGAATA GGATTTCATC
82501 TTAGAGAGGG AAAAAAAGAG GATCTTGAAT ATGGATTTAC AGAAGGCCAG
82551 AGTTACCTAG CTACAGAGAG AAGGAACAGA TGTTAGAGTA GATGAAGGGA
82601 GAGCGTAGAT ACAGTGGCTG TAGTGCTCTG TTCTTCCTAC ATTCACATTA
82651 AAATCATGGT CAGTCCAGGT CTCAGTGATA GGGCTGTTTA GATCACTCAG
82701 CCTTTGTTCT CAGCGTTTAG TACCAGAACA TCAATTTTTA GAAATACTTC
82751 ATTGTTAATG TTCTTCCTAC ATATATTATA TTCAAGTGCA AGAAAATACA
82801 ATTAATAGAC TATATGCAGT TGTTTTTTAA AGAATTATTT AAAATTACAT
82851 GTTACCATAA TCAGTTTTAT ATATATATAT ATAACTATAT ATATACATAC
82901 ATATATAGAT ACATGCATAT ATATATATAT ACACACACAT ACATAAGCAA
82951 TCACTTGAAA ATAGTAACAA ATATTTGTTT GTTTTAGGTT TACGCAGTCA
83001 ATAGTGCTGG TGCAGGTCCA AAGGTTCCGA TGAGAATAAC CATGGATATC
83051 AAAGGTACAT ACATGAGCTA CCTTCCTATG AAATGCTATT AATCAGTGAT
83101 TATAATTTAA ATTCCATACT TGAAATAAGG ATGTAGACAA GCCTTTAAGT
83151 GATAAATATG CATATATTAA GCACATACTA AGTAAAAATG TGTGGTTATT
83201 AAAGCTATAG TTAAAAACGT TTAAATGATG ATGTGAATTA CCATGTTAAA
83251 TAAGGAGAAT GTCTTTATTT TATATTTCTT TAATATATTT TATATTTCTA
83301 AGTTTAAATT TTTAAAGACA AATTTTATAG TCCGTTATTT GATGTTTCTT
83351 TAAATGTTAT CGAAAAGAAA GTGTGTTTAA ATTGCCTATC ATTAGACTTT
83401 GACTAGGTCT AATTAGATTA TTAGATTGTT TGACTGATTT TTATTTTGGA
83451 AGTGAGATTC TTTCAGTTAA TTAAATAGTG TTTTTTGAAC TACCATGTAG
83501 GTTGGTTTAT GATTCTGACA GTAAAGTAAA TCTATCAATT CATGATTCTG
83551 GCAAGTATTT TTTATAGAAA ATATAACTAA AATTTGGGTC ATCCTTTCAA
83601 AATAAAACAA ACAAACAAAC CATGGAAACC NNNNNNNNNN NNNNNNNNNN
83651 NNNNNNNNNN NNNNNNNNNN NNNNNNNNNN NNNNNNNNNN NNNNNNNNNN
83701 NNNNNNNNNN NNNNNNNNNN NNNNNNNNNN NNNNNNNNNN NNNNNNNNNN
83751 NNNNNNNNNN NNNNNNNNNN NNNNNNNNNN NNNNNNNNNN NNNNNNNNNN
83801 NNNNNNNNNN NNNNNNNNNN NNNNNNNNNN NNNNNNNNNN NNNNNNNNNN
83851 NNNNNNNNNN NNNNNNNNNN NNNNNNNNNN NNNNNNNNNN NNNNTGATTA
83901 AAGGTGACAG CATTAGGCTG GGTTTAGGGT CAAACTGCTG GTATTGAATC
83951 ATGGATTAGC CACTTGATAT CTATTTGACT TTGAGAAAGT TTCTTAACCT
84001 CTATAGGCCT GAAAAATGGA GATAATACTA GTTCCTATCT CAAAGTTACT
84051 AACTTTGAGG ATTAAAAGAG AATCTGAAAA AACCCTTAAG ACCCCTGCCT
84101 GGAAACATGT ACTATTAAGA ATAAAAAATA TTCACTGTTA GATGAAACTG
84151 ATAAATTTTA TCTTTTTGTC AATGGATTAT TTATATAATT GTGATACTCT
84201 TTATAAGTGT TTGATTTAAA TTGATAAATT ATTTACTTTG GGAAGTACAA
84251 ATGCATAAGG TCTTTAAAAA CATCAATTAT TTCACAAAAT GACTTCACAA
84301 AGAATAGTAT GAGTCATACC TTTTAAATTT ATCTTTGTTA TTCAGTGGCA
84351 GACGTGTAGG TGTACAGATA GCAATACATG CATCACTTTT ATGCTTTAGT
84401 AAAACTTCCC ATTTCAGATG CTATTCCCAT CCCCATGCCA GGTTGGTTAA
84451 TCTTGACTTT TACTCCTTAC CTAAGGCAGG CAGACTTACG ACTTCTAGTC
84501 TAGAGAAGAT ATATGAACAA TGTCTTAGTG GTGGGATCCT AGAGAAATTA
84551 TGTTTTCTCT ACTAATACAC ATTATTTTAT TAATGATGTG GAATATTCAA
84601 TTGGTAGTAG TCTCATGAAA TTTGCATTTG ACAGATATTA TGAAGTTGGA
84651 TAGTAATGTC CAATGCTGGA TTCCTCTAAC TGGAAATCTT TTCCTGGGGA
84701 CTCCCAAGTG GCCTGGCTGA GAATCTCAGA ACTACCTGAA ACCTGAGCCT
84751 CTTCCTACTG AATCCTGCCT TTCATCTTCC CTTTTACAGG TGTCATACCT
84801 GTGATCTGTG GCACTTACTC CTTCCCTCTG TCCCTTAATT CTTCACAGAT
84851 AATTCCCCCA AAAAACCTCT TACACATCCA GTCTCATTTT AGCCTTTATT
84901 TCTCTTAGTA CCCAAACTGA TACATTGAGT AAGAAATTTG CATTTGAATC
84951 TGATGCTCAA AAAAGAGTGA ACTACAGAAC CGAGTCAAAA AAATGTGATT
85001 CAAATGTTGA TAGTTATCTT TGATAACTGT ATGACATAAG CTCTTTTCCC
85051 TATCTACAAA ATAAAAACAA TGTTGATAAT CCTGTGGGAT TATTGAGAAG
85101 CTTTTTAAAA AAGATTCTTA AAAATATGGA AATTGAAATT TGGTTAAGTA
```

FIGURE 3, page 24 of 87

85151 ACTTACTGAT GCTCAAGCAC TACATTCACA CACACACACA CACACACACA
85201 CACACACACA CACACACACA GTGAGCTATA AGACCAAATG AAACAAGCAG
85251 AGCTTCTATA CATATATTTT GGAGATATTT GTATGCATTG ATGACAAATT
85301 ATGAATTATC ATGGCTCTTC TAGAAGTTAT TCTGTTAATC TGTTAAGGTT
85351 AAAAGTACAT ATATCTTTTG TTCTAGAAAT TCTGCTCTTA GGAATCTATT
85401 TCATAGAGAC AAAAAGATCA GTAAATAAAG CTCATTGTAA AACAAAGCTA
85451 ATTATTGTAA AACATGTTTA AAAACTGGAG GAAAAGTGAA TTCCCATCAC
85501 CAGATGAACG GTTGAATAAA TATGATGCAG CTGCACCATG ATATATAATA
85551 TAGTCATTAA GAAGAATGAG TTAGCTCTGT ACCTGGTCAC TTGGAAACAT
85601 TTAACCAAGT TATATTTAAG CAAAAAAAGC AATATGAGGG GTAATTATAA
85651 TACATACTAG AGCCCCATTA GAAAAAGCAA ACAGTGAGAA GAGTGTGTTG
85701 TGCATGACTA TTTATGTATT TTTATATGAT TATGTGAACA TGGAAAAAAA
85751 TATGGGATGC TATCATCTAG ATGTTTAGCA TGGATTAACT GTGGGAGGGG
85801 TGCTAGTATG ACTAGAACAG AAATTAGTAA ACCAGCTAAA AGAAGCAAAA
85851 GAAACTACAC TAAAATTATA GTAAAAAGTA AATATGTTTA TGCATTTATA
85901 AAAAATATAT ATGAGTGAGA GCATGTATAA ATTGAATTTT TAATATGCAA
85951 AGAGGAGTCA GGTGCCTGAA AATCACACCT GGGCTCTATT ATCTCAGGGA
86001 AGTCTCAAAT GTATAATTAT GCTTTCAGGA GATAATAATT GCTAAATGTC
86051 TGCTGTCTCC AAGCACAATT CTCTATAATT TGTTATTTAT GTTTGTCATC
86101 ACTTTATCTG TAAATTAACT GCATGAAAGG AGAAAGATTT TTTCTTTTGT
86151 TGATGAAACA ATAACATCAA TTGCAGTGAT ATTTCTTCTT TGTTTATAGC
86201 TCCAGCACGA CCAAAAACCA AACCAACCCC TATTTATGAT GCCACAGGAA
86251 AACTGCTTGT GACTTCAACA ACAATTACAA TCAGAATGCC AATATGTTAC
86301 TACAGTGATG ATCATGGACC AATAAAAAAT GTACAAGTGC TTGTGACAGA
86351 AACAGGAGGT ATCATCACAT GTCAATTTAT CTTGTTAAAT TGTGGAGTGT
86401 AGATTACTGA GTGCTAAAAA GAATTTAGTT CAAATTAAGA TTGACTCCCA
86451 GTTATCACAC ACCTCTTGAG ATTAATAGAT TGTCAATATT ATTATTAATG
86501 ATACCAATCA TTTCTTTGTA AATAAATAAA TTATTTATTT ATTTTATTTG
86551 TAAAACTTTT ATAAATGTCA TTTATTTATA CCAATTATTT ATTCTTTTTT
86601 ACCTATCAAG AAAGGCACAG TTAAAATATG TGATTTATTA ATTCCATATA
86651 CTAGTAGATA AACATGTTTT GATTTTGGTA AGATGGAATC TTGATAGCTT
86701 CTTTGGAGGG GTGAACAAGT GAGTTACTCT TGATTGAGGG ATGCTCTTTC
86751 TCTACCTGAT AAATCATCCT TTATAACAGT TCCTGTAGAT TCACATGTAA
86801 CAGAGAAGAA CAGGGTTACC TGCCTATACA GGTGGATCAC TTGAATTATC
86851 TCTGGTGACT GATGTTGCAT CGAGAGTCCC CTTATACAAT TATAAAAACA
86901 CTATTTATAA TTGTAAAAAT ATATTCATAT GTTACTTGGA ATTATTGTTC
86951 TCTTTGTTTC TGAAAACAGC TCAGCATGAT GGAAATGTAA CAAAGTGGTA
87001 TGATGCATAT TTTAATAAAG CAAGGCCATA TTTTACAAAT GAAGGCTTTC
87051 CTAACCCTCC ATGTACAGAA GGAAAGACAA AGTTTAGTGG CAATGAAGAA
87101 ATCTACATCA TAGGTGCTGA TAATGCATGC ATGATTCCTG GCAATGAAGA
87151 CAAAATTTGC AATGGACCAC TGAAACCAAA AAAGCAATAC TTGTAAGTAT
87201 AGGTTATATC TACCATGCAT TCTGTTAGCA AGCTAGTTAG TATCTTTCAT
87251 CCATCCATCT GCCTGTCCTT TCATCTTTCC AATAAGCACT GGATGTCCGC
87301 CACGTATAGT GACCTGATTT TTCTGGCACT AGGAATAGAA AGATAAACTG
87351 AAAATTATTC TTACATTCCA TAAACATACA GTATTATAGG GGAAGCAGGC
87401 AACCCTAAGA GTAATTATGA TTTGATATAA GTTACATAAA GACCATATGA
87451 AAAATGTGCT ATTGGAGAAC ATAGGTATAT AGGAGAATTT AATTCTTTCT
87501 GTAGAGGACA ATGTGACTAA TGTGTTTTTC ACTTATTATT TTACCATCCA
87551 TGCTGATGTA CAGGATTTTT GAAACACTAT CCTATCCTTT GATTTAACAG
87601 TGGCTTCCCT TTATGTCACT CATAACAATA ACTCTCTGCT TTTTATCTCA
87651 TGAATGAGTG ATAGAAATAT TTAATACCAC CTTTAATATT TAGCTTTTTG
87701 TAGCCCCTAA AAACCCAACA TTTTAAAATC AATTTGATAT TTTGGCTGTA
87751 TTAAATTATT TGCTAAATTG ATTATCTTCC TTTTGAATTG ATTATGTTAT
87801 TTTTGTATTG TAAGACTACA ATTTTTAAAA GAATCATCTT ATCCTTGTGT
87851 GATTTTCAAA ATATAATTTT TACTAGTAAT TTTTTAAATG CAGGTGCTTT
87901 CATTTGTGCC TGTTAGTTAA AACATTATCA AATTCTTTAC AAATATCCTA
87951 AGCCAAGTTA ACATTGGAAA AATTAGAGAA ATTAGGCAAA TAAAAATAAT
88001 GCTTTATCAT CTCTATTAAA TGCAATTACT TTGGTTCAAA TTCTAGGTTA
88051 TTGCCTGAAT AGCTATACAC ATATGATAGT TATAAAAATG ATATACTACC
88101 AAGTATCATG TTTATTCATA TTTATAGTTT ATTTATTTTG CATATTTGTT
88151 CCTGAAACAG ACTCTTCATA TAACAAATAA AATCATAAGA ATTTTATAAT
88201 GGTAGAGGTT CAATCATGTA TTGCAACGTA TTGGTTTTAT GTTTTTAAAT
88251 GCCCTTGTGC CTTTATTTTT AAATTAAGTA AATTTCAATT GTCTCTGAGG
88301 ATCTTAGATT CTTTTTGTAA TTTTTAAGCT TGATCTTCTT CTGTATCCTT
88351 TACTTCAAAT GCTATGGAAG CAAAAAAGTA TACAAATGCA ACTGTGCACA
88401 CACAGAAATA ACAAACATTT TCTTAATGTG TTTATATGTG AACAAGACAA
88451 GTTCTATATC ATCATTTTAA TCTAATTCAC TAGCATTTGC AAAAGTGATT
88501 GAGGTATAAC AGTTATGCCT TTTATTTATA AATTATGTTA GTGTAACACC
88551 CTTCACAGAT ATCAAATCAT TCCATCTAAA CAAATCCTTG AAGGAGGTGA
88601 GCTGATTCAG TTGTTCAAAC TGCTAACTGC TCACGAGTTT ACCAAATTTT
88651 TAGCCCCTGC CTCATCAAAT TCAATGGGTC AAAGTACGAG ATAATTATTT

FIGURE 3, page 25 of 87

88701 GTCTCATATA AATATAGCAT ATATTTCTCC TGATGATGAT TCCATTCCAA
88751 ATTTTCATCT TGTAAATTCA TTTTCTTTTG AATTAAATAA ATAGTTTTTA
88801 TAATTACTTC TTGAGTTATT CATAGGAAAA ATCACATGAT ATGCAAAGTG
88851 TTGATTTTTC TTTTTTTATT TTATAGATTT AAATTTAGAG CTACAAATAT
88901 TATGGGACAA TTTACTGACT CTGATTATTC TGACCCTGTT AAGACTTTAG
88951 GTAAGACATT TTTGTAATTC ATTTATAATC TCAACATATT TATCAAAGTT
89001 GGAACATTTA TTAGTAAATG TATTAATCCA TGTCTAGATG TTTTAAAATA
89051 TAAACTCATT TAAATGTTAA TTAGCCTCTC TAGTAATATT TGTGGGTTTT
89101 TAAAATTTTT TCTTTTAGGT TTAGGAGTAC CTGTGAAGGT TTGTTACACA
89151 AACATCTGTC ATCTCATCTT AACTATCCTT TAAGTTAGGT CAGTGCTTCT
89201 CAGAGGGATT TTATACCCCA GGGGATATTT GGCAAAGTCT GGAGCCATTT
89251 TTGGCTGCCA TAACAGGATG GTAGTGGTGG TGGTGCATGC TACTGGCATC
89301 TAGTGGGCAA AGATTAGGAA TGCTGCTAAA TTTCCACAAT GCACAAAACA
89351 GCCCGTAATG TCAGTGGTCC TGAGGATGAG AAACTCTGAC TTAAGCCCTA
89401 ATGTTGACTC CATTTTACAG ATGAGGAAAC CAACACCCAG ATTCTTTCAG
89451 TATTTAAGTG GCTAGGCCAG GATTCCAACA TTACAGAACA GGATTTCATA
89501 ACATTACATT ACAAATATGG GATTTAGACC TGGGTTCAAA TCTTGGCTCT
89551 GTCACTTGAG AAAATAATTT AATTTCTATA AATCTGAGTT TCCTTTGTTG
89601 GGAAAATATT GATAAGAGTA TCATCCTTGA GGGGTTGTTG AAGTTTTGTG
89651 TAAAACAACA TATATAAATA TATTAATATT TTATAGTTAG TAAATTTTTA
89701 AAGTTTAATA GCTTTTTTGG ATAGGTTATA ATAAAATATT TTAGAAACAT
89751 TTTTATTTAG GAGAAATTAT TTCTCTAGAA TTTCACTGAG AGGATCACAA
89801 CATTCTACAT TGTTTGTGCC AGGCCCTCAA AAGCCCCAGT TTATTCGTCT
89851 TAAAGAATTG CATGAACAGG GTATTTCTGG GGCACCACTT GAAAATGTAA
89901 GACTTCATGT GTTGCCCAGA TCCTGGCGAG CTGTTGCTCA GTGTATCTTG
89951 AACTGCTAAT AGACTTCAGT GAGAGTTATG ACTGGAGAAA GACGGATTGT
90001 CCCACCATTT TTAGCCAGAA ATTCTCATTG GGTTATGGAA ATACTAATTG
90051 TATAAAAAGC CAGCCTCCAC AGCCTCTACA TGTAGTCAAG GAAACTTTGC
90101 ATCTTGAAGA AATAGAGGGG GCATGTAGTT TGCTACATAG ATGTTTGTAG
90151 AGAAATAACA AATTTCTTTG GCTAAAATGT TTGTTTAATT TTATACAAAT
90201 CATTGGTTTG ATTAATTTTA CCCAATAATT TCATCATTTT AAAGCTAGCT
90251 GATTAGTTTT GTGGTTTTGA AATTGTATCA AGTGTTTCTT CATTTGATAG
90301 GTGAGTCTAT CACACTCTGA TGCCACCACA GTAAAATAAA TGTCTTCTTG
90351 TCATCAGCAT AATTTCCTAT AGGTTACAGC ATTCATAAGC CATTACTTCA
90401 GCTAAGTAGT GATCCTGGTG CATTTGCCAA TGGAAGGTAA AAGACCTAGA
90451 CAAGATAGAT AACCCATGTG TCTTAGGAGA TAATATTTTA TAGGAGCAGT
90501 GCTGAAAGGA GCTAGCCTTG CTGTATTGTA TGATGTTGTC TTTCATCAAC
90551 TTACTGGTTT CATACAGATT ATTCATGGGA AGGCAACATG TTCCGTCAGT
90601 TATCTGAGAG GCAAAGTTGA GACATTCAGG GTAATGGAAA TGAGAAAGAA
90651 AAGCTATAAA AGGGGGGGAG CGCCAAGCAT CAGGAACCAC AGTGCACAGG
90701 AGCATGATTC CTTAGATTCT GCTAAATGGC TTCTCTCTGC CCAATGATGG
90751 CCTCATCCAG CACTATAAGT AATCTCAAAG AGCTCCTCAG CAATGGTCTT
90801 CTCTTTCTTC TTTCCACTCA CAGTCAAGGT GGTGGAATAC AACCATTAAT
90851 CCTGGAATGT AGCAGAAATA CACAGTCAGG TTTTTGATTC CTTCTTTGGA
90901 AGTATAACCA CTGCCACCCC AATCATCTAG GTATGAATCT TTGTGTGCTC
90951 TGGAAACAGA AGGAGTCTAC AGTGAGTAAA AGATGTGTAA TGAAGGACAG
91001 AGCACAGGAT CCTGCCAAGA CTAAGGAAGG AGGGACTGGT GAAATGTAGA
91051 CTGGACACAA TATATAGAAA GGCACTGGGC TGCTGAGGGA TAGTGACAAG
91101 GAAGGGTCCT ATGTGTCTAT GATCAAATTA CTCAGAGTTC AGTGTATTTT
91151 TTGTAGACCA GTGACATGAT GACAGTCTTT TAGGTTGCTC CTTAGAGTGA
91201 TCTTCCAGGG ACTCTCTCCT GAGATACAGC AGCTTTGTTA ATTGGCCTTT
91251 GCCCTACAGT GCTTATTCTG GATTGACCAC ATGGAGTTCT GCTATTTAGA
91301 TAGTCATTTA TAGCGAGTAA GACAGTGACA AGTGGAATCA AAGGAACTTG
91351 CTTGGTTTGT AATCGTTAGT TGTAGTGAAA TGAGAATGCA CCCCTGGAGC
91401 AGAATTCCTC AATGACTAGC AAAGCAGCCC AGCCATTTCT CTGGTTAATG
91451 GATTTAACAC CATCAATTAC TGTTGTCATA TTTGCTTTCT ACCAGACTAT
91501 TGAGTGTCGT GGTTCTATGG AGATTAGAGT CACTTTCATA GGTCAAGAAA
91551 CAAACAACAT CCCCTAGAAG TGGTCCTGGT CCATTTGACA TTGATAGAAC
91601 GCTGTAGATC AGGGGTGTCC AATCTATTGG CTTTTCTAGG CCACATTGGA
91651 ATAAGAAGAA TTGTCTTGGA CTACATATAA AATACATCAA CACTAACAAT
91701 AGCCGATGAA CCAAAAAAAA TTGTAAAACC ATATCCTAAT GTTTTAAGAA
91751 AGTTTACAAA TTTCTGTTGG CCCACGTCCA AAGTTGTCCT GGGCCACATG
91801 CAGCCCATGA GCTGCGAGTT GGACAAGCTC GCCACAGATT CAAAAGAGTT
91851 CTTAGTAAAA GAACATTGCC AGGGAAGAAA CTCTAGAAGA ACTCAAAAAG
91901 AAAACAAAGT TGATCAATTC TCCAATGGTT AGTGGCAAGA ATGGTTTCAT
91951 GGTTGTGAGA ATGAAGGCAG GCAAATAATA AAGTGCATTC ATATAATACC
92001 CCTGGTGTCA TCAGAAGATG ACAAAGGGTG ATTGAGTCCT TTTTTTCTCT
92051 CAAATATGTC ATGTGTTGGG ATATATGAAT CATTTGCAGC AGGCTAGGGA
92101 CTCAAACATT CCTGGTAAGC TGCTGAAGAC ATATGTGTGC ATGTAATCCC
92151 AGACTACAGA GAGAAGTCTA GGTCCCATCA AGGTCATCCA CCCACCAGGG
92201 GATAAGCATT CATTCACTGG TATTTTGCAC ACCACAGGCA ATGAGCACTA

FIGURE 3, page 26 of 87

92251 AGCCGAGTTG CCTGTCTGTT GAAACTTTGG GATTTAAGAG CTTTTGCACG
92301 ACTCTGTTTC CACAGACCAT TGTAGTGGTA ATTATGCCTC TCAGAGACGT
92351 TATTATTTGG AGTTTAAAAT TAGGGGCAAA AGAATCACCA TAGACTGATA
92401 ATCTTAAAAA TGTTTAAGTT TAGTGAAAGG GACTAATGAA AGTACAAGTG
92451 AGAGATGGCC AGGTAGAACT TCACTGGATG GATAAGTATG AGTCTGTGGA
92501 AGAGCAGTTT GCATTTAGGG AAACCTTTCT GGCCTGTAGG GATAAACAGG
92551 GAAGATAACG TATGCATTAT TTTAATCCTA AATAAATACT TGAAACTTAT
92601 TTGATTTCGT TTTTACTCAA GATTGAGTAT TGGCATTTTT ATTATCAAAA
92651 TTCACAAAAA ACCCTCTTAA ACTTTTTGAA AAAATCTTCC CTAGGCACAT
92701 CAGTTTATGG AAAGTGCTTG TAGGCAATGT TTTGATTACA AGGTTTAATT
92751 ATAGAGGGAT CCTGTGATTT GAAAACCAGA CACCCGTTTC TGTACCTTAC
92801 AGGGCTCTCA TTAAAGCTGA ACATGATGAA ATCTTAAACC CCATGGCAAA
92851 GGCACTCTGT GATTGTTTTC TTTTGTCATA ACACTTCTCA TTTAATTACT
92901 ATGCTAACAA TGAAAAGTTC CAATGTGCTC ACTTAGATTC AGAAATAGGG
92951 AGTTGCTATG TATCTTTTGC ATCCAAAGGA TTACTTCCCT AAAGTCACCA
93001 GAGGAACAGA GGAAGATTGT ATTTTGTTAA CGAGACAGTG GTAATGTGGT
93051 GGTGAACCTC ACATACTCTG TAGTCAAGAC AGACGTATTT CAGGCAGGCT
93101 TGGTATATAT TGAATTTATG AGATTGTGGG TTAGTTACTT AAAAAATTAT
93151 TTTTAAGTTC TGAAATCTTA TTTCTAAAAT GAGAATACTA ATACTCCATT
93201 TTAGAAGCTA ACTAGGAGAT TAAATCAGAT GAATAAAATG GATGAATAAA
93251 TATGAAATGT TTGTTAATAA AGATACCTGT CATTGTTTAT GTACCAAGTC
93301 TTTAAGGGGT TTTACATATA AACTCATGCA TCTTCACTGC AACTCTGTAA
93351 CAACACCTCC TATTTACATA GCGCCAATTT CTAGGTAAGA AGTTTGAAGC
93401 ATTGTGTTTT TTACTAACTT GACCAAGCTT TTTAACCATC CCAAAGGTGG
93451 TGGCAGAACC TGCTTTCAGA CCCAGGCAGC GTGACCTCAG TCAGTGCTGT
93501 ACTTGTAACC ACTGCACACA CTACCTGCAA ATCACTAAGT CCCCAAGTAG
93551 CCCCCAGTTC ATTACTATGG GTGATGTTTC TGCTCCCACA ACCTATCTTT
93601 GCTGTACCAT TTTCTCTTCT TGATAGTTTT AATTATTTCT AGCAGCTCTC
93651 TTTTCTCACA CTTTGTCTTG GCTTTTGAGG TTAGTGTTCA CAGATAAGCA
93701 TGTGTTGCTT TTGTGTTTAG AGATATGGTT TCTTTTTATT TTTTTAACAC
93751 CGAATAATGT GACTTTTCTC ACACCCTAGC AAACACTTTA TTAGCTACCT
93801 TTAAATTTTT TCCTGTCTGT ATGGATGAAA ATGATGTTCA TCCCAATGGG
93851 GTGTTTTAAT CTATATGTTT AAAATTTTAT TGAATATTGA CAAATTATAC
93901 ACGTATATAT TTATGGGGAA CAGAGTGATG CCATGATATA TGTATACCAT
93951 GTGCAATTAT TGAATCAAGT TAATTAACAA ATCCATCACC TCAAGCACTT
94001 ATCATTTATT CCTCCTATCT AACTCTATTT CTTGACTTAT GGAATTGAGT
94051 AACTTTTAGT AAATTATTTG CTCAGTGTTT GAATACCCTA GGTGACTAGC
94101 ACTGGGCCAA AAGAGAAGAT GAACTCCCTA TACTTTAGTC CTGTTATAAG
94151 AACTCAATTT TTATAATAAT AATAATAATA ATAATAATAA TAATAATAAA
94201 GAAGGAGGAA GAGGAGGAGG AGGAGGAAGG GGAGGAGGAG AAGAAGGAGA
94251 GGGAGAAATA AGGAGGAAAA GACTTTCCAT TTTATATGCA TCTTATCAG
94301 GAGCCAGGCA TTGTACTATG AGCTTTATAT CTAATTGAAT TCAAGTTTCT
94351 CCTTAGAGAA TAGGCTTAAA AACAGACTTA AAAAGTTGGA TACATATGCT
94401 GAATTTAAAT AATGATAACT TCAGTCAGAA GATAATACTT ATGAAAAATT
94451 AGTGCTTTAG AATTATGATT TGCCAAATTA TAGTAGTACA ATTTATTATG
94501 TAAACAGACC AATTTAATGT GATTTGTCAC AGGATTTTAA GTCTAGTCAG
94551 AAATGACTTG CACCTACTAC AAAAAGAAAC ATGTTTATAT TTTTAAGTAA
94601 AAGAATTCCA TTTTCTATTA AAGGATTTGG AGAAGTGACA TCATTCTCTA
94651 CTGTTAATGC TCTGTGGGTC CATGCATAAC AGTGAATCAG AAAGTGTACT
94701 TGATAATCAG GGAACATTTT GTCCTCTCTT AGTGACACTT TTGTAATTCA
94751 TGTGCCCAAA GGATTACATA TTGTTTATTA ATATATTATA TGTCATTTCC
94801 TCATTTGGCC AGTGCTTTGA AATGGTAATC TAATCTAAAA AAAATTTTTT
94851 GTGTGGTCTA TGAGAACATT TTTTTCCCAC TGAGTTCTAA GGCCCAGTGA
94901 TTCATTATTA CCTAATAAAG AGGATTCTTT ATTCATCTTC ATGCCTCCTT
94951 TCCCAAGCAT ATCCAATTAG AGTCACCATG TGAAAATTCA TAAATCAAAC
95001 CGTTCGTATT TTAATGTATA AAAAAATGTA CCTAAAATAC TTTAGGTGAT
95051 ACATGCTGCT TTCTCATTTT TTAAATTTAG CAGGAGATTC TAGCAGACCA
95101 TGAAGTGCTG ATAACTGTTT TAAATTCAGT ATTTATTCAA ATCCACCATG
95151 CAGGATAGCC ACAGGAACTC TTTTATATTG GTAACATTAC ATAAGTACCA
95201 ATACAGGACA AAAAGATGAA GCATTAATAC GTGCCTATTT TACACATTGG
95251 TAACCTATTT TGTCACTTGA CTGTAATACT TTGTGCAGTA AAATTATAAA
95301 TTATGTAACT TAAAATTGAT TACAATTATA ATTAGTAGTT GTGCTTAATA
95351 ATTTTTATAT TCTTATTTGG TTCAATGCCT GATCTTCAAA CACGAACATT
95401 TTTAATCTTT TTCAAAATCA ATATATTTGT TCATTAGTAA ATTTAGCAAA
95451 TATTTATTTA ATATTTACTC TGTGCCCAGT ACATCTCTCA GACCGTGGAA
95501 TAGTTTTGTA TAAAACAAAA ACCCCTGTAC TCAAGGGGGC TTACATTCTG
95551 GAGGAAAGGA CAGAGAATAA ATAGTAAGAA TAATAAATAA GTGATTTATA
95601 TGTTAAAATA AGATAAAGTT ATGGAGGAAA AAAGTAGAAC AGAGGGAAGA
95651 AGGAGGGGGA GGAGGAGGCA GAAAATGCAG GGAGTTGTGT CTTTCAATTT
95701 TAAATAGTGT GCTGTGTTAG TCTGCTCAGG CTGCCATCAC AAAATATCAT
95751 AGATGGGGTG TGTTAAACAA TAGAAGTTTA TTTCCTCACA GTCCAGAAGG

FIGURE 3, page 27 of 87

95801 CTAGAAATCT AGGATCAAGT TTCCTGCCCA TTTGGTATCA GGTGAGGGCT
95851 CTCTTTCTGG CTTACAGATG GTTGCCTTCT TGCAGTGTTC TTACATGGCC
95901 TTTCCTTGGT GCATGGATGG AGATAGAGAA AATATGGTGG GGGGAGGAGG
95951 AGGAGAAAGG AGTGAGTGGC ACACACACAC ACACACACAC AGAGAGAGAG
96001 AAAGAGAGAG AGAGAGATGG AGAACAAGCT CTCTGTGTCT CTTCTTATAA
96051 GTCACTAATC CCATCAGATC GGGGCCTCAC CCTATGGCCT CATTTAACTG
96101 TAATTCCTTT CTTACTCCAA ATACAGCCAC ACTGGGGATT AGGGCTTCAA
96151 CATATTAATT TGGGGGAAAC ACATGTATTC AGCCCATAAT ATATGATCAT
96201 TGAGAAGGTA TTTCAGCAAA CCTTTAAAGG AAGTGAAGTG GCTACCCAGA
96251 AAGATATACA AGGCATACAC ACCTTTGCAG GCAGAGGAAG AAGCTGCTGC
96301 AAAAGCCATG TGTCAACAAT GGCCTTGTGT TATTCATCAA TAAGGAGGCT
96351 AATCTGGCTC CCTAGGAGTG AGCAAGCAAG GTGGGGACTG GAAGGGAAAT
96401 CAGAGGGGTA ACAGGGGACC AGACAGTTAA TGAGGGACCA GATCACACAT
96451 GCCACTGGAA GGATATGGGC TTTTCTCAGT GGGAGATGAG GAGGATTTTA
96501 AGCAGAGAAA TAATGTTTTA AAACGATTGT CCTTGCTTGT ATGTTGAAAA
96551 TAGGTGGAAC AAGGACAAAG GTGGATACAG GCAGACTTGC TAAGTTTTTA
96601 ATTCATGCAA GACAGGATGG TGGCCTAGAT CAGATTATCA GCAGCAAAGG
96651 TGGAGCAAAG TGAATGGAAC ATACATAAAA CTAGAAAAAA TGGTGTCATG
96701 AACCCCCAAA TACCTACTAA CTCAATTTAA TAATAATTAA CATTTGGCCA
96751 CATTTGTTTT ATTTAGACAT TGTTCACTTA TTTCTGAAGT AAAGTAAGTC
96801 ACATAACGCA TATTCCACTC CTAAATACTT TAGTATGTTT CTCTAATAAG
96851 TACATTTTTA TTATATTGCT GTGATTAAAC TTAACAATAA ATTATTGATA
96901 TTATTTAAGC TACTTGTATA TACGTTTTCA AATCAGTCTT TGATTTTTTT
96951 CTTTAAAGTT AATTTATTTG AATCAGGATC CAAATAGGAA TTTACACATT
97001 ATCTTTGATT GTTCTGTTTC TTCTATTATT TTTTTAAAGA GCCTTCTTTT
97051 CTCCTTTCCT TCCCCCCTAT GTCATAGACT CCCTGAAGCA ATCAGATAGG
97101 TTGTCACGTA GGAAGTCCCA TATTTTGGAT CTGTCTGGTG GTTTTCTCTT
97151 GATGTCCTTT AATTTTTTTT CTTTCCACCA CTTTCTTATA AATTAGAAAT
97201 AAGATCTAAA GCTTTGAGTA TTCGCAGTCA ACATTTTTGT CAGAAGTACT
97251 TTATAGGTCT TGCTCACTAG ATCAAAATAC CTTCCATCAG GAAGTGTAGA
97301 ATATCTGATT GTTACACGTG ATGCTAAAAT TGATCAGTAG GCTTGGTGGC
97351 AGCAACAGCA TGATCCTTCA TTGGAAAGTT GGTTTTGACC ACTTATAACA
97401 AGCGTATAAT CTATACAGCG ATATTTTGTC ATCCTGTAAA TGTCCAATTC
97451 CCCATTAACT TTCCTCCTAA TCATTTTAGA ATACATTTAT GTTTGTTACC
97501 TGAATCAACT ATTTCGTTAG AAATACTGAT TATTAATTTT TTTTTATTTT
97551 GAGCTGGTGT TTTGCTCTTG TTACCCAGGC TGGAGTGCAG TGGCACGATG
97601 TCGGCTCACT GCAACCTCCA CCTTCCGATT TCAAGCTATT CTCCTGCCTC
97651 AGCCTACCGA GTAGCTGGGA TTACAGGCGC CTGCCACCAC GCCCAGCTAA
97701 TTTTTGTATT TTTAGTAGAG ACGGGGTTTC ACCATGTTGG CCAGGTTGTC
97751 TCGAACTCCT AACCTTGGGA TCTGCCTGCC TCGGCTTCCC AAAGTGCTGG
97801 GATTATAGGC ATGAGCCACC GTGCCCAGCC CTGTTTATTA ATTTCTAATT
97851 TTGTCACTCC TTTAACATTT ATGCAGCAAA ATTATCTTCT AATAATGAGC
97901 TTTATCTCCT TAACTAGGGC TATTTTTAAA AAGTCATAAA ATGTAGTTCA
97951 GATAAGAAAC CNNNNNNNNN NNNNNNNNNN NNNNNNNNNN NNNNNNNNNN
98001 NNNNNNNNNN NATTTTTGTT ATTTGTATTT CTTTTATTAA ATAATCTTAT
98051 TTTTTATTTC TGATCAATTT CCATTTTTAT TAAATATAAG GCTTGAATTC
98101 TTCCCTCTTT GGCCAGTAGG AGCCCCTTCA GGAGGATCAT TTGTTCCTTT
98151 TATACCAGTA GCCTTTTGTT AGCTTCCTAG ATCTCTAGCA CCATTATATG
98201 TCTTGAATTT GTTTAGTTCC TTCCTCCCAC TTTGCAATTA CCATCTTTCC
98251 AAAGTTACAT AGTTTCTTTG GTGAAAATTA CAAATATGTT GAAGATAGAG
98301 CCTACAGGAT TTCCTCACAT GTTTTGGATG TATTCTATGA AAGAGAGTCA
98351 AAGATGACTC CAGGGTTTTG GCCTTAGCAA CTACAGTAAT GGAGTGTCCA
98401 TCAACTGAGA GGTGGGAGGA TACAGTTGAA AGGAGGGAAG TGTACATGTT
98451 CAGTTTTGGA CATATCAATT TAACATTTTA AGTATACTTC AAAATAAAGA
98501 CGTCTGGTAG GCAGTTAGAT ATATAAGTCT GAAGTCTGGT GGATAAAAAC
98551 TAAGTAGTCA TCATCATATA GATGAAATTA AAACTGTGAG GCTAGATGGG
98601 CTCACACTGG GGAGTGAGTT TAGATAGAAA AAGCAAGAAG ACCCGGGACT
98651 GAGCCCCAAA GTTAAAAAAT CTAGGAGAAG AGGAACAAAC AAGCTGCTAC
98701 ATTTTACTAG TATTCTTCAG CAAAGAATAT TTTCTTATGC CAAGATAATA
98751 TTTTTTGGTA GTTTGGGATT CAAAATAAGA TTCCATAATA ATATTTAATG
98801 ATCCTGTTAT CCCTCTTCTC CAGGGGAAGG ACTTTCAGAA AGAACCGTAG
98851 AGATCATTCT TTCCGTCACT TTGTGTATCC TTTCAATAAT TCTCCTTGGA
98901 ACAGCTATTT TTGCATTTGC AAGGTAAGAT TTATTTGCGC TTACATTCCA
98951 GGATGCTTTA TGGGCATTAT ATCAGTCATA GTCCAATCAG GAGACAGAAG
99001 CCACAACAGT TACTTGAATG GGAAACATTT TTATTTTTAA TAGACAGATA
99051 AAAATGTATT TATCATGTAC AATATGATAC TTTAAAGTGT ATATGCGTTG
99101 TGTAGTGACT AAATCTAGCC ATAAAAGGAA AGAAATCCTG CCATTTGAAC
99151 AGAAAACATT TAATGTAAAG AATTGTTAAC TAGCAGAAAT GGCTAACTAC
99201 TAAAGAGAGT AAAAGAGAAA TCTAAGAGTC CAGAAGTAGC AAGCAAAACA
99251 AAGCAGCTAC TCTCTTTAAC TTGAAGGAGA GAGGACAGTA AACAACTAAG
99301 AACTGAAAGA AGTTGTCTCC CAAGACTTAC ATGGAATCGC TACTTCTAGC

FIGURE 3, page 28 of 87

99351 ACATGCAACC TATCACCAAA CAGTGAGCAA AGAAATATGA CAGAGGGAAG
99401 GGGTTGGAGC TGTTCCGTAG AAGCTACCCG TCATTATTAG ATGGTAGGCA
99451 GGCTGAAATT GGTAATAGAA GCATCCCATT CTTGCTGAAT GGTGTAGGTG
99501 AGCTGGTACT ACTTGAGACT GTTCACGAAT GGCATGGGCA GAACGTTCAC
99551 TTCAGAGGCA ACAAGAGCTC ATCCAAGTGA GCTGCTGGGC TCTCACAATG
99601 AATAACAATA ATGCAGGATT GGATCCCACA AGGGCAGTGT TTTCCTCTTC
99651 CTACTGCCTC TCAGGGTCAC TCTAGTGCCC TCTATTGACA AAGCCTCACT
99701 TTCGGCCGGC TGGCAAAGGA GAAATGCAGG TTCCAGCTCC AATATCAAAG
99751 AGCACAGCAA AAAAAAGGAG GTTTGGAGAT GAGAGACAAC AAGGTGAAAA
99801 CACAAAAGCA GAAGCTTTCA GGCCACCTAC ATCTTTTAAA GTAATTTGTA
99851 ACTCTTATAG GTTTAATTTA AAATATCTCA ATCAGGTCTA AATATTAAAG
99901 TTTATACAGA AAGAGATCTT TTTTATAGTT AGAACAACAC TTGTAAAATA
99951 TCCAGCTTCC TTATATGGTA GACCCCCTTC TCATGCTTAC TTTCTGAACA
100001 TGTCTGTGCT GAATTTTCCA AGTGTATCTT TCCATTCTCA GCATCAGCAT
100051 CCTACTTCCC TTATTATTTA CAGGGCCTCG TTGGAAATCT TACTTCTGAC
100101 CTCAAAATCT AGCTTCTTAA GGCAGATTGC CGAGTTAAAG GGACCTTACA
100151 TTTGTAAAGT AAACTTTCTA CCAATTTCCT AAATAGTTCA ATAGACTATT
100201 TTTATTTCAA CTGAAGAATG TAGTTCTGTA TTCTAAATGC CATGCATTAT
100251 GGTTCATCTT GACTCTCTTA AAGCATAATT TTAATAGATA ATTTGAAAGG
100301 CTCTTGAAAA AGATATTTTC TCTATACCAC ATAACTATTT GCAGATTTAG
100351 CCAGAAGACA GTGAGAGAGT TATCATTCGA GGCACTTTGA ATGCTATAAT
100401 GTGTAAAATA TGGGCCTTTC CCTAAGGAGT ATGGACTGGC CACATTTATG
100451 TAATTTCCCT GCTCTAAAAT CTTTTCTGAC TTCTCATTTC TCTACAAGAT
100501 GAACTCCTTG TGTGAGTAGG AAATGGTCCT CCTTATTCCC CACAACTTGC
100551 CTACTCACTA GCTAAAGAGA TCTATTCTCA CCTGAACATT CCTTGGGCTT
100601 TTATACATTC TGCTTTTGTT CAGTCACCCT GAAATGTGCT TCCTCCTCCT
100651 TCTCATCCTG GGACATCCAA GTCAAATTCT ACTTCTTTAC CTCCTCTAAA
100701 TAATAATAAC TATTTATGTA ACTAATCAGG CACTGTCTTA TGTGTTGTAA
100751 TTTGAATCTT TTTTTCTCTT TTCATGTTTT TTCTGCATTG AAATCTTGCC
100801 TCTCAACTAA ATTGTAATGT CTTTGAGGGT AGGGAACATG TTTTATACTT
100851 TCCATATCAT CCTTGATGTC CAACTCTTAA TAAATACTAA ATATTTGAAA
100901 TGTGAAAGAT AGAATAGCTA AACATTACTT TGTAATATAC CATACTGTGT
100951 CATGGAGAAA TAAGCATTTA AAGGGTTTAA GATGAAAAGA ATCTGATTTG
101001 ATTCTCAGAT TCATGTGGCT TTTATTTTTG AACCTAAGTT TTCTGATTGT
101051 AAAGATAATA TCTACTCACA ATATTTTTAT AAAAATTCAA TAAGATAATT
101101 TGAAAATAAT TTTTAAGTAT TTTCATGCAT GTAAAAATAT TTCATATATG
101151 TGAACACAAT GGGGCATTAT CTGTTAGCAA TACTATTGAT AGCATTGAAC
101201 TATTTTCACT TTGGCATAGT TCCTTTATAT GACAAATCAA TGACATAGCT
101251 AGAGAGAAGA GAAACAAGAT CACAACGTAA GTCTTCTTGG CTCTATATTT
101301 AAATGTACCA ATGGCTCAGG CCTTCGTCAA CTAATTCTTC TTAAATTTAG
101351 AACTTCATCC CAATAACTTA TTAGAAAAAA AAGAAAGTAG AATAGGTTCT
101401 ATGGAATTAA AACAAGAAAA AGAAGTCGAG TAGCTATAAA TTTGCAACAT
101451 ATTCAGAGAG GTGATTTTAA CAAGGAAATT ATTTGACTAA ATGTCTTTAC
101501 TTAAAAAGAA AACTAAACCT AATTTTATAT ACTTTGTGTG AAACTCCCTT
101551 CTTGGACTTT ACTCCGCTTG TTTTAGAATT CGACAGAAGC AGAAAGAAGG
101601 TGGCACATAC TCTCCTCAGG ATGCAGAAAT TATTGACACT AAATTGAAGC
101651 TGGATCAGCT CATCACAGTG GCAGACCTGG AACTGAAGGA CGAGAGATTA
101701 ACGCGGTGAG CACACTCCTC TGGGTGAACT GTGGTCCAGA GGGCCTGGAG
101751 CCATGACCCT ATTCTGACCT ATGCTTGTTG GAAGTGTTTG TGGGGCTCTA
101801 ATTTACACAG GTCACAGAGA TCTTCTTTCA AAGAGTGACC TCCGTCTTCT
101851 ACACACTTCT CACTGCTGTT CAGAGAATCA CTTAATCTTC CTAATATTTT
101901 GAGTTAAATA TGAACTTTGG ACTATAATGT TCAATCAGGA TTATTTTCCT
101951 GGGACAAATA TTTTTCCACA TTAAACCTTT GACATTATGT TTAATAATTC
102001 ATTTCATATG ATAGATTTTT ACATTAAACT TTTCTGGAAG TGTCCACATT
102051 TTCAATCACA GGTTTAAATT AATTAAATTT ATAACTACTT GATATTATTT
102101 ATATCCATTT TTATAAAAGC TTTTTAATAA CTATTTCAGT ATAAAAGTAC
102151 ATAAAAGTCT AAGTTGTATA TGATATCATT TTTACATTTC TTTGTATTTA
102201 AAAATTAAAT ATAAAGTAAA AAGTTACCTT CAGAGGGAAA AGTAAAAACA
102251 TGTGTACTAA ATATGTTTCA TTGGTACCTA TTGGAAATAG TAAAGTACAT
102301 AATTTTAAAG AAAAAATAAT TATAAATCCT TTTAAAAGCA TTATCAATTA
102351 TTCAAAATGT TGGCACATTA TAAAAACTTG TCTATTAAGA TAATTCATCA
102401 AATTCTTAAT GAAAACTACC ATCAGGCTAT TTTAACGTTT GCATTTTTAT
102451 AAGATTCAAT AACATGTAAT GCTTATAAGC ACAAAGTAGT TGTTACCAAG
102501 TATTTGCTCA GCTCTGTTAA AATTAAAAAA ATTATTATTA ATTTTGAAAA
102551 TATGGCATCA AATGTCTTGG ACTCAAAAAG TTATTCATTT GTAGTTGTCA
102601 CTTGTTAAAG TTGGTCTTTA TCTAATAGAT GGACTTTGCA AGTATATTTC
102651 CAGCATATCT AAAAATACCT AATATGTGCT ATAGAGGGAA GTGTCATCTG
102701 ATAAGCAAAG TCCTTCCAAA TGCTACAAAA TGAAGGTTAT TCAATGTTAT
102751 CACTAAATTG CAGGGAAATG TGTTTTCTTG GATATGACAG CTGACTTTTT
102801 AAACATTCAG ATGTTGATCT TTGTGTTCTA ATACAGTGGT CCTATCCACA
102851 AATGGATAGT ACTCCAAAGA TTTAAGTGTC AGATGATTGT AAGTTATCCA

FIGURE 3, page 29 of 87

102901 AGACATAGTT TTCTATATAA GAAATATTAT GTACAAAATA TCAAATATGT
102951 AAAAAGAATC AATAAAAGAT TCCCAGGGTA ACTCATCTAA GTAAAACCAT
103001 ATCATAGGAA CACAAGCACT GCTACTACTA GACTGTGTCT CAGCCCTTAA
103051 GGAATCATTC TGCATCATCA AAGAAAGTTT TTCCTCCTTT TCCCCTATGG
103101 GCCAAATGAA TTTTAGTGGT ATCCTCCTAG CCTCCTTCCT GCACTCCATC
103151 GTCAGTTCCT TTTGCCCCTC CTCAGGCCTG TGTGGCCCAT CCCTTTATTC
103201 TACAACTGAA AATGCACAAG GGAAAAAATT CAAATCTCTC AATGCAATTA
103251 ATTTTAGCTA TTTGAACAAT ATAGTTGAAT CTGTTCATAC TAAAATGTAA
103301 ACTTCTAAGA CCGACCCCCT CCCCAACACT GGTAGGCATT TTCATTTTGT
103351 TAAAAGAATA CTTAGTAGCC CGTGAAAAAT CCTGAATAAG TATATCTTCA
103401 GCAAATGTAA TAACGTGAAA AAGCACTCTT TTTGTTTATT ATGTCATGTT
103451 TTTAAACAGT CAATATTGGA GAAAGTATTA TTTATCGAAG AGGTTACATT
103501 CGAGGCAGAC TGTGGTGAGA TTCAATCCCC TAAGCACTAT ATATTTTCAC
103551 AGCTTGCCCC TTTCTCTACT TCTGAACACT AAATACATCA TCATAAAAAA
103601 ATTAGAAAAG GTCGGGTGTG GTGACTCATG CCTGTAATCC CAGCACTTTG
103651 GGAGGCTGTG GAGGGTGAAT AACCTGAGGT CAGGAGTTTG AAACCAGCCT
103701 GGCTAGCATG GTGAAACCCC ATCTCTATTA AAAATTTAAA ATTAGCCCAG
103751 CATGGTGGCA TGTGCCTGTA GTCCCAGCTA CTCCAGCCTG GGTGACAGAG
103801 CGAGACTCCA TGTCAAACAA AAAGAGTAGA TTTTTTTTTT TTAAGAATGA
103851 CTGTCATGGC AGCTACAGAA AAGTTTCAGA TCATGAAAAA GGTGGGCAAG
103901 GAATGTATAG ATTGTTTACT ATTGGTTATT TATAATTCAG GGTCTACTTT
103951 ATTTGACCTT CACTCTTCAT TATTTATTTT TCCACTTCTG TGTTTATTTA
104001 CATATTGCAT TATTTGTAAA AGGGTTTAAA AGTGAAATAA TATTTCAGAT
104051 AATTTTTATT TTGTTACACA CAGAGAATTA GTATATATTA CCCATGATAA
104101 TAGCAAAATT GGAAATATTA GTTTCCATGC TTTTCACTTT TTCACTTGTT
104151 TGTTGTGATT CTGGTATTCA CAATTGTTTG TAATTCCAAT GGCACATAAT
104201 AACATGCTTT GCTGGACTTA TTACAGAAAT GCATTAAAAT AACAATTAAG
104251 TGATTTGGGC ATTAATTCTT CAGTACAGAG ATCTGTGTCC AGCTTTACTA
104301 TTTATGCAAT ATTTTTATGT TAATAAAGTC ACTAAAACAT TAGACAATAA
104351 GACTGGAAAA AATAACAAAT ATAATTAGCT GCATGTACAT ATGCGTGGAT
104401 CCTGTCATTT GGTGAAGCTC TAAAACTCTT CATCTGTTTT GAGGTGTTTG
104451 AAGATCTAAA TCTGTTCAAA GTCAATCAGA GACTGATGGT AGATTCTAGG
104501 AGTGAGAATC AAGAAGTCTG ATTTAGCTCC CTAAATTGTT GGCAGACTTC
104551 CACCATATGT CTTTGTTATC TGCAGGAAAG AACTTCCATA ATTTCTCTTA
104601 AATCTACCCA GCTAATAGGC TGGGCATAGT GGCTCATGCC TGTAATCTCA
104651 GCACTTTGGG AGGCCTAGGT GGGTGGATCA CCTGAGGTCA GGATTTTGAG
104701 ACCAGCCGGC CCAACATGGT GAAACCCCAT CTCTACTAAA AATACAAAAA
104751 TTAGCCAGGC ATGGTGGCGC ATGCCTGTAA TCCCAGCTAC TCAGGAGGCT
104801 GAGGCAGGAG AATCACTTGA ACCCAGGAGG CTGAAAGTGG CAGTGAGCCA
104851 AGATCACACC ATTGCACTCC AGCCTGGGCA ACAAGAGTGA AACTCCGTTA
104901 AAAAAAAAAA AAAAAAATCT ACCCAGCTAA CATACGCTCT CTCTACTTGA
104951 TTCTTAGGCA TGTCCTTTTT ATTCCAACCT GCTAAATTTT TCATGCAAAA
105001 TTGAGCTCAT AACTTTTCTG AGTCCTGTAT GTTTTCCCAT GTCCAAAAGA
105051 TAAATGATAA AAGAAGAATC TCTAATCAAT AATTAAAATA TTAATTTTAG
105101 GAAGTTACCA ACTAGGCAAA AATAAAACAA AAAACAAACA TGGTGCTTGG
105151 TACTAAGTCC TTTCAATGAT TTGTGGTTTC ATATTTTAGA AATTATTTAA
105201 CTATTTTATA CTCTCTGCCT GTATATTTAC ACTTTAAAAC CCATTCTGTA
105251 ATTTTTGTTA TTTGTAAACT CATTATTTAA TTATGCTCCA CTTTGTTTCA
105301 CAAAACTTTT GAAAATGCCT TCTCTCACTC TATCATTCTA TACTATTTCT
105351 TCCCAAATGA GAGCAGGAGT CAAATAAAGA TGTAGTACTC TTTAATTCTA
105401 TGAAAACATT CAAGGATATA CTAAAATAAC GTTTTAAATT CTCAATTTGA
105451 ATGATAATTA TATTATGTAC AAAGATTATT CACATTTTAT GTTTAAGTTT
105501 AGATAACACA AACTATAATT CTTAGGAAGA ATATGTAACA TTTTGGGCTC
105551 ATCTGTTTCA CACTTACCGA ATTAGGAAAT GATCCTTGGG TTTTGTTATC
105601 TAATAAACAT ACAGAACAAC ATTTTGTGAT GGCTCCTGCA AAACACCACC
105651 ACTTAGCCCA CTGAAGTTAG AAAGGTTTCT TAGAGCTCTT ATTGGCAAGA
105701 TCAGCAGACA CAGACACGCA CAGTAAGACA CAGACCTGTA TCACTGAGAC
105751 TGACTCACCT TGTGGATTGC CTTTAACTAC TTTAACTGTA CAACGATTAC
105801 CTTCCCATGA GAGTCACATC ACTTATAATT AAATAACCCA ACAGAATTTT
105851 CGTAAGCTAA AAATGCTATT TGCTAAATAA GCTTATTTTT TACTATCTTC
105901 TTTCCGCATT TAAGTCACGG AAGTTTTGTT TCTTATGCCG ACTAAATCAG
105951 AAAAGAATAG TAAAACAACA TTAATCAATG TCACTAATAT TCTTACTTGA
106001 CAGAAACTCA GTTTCTTTTA GTCCTCAATT TTTTTTCAAA AATTTTATGC
106051 ACCACTTCAT ATTAATTACC CTGCCTATTT TAGTTGAGTG AATGTAATGG
106101 CACATTATTT TAAGCCTCAA AGCCCAATCC AATAATCACG AATAGAATTA
106151 AAATTCACAA GATAAAGTAA ACAATCTAAT GAGTTGGAAA AATTTCTATT
106201 TTAAGAGAAG TCTTCTTCAA TAATTTTCTT TCTTCAGTAA CTTCAGAAGT
106251 GTACATGTTG AATTTTTGTT AAATACACAG TTATGTCTTC AGGAAGATTA
106301 CTGCTTAAAA AAATTCTACA TATGTACTTT GTAAACTGTA AACCAGAATA
106351 CCTTTGGTAT TGTTACTATT GTGATTTATA TTTGTAATAT TGAATACTAC
106401 CCCGGTCTAC TTTCATATAT AGAGTTTGCT AACAAAATAA TAGCTACTGT

FIGURE 3, page 30 of 87

106451 TTATGAGCAA CTCCTGTGTT AAACTCTGCA TGTAGTGATT TCACTTAACT
106501 CTTTCAAACC TTAGTGGTAG GTACACCTAT CCCCATTTTA CAGATGGATT
106551 AAAAAATGAT GATAGGACAG GTTTATGTAA ATGTCTAAGG TCATACAGCT
106601 AATAAGCAGG AGAGCTACAA GCTAGCCCAG GTCTTTCTCT GAGGTATGAA
106651 GATACACGTG TGTGTGTGTG TGTGTGTGTG TGTGTGTGTG TGTGTGTGTG
106701 TTTAACTTCG AAGCATACTA GAGAAGATTA ATGTAAACTT TTCTTAAATA
106751 GACAAAGACC CATGGAATTC TTCCTCAGCA GCATTTTCTA TGATGAGAAT
106801 GAGTCTAAAG AAAGAGGTTC CTCTTTGGAT TTCTTTGTTG TCTCATGATA
106851 TGAAGCAAAG AAGTGATGGC ATTTAATGTT GACTCAAACT TGCAGGAACT
106901 GGAAAACTTT TAGTAGTGTA ATTTTTATTT TGGCTTCAAT AATAACTCAT
106951 AATTTTTGAC TGATATATGA AATTCTAATA GTTCACATTT TAAGTGTCAT
107001 CATTCTTTGA CAAATTCTGT TCATATATTT TACTTCCGTT CTAAACTTAA
107051 GCTATCTTTG CAAACAATGG CAAAAATTTG TGAATTCGGA ATACAAGAAA
107101 TGTTCTATGC TTAGAATGAA ATTGGAGATA CTTAATGCTC ATATTCTTGT
107151 AATAACAAAT CAAAAATAAT TCAGTGTGTT TGTATACTAA ATAATGAATC
107201 TTTACTTGCA GATACTCTTC ATTTTTCTTT AGACGCAAGG AGATTTTTGT
107251 CATCCAGTAA GTTACTGTGG TAATGCAGAA CTCTGCTGTG ATTATTTTAA
107301 TCTTGTCAGG TGGTGTGCTC TATATTTTAA AATACATAAT ATTGAACATC
107351 TTGTTGTTTA ATGCACTATT TTTTCCAAAG CTCCCCCCAA AAGCTATATT
107401 TCTATTTACA ACATGTCCTT TATAATATTG CATGCTATTG ATAATGGTCA
107451 AGTTAATCTT ATCAAAATGC ACATTGACTC ATAATGTGCA TGTCCTGAGA
107501 ATTTGCTGTG TTCTCATGTT GTGTTAGATT TGATAGCAAA TTAAGTTTGC
107551 ACCTAGATTC CTGTACAGGC TTCTCATTCT GTTATCAACA TGACGCAAGA
107601 GTTGAGCTCT ACATCTGATG GGTGGAAACT ATATTTACAT TTCATACAAG
107651 CTCATTTTTG CAACTGTAGA TGGTTAACCT GTAAGGACCA AGACAATGAC
107701 ATTTCTTGTT CCCTGACTCT CTAGTGCATA CACAGAATGG CATATTTCAT
107751 GGAAACGTTA TTTCTCCACT GACCAATGGG TAGCCAACTG TGCACGCTTC
107801 CAGGCACTCC CCTGATGCTC AGAAATGCCA TTTGTATCCT GGCACAAACA
107851 TTTTTTGTTA CATTCTGAGA GTAGCATAGC AGAATATCAG CACTAGCAGG
107901 GACCCCAGTA ACTGATTGAG CGTCCCAAAC ATAATAAATT TCTTCATGCA
107951 AAGAATGTAA ATGAAGGAAT ATGAATGGAG GCAGAGAATA AAAAGGCATT
108001 TGATTTCAAA ATCACACGCC TTACTAAAGA AGAATCCGTC TTCATGAGCT
108051 ATAAGGCTGA ATGGGGCCAA AGCTCCTGAT AGTCTGGTTA ACCATGAATA
108101 ATACTCTGCA TTATTAAAAT CAAGGAAGCC CGGTCTATTT CTAATCTAAT
108151 CACATTTAGC ATTTGGGAAT CATAAGTAAC CTTGTTTTAA CTTCAGATTA
108201 ACTAGTTACC AAGTTCCCAT TGACAGAATT AAAATACTTT AATGAAAATA
108251 CATTTCCTTC AGAGGACCTG CTTGATGGGG TTCAAACATT TGTCAAAGTA
108301 AGACACTGTT AAACTGAAGA TTTAATTGAT CACATTACAC ATAAAATATC
108351 AATTTTCAAC CAGCACTCAA AGTTAACCTC TGGGCCATTC CAGACTCAGA
108401 GGCGGTTTGG TTGAGCAACT CTGCTGAATG TCTTTCTTCA TCATCATAAA
108451 ATAGAATCCT TTTCCTATTC TTTTTCTCCT TCTCTCTTTC TCTCTCTCTC
108501 ACTCTCTCTC TCTCTCTCTT GCTCTCTCTC TCTCGCTCTC TCTCTTTCTC
108551 TCCCTCCTTC CNNNNNNNNN NNNNNNNNNN NNNNNNNNNN NNNNNNNNNN
108601 NNNNNNNNNN NNNNNNNNNN NNNNNNNNNN NNNNNNNNNN NNNNNNNNNN
108651 NNNNNNNNNN NNNNNNNNNN NNNNNNNNNN NNNNNNNNNN NNNNNNNNNN
108701 NNNNNNNNNN NNNNNNNNNN NNNNNNNNNN NNNNNNNNNN NNNNNNNNNN
108751 NNNNNNNNNN NNNNNNNNNN NNNNNNNNNN NNNNNNNNNN NNNNNNNNNN
108801 NNNNNNNNNN NNNNNNNNNN NNNNNNNNNN NNNNNNNNNN NNNNNNNNNN
108851 NNNNNNNNNN NNNNNNNNNN NNTATTCATT GAGTCCCTTG CTCAGGGCCC
108901 CATCCATCTC TTCACATAAC TTTGATCAGT CTCTTTCTCC TCTCTATCTA
108951 CAAATTCTAC CCTGTTGCCC CGGATGTAGC TAAACAATGC CCATGGTTTT
109001 CATTTAGAAT ACATGGTTGA CAAAAGAAGA CTTCTGGCAA GAATATTTCT
109051 TCAAATGTGC TAATGTGGAA AGGCTTAGTA ATAAGGAAAA TTCAACTTCT
109101 GCCACACTGG GGATCATACC TCTGAGCTTT TTGACATCAG CAAGAATATT
109151 GCATTCACTT CTCATCTAAA AGGCCATTTC ATCTTGTTTA AATAAAAATA
109201 AATAACAATT GAGGGCCGGG CGCGGTGGCT CACGCCTGTA ATCCCAGCAC
109251 TTTGGGAGGC CGAGGCGGGC GGATCACGAG GTCAGGAGAT CGAGACCATC
109301 CCGGCTAAAA CGGTGAAACC CCGTCTCTAC TAAAAATACA AAAAATTAGC
109351 CGGGCGTAGT GGCGGGCGCC TGTAGTCCCA GCTACTCGGG AGGCTGAGGC
109401 AGGAGAATGG CGTGAACCCG GGAGGCGGAG CTTGCAGTGA GCCGAGATCC
109451 CGCCACTGCA CTCCAGCCTG GGCGACAGAG CGAGACTCCG TCTTAAAAAA
109501 AAAAAAAAAA AAAAAAAAAA CCAATTGAGT ATCTCTCAAG TGCTAGGCAC
109551 TGTTTTAGGC ACTGGGAATA GTGTGATGAG AAAGGAAGAA ACATTGCCTC
109601 CAAAGAGCTA TCCTTCAAAT TTAATGCTTC TTTTAAACTG ATTTGTCCTA
109651 CACATATGAG AAGATATGTT GAGAAGGTAA TACATATCAT TTACTATTAA
109701 TTGTTTTCCT GATTTAAAAA AGTATTACAT GGCCAGGCGC GGTGGCTCAT
109751 GCCTGTAATC CCAGCACTTT GGGAGGTCGA GGCGGGTAGA TCCCCTGAGG
109801 TCAGGAGTTC GAGACCAGCC TGGCCAACAT GGCAAAATCC CGTCTCTACT
109851 AAAAGTACAA AAATTAGCCA GGCATAGTGG CAGACACCTG TAATCCCAGC
109901 TACTCAGGAG GCTGAGGCAG GAGAATCGCT TGAACCCAGG AGGCAGAGGT
109951 TGCAATGAGC CGAGTTTGCA CCATTGCACT CCAGCCTGGG CAACAATCGT

FIGURE 3, page 31 of 87

110001 GAAATCCCAT CTCAAAAAAA AAAAAAAGGA AGTATTCTAT TACTCACTTA
110051 TGGTATATTT CTCTTATAAA ATTTTAGAAT CAGCTGTATA GGACCAACCA
110101 TGGGTTAGGA TATTTTAAAT TTATATTGAG CACCACGGAA ACATCAATGA
110151 TTTGGTAAAA GAATACAGAA GGATGTGACA GAATGCAGAA GGATGTGAAA
110201 GAATGCAGAA GGATGTGAAA GAACAAAATA AAGAAAACTA ATAGGAAATA
110251 ACAAAAATTA AGGCACCTTT AAAAGTATTA AAATAGATGC TTTGGATAAG
110301 CGATAGAATA TTGTAGAAGT AGATGTAATT TATGTGTCAT TAGTGACTTG
110351 ATGAAATATA TAAACTAAAA ACTCACACTC AGTATCATAC AAAACTTGGA
110401 AATATTAATA TTGTACCAGA GAAATAGATT CTTCACAAAT TTAATCTAAG
110451 TAGCAAGTAC ATGCTATGGG ATACAAATAC ATATTTTTAC ACCAATTGAC
110501 AAATTTGAGA TTCTTTTTATT TTTAACTTAA CATCACTGGT TAAGTAGAAG
110551 AAAAGTTTCT CAGTTTGTCC CATACCACTG GTAATGCTGG TTGAAGCTGC
110601 TCAGCTATAG GTTATCATCT GTGGCTCTCT ATTAGGACTA TATTTTAATT
110651 CCCTATAGAT TTCAACTAAT TGACCTTGAG GGAAAGCTGA GTCTCTGTGA
110701 CAATATGGTC TTCAATCACC ACTGCCAACA TAAATAAATG CTTCCTTTCT
110751 AGATCCATCA AGAGTAATCT GAGTGGAATT TAAGTTTTTG ATAGGCTTTA
110801 AAGAAATGAG TCCAGACGTG AAATAAGACA CTTTTCAACC AAAAGGATAT
110851 AGAATTTAAG ACAGTTAAGA TTCGTGTAAT AAAAAGTGTT TAGCCCTTTC
110901 TATTGGAAAT TAGTCAGTTA TCTTATTGAA ATCTGGACAG TTCCCAAATT
110951 GATTTATCCA GTAATGAACT GATTATAGTC TGACAGTAAC CTTCACTATC
111001 ATAAATGAAT ATCCTACCAG TCTAAAAATG CTTTCCATTT AACAGTTTTT
111051 TTTTAAGTTT TTAAAATGTT AATAAAAAGT TTTCTATTTG AGTATGTTTG
111101 AGTATCTCCT TGGATCACTT CATTCGAAAC TAGCACTCCT GAAATAGCAT
111151 TGTTGATTTT CATGCACATC AATTTCTGTG AGTTTCTAGT GCTTATTTAA
111201 GCAAACAGTT TTTCCTATTA GGAATTTAAT TATACCTCTC AGTGATAAGT
111251 TAGTGCATTT TCCTTATAGT ATGTCCCATT TTCTTTTCTA ATTCTCTCTA
111301 TAAATCAGTC AAATTAATTT TTTTGTATAT AAACATTAAA GCTTAAAACC
111351 TCAAAGAAAA ATACAATTTA GAATGTAGCC AACACCTAAG GGAGAAATAC
111401 ACCTATACAA CATGAGGCTA AGAACGAAAG CAATGATAAG TATACTACAG
111451 ACAACAATGA GGAAGGAAAT ATCTAACTTT TATTTGAAAT AGTCAGGTAA
111501 TGTACCTCAA AATGTCTTCT CAATTTGAGC ATTCCTAATA GGTATTTGAA
111551 GATTTCAACT CACAAATGAT TGTGACATAA GTACAGACTA GAAAATTACA
111601 TAAAAACTGG ACTACTAGAA GCTTTCTTAT CTTATATAAA CATAAATGTG
111651 AAGAACAGAT TCTAAAAAGT GATTGGATTT AGATAAAAAA GAGTGATACA
111701 AAAGAAAATA AAGCCAAATC AGATTCCACC TCTCTTTTTC TTAAAGTGTG
111751 TGCCTATTTG TTTATCACTT GAGTAGGCAA GAGCAATTTT ATTGTTCATT
111801 TATCTAACTT CCTAACAAAG TACACCTGTT AATTTATAAC GTTAGGTTAT
111851 CTGCTATGGC TTTTGCTTAG ACTCACATGC TTTTTGTTGA TAAATCTATT
111901 GATTATACGT ATTTAAAGCT TTGAGTTAGG ACCTCTTGAG AATTCTCAGT
111951 TTCTTAATAA TTTAGTGTGA AAATGTATTC AATTCAGATA TTCCCTCACA
112001 ATAAAGCCAG AATATTCATA TTTTGCTTTC TGTGTATCTT AATCTGAATT
112051 CATCCACAAT TTTATATTTG ATATGTTTTA TTTAATGTTT ACTGTGAATA
112101 ATGTTATGAG GGACATCTAG TAAGCCAAGT GTTAATCCTG CCCCAGCCCT
112151 GAAGTATATA TGAGCCCAAA CACTTGTATC CTTAATGCAG GGACTTAAAT
112201 AGCCATAATA CAACATAGAA GATGATTTGT CCTTGGAAAT TTGATTTTAC
112251 AGGCAAAGGA AATTATTTTC TTTTTAGTAG AACAGAGTAA GATCGATAGG
112301 GTTGTTAACA TTTGAATCAG GTATTAAAGA ATAAGTAAAA TTTCCGTTGT
112351 ACGAAGAATG CCTGGAATGG TATAAAATTG AGAGGGAGGG ATATATAGAG
112401 AATATCTGGA GTGCAAACAG GATGCATGAA GAGGAGTTAC AAGGAATAAT
112451 GTCAGAAATG TGGGCATGGT TAGAAATGTT TTACATGATT ATATGAAAAC
112501 TGAATTATTA TGGTCATTGT ATTAGAGATT TGTTTGGGAT CTCGAATTGA
112551 GAGCTAGAAA TCCAGACTTG GATTTGAAAG CTAGATATTC GTGACTACTA
112601 TATTTTAGCA CAATATAGTC TATCCATCTT TGAGTAAAAT TAAGAGAATA
112651 TTCTTTTGGA AATAATGGAA AAAATCCCTT CCTTATATCA GTATCAATTG
112701 TAGAACAGTA TGGATAGGAG CAGCTTGAGA TGAACAAACT AAATTAGCAA
112751 TAGTAATTAT CATACTATTG ATAGTAACCA ATACTTATGT ATTGCTTACT
112801 AAAGGCAGAG ACCTTTAAAT ATATGAACTT AATTTAATAC ATTTCCCAAA
112851 CTAGGAAACT GAGGCACAGA AAAATTAAGT ATTGCACATG ATAATATAAC
112901 TAGTAATTGT TCAAGCAGGT ATTTGAAACC AATAAAGGCA TCATATTTTC
112951 TAATAAGGCA ATAATTCACA AATATCCACC CAAACCCATT ATAGCCAGTT
113001 ATGGTTTAAA ATATCTTTAG GCGGACATCA TGAAATGCAC ATCTTTATTA
113051 TCCCCCTTGA GGGGTGAGGG AGCTGGGGTA TTTATCCACC AACTCTGGTT
113101 AGTCATTGGT TGATGGATGT TTCTTGGAAT ATTTACCCTC CGATGCTTCT
113151 AGCCTGGATG CAGGAGACAC TCGAGGAGAG TGGCAGGTCC TTGTAGTAGG
113201 AAACTATCTC CTTGCATGCG AATGTTGAGT GCCCAGGCGA TGTGGGTTAG
113251 GCACCAATGA CATCTGCACA AACTTTTAAA AATCTGAATT TCACAGCACT
113301 TAATAAATTT ACGATGATGT ATTTCTGCGA AAAAAAAAAT CTTTAGGGAG
113351 AGATTTTAAA TGCAAAATGA ATTAAGAATA GTGAAACAGC AACTTTTGGT
113401 AGAGTTTTTC ACTGAAAAGA CATGAACTTA AAACAAAAAA ATGTATATTT
113451 ATTCAATTAA TCATAACTTC TGAAATGAAG AATAGAGATG ATTAAAGAAG
113501 AGCAATAATA TGAATAATAT TTTGCTTTAG CTATTTCTTG CTCACTTTTC

FIGURE 3, page 32 of 87

113551 TTTAATATGA TTATTCACAT TTAATGTCTC TTAGGGATTT CACAAATGTA
113601 TACTGATGCT TCAAATGGTT TATTGACATT TTCCCAGAAA CCAACATCTA
113651 CTTTAGATTC TAGTTATCTC AGTAAAAATA CTTTTGCAGT ACCGGCTCAA
113701 ATGATCCTCT AGGAAAAAGG AATCTCTCTG CGATGGGTGG CAGTCTCACT
113751 GTCCTTATAT AGGTGGACTA CTAGCCTGTC ACTAAATCAT ATATATTGTG
113801 CTTAAATTTT GCCAATCACA ATGGAATAAT ATTTGCTGTT ATTATAAAAG
113851 TTATTTCCAC AAAGTTCAAG AGTTTCTATG TCCATGTGGT AGCAGGGAAA
113901 TAGACCTTGG TAATCAAAGC ATCTCAGTCA TTTATATCTT AAGTTCAGTT
113951 GATCAGAATT TACCCAACAC AACCTTCTAT TCTTTCCTAT TTCTGAAGAA
114001 CAAGGTATCA TAGGGGCACT GGGCAACAAG TTATCTTAAG GGAGCTAGGT
114051 AGTATGTGTG GATGTAGCCT GTAGTTTATC TTTCTTTCTT GCTGGTCTTC
114101 GCTGAGGGGT AATTATTTTT AACAAAGATT GATTGTGGCT TCAGTCCCCA
114151 CTGCAACTGT TACTATGTCA GAGATATTTC CAGGGCCTCC AATATTCAGA
114201 CATTCTATTT TCCCTTCCCC AAATCAAAGA TTCTTCTCAT TTGGTAGCCC
114251 TTTCAGCCAT CTCCATATCC ATCTAGAATA AGGAATTCTT TCTTGCTTTC
114301 TTTAAATCAC TCTAGGGTAT TGTGGGGCAC TCTTAAGCTT ATCCACCAAG
114351 ACTCTTTGTT AGTCACTGCT ACTTTGTCAC TTAGATGCCC TGTTTGGCAA
114401 TGGAATAGTC TATCACTTTA TGTTTACCCT GAGAAGCTGG AAGATACAAC
114451 ATCTCTTTCT GCTTGGGGGG CACCCATCAT TAACTGAGAA TTCTAACATT
114501 CTACTTTGTA ATACCTGGTC CAGCATCCCC ATATTTTTCA ACAATTCCTG
114551 TATTGTAATG AAATATACTT CCTTTTAAAT CCTGTTTTCT TCATTGAATA
114601 CACCTCTTTT TGACCATTTT CATATTTATT ATGCTCTGTT TTTCAAACCA
114651 TTTTTTTTCT TTTATTCATT CTTTGCTTCA AAAAACATAT CTTCTTACAA
114701 ATATTCTTCA ATTAAAGAAT ATAGTAAAAT CCCTAATATT ATTCTAGATT
114751 TAAAACTTTG AAAAAGTCAT ATGTTCCTTA GTTCATTTCA TTATATTTTG
114801 TGCCTTTTGT GTTTTTTGCA GTGCTAATTT GTTGTGCATG ACGTAAGTGT
114851 TATTAATGAT ACGCCCCTCT CTAAGTTTGT GTATGTTGTG TAGCCTATTT
114901 AGCTGTTAAA ATTATTTTTG TTTACAGAGT ATAAGTAATT TGGCCAATGA
114951 TCTGTCACAA AAGATAGGTC TAAAATAATG GAAATAGTTA TAATTTGTTG
115001 TTGCTGTGTA TTTATCCAAA CTCACTCATG AAACAATACT TAACCAATGT
115051 GATGTCATGT TTCATGGATT CATTCTGTCT GGTTCAACAC TTTCTATATA
115101 TAGAGGAAAT ATTTTTAAAA TCCACATTAG CTCTTTTAGA CCACTAAATA
115151 CCATGCAATA TATTAAAAAG TGATCTATTT TTAATGTAGT ATCCTAAATG
115201 CCTAACATTT TTAAGCATTT ATAATGACAT TTATAATAAC AACAACATCT
115251 TTTCAGCTCG AGAAAGAATG TAAATTATTT GCCATGTTTG AGTCCAAATA
115301 ATGTAATTTC AAAAAAATAA ATAAAATTTA AAATAATGAT CATATATTAG
115351 TTAAAGGCAT AGCACATTTT ACATTATTGA TTTATTATAA TTTTCTGACT
115401 TTAATCTACA CTTCTTTCAG AATTAGCTGT CCACTCTGAC TCACAATGCA
115451 TTTAACACAA TCTCTATTGC AGGTTACTTA GTTATAGAAA ATCCATCAAG
115501 TAAGTTTGTT AAATATTTTC TTTCTTCTTT TTGAATATCA AAGTTAGATG
115551 CACTGACTCA GTAGAACCTT AATGTGTGAT TCACTTTTTG TATGTTTGTT
115601 GGAAAAACCT CCAAGCTGGA TATAAATCAT AAAAGCATGA CTAATTGCAT
115651 GGTAACTGGA GAAATGCTTT CTCTCTCTCT GGGGTGAAGC CTGCATGTCT
115701 GTATTTTAGC TTGGGAAGTA ATACGGGGAT ATTTAAACTC CTTGGGGTTT
115751 GAAAACCATG TCATTATGAG AATGAGGTCA CTGCAATATT TTATATCTTC
115801 TAAAACCTTG TAATGTATAA AATGTTTTCT GTCTGACAAA GAGGTATTAT
115851 GTGCTTTAGG AGTCAATGAT AACTTCATGC CCTTACATTT ACTTGAAAAA
115901 TTTTCTTCAT TAAAATGCTA AATCCTTTAT TTAATGTCAC TAAAAAATTG
115951 AAGGAATTTT GTGCCATGAA TACAAAGAAA GTGAGCTTAA AGAAGAAAAG
116001 TTAATTTTAT AAGTATAACA GAGTGACTTT AAAAAGCTGT GTTGTTTGTG
116051 ATTTTGGGGA TGTCCATTGT TCTTTAACTT GTTAAAAGTG AAGCCAGTGC
116101 CAATGCTAAC GCGAACAAAT ACAATCTAAC ATGACCCTAT TTTATACCTT
116151 TCTTTACTTG GAGGCCAATA AGCAAGAAAT CCTTCCTGCA ACATGTTGAA
116201 GAGCTTTGCA CAAACAACAA CCTAAAGTTT CAAGAAGAAT TTTCGGTATG
116251 TTACTAGCAG TTGTCACAAC ATTGCAAGAC CTCCAGTCGT TTCATGTGTC
116301 ACATTTCATG TCCATTTTAA GCAAGCAAGG CCATGAAGGA CTCTGGCCTT
116351 GATAATCAAT ACCCAATTAC CAGGTTGATT GTTTTGATAG TAATGTTACA
116401 CTGGGCCGCC TCTGGTGCAA CCTGATCAGA ATTATTCACC TACTGTGTCA
116451 GGAAAAGGTG GTCTTCTTCA GACCTCCCCT GTATTGGCAG CATGACCTTG
116501 TCTATTCTCT GCTCTTTCAT CCAGATGTAG GTGCAAATGT AGAATGCCAT
116551 ATTCATTAGT TTGTTTTGTA TTCAAGGTTT AGGTCATACT ATAAGTGTAG
116601 TTTTATATTT AAGTAATTAT TTTACATTTG GACACTAAAT TATTTCATTT
116651 TACGTTTACC TACTTGGTTT ACATTAGTGA TATAGATGAA TGTGAGATCA
116701 AAACTTGAAG CTTCCAGAAA CTATAAGAAA ATTATTTCTA GAACTGTCTA
116751 AAAATAAAAA AAAAGATAAG TAATGTCCAC GTTTTACAGG GGGCCTTTTT
116801 AAAGTTACTA TGGAATAAAT GCTGTATCAT ATAATGAAAA TGTATAAAAT
116851 TAAGAATTTG TCACTTTAAA TCTACTTAAA AGTTGGGAAT AGTTTTTTTT
116901 TTAACATTTT GTATATCTAT AAAATTGAAA TTATTTAAAA ACATAAGGTA
116951 GATATCAAAT CTTCAAGCTA CTTTAAGAGT TATAAGCATC TTTTCTAACT
117001 TAGATGATTA TTTTGTTATT AAGAAAGACA GATTTCTACA TGTCACCAAA
117051 AACATTATTT CTATTTTATT TTTTTCCATG AAATTTCCAG TGTGTGAACT

FIGURE 3, page 33 of 87

117101 CCTGAAACAA AGAATAAAAC AATTGGGTTA AATAATTCAG AATTATAATA
117151 TTTCAGTCTC TTAGGGAATA ATAACAAAAA TGAGAGAAGA TTAATGGTAT
117201 TTCCTGCAGC CTTTTGGTTA TGCTTCTTAA GAAATATTGG TCTGGACTTA
117251 ACAAAATCAA TAGTGCCATA AAATTCTTCC TAGCATTTAG ACAGCAAGAA
117301 TTCTCAATTT TTCAGGAGCA AAAGTGTAAT TTCCCTAGAA TAAGAGTGAA
117351 TGTAATTACA TTATGCATGA CCAAGTAGAT AAAAAGTTTT ATTAGCAATA
117401 ACATTTTCAC ATATATGAGA AAGTTTCTAG TTTAAGTTTT TTGAAGACCA
117451 TAGTTTGAAG AACTTTTTAA AAATTTCATT TTGTCTAATG CTTTGTTAAG
117501 AATTTCTAAA GCAAATTATT AAATTATGTT TTAATAAATA CATTTTTGGT
117551 GCATATATTT GATAAACCTT TTAACTCAGG ACATATTCAC TCATATCTTA
117601 AATATTTATA AGTTCCTACT ATGTGATAGG CATTGTATTT GGCACATACA
117651 ATCAGCACTT ACCAGCTAAG TGACTTTGGG CAAATTTCTT AAACTCTCTT
117701 TGCCTCAATA TCTTCATTTG TAAAATTATA ATATCTACTT TATTAAATTA
117751 TGAATATAAA ATGATTGAAT ATAAGCAATA CTAAGAACAG TAGCTGGCAC
117801 AAGTATTAGC TATTACGATG ATAAATTCTA CCATAAAGAA GCTCATATTA
117851 TGGTAAGAAC TGCAGATGTG TAAAAATTGC AAATTTACTG TATCTTGATG
117901 GAGATATGCA TGAAGATTGA GGATCAAATC TGTTTGTATA TCAACCAGAA
117951 AAGAGTTTAT AAAAAAGGTG TCTTTCAGGA TGAACTTTAG GATGAGCAGA
118001 AGTCTAATGA GAAGGTAAAG GAAAAAAGGT GTTCCAGAGA CAGGAAAAGG
118051 ATAGGAATGC AAAAACGGTC TAACTCATCT GTGGTCCCAC TGAAAAGAGA
118101 GAAAGCAATA GGAGAAAGAG CTAAATAGGG AGAATTGTGG CCTTGTGCAC
118151 CCTGATAAGG ATAACACTGC CCAGTGTAAC ATTACCATCT AAACAATCAA
118201 CCTAGTGTTT GAGCATTGCT TACCAAAGCC AGAGCTGCTT AAGTCTAGAA
118251 ATGGAAACTT TTATGTGAAA TAATTATAAA ATATAAGTGC TCTTTCAGTC
118301 TATTTAAACT CACCTTTTTT CTCCCTTCTT TATGTATTTC CAAAACTTTG
118351 ACACAAGGAA GCTGTTCTAG GACTCCTTAT TGGGTTAAAA AAATTTTGTA
118401 AGCCTTTGGT GCCAACACAT CAGAATTCAG ATCTTACACC ATTCCTGTCC
118451 CTTAATACAT ACCCATATGT AAACAATTGT CCAGATTTTA ATTTTGAGAA
118501 AAAAAAATAA GAAAGGGAAA CTTATCCAAT TAAAAGAAAT AATTTATATT
118551 GATGTTGAAA AATTGTTAAA ACACATATTT TTAGTGCTTT TTATGGAATT
118601 TGGCAAGTTG AGATTTCTAA AATGGAAAAC TATAAATTTC ACACATGTAA
118651 ATTTTCAGCT CAACAAAATA ATGAACATAT TTTCTTATGC CAGACTTTTT
118701 AATGATGCTT GCTTTGCCAA GAGCAAGGTA GATAGATAAT ATCATAAATT
118751 TTCATCAAAT GTCAATAATA GATCTTCTTG ACCCTTCATC TATATCTGAT
118801 AATTCTTAAT TGCACCTTTG CATTCCATTA TTGATTTAGC AATGCTTATT
118851 AAGAGCAGGA ATTGACCTCT GGCATCTTCT CAAACTGACC AATGTTGTAC
118901 CAATTAATAG GCATGAAATC ACACTGCCTG AGGAGAGAAA ACAAAAAATA
118951 AATCATTGAA ATCCCTTTTC CTACTAAGTA GACATTAAAA TATTAAACAA
119001 TAGTGTGTAC CTGATGAAAC CATTAGTAAC ATATGTAAAA TGGTCACTAA
119051 CATGGTTGCC ACATCTTAAG GCTTCCCAAA GTGCAAAGAA ATTATCTCCG
119101 AAAGAGCAAA ACCCAGCTGA CCAACTTTAT TCAGGATATT TTTGGTGAAA
119151 GCCTAGGTAA ACTCATTACT GTTAACTTGA CCTTGTTTCC ACAGTTATGA
119201 TAGGTGTTTT TAATTTAAAA ATTAAAAAAA AAGTTTAGGA CAAATAACTG
119251 TCTTTTAATA AGTGAAATTT CTTGTTTACC TCTGATAAAT GTAAACTTTG
119301 TAATGACTTT ATTTTACAGG AATTACCAAA ATTTCTTCAG GATCTTTCTT
119351 CAACTGATGC TGATCTGCCT TGGAATAGAG CAAAAAACCG CTTCCCAAAC
119401 ATAAAACCAT GTATGTGCAT TTGTTGGTTT TGGTTTAGCT AGGAAATATT
119451 TTTAAATGCC TACCATCTTA ACTTTTTTGT TTCCTTAATA TATTTTATTT
119501 TATATTGTTT GAATTATAAT AATGTATTTT ATTGGCAGTG ACTACCAAAT
119551 TATATATCTT TTGCTTTGTT CATATTTAAC TAAAGTTAGT ATACGTGGTT
119601 TTCAGTTTGT TCACACAAGT TCACTTATGC AGGTGCAAGA AACTGTAGAC
119651 CTAATAGTTT CTTAGCTTTG TAATTAAACC CAAGTAATGA ACCTGTTTAA
119701 CATCTTCCTA CAGACCTAGC ATCAAATGCA AAGGGAATAT TCTCACTTAG
119751 CTTTGTGCAT TAGTTTCCCT TCACAGCATA GCAGTGTTTT CCTATGGAAC
119801 ATAAAAAAAA TGCATTGTAA AATATTCATT GAAGACCAGA GTAAATGCGC
119851 ACTTACATGA ATTCATTTTA CATATGAGGC AGAATGAGCT TCACCATAGT
119901 ACATACAGCT TCATTTTTCA ATCAATAAGA AAATAAACAG TGTTATTGCT
119951 TAAAGAATTA ACAGTGATGT GAAAGGAAAA TAGGACATTT CTCTGTTACT
120001 AATAACTATA TGTTTGCTAT TATATTTTTG AACAGATATC CCTATTTTCA
120051 ATATTCTGAT TCAATACATT TTACACTATG AAATTAAAAA GTGACATTGT
120101 GATGTCCTGA AACGTTTCAA AGTCTAGAGT TTTGAAATGT TCCCAATTTT
120151 AAAGATAATA TACATCTGTG TGTGTATATA TATATTTTTG TCTATGCTTT
120201 TTCAAATGTA TATTGGGGGA ATAGCTACAC TTCTTAAAAA TTGAATTCTT
120251 CTTTCTAGAA AGACGTAGAC CTAGAGAAGG ATGTGATCAT AGAATGTCGA
120301 ATTGTAAAGG ACATGCATAG GAAGAAACAG ACCAAATTCT GATATTCTAG
120351 AACTAGGGAA TAACTTATGA AGTTCACGAA GGAAACAAAT GTAAGGAAAC
120401 ATGATATAGG AAGTAGTAAT CTACTAGAAC CTGTTAATTT CTAAGAAGTA
120451 GAATAGGATG AAAATACAAA TAGCTTTAAC CACCTAAATC CTTTCTGCAA
120501 CAAAACAAAT CATAAGTAAA TGATTTTAAG AGCAAGATAA CAAGACTCAG
120551 TCAGAGGAAA TAAACATTCA TAATTTCTTT TTCTTTCTTT CTTTTTTTCT
120601 TTCTTTCTTT TTTTTCTTTC TTTCTTTTCT TTCTTTCTCT CTTTCTTATC

FIGURE 3, page 34 of 87

120651 TCTCTTCCTT TCTTTTCTTT TCTCTTTTCT TTTCTTTCTT TTTGGACTTT
120701 TGATCTTGTT GTCCAGGCTG GAGTGCGGTA GTGCAACCTT GGCTCACTGC
120751 AACTTCTGCC TCCTGGGTTC AAGCAATCTC CTGCCTCAGC CTCCCAAGTA
120801 GCTGGGATTA CAGGCATGTG CCGCCATGCC CAGCTAATTT TGTATTTTAA
120851 GTGGAGATGG TTTTTCACCA TGTTTGTCAG GCTGGTTAAA TTTCTAAGAC
120901 CAGGACATTT TTCAACGCAT CCTTTTATTC TTTCTTTTAG AGAGTTAACC
120951 TAGGTTGGAT GCAATGTAAG TATAAAAGTT ATGGACATTC CCATGTCTTT
121001 ATATTTATCT GCACCTAAAT TTCATCCAGA CTGTTTGCTT CATGCTTATT
121051 TGGTGATATT CTGTGAAAAT AAATACTGTA ATCTGATTAA GGGACAGTAA
121101 CTGTGGAATA ATTAGTATTT TTTCAATTGT ATAGAATTAA TGGCCTGGCG
121151 CGGTGGCTCA CGCCTGTAAT CCCAGCACGT TGGGAGGCTG AGGCGGGCAG
121201 ATCACTTGAG GTCAGAAGTT CAAGACTAGC CTGGCAAATG TGGTGAAACC
121251 CCATCTGTAC TAAAAATCCA AAAAAAAAAA AAAAAATTAG CCGGGCGTGA
121301 TGGCAGGTGC CTGTAATCCC AGCTACTCGA GAGGCTGAGG CAGGAGACTT
121351 GCTTGAACCT GGGAGGCAGA GGTTGCAGTG AGCCCGAGAT CGCACCATTG
121401 CATTCCATCC TGGGTGACAG AGCGAGACTC TATCTCAAAA AATAATAATA
121451 ATAATTAATT TATAATATAT CAGTATATAT AAAGTAAGTA ATTCAAATAT
121501 GTCTAACTTA CTTCCAAGGG AGTGTCTAAT TTGAAATATG TAAAATTTGA
121551 TAGATCAGAA AGTTTTTTTG CTGTGTGACT TTTNNNNNNN NNNNNNNNNN
121601 NNNNNNNNNN NNNNNNNNNN NNNNNNNNNN NNNNNNNNNN NNNNNNNNNN
121651 NNNNNNNNNN NNNNNNNNNN NNNNNNNNNN NNNNNNNNNN NNNNNNNNNN
121701 NNNNNNNNNN NNNNNNNNNN NNNNNNNNNN NNNNNNNNNN NNNNNNNNNN
121751 NNNNNNNNNN NNNNNNNNNN NNNNNNNNNN NNNNNNNNNN NNNNNNNNNN
121801 NNNNNNNNNN NNNNNNNNNN NNNNNNNNNN NNNNNNNNNN NNNNNNNNNN
121851 NNNNNNNNNN NNNNNNNNNN NNNNNNNNNN NNNNNNNNNN NNNNNNNNNN
121901 NNNNNNNNNN NNNNNNNNNN NNNNNNNNNN NNNNNNNNNN NNNNNNNNNN
121951 NNNNNNNNNN NNNNNNNNNN NNNNNNNNNN NNNNNNNNNN NNNNNNNNNN
122001 NNNNNNNNNN NNNNNNNNNN NNNNNNNNNN NNNNNNNNNN NNNNNNNNNN
122051 NNNNNNNNNN NNNNNNNNNN NNNNNNNNNN NNNNNNNNNN NNNNNNNNNN
122101 NNNNNNNNNN NNNNNNNNNN NNNNNNNNNN NNNNNNNNNN NNNNNNNNNN
122151 NNNNNNNNNN NNNNNNNNNN NNNNNNNNNN NNNNNNNNNN NNNNNNNNNN
122201 NNNNNNNNNN NNNNNNNNNN NNNNNNNNNN NNNNNNNNNN NNNNNNNNNN
122251 NNNNNNNNNN NNNNNNNNNN NNNNNNNNNN NNNNCAGAGA TTGATTTCAT
122301 TTTAATAGAA TTTGAATTTT AGCTAATAGA ATTTGAATTT TAGCTTGAGC
122351 CAGCTAAATG AAGTCCATTG TTTCTCTCCC CCTGAGTAAT GTAAGAAGCA
122401 GAATGCCAAA TATCACAGCA TGTTTTAGAA GACATTAGCT TAAAACACTT
122451 TAAGATGCTA GAATTAGCAG CAAATACTTG CAGAAGAGAT TTCCAAATCT
122501 CCGTTTGACA GACGACCTAT GACCTTCAGA AATATTCCAA CACCACAAAG
122551 AAAAGTTTAG CTTGTAGTTG ACTCAGATAG TTATAAGGAG GTGTATCTAG
122601 TGAATAGAAA CATAATGATT CTCTTCCTTA GTAACAGGAC TAGTTACAAT
122651 GTCATTAAAC TAGATCATAT AAAATTCTAT ATTTGGGACA TAAATCATTT
122701 GCAGAAATGT GTTTAATCAT TCCCATTTCT AAACATAACC ACATTGGGCA
122751 AGTAATTGTG ATTACTAACA ATACAACTAA TTCATTTTAA CATATTATGT
122801 GCTTAAGTTT TAAGAATGTA AGAACATGTA TTGAGTGCCT ATTATAAGCT
122851 TTCATGTAAA TTTTCTTCAA GAGGATTATA CAAAATCTGT GTTATAATGA
122901 CATCTTGTAG CTGAGGTAAC CAAGGAGCAG AGAAGCTTAG CAATTTACCC
122951 AAGCCCATAT GTATGGTAGG CAGATCATCT AGAATTCAGA CCCAATCCTG
123001 TTTACCCATT TTTCCTCCTT GAAAACAAAC AACCCATCAA AACAATTAAG
123051 TAGTGGATAT TTCATGTTTA GTTAAAAATC ATTACTGGAT GTTTCAATTA
123101 TAATATCAAC TTGGTAAAAT TTCTCAGGAA AAATAGTTTC TGACATTTTT
123151 CTCTGAAGAA AAGTAATGAG TACAGGGTAT CTAGTTTTAC TAGCTCTTAA
123201 AATATTCTAA AAAGTAGTAA TTAGAAATTT GAAAGAAAGA ATAGGCAGAT
123251 GAATTAATGG AAAAGAATGA ATGGTCTAGA AATAGACCTA ACTACCTAGA
123301 AAACAAAGTG GTGTTCCAAA TCAGGGACAA AAGATGGAAA TGTTAAAAAA
123351 TTGATACTAT TTGTTGTTCC AACGACANNN NNNNNNNNNN NNNNNNNNNN
123401 NNNNNNNNNN NNNNNNNNNN NNNNNNNNNN NNNNNNNNNN NNNNNNNNNN
123451 NNNNNNNNNN NNNNNNNNNN NNNNNNNNNN NNNNNNNNNN NNNNNNNNNN
123501 NNNNNNNNNN NNNNNNNNNN NNNNNNNNNN NNNNNNNNNN NNNNNNNNNN
123551 NNNNNNNNNN NNNNNNNNNN NNNNNNNNNN NNNNNNNNNN NNNNNNNNNN
123601 NNNNNNNNNN NNNNNNNNNN NNNNNNNNNN NNNNNNNNNN NNNNNNNNNN
123651 NNNNNNNNNN NNNNNNNNNN NNNNNNNNNN NNNNNNNNNN NNNNNNNNNN
123701 NNNNNNNNNN NNNNNNNNNN NNNNNNNNNC AGTTTCACTT GTATTTAAGG
123751 AAATCAAAAT AAATATTATG AGACATCAAT TTGTATTTGT ACAAAGAACA
123801 TAAAGTGTTT AATAATACCT TGTGATAATG AAAGTAAGAG AAAACAGAAT
123851 TTTTCAAACA CTTTGGTTCA GAGTATGAAT TGTTAGAGAA CAATTGAGAA
123901 ATGTTTTTCA AAATTTGGAA TGCATATATA TAAAATCTAA AAATTTTACT
123951 GCTGGTAGTA TATTCTACAA GTACACTCCT ATATATATGC AATATGCAAA
124001 AATTTCAATT ATATCTATTC AACATTTTAT AATTACAAAG TGAATCATTT
124051 AAATAATAAT AAAAGGTTAA ATAACTACAT TATTATATAT TCAAACAGTG
124101 AAATACTGTA TAGCTTTTAA AAATAATTAA CTACATATCT TTGTTTATGC
124151 TGATACGGAA AGACATAGGT AAATGAAAAA AACGATTTGC AGAACAGATT

FIGURE 3, page 35 of 87

124201 GTATATCACT CCATTTGTAG CTAAAGAAAA TTAGAATATA AAGAATATGT
124251 ATAGAAAATT CTGGAAATAT ATACAAGGAC ATATTAATAG TCATTGTCTC
124301 TGGGTGGTAG AAATATGGGA GAAGAAATAA CTTTTTAAAA TTTACCGCCA
124351 TCTGTGAAAT TGGAATGTTA TATTATGAAC TCCTTTGTAT TACTTTTATA
124401 GTAAAAAAAG TAGTAACAAT TTAAAAAGCC AATTAACATT GATTCCTTAT
124451 ATTTTCTTCT AGATAATAAT AACAGAGTAA AGCTGATAGC TGACGCTAGT
124501 GTTCCAGGTT CGGATTATAT TAATGCCAGC TATATTTCTG TAAGTTACTA
124551 TTTTATATAT TTTATAATTG TATAAAACAT AATTACTGAA ATTGTATTAT
124601 CTTTCCAATT ACTTAAAACA ACAAATTTAT TACAACTCCT ATGGATCTTA
124651 ATATGCTAGT TATTTACAGC CACATTGTGT ACCCTTATTT TATAGATGTG
124701 GATATGGATA TGCCTAACAG AGATACTAAC TTATCAAAAA TTATTTCACC
124751 AGTGCGCGGC AGATGTTCAA CTTCAGGCTA CACATCCCTG ATCTTTCCAC
124801 TAATTCATAT GCTTTGTTAA TGTATTCTCC ATATGCAATG AAGTTTGCCA
124851 ATCTCTGTGA ATTAAAAATT ATCAAATGGA CAGTTATGTC CATATAACAT
124901 GAAAATTTAT TATGCAGCTC TTCCCTTCTA GATCTGCAGT CCTTCAAGCG
124951 GGTAATAATG CCATCACCAT CATAGGTACA TTGAAACCTT ATATGCACTC
125001 AAGATCTCCA CTTGGTTTGC AAATTCATGG AATCTTAAAG AAGGAAGTGC
125051 CTTGAATTTG ACCATTCACC TTGAAACTCT AAAAAATTCC TGTCAGCCTC
125101 TTTTGGCATT GATTCATCCA CTTCTTCCTA AGACGGGATT CTATCTCTAA
125151 ACAACTCTGC TTTACAGTTG TTGGGTTTTT TTTTAACCAA GTTATGTCTC
125201 TTTATATTCT TACCCACTGA CTTAAATTCT AATGCATAGC AAGCTTAACC
125251 ATCTTCATTA TGGTGAATCT ACAAATACAT GAAGATTTCC TCTGCTGCCC
125301 ACACTCTCCA TAGGCTTTTT CTTATCCATA GGTCTTCTCA TCCATGCCCT
125351 CTATTTCCTT CAGTTCTATT AAGGCTCTTG TTATATGACG TTCCACCCTT
125401 TCTCCAACGT CAAACATACT TGTGCTGTGT CTCATTCCCT CCAAGCCTTT
125451 GTCATGGAGG AAAAAAACGA ATTAGTTCTA AATCTGATAT TGGTTGATAA
125501 CTAATCTAAA ATTACAATCA TATATTGGGT CCTGTTGTCA AAGGAGTGAA
125551 TAATGGGAGA ATTTAAGACT TTAAGACTTT TTAACCAGAG AAGTGAAGGA
125601 AAGTTTAGAG AAGCTAAGGT ATTCTTTAAA TTTCATTCTA TTTTAATGCT
125651 AGAACTTTAA ATCTGTATTT AAAGAATTAC ATGAATTTAC TATTATGGTA
125701 ACATTTTATT CATTTATCAA ATGATTGATT CCCTCTAAAA TGTAATTCAA
125751 AATGTAAACA TTTTGGTGAA ATCTTATGCT TACAATTTCC ATTAAAATCT
125801 AAACTCTACA GCATGTTAAA GTTTTACTTG GATTTACAAA ATGATGCATA
125851 TATGCATTTA GATATTTACA TTTCATCACT ACTCTGATAA TCAAATGCCA
125901 TCAAGCAGGA CAAGGACAAC TGGTTGTATC AGTGACCTAT TGATTTGTAT
125951 CATTTTTTAT TCACCAATAA GTAGATACAA ATCAACAGCT CATATTGTCT
126001 AATGTTCCAT AAGGCATGAC AGTACAGGAT ATGAATATAA TTAAGAAGAA
126051 AAACAGACAA TTTTAGTAGG TGTAGCTGAA CCACACAGAT TATGTAAGCA
126101 AAGTAATTTT CGCAAACCCC CAGTGTCCCC TTGAAATATG GTAGGTTGTC
126151 AGCATACAAC TATGAGCAAA TGATAACGTG GTATGAGCAA TAAACTAGGA
126201 AGCCTGAAGA TATATATTCT GCTGTAATCA AGTGATGTTG TAATATAATA
126251 AATCTTACAA CAACGTCACT ATGACCCAAT GTAATGATAT GCATAATCAT
126301 TGCTGAGCTG CATGGTAAGC AGGCTCAGAT GGAAGGCACT TTACAAGAAG
126351 GCGGATTTCT ATATTGGGGC TGGCAGTGTA CTGTAGCACT CAGAGAAATC
126401 TCCTTTGCTC AGGATGTCAA GAACAGATGG GAACAGATGT AGCAATGATA
126451 CTGCAGTGGC CCTCACTTTC CACCTACGTA TTCCTACAAT CTTCACCTTA
126501 GAAAGAATGT CTGGTATATC AATTTCCGCC TACCCCCAAA TTTTATTCGA
126551 AAGCACTTCC AATTGAAAGT TTATGAACAC TTGTCCCAGG AGCAAAAGAC
126601 AGAGGTCATC TATGAATGGA TTCCGGGTTT CAATTTCTTT GGAAGCTATG
126651 GCAAAGGGAA GAGAACTATA GAGGGAGGTA GGAAAGAAAG CAAAATAACT
126701 AGTGTTCAGA TAGAAACATG AAAAACTGAA GTCTGGGGAA GAGACAGAGG
126751 AGGACCAGCA TATGGTCTGA GGGATGTATG TTAAGACTGG GACCCTCCAG
126801 CCCAGGGTTT ATAACTAGGT TAACATGCCA ATGTGTGTTT TCCTCTGCCG
126851 TTGGCCATTC TCGAGAATGG TGCTCCCAGA GTTAGGACTT GGAAAGGCTG
126901 GAAGATTTTG ATGAAGGATA GACTGTGAAA GAGGTAGGAA GAAGTGATAT
126951 TGCAGCCCCA TAATCTGCCA CCAACTGTAC AAATGAGTTT AGAAAGGTTT
127001 TCAAGAGAGT CAAAAATGAA AATACTGTGA TTTTAGGTAT AAGAGGAAGG
127051 CTTATAATTA ATTTGAGGA AGGCTCGTCA AAATTATCTC TCCTGTCAAT
127101 TTCAGATGCC TGCAATTACT TTAATTTGAT GACAGCTTTT AACACAACTA
127151 GAGATTAAAG GCTATCATGC AAATGGTTGC AGTAACATTA GAAACATCAG
127201 AATTTGTTCC TATGTTGACA GAGCATTATA ATANNNNNNN NNNNNNNNNN
127251 NNNNNNNNNN NNNNNNNNNN NNNNNNNNNN NNNAATTTAT TAATATTGAT
127301 CGTCCTCTCT TCTTTGATCC CTCCAAACTT TGTATATTTA GCATAGCCTT
127351 TGTCAGATTC TAACTCACAG TGATCTCATT TATTAACTGC CTTCTCTGTG
127401 TGAGGAAGAG CATAAGGTAC TGGGCACTAC ATGAGGATAA GCATGTATAT
127451 TTCCTCTTAT CTTAGTACCA CGTAAGGATG GAGATTCAGT CTTCATGATC
127501 TTACTATCAA TCCTTCAATA TGAATTGAGG ACCCCTAAAA CACATACATA
127551 TGAAAACACA AACACACATG CATGTTTATA TACATCATTT ACAAGGATTT
127601 GCTAGACAGT TTGGGGGATA TTAAGATGAA GAATCTCTGC TTTTAATGAC
127651 ATCATAATCA TACAAAAGGA AAAAATATAT ATATATAAAC ACATATATGT
127701 GTGTATACAT AAATATATTT GTATATGTGT ATATACAGTT ATATTTTATA

FIGURE 3, page 36 of 87

127751 TGTCTATATT TTATATATGT ATATATATAA TATAAACATA TATACATTTT
127801 GTATGTATGT ATCTAGATAT GTATATGCAT GTATATAAAT TCTCCCACTA
127851 TTCACTCCTT TAGCAATAGG ACCCAATATA TATATTGTAA TTTTGGAATA
127901 ATTATCAAAC AATATAGAAT ATGGTGATAT ATTTTTATAT GCCGATATGT
127951 ATACATTTGT ATATAAACAT ATACATATAT GTGTATATGT ACACACATAT
128001 ATGTACACAT ACACACATAT ACTTATAGGC ATATACAAAT ATATCACCAT
128051 CAATGCCCAA CACATTTTCT TTAGCATAAT AAAGCAATTG AGGGTGTTTG
128101 CAGGAGTAAA TATAAACTGC ACATTTTACA TTTTTTTTCC CTAGAGCTTA
128151 TATGGGTAAA TAAAGAAAAC CTGTTCAAGG ACATTGATAG GCACTAAAAT
128201 GTCATTATTT CCTGTATAAT ATGGATAAAC TTTAACATAA AAAAATCTGC
128251 AATTTTTGGA AACCTTTACA TTTATAGAGC ACTTCAAAAT TTTCAAAGCA
128301 ATTTCACATT CCTTATTTTA CAAATAGTAT TCAAAATGAC TCTCTGAGGT
128351 GTGCAAGAAA ATAATGATTA TCTCTAATTT ATAATTAGGA AACTGAAGAT
128401 TAGCTTATTT AAGTAGCCTG CTCTACAGGG TACACTATTA GAAAGGACTA
128451 AAGTCAAAAC CAGTGTTCTA GTCTCTAGGC CTATACATTG TTTTCATTAT
128501 TCAAACTTAC TGCCTTCTTC TATACAAATT TAATGAAATA CCTTATCTTC
128551 ACTAAACTTA ATGCTAGAAT TATTGAGAAA GTATGCAGAT AATTAGGTTT
128601 GCACCATTCA ACATTCACAA TAGTTAAATC TCAAAGGATG AAAAGAAGGA
128651 TTGGTCTGAC CTTCTCCATC TCATATGCTA TTCTAAAACT AATTGTATCT
128701 GCATATACAA ATTCACTGGA TATAACTGAA TAACTGCTGT ATGAGATTAG
128751 AATAAAGCAT AAAAATATTG ATTTGGAAGC AATATTTAAA TTACTTTTTT
128801 AGCATGTAGT TCCACAATAC CTGAGATGTA GTAGGCATTT AATAATTGAG
128851 TTCATAAAAA GGAGGATTAT ATTTAGATGG GTAAATACAT ATGCTTCAGA
128901 GTTCAAATGG ACCTGAGTTC AAATTCCTTC TCTGCATTTT TGTAGCTGTA
128951 TGACCTGAAA CTTTCTGAGT GAAGTTTCTA CACTGATAAA GTAGGAATAA
129001 TAATCAACCC TACTTTATTC ATTGCTGCTA AATCATATTT CAATTATTCA
129051 CTGAATTACA CATTGGAAGC ATTTAATAAA TACATGTTAT TTTTATTGCT
129101 GTTGATGTTT CATGGTAGTA GATTCTACAT TTTCCTGGCT GATAATCCAG
129151 AGGAAAATCT CTGAGCTAAT TTAAGGACTG CAATGAAAAG TGGCATCCAT
129201 GGGTAAAGGT CATAATGAAA GTTGACCTGT GGAATGAAAC TTACACTTTG
129251 TTCCATGTAT CACAGAGCTT TAAAAACCAG TAAACTCTAT ATTCCAATTA
129301 AAGGGCAAAA GTCCAGGCAA GAAGTTTCCT CTCAGAAAAA CTCAAAAGTT
129351 TGCACACACA TATTCAAAGG TAGAAGCAGA AATAGCAAAC AGAATTGACA
129401 TACTTTCTTC ATTTTCATAA GATACAATGG AAATATCTCC AAAACACCTT
129451 TGGGCAAACA TTTTACCTGG TGCTTTACCA TTTTCTGAAA TAAATTAGCC
129501 ATTACAGGAA GAAAACTTAA ATGTGTCTTA GCTTCTTTAC ATGAGAATCA
129551 AGGGGGGAAA TGTGACCATA TAAAGATATA TTTAAATAAC AGATAATACA
129601 TAGATATATG TATTAAAAAG AAATATAAAA TAATATTTCA AATCCTGGAA
129651 AACTGAGATC ATATAATGTT AGTTTTGTAA ATAAGTTGTA ACAAGATTGT
129701 ATAGGAATAA TCCCAATTAT TTATATATGT GTATGTATAT AAAATATACA
129751 GTATAATATT TAGTATACAA TATGTGATAT ATTGTCTATA TTACTCTGTG
129801 TGGAACCTAC TCCTCCCTTA CAGGTACTGG CTTTCTGGCC TTGCTCACCA
129851 GTGGGTCTGC ATACCCTCCC GTACGTACTC AGCATAGAGA AGGGTCAAGT
129901 TGCCTCAATC CTCAGTGCCA CCTCCACATC ATTCTCTATC CCTCTGCCCT
129951 AAAATTGCCA GCTTGAATTC ATGCTATCAA GCATAGGACA CACCATTGCT
130001 CTTTTTGGAA GTTAATTACC ATCCCCTAAG TCACTTTCTC TTGTTTCTTA
130051 AAGATTTCAC TCCGGGATCA CTGCTTCTCT CTCATCACTC TTCTGTCATA
130101 ATTATTGATG ATGTCAAAAT TCATATAAAA TATTGACCCA TAGCCCTGCT
130151 CATCACTTTC TGGACCTCTT CTCTTGCAGT GACTTGCCTT CCACATGACC
130201 TCATCACTTT CTGCCATGTT CACAACCTAG ACCTTTTCAC CACCAAGAAT
130251 TGTAGCCTCT CCATAATCTT GATTGCAGAT GTCTCACTAT CTGTCCAAAT
130301 CCTTCTTTCC AGATCACTGG ACTCTGATAA TTCTTCAACC CTGCTCTGCC
130351 CTACAGCTCT TTGATTCTAT CGAATTTTCC ATTTCTCCTA ACCCAATCAA
130401 GACTTCATTT TTTCTCTTGC TCAGCTTGAA CTGCATGCCT ATTTGTTTCC
130451 TTTCCTCTAT TGTATATATC CTCAACTCTC AAATTTATCT CTTATAGTCT
130501 CGACCTTTTG ATAAATCCCC AAACTTTGCT AAATAAAACC CTCCATGGAT
130551 TCTTCTCTGT GTTACTAGAA GTGTATTGGA GAAAAATTCA TGATCACGCC
130601 AAAATATCTC ACTTTAAACT CATGGCCACT AACCTCAAAA ACACAGCCTC
130651 CTAATCTATT CAATCTCCCT TTCTTCTAGG AGATTCTTTC TCCTTCTTCT
130701 TTCTTCTCTG GCCTCTAACA CTATATTCCT CATTTTCACC TACATCTGAT
130751 AGCCTTGTTT ATATTTCACT GATAAAACAA AAGCAATTAA AAGAGAACAT
130801 TCACAAGGTC CCCTACTTGT CTGCATCTGT GTCCATATAC TCAGTCTTTC
130851 TCCTGTGGCT GCATATGAAC TGTCCTAGTC CCTGATAACA GCCAACCCTC
130901 TCACTTGGAC ACTACATGAC CTCTCCCTTT GCCTCTCAAG AACATGGGTT
130951 GAGGAATTCT CCCTTCTGCA TCATCATTTT TTCTCTTTTA GCAGCTAAAC
131001 AAATCTATTG TAATTTCTTA CATCATAAAA ATATCTTGAT ATTATAGGTT
131051 TCTCTCTACT TCTTTATTGT TCTTTTTATT TACATTATAG CCCCTTGAAG
131101 AATTGTCAAC ACTTACTATC TTCAATTCCC TTCTCTTATT TCTTCAGCAC
131151 CCTCAAATAA GACTTGGATA CTAAGCAAGC ACAACACTGA ATCAGCTATT
131201 TTCAAGGTCA TCAATTAACT ACTCAGAAAA TTAGCCTTAA GTCTCAGTCT
131251 CCAATTTATT TGACTTTTCA GCAGCTCTGA CTCTTTCATC TTAGTCTCAT

FIGURE 3, page 37 of 87

131301 AGGTTCTATC TCATCTTCTA GACCTGCAAA CAAAATAATT TAGAGCTCAG
131351 TACTTGAATT TACTATCTCT TTCTAAACTC TTTTTCTTGG TGATTGTAAG
131401 AGTCAGGGTT CTCTAGAGGG ACAGAACTAA CAGGATAGAT GTATATATGA
131451 AGGGGCGTTT ATTAAGGAGT GTTGACTCAC ACAATCACAA GGTGAAGCCC
131501 CAAAATAGGC CATCTGCAAG CTGAGGAGCA AGGAAGCCAG TCTAAGTCCC
131551 AAAATCTCAA AAGTAGGGAA GCTGATAGTG CAGCCTTCAG TCTATGACCA
131601 AAGGGCCATG GCAAATTACT GGTGCAAGTC CCAGAGTCCA AAAGCTGAAG
131651 TACGTGGAGT CCGATGTTCT AGGGCAGGAA GCATCCAGCA TTTCCCAGTC
131701 CACTGACTCA AATGTTAATC TCCTTTGGCA ATACCCTCAC AGACACACCC
131751 AGAAACAATA CTTTGTGTTC TTCAATCCAA TCAAGATGAC ACTCAATATT
131801 GACCATCGCA GTGATGTCAT CCAATTTTCA TGACTTTAAG TAAGAGATAT
131851 GAGCTGATTA CTTTCAAATT TATGTCTCTA GTTTGGACTT CTTACTGAAT
131901 TCTAAAGTCA TATATCTAAT TGCCTTCGTG GCATTCCTAC CTGAATATCT
131951 AATAGTGATT TCAAACATAA TATGTCCAAT GTGAGTTTTT TATTTTCCCT
132001 GCAAATCTGT TCATACTAAA ACCTCAAAAA CACAGGCAGT AAAAGCAAAA
132051 ATATACAAAT GGGATTATAT CAAAGTAAAA ATCATATGCA CACAAAGGAA
132101 ACAATCAACA GAATGAATAG ACAATCTGCA AAATGGGAGA AAATATTTGC
132151 AAACTATTCA TCCAACAAGG GATTAATATC CAAAATATAC CAGGAACTCA
132201 ACTCAATAGC AGAAAAAAAA TCCAATTTAA AAATGGGCAA ATGAGCTGAA
132251 TGAACATCTC TCAAAAGAAG ACATACAAAT GGCCAACAGG CATATGAAAG
132301 ATTGCTCAAC ATCACTAATC ATCAAGGAAA TACAAATCAA AACCACAATG
132351 AAACACCATC TCTCCCCATT TAGAATGGTT ATTATCAAAA AGACAAAAAA
132401 ATAACAAATG CCAGCAAGAA TGCAGAGAAA GTGGAATTAT TATACACTAT
132451 TATACACTAT TTAGTTTTCC TCAGAAAACT AAAATACAAC CATCATTATG
132501 ACCCAGCAAT ACCACTACTG GGTATATATC CAAAGGGAAG AAAATCAGTA
132551 TGTCAAAGGC ATATCTATGC TTACGCAGTA AGTGCTGCAG CACTATTCAC
132601 AATAGATGAG ATAAAGAATC AGCCTAAGTA TTCATCAACA GATGAATGAA
132651 TAAAGAAAAT ATGCTGTATA TACGCAATGG AATACTATTT AGCCATGTAA
132701 AAGAATAAAG TCCTGTCATT TGTGGCAATA TGGATGAGCT TGGAGAACAT
132751 TATGATAATT GAAATAATCC AGGAACAGAA AAATAAATAC CACATGTTCT
132801 CACTTATGCA GAGGCTGAAA AAGTTGATCT CGTGAAAGTA GAGAGTAGAA
132851 TAGTGGTTAA AAGCTGGGAA GGGGAAGAGG TGAGAGTAAG AGATTGGTTA
132901 ACGAATGCAA AATTACAGCT AGATAGGAGA AATAAATACT GGTGTCTATA
132951 GCTCTGTAGT GTGACTATAA CAAACCACAA TTTATTGTAT ATTTTCAAAT
133001 AGCTAGAAGA GCAGAATTTG ATGTTCCCAA CATAAAGAAA TTATAAATGT
133051 TTAAGGAGAT GGATGTGCTC ATTACCCTGA CTTGAGTATT ACACATTGCA
133101 TACATGTATG AAAATTTTCA CACTGTATTC CATAAAAAATG TGCAATTATT
133151 ATGTGTCAAA ATAATAAGAA AAGATTATTA AAAACTGCTC ATCTGGAGTC
133201 TTCCCCATCT TCCTTTGGAG TCGTTATTGA TTTCTCTGTT TCTCTCATAC
133251 CTCATATCAA ATCTATTAGC AAATTCAGTT GGTTTTGCCT TCAAAATGTA
133301 TCCATATCTG ATCACTTCTC ACCATCTCCA TTGATATCAC CCATGCCACC
133351 AATATTTCTT GGCTGAATTG TTACAATAAC CCTCTAACTA TTCTCCCTCC
133401 TTTCACCTTT TAAACTCCCA TAGGTTGGTC TATGGAAGCC CACGTGAAAC
133451 TGTTAAACCA CACACTATGT TTGAAACCTT TCAGTGACTT TCTGTGTCAT
133501 TCAGAGTAAA AAGCAAAGTC TTATAATTAC TTTTTAGGAC CTAAAGCACC
133551 ACTTATACTC CCTGCTTTTT CTAGCCATTA TCTGTTACTC TTCCCCCTCA
133601 TTTACTCTAC TCCAGGCACC TGCTGTTCCT AGAACATTCC TGACACCCTT
133651 CTCCTTTAAG GTCGTTGGAC TTGATTTTCC TTCTACCCAC AATTCTTTTC
133701 CCCCGAATCC TGCAGGCCTC ACTTCTTTCC TTCTTCAAAA CTGTCTTCAC
133751 ATTATCACCA GTGATATGTG AAGTTTGGAG ATGGGCTGGA GAACACTATG
133801 ATAAGTGAAA TAAGCCAGGA ACAGAAAAAT AAATACCGCA TATTCTCATG
133851 AAGTATTTAT TTTTTCTGAA TAACCTATTT CTGAACAGCC TATTTTCTGA
133901 AAAGCCTATT TTCTGAAAAC TTTCTCTCAT AGCCCTTATC ACTTTTATAA
133951 ATTCTATGTA ATTTGCATAC ATAATATACA TTAATAGACA ATGTCTATTT
134001 CTCCTAATGA TAAAATAAAC GAGGGTAGGA ATTTCAGTGT CTTTGGTCAG
134051 TGATGAACCC CCAGCTCCTA AAATAGTGCC TGGAATGTAA TAGTCACTCA
134101 CAAATATTGA TTCAGTGGAG AATGTGCATA TTTAAAAAAT CTGTAAAGAA
134151 ATCAACCAAA ATGTTAATGG TCCTTCACTC TGGATAGTGG GATTACAGGT
134201 GAATTCTACT TTCTATTATG TATTTTTCTA AATTTTCAAA ATATTCTACA
134251 TTAACATATA TTATTTTTAA TAAGAAAAGA TCCCTCACAC TTTAACTACA
134301 TATTTAGGTC TTTCGGTTGA GACTGGAAAG ACAGAAAAGC TGCAGTATAC
134351 TGTGTATTTA AGAGAATCAA GATTTTCTAC AAGCAAATGT TCCTGGCTTG
134401 CACTGTAATT TGGGAAAATC ACCTAAAGTG CCTCCTCATT GTTCCTTAAA
134451 GTAAAATAAA CTTGCTGGAT TACATTTTAG AGTCCCTGGA AAATTTAAAT
134501 ATATGTTATT TTTTGTATAT TACTATTCTC TGACTACTGA GACAATTTCA
134551 ATGTAAAAAA GTAAATGTTA CCTTTTATTC CATATTCCTT AAAGCATCTT
134601 CCTGTTTGAA ATAGATGTCA TTCCATTACT ACTTTTTAAC TTATACATTA
134651 CCTTTCTTTA AAAGAAATCC ACAGATACTG TTCACAATTA TATAAACTCA
134701 AGTGTCATGC TTTTATGTTC CAGGTAAATA GACCAAATTT CAGAGAAATT
134751 TGATAAATAT ACACAAGGAT GTCATAATAG ATTTAAGACA GATCTCATGT
134801 CCTATGAGTT TACTGTATTA GCAAAATGAA ACTTCATATT ACCATGTTTT

FIGURE 3, page 38 of 87

134851 TCTTGGGTCA GAACTCCAGA CAGTAAATGC CACTAGACTA ATGACTAATG
134901 CCACAGTTTA AGTAGATAAG TAATTTCTTA GAGGAAGAGT GTACATATAT
134951 CTGCACAACC AATAAATACA TGGCAGAAAC ATCATGGAGT GGGTTTAGAG
135001 AGCTGGTTCT GGGCTCAACC TGCCTTACCA ATTTTGAGAT CTTGGCAAGT
135051 TACTTCACCT TTCTAAGCTT CAATATCTTC ATCTATAAAA TGAGCATAAT
135101 ATTAGTACTA ATTCACAATG ATTTTATAAG AATATTGAAT ATAAGATGCT
135151 TAGCAAACTG CTACAAAGAC TCAGACTTAA GACCTTTATT AAGTTCTGTT
135201 ATTATTGTAA ATATTATTAT GTAGTCCTTA ATGTTTTATT CAAAAGTTAG
135251 ACATAAATTT TGAGAACCAT TTGTTGTGTA GTATATCAGA TTGTGAGGAT
135301 AAATTTAGAC GTTGGAAATT TTGAGTATTT AAGATTATCT AGTATTTACG
135351 GTATTCTAAA ATATTAGGTA ATTTTACAAC CAGCATATGT TTCATGCATT
135401 GATCGAAAAC TAAAACACTG TATCTGTGAA CACAGTGATG CAGTGTTTGT
135451 AATTATATCC TTCTAGGGTT ATTTATGTCC AAATGAATTT ATTGCTACTC
135501 AAGGTCCACT ACCAGGAACA GTTGGAGATT TTTGGAGAAT GGTGTGGGAA
135551 ACCAGAGCAA AAACATTAGT AATGCTAACA CAGTGTTTTG AAAAAGGACG
135601 GGTAAGTTAT TTGAAAATGT TTTACAAATG TTGTTTTACG ATTGTGTTAA
135651 CATATGTGTG AATATTTCAT CTAATACTGT GAGTCATCAA TAACCTGGAC
135701 ATCTATAAAG TAATTTTAAC TTAGTCGTAA TAACTGTGGT ATACATATAT
135751 ATCAATATAA CAATGACGCT TATGACTGAT GATTTTCTCT GAATGCAGAT
135801 CAGATGCCAT CAGTATTGGC CAGAGGACAA CAAGCCAGTT ACTGTCTTTG
135851 GAGATATAGT GATTACAAAG CTAATGGAGG ATGTTCAAAT AGATTGGACT
135901 ATCAGGGATC TGAAAATTGA AAGGGTAAAA AAAAAAGGGG GGGACGAGAG
135951 AACATGATAT AAAATATGAT TGATCTAAAT GTCTAAAATA AAATTAATTT
136001 CTAGAACTAT CCCTTTCAAG GATACCTGTA TATTCAACAA TGCTTTTGTA
136051 TTGTCTTCTG AACAGAATTT TGAATCGATA TCCAACTTTA GTATCAATGT
136101 CACTGTATTT GTTCCAGATC ACTCTAGTTA AAGTCTGTAT TAACCAATTA
136151 GCATCACATT CTTAGGTTGA CAAGAGCAGA AAAAGGAGAG AAAATGATGA
136201 GATCACTAGC TTTATTTTAT CTAATGAAGA AACTGTAATA TCTGACTTGA
136251 GACAGCAATT TCCCAAGTCA CTCATCTCCT GAATCCTAAT AATTTGATTT
136301 TCTATTTAAT CTGCAGCCAG ATAGAAAAGG TAGTATGGGA TCTCACTTTA
136351 TGAGATCTTT ATGGGATCAC TTTATGGGAT CTCAGTTTAT ATAAATGCCT
136401 ATACACACAG AAGATGATAT AAGGATCTTT ATACTTTTCA CATAACAGAT
136451 GCTCAATACC TGTGTATGGA ATAATTTGTG AATGTGTTCA TTTAAGTTTT
136501 GGGTCAAAAG TGTTTCAATA CCTATTATTC TGAGTGCTAC AAAATGGCAT
136551 ACTATATTTG AATATTAATG TCCTATATTA ACATTTATTT CCAAGCTTTC
136601 TTATGTTTTC ATTCATATTG AAAGGCAATT CTCTTTATTG TAACAATAAA
136651 AATCTCTCTT ATAGGAAATA ATGAAAACAT TTTATTTGGT TTGGTAAATA
136701 GTCATTTTTA AAAGATCACC TTCAAAAACT GGGACTATTG CCTTCAACCT
136751 TCATTGTGGA ACTTAAATAA TTTTGTCATT CATTAATCCG TCCCTTTGTC
136801 TAGCATGGGG ATTGCATGAC TGTTCGACAG TGTAACTTTA CTGCCTGGCC
136851 AGAGCATGGG GTTCCCTGAG AACAGCGCCC CTCTAATTCA CTTTGTGAAG
136901 TTGGTTCGAG CAAGCAGGGC ACATGACACC ACACCTATGA TTGTTCACTG
136951 CAGGTGAGAA AGTGATCAGA AATGGCCTTT GAACCCATTG GTCTTTTTAT
137001 TATTAAAATT CCATTGGTTA TTTTTTATAA AATGTTCATG TAAATTTCTT
137051 CCAGCTTGCC GTCTTCAGAG ATTTCACATT TAGCATTTCT AGACACATTG
137101 GTATGATTTA TGTTTTCTGA CATGATAGAT CTAAACCAGT CTTGACTCGA
137151 GTCTTTTTCA CAGTTGAAGT TTGGAGATTA GAGGAAAATG TAGTATGAAT
137201 TCTACTTAAA TGAGATACTC AGAATAGGTA AATAAATAGA AACAGAAAGT
137251 AGAGTTGTGG TTATTAGTGA GGAGGGAGAT GAAAAATTAT TATCTAATGG
137301 GTACAGACCT TCTATTTGGG ATGATGAAAA GTTCTGGAAA TATACTGTGT
137351 TGATATTTGC ACAACATTGA GAATATACTT AATGCCACTG AATTGTACAT
137401 GTAAAATGGT CAAAATGGTA GATTCTCTGT TATTCATCTT TCACCACAAT
137451 AAAAAGATTT TTTTAAAGTA ACAATAACTT TTAATATTTT TAACAGGAGT
137501 GTACTATAAT TAATGTGGTT AAATACTGTA CATAAGAAAA GATAAATTCA
137551 TTCAGTTTTT AAACTTTTAT TTTAAAAAAC TCAATATGTA ATTTAAATGA
137601 TTATACATTT TCCATAAATT TCTGGATTTT TAAAATTATA AGACTAATAC
137651 GTAAATGCTT GCTCATTATA AAATATATGA ACAATGCTTA TATTTATAAA
137701 ACATGTAGAA CAAAAAGTAA AAGCCTCATT TTTACCTTCT CAATTTTAAA
137751 TCCCTCCATA TAGGTATAAA GCTTAATATA ATAGTATATA CTAAAAACAG
137801 TATAACAATT TGCTTCTACA GTCAATGATT GATTTTATGC TGGCATCACT
137851 GATGATTAAA ACCTTTGATG GACAGTAGCT GTCTTCAATT TCTCTGTATC
137901 ATGCAAATAC ACTGCCATGG GCACTAAAAG AAAAGTACTT TCTCCTTTTT
137951 AGCCTCAAAA AGAATAGAGT CTCCTCCTTT GTGATTTAAA TAAGAGATAA
138001 GAAGAAAGTT GTTCATATTA TTGACCATNN NNNNNNNNNN NNNNNNNNNN
138051 NNNNNNNNNN NNNNNNNNNN NNNNNNNNNN NNNNNNNNNN NNNNNNNNNN
138101 NNNNNNNNNN NNNNNNNNNN NNNNNNNNNN NNNNNNNNNN NNNNNNNNNN
138151 NNNNNNNNNN NNNNNNNNNN NNNNNNNNNN NNNNNNNNNN NNNNNNNNNN
138201 NNNNNNNNNN NNNNNNNNNN NNNNNNNNNN NNNNNNNNNN NNNNNNNNNN
138251 NNNNNNNNNN NNNNNNNNNN NNNNNNNNNN NNNNNNNNNN NNNNNNNNNN
138301 NNNNNNNNNN NNNNNNNNNN NNNNNNNNNN NNNNNNNNNN NNNNNNNNNN
138351 NNNNNNNNNN NNNNNNNNNN NNNNNNNNNN NNNNNNNNNN NNNNNNNNNN

FIGURE 3, page 39 of 87

```
138401 NNNNNNNNNN NNNNNNNNNN NNNNNNNNNN NNNNNNNNNN NNNNNNNNNN
138451 NNNNNNNNNN NNNNNNNNNN NNNNNNNNNN NNNNNNNNNN NNNNNNNNNN
138501 NNNNNNNNNN NNNNNNNNNN NNNNNNNNNN NNNNNNNNNN NNNNNNNNNN
138551 NNNNNNNNNN NNNNNNNNNN NNNNNNNNNN NNNNNNNNNN NNNNNNNNNN
138601 NNNNNNNNNN NNNNNNNNNN NNNNNNNNNN NNNNNNNNNN NNNNNNNNNN
138651 NNNNNNNNNN NNNNNNNNNN NNNNNNNNNN NNNNNNNNNN NNNNNNNNNN
138701 NNNNNNNNNN NNNNNNNNNN NNNNNNNNNN NNNNNNNNNN NNNNNNNNNN
138751 NNNNNNNNNN NNNNNNNNNN NNNNNNNNNN NNNNNNNNNN NNNNNNNNNN
138801 NNNNNNNNNN NNNNNNNNCA TATACCTGTC TTTGAGTATT GATGTAATTT
138851 TTTAAATGAA AATAGTTTTT CAATTTTATT ATCTATAGGA GGCAAAATAA
138901 ATTCTAGAGA AAGAAAGTGA AAAGGACAAT TGCAACACTA TTTTTCAAAA
138951 TGAAACAAAG AAAATGCTAT ATAAGCTAAA TATTCTACAT TTGTAACATT
139001 TAGCATTTCT GCTGGTAACT GAATATTTGG TCAATACAGA GTCTCTGGTA
139051 TTAAGAATTT TCAATGATTT TAAAAAAATC TCTATACTTC AACAACACAC
139101 CCTAAAATAT TAAGAAATAA GAGGTTAAGT TCCACTGATT AAAGAAAGAC
139151 AAACTCAAAT ATTTGATAGC ATATTAATGA TAATCATCTT GCCTTGTTTA
139201 AACACAATCT TGGTAACCAT AAAAAATCCA AAGACACTCC AAAGAAAATC
139251 TGCCTCCAAA TAAGAGAAGA AACTATTAGA ATTTATTGCT ATCATAGCTC
139301 ATTATCTTTA TCCCCATCAA AATGAACAAC CCTTTGCTGA ATAATTTTCA
139351 TGTAATTTAC CCTTCCTGTA GTGCTGGAGT TGGAAGAACT GGAGTTTTTA
139401 TTGCTCTGGA CCATTTAACA CAACATATAA ATGACCATGA TTTTGTGGAT
139451 ATATATGGAC TAGTAGCTGA ACTGAGAAGT GAAAGAATGT GCATGGTGCA
139501 GAATCTGGTA AGATCTCTAA ACCTGCACTG CATTCTAAAG TTCTAGAATT
139551 TCCACATGGG AGATCCTTAG TGGCAGCAAT CTGGATGGAC ATGAGCTTGA
139601 AGCTGTGGAC ACCTTCTTTT CCTACATTAT AAGCCTTTTG GGGAGGATTC
139651 GGGAGGGCAG CTGATAGAGA TTATAGGAGA ACTAATGCCC ACATGCCATA
139701 GTCACCCTGC AGCATTGTTA CTGATGGCTC ATCTTAACTT GTTATACTGA
139751 TAGGCATGTA GGCAGTAACA TAAAATTGAT TTATCTTTAT CGTTTAGCAA
139801 CTTTGGGATA TCTGGAAATG AACTCAAATC AATATCTTTT GAATATCATT
139851 ATCTTTTGAA AAGTTATAAA TGGGAAAACA GTTTAAAATA TTGACTGTAA
139901 TAAAGTTCTA TGGGTTTTAC TTCTCCATAT TTATCCCTAT TGCATACCAG
139951 TACTAATAAT GATTATTGTA GCACGCTATC AACTATTAAC TGTGAGGTTT
140001 TTGTTTGTTG TTTTGGCTTA TAGGCAAAAA ATATTTACAA AATATATACA
140051 ATTNNNNNNN NNNNNNNNNN NNNNNNNNNN NNNNNNNNNN NNNNNNNNNN
140101 NNNNNNNNNN NNNNNNNNNN NNNNNNNNNN NNNNNNNNNN NNNNNNNNNN
140151 NNNNNNNNNN NNNNNNNNNN NNNNNNNNNN NNNNNNNNNN NNNNNNNNNN
140201 NNNNNNNNNN NNNNNNNNNN NNNNNNNNNN NNNNNNNNNN NNNNNNNNNN
140251 NNNNNNNNNN NNNNNNNNNN NNNNNNNNNN NNNNNNNNNN NNNNNNNNNN
140301 NNNNNNNNNN NNNNNNNNNN NNNNNNNNNN NNNNNNNNNN NNNNNNNNNN
140351 NNNNNNNNNN NNNNNNNNNN NNNNNNNNNN NNNNNNNNNN NNNNNNNNNN
140401 NNNNNNNNNN NNNNNNNNNN NNNNNNNNNN NNNNNNNNNN NNNNNNNNNN
140451 NNNNNNNNNN NNNNNNNNNN NNNNNNNNNN NNNNNNNNNN NNNNNNNNNN
140501 NNNNNNNNNN NNNNNNNNNN NNNNNNNNNN NNNNNNNNNN NNNNNNNNNN
140551 NNNNNNNNNN NNNNNNNNNN NNNNNNNNNN NNNNNNNNNN NNNNNNNNNN
140601 NNNNNNNNNN NNNNNNNNNN NNNNNNNNNN NNNNNNNNNN NNNNNNNNNN
140651 NNNNNNNNNN NNNNNNNNNN NNNNNNNNNN NNNNNNNNNN NNNNNNNNNN
140701 NNNNNNNNNN NNNNNNNNNN NNNNNNNNNN NNNNNNNNNN NNNNNNNNNN
140751 NNNNNNNNNN NNNNNNNNNN NNNNNNNNNN NNNNNNNNNN NNNNNNNNNN
140801 NNNNNNNNNN NNNNNNNNNN NNNNNNNNNN NNNNNNNNNN NNNNNNNNNN
140851 NNNNNNNNNN NNNNNNNNNN NNNNNNNNNN NNNNNNNNNN NNNNNNNNNN
140901 NNNNNNNNNN NNNNNNNNNN NNNNNNNNNN NNNNNNNNNN NNNNNNNNNN
140951 NNNNNNNNNN NNNNNNNNNN NNNNNNNNNN NNNNNNNNNN NNNNNNNNNN
141001 NNNNNNNNNN NNNNNNNNNN NNNNNNNNNN NNNNNNNNNN NNNNNNNNNN
141051 NNNNNNNNNN NNNNNNNNNN NNNNNNNNNN NNNNNNNNNN NNNNNNNNNN
141101 NNNNNNNNNN NNNNNNNNNN NNNNNNNNNN NNNNNNNNNN NNNNNNNNNN
141151 NNNNNNNNNN NNNNNNNNNN NNNNNNNNNN NNNNNNNNNN NNNNNNNNNN
141201 NNNNNNNNNN NNNNNNNNNN NNNNNNNNNN NNNNNNNNNN NNNNNNNNNN
141251 NNNNNNNNNN NNNNNNNNNN NNNNNNNNNN NNNNNNNNNN NNNNNNNNNN
141301 NNNNNNNNNN NNNNNNNNNN NNNNNNNNNN NNNNNNNNNN NNNNNNNNNN
141351 NNNNNNNNNN NNNNNNNNNN NNNNNNNNNN NNNNNNNNNN NNNNNNNNNN
141401 NNNNNNNNNN NNNNNNNNNN NNNNNNNNNN NNNNNNNNNN NNNNNNNNNN
141451 NNNNNNNNNN NNNNNNNNNN NNNNNNNNNN NNNNNNNNNN NNNNNNNNNN
141501 NNNNNNNNNN NNNNNNNNNN NNNNNNNNNN NNNNNNNNNN NNNNNNNNNN
141551 NNNNNNNNNN NNNNNNNNNN NNNNNNNNNN NNNNNNNNNN NNNNNNNNNN
141601 NNNNNNNNNN NNNNNNNNNN NNNNNNNNNN NNNNNNNNNN NNNNNNNNNN
141651 NNNNNNNNNN NNNNNNNNNN NNNNNNNNNN NNNNNNNNNN NNNNNNNNNN
141701 NNNNNNNNNN NNNNNNNNNN NNNNNNNNNN NNNNNNNNNN NNNNNNNNNN
141751 NNNNNNNNNN NNNNNNNNNN NNNNNNNNNN NNNNNNNNNN NNNNNNNNNN
141801 NNNNNNNNNN NNNNNNNNNN NNNNNNNNNN NNNNNNNNNN NNNNNNNNNN
141851 NNNNNNNNNN NNNNNNNNNN NNNNNNNNNN NNNNNNNNNN NNNNNNNNNN
141901 NNNNNNNNNN NNNNNNNNNN NNNNNNNNNN NNNNNNNNNN NNNNNNNNNN
```

FIGURE 3, page 40 of 87

141951 NNNNNNNNNN NNNNNNNNNN NNNNNNNNNN NNNNNNNNNN NNNNNNNNNN
142001 NNNNNNNNNN NNNNNNNNNN NNNNNNNNNN NNNNNNNNNN NNNNNNNNNN
142051 NNNNNNNNNN NNNNNNNNNN NNNNNNNNNN NNNNNNNNNN NNNNNNNNNN
142101 NNNNNNNNNN NNNNNNNNNN NNNNNNNNNN NNNNNNNNNN NNNNNNNNNN
142151 NNNNNNNNNN NNNNNNNNNN NNNNNNNNNN NNNNNNNNNN NNNNNNNNNN
142201 NNNNNNNNNN NNNNNNNNNN NNNNNNNNNN NNNNNNNNNN NNNNNNNNNN
142251 NNNNNNNNNN NNNNNNNNNN NNNNNNNNNN NNNNNNNNNN NNNNNNNNNN
142301 NNNNNNNNNN NNNNNNNNNN NNNNNNNNNN NNNNNNNNNN NNNNNNNNNN
142351 NNNNNNNNNN NNNNNNNNNN NNNNNNNNNN NNNNNNNNNN NNNNNNNNNN
142401 NNNNNNNNNN NNNNNNNNNN NNNNNNNNNN NNNNNNNNNN NNNNNNNNNN
142451 NNNNNNNNNN NNNNNNNNNN NNNNNNNNNN NNNNNNNNNN NNNNNNNNNN
142501 NNNNNNNNNN NNNNNNNNNN NNNNNNNNNN NNNNNNNNNN NNNNNNNNNN
142551 NNNNNNNNNN NNNNNNNNNN NNNNNNNNNN NNNNNNNNNN NNNNNNNNNN
142601 NNNNNNNNNN NNNNNNNNNN NNNNNNNNNN NNNNNNNNNN NNNNNNNNNN
142651 NNNNNNNNNN NNNNNNNNNN NNNNNNNNNN NNNNNNNNNN NNNNNNNNNN
142701 NNNNNNNNNN NNNNNNNNNN NNNNNNNNNN NNNNNNNNNN NNNNNNNNNN
142751 NNNNNNNNNN NNNNNNNNNN NNNNNNNNNN NNNNNNNNNN NNNNNNNNNN
142801 NNNNNNNNNN NNNNNNNNNN NNNNNNNNNN NNNNNNNNNN NNNNNNNNNN
142851 NNNNNNNNNN NNNNNNNNNN NNNNNNNNNN NNNNNNNNNN NNNNNNNNNN
142901 NNNNNNNNNN NNNNNNNNNN NNNNNNNNNN NNNNNNNNNN NNNNNNNNNN
142951 NNNNNNNNNN NNNNNNNNNN NNNNNNNNNN NNNNNNNNNN NNNNNNNNNN
143001 NNNNNNNNNN NNNNNNNNNN NNNNNNNNNN NNNNNNNNNN NNNNNNNNNN
143051 NNNNNNNNNN NNNNNNNNNN NNNNNNNNNN NNNNNNNNNN NNNNNNNNNN
143101 NNNNNNNNNN NNNNNNNNNN NNNNNNNNNN NNNNNNNNNN NNNNNNNNNN
143151 NNNNNNNNNN NNNNNNNNNN NNNNNNNNNN NNNNNNNNNN NNNNNNNNNN
143201 NNNNNNNNNN NNNNNNNNNN NNNNNNNNNN NNNNNNNNNN NNNNNNNNNN
143251 NNNNNNNNNN NNNNNNNNNN NNNNNNNNNN NNNNNNNNNN NNNNNNNNNN
143301 NNNNNNNAAC AACAACAAAA CCAACAACAA CACATTGTAG CCCCAGGAAA
143351 TTTGAAAGGC CTTTATGAGA GAACTCTCCT GTAGTGAGCT AATATCCTAA
143401 GATACTTTTA GTGCCTCAAG GAAGTGGAAA TTTACTGGTG TGAACTCATA
143451 TAGGGGAAGA AAAAGAAAAA AAGTCAACAT ATTTTGGATG TCCAGTTTTT
143501 TGTCGGGCAT TTTATGTATG TTAAATCCTT TAAATCTTAC AATACAGGAT
143551 TTATGACACA CACTCCCACC CCCAGATGAG GAAATTGTGC ATCAGAAGAG
143601 TTTAATTCTT AAGGTAATAT GGCTCTCTAG GGCAGAAACT GGAATTAAAC
143651 TTTTTTCACA ACAGTATGCT GCTTTCTTGG CAATAACACA TAACGGCAGA
143701 AGGACCTTGG AACCTGTAGG ACTGTCTCAC AGAGTTCAGC CTGCTCTGCT
143751 GGCAAAGTTT ACACCTATCA TTCTTTCCAG TGGAGAAGAT GAAATCAGGA
143801 CAGTCAGAAG TTTCACATAT CAAATGTGAC TTCACATATT TTTTTAAATA
143851 CTAGAACTCA TAAATTTAAA TGATTTCCAA AAAGATTATA TTGTGTCAAC
143901 ATATTTCTGT CAATAATGTA ATTCACTGTG TCATGTATGT TTGAAAACAC
143951 ACTCTTGGAA TTACCTCGAG AAGTAACTTA CTAGCAATTT CAGTAGAAAT
144001 TTTATTGCTT TATAACAACA CTTCAATTCT TACCAAAATT GAATTCTATA
144051 AACTAGATCA TCCACCTCAT TTACAAAACT TAACACCTAA TGACATTTGA
144101 ATTTTCTTTA AATTACATCT GCCCTTAAAT GGTAAAGGTT GACTAGCTGT
144151 GAGAATTAAA TGAGACTAAG TCAACAAACA CTTATTATAC AACTACTATG
144201 TGCCCGGCAC TATTATAGGT AATCAGAATA TAGCAGTGAA TATGACAGAG
144251 TTCTGCCTTT ATAAAACTGA CGTTCCAGTA ATGAGATGTT CTTGGAAACA
144301 TTTTGTAATC CACAAAGAAA TAGATATTCC TAATAATGAC AAACAATTTC
144351 TGAAGACAAT TTCAATAGAG GAGTTCCAAA AGGTTTTGAG GTACAGTAGC
144401 AATAGATACG AATATAACCT CTGAGGCTGA TCACTTTTGA GAATGTTCTA
144451 TTTAAATCAT TGTCAATTTG AATATATGTC TTAAACATTT GATGATATTC
144501 CTTTAAAGTC AGATATGTTT GTTATGTGCA AATGAGGGTG ATTTGAAATA
144551 TACTTTTTTT TTTAGCTTTA ACTACTTTTG ATAAGGTCCA AACTCAGAGA
144601 TGCTAGTAGG TTATTGAATT ATATTGAAAA CATTTAAAGG ATCCAAATGG
144651 TACTGAATTT AGCCCAAACA TTCAGATGCA ATGGTAGGAG TCCTTGTCCA
144701 GCACCTGGAT GTTTGGGTAC TTCAATGACC CACTGCCTTG TATTTACAAA
144751 TCAGGACCAG ATACTTGATC TTAAGCAGGC CACATATCCA GGTGACTAAC
144801 AGATTTATTG GTTAAACATA TTTTAAATGC GCTGATGATG TATAGATATG
144851 CTGACTCACA GATTTCAAAA GTAAATTTAG CATTTGTATT CCAACAGTCA
144901 TTCTAACAAG AAAACTGTAA GAGAATTTAC CAATTAGGTC TAACAGGAAA
144951 AAAACTCATA AACAAATTTA TGTAATATAA TTTTCTACTT CTTATGATAA
145001 CAGCAAGAAA GAATATATTA ATACTTGGTG TTTAGTGACA AGTGTTAGAA
145051 AAAAACTTGA AGCTTCAAGA GACCACAGGA ATTTAGAAAG CCTCCTATTT
145101 GAAATGGTAG AAAATCATAT CTATACTATG ATAAATTCTG TGTCTGTAAC
145151 TTAGCTATTT ATTTGATGAA TTCAGTACTG CTTTTAGCTT TAACAATATA
145201 ACTCCCTTTA TGAAACTCTT CATCAATATA TTTGTTTAAC CACTCTGTCT
145251 TTGGTGTCTA GGCACAGTAT ATCTTTTTAC ACCAGTGCAT TCTGGATCTC
145301 TTATCAAATA AGGGAAGTAA TCAGCCCATC TGTTTTGTTA ACTATTCAGC
145351 ACTTCAGAAG ATGGACTCTT TGGACGCCAT GGAAGGTAAA CAGAAACAAC
145401 AGTATATGCC CAGCTTACTA GTTTACCACC TACGGTAAGA ACATAAATTT
145451 CAGAATAACC ATATGTTAAA AATGTTTAAG AAGCTGGATT AGTGCACAGA

FIGURE 3, page 41 of 87

145501 TCAGGTTTTT TTTCTTTAAC TTTTCTCTAA TCCAAGTTGG GCTAATAATA
145551 CCCTTTCTGT CTACATTATA TTTTTATCAT GAAACATTTC AATTTTGAAC
145601 TGTTAACTTC AACACTCTCT TGTAACATGT TACTTTCTGT TATAGGTGAT
145651 GTTGAGCTTG AATGGGAAGA AACCACTATG TAAATATTCA GACCAAAGGA
145701 TACAATTGGA AGAGATTTTT AAATCCCAGG GGCCAAAGTT ACCCCCTCAT
145751 TCTTCCGAAT TGAAATGTGC AACCTTAAAG AAATATCTAT GCTTCTCTCA
145801 CTGTGCCTTT CCAAACGGAT TGAACATTTT AAGNNNNNNN NNNNNNNNNN
145851 NNNNNNNNNN NNNNNNNNNN NNNNNNNNNN NNNNNNNNNN NNNNNNNNNN
145901 NNNNNNNNNN NNNNNNNNNN NNNNNNNNNN NNNNNNNNNN NNNNNNNNNN
145951 NNNNNNNNNN NNNNNNNNNN NNNNNNNNNN NNNNNNNNNN NNNNNNNNNN
146001 NNNNNNNNNN NNNNNNNNNN NNNNNNNNNN NNNNNNNNNN NNNNNNNNNN
146051 NNNNNNNNNN NNNNNNNNNN NNNNNNNNNN NNNNNNNNNN NNNNNNNNNN
146101 NNNNNNNNNN NNNNNNNNNN NNNNNNNNNN NNNNNNNNNN NNNNNNNNNN
146151 NNNNNNNNNN NNNNNNNNNN NNNNNNNNNN NNNNNNNNNN NNNNNNNNNN
146201 NNNNNNNNNN NNNNNNNNNN NNNNNNNNNN NNNNNNNNNN NNNNNNNNNN
146251 NNNNNNNNNN NNNNNNNNNN NNNNNNNNNN NNNNNNNNNN NNNNNNNNNN
146301 NNNNNNNNNN NNNNNNNNNN NNNNNNNNNN NNNNNNNNNN NNNNNNNNNN
146351 NNNNNNNNNN NNNNNNNNNN NNNNNNNNNN NNNNNNNNNN NNNNNNNNNN
146401 NNNNNNNNNN NNNNNNNNNN NNNNNNNNNN NNNNNNNNNN NNNNNNNNNN
146451 NNNNNNNNNN NNNNNNNNNN NNNNNNNNNN NNNNNNNNNN NNNNNNNNNN
146501 NNNNNNNNNN NNNNNNNNNN NNNNNNNNNN NNNNNNNNNN NNNNNNNNNN
146551 NNNNNNNNNN NNNNNNNNNN NNNNNNNNNN NNNNNNNNNN NNNNNNNNNN
146601 NNNNNNNNNN NNNNNNNNNN NNNNNNNNNN NNNNNNNNNN NNNNNNNNNN
146651 NNNNNNNNNN NNNNNNNNNN NNNNNNNNNN NNNNNNNNNN NNNNNNNNNN
146701 NNNNNNNNNN NNNNNNNNNN NNNNNNNNNN NNNNNNNNNN NNNNNNNNNN
146751 NNNNNNNNNN NNNNNNNNNN NNNNNNNNNN NNNNNNNNNN NNNNNNNNNN
146801 NNNNNNNNNN NNNNNNNNNN NNNNNNNNNN NNNNNNNNNN NNNNNNNNNN
146851 NNNNNNNNNN NNNNNNNNNN NNNNNNNNNN NNNNNNNNNN NNNNNNNNNN
146901 NNNNNNNNNN NNNNNNNNNN NNNNNNNNNN NNNNNNNNNN NNNNNNNNNN
146951 NNNNNNNNNN NNNNNNNNNN NNNNNNNNNN NNNNNNNNNN NNNNNNNNNN
147001 NNNNNNNNNN NNNNNNNNNN NNNNNNNNNN NNNNNNNNNN NNNNNNNNNN
147051 NNNNNNNNNN NNNNNNNNNN NNNNNNNNNN NNNNNNNNNN NNNNNNNNNN
147101 NNNNNNNNNN NNNNNNNNNN NNNNNNNNNN NNNNNNNNNN NNNNNNNNNN
147151 NNNNNNNNNN NNNNNNNNNN NNNNNNNNNN NNNNNNNNNN NNNNNNNNNN
147201 NNNNNNNNNN NNNNNNNNNN NNNNNNNNNN NNNNNNNNNN NNNNNNNNNN
147251 NNNNNNNNNN NNNNNNNNNN NNNNNNNNNN NNNNNNNNNN NNNNNNNNNN
147301 NNNNNNNNNN NNNNNNNNNN NNNNNNNNNN NNNNNNNNNN NNNNNNNNNN
147351 NNNNNNNNNN NNNNNNNNNN NNNNNNNNNN NNNNNNNNNN NNNNNNNNNN
147401 NNNNNNNNNN NNNNNNNNNN NNNNNNNNNN NNNNNNNNNN NNNNNNNNNN
147451 NNNNNNNNNN NNNNNNNNNN NNNNNNNNNN NNNNNNNNNN NNNNNNNNNN
147501 NNNNNNNNNN NNNNNNNNNN NNNNNNNNNN NNNNNNNNNN NNNNNNNNNN
147551 NNNNNNNNNN NNNNNNNNNN NNNNNNNNNN NNNNNNNNNN NNNNNNNNNN
147601 NNNNNNNNNN NNNNNNNNNN NNNNNNNNNN NNNNNNNNNN NNNNNNNNNN
147651 NNNNNNNNNN NNNNNNNNNN NNNNNNNNNN NNNNNNNNNN NNNNNNNNNN
147701 NNNNNNNNNN NNNNNNNNNN NNNNNNNNNN NNNNNNNNNN NNNNNNNNNN
147751 NNNNNNNNNN NNNNNNNNNN NNNNNNNNNN NNNNNNNNNN NNNNNNNNNN
147801 NNNNNNNNNN TATCTTCATT AGTTTCTTGT CTAAGACTTC ATAGATACTA
147851 GTTACTCTCT GGGGTCCCTG AAGCAATAGT ATTAACCCTC ACACAAATCA
147901 GTAAATGTGA GTAGTAGTTG GTTAGACGGA TCAGTCATGG TAGATTTTTG
147951 TGTATTTTAA TGTAGCAGAT AGGAGATTCA AGCTTTTTTT CTCTCAAGCT
148001 TGAGAATACA GAGGGCATAG GTCTGGCTTA CCTTGTAAAA AATGCCAGCA
148051 GCTAACAATG AAATTCTACC CAACACAGGC TGGGTATTTC TCTGATTTTT
148101 TGCCTTGGGT TTACAGTATT CCTAGAGTTA CCAGAAAACT ATAGTGGACA
148151 ATTAGCGGTG GATGCCAAGA GAATGCTTGG AACTTTGAGA ATGTTGGGGT
148201 GGACATTAAT CAATTGATAT AAGCTTTGGG TATGGAGGAC AACGTTATGT
148251 TATAATCATT AGAAGAAATT TCAAAGGCGA TAAAGAAAAA CTATTTCAGA
148301 AACGCTCTTC CCTGAAACAC CAAGAAAGTG ACCTATTATG TTAATATTTT
148351 TGTTATATGC AATGTGCCCT GTTAGTTTTG TTAGAAAATG TACATTTTAT
148401 TATATCCATT TTCAAATCGT TTCTGGTAGT GGGGTTTTAA AATGATAAAT
148451 GAGGTTCAAA ATTAATTCCA GCCTCCTTTC TTTTAGAAAC AGTGTTAGAT
148501 TGAATCTGCA TCAGGCGTGT TTTCACATGC TTGGCTTCAT AATCTCTCTT
148551 CCTCCCCCTA TATTGTTTGC CTGGAATCTG CACTAAAGAT AAGGCAGAGT
148601 GCAAACCTGA CTCATTGGCA ACCAATCAGA AGAACTTTAT GTGGAAAACT
148651 CCCTTCGAGG AGGTACAGGC AGCATGAACA AAATTTTTGA AAAAGTGGAA
148701 GCAAAGGTAG AAAAATATGG TTGAAATGGC TAAAACAATT GGTACTTGTT
148751 TTAAAACTAT ATTTCATTTC TGATATGAAA CCTTATCTTT TCTTTTAAAG
148801 AAACACCTAA CAAAATATTT ATCAGATCAG CACCACAGTA AAGGGAAAAA
148851 GACATTAAAA ATTAAAAAAG ATAAAATAAC AAATATTTAT CAGAAATGCT
148901 CACCCTTCAA AAAATCTGGA AGATTTTGAT TATATATTTT TCCAATTATC
148951 TTCTGTTTGG TAAATTTCCA AGTAATTGGA TAAATAGTTT ATATTTACTT
149001 TGTTTTAAAA TGACTCAAAT TTTCAATTAG AGCATAAGCT TTCAAAAACA

FIGURE 3, page 42 of 87

149051 ATCTGGTCAA CTAGCAGACT TTTAGCAAAT AAGACATATT TCAGAAACAG
149101 AAAATTAATT GTTATATTAT TTATGATAGT TATACCTAAA ACCTAGGTGT
149151 TGTTAAATAT TTACATGTTT AACACCCAAG TATACTTAGA GATCATTTAT
149201 TGTACTCAGT GATTTCTAAC AACATGATTA TTTTGGAACT TGAACCTATA
149251 CTATTTGTTT TCATTTTTTT GAAACTTTAG GAGAATAACT TTATTTTAAA
149301 CCTCTATTTT TCAATATCAG AACCAGAACA ACCTGAGAAA CTTAGAGCCT
149351 TCAATATTTC CACACATTCC TTTTCTCTGC ACTGGAGCCT ACCCTCTGGT
149401 CATGTGGAAA GGTATCAAGT GGATCTTGTT CCTGACAGTG GCTTTGTTAC
149451 TATCAGAGAT CTTGGAGGTG GAGAATATCA GGTATAGTTT TCATTATTGT
149501 ACTTGCCGAG CCTACTTGTA TTTATATTTT GCTCCTAATA GGAAAGTTCT
149551 TTATTTTATG AAACCCATCT ACCACAAAAA CTTACTCCTT GTTGGGTTTT
149601 TGAAAGCATA AGTTGAAGAC AAAAACGTTG ATGTCAAACT GATGAGTGTT
149651 AAGTTTCAGC ATTGGTGGAC TGTTACCTTA GCAACATCTA TGCTGCTTTT
149701 TTTTTTTTTT TTTTTTTTTT AAGTTCACCC TGAACCTACA GCCAGTCATC
149751 CAAGGGTTCA TGAATAGTTT AACAAAGAAA AGGCAGAGCT ATTGAGTAAT
149801 ACGGGCTCAT TAATTGTGTA CTTGCCAGAA GGATCTGTCT TTAAATCATT
149851 AATGCAGGCA ACATTTCTCT CTAGAGCCAT CAATGTGATT CTACTGGCTG
149901 AAAAATGTAA TAAAGATGGA TTTTCTTATC ATTTTTCTTT TACTTTTTAT
149951 TGGGACTTCA GAGACACAGG TATTTCGTAT ACACTCTTTA AAAACAAGGG
150001 CTAAGTCATG GGCTGTAGAT TTCTCAAGAC TTGAATAGTT GTTCCTTGTG
150051 ACAGTGAACT AGGATAGATA GAAATGCTGA CTTAGGCTGT GATAACGCAG
150101 TACGTTTTGT AAGTTTTTAT TTTAAAGTCA TTTGGTAAAA AGTTATATAA
150151 CATATTTGTA TCTTACAATA ATATGGAACT TATTGTGATG TTATAAACAG
150201 TGCAGAGTTA TATAGTGAAG AGTTAATTTT TGTTATAGTG ATAGATTTAT
150251 TTTAGCTTGC TTGCTTTCCA GAAAGAATTT TAATGCAACT ATTTGTTTGT
150301 GNNNNNNNNN NNNNNNNNNN NNNNNNNNNN NNNNNNNNNN NNNNNNNNNN
150351 NNNNNNNNNN NNNNNNNNNN NNNNNNNNNN NNNNNNNNNN NNNNNNNNNN
150401 NNNNNNNNNN NNNNNNNNNN NNNNNNNNNN NNNNNNNNNN NNNNNNNNNN
150451 NNNNNNNNNN NNNNNNNNNN NNNNNNNNNN NNNNNNNNNN NNNNNNNNNN
150501 NNNNNNNNNN NNNNNNNNNN NNNNNNNNNN NNNNNNNNNN NNNNNNNNNN
150551 NNNNNNNNNN NNNNNNNNNN NNNNNNNNNN NNNNNNNNNN NNNNNNNNNN
150601 NNNNNNNNNN NNNNNNNNNN NNNNNNNNNN NNNNNNNNNN NNNNNNNNNN
150651 NNNNNNNNNN NNNNNNNNNN NNNNNNNNNN NNNNNNNNNN NNNNNNNNNN
150701 NNNNNNNNNN NNNNNNNNNN NNNNNNNNNN NNNNNNNNNN NNNNNNNNNN
150751 NNNNNNNNNN NNNNNNNNNN NNNNNNNNNN NNNNNNNNNN NNNNNNNNNN
150801 NNNNNNNNNN NNNNNNNNNN NNNNNNNNNN NNNNNNNNNN NNNNNNNNNN
150851 NNNNNNNNNN NNNNNNNNNN NNNNNNNNNN NNNNNNNNNN NNNNNNNNNN
150901 NNNNNNNNNN NNNNNNNNNN NNNNNNNNNN NNNNNNNNNN NNNNNNNNNN
150951 NNNNNNNNNN NNNNNNNNNN NNNNNNNNNN NNNNNNNNNN NNNNNNNNNN
151001 NNNNNNNNNN NNNNNNNNNN NNNNNNNNNN NNNNNNNNNN NNNNNNNNNN
151051 NNNNNNNNNN NNNNNNNNNN NNNNNNNNNN NNNNNNNNNN NNNNNNNNNN
151101 NNNNNNNNNN NNNNNNNNNN NNNNNNNNNN NNNNNNNNNN NNNNNNNNNN
151151 NNNNNNNNNN NNNNNNNNNN NNNNNNNNNN NNNNNNNNNN NNNNNNNNNN
151201 NNNNNNNNNN NNNNNNNNNN NNNNNNNNNN NNNNNNNNNN NNNNNNNNNN
151251 NNNNNNNNNN NNNNNNNNNN NNNNNNNNNN NNNNNNNNNN NNNNNNNNNN
151301 NNNNNNNNNN NNNNNNNNNN NNNNNNNNNN NNNNNNNNNN NNNNNNNNNN
151351 NNNNNNNNNN NNNNNNNNNN NNNNNNNNNN NNNNNNNNNN NNNNNNNNNN
151401 NNNNNNNNNN NNNNNNNNNN NNNNNNNNNN NNNNNNNNNN NNNNNNNNNN
151451 NNNNNNNNNN NNNNNNNNNN NNNNNNNNNN NNNNNNNNNN NNNNNNNNNN
151501 NNNNNNNNNN NNNNNNNNNN NNNNNNNNNN NNNNNNNNNN NNNNNNNNNN
151551 NNNNNNNNNN NNNNNNNNNN NNNNNNNNNN NNNNNNNNNN NNNNNNNNNN
151601 NNNNNNNNNN NNNNNNNNNN NNNNNNNNNN NNNNNNNNNN NNNNNNNNNN
151651 NNNNNNNNNN NNNNNNNNNN NNNNNNNNNN NNNNNNNNNN NNNNNNNNNN
151701 NNNNNNNNNN NNNNNNNNNN NNNNNNNNNN NNNNNNNNNN NNNNNNNNNN
151751 NNNNNNNNNN NNNNNNNNNN NNNNNNNNNN NNNNNNNNNN NNNNNNNNNN
151801 NNNNNNNNNN NNNNNNNNNN NNNNNNNNNN NNNNNNNNNN NNNNNNNNNN
151851 NNNNNNNNNN NNNNNNNNNN NNNNNNNNNN NNNNNNNNNN NNNNNNNNNN
151901 NNNNNNNNNN NNNNNNNNNN NNNNNNNNNN NNNNNNNNNN NNNNNNNNNN
151951 NNNNNNNNNN NNNNNNNNNN NNNNNNNNNN NNNNNNNNNN NNNNNNNNNN
152001 NNNNNNNNNN NNNNNNNNNN NNNNNNNNNN NNNNNNNNNN NNNNNNNNNN
152051 NNNNNNNNNN NNNNNNNNNN NNNNNNNNNN NNNNNNNNNN NNNNNNNNNN
152101 NNNNNNNNNN NNNNNNNNNN NNNNNNNNNN NNNNNNNNNN NNNNNNNNNN
152151 NNNNNNNNNN NNNNNNNNNN NNNNNNNNNN NNNNNNNNNN NNNNNNNNNN
152201 NNNNNNNNNN NNNNNNNNNN NNNNNNNNNN NNNNNNNNNN NNNNNNNNNN
152251 NNNNNNNNNN NNNNNNNNNN NNNNNNNNNN NNNNNNNNNN NNNNNNNNNN
152301 NNNNNNNNNN NNNNNNNNNN NNNNNNNNNN NNNNNNNNNN NNNNNNNNNN
152351 NNNNNNNNNN NNNNNNNNNN NNNNNNNNNN NNNNNNNNNN NNNNNNNNNN
152401 NNNNNNNNNN NNNNNNNNNN NNNNNNNNNN NNNNNNNNNN NNNNNNNNNN
152451 NNNNNNNNNN NNNNNNNNNN NNNNNNNNNN NNNNNNNNNN NNNNNNNNNN
152501 NNNNNNNNNN NNNNNNNNNN NNNNNNNNNN NNNNNNNNNN NNNNNNNNNN
152551 NNNNNNNNNN NNNNNNNNNN NNNNNNNNNN NNNNNNNNNN NNNNNNNNNN

FIGURE 3, page 43 of 87

152601 NNNNNNNNNN NNNNNNNNNN NNNNNNNNNN NNNNNNNNNN NNNNNNNNNN
152651 NNNNNNNNNN NNNNNNNNNN NNNNNNNNNN NNNNNNNNNN NNNNNNNNNN
152701 NNNNNNNNNN NNNNNNNNNN NNNNNNNNNN NNNNNNNNNN NNNNNNNNNN
152751 NNNNNNNNNN NNNNNNNNNN NNNNNNNNNN NNNNNNNNNN NNNNNNNNNN
152801 NNNNNNNNNN NNNNNNNNNN NNNNNNNNNN NNNNNNNNNN NNNNNNNNNN
152851 NNNNNNNNNN NNNNNNNNNN NNNNNNNNNN NNNNNNNNNN NNNNNNNNNN
152901 NNNNNNNNNN NNNNNNNNNN NNNNNNNNNN NNNNNNNNNN NNNNNNNNNN
152951 NNNNNNNNNN NNNNNNNNNN NNNNNNNNNN NNNNNNNNNN NNNNNNNNNN
153001 NNNNNNNNNN NNNNNNNNNN NNNNNNNNNN NNNNNNNNNN NNNNNNNNNN
153051 NNNNNNNNNN NNNNNNNNNN NNNNNNNNNN NNNNNNNNNN NNNNNNNNNN
153101 NNNNNNNNNN NNNNNNNNNN NNNNNNNNNN NNNNNNNNNN NNNNNNNNNN
153151 NNNNNNNNNN NNNNNNNNNN NNNNNNNNNN NNNNNNNNNN NNNNNNNNNN
153201 NNNNNNNNNN NNNNNNNNNN NNNNNNNNNN NNNNNNNNNN NNNNNNNNNN
153251 NNNNNNNNNN NNNNNNNNNN NNNNNNNNNN NNNNNNNNNN NNNNNNNNNN
153301 NNNNNNNNNN NNNNNNNNNN NNNNNNNNNN NNNNNNNNNN NNNNNNNNNN
153351 NNNNNNNNNN NNNNNNNNNN NNNNNNNNNN NNNNNNNNNN NNNNNNNNNN
153401 NNNNNNNNNN NNNNNNNNNN NNNNNNNNNN NNNNNNNNNN NNNNNNNNNN
153451 NNNNNNNNNN NNNNNNNNNN NNNNNNNNNN NNNNNNNNNN NNNNNNNNNN
153501 NNNNNNNNNN NNNNNNNNNN NNNNNNNNNN NNNNNNNNNN NNNNNNNNNN
153551 NNNNNNNNNN NNNNNNNNNN NNNNNNNNNN NNNNNNNNNN NNNNNNNNNN
153601 NNNNNNNNNN NNNNNNNNNN NNNNNNNNNN NNNNNNNNNN NNNNNNNNNN
153651 NNNNNNNNNN NNNNNNNNNN NNNNNNNNNN NNNNNNNNNN NNNNNNNNNN
153701 NNNNNNNNNN NNNNNNNNNN NNNNNNNNNN NNNNNNNNNN NNNNNNNNNN
153751 NNNNNNNNNN NNNNNNNNNN NNNNNNNNNN NNNNNNNNNN NNNNNNNNNN
153801 NNNNNNNNNN NNNNNNNNNN NNNNNNNNNN NNNNNNNNNN NNNNNNNNNN
153851 NNNNNNNNNN NNNNNNNNNN NNNNNNNNNN NNNNNNNNNN NNNNNNNNNN
153901 NNNNNNNNNN NNNNNNNNNN NNNNNNNNNN NNNNNNNNNN NNNNNNNNNN
153951 NNNNNNNNNN NNNNNNNNNN NNNNNNNNNN NNNNNNNNNN NNNNNNNNNN
154001 NNNNNNNNNN NNNNNNNNNN NNNNNNNNNN NNNNNNNNNN NNNNNNNNNN
154051 NNNNNNNNNN NNNNNNNNNN NNNNNNNNNN NNNNNNNNNN NNNNNNNNNN
154101 NNNNNNNNNN NNNNNNNNNN NNNNNNNNNN NNNNNNNNNN NNNNNNNNNN
154151 NNNNNNNNNN NNNNNNNNNN NNNNNNNNNN NNNNNNNNNN NNNNNNNNNN
154201 NNNNNNNNNN NNNNNNNNNN NNNNNNNNNN NNNNNNNNNN NNNNNNNNNN
154251 NNNNNNNNNN NNNNNNNNNN NNNNNNNNNN NNNNNNNNNN NNNNNNNNNN
154301 NNNNNNNNNN NNNNNNNNNN NNNNNNNNNN NNNNNNNNNN NNNNNNNNNN
154351 NNNNNNNNNN NNNNNNNNNN NNNNNNNNNN NNNNNNNNNN NNNNNNNNNN
154401 NNNNNNNNNN NNNNNNNNNN NNNNNNNNNN NNNNNNNNNN NNNNNNNNNN
154451 NNNNNNNNNN NNNNNNNNNN NNNNNNNNNN NNNNNNNNNN NNNNNNNNNN
154501 NNNNNNNNNN NNNNNNNNNN NNNNNNNNNN NNNNNNNNNN NNNNNNNNNN
154551 NNNNNNNNNN NNNNNNNNNN NNNNNNNNNN NNNNNNNNNN NNNNNNNNNN
154601 NNNNNNNNNN NNNNNNNNNN NNNNNNNNNN NNNNNNNNNN NNNNNNNNNN
154651 NNNNNNNNNN NNNNNNNNNN NNNNNNNNNN NNNNNNNNNN NNNNNNNNNN
154701 NNNNNNNNNN NNNNNNNNNN NNNNNNNNNN NNNNNNNNNN NNNNNNNNNN
154751 NNNNNNNNNN NNNNNNNNNN NNNNNNNNNN NNNNNNNNNN NNNNNNNNNN
154801 NNNNNNNNNN NNNNNNNNNN NNNNNNNNNN NNNNNNNNNN NNNNNNNNNN
154851 NNNNNNNNNN NNNNNNNNNN NNNNNNNNNN NNNNNNNNNN NNNNNNNNNN
154901 NNNNNNNNNN NNNNNNNNNN NNNNNNNNNN NNNNNNNNNN NNNNNNNNNN
154951 NNNNNNNNNN NNNNNNNNNN NNNNNNNNNN NNNNNNNNNN NNNNNNNNNN
155001 NNNNNNNNNN NNNNNNNNNN NNNNNNNNNN NNNNNNNNNN NNNNNNNNNN
155051 NNNNNNNNNN NNNNNNNNNN NNNNNNNNNN NNNNNNNNNN NNNNNNNNNN
155101 NNNNNNNNNN NNNNNNNNNN NNNNNNNNNN NNNNNNNNNN NNNNNNNNNN
155151 NNNNNNNNNN NNNNNNNNNN NNNNNNNNNN NNNNNNNNNN NNNNNNNNNN
155201 NNNNNNNNNN NNNNNNNNNN NNNNNNNNNN NNNNNNNNNN NNNNNNNNNN
155251 NNNNNNNNNN NNNNNNNNNN NNNNNNNNNN NNNNNNNNNN NNNNNNNNNN
155301 NNNNNNNNNN NNNNNNNNNN NNNNNNNNNN NNNNNNNNNN NNNNNNNNNN
155351 NNNNNNNNNN NNNNNNNNNN NNNNNNNNNN NNNNNNNNNN NNNNNNNNNN
155401 NNNNNNNNNN NNNNNNNNNN NNNNNNNNNN NNNNNNNNNN NNNNNNNNNN
155451 NNNNNNNNNN NNNNNNNNNN NNNNNNNNNN NNNNNNNNNN NNNNNNNNNN
155501 NNNNNNNNNN NNNNNNNNNN NNNNNNNNNN NNNNNNNNNN NNNNNNNNNN
155551 NNNNNNNNNN NNNNNNNNNN NNNNNNNNNN NNNNNNNNNN NNNNNNNNNN
155601 NNNNNNNNNN NNNNNNNNNN NNNNNNNNNN NNNNNNNNNN NNNNNNNNNN
155651 NNNNNNNNNN NNNNNNNNNN NNNNNNNNNN NNNNNNNNNN NNNNNNNNNN
155701 NNNNNNNNNN NNNNNNNNNN NNNNNNNNNN NNNNNNNNNN NNNNNNNNNN
155751 NNNNNNNNNN NNNNNNNNNN NNNNNNNNNN NNNNNNNNNN NNNNNNNNNN
155801 NNNNNNNNNN NNNNNNNNNN NNNNNNNNNN NNNNNNNNNN NNNNNNNNNN
155851 NNNNNNNNNN NNNNNNNNNN NNNNNNNNNN NNNNNNNNNN NNNNNNNNNN
155901 NNNNNNNNNN NNNNNNNNNN NNNNNNNNNN NNNNNNNNNN NNNNNNNNNN
155951 NNNNNNNNNN NNNNNNNNNN NNNNNNNNNN NNNNNNNNNN NNNNNNNNNN
156001 NNNNNNNNNN NNNNNNNNNN NNNNNNNNNN NNNNNNNNNN NNNNNNNNNN
156051 NNNNNNNNNN NNNNNNNNNN NNNNNNNNNN NNNNNNNNNN NNNNNNNNNN
156101 NNNNNNNNNN NNNNNNNNNN NNNNNNNNNN NNNNNNNNNN NNNNNNNNNN

FIGURE 3, page 44 of 87

156151 NNNNNNNNNN NNNNNNNNNN NNNNNNNNNN NNNNNNNNNN NNNNNNNNNN
156201 NNNNNNNNNN NNNNNNNNNN NNNNNNNNNN NNNNNNNNNN NNNNNNNNNN
156251 NNNNNNNNNN NNNNNNNNNN NNNNNNNNNN NNNNNNNNNN NNNNNNNNNN
156301 NNNNNNNNNN NNNNNNNNNN NNNNNNNNNN NNNNNNNNNN NNNNNNNNNN
156351 NNNNNNNNNN NNNNNNNNNN NNNNNNNNNN NNNNNNNNNN NNNNNNNNNN
156401 NNNNNNNNNN NNNNNNNNNN NNNNNNNNNN NNNNNNNNNN NNNNNNNNNN
156451 NNNNNNNNNN NNNNNNNNNN NNNNNNNNNN NNNNNNNNNN NNNNNNNNNN
156501 NNNNNNNNNN NNNNNNNNNN NNNNNNNNNN NNNNNNNNNN NNNNNNNNNN
156551 NNNNNNNNNN NNNNNNNNNN NNNNNNNNNN NNNNNNNNNN NNNNNNNNNN
156601 NNNNNNNNNN NNNNNNNNNN NNNNNNNNNN NNNNNNNNNN NNNNNNNNNN
156651 NNNNNNNNNN NNNNNNNNNN NNNNNNNNNN NNNNNNNNNN NNNNNNNNNN
156701 NNNNNNNNNN NNNNNNNNNN NNNNNNNNNN NNNNNNNNNN NNNNNNNNNN
156751 NNNNNNNNNN NNNNNNNNNN NNNNNNNNNN NNNNNNNNNN NNNNNNNNNN
156801 NNNNNNNNNN NNNNNNNNNN NNNNNNNNNN NNNNNNNNNN NNNNNNNNNN
156851 NNNNNNNNNN NNNNNNNNNN NNNNNNNNNN NNNNNNNNNN NNNNNNNNNN
156901 NNNNNNNNNN NNNNNNNNNN NNNNNNNNNN NNNNNNNNNN NNNNNNNNNN
156951 NNNNNNNNNN NNNNNNNNNN NNNNNNNNNN NNNNNNNNNN NNNNNNNNNN
157001 NNNNNNNNNN NNNNNNNNNN NNNNNNNNNN NNNNNNNNNN NNNNNNNNNN
157051 NNNNNNNNNN NNNNNNNNNN NNNNNNNNNN NNNNNNNNNN NNNNNNNNNN
157101 NNNNNNNNNN NNNNNNNNNN NNNNNNNNNN NNNNNNNNNN NNNNNNNNNN
157151 NNNNNNNNNN NNNNNNNNNN NNNNNNNNNN NNNNNNNNNN NNNNNNNNNN
157201 NNNNNNNNNN NNNNNNNNNN NNNNNNNNNN NNNNNNNNNN NNNNNNNNNN
157251 NNNNNNNNNN NNNNNNNNNN NNNNNNNNNN NNNNNNNNNN NNNNNNNNNN
157301 NNNNNNNNNN NNNNNNNNNN NNNNNNNNNN NNNNNNNNNN NNNNNNNNNN
157351 NNNNNNNNNN NNNNNNNNNN NNNNNNNNNN NNNNNNNNNN NNNNNNNNNN
157401 NNNNNNNNNN NNNNNNNNNN NNNNNNNNNN NNNNNNNNNN NNNNNNNNNN
157451 NNNNNNNNNN NNNNNNNNNN NNNNNNNNNN NNNNNNNNNN NNNNNNNNNN
157501 NNNNNNNNNN NNNNNNNNNN NNNNNNNNNN NNNNNNNNNN NNNNNNNNNN
157551 NNNNNNNNNN NNNNNNNNNN NNNNNNNNNN NNNNNNNNNN NNNNNNNNNN
157601 NNNNNNNNNN NNNNNNNNNN NNNNNNNNNN NNNNNNNNNN NNNNNNNNNN
157651 NNNNNNNNNN NNNNNNNNNN NNNNNNNNNN NNNNNNNNNN NNNNNNNNNN
157701 NNNNNNNNNN NNNNNNNNNN NNNNNNNNNN NNNNNNNNNN NNNNNNNNNN
157751 NNNNNNNNNN NNNNNNNNNN NNNNNNNNNN NNNNNNNNNN NNNNNNNNNN
157801 NNNNNNNNNN NNNNNNNNNN NNNNNNNNNN NNNNNNNNNN NNNNNNNNNN
157851 NNNNNNNNNN NNNNNNNNNN NNNNNNNNNN NNNNNNNNNN NNNNNNNNNN
157901 NNNNNNNNNN NNNNNNNNNN NNNNNNNNNN NNNNNNNNNN NNNNNNNNNN
157951 NNNNNNNNNN NNNNNNNNNN NNNNNNNNNN NNNNNNNNNN NNNNNNNNNN
158001 NNNNNNNNNN NNNNNNNNNN NNNNNNNNNN NNNNNNNNNN NNNNNNNNNN
158051 NNNNNNNNNN NNNNNNNNNN NNNNNNNNNN NNNNNNNNNN NNNNNNNNNN
158101 NNNNNNNNNN NNNNNNNNNN NNNNNNNNNN NNNNNNNNNN NNNNNNNNNN
158151 NNNNNNNNNN NNNNNNNNNN NNNNNNNNNN NNNNNNNNNN NNNNNNNNNN
158201 NNNNNNNNNN NNNNNNNNNN NNNNNNNNNN NNNNNNNNNN NNNNNNNNNN
158251 NNNNNNNNNN NNNNNNNNNN NNNNNNNNNN NNNNNNNNNN NNNNNNNNNN
158301 NNNNNNNNNN NNNNNNNNNN NNNNNNNNNN NNNNNNNNNN NNNNNNNNNN
158351 NNNNNNNNNN NNNNNNNNNN NNNNNNNNNN NNNNNNNNNN NNNNNNNNNN
158401 NNNNNNNNNN NNNNNNNNNN NNNNNNNNNN NNNNNNNNNN NNNNNNNNNN
158451 NNNNNNNNNN NNNNNNNNNN NNNNNNNNNN NNNNNNNNNN NNNNNNNNNN
158501 NNNNNNNNNN NNNNNNNNNN NNNNNNNNNN NNNNNNNNNN NNNNNNNNNN
158551 NNNNNNNNNN NNNNNNNNNN NNNNNNNNNN NNNNNNNNNN NNNNNNNNNN
158601 NNNNNNNNNN NNNNNNNNNN NNNNNNNNNN NNNNNNNNNN NNNNNNNNNN
158651 NNNNNNNNNN NNNNNNNNNN NNNNNNNNNN NNNNNNNNNN NNNNNNNNNN
158701 NNNNNNNNNN NNNNNNNNNN NNNNNNNNNN NNNNNNNNNN NNNNNNNNNN
158751 NNNNNNNNNN NNNNNNNNNN NNNNNNNNNN NNNNNNNNNN NNNNNNNNNN
158801 NNNNNNNNNN NNNNNNNNNN NNNNNNNNNN NNNNNNNNNN NNNNNNNNNN
158851 NNNNNNNNNN NNNNNNNNNN NNNNNNNNNN NNNNNNNNNN NNNNNNNNNN
158901 NNNNNNNNNN NNNNNNNNNN NNNNNNNNNN NNNNNNNNNN NNNNNNNNNN
158951 NNNNNNNNNN NNNNNNNNNN NNNNNNNNNN NNNNNNNNNN NNNNNNNNNN
159001 NNNNNNNNNN NNNNNNNNNN NNNNNNNNNN NNNNNNNNNN NNNNNNNNNN
159051 NNNNNNNNNN NNNNNNNNNN NNNNNNNNNN NNNNNNNNNN NNNNNNNNNN
159101 NNNNNNNNNN NNNNNNNNNN NNNNNNNNNN NNNNNNNNNN NNNNNNNNNN
159151 NNNNNNNNNN NNNNNNNNNN NNNNNNNNNN NNNNNNNNNN NNNNNNNNNN
159201 NNNNNNNNNN NNNNNNNNNN NNNNNNNNNN NNNNNNNNNN NNNNNNNNNN
159251 NNNNNNNNNN NNNNNNNNNN NNNNNNNNNN NNNNNNNNNN NNNNNNNNNN
159301 NNNNNNNNNN NNNNNNNNNN NNNNNNNNNN NNNNNNNNNN NNNNNNNNNN
159351 NNNNNNNNNN NNNNNNNNNN NNNNNNNNNN NNNNNNNNNN NNNNNNNNNN
159401 NNNNNNNNNN NNNNNNNNNN NNNNNNNNNN NNNNNNNNNN NNNNNNNNNN
159451 NNNNNNNNNN NNNNNNNNNN NNNNNNNNNN NNNNNNNNNN NNNNNNNNNN
159501 NNNNNNNNNN NNNNNNNNNN NNNNNNNNNN NNNNNNNNNN NNNNNNNNNN
159551 NNNNNNNNNN NNNNNNNNNN NNNNNNNNNN NNNNNNNNNN NNNNNNNNNN
159601 NNNNNNNNNN NNNNNNNNNN NNNNNNNNNN NNNNNNNNNN NNNNNNNNNN
159651 NNNNNNNNNN NNNNNNNNNN NNNNNNNNNN NNNNNNNNNN NNNNNNNNNN

FIGURE 3, page 45 of 87

```
159701 NNNNNNNNNN NNNNNNNNNN NNNNNNNNNN NNNNNNNNNN NNNNNNNNNN
159751 NNNNNNNNNN NNNNNNNNNN NNNNNNNNNN NNNNNNNNNN NNNNNNNNNN
159801 NNNNNNNNNN NNNNNNNNNN NNNNNNNNNN NNNNNNNNNN NNNNNNNNNN
159851 NNNNNNNNNN NNNNNNNNNN NNNNNNNNNN NNNNNNNNNN NNNNNNNNNN
159901 NNNNNNNNNN NNNNNNNNNN NNNNNNNNNN NNNNNNNNNN NNNNNNNNNN
159951 NNNNNNNNNN NNNNNNNNNN NNNNNNNNNN NNNNNNNNNN NNNNNNNNNN
160001 NNNNNNNNNN NNNNNNNNNN NNNNNNNNNN NNNNNNNNNN NNNNNNNNNN
160051 NNNNNNNNNN NNNNNNNNNN NNNNNNNNNN NNNNNNNNNN NNNNNNNNNN
160101 NNNNNNNNNN NNNNNNNNNN NNNNNNNNNN NNNNNNNNNN NNNNNNNNNN
160151 NNNNNNNNNN NNNNNNNNNN NNNNNNNNNN NNNNNNNNNN NNNNNNNNNN
160201 NNNNNNNNNN NNNNNNNNNN NNNNNNNNNN NNNNNNNNNN NNNNNNNNNN
160251 NNNNNNNNNN NNNNNNNNNN NNNNNNNNNN NNNNNNNNNN NNNNNNNNNN
160301 NNNNNNNNNN NNNNNNNNNN NNNNNNNNNN NNNNNNNNNN NNNNNNNNNN
160351 NNNNNNNNNN NNNNNNNNNN NNNNNNNNNN NNNNNNNNNN NNNNNNNNNN
160401 NNNNNNNNNN NNNNNNNNNN NNNNNNNNNN NNNNNNNNNN NNNNNNNNNN
160451 NNNNNNNNNN NNNNNNNNNN NNNNNNNNNN NNNNNNNNNN NNNNNNNNNN
160501 NNNNNNNNNN NNNNNNNNNN NNNNNNNNNN NNNNNNNNNN NNNNNNNNNN
160551 NNNNNNNNNN NNNNNNNNNN NNNNNNNNNN NNNNNNNNNN NNNNNNNNNN
160601 NNNNNNNNNN NNNNNNNNNN NNNNNNNNNN NNNNNNNNNN NNNNNNNNNN
160651 NNNNNNNNNN NNNNNNNNNN NNNNNNNNNN NNNNNNNNNN NNNNNNNNNN
160701 NNNNNNNNNN NNNNNNNNNN NNNNNNNNNN NNNNNNNNNN NNNNNNNNNN
160751 NNNNNNNNNN NNNNNNNNNN NNNNNNNNNN NNNNNNNNNN NNNNNNNNNN
160801 NNNNNNNNNN NNNNNNNNNN NNNNNNNNNN NNNNNNNNNN NNNNNNNNNN
160851 NNNNNNNNNN NNNNNNNNNN NNNNNNNNNN NNNNNNNNNN NNNNNNNNNN
160901 NNNNNNNNNN NNNNNNNNNN NNNNNNNNNN NNNNNNNNNN NNNNNNNNNN
160951 NNNNNNNNNN NNNNNNNNNN NNNNNNNNNN NNNNNNNNNN NNNNNNNNNN
161001 NNNNNNNNNN NNNNNNNNNN NNNNNNNNNN NNNNNNNNNN NNNNNNNNNN
161051 NNNNNNNNNN NNNNNNNNNN NNNNNNNNNN NNNNNNNNNN NNNNNNNNNN
161101 NNNNNNNNNN NNNNNNNNNN NNNNNNNNNN NNNNNNNNNN NNNNNNNNNN
161151 NNNNNNNNNN NNNNNNNNNN NNNNNNNNNN NNNNNNNNNN NNNNNNNNNN
161201 NNNNNNNNNN NNNNNNNNNN NNNNNNNNNN NNNNNNNNNN NNNNNNNNNN
161251 NNNNNNNNNN NNNNNNNNNN NNNNNNNNNN NNNNNNNNNN NNNNNNNNNN
161301 NNNNNNNNNN NNNNNNNNNN NNNNNNNNNN NNNNNNNNNN NNNNNNNNNN
161351 NNNNNNNNNN NNNNNNNNNN NNNNNNNNNN NNNNNNNNNN NNNNNNNNNN
161401 NNNNNNNNNN NNNNNNNNNN NNNNNNNNNN NNNNNNNNNN NNNNNNNNNN
161451 NNNNNNNNNN NNNNNNNNNN NNNNNNNNNN NNNNNNNNNN NNNNNNNNNN
161501 NNNNNNNNNN NNNNNNNNNN NNNNNNNNNN NNNNNNNNNN NNNNNNNNNN
161551 NNNNNNNNNN NNNNNNNNNN NNNNNNNNNN NNNNNNNNNN NNNNNNNNNN
161601 NNNNNNNNNN NNNNNNNNNN NNNNNNNNNN NNNNNNNNNN NNNNNNNNNN
161651 NNNNNNNNNN NNNNNNNNNN NNNNNNNNNN NNNNNNNNNN NNNNNNNNNN
161701 NNNNNNNNNN NNNNNNNNNN NNNNNNNNNN NNNNNNNNNN NNNNNNNNNN
161751 NNNNNNNNNN NNNNNNNNNN NNNNNNNNNN NNNNNNNNNN NNNNNNNNNN
161801 NNNNNNNNNN NNNNNNNNNN NNNNNNNNNN NNNNNNNNNN NNNNNNNNNN
161851 NNNNNNNNNN NNNNNNNNNN NNNNNNNNNN NNNNNNNNNN NNNNNNNNNN
161901 NNNNNNNNNN NNNNNNNNNN NNNNNNNNNN NNNNNNNNNN NNNNNNNNNN
161951 NNNNNNNNNN NNNNNNNNNN NNNNNNNNNN NNNNNNNNNN NNNNNNNNNN
162001 NNNNNNNNNN NNNNNNNNNN NNNNNNNNNN NNNNNNNNNN NNNNNNNNNN
162051 NNNNNNNNNN NNNNNNNNNN NNNNNNNNNN NNNNNNNNNN NNNNNNNNNN
162101 NNNNNNNNNN NNNNNNNNNN NNNNNNNNNN NNNNNNNNNN NNNNNNNNNN
162151 NNNNNNNNNN NNNNNNNNNN NNNNNNNNNN NNNNNNNNNN NNNNNNNNNN
162201 NNNNNNNNNN NNNNNNNNNN NNNNNNNNNN NNNNNNNNNN NNNNNNNNNN
162251 NNNNNNNNNN NNNNNNNNNN NNNNNNNNNN NNNNNNNNNN NNNNNNNNNN
162301 NNNNNNNNNN NNNNNNNNNN NNNNNNNNNN NNNNNNNNNN NNNNNNNNNN
162351 NNNNNNNNNN NNNNNNNNNN NNNNNNNNNN NNNNNNNNNN NNNNNNNNNN
162401 NNNNNNNNNN NNNNNNNNNN NNNNNNNNNN NNNNNNNNNN NNNNNNNNNN
162451 NNNNNNNNNN NNNNNNNNNN NNNNNNNNNN NNNNNNNNNN NNNNNNNNNN
162501 NNNNNNNNNN NNNNNNNNNN NNNNNNNNNN NNNNNNNNNN NNNNNNNNNN
162551 NNNNNNNNNN NNNNNNNNNN NNNNNNNNNN NNNNNNNNNN NNNNNNNNNN
162601 NNNNNNNNNN NNNNNNNNNN NNNNNNNNNN NNNNNNNNNN NNNNNNNNNN
162651 NNNNNNNNNN NNNNNNNNNN NNNNNNNNNN NNNNNNNNNN NNNNNNNNNN
162701 NNNNNNNNNN NNNNNNNNNN NNNNNNNNNN NNNNNNNNNN NNNNNNNNNN
162751 NNNNNNNNNN NNNNNNNNNN NNNNNNNNNN NNNNNNNNNN NNNNNNNNNN
162801 NNNNNNNNNN NNNNNNNNNN NNNNNNNNNN NNNNNNNNNN NNNNNNNNNN
162851 NNNNNNNNNN NNNNNNNNNN NNNNNNNNNN NNNNNNNNNN NNNNNNNNNN
162901 NNNNNNNNNN NNNNNNNNNN NNNNNNNNNN NNNNNNNNNN NNNNNNNNNN
162951 NNNNNNNNNN NNNNNNNNNN NNNNNNNNNN NNNNNNNNNN NNNNNNNNNN
163001 NNNNNNNNNN NNNNNNNNNN NNNNNNNNNN NNNNNNNNNN NNNNNNNNNN
163051 NNNNNNNNNN NNNNNNNNNN NNNNNNNNNN NNNNNNNNNN NNNNNNNNNN
163101 NNNNNNNNNN NNNNNNNNNN NNNNNNNNNN NNNNNNNNNN NNNNNNNNNN
163151 NNNNNNNNNN NNNNNNNNNN NNNNNNNNNN NNNNNNNNNN NNNNNNNNNN
163201 NNNNNNNNNN NNNNNNNNNN NNNNNNNNNN NNNNNNNNNN NNNNNNNNNN
```

FIGURE 3, page 46 of 87

```
163251 NNNNNNNNNN NNNNNNNNNN NNNNNNNNNN NNNNNNNNNN NNNNNNNNNN
163301 NNNNNNNNNN NNNNNNNNNN NNNNNNNNNN NNNNNNNNNN NNNNNNNNNN
163351 NNNNNNNNNN NNNNNNNNNN NNNNNNNNNN NNNNNNNNNN NNNNNNNNNN
163401 NNNNNNNNNN NNNNNNNNNN NNNNNNNNNN NNNNNNNNNN NNNNNNNNNN
163451 NNNNNNNNNN NNNNNNNNNN NNNNNNNNNN NNNNNNNNNN NNNNNNNNNN
163501 NNNNNNNNNN NNNNNNNNNN NNNNNNNNNN NNNNNNNNNN NNNNNNNNNN
163551 NNNNNNNNNN NNNNNNNNNN NNNNNNNNNN NNNNNNNNNN NNNNNNNNNN
163601 NNNNNNNNNN NNNNNNNNNN NNNNNNNNNN NNNNNNNNNN NNNNNNNNNN
163651 NNNNNNNNNN NNNNNNNNNN NNNNNNNNNN NNNNNNNNNN NNNNNNNNNN
163701 NNNNNNNNNN NNNNNNNNNN NNNNNNNNNN NNNNNNNNNN NNNNNNNNNN
163751 NNNNNNNNNN NNNNNNNNNN NNNNNNNNNN NNNNNNNNNN NNNNNNNNNN
163801 NNNNNNNNNN NNNNNNNNNN NNNNNNNNNN NNNNNNNNNN NNNNNNNNNN
163851 NNNNNNNNNN NNNNNNNNNN NNNNNNNNNN NNNNNNNNNN NNNNNNNNNN
163901 NNNNNNNNNN NNNNNNNNNN NNNNNNNNNN NNNNNNNNNN NNNNNNNNNN
163951 NNNNNNNNNN NNNNNNNNNN NNNNNNNNNN NNNNNNNNNN NNNNNNNNNN
164001 NNNNNNNNNN NNNNNNNNNN NNNNNNNNNN NNNNNNNNNN NNNNNNNNNN
164051 NNNNNNNNNN NNNNNNNNNN NNNNNNNNNN NNNNNNNNNN NNNNNNNNNN
164101 NNNNNNNNNN NNNNNNNNNN NNNNNNNNNN NNNNNNNNNN NNNNNNNNNN
164151 NNNNNNNNNN NNNNNNNNNN NNNNNNNNNN NNNNNNNNNN NNNNNNNNNN
164201 NNNNNNNNNN NNNNNNNNNN NNNNNNNNNN NNNNNNNNNN NNNNNNNNNN
164251 NNNNNNNNNN NNNNNNNNNN NNNNNNNNNN NNNNNNNNNN NNNNNNNNNN
164301 NNNNNNNNNN NNNNNNNNNN NNNNNNNNNN NNNNNNNNNN NNNNNNNNNN
164351 NNNNNNNNNN NNNNNNNNNN NNNNNNNNNN NNNNNNNNNN NNNNNNNNNN
164401 NNNNNNNNNN NNNNNNNNNN NNNNNNNNNN NNNNNNNNNN NNNNNNNNNN
164451 NNNNNNNNNN NNNNNNNNNN NNNNNNNNNN NNNNNNNNNN NNNNNNNNNN
164501 NNNNNNNNNN NNNNNNNNNN NNNNNNNNNN NNNNNNNNNN NNNNNNNNNN
164551 NNNNNNNNNN NNNNNNNNNN NNNNNNNNNN NNNNNNNNNN NNNNNNNNNN
164601 NNNNNNNNNN NNNNNNNNNN NNNNNNNNNN NNNNNNNNNN NNNNNNNNNN
164651 NNNNNNNNNN NNNNNNNNNN NNNNNNNNNN NNNNNNNNNN NNNNNNNNNN
164701 NNNNNNNNNN NNNNNNNNNN NNNNNNNNNN NNNNNNNNNN NNNNNNNNNN
164751 NNNNNNNNNN NNNNNNNNNN NNNNNNNNNN NNNNNNNNNN NNNNNNNNNN
164801 NNNNNNNNNN NNNNNNNNNN NNNNNNNNNN NNNNNNNNNN NNNNNNNNNN
164851 NNNNNNNNNN NNNNNNNNNN NNNNNNNNNN NNNNNNNNNN NNNNNNNNNN
164901 NNNNNNNNNN NNNNNNNNNN NNNNNNNNNN NNNNNNNNNN NNNNNNNNNN
164951 NNNNNNNNNN NNNNNNNNNN NNNNNNNNNN NNNNNNNNNN NNNNNNNNNN
165001 NNNNNNNNNN NNNNNNNNNN NNNNNNNNNN NNNNNNNNNN NNNNNNNNNN
165051 NNNNNNNNNN NNNNNNNNNN NNNNNNNNNN NNNNNNNNNN NNNNNNNNNN
165101 NNNNNNNNNN NNNNNNNNNN NNNNNNNNNN NNNNNNNNNN NNNNNNNNNN
165151 NNNNNNNNNN NNNNNNNNNN NNNNNNNNNN NNNNNNNNNN NNNNNNNNNN
165201 NNNNNNNNNN NNNNNNNNNN NNNNNNNNNN NNNNNNNNNN NNNNNNNNNN
165251 NNNNNNNNNN NNNNNNNNNN NNNNNNNNNN NNNNNNNNNN NNNNNNNNNN
165301 NNNNNNNNNN NNNNNNNNNN NNNNNNNNNN NNNNNNNNNN NNNNNNNNNN
165351 NNNNNNNNNN NNNNNNNNNN NNNNNNNNNN NNNNNNNNNN NNNNNNNNNN
165401 NNNNNNNNNN NNNNNNNNNN NNNNNNNNNN NNNNNNNNNN NNNNNNNNNN
165451 NNNNNNNNNN NNNNNNNNNN NNNNNNNNNN NNNNNNNNNN NNNNNNNNNN
165501 NNNNNNNNNN NNNNNNNNNN NNNNNNNNNN NNNNNNNNNN NNNNNNNNNN
165551 NNNNNNNNNN NNNNNNNNNN NNNNNNNNNN NNNNNNNNNN NNNNNNNNNN
165601 NNNNNNNNNN NNNNNNNNNN NNNNNNNNNN NNNNNNNNNN NNNNNNNNNN
165651 NNNNNNNNNN NNNNNNNNNN NNNNNNNNNN NNNNNNNNNN NNNNNNNNNN
165701 NNNNNNNNNN NNNNNNNNNN NNNNNNNNNN NNNNNNNNNN NNNNNNNNNN
165751 NNNNNNNNNN NNNNNNNNNN NNNNNNNNNN NNNNNNNNNN NNNNNNNNNN
165801 NNNNNNNNNN NNNNNNNNNN NNNNNNNNNN NNNNNNNNNN NNNNNNNNNN
165851 NNNNNNNNNN NNNNNNNNNN NNNNNNNNNN NNNNNNNNNN NNNNNNNNNN
165901 NNNNNNNNNN NNNNNNNNNN NNNNNNNNNN NNNNNNNNNN NNNNNNNNNN
165951 NNNNNNNNNN NNNNNNNNNN NNNNNNNNNN NNNNNNNNNN NNNNNNNNNN
166001 NNNNNNNNNN NNNNNNNNNN NNNNNNNNNN NNNNNNNNNN NNNNNNNNNN
166051 NNNNNNNNNN NNNNNNNNNN NNNNNNNNNN NNNNNNNNNN NNNNNNNNNN
166101 NNNNNNNNNN NNNNNNNNNN NNNNNNNNNN NNNNNNNNNN NNNNNNNNNN
166151 NNNNNNNNNN NNNNNNNNNN NNNNNNNNNN NNNNNNNNNN NNNNNNNNNN
166201 NNNNNNNNNN NNNNNNNNNN NNNNNNNNNN NNNNNNNNNN NNNNNNNNNN
166251 NNNNNNNNNN NNNNNNNNNN NNNNNNNNNN NNNNNNNNNN NNNNNNNNNN
166301 NNNNNNNNNN NNNNNNNNNN NNNNNNNNNN NNNNNNNNNN NNNNNNNNNN
166351 NNNNNNNNNN NNNNNNNNNN NNNNNNNNNN NNNNNNNNNN NNNNNNNNNN
166401 NNNNNNNNNN NNNNNNNNNN NNNNNNNNNN NNNNNNNNNN NNNNNNNNNN
166451 NNNNNNNNNN NNNNNNNNNN NNNNNNNNNN NNNNNNNNNN NNNNNNNNNN
166501 NNNNNNNNNN NNNNNNNNNN NNNNNNNNNN NNNNNNNNNN NNNNNNNNNN
166551 NNNNNNNNNN NNNNNNNNNN NNNNNNNNNN NNNNNNNNNN NNNNNNNNNN
166601 NNNNNNNNNN NNNNNNNNNN NNNNNNNNNN NNNNNNNNNN NNNNNNNNNN
166651 NNNNNNNNNN NNNNNNNNNN NNNNNNNNNN NNNNNNNNNN NNNNNNNNNN
166701 NNNNNNNNNN NNNNNNNNNN NNNNNNNNNN NNNNNNNNNN NNNNNNNNNN
166751 NNNNNNNNNN NNNNNNNNNN NNNNNNNNNN NNNNNNNNNN NNNNNNNNNN
```

FIGURE 3, page 47 of 87

166801 NNNNNNNNNN NNNNNNNNNN NNNNNNNNNN NNNNNNNNNN NNNNNNNNNN
166851 NNNNNNNNNN NNNNNNNNNN NNNNNNNNNN NNNNNNNNNN NNNNNNNNNN
166901 NNNNNNNNNN NNNNNNNNNN NNNNNNNNNN NNNNNNNNNN NNNNNNNNNN
166951 NNNNNNNNNN NNNNNNNNNN NNNNNNNNNN NNNNNNNNNN NNNNNNNNNN
167001 NNNNNNNNNN NNNNNNNNNN NNNNNNNNNN NNNNNNNNNN NNNNNNNNNN
167051 NNNNNNNNNN NNNNNNNNNN NNNNNNNNNN NNNNNNNNNN NNNNNNNNNN
167101 NNNNNNNNNN NNNNNNNNNN NNNNNNNNNN NNNNNNNNNN NNNNNNNNNN
167151 NNNNNNNNNN NNNNNNNNNN NNNNNNNNNN NNNNNNNNNN NNNNNNNNNN
167201 NNNNNNNNNN NNNNNNNNNN NNNNNNNNNN NNNNNNNNNN NNNNNNNNNN
167251 NNNNNNNNNN NNNNNNNNNN NNNNNNNNNN NNNNNNNNNN NNNNNNNNNN
167301 NNNNNNNNNN NNNNNNNNNN NNNNNNNNNN NNNNNNNNNN NNNNNNNNNN
167351 NNNNNNNNNN NNNNNNNNNN NNNNNNNNNN NNNNNNNNNN NNNNNNNNNN
167401 NNNNNNNNNN NNNNNNNNNN NNNNNNNNNN NNNNNNNNNN NNNNNNNNNN
167451 NNNNNNNNNN NNNNNNNNNN NNNNNNNNNN NNNNNNNNNN NNNNNNNNNN
167501 NNNNNNNNNN NNNNNNNNNN NNNNNNNNNN NNNNNNNNNN NNNNNNNNNN
167551 NNNNNNNNNN NNNNNNNNNN NNNNNNNNNN NNNNNNNNNN NNNNNNNNNN
167601 NNNNNNNNNN NNNNNNNNNN NNNNNNNNNN NNNNNNNNNN NNNNNNNNNN
167651 NNNNNNNNNN NNNNNNNNNN NNNNNNNNNN NNNNNNNNNN NNNNNNNNNN
167701 NNNNNNNNNN NNNNNNNNNN NNNNNNNNNN NNNNNNNNNN NNNNNNNNNN
167751 NNNNNNNNNN NNNNNNNNNN NNNNNNNNNN NNNNNNNNNN NNNNNNNNNN
167801 NNNNNNNNNN NNNNNNNNNN NNNNNNNNNN NNNNNNNNNN NNNNNNNNNN
167851 NNNNNNNNNN NNNNNNNNNN NNNNNNNNNN NNNNNNNNNN NNNNNNNNNN
167901 NNNNNNNNNN NNNNNNNNNN NNNNNNNNNN NNNNNNNNNN NNNNNNNNNN
167951 NNNNNNNNNN NNNNNNNNNN NNNNNNNNNN NNNNNNNNNN NNNNNNNNNN
168001 NNNNNNNNNN NNNNNNNNNN NNNNNNNNNN NNNNNNNNNN NNNNNNNNNN
168051 NNNNNNNNNN NNNNNNNNNN NNNNNNNNNN NNNNNNNNNN NNNNNNNNNN
168101 NNNNNNNNNN NNNNNNNNNN NNNNNNNNNN NNNNNNNNNN NNNNNNNNNN
168151 NNNNNNNNNN NNNNNNNNNN NNNNNNNNNN NNNNNNNNNN NNNNNNNNNN
168201 NNNNNNNNNN NNNNNNNNNN NNNNNNNNNN NNNNNNNNNN NNNNNNNNNN
168251 NNNNNNNNNN NNNNNNNNNN NNNNNNNNNN NNNNNNNNNN NNNNNNNNNN
168301 NNNNNNNNNN NNNNNNNNNN NNNNNNNNNN NNNNNNNNNN NNNNNNNNNN
168351 NNNNNNNNNN NNNNNNNNNN NNNNNNNNNN NNNNNNNNNN NNNNNNNNNN
168401 NNNNNNNNNN NNNNNNNNNN NNNNNNNNNN NNNNNNNNNN NNNNNNNNNN
168451 NNNNNNNNNN NNNNNNNNNN NNNNNNNNNN NNNNNNNNNN NNNNNNNNNN
168501 NNNNNNNNNN NNNNNNNNNN NNNNNNNNNN NNNNNNNNNN NNNNNNNNNN
168551 NNNNNNNNNN NNNNNNNNNN NNNNNNNNNN NNNNNNNNNN NNNNNNNNNN
168601 NNNNNNNNNN NNNNNNNNNN NNNNNNNNNN NNNNNNNNNN NNNNNNNNNN
168651 NNNNNNNNNN NNNNNNNNNN NNNNNNNNNN NNNNNNNNNN NNNNNNNNNN
168701 NNNNNNNNNN NNNNNNNNNN NNNNNNNNNN NNNNNNNNNN NNNNNNNNNN
168751 NNNNNNNNNN NNNNNNNNNN NNNNNNNNNN NNNNNNNNNN NNNNNNNNNN
168801 NNNNNNNNNN NNNNNNNNNN NNNNNNNNNN NNNNNNNNNN NNNNNNNNNN
168851 NNNNNNNNNN NNNNNNNNNN NNNNNNNNNN NNNNNNNNNN NNNNNNNNNN
168901 NNNNNNNNNN NNNNNNNNNN NNNNNNNNNN NNNNNNNNNN NNNNNNNNNN
168951 NNNNNNNNNN NNNNNNNNNN NNNNNNNNNN NNNNNNNNNN NNNNNNNNNN
169001 NNNNNNNNNN NNNNNNNNNN NNNNNNNNNN NNNNNNNNNN NNNNNNNNNN
169051 NNNNNNNNNN NNNNNNNNNN NNNNNNNNNN NNNNNNNNNN NNNNNNNNNN
169101 NNNNNNNNNN NNNNNNNNNN NNNNNNNNNN NNNNNNNNNN NNNNNNNNNN
169151 NNNNNNNNNN NNNNNNNNNN NNNNNNNNNN NNNNNNNNNN NNNNNNNNNN
169201 NNNNNNNNNN NNNNNNNNNN NNNNNNNNNN NNNNNNNNNN NNNNNNNNNN
169251 NNNNNNNNNN NNNNNNNNNN NNNNNNNNNN NNNNNNNNNN NNNNNNNNNN
169301 NNNNNNNNNN NNNNNNNNNN NNNNNNNNNN NNNNNNNNNN NNNNNNNNNN
169351 NNNNNNNNNN NNNNNNNNNN NNNNNNNNNN NNNNNNNNNN NNNNNNNNNN
169401 NNNNNNNNNN NNNNNNNNNN NNNNNNNNNN NNNNNNNNNN NNNNNNNNNN
169451 NNNNNNNNNN NNNNNNNNNN NNNNNNNNNN NNNNNNNNNN NNNNNNNNNN
169501 NNNNNNNNNN NNNNNNNNNN NNNNNNNNNN NNNNNNNNNN NNNNNNNNNN
169551 NNNNNNNNNN NNNNNNNNNN NNNNNNNNNN NNNNNNNNNN NNNNNNNNNN
169601 NNNNNNNNNN NNNNNNNNNN NNNNNNNNNN NNNNNNNNNN NNNNNNNNNN
169651 NNNNNNNNNN NNNNNNNNNN NNNNNNNNNN NNNNNNNNNN NNNNNNNNNN
169701 NNNNNNNNNN NNNNNNNNNN NNNNNNNNNN NNNNNNNNNN NNNNNNNNNN
169751 NNNNNNNNNN NNNNNNNNNN NNNNNNNNNN NNNNNNNNNN NNNNNNNNNN
169801 NNNNNNNNNN NNNNNNNNNN NNNNNNNNNN NNNNNNNNNN NNNNNNNNNN
169851 NNNNNNNNNN NNNNNNNNNN NNNNNNNNNN NNNNNNNNNN NNNNNNNNNN
169901 NNNNNNNNNN NNNNNNNNNN NNNNNNNNNN NNNNNNNNNN NNNNNNNNNN
169951 NNNNNNNNNN NNNNNNNNNN NNNNNNNNNN NNNNNNNNNN NNNNNNNNNN
170001 NNNNNNNNNN NNNNNNNNNN NNNNNNNNNN NNNNNNNNNN NNNNNNNNNN
170051 NNNNNNNNNN NNNNNNNNNN NNNNNNNNNN NNNNNNNNNN NNNNNNNNNN
170101 NNNNNNNNNN NNNNNNNNNN NNNNNNNNNN NNNNNNNNNN NNNNNNNNNN
170151 NNNNNNNNNN NNNNNNNNNN NNNNNNNNNN NNNNNNNNNN NNNNNNNNNN
170201 NNNNNNNNNN NNNNNNNNNN NNNNNNNNNN NNNNNNNNNN NNNNNNNNNN
170251 NNNNNNNNNN NNNNNNNNNN NNNNNNNNNN NNNNNNNNNN NNNNNNNNNN
170301 NNNNNNNNNN NNNNNNNNNN NNNNNNNNNN NNNNNNNNNN NNNNNNNNNN

FIGURE 3, page 48 of 87

```
170351 NNNNNNNNNN NNNNNNNNNN NNNNNNNNNN NNNNNNNNNN NNNNNNNNNN
170401 NNNNNNNNNN NNNNNNNNNN NNNNNNNNNN NNNNNNNNNN NNNNNNNNNN
170451 NNNNNNNNNN NNNNNNNNNN NNNNNNNNNN NNNNNNNNNN NNNNNNNNNN
170501 NNNNNNNNNN NNNNNNNNNN NNNNNNNNNN NNNNNNNNNN NNNNNNNNNN
170551 NNNNNNNNNN NNNNNNNNNN NNNNNNNNNN NNNNNNNNNN NNNNNNNNNN
170601 NNNNNNNNNN NNNNNNNNNN NNNNNNNNNN NNNNNNNNNN NNNNNNNNNN
170651 NNNNNNNNNN NNNNNNNNNN NNNNNNNNNN NNNNNNNNNN NNNNNNNNNN
170701 NNNNNNNNNN NNNNNNNNNN NNNNNNNNNN NNNNNNNNNN NNNNNNNNNN
170751 NNNNNNNNNN NNNNNNNNNN NNNNNNNNNN NNNNNNNNNN NNNNNNNNNN
170801 NNNNNNNNNN NNNNNNNNNN NNNNNNNNNN NNNNNNNNNN NNNNNNNNNN
170851 NNNNNNNNNN NNNNNNNNNN NNNNNNNNNN NNNNNNNNNN NNNNNNNNNN
170901 NNNNNNNNNN NNNNNNNNNN NNNNNNNNNN NNNNNNNNNN NNNNNNNNNN
170951 NNNNNNNNNN NNNNNNNNNN NNNNNNNNNN NNNNNNNNNN NNNNNNNNNN
171001 NNNNNNNNNN NNNNNNNNNN NNNNNNNNNN NNNNNNNNNN NNNNNNNNNN
171051 NNNNNNNNNN NNNNNNNNNN NNNNNNNNNN NNNNNNNNNN NNNNNNNNNN
171101 NNNNNNNNNN NNNNNNNNNN NNNNNNNNNN NNNNNNNNNN NNNNNNNNNN
171151 NNNNNNNNNN NNNNNNNNNN NNNNNNNNNN NNNNNNNNNN NNNNNNNNNN
171201 NNNNNNNNNN NNNNNNNNNN NNNNNNNNNN NNNNNNNNNN NNNNNNNNNN
171251 NNNNNNNNNN NNNNNNNNNN NNNNNNNNNN NNNNNNNNNN NNNNNNNNNN
171301 NNNNNNNNNN NNNNNNNNNN NNNNNNNNNN NNNNNNNNNN NNNNNNNNNN
171351 NNNNNNNNNN NNNNNNNNNN NNNNNNNNNN NNNNNNNNNN NNNNNNNNNN
171401 NNNNNNNNNN NNNNNNNNNN NNNNNNNNNN NNNNNNNNNN NNNNNNNNNN
171451 NNNNNNNNNN NNNNNNNNNN NNNNNNNNNN NNNNNNNNNN NNNNNNNNNN
171501 NNNNNNNNNN NNNNNNNNNN NNNNNNNNNN NNNNNNNNNN NNNNNNNNNN
171551 NNNNNNNNNN NNNNNNNNNN NNNNNNNNNN NNNNNNNNNN NNNNNNNNNN
171601 NNNNNNNNNN NNNNNNNNNN NNNNNNNNNN NNNNNNNNNN NNNNNNNNNN
171651 NNNNNNNNNN NNNNNNNNNN NNNNNNNNNN NNNNNNNNNN NNNNNNNNNN
171701 NNNNNNNNNN NNNNNNNNNN NNNNNNNNNN NNNNNNNNNN NNNNNNNNNN
171751 NNNNNNNNNN NNNNNNNNNN NNNNNNNNNN NNNNNNNNNN NNNNNNNNNN
171801 NNNNNNNNNN NNNNNNNNNN NNNNNNNNNN NNNNNNNNNN NNNNNNNNNN
171851 NNNNNNNNNN NNNNNNNNNN NNNNNNNNNN NNNNNNNNNN NNNNNNNNNN
171901 NNNNNNNNNN NNNNNNNNNN NNNNNNNNNN NNNNNNNNNN NNNNNNNNNN
171951 NNNNNNNNNN NNNNNNNNNN NNNNNNNNNN NNNNNNNNNN NNNNNNNNNN
172001 NNNNNNNNNN NNNNNNNNNN NNNNNNNNNN NNNNNNNNNN NNNNNNNNNN
172051 NNNNNNNNNN NNNNNNNNNN NNNNNNNNNN NNNNNNNNNN NNNNNNNNNN
172101 NNNNNNNNNN NNNNNNNNNN NNNNNNNNNN NNNNNNNNNN NNNNNNNNNN
172151 NNNNNNNNNN NNNNNNNNNN NNNNNNNNNN NNNNNNNNNN NNNNNNNNNN
172201 NNNNNNNNNN NNNNNNNNNN NNNNNNNNNN NNNNNNNNNN NNNNNNNNNN
172251 NNNNNNNNNN NNNNNNNNNN NNNNNNNNNN NNNNNNNNNN NNNNNNNNNN
172301 NNNNNNNNNN NNNNNNNNNN NNNNNNNNNN NNNNNNNNNN NNNNNNNNNN
172351 NNNNNNNNNN NNNNNNNNNN NNNNNNNNNN NNNNNNNNNN NNNNNNNNNN
172401 NNNNNNNNNN NNNNNNNNNN NNNNNNNNNN NNNNNNNNNN NNNNNNNNNN
172451 NNNNNNNNNN NNNNNNNNNN NNNNNNNNNN NNNNNNNNNN NNNNNNNNNN
172501 NNNNNNNNNN NNNNNNNNNN NNNNNNNNNN NNNNNNNNNN NNNNNNNNNN
172551 NNNNNNNNNN NNNNNNNNNN NNNNNNNNNN NNNNNNNNNN NNNNNNNNNN
172601 NNNNNNNNNN NNNNNNNNNN NNNNNNNNNN NNNNNNNNNN NNNNNNNNNN
172651 NNNNNNNNNN NNNNNNNNNN NNNNNNNNNN NNNNNNNNNN NNNNNNNNNN
172701 NNNNNNNNNN NNNNNNNNNN NNNNNNNNNN NNNNNNNNNN NNNNNNNNNN
172751 NNNNNNNNNN NNNNNNNNNN NNNNNNNNNN NNNNNNNNNN NNNNNNNNNN
172801 NNNNNNNNNN NNNNNNNNNN NNNNNNNNNN NNNNNNNNNN NNNNNNNNNN
172851 NNNNNNNNNN NNNNNNNNNN NNNNNNNNNN NNNNNNNNNN NNNNNNNNNN
172901 NNNNNNNNNN NNNNNNNNNN NNNNNNNNNN NNNNNNNNNN NNNNNNNNNN
172951 NNNNNNNNNN NNNNNNNNNN NNNNNNNNNN NNNNNNNNNN NNNNNNNNNN
173001 NNNNNNNNNN NNNNNNNNNN NNNNNNNNNN NNNNNNNNNN NNNNNNNNNN
173051 NNNNNNNNNN NNNNNNNNNN NNNNNNNNNN NNNNNNNNNN NNNNNNNNNN
173101 NNNNNNNNNN NNNNNNNNNN NNNNNNNNNN NNNNNNNNNN NNNNNNNNNN
173151 NNNNNNNNNN NNNNNNNNNN NNNNNNNNNN NNNNNNNNNN NNNNNNNNNN
173201 NNNNNNNNNN NNNNNNNNNN NNNNNNNNNN NNNNNNNNNN NNNNNNNNNN
173251 NNNNNNNNNN NNNNNNNNNN NNNNNNNNNN NNNNNNNNNN NNNNNNNNNN
173301 NNNNNNNNNN NNNNNNNNNN NNNNNNNNNN NNNNNNNNNN NNNNNNNNNN
173351 NNNNNNNNNN NNNNNNNNNN NNNNNNNNNN NNNNNNNNNN NNNNNNNNNN
173401 NNNNNNNNNN NNNNNNNNNN NNNNNNNNNN NNNNNNNNNN NNNNNNNNNN
173451 NNNNNNNNNN NNNNNNNNNN NNNNNNNNNN NNNNNNNNNN NNNNNNNNNN
173501 NNNNNNNNNN NNNNNNNNNN NNNNNNNNNN NNNNNNNNNN NNNNNNNNNN
173551 NNNNNNNNNN NNNNNNNNNN NNNNNNNNNN NNNNNNNNNN NNNNNNNNNN
173601 NNNNNNNNNN NNNNNNNNNN NNNNNNNNNN NNNNNNNNNN NNNNNNNNNN
173651 NNNNNNNNNN NNNNNNNNNN NNNNNNNNNN NNNNNNNNNN NNNNNNNNNN
173701 NNNNNNNNNN NNNNNNNNNN NNNNNNNNNN NNNNNNNNNN NNNNNNNNNN
173751 NNNNNNNNNN NNNNNNNNNN NNNNNNNNNN NNNNNNNNNN NNNNNNNNNN
173801 NNNNNNNNNN NNNNNNNNNN NNNNNNNNNN NNNNNNNNNN NNNNNNNNNN
173851 NNNNNNNNNN NNNNNNNNNN NNNNNNNNNN NNNNNNNNNN NNNNNNNNNN
```

FIGURE 3, page 49 of 87

```
173901 NNNNNNNNNN NNNNNNNNNN NNNNNNNNNN NNNNNNNNNN NNNNNNNNNN
173951 NNNNNNNNNN NNNNNNNNNN NNNNNNNNNN NNNNNNNNNN NNNNNNNNNN
174001 NNNNNNNNNN NNNNNNNNNN NNNNNNNNNN NNNNNNNNNN NNNNNNNNNN
174051 NNNNNNNNNN NNNNNNNNNN NNNNNNNNNN NNNNNNNNNN NNNNNNNNNN
174101 NNNNNNNNNN NNNNNNNNNN NNNNNNNNNN NNNNNNNNNN NNNNNNNNNN
174151 NNNNNNNNNN NNNNNNNNNN NNNNNNNNNN NNNNNNNNNN NNNNNNNNNN
174201 NNNNNNNNNN NNNNNNNNNN NNNNNNNNNN NNNNNNNNNN NNNNNNNNNN
174251 NNNNNNNNNN NNNNNNNNNN NNNNNNNNNN NNNNNNNNNN NNNNNNNNNN
174301 NNNNNNNNNN NNNNNNNNNN NNNNNNNNNN NNNNNNNNNN NNNNNNNNNN
174351 NNNNNNNNNN NNNNNNNNNN NNNNNNNNNN NNNNNNNNNN NNNNNNNNNN
174401 NNNNNNNNNN NNNNNNNNNN NNNNNNNNNN NNNNNNNNNN NNNNNNNNNN
174451 NNNNNNNNNN NNNNNNNNNN NNNNNNNNNN NNNNNNNNNN NNNNNNNNNN
174501 NNNNNNNNNN NNNNNNNNNN NNNNNNNNNN NNNNNNNNNN NNNNNNNNNN
174551 NNNNNNNNNN NNNNNNNNNN NNNNNNNNNN NNNNNNNNNN NNNNNNNNNN
174601 NNNNNNNNNN NNNNNNNNNN NNNNNNNNNN NNNNNNNNNN NNNNNNNNNN
174651 NNNNNNNNNN NNNNNNNNNN NNNNNNNNNN NNNNNNNNNN NNNNNNNNNN
174701 NNNNNNNNNN NNNNNNNNNN NNNNNNNNNN NNNNNNNNNN NNNNNNNNNN
174751 NNNNNNNNNN NNNNNNNNNN NNNNNNNNNN NNNNNNNNNN NNNNNNNNNN
174801 NNNNNNNNNN NNNNNNNNNN NNNNNNNNNN NNNNNNNNNN NNNNNNNNNN
174851 NNNNNNNNNN NNNNNNNNNN NNNNNNNNNN NNNNNNNNNN NNNNNNNNNN
174901 NNNNNNNNNN NNNNNNNNNN NNNNNNNNNN NNNNNNNNNN NNNNNNNNNN
174951 NNNNNNNNNN NNNNNNNNNN NNNNNNNNNN NNNNNNNNNN NNNNNNNNNN
175001 NNNNNNNNNN NNNNNNNNNN NNNNNNNNNN NNNNNNNNNN NNNNNNNNNN
175051 NNNNNNNNNN NNNNNNNNNN NNNNNNNNNN NNNNNNNNNN NNNNNNNNNN
175101 NNNNNNNNNN NNNNNNNNNN NNNNNNNNNN NNNNNNNNNN NNNNNNNNNN
175151 NNNNNNNNNN NNNNNNNNNN NNNNNNNNNN NNNNNNNNNN NNNNNNNNNN
175201 NNNNNNNNNN NNNNNNNNNN NNNNNNNNNN NNNNNNNNNN NNNNNNNNNN
175251 NNNNNNNNNN NNNNNNNNNN NNNNNNNNNN NNNNNNNNNN NNNNNNNNNN
175301 NNNNNNNNNN NNNNNNNNNN NNNNNNNNNN NNNNNNNNNN NNNNNNNNNN
175351 NNNNNNNNNN NNNNNNNNNN NNNNNNNNNN NNNNNNNNNN NNNNNNNNNN
175401 NNNNNNNNNN NNNNNNNNNN NNNNNNNNNN NNNNNNNNNN NNNNNNNNNN
175451 NNNNNNNNNN NNNNNNNNNN NNNNNNNNNN NNNNNNNNNN NNNNNNNNNN
175501 NNNNNNNNNN NNNNNNNNNN NNNNNNNNNN NNNNNNNNNN NNNNNNNNNN
175551 NNNNNNNNNN NNNNNNNNNN NNNNNNNNNN NNNNNNNNNN NNNNNNNNNN
175601 NNNNNNNNNN NNNNNNNNNN NNNNNNNNNN NNNNNNNNNN NNNNNNNNNN
175651 NNNNNNNNNN NNNNNNNNNN NNNNNNNNNN NNNNNNNNNN NNNNNNNNNN
175701 NNNNNNNNNN NNNNNNNNNN NNNNNNNNNN NNNNNNNNNN NNNNNNNNNN
175751 NNNNNNNNNN NNNNNNNNNN NNNNNNNNNN NNNNNNNNNN NNNNNNNNNN
175801 NNNNNNNNNN NNNNNNNNNN NNNNNNNNNN NNNNNNNNNN NNNNNNNNNN
175851 NNNNNNNNNN NNNNNNNNNN NNNNNNNNNN NNNNNNNNNN NNNNNNNNNN
175901 NNNNNNNNNN NNNNNNNNNN NNNNNNNNNN NNNNNNNNNN NNNNNNNNNN
175951 NNNNNNNNNN NNNNNNNNNN NNNNNNNNNN NNNNNNNNNN NNNNNNNNNN
176001 NNNNNNNNNN NNNNNNNNNN NNNNNNNNNN NNNNNNNNNN NNNNNNNNNN
176051 NNNNNNNNNN NNNNNNNNNN NNNNNNNNNN NNNNNNNNNN NNNNNNNNNN
176101 NNNNNNNNNN NNNNNNNNNN NNNNNNNNNN NNNNNNNNNN NNNNNNNNNN
176151 NNNNNNNNNN NNNNNNNNNN NNNNNNNNNN NNNNNNNNNN NNNNNNNNNN
176201 NNNNNNNNNN NNNNNNNNNN NNNNNNNNNN NNNNNNNNNN NNNNNNNNNN
176251 NNNNNNNNNN NNNNNNNNNN NNNNNNNNNN NNNNNNNNNN NNNNNNNNNN
176301 NNNNNNNNNN NNNNNNNNNN NNNNNNNNNN NNNNNNNNNN NNNNNNNNNN
176351 NNNNNNNNNN NNNNNNNNNN NNNNNNNNNN NNNNNNNNNN NNNNNNNNNN
176401 NNNNNNNNNN NNNNNNNNNN NNNNNNNNNN NNNNNNNNNN NNNNNNNNNN
176451 NNNNNNNNNN NNNNNNNNNN NNNNNNNNNN NNNNNNNNNN NNNNNNNNNN
176501 NNNNNNNNNN NNNNNNNNNN NNNNNNNNNN NNNNNNNNNN NNNNNNNNNN
176551 NNNNNNNNNN NNNNNNNNNN NNNNNNNNNN NNNNNNNNNN NNNNNNNNNN
176601 NNNNNNNNNN NNNNNNNNNN NNNNNNNNNN NNNNNNNNNN NNNNNNNNNN
176651 NNNNNNNNNN NNNNNNNNNN NNNNNNNNNN NNNNNNNNNN NNNNNNNNNN
176701 NNNNNNNNNN NNNNNNNNNN NNNNNNNNNN NNNNNNNNNN NNNNNNNNNN
176751 NNNNNNNNNN NNNNNNNNNN NNNNNNNNNN NNNNNNNNNN NNNNNNNNNN
176801 NNNNNNNNNN NNNNNNNNNN NNNNNNNNNN NNNNNNNNNN NNNNNNNNNN
176851 NNNNNNNNNN NNNNNNNNNN NNNNNNNNNN NNNNNNNNNN NNNNNNNNNN
176901 NNNNNNNNNN NNNNNNNNNN NNNNNNNNNN NNNNNNNNNN NNNNNNNNNN
176951 NNNNNNNNNN NNNNNNNNNN NNNNNNNNNN NNNNNNNNNN NNNNNNNNNN
177001 NNNNNNNNNN NNNNNNNNNN NNNNNNNNNN NNNNNNNNNN NNNNNNNNNN
177051 NNNNNNNNNN NNNNNNNNNN NNNNNNNNNN NNNNNNNNNN NNNNNNNNNN
177101 NNNNNNNNNN NNNNNNNNNN NNNNNNNNNN NNNNNNNNNN NNNNNNNNNN
177151 NNNNNNNNNN NNNNNNNNNN NNNNNNNNNN NNNNNNNNNN NNNNNNNNNN
177201 NNNNNNNNNN NNNNNNNNNN NNNNNNNNNN NNNNNNNNNN NNNNNNNNNN
177251 NNNNNNNNNN NNNNNNNNNN NNNNNNNNNN NNNNNNNNNN NNNNNNNNNN
177301 NNNNNNNNNN NNNNNNNNNN NNNNNNNNNN NNNNNNNNNN NNNNNNNNNN
177351 NNNNNNNNNN NNNNNNNNNN NNNNNNNNNN NNNNNNNNNN NNNNNNNNNN
177401 NNNNNNNNNN NNNNNNNNNN NNNNNNNNNN NNNNNNNNNN NNNNNNNNNN
```

FIGURE 3, page 50 of 87

```
177451 NNNNNNNNNN NNNNNNNNNN NNNNNNNNNN NNNNNNNNNN NNNNNNNNNN
177501 NNNNNNNNNN NNNNNNNNNN NNNNNNNNNN NNNNNNNNNN NNNNNNNNNN
177551 NNNNNNNNNN NNNNNNNNNN NNNNNNNNNN NNNNNNNNNN NNNNNNNNNN
177601 NNNNNNNNNN NNNNNNNNNN NNNNNNNNNN NNNNNNNNNN NNNNNNNNNN
177651 NNNNNNNNNN NNNNNNNNNN NNNNNNNNNN NNNNNNNNNN NNNNNNNNNN
177701 NNNNNNNNNN NNNNNNNNNN NNNNNNNNNN NNNNNNNNNN NNNNNNNNNN
177751 NNNNNNNNNN NNNNNNNNNN NNNNNNNNNN NNNNNNNNNN NNNNNNNNNN
177801 NNNNNNNNNN NNNNNNNNNN NNNNNNNNNN NNNNNNNNNN NNNNNNNNNN
177851 NNNNNNNNNN NNNNNNNNNN NNNNNNNNNN NNNNNNNNNN NNNNNNNNNN
177901 NNNNNNNNNN NNNNNNNNNN NNNNNNNNNN NNNNNNNNNN NNNNNNNNNN
177951 NNNNNNNNNN NNNNNNNNNN NNNNNNNNNN NNNNNNNNNN NNNNNNNNNN
178001 NNNNNNNNNN NNNNNNNNNN NNNNNNNNNN NNNNNNNNNN NNNNNNNNNN
178051 NNNNNNNNNN NNNNNNNNNN NNNNNNNNNN NNNNNNNNNN NNNNNNNNNN
178101 NNNNNNNNNN NNNNNNNNNN NNNNNNNNNN NNNNNNNNNN NNNNNNNNNN
178151 NNNNNNNNNN NNNNNNNNNN NNNNNNNNNN NNNNNNNNNN NNNNNNNNNN
178201 NNNNNNNNNN NNNNNNNNNN NNNNNNNNNN NNNNNNNNNN NNNNNNNNNN
178251 NNNNNNNNNN NNNNNNNNNN NNNNNNNNNN NNNNNNNNNN NNNNNNNNNN
178301 NNNNNNNNNN NNNNNNNNNN NNNNNNNNNN NNNNNNNNNN NNNNNNNNNN
178351 NNNNNNNNNN NNNNNNNNNN NNNNNNNNNN NNNNNNNNNN NNNNNNNNNN
178401 NNNNNNNNNN NNNNNNNNNN NNNNNNNNNN NNNNNNNNNN NNNNNNNNNN
178451 NNNNNNNNNN NNNNNNNNNN NNNNNNNNNN NNNNNNNNNN NNNNNNNNNN
178501 NNNNNNNNNN NNNNNNNNNN NNNNNNNNNN NNNNNNNNNN NNNNNNNNNN
178551 NNNNNNNNNN NNNNNNNNNN NNNNNNNNNN NNNNNNNNNN NNNNNNNNNN
178601 NNNNNNNNNN NNNNNNNNNN NNNNNNNNNN NNNNNNNNNN NNNNNNNNNN
178651 NNNNNNNNNN NNNNNNNNNN NNNNNNNNNN NNNNNNNNNN NNNNNNNNNN
178701 NNNNNNNNNN NNNNNNNNNN NNNNNNNNNN NNNNNNNNNN NNNNNNNNNN
178751 NNNNNNNNNN NNNNNNNNNN NNNNNNNNNN NNNNNNNNNN NNNNNNNNNN
178801 NNNNNNNNNN NNNNNNNNNN NNNNNNNNNN NNNNNNNNNN NNNNNNNNNN
178851 NNNNNNNNNN NNNNNNNNNN NNNNNNNNNN NNNNNNNNNN NNNNNNNNNN
178901 NNNNNNNNNN NNNNNNNNNN NNNNNNNNNN NNNNNNNNNN NNNNNNNNNN
178951 NNNNNNNNNN NNNNNNNNNN NNNNNNNNNN NNNNNNNNNN NNNNNNNNNN
179001 NNNNNNNNNN NNNNNNNNNN NNNNNNNNNN NNNNNNNNNN NNNNNNNNNN
179051 NNNNNNNNNN NNNNNNNNNN NNNNNNNNNN NNNNNNNNNN NNNNNNNNNN
179101 NNNNNNNNNN NNNNNNNNNN NNNNNNNNNN NNNNNNNNNN NNNNNNNNNN
179151 NNNNNNNNNN NNNNNNNNNN NNNNNNNNNN NNNNNNNNNN NNNNNNNNNN
179201 NNNNNNNNNN NNNNNNNNNN NNNNNNNNNN NNNNNNNNNN NNNNNNNNNN
179251 NNNNNNNNNN NNNNNNNNNN NNNNNNNNNN NNNNNNNNNN NNNNNNNNNN
179301 NNNNNNNNNN NNNNNNNNNN NNNNNNNNNN NNNNNNNNNN NNNNNNNNNN
179351 NNNNNNNNNN NNNNNNNNNN NNNNNNNNNN NNNNNNNNNN NNNNNNNNNN
179401 NNNNNNNNNN NNNNNNNNNN NNNNNNNNNN NNNNNNNNNN NNNNNNNNNN
179451 NNNNNNNNNN NNNNNNNNNN NNNNNNNNNN NNNNNNNNNN NNNNNNNNNN
179501 NNNNNNNNNN NNNNNNNNNN NNNNNNNNNN NNNNNNNNNN NNNNNNNNNN
179551 NNNNNNNNNN NNNNNNNNNN NNNNNNNNNN NNNNNNNNNN NNNNNNNNNN
179601 NNNNNNNNNN NNNNNNNNNN NNNNNNNNNN NNNNNNNNNN NNNNNNNNNN
179651 NNNNNNNNNN NNNNNNNNNN NNNNNNNNNN NNNNNNNNNN NNNNNNNNNN
179701 NNNNNNNNNN NNNNNNNNNN NNNNNNNNNN NNNNNNNNNN NNNNNNNNNN
179751 NNNNNNNNNN NNNNNNNNNN NNNNNNNNNN NNNNNNNNNN NNNNNNNNNN
179801 NNNNNNNNNN NNNNNNNNNN NNNNNNNNNN NNNNNNNNNN NNNNNNNNNN
179851 NNNNNNNNNN NNNNNNNNNN NNNNNNNNNN NNNNNNNNNN NNNNNNNNNN
179901 NNNNNNNNNN NNNNNNNNNN NNNNNNNNNN NNNNNNNNNN NNNNNNNNNN
179951 NNNNNNNNNN NNNNNNNNNN NNNNNNNNNN NNNNNNNNNN NNNNNNNNNN
180001 NNNNNNNNNN NNNNNNNNNN NNNNNNNNNN NNNNNNNNNN NNNNNNNNNN
180051 NNNNNNNNNN NNNNNNNNNN NNNNNNNNNN NNNNNNNNNN NNNNNNNNNN
180101 NNNNNNNNNN NNNNNNNNNN NNNNNNNNNN NNNNNNNNNN NNNNNNNNNN
180151 NNNNNNNNNN NNNNNNNNNN NNNNNNNNNN NNNNNNNNNN NNNNNNNNNN
180201 NNNNNNNNNN NNNNNNNNNN NNNNNNNNNN NNNNNNNNNN NNNNNNNNNN
180251 NNNNNNNNNN NNNNNNNNNN NNNNNNNNNN NNNNNNNNNN NNNNNNNNNN
180301 NNNNNNNNNN NNNNNNNNNN NNNNNNNNNN NNNNNNNNNN NNNNNNNNNN
180351 NNNNNNNNNN NNNNNNNNNN NNNNNNNNNN NNNNNNNNNN NNNNNNNNNN
180401 NNNNNNNNNN NNNNNNNNNN NNNNNNNNNN NNNNNNNNNN NNNNNNNNNN
180451 NNNNNNNNNN NNNNNNNNNN NNNNNNNNNN NNNNNNNNNN NNNNNNNNNN
180501 NNNNNNNNNN NNNNNNNNNN NNNNNNNNNN NNNNNNNNNN NNNNNNNNNN
180551 NNNNNNNNNN NNNNNNNNNN NNNNNNNNNN NNNNNNNNNN NNNNNNNNNN
180601 NNNNNNNNNN NNNNNNNNNN NNNNNNNNNN NNNNNNNNNN NNNNNNNNNN
180651 NNNNNNNNNN NNNNNNNNNN NNNNNNNNNN NNNNNNNNNN NNNNNNNNNN
180701 NNNNNNNNNN NNNNNNNNNN NNNNNNNNNN NNNNNNNNNN NNNNNNNNNN
180751 NNNNNNNNNN NNNNNNNNNN NNNNNNNNNN NNNNNNNNNN NNNNNNNNNN
180801 NNNNNNNNNN NNNNNNNNNN NNNNNNNNNN NNNNNNNNNN NNNNNNNNNN
180851 NNNNNNNNNN NNNNNNNNNN NNNNNNNNNN NNNNNNNNNN NNNNNNNNNN
180901 NNNNNNNNNN NNNNNNNNNN NNNNNNNNNN NNNNNNNNNN NNNNNNNNNN
180951 NNNNNNNNNN NNNNNNNNNN NNNNNNNNNN NNNNNNNNNN NNNNNNNNNN
```

FIGURE 3, page 51 of 87

181001 NNNNNNNNNN NNNNNNNNNN NNNNNNNNNN NNNNNNNNNN NNNNNNNNNN
181051 NNNNNNNNNN NNNNNNNNNN NNNNNNNNNN NNNNNNNNNN NNNNNNNNNN
181101 NNNNNNNNNN NNNNNNNNNN NNNNNNNNNN NNNNNNNNNN NNNNNNNNNN
181151 NNNNNNNNNN NNNNNNNNNN NNNNNNNNNN NNNNNNNNNN NNNNNNNNNN
181201 NNNNNNNNNN NNNNNNNNNN NNNNNNNNNN NNNNNNNNNN NNNNNNNNNN
181251 NNNNNNNNNN NNNNNNNNNN NNNNNNNNNN NNNNNNNNNN NNNNNNNNNN
181301 NNNNNNNNNN NNNNNNNNNN NNNNNNNNNN NNNNNNNNNN NNNNNNNNNN
181351 NNNNNNNNNN NNNNNNNNNN NNNNNNNNNN NNNNNNNNNN NNNNNNNNNN
181401 NNNNNNNNNN NNNNNNNNNN NNNNNNNNNN NNNNNNNNNN NNNNNNNNNN
181451 NNNNNNNNNN NNNNNNNNNN NNNNNNNNNN NNNNNNNNNN NNNNNNNNNN
181501 NNNNNNNNNN NNNNNNNNNN NNNNNNNNNN NNNNNNNNNN NNNNNNNNNN
181551 NNNNNNNNNN NNNNNNNNNN NNNNNNNNNN NNNNNNNNNN NNNNNNNNNN
181601 NNNNNNNNNN NNNNNNNNNN NNNNNNNNNN NNNNNNNNNN NNNNNNNNNN
181651 NNNNNNNNNN NNNNNNNNNN NNNNNNNNNN NNNNNNNNNN NNNNNNNNNN
181701 NNNNNNNNNN NNNNNNNNNN NNNNNNNNNN NNNNNNNNNN NNNNNNNNNN
181751 NNNNNNNNNN NNNNNNNNNN NNNNNNNNNN NNNNNNNNNN NNNNNNNNNN
181801 NNNNNNNNNN NNNNNNNNNN NNNNNNNNNN NNNNNNNNNN NNNNNNNNNN
181851 NNNNNNNNNN NNNNNNNNNN NNNNNNNNNN NNNNNNNNNN NNNNNNNNNN
181901 NNNNNNNNNN NNNNNNNNNN NNNNNNNNNN NNNNNNNNNN NNNNNNNNNN
181951 NNNNNNNNNN NNNNNNNNNN NNNNNNNNNN NNNNNNNNNN NNNNNNNNNN
182001 NNNNNNNNNN NNNNNNNNNN NNNNNNNNNN NNNNNNNNNN NNNNNNNNNN
182051 NNNNNNNNNN NNNNNNNNNN NNNNNNNNNN NNNNNNNNNN NNNNNNNNNN
182101 NNNNNNNNNN NNNNNNNNNN NNNNNNNNNN NNNNNNNNNN NNNNNNNNNN
182151 NNNNNNNNNN NNNNNNNNNN NNNNNNNNNN NNNNNNNNNN NNNNNNNNNN
182201 NNNNNNNNNN NNNNNNNNNN NNNNNNNNNN NNNNNNNNNN NNNNNNNNNN
182251 NNNNNNNNNN NNNNNNNNNN NNNNNNNNNN NNNNNNNNNN NNNNNNNNNN
182301 NNNNNNNNNN NNNNNNNNNN NNNNNNNNNN NNNNNNNNNN NNNNNNNNNN
182351 NNNNNNNNNN NNNNNNNNNN NNNNNNNNNN NNNNNNNNNN NNNNNNNNNN
182401 NNNNNNNNNN NNNNNNNNNN NNNNNNNNNN NNNNNNNNNN NNNNNNNNNN
182451 NNNNNNNNNN NNNNNNNNNN NNNNNNNNNN NNNNNNNNNN NNNNNNNNNN
182501 NNNNNNNNNN NNNNNNNNNN NNNNNNNNNN NNNNNNNNNN NNNNNNNNNN
182551 NNNNNNNNNN NNNNNNNNNN NNNNNNNNNN NNNNNNNNNN NNNNNNNNNN
182601 NNNNNNNNNN NNNNNNNNNN NNNNNNNNNN NNNNNNNNNN NNNNNNNNNN
182651 NNNNNNNNNN NNNNNNNNNN NNNNNNNNNN NNNNNNNNNN NNNNNNNNNN
182701 NNNNNNNNNN NNNNNNNNNN NNNNNNNNNN NNNNNNNNNN NNNNNNNNNN
182751 NNNNNNNNNN NNNNNNNNNN NNNNNNNNNN NNNNNNNNNN NNNNNNNNNN
182801 NNNNNNNNNN NNNNNNNNNN NNNNNNNNNN NNNNNNNNNN NNNNNNNNNN
182851 NNNNNNNNNN NNNNNNNNNN NNNNNNNNNN NNNNNNNNNN NNNNNNNNNN
182901 NNNNNNNNNN NNNNNNNNNN NNNNNNNNNN NNNNNNNNNN NNNNNNNNNN
182951 NNNNNNNNNN NNNNNNNNNN NNNNNNNNNN NNNNNNNNNN NNNNNNNNNN
183001 NNNNNNNNNN NNNNNNNNNN NNNNNNNNNN NNNNNNNNNN NNNNNNNNNN
183051 NNNNNNNNNN NNNNNNNNNN NNNNNNNNNN NNNNNNNNNN NNNNNNNNNN
183101 NNNNNNNNNN NNNNNNNNNN NNNNNNNNNN NNNNNNNNNN NNNNNNNNNN
183151 NNNNNNNNNN NNNNNNNNNN NNNNNNNNNN NNNNNNNNNN NNNNNNNNNN
183201 NNNNNNNNNN NNNNNNNNNN NNNNNNNNNN NNNNNNNNNN NNNNNNNNNN
183251 NNNNNNNNNN NNNNNNNNNN NNNNNNNNNN NNNNNNNNNN NNNNNNNNNN
183301 NNNNNNNNNN NNNNNNNNNN NNNNNNNNNN NNNNNNNNNN NNNNNNNNNN
183351 NNNNNNNNNN NNNNNNNNNN NNNNNNNNNN NNNNNNNNNN NNNNNNNNNN
183401 NNNNNNNNNN NNNNNNNNNN NNNNNNNNNN NNNNNNNNNN NNNNNNNNNN
183451 NNNNNNNNNN NNNNNNNNNN NNNNNNNNNN NNNNNNNNNN NNNNNNNNNN
183501 NNNNNNNNNN NNNNNNNNNN NNNNNNNNNN NNNNNNNNNN NNNNNNNNNN
183551 NNNNNNNNNN NNNNNNNNNN NNNNNNNNNN NNNNNNNNNN NNNNNNNNNN
183601 NNNNNNNNNN NNNNNNNNNN NNNNNNNNNN NNNNNNNNNN NNNNNNNNNN
183651 NNNNNNNNNN NNNNNNNNNN NNNNNNNNNN NNNNNNNNNN NNNNNNNNNN
183701 NNNNNNNNNN NNNNNNNNNN NNNNNNNNNN NNNNNNNNNN NNNNNNNNNN
183751 NNNNNNNNNN NNNNNNNNNN NNNNNNNNNN NNNNNNNNNN NNNNNNNNNN
183801 NNNNNNNNNN NNNNNNNNNN NNNNNNNNNN NNNNNNNNNN NNNNNNNNNN
183851 NNNNNNNNNN NNNNNNNNNN NNNNNNNNNN NNNNNNNNNN NNNNNNNNNN
183901 NNNNNNNNNN NNNNNNNNNN NNNNNNNNNN NNNNNNNNNN NNNNNNNNNN
183951 NNNNNNNNNN NNNNNNNNNN NNNNNNNNNN NNNNNNNNNN NNNNNNNNNN
184001 NNNNNNNNNN NNNNNNNNNN NNNNNNNNNN NNNNNNNNNN NNNNNNNNNN
184051 NNNNNNNNNN NNNNNNNNNN NNNNNNNNNN NNNNNNNNNN NNNNNNNNNN
184101 NNNNNNNNNN NNNNNNNNNN NNNNNNNNNN NNNNNNNNNN NNNNNNNNNN
184151 NNNNNNNNNN NNNNNNNNNN NNNNNNNNNN NNNNNNNNNN NNNNNNNNNN
184201 NNNNNNNNNN NNNNNNNNNN NNNNNNNNNN NNNNNNNNNN NNNNNNNNNN
184251 NNNNNNNNNN NNNNNNNNNN NNNNNNNNNN NNNNNNNNNN NNNNNNNNNN
184301 NNNNNNNNNN NNNNNNNNNN NNNNNNNNNN NNNNNNNNNN NNNNNNNNNN
184351 NNNNNNNNNN NNNNNNNNNN NNNNNNNNNN NNNNNNNNNN NNNNNNNNNN
184401 NNNNNNNNNN NNNNNNNNNN NNNNNNNNNN NNNNNNNNNN NNNNNNNNNN
184451 NNNNNNNNNN NNNNNNNNNN NNNNNNNNNN NNNNNNNNNN NNNNNNNNNN
184501 NNNNNNNNNN NNNNNNNNNN NNNNNNNNNN NNNNNNNNNN NNNNNNNNNN

FIGURE 3, page 52 of 87

184551 NNNNNNNNNN NNNNNNNNNN NNNNNNNNNN NNNNNNNNNN NNNNNNNNNN
184601 NNNNNNNNNN NNNNNNNNNN NNNNNNNNNN NNNNNNNNNN NNNNNNNNNN
184651 NNNNNNNNNN NNNNNNNNNN NNNNNNNNNN NNNNNNNNNN NNNNNNNNNN
184701 NNNNNNNNNN NNNNNNNNNN NNNNNNNNNN NNNNNNNNNN NNNNNNNNNN
184751 NNNNNNNNNN NNNNNNNNNN NNNNNNNNNN NNNNNNNNNN NNNNNNNNNN
184801 NNNNNNNNNN NNNNNNNNNN NNNNNNNNNN NNNNNNNNNN NNNNNNNNNN
184851 NNNNNNNNNN NNNNNNNNNN NNNNNNNNNN NNNNNNNNNN NNNNNNNNNN
184901 NNNNNNNNNN NNNNNNNNNN NNNNNNNNNN NNNNNNNNNN NNNNNNNNNN
184951 NNNNNNNNNN NNNNNNNNNN NNNNNNNNNN NNNNNNNNNN NNNNNNNNNN
185001 NNNNNNNNNN NNNNNNNNNN NNNNNNNNNN NNNNNNNNNN NNNNNNNNNN
185051 NNNNNNNNNN NNNNNNNNNN NNNNNNNNNN NNNNNNNNNN NNNNNNNNNN
185101 NNNNNNNNNN NNNNNNNNNN NNNNNNNNNN NNNNNNNNNN NNNNNNNNNN
185151 NNNNNNNNNN NNNNNNNNNN NNNNNNNNNN NNNNNNNNNN NNNNNNNNNN
185201 NNNNNNNNNN NNNNNNNNNN NNNNNNNNNN NNNNNNNNNN NNNNNNNNNN
185251 NNNNNNNNNN NNNNNNNNNN NNNNNNNNNN NNNNNNNNNN NNNNNNNNNN
185301 NNNNNNNNNN NNNNNNNNNN NNNNNNNNNN NNNNNNNNNN NNNNNNNNNN
185351 NNNNNNNNNN NNNNNNNNNN NNNNNNNNNN NNNNNNNNNN NNNNNNNNNN
185401 NNNNNNNNNN NNNNNNNNNN NNNNNNNNNN NNNNNNNNNN NNNNNNNNNN
185451 NNNNNNNNNN NNNNNNNNNN NNNNNNNNNN NNNNNNNNNN NNNNNNNNNN
185501 NNNNNNNNNN NNNNNNNNNN NNNNNNNNNN NNNNNNNNNN NNNNNNNNNN
185551 NNNNNNNNNN NNNNNNNNNN NNNNNNNNNN NNNNNNNNNN NNNNNNNNNN
185601 NNNNNNNNNN NNNNNNNNNN NNNNNNNNNN NNNNNNNNNN NNNNNNNNNN
185651 NNNNNNNNNN NNNNNNNNNN NNNNNNNNNN NNNNNNNNNN NNNNNNNNNN
185701 NNNNNNNNNN NNNNNNNNNN NNNNNNNNNN NNNNNNNNNN NNNNNNNNNN
185751 NNNNNNNNNN NNNNNNNNNN NNNNNNNNNN NNNNNNNNNN NNNNNNNNNN
185801 NNNNNNNNNN NNNNNNNNNN NNNNNNNNNN NNNNNNNNNN NNNNNNNNNN
185851 NNNNNNNNNN NNNNNNNNNN NNNNNNNNNN NNNNNNNNNN NNNNNNNNNN
185901 NNNNNNNNNN NNNNNNNNNN NNNNNNNNNN NNNNNNNNNN NNNNNNNNNN
185951 NNNNNNNNNN NNNNNNNNNN NNNNNNNNNN NNNNNNNNNN NNNNNNNNNN
186001 NNNNNNNNNN NNNNNNNNNN NNNNNNNNNN NNNNNNNNNN NNNNNNNNNN
186051 NNNNNNNNNN NNNNNNNNNN NNNNNNNNNN NNNNNNNNNN NNNNNNNNNN
186101 NNNNNNNNNN NNNNNNNNNN NNNNNNNNNN NNNNNNNNNN NNNNNNNNNN
186151 NNNNNNNNNN NNNNNNNNNN NNNNNNNNNN NNNNNNNNNN NNNNNNNNNN
186201 NNNNNNNNNN NNNNNNNNNN NNNNNNNNNN NNNNNNNNNN NNNNNNNNNN
186251 NNNNNNNNNN NNNNNNNNNN NNNNNNNNNN NNNNNNNNNN NNNNNNNNNN
186301 NNNNNNNNNN NNNNNNNNNN NNNNNNNNNN NNNNNNNNNN NNNNNNNNNN
186351 NNNNNNNNNN NNNNNNNNNN NNNNNNNNNN NNNNNNNNNN NNNNNNNNNN
186401 NNNNNNNNNN NNNNNNNNNN NNNNNNNNNN NNNNNNNNNN NNNNNNNNNN
186451 NNNNNNNNNN NNNNNNNNNN NNNNNNNNNN NNNNNNNNNN NNNNNNNNNN
186501 NNNNNNNNNN NNNNNNNNNN NNNNNNNNNN NNNNNNNNNN NNNNNNNNNN
186551 NNNNNNNNNN NNNNNNNNNN NNNNNNNNNN NNNNNNNNNN NNNNNNNNNN
186601 NNNNNNNNNN NNNNNNNNNN NNNNNNNNNN NNNNNNNNNN NNNNNNNNNN
186651 NNNNNNNNNN NNNNNNNNNN NNNNNNNNNN NNNNNNNNNN NNNNNNNNNN
186701 NNNNNNNNNN NNNNNNNNNN NNNNNNNNNN NNNNNNNNNN NNNNNNNNNN
186751 NNNNNNNNNN NNNNNNNNNN NNNNNNNNNN NNNNNNNNNN NNNNNNNNNN
186801 NNNNNNNNNN NNNNNNNNNN NNNNNNNNNN NNNNNNNNNN NNNNNNNNNN
186851 NNNNNNNNNN NNNNNNNNNN NNNNNNNNNN NNNNNNNNNN NNNNNNNNNN
186901 NNNNNNNNNN NNNNNNNNNN NNNNNNNNNN NNNNNNNNNN NNNNNNNNNN
186951 NNNNNNNNNN NNNNNNNNNN NNNNNNNNNN NNNNNNNNNN NNNNNNNNNN
187001 NNNNNNNNNN NNNNNNNNNN NNNNNNNNNN NNNNNNNNNN NNNNNNNNNN
187051 NNNNNNNNNN NNNNNNNNNN NNNNNNNNNN NNNNNNNNNN NNNNNNNNNN
187101 NNNNNNNNNN NNNNNNNNNN NNNNNNNNNN NNNNNNNNNN NNNNNNNNNN
187151 NNNNNNNNNN NNNNNNNNNN NNNNNNNNNN NNNNNNNNNN NNNNNNNNNN
187201 NNNNNNNNNN NNNNNNNNNN NNNNNNNNNN NNNNNNNNNN NNNNNNNNNN
187251 NNNNNNNNNN NNNNNNNNNN NNNNNNNNNN NNNNNNNNNN NNNNNNNNNN
187301 NNNNNNNNNN NNNNNNNNNN NNNNNNNNNN NNNNNNNNNN NNNNNNNNNN
187351 NNNNNNNNNN NNNNNNNNNN NNNNNNNNNN NNNNNNNNNN NNNNNNNNNN
187401 NNNNNNNNNN NNNNNNNNNN NNNNNNNNNN NNNNNNNNNN NNNNNNNNNN
187451 NNNNNNNNNN NNNNNNNNNN NNNNNNNNNN NNNNNNNNNN NNNNNNNNNN
187501 NNNNNNNNNN NNNNNNNNNN NNNNNNNNNN NNNNNNNNNN NNNNNNNNNN
187551 NNNNNNNNNN NNNNNNNNNN NNNNNNNNNN NNNNNNNNNN NNNNNNNNNN
187601 NNNNNNNNNN NNNNNNNNNN NNNNNNNNNN NNNNNNNNNN NNNNNNNNNN
187651 NNNNNNNNNN NNNNNNNNNN NNNNNNNNNN NNNNNNNNNN NNNNNNNNNN
187701 NNNNNNNNNN NNNNNNNNNN NNNNNNNNNN NNNNNNNNNN NNNNNNNNNN
187751 NNNNNNNNNN NNNNNNNNNN NNNNNNNNNN NNNNNNNNNN NNNNNNNNNN
187801 NNNNNNNNNN NNNNNNNNNN NNNNNNNNNN NNNNNNNNNN NNNNNNNNNN
187851 NNNNNNNNNN NNNNNNNNNN NNNNNNNNNN NNNNNNNNNN NNNNNNNNNN
187901 NNNNNNNNNN NNNNNNNNNN NNNNNNNNNN NNNNNNNNNN NNNNNNNNNN
187951 NNNNNNNNNN NNNNNNNNNN NNNNNNNNNN NNNNNNNNNN NNNNNNNNNN
188001 NNNNNNNNNN NNNNNNNNNN NNNNNNNNNN NNNNNNNNNN NNNNNNNNNN
188051 NNNNNNNNNN NNNNNNNNNN NNNNNNNNNN NNNNNNNNNN NNNNNNNNNN

FIGURE 3, page 53 of 87

188101 NNNNNNNNNN NNNNNNNNNN NNNNNNNNNN NNNNNNNNNN NNNNNNNNNN
188151 NNNNNNNNNN NNNNNNNNNN NNNNNNNNNN NNNNNNNNNN NNNNNNNNNN
188201 NNNNNNNNNN NNNNNNNNNN NNNNNNNNNN NNNNNNNNNN NNNNNNNNNN
188251 NNNNNNNNNN NNNNNNNNNN NNNNNNNNNN NNNNNNNNNN NNNNNNNNNN
188301 NNNNNNNNNN NNNNNNNNNN NNNNNNNNNN NNNNNNNNNN NNNNNNNNNN
188351 NNNNNNNNNN NNNNNNNNNN NNNNNNNNNN NNNNNNNNNN NNNNNNNNNN
188401 NNNNNNNNNN NNNNNNNNNN NNNNNNNNNN NNNNNNNNNN NNNNNNNNNN
188451 NNNNNNNNNN NNNNNNNNNN NNNNNNNNNN NNNNNNNNNN NNNNNNNNNN
188501 NNNNNNNNNN NNNNNNNNNN NNNNNNNNNN NNNNNNNNNN NNNNNNNNNN
188551 NNNNNNNNNN NNNNNNNNNN NNNNNNNNNN NNNNNNNNNN NNNNNNNNNN
188601 NNNNNNNNNN NNNNNNNNNN NNNNNNNNNN NNNNNNNNNN NNNNNNNNNN
188651 NNNNNNNNNN NNNNNNNNNN NNNNNNNNNN NNNNNNNNNN NNNNNNNNNN
188701 NNNNNNNNNN NNNNNNNNNN NNNNNNNNNN NNNNNNNNNN NNNNNNNNNN
188751 NNNNNNNNNN NNNNNNNNNN NNNNNNNNNN NNNNNNNNNN NNNNNNNNNN
188801 NNNNNNNNNN NNNNNNNNNN NNNNNNNNNN NNNNNNNNNN NNNNNNNNNN
188851 NNNNNNNNNN NNNNNNNNNN NNNNNNNNNN NNNNNNNNNN NNNNNNNNNN
188901 NNNNNNNNNN NNNNNNNNNN NNNNNNNNNN NNNNNNNNNN NNNNNNNNNN
188951 NNNNNNNNNN NNNNNNNNNN NNNNNNNNNN NNNNNNNNNN NNNNNNNNNN
189001 NNNNNNNNNN NNNNNNNNNN NNNNNNNNNN NNNNNNNNNN NNNNNNNNNN
189051 NNNNNNNNNN NNNNNNNNNN NNNNNNNNNN NNNNNNNNNN NNNNNNNNNN
189101 NNNNNNNNNN NNNNNNNNNN NNNNNNNNNN NNNNNNNNNN NNNNNNNNNN
189151 NNNNNNNNNN NNNNNNNNNN NNNNNNNNNN NNNNNNNNNN NNNNNNNNNN
189201 NNNNNNNNNN NNNNNNNNNN NNNNNNNNNN NNNNNNNNNN NNNNNNNNNN
189251 NNNNNNNNNN NNNNNNNNNN NNNNNNNNNN NNNNNNNNNN NNNNNNNNNN
189301 NNNNNNNNNN NNNNNNNNNN NNNNNNNNNN NNNNNNNNNN NNNNNNNNNN
189351 NNNNNNNNNN NNNNNNNNNN NNNNNNNNNN NNNNNNNNNN NNNNNNNNNN
189401 NNNNNNNNNN NNNNNNNNNN NNNNNNNNNN NNNNNNNNNN NNNNNNNNNN
189451 NNNNNNNNNN NNNNNNNNNN NNNNNNNNNN NNNNNNNNNN NNNNNNNNNN
189501 NNNNNNNNNN NNNNNNNNNN NNNNNNNNNN NNNNNNNNNN NNNNNNNNNN
189551 NNNNNNNNNN NNNNNNNNNN NNNNNNNNNN NNNNNNNNNN NNNNNNNNNN
189601 NNNNNNNNNN NNNNNNNNNN NNNNNNNNNN NNNNNNNNNN NNNNNNNNNN
189651 NNNNNNNNNN NNNNNNNNNN NNNNNNNNNN NNNNNNNNNN NNNNNNNNNN
189701 NNNNNNNNNN NNNNNNNNNN NNNNNNNNNN NNNNNNNNNN NNNNNNNNNN
189751 NNNNNNNNNN NNNNNNNNNN NNNNNNNNNN NNNNNNNNNN NNNNNNNNNN
189801 NNNNNNNNNN NNNNNNNNNN NNNNNNNNNN NNNNNNNNNN NNNNNNNNNN
189851 NNNNNNNNNN NNNNNNNNNN NNNNNNNNNN NNNNNNNNNN NNNNNNNNNN
189901 NNNNNNNNNN NNNNNNNNNN NNNNNNNNNN NNNNNNNNNN NNNNNNNNNN
189951 NNNNNNNNNN NNNNNNNNNN NNNNNNNNNN NNNNNNNNNN NNNNNNNNNN
190001 NNNNNNNNNN NNNNNNNNNN NNNNNNNNNN NNNNNNNNNN NNNNNNNNNN
190051 NNNNNNNNNN NNNNNNNNNN NNNNNNNNNN NNNNNNNNNN NNNNNNNNNN
190101 NNNNNNNNNN NNNNNNNNNN NNNNNNNNNN NNNNNNNNNN NNNNNNNNNN
190151 NNNNNNNNNN NNNNNNNNNN NNNNNNNNNN NNNNNNNNNN NNNNNNNNNN
190201 NNNNNNNNNN NNNNNNNNNN NNNNNNNNNN NNNNNNNNNN NNNNNNNNNN
190251 NNNNNNNNNN NNNNNNNNNN NNNNNNNNNN NNNNNNNNNN NNNNNNNNNN
190301 NNNNNNNNNN NNNNNNNNNN NNNNNNNNNN NNNNNNNNNN NNNNNNNNNN
190351 NNNNNNNNNN NNNNNNNNNN NNNNNNNNNN NNNNNNNNNN NNNNNNNNNN
190401 NNNNNNNNNN NNNNNNNNNN NNNNNNNNNN NNNNNNNNNN NNNNNNNNNN
190451 NNNNNNNNNN NNNNNNNNNN NNNNNNNNNN NNNNNNNNNN NNNNNNNNNN
190501 NNNNNNNNNN NNNNNNNNNN NNNNNNNNNN NNNNNNNNNN NNNNNNNNNN
190551 NNNNNNNNNN NNNNNNNNNN NNNNNNNNNN NNNNNNNNNN NNNNNNNNNN
190601 NNNNNNNNNN NNNNNNNNNN NNNNNNNNNN NNNNNNNNNN NNNNNNNNNN
190651 NNNNNNNNNN NNNNNNNNNN NNNNNNNNNN NNNNNNNNNN NNNNNNNNNN
190701 NNNNNNNNNN NNNNNNNNNN NNNNNNNNNN NNNNNNNNNN NNNNNNNNNN
190751 NNNNNNNNNN NNNNNNNNNN NNNNNNNNNN NNNNNNNNNN NNNNNNNNNN
190801 NNNNNNNNNN NNNNNNNNNN NNNNNNNNNN NNNNNNNNNN NNNNNNNNNN
190851 NNNNNNNNNN NNNNNNNNNN NNNNNNNNNN NNNNNNNNNN NNNNNNNNNN
190901 NNNNNNNNNN NNNNNNNNNN NNNNNNNNNN NNNNNNNNNN NNNNNNNNNN
190951 NNNNNNNNNN NNNNNNNNNN NNNNNNNNNN NNNNNNNNNN NNNNNNNNNN
191001 NNNNNNNNNN NNNNNNNNNN NNNNNNNNNN NNNNNNNNNN NNNNNNNNNN
191051 NNNNNNNNNN NNNNNNNNNN NNNNNNNNNN NNNNNNNNNN NNNNNNNNNN
191101 NNNNNNNNNN NNNNNNNNNN NNNNNNNNNN NNNNNNNNNN NNNNNNNNNN
191151 NNNNNNNNNN NNNNNNNNNN NNNNNNNNNN NNNNNNNNNN NNNNNNNNNN
191201 NNNNNNNNNN NNNNNNNNNN NNNNNNNNNN NNNNNNNNNN NNNNNNNNNN
191251 NNNNNNNNNN NNNNNNNNNN NNNNNNNNNN NNNNNNNNNN NNNNNNNNNN
191301 NNNNNNNNNN NNNNNNNNNN NNNNNNNNNN NNNNNNNNNN NNNNNNNNNN
191351 NNNNNNNNNN NNNNNNNNNN NNNNNNNNNN NNNNNNNNNN NNNNNNNNNN
191401 NNNNNNNNNN NNNNNNNNNN NNNNNNNNNN NNNNNNNNNN NNNNNNNNNN
191451 NNNNNNNNNN NNNNNNNNNN NNNNNNNNNN NNNNNNNNNN NNNNNNNNNN
191501 NNNNNNNNNN NNNNNNNNNN NNNNNNNNNN NNNNNNNNNN NNNNNNNNNN
191551 NNNNNNNNNN NNNNNNNNNN NNNNNNNNNN NNNNNNNNNN NNNNNNNNNN
191601 NNNNNNNNNN NNNNNNNNNN NNNNNNNNNN NNNNNNNNNN NNNNNNNNNN

FIGURE 3, page 54 of 87

191651 NNNNNNNNNN NNNNNNNNNN NNNNNNNNNN NNNNNNNNNN NNNNNNNNNN
191701 NNNNNNNNNN NNNNNNNNNN NNNNNNNNNN NNNNNNNNNN NNNNNNNNNN
191751 NNNNNNNNNN NNNNNNNNNN NNNNNNNNNN NNNNNNNNNN NNNNNNNNNN
191801 NNNNNNNNNN NNNNNNNNNN NNNNNNNNNN NNNNNNNNNN NNNNNNNNNN
191851 NNNNNNNNNN NNNNNNNNNN NNNNNNNNNN NNNNNNNNNN NNNNNNNNNN
191901 NNNNNNNNNN NNNNNNNNNN NNNNNNNNNN NNNNNNNNNN NNNNNNNNNN
191951 NNNNNNNNNN NNNNNNNNNN NNNNNNNNNN NNNNNNNNNN NNNNNNNNNN
192001 NNNNNNNNNN NNNNNNNNNN NNNNNNNNNN NNNNNNNNNN NNNNNNNNNN
192051 NNNNNNNNNN NNNNNNNNNN NNNNNNNNNN NNNNNNNNNN NNNNNNNNNN
192101 NNNNNNNNNN NNNNNNNNNN NNNNNNNNNN NNNNNNNNNN NNNNNNNNNN
192151 NNNNNNNNNN NNNNNNNNNN NNNNNNNNNN NNNNNNNNNN NNNNNNNNNN
192201 NNNNNNNNNN NNNNNNNNNN NNNNNNNNNN NNNNNNNNNN NNNNNNNNNN
192251 NNNNNNNNNN NNNNNNNNNN NNNNNNNNNN NNNNNNNNNN NNNNNNNNNN
192301 NNNNNNNNNN NNNNNNNNNN NNNNNNNNNN NNNNNNNNNN NNNNNNNNNN
192351 NNNNNNNNNN NNNNNNNNNN NNNNNNNNNN NNNNNNNNNN NNNNNNNNNN
192401 NNNNNNNNNN NNNNNNNNNN NNNNNNNNNN NNNNNNNNNN NNNNNNNNNN
192451 NNNNNNNNNN NNNNNNNNNN NNNNNNNNNN NNNNNNNNNN NNNNNNNNNN
192501 NNNNNNNNNN NNNNNNNNNN NNNNNNNNNN NNNNNNNNNN NNNNNNNNNN
192551 NNNNNNNNNN NNNNNNNNNN NNNNNNNNNN NNNNNNNNNN NNNNNNNNNN
192601 NNNNNNNNNN NNNNNNNNNN NNNNNNNNNN NNNNNNNNNN NNNNNNNNNN
192651 NNNNNNNNNN NNNNNNNNNN NNNNNNNNNN NNNNNNNNNN NNNNNNNNNN
192701 NNNNNNNNNN NNNNNNNNNN NNNNNNNNNN NNNNNNNNNN NNNNNNNNNN
192751 NNNNNNNNNN NNNNNNNNNN NNNNNNNNNN NNNNNNNNNN NNNNNNNNNN
192801 NNNNNNNNNN NNNNNNNNNN NNNNNNNNNN NNNNNNNNNN NNNNNNNNNN
192851 NNNNNNNNNN NNNNNNNNNN NNNNNNNNNN NNNNNNNNNN NNNNNNNNNN
192901 NNNNNNNNNN NNNNNNNNNN NNNNNNNNNN NNNNNNNNNN NNNNNNNNNN
192951 NNNNNNNNNN NNNNNNNNNN NNNNNNNNNN NNNNNNNNNN NNNNNNNNNN
193001 NNNNNNNNNN NNNNNNNNNN NNNNNNNNNN NNNNNNNNNN NNNNNNNNNN
193051 NNNNNNNNNN NNNNNNNNNN NNNNNNNNNN NNNNNNNNNN NNNNNNNNNN
193101 NNNNNNNNNN NNNNNNNNNN NNNNNNNNNN NNNNNNNNNN NNNNNNNNNN
193151 NNNNNNNNNN NNNNNNNNNN NNNNNNNNNN NNNNNNNNNN NNNNNNNNNN
193201 NNNNNNNNNN NNNNNNNNNN NNNNNNNNNN NNNNNNNNNN NNNNNNNNNN
193251 NNNNNNNNNN NNNNNNNNNN NNNNNNNNNN NNNNNNNNNN NNNNNNNNNN
193301 NNNNNNNNNN NNNNNNNNNN NNNNNNNNNN NNNNNNNNNN NNNNNNNNNN
193351 NNNNNNNNNN NNNNNNNNNN NNNNNNNNNN NNNNNNNNNN NNNNNNNNNN
193401 NNNNNNNNNN NNNNNNNNNN NNNNNNNNNN NNNNNNNNNN NNNNNNNNNN
193451 NNNNNNNNNN NNNNNNNNNN NNNNNNNNNN NNNNNNNNNN NNNNNNNNNN
193501 NNNNNNNNNN NNNNNNNNNN NNNNNNNNNN NNNNNNNNNN NNNNNNNNNN
193551 NNNNNNNNNN NNNNNNNNNN NNNNNNNNNN NNNNNNNNNN NNNNNNNNNN
193601 NNNNNNNNNN NNNNNNNNNN NNNNNNNNNN NNNNNNNNNN NNNNNNNNNN
193651 NNNNNNNNNN NNNNNNNNNN NNNNNNNNNN NNNNNNNNNN NNNNNNNNNN
193701 NNNNNNNNNN NNNNNNNNNN NNNNNNNNNN NNNNNNNNNN NNNNNNNNNN
193751 NNNNNNNNNN NNNNNNNNNN NNNNNNNNNN NNNNNNNNNN NNNNNNNNNN
193801 NNNNNNNNNN NNNNNNNNNN NNNNNNNNNN NNNNNNNNNN NNNNNNNNNN
193851 NNNNNNNNNN NNNNNNNNNN NNNNNNNNNN NNNNNNNNNN NNNNNNNNNN
193901 NNNNNNNNNN NNNNNNNNNN NNNNNNNNNN NNNNNNNNNN NNNNNNNNNN
193951 NNNNNNNNNN NNNNNNNNNN NNNNNNNNNN NNNNNNNNNN NNNNNNNNNN
194001 NNNNNNNNNN NNNNNNNNNN NNNNNNNNNN NNNNNNNNNN NNNNNNNNNN
194051 NNNNNNNNNN NNNNNNNNNN NNNNNNNNNN NNNNNNNNNN NNNNNNNNNN
194101 NNNNNNNNNN NNNNNNNNNN NNNNNNNNNN NNNNNNNNNN NNNNNNNNNN
194151 NNNNNNNNNN NNNNNNNNNN NNNNNNNNNN NNNNNNNNNN NNNNNNNNNN
194201 NNNNNNNNNN NNNNNNNNNN NNNNNNNNNN NNNNNNNNNN NNNNNNNNNN
194251 NNNNNNNNNN NNNNNNNNNN NNNNNNNNNN NNNNNNNNNN NNNNNNNNNN
194301 NNNNNNNNNN NNNNNNNNNN NNNNNNNNNN NNNNNNNNNN NNNNNNNNNN
194351 NNNNNNNNNN NNNNNNNNNN NNNNNNNNNN NNNNNNNNNN NNNNNNNNNN
194401 NNNNNNNNNN NNNNNNNNNN NNNNNNNNNN NNNNNNNNNN NNNNNNNNNN
194451 NNNNNNNNNN NNNNNNNNNN NNNNNNNNNN NNNNNNNNNN NNNNNNNNNN
194501 NNNNNNNNNN NNNNNNNNNN NNNNNNNNNN NNNNNNNNNN NNNNNNNNNN
194551 NNNNNNNNNN NNNNNNNNNN NNNNNNNNNN NNNNNNNNNN NNNNNNNNNN
194601 NNNNNNNNNN NNNNNNNNNN NNNNNNNNNN NNNNNNNNNN NNNNNNNNNN
194651 NNNNNNNNNN NNNNNNNNNN NNNNNNNNNN NNNNNNNNNN NNNNNNNNNN
194701 NNNNNNNNNN NNNNNNNNNN NNNNNNNNNN NNNNNNNNNN NNNNNNNNNN
194751 NNNNNNNNNN NNNNNNNNNN NNNNNNNNNN NNNNNNNNNN NNNNNNNNNN
194801 NNNNNNNNNN NNNNNNNNNN NNNNNNNNNN NNNNNNNNNN NNNNNNNNNN
194851 NNNNNNNNNN NNNNNNNNNN NNNNNNNNNN NNNNNNNNNN NNNNNNNNNN
194901 NNNNNNNNNN NNNNNNNNNN NNNNNNNNNN NNNNNNNNNN NNNNNNNNNN
194951 NNNNNNNNNN NNNNNNNNNN NNNNNNNNNN NNNNNNNNNN NNNNNNNNNN
195001 NNNNNNNNNN NNNNNNNNNN NNNNNNNNNN NNNNNNNNNN NNNNNNNNNN
195051 NNNNNNNNNN NNNNNNNNNN NNNNNNNNNN NNNNNNNNNN NNNNNNNNNN
195101 NNNNNNNNNN NNNNNNNNNN NNNNNNNNNN NNNNNNNNNN NNNNNNNNNN
195151 NNNNNNNNNN NNNNNNNNNN NNNNNNNNNN NNNNNNNNNN NNNNNNNNNN

FIGURE 3, page 55 of 87

```
195201 NNNNNNNNNN NNNNNNNNNN NNNNNNNNNN NNNNNNNNNN NNNNNNNNNN
195251 NNNNNNNNNN NNNNNNNNNN NNNNNNNNNN NNNNNNNNNN NNNNNNNNNN
195301 NNNNNNNNNN NNNNNNNNNN NNNNNNNNNN NNNNNNNNNN NNNNNNNNNN
195351 NNNNNNNNNN NNNNNNNNNN NNNNNNNNNN NNNNNNNNNN NNNNNNNNNN
195401 NNNNNNNNNN NNNNNNNNNN NNNNNNNNNN NNNNNNNNNN NNNNNNNNNN
195451 NNNNNNNNNN NNNNNNNNNN NNNNNNNNNN NNNNNNNNNN NNNNNNNNNN
195501 NNNNNNNNNN NNNNNNNNNN NNNNNNNNNN NNNNNNNNNN NNNNNNNNNN
195551 NNNNNNNNNN NNNNNNNNNN NNNNNNNNNN NNNNNNNNNN NNNNNNNNNN
195601 NNNNNNNNNN NNNNNNNNNN NNNNNNNNNN NNNNNNNNNN NNNNNNNNNN
195651 NNNNNNNNNN NNNNNNNNNN NNNNNNNNNN NNNNNNNNNN NNNNNNNNNN
195701 NNNNNNNNNN NNNNNNNNNN NNNNNNNNNN NNNNNNNNNN NNNNNNNNNN
195751 NNNNNNNNNN NNNNNNNNNN NNNNNNNNNN NNNNNNNNNN NNNNNNNNNN
195801 NNNNNNNNNN NNNNNNNNNN NNNNNNNNNN NNNNNNNNNN NNNNNNNNNN
195851 NNNNNNNNNN NNNNNNNNNN NNNNNNNNNN NNNNNNNNNN NNNNNNNNNN
195901 NNNNNNNNNN NNNNNNNNNN NNNNNNNNNN NNNNNNNNNN NNNNNNNNNN
195951 NNNNNNNNNN NNNNNNNNNN NNNNNNNNNN NNNNNNNNNN NNNNNNNNNN
196001 NNNNNNNNNN NNNNNNNNNN NNNNNNNNNN NNNNNNNNNN NNNNNNNNNN
196051 NNNNNNNNNN NNNNNNNNNN NNNNNNNNNN NNNNNNNNNN NNNNNNNNNN
196101 NNNNNNNNNN NNNNNNNNNN NNNNNNNNNN NNNNNNNNNN NNNNNNNNNN
196151 NNNNNNNNNN NNNNNNNNNN NNNNNNNNNN NNNNNNNNNN NNNNNNNNNN
196201 NNNNNNNNNN NNNNNNNNNN NNNNNNNNNN NNNNNNNNNN NNNNNNNNNN
196251 NNNNNNNNNN NNNNNNNNNN NNNNNNNNNN NNNNNNNNNN NNNNNNNNNN
196301 NNNNNNNNNN NNNNNNNNNN NNNNNNNNNN NNNNNNNNNN NNNNNNNNNN
196351 NNNNNNNNNN NNNNNNNNNN NNNNNNNNNN NNNNNNNNNN NNNNNNNNNN
196401 NNNNNNNNNN NNNNNNNNNN NNNNNNNNNN NNNNNNNNNN NNNNNNNNNN
196451 NNNNNNNNNN NNNNNNNNNN NNNNNNNNNN NNNNNNNNNN NNNNNNNNNN
196501 NNNNNNNNNN NNNNNNNNNN NNNNNNNNNN NNNNNNNNNN NNNNNNNNNN
196551 NNNNNNNNNN NNNNNNNNNN NNNNNNNNNN NNNNNNNNNN NNNNNNNNNN
196601 NNNNNNNNNN NNNNNNNNNN NNNNNNNNNN NNNNNNNNNN NNNNNNNNNN
196651 NNNNNNNNNN NNNNNNNNNN NNNNNNNNNN NNNNNNNNNN NNNNNNNNNN
196701 NNNNNNNNNN NNNNNNNNNN NNNNNNNNNN NNNNNNNNNN NNNNNNNNNN
196751 NNNNNNNNNN NNNNNNNNNN NNNNNNNNNN NNNNNNNNNN NNNNNNNNNN
196801 NNNNNNNNNN NNNNNNNNNN NNNNNNNNNN NNNNNNNNNN NNNNNNNNNN
196851 NNNNNNNNNN NNNNNNNNNN NNNNNNNNNN NNNNNNNNNN NNNNNNNNNN
196901 NNNNNNNNNN NNNNNNNNNN NNNNNNNNNN NNNNNNNNNN NNNNNNNNNN
196951 NNNNNNNNNN NNNNNNNNNN NNNNNNNNNN NNNNNNNNNN NNNNNNNNNN
197001 NNNNNNNNNN NNNNNNNNNN NNNNNNNNNN NNNNNNNNNN NNNNNNNNNN
197051 NNNNNNNNNN NNNNNNNNNN NNNNNNNNNN NNNNNNNNNN NNNNNNNNNN
197101 NNNNNNNNNN NNNNNNNNNN NNNNNNNNNN NNNNNNNNNN NNNNNNNNNN
197151 NNNNNNNNNN NNNNNNNNNN NNNNNNNNNN NNNNNNNNNN NNNNNNNNNN
197201 NNNNNNNNNN NNNNNNNNNN NNNNNNNNNN NNNNNNNNNN NNNNNNNNNN
197251 NNNNNNNNNN NNNNNNNNNN NNNNNNNNNN NNNNNNNNNN NNNNNNNNNN
197301 NNNNNNNNNN NNNNNNNNNN NNNNNNNNNN NNNNNNNNNN NNNNNNNNNN
197351 NNNNNNNNNN NNNNNNNNNN NNNNNNNNNN NNNNNNNNNN NNNNNNNNNN
197401 NNNNNNNNNN NNNNNNNNNN NNNNNNNNNN NNNNNNNNNN NNNNNNNNNN
197451 NNNNNNNNNN NNNNNNNNNN NNNNNNNNNN NNNNNNNNNN NNNNNNNNNN
197501 NNNNNNNNNN NNNNNNNNNN NNNNNNNNNN NNNNNNNNNN NNNNNNNNNN
197551 NNNNNNNNNN NNNNNNNNNN NNNNNNNNNN NNNNNNNNNN NNNNNNNNNN
197601 NNNNNNNNNN NNNNNNNNNN NNNNNNNNNN NNNNNNNNNN NNNNNNNNNN
197651 NNNNNNNNNN NNNNNNNNNN NNNNNNNNNN NNNNNNNNNN NNNNNNNNNN
197701 NNNNNNNNNN NNNNNNNNNN NNNNNNNNNN NNNNNNNNNN NNNNNNNNNN
197751 NNNNNNNNNN NNNNNNNNNN NNNNNNNNNN NNNNNNNNNN NNNNNNNNNN
197801 NNNNNNNNNN NNNNNNNNNN NNNNNNNNNN NNNNNNNNNN NNNNNNNNNN
197851 NNNNNNNNNN NNNNNNNNNN NNNNNNNNNN NNNNNNNNNN NNNNNNNNNN
197901 NNNNNNNNNN NNNNNNNNNN NNNNNNNNNN NNNNNNNNNN NNNNNNNNNN
197951 NNNNNNNNNN NNNNNNNNNN NNNNNNNNNN NNNNNNNNNN NNNNNNNNNN
198001 NNNNNNNNNN NNNNNNNNNN NNNNNNNNNN NNNNNNNNNN NNNNNNNNNN
198051 NNNNNNNNNN NNNNNNNNNN NNNNNNNNNN NNNNNNNNNN NNNNNNNNNN
198101 NNNNNNNNNN NNNNNNNNNN NNNNNNNNNN NNNNNNNNNN NNNNNNNNNN
198151 NNNNNNNNNN NNNNNNNNNN NNNNNNNNNN NNNNNNNNNN NNNNNNNNNN
198201 NNNNNNNNNN NNNNNNNNNN NNNNNNNNNN NNNNNNNNNN NNNNNNNNNN
198251 NNNNNNNNNN NNNNNNNNNN NNNNNNNNNN NNNNNNNNNN NNNNNNNNNN
198301 NNNNNNNNNN NNNNNNNNNN NNNNNNNNNN NNNNNNNNNN NNNNNNNNNN
198351 NNNNNNNNNN NNNNNNNNNN NNNNNNNNNN NNNNNNNNNN NNNNNNNNNN
198401 NNNNNNNNNN NNNNNNNNNN NNNNNNNNNN NNNNNNNNNN NNNNNNNNNN
198451 NNNNNNNNNN NNNNNNNNNN NNNNNNNNNN NNNNNNNNNN NNNNNNNNNN
198501 NNNNNNNNNN NNNNNNNNNN NNNNNNNNNN NNNNNNNNNN NNNNNNNNNN
198551 NNNNNNNNNN NNNNNNNNNN NNNNNNNNNN NNNNNNNNNN NNNNNNNNNN
198601 NNNNNNNNNN NNNNNNNNNN NNNNNNNNNN NNNNNNNNNN NNNNNNNNNN
198651 NNNNNNNNNN NNNNNNNNNN NNNNNNNNNN NNNNNNNNNN NNNNNNNNNN
198701 NNNNNNNNNN NNNNNNNNNN NNNNNNNNNN NNNNNNNNNN NNNNNNNNNN
```

FIGURE 3, page 56 of 87

198751 NNNNNNNNNN NNNNNNNNNN NNNNNNNNNN NNNNNNNNNN NNNNNNNNNN
198801 NNNNNNNNNN NNNNNNNNNN NNNNNNNNNN NNNNNNNNNN NNNNNNNNNN
198851 NNNNNNNNNN NNNNNNNNNN NNNNNNNNNN NNNNNNNNNN NNNNNNNNNN
198901 NNNNNNNNNN NNNNNNNNNN NNNNNNNNNN NNNNNNNNNN NNNNNNNNNN
198951 NNNNNNNNNN NNNNNNNNNN NNNNNNNNNN NNNNNNNNNN NNNNNNTTTC
199001 TTTGACCTTG GTACCTCTCT CAGGGATGAG GACTCTCTTC CCATTTCTAT
199051 TGATCTTCTG AAAAAGTAGC CTCATTCCCC AACTCAAGGA ACTCTTTAAA
199101 TGCTTGAAAT CTTATTAGAA GTCACCAGTG ACCTCCCCAG TGTGCAACAC
199151 AAGTAATTAA ATATTTTTAA CCACCCTTGT GTTCTTATCT CCTTCAAAAT
199201 CCATCCCTCT GTCCCCCCAC TTTTCAGCTT TTGAAACTAT TTGTTCCTTA
199251 ATACTTTCTG CAATTTTATG TACTGTGACA TTGCAATTCT TTGGCCTTGC
199301 ACAATTAAAA ATGAAAGTTC AAAAAGCTAA CTCTCTCTAT TTTCTAACTT
199351 TTTAGTGAAG ATGTTCCACA GAGCTTTGGT TTCAGCCATC TCATAACATT
199401 TTCTTTTGAA GACCTAACAG TTTCAATCAC TGCTTCCTAT TTGTCTGACT
199451 CTTTTGCCTT ACTTTCTACT CTGATCCTTC TCTCTGACGC TCTGGATTCC
199501 TAATTGCAGC CATTTGTGGG AAGAGTCCAC CAGGGCTCAT TACATCTAAA
199551 TAAATTTCTC CCCATAAAAC AAAACAGAAA TCTTCTCTGA GATAATAGGG
199601 GCTTCATGAT GGGAGGGAAG ATGTGACATT GGAATGAGGA CAGAGATCTT
199651 GGGACAGTGA TAGTGACCTG TGCAGGTTCC CACAGGGCAC CCATAAGGTC
199701 TGTCCAGGCA ATTAATAGTG TCAGTGTGTC AAGAATAAGG CCTAAAGAGC
199751 GGCTGACTTG AAGTCTTGGT ACCTGGGTTT AGAATTTTCT AATCCCTCTG
199801 ACTGGACATA ACACAAATCT CTGACCTCAA GGTCATTTGT CTANNNNNNN
199851 NNNNNNNNNN NNNNNNNNNN NNNNNNNNNN NNNNNNNNNN NNNNNNNNNN
199901 NNNNNNNNNN NNNNNNNNNN NNNNNNNNNN NNNNNNNNNN NNNNNNNNNN
199951 NNNNNNNNNN NNNNNNNNNN NNNNNNNNNN NNNNNNNNNN NNNNNNNNNN
200001 NNNNNNNNNN NNNNNNNNNN NNNNNNNNNN NNNNNNNNNN NNNNNNNNNN
200051 NNNNNNNNNN NNNNNNNNNN NNNNNNNNNN NNNNNNNNNN NNNNNNNNNN
200101 NNNNNNNNNN NNNNNNNNNN NNNNNNNNNN NNNNNNNNNN NNNNNNNNNN
200151 NNNNNNNNNN NNNNNNNNNN NNNNNNNNNN NNNNNNNNNN NNNNNNNNNN
200201 NNNNNNNNNN NNNNNNNNNN NNNNNNNNNN NNNNNNNNNN NNNNNNNNNN
200251 NNNNNNNNNN NNNNNNNNNN NNNNNNNNNN NNNNNNNNNN NNNNNNNNNN
200301 NNNNNNNNNN NNNNNNNNNN NNNNNNNNNN NNNNNNNNNN NNNNNNNNNN
200351 NNNNNNNNNN NNNNNNNNNN NNNNNNNNNN NNNNNNNNNN NNNNNNNNNN
200401 NNNNNNNNNN NNNNNNNNNN NNNNNNNNNN NNNNNNNNNN NNNNNNNNNN
200451 NNNNNNNNNN NNNNNNNNNN NNNNNNNNNN NNNNTCATCA AGCTAGTAAG
200501 AAGGGTCTAT ATAATGTGAT CATGGGAGAG ACATGTTATT CCTTTTGCCT
200551 TATTCTATTG GTTAGATACA AATCATAGGT CCCAACTAAC TAAAGAAGAG
200601 GAGATTTTAC AAAGCAGGAA CAACAGGAGG TGGGTATAGT GGGTATCTAC
200651 CTGAGAGGCC ATGCACTACA CTCCCCCAGC CTACTATTTT ATATTTCAAA
200701 CACTTATTAG AATAATCCTT CCAGATTTAA GTATGTTATT TACATTATGA
200751 AAGTAACCTA ATAAGAATTG AGAACAGATG ACGAAGGTAT ATATGTGTTT
200801 AAGTAACCTA ACTCTTCACT ATCATTGCAG AAAATCAATA GATTCTAAAA
200851 ATGAGTGTTA ACAGAGCAGT ATATGCATAT TATTTAGTGT TTTAGGGGTA
200901 AACACCATAA GAACTGAAAA CAGGAGTGGT TTAAAGTGTT GCTTCTGGGA
200951 AGTAAGAGGT AGGGAGGGTA TAAACAGGGA ATTGTTATTT TCATTATAAA
201001 CCCTTCATCA TCTTTTTTTG TAGCCATGTA GATATAACAT GATGATTAAA
201051 CTTAAAAATA TAACCCTCCT ATGCTAGGCA TGATTTGATC TCATTACCCT
201101 TATTGAATTT TTTTCCAGTG AATCCCATGA TCTATTTGTT TCTGAATAAA
201151 TATGGATTAT TTAAACAAGC TGAAATATGT ATAAGATTTT ACTGTTAATA
201201 TTTAAACAAA TATTTGAAAA TTACATTAGC AAAATGAGTC TCAGGGTTTG
201251 AGATCTTTTA TTTCAACTTC CACACTTATA TATGTATCTG ATCTATAACA
201301 TTCCTAATAA ATGAGGTGAA TCCAGCCTCT GCTAAAATAT TTGATCAACT
201351 GTTATAGGAT ATCTACCACT GCAAAAGTAG CTCCTATCCT ATAAGCTTTG
201401 AAGTATTCTT TGTTATGGTC CCATAAGCAT CTATTTCTTA AGTAATCATG
201451 AGGTTTTAGG CACTCTGTTA GGTACAGAAA CCCATAGATG AATAAGAAAC
201501 TACGGTGTTC TTTACTTTGA ACTGAAATAC CTGTCTTTTA ATTTTCATCA
201551 GTTCGTCCTA AGTCTCCTCT CTAGACCAAC ACAGTAGATT CCAGTGGTTA
201601 TGAACATGAA CTTTGGAGCC AGGAAAAATG TTCCAATCCT ACCTCTGCTG
201651 TCACTAGTTT TGTGAACTTG AACAGATGAC TGTAAAATGG AGATAAAAAT
201701 CATCTATCTC TTTGGGGGAC AATAAAGCAA GATCACATGA GTAAAAGTAT
201751 TTAACACTCT GTAACACACA GTAGCTTAAA ATGTTAGCCT TTGCAGTAAC
201801 AACAATAATA AACAATGATT TAACTCTTTC TCATTGAAGA TAATGGTCAG
201851 AGTTTTCCGA AGACTTAATA TCCTTAGTTT TTATTAGTCA TGGCTTCTAG
201901 GTCCTTCATA TCATGGATTA TATTCCTGTG CATATTTTCC AGTTTGTCAA
201951 GGATCCTCTT ACTCACCCTG AACACAATAT TCTGTATGGA GTTTGAATGG
202001 AGCCAAATTG AGCATAATTA TTTTCTCCTT CGAAGTAAAT TTCTTCCTTC
202051 TTTCAAAACA GTGAAATAAA AAAAAATCAT TTCATTGGGA GCCTCATTCC
202101 ACTGAGACTG AAGTCTAAAA AACCCTGAAG TCATTTCCGT GGACTGCTCT
202151 TTGCTTGAAC TTCACAGTCA GATCCCATCC AGTACTTGTT CAATTAGAAA
202201 CCTGAGACAT TTTTCTCCAA CAGACATATT GCTGCCTAGT ATTACAGACT
202251 TCTGAGATTG ATATAGATGC ATCTTTTTCA TCCAACATAT TCCTTGAGAA

FIGURE 3, page 57 of 87

```
202301 TATCAACGTT TGTCACTGGT GAATGTAAGT CTTGTGCTAA GTCTTGTGCC
202351 AAGTCTTGTG CTAAGGGCTT GGCTGGTTGC TAGGAATGAG GCTGAGGACA
202401 GAACCCAAGA GTAGTTTAGG AATGTCTTGA GATAGGTTTA TTTTATTCAG
202451 CATTAGGAAC ATAAACGGAG TCAAGACTTA AAGATTTGTT CACCTGAATA
202501 ATGTGTTGAA TGATACGGTA TCCTTTAGAA AATTTCCCAG CATATGCTAA
202551 TTAAAAAAAT TTTTCTTTTT ACCACTTCTT GATAACAGCA CAAATCATGT
202601 TTTAGTCTAC ATTAAAATAT AGAAGCATTT CTTAAGAATA AGTCAAACAT
202651 TTCATTAATT CAATTCAGCA GACCTCCAGT GACCCCAAAC TGATAGATGT
202701 GATAGGGTTT TTTAGAAAAT ACAATTACAT TCACTATAAT GAAGATTACT
202751 ACATGTAAAA TCAAGTTGGT TTATTCAGGT GGATTAGGAA TTTATCTCTG
202801 AAGACTCCTA ATTCTTTCAC ATAAATTCCA AGAATTCCTG GGCAGCATAG
202851 GCAAGGCCTT TCATGTTGAC AAATTGTGAC ATTCCCTAAC TCAATGGTGC
202901 TCAACCAGCG GCAGTTTTGC TCTCCAAGAA ACATGTGTTA ATCTTTGAAG
202951 ACATGTTCAT TGTCACAACT GAGGTAGCTG GGGGCCAGGG AAGCTGCTAA
203001 ACATCCTACA ATGTACAGGA CAGCCTCCGC AACAGAAAAA TATCTAATTC
203051 AGAATGTCAG TAGTGCTGAG GTTGGGAACC CTGTATTAAA TCAGTGAGTT
203101 GCAAATTTTT AGGTGTTGCA ATGGACTTTT TTCCCTCCTA TTTCTCTCAT
203151 TTCTACTGCT GCTTCTCTCT GCCCCTTCCC ACTACTCTCT TAAGTCCAAA
203201 TTCTTTCCCA ACATTTTTGC TTTTAATATT ATTACTTTTT TTCTCATTAT
203251 GAAAACTTAA CTANNNNNNN NNNNNNNNNN NNNNNNNNNN NNNNNNNNNN
203301 NNNNNNNNNN NNNNNNNNNN NNNNNNNNNN NNNNNNNNNN NNNNNNNNNN
203351 NNNNNNNNNN NNNNNNNNNN NNNNNNNNNN NNNNNNNNNN NNNNNNNNNN
203401 NNNNNNNNNN NNNNNNNNNN NNNNNNNNNN NNNNNNNNNN NNNNNNNNNN
203451 NNNNNNNNNN NNNNNNNNNN NNNNNNNNNN NNNNNNNNNN NNNNNNNNNN
203501 NNNNNNNNNN NNNNNNNNNN NNNNNNNNNN NNNNNNNNNN NNNNNNNNNN
203551 NNNNNNNNNN NNNNNNNNNN NNNNNNNNNN NNNNNNNNNN NNNNNNNNNN
203601 NNNNNNNNNN NNNNNNNNNN NNNCATATAG AGTTCCCTAT CCATAGTTCT
203651 TTATCACAAC TTTTAAAAAG TAGCTTTTAT GGGAAACCTG TTGCTTTTCA
203701 TGACAGCACT TTTCTGGGTA GAGTTGTAAC AAGATTTAGA CAATTGCATT
203751 TTGTAAATAT TTGGAGGACT GAAGATTTTT TGACTCATTT CTCCATTCTT
203801 TTATCTTTCA GAAGAATTAA TATTTAAGTA ACTTGCCATT GTAGATAGTT
203851 AACTGAAATG CCATAAAATT TCTTGCTTTA CTGAACTTTT TCCTGAGCAC
203901 CTACTTTCTT TTTTGGAAAG TATTAAGTGC TTTGATATTC CTAAGGCCTA
203951 GAAAACCTGT TTTTGGCTCT CTGAGTGAAG ACAACTCCAA AACATGTAAG
204001 ATAATTAAAA GACAGATATA CCAAAACTTA TAAACAACTG AAACCTATAT
204051 TATGAATTAA TATAAACTCT GAGGGTAAAA GAGCATGGAA TTGATAAGGA
204101 ATAGAATTTT TTTAAAAAAA GGGGTTTTGG AGGTAAGTTT TGAAGCAGAA
204151 CTTGAAAAAA ATTAGTAAAA GAGAGTAGAT TTTTCAGCAT ATTCTTTTTT
204201 CAAAACTGTT TGATTTTGGA AAATTTTGAA CAGGTTTAAA AGTACAGAAA
204251 AGAGTCTAAT AAGCCTCCAT ATACCTGCCA CCTGGATTCA GTAATCATCA
204301 ATAGGCTGCC ATTCTTGCCT CCGGTTTTTA AATAAATTCC AGACTTAACA
204351 TCATTTTGTT CCTATATGCC TAAGCACGAA TTTCTAAAAA CCATGGACAT
204401 TTCCACCCAT AAAATAATGC CATGACCACA ATGAACAAAA TTACTAATAC
204451 CATCCTGGTA TCATTTAATA CCTAGAACAC ATTCAGATTT CCTTGATTAT
204501 CTTCACATCC TATGTTGATT AGGTATGTTC TAATTAGACT CCAAACAAAG
204551 CAACATTTTC TTTGATTAAT GTGTAGTCTT ATTTCCAAAG TCAACATTCT
204601 ACACAAATAT CCAATATTAT TTGGCCATAA CACCTTTTCC CCATTTTGTT
204651 TCAATCAATT ATGCTAGTGG GGATGAAGAA ATGAGAATCA TCTAGTTAGC
204701 TCAATGAAAA CCTCTACTGT ATTCATCCAT AATCTGTTCC TGATGTTTTC
204751 ACCTCAGTGT TTGCCATTTT GGTGAACTTG ACATGTGTGA ATTACATTAT
204801 AGGATCTAGG AACAATTGCA GTTACTTTAA ATATTCCTTA TGTCCAGAGT
204851 CTTGACAGGT ATGCCATGAA TCCTGTGTGA AAACTATTAA TATTACCATG
204901 TAGTTTTATT CTGGTATGTA ACTTCACTCT ATTATAAACT ATTATCATTA
204951 ATGTATATCA AGCAGGCATA TAGACCTCTC ATGTATGGTA TACAAATGAG
205001 GACAGGTAAT TAGAGAAGCA AAACACATTC TAATACATCA GTATGCCTAG
205051 AACACTTACC ATTTGGGGGT GATCAGTTAC AATATCTCAG TCATGAAACC
205101 TTTGCATGAG GACGTCTTAT CTTACCATAA AGAAACTAAC TCAAGTCAGA
205151 ACAAAATCTG TTTCTTCCCA AAATACAGTA TTGTTCTCTT AGGAAATACA
205201 ATGATCACAA TGTGTTACAA TGATTCAGGG TATTAGTAGC CGGAGAATGA
205251 AATTTTGGAA TCTAAAGAAG ACAGTGGTCA TGGAAATATG TTATCTTTTA
205301 TAACAGCATG ATTCCAAAGT TATAGGTTTT TTAGAACTAA TACTTGATTT
205351 AAGTCATGAA GTGTAACTGT CACAGTCTTT TAAAATATCT ACTTTTAATT
205401 ACAGTATATA AATGACCCCA TGGCTCCAGA AATTGTGAAC ATAGTAGAGC
205451 CAATGGTAGG ATTATATGAG GGTTCAGCAG AGATGTCGTC TGACCTTCAC
205501 TCACTTGCTA CATTTATATA TAACAGCCAT CCAGATAAAA ACTTTCCTGC
205551 AAGGAATAGA GCTGAAGACC AGACTTCACC AGTTGGTAGG TAGAATTTTG
205601 ATTTTCTATA AAGTTCATTT AAACCACCAG TGCTAGCTAG CACAGAAATG
205651 AACCTAAGCT TAGAGTTCAG CCATATTATT AATGGTCTTT GGGCTGGAGT
205701 CGGATTTTTT TTTAGCTGTC GGAAAACCTC ATGCAACAAA TGGAAATGCC
205751 ACACAGGCAG AAGCTGGCCC CTCCTAACCC ATTTGACCTT CTTCCTGGAG
205801 AAAGTAGCAC CCTAGAGTCT CTGGCCAAGC TGCATAGACA ATCAGTTATT
```

FIGURE 3, page 58 of 87

205851 ACAGTTGCCA AAGCAGGTGT GATGGGAAGG GATTAACATA TCTTCAAATC
205901 ATTTACAGGC CTCACATTCT CTACAGCTTT TGACTAATAG GTTTTCAAGT
205951 GTCACTAAAG GTAAATAGGT CAGAAAGTTA CAAATCTAGT GCATGGTGTG
206001 ATAAACAGGT GTAGGTGACC CCAACGATGT GGTGATGTCA TTAGTGTATA
206051 CACTTGCTCT TCAGTGTCAG TGGCTCTTAC AGTTTCTAAA AGGAGAATGT
206101 CATACGTGGC AAATTAAAAA TACTCACCTG ACACATATTA TCTCTCTAGT
206151 TTTTCTAAAA TGTTAAATGA GAAAAACATT TTATTACCTT TTCTCTAATT
206201 TGGTACTTGT CCCATTCAAA ATTAAAAGTG TTATTCTATT TATGGTAGAA
206251 TTAGTAAAAA AAAATCACAT TACATTCAAT AGATGTTTAT ATTTCACTTA
206301 CTGATCCATT TTTCTTGTGC AAAGAAGACT GGAGGGCAAC ACTGAAAATT
206351 AAGAGTCCCA TGATTTCTGA TGCAGACATT CCCTTAAATA TTTCAAGTTT
206401 GGCCTAATTG CTACTTAAGA GTTTTAGAAG CACAAATTCT AAATAAAGCG
206451 AAAATCTAAC ATTTGAAATT CTTCTGGGAT ATTTATTTGT CAGTTATCCA
206501 AGCATGCTTG CTTTCAAGAA TTATTTTGGT TTACTGAATG TATGAACATA
206551 TGGTGAAATT TGAGTCCAAA TAAAACTCTT TATTTATTTA ACTCTTTTAC
206601 TAAAACCTGG TATTGATTTA TAATATCTCA ATTATATATT TCTTTAACTC
206651 TTCTACTAAA TCCTGGTATT GATTTATAAT ATTTCATTTA TATATTATTG
206701 CCTACTCTTT CTTTTCAGAA AACATTCCTA ACCAGCCTCT TTAAGAAAGT
206751 TGTTTTCTTA AAAACACTAA TGTCATGTTT CAGAGTAATG TGTAAAAACT
206801 AACAAAATTA TATTATGAAC ACAAAATGTT TGTGGTTATT ATTGGGAGGT
206851 ACTCAGAAAT TCATAGTAAT ATTCAATACG ATCTCTAAAA TTAATATTTT
206901 TATGTTTACT ATTATTACAC ATCTAACTTT AATAGAGGTG TGCATGGAGA
206951 GATTAATGAA TACGGAGAAA TCAGGTTTAA GATTTTATAG TCTAAGAAAA
207001 AAATAATTTT GATTGTGAAG CCAAACACCT TTCTTTTTTT CTCTTTTTAC
207051 TGAATTCAAA CAGTAACTAC AAGGAATCAG TATATTACTG ACATTGCAGC
207101 TGAACAGCTG TCTTATGTTA TCAGGAGACT TGTACCTTTC ACTGAGCACA
207151 TGATTAGTGT ATCTGCTTTC ACCATCATGG GAGAAGGACC ACCAACAGTT
207201 CTCAGTGTTA GGACACGTCA GCAAGGTAAG GATGTATTTC CTTTGAAACA
207251 ATTAACTGCA AATATTGCTG TTGTACACTG TGATACTTTT TTTTCATTCA
207301 TATGTTCATT CTTCTTTTTA AGTGCCAAGC TCCATTAAAA TTATAAACTA
207351 TAAAAATATT AGTTCTTCAT CTATTTTGTT ATATTGGGAT CCTCCAGAAT
207401 ATCCCAATGG AAAAATAACT CACTATACGA TTTATGCAAT GGAATTGGAT
207451 ACAAACAGAG CATTCCAGAT AACTACCATA GATAACAGCT TTCTCATAAC
207501 AGGTAGAAAA CAATGTTTTG TTGTTGTTGT TGTTGTTGTT CATTTTACAT
207551 TTCTATTCTG GTGGAAAATA TGCCCATCTC CCTGTGCCTT ATATACTACA
207601 GAACACATGC TATGTCACTT CATATTTTGT TGTTTTGTGT CACCATGAAT
207651 CTTTTTAAAA TACCTGCATA CATAACTCGA TTAAATGTGT TTTTCTTTTA
207701 CTAGATTTAC CCACAATGAA GTAAAAAGCA TCAGATCACA AGCTTCATAG
207751 AAATTTACTT AACTGAAGGA ATACTGTATC TGGTATATCA AAATAACTCA
207801 TTATTGAAGA CTAAAATGTA CGAATGCAAA AATCAGCTGA AGTAATTCAG
207851 CTGACATGGT ATTTGTGCCA AGTCAACTAT ACACCCTGCA GTGTGCCAAA
207901 AAGTTACTTT TGCAACTTTA AATTATTGCC TTAATATTTT AGGAGAGAAC
207951 TTGAAGTCAC CAACATAGAA AGGCCTATAA GCCCAAGAAT TTGAGGAGAC
208001 TGCAATTATT TGGAAGCGAT ATAGATATCT AGTCCCCCGT ATAAATTCTT
208051 CTTACTGGCC TTATATTAAA TGGCACCAAT CCCAAGAGTA TTATTTTAAG
208101 GACATTAAAC AGTTTGTCTC TTGTCCTTAT AGGGTTAAAG AAATACACAA
208151 AATACAAAAT GAGAGTGGCA GCCTCAACCC ACGATGGAGA AAGTTCTTTG
208201 TCTGAAGAAA ATGACATCTT TGTGAGAACT TCAGAAGATG GTAAGAATAT
208251 CAATTGCAGC TTTAATTTTT TTAAAAAAGT GGTTGTAAAT GCTCACTGCC
208301 TTCACTTCAT GCTACCTCTA GGGTCTAAAG CAACAAACAT CAATAAAAAT
208351 ATAGGTACTA CAAATGTTCT TTTCTTCCCC TAGAACCGGA ATCATCACCT
208401 CAAGATGTCG AAGTAATTGA TGTTACCGCA GATGAAATAA GGTTGAAGTG
208451 GTCACCACCC GAAAAGCCCA ATGGGATCAT TATTGCTTAT GAAGTGCTAT
208501 ATAAAAATAT AGATACTTTA TATATGAAGA ACACATCAAC AACAGACATA
208551 ATATTAAGGA ACTTAAGACC TCACACCCTC TATAACATTT CTGTAAGGTC
208601 TTACACCAGA TTTGGTCATG GCAATCAGGT ATCTTCTTTA CTCTCTGTAA
208651 GGACTTCGGA GACTGGTGAG CTTTTGTTTT GCTTTGTTTG TTTAATAATA
208701 CACAGTGATA TAGTAAGCAA AGCTGATAAT CGCCATGTTG TTTACATTTT
208751 ACATAACCTA AAATCCCTCA TTATTTTGTT TTGTATAATC CAGAAATTAA
208801 TTTTCTTTTT CAGGCAAAAG TGCAGGAAAA GGTTTATTGT ACAAATTTTT
208851 AAGTCTGATT TATATAAGGG AACTTCTAAT CAAAATCTGT GAATTTTCAA
208901 ATGAAAAGAC CTTGAGAAAC CAAGGATTCT TTCAATGTAC CTATAAATTT
208951 TAGATTGAAT GGCTACTTGC TTTCGAGTTA GGTAAAACTG AGACATACTC
209001 ATAGGAATAG ATTCTGAGAT TCTAATGAGG TATGTGTATA GATAGTGGTG
209051 CAGAGTGGGA GCACGAAAAT GGCATGCCTG GAGAAGACTT ATGGAGGAGA
209101 CAGCATTTGG CCTGGATCTT AATGAGGAGG TTGGAATGGG CAGAAGGATG
209151 TTATAGAGCA GGGGTCCCCA ACCTTTTTGG CACTGGGGAC CAGTTTCATG
209201 GAAGAAAATT TTTCCCCTCC CTCCGGACTA GGGAGGGGAG TGAGGTTGGT
209251 TTCTGGATGA TTCAAGCACG TTACGTTTGT TGTGCACTTT ATTTCTATTA
209301 TTATTACATT GTAACATATA ATGAAATAAT TATACAACTC ACCATAATGC
209351 AGAATCAATG GGAGCCCTGA GCTTGTTTTC CTGCAACTAG ATGGTCCTAT

FIGURE 3, page 59 of 87

209401 CTGGGGGGTA ATGGGAGACA ATGACAGATC ATCAGGCATT AAATTCTCAT
209451 AAGAAGCACA CAACATAGAT CCCTTGCATG GGCAATTCAC AATAGAGTTT
209501 GCGCTCCTAT GAAAATCTAA TGTCGACACT GATCTGACAG GAGGCAGAGC
209551 TCAGGCAGTA ATTCAGGCGA TAGGGAGTGG CTGTAAATAC AGAAGCTTTA
209601 TGATGCTCAC CTGCTGTGTG GCCCAGTTCC TAACAGGCCA TCAGCTGGTA
209651 CTAGTCCGTG GCGCTGGGAT TGGGGACCCC TGTTATAGAG GTTGCTGGAT
209701 GGGTTGGGAG AGGATATCCC ATCTAAAGGA AGTAAAACAA GCAAGGAATT
209751 ACTTGTGTTT TAGTTTCGGT GAAACTAGAG TAAGACAGTT TGTCTGTTAA
209801 TCTTATTTTG TTGTTTATAT TGTGTTATAA TTATATATTG GTGGCATAAC
209851 TATTAGGCCA ATTCTACAAT GTATTTTGAG AATTAATAAC TAAATATAAA
209901 GTTACTATTT TAATTGTACG TTTAAAACAA TAAATATTTA CTGACTAGAT
209951 ACTGGTGGAA CCACATGAAA TAATTTTTAT AGGTCACAAA TGGCCAAATA
210001 TCAGCAATTT CATATAGTTC AGCCAGATAC TATATACGAA TTTCTGTCTT
210051 GACCTTGAGG ATCTAGAAAT CTAGTAAAGT AGCTTACTTT TGTAGAAAAG
210101 TATCCTGTTG AGACTATTCA CAGAAATGAA TACAATGAGA TGATACAAAA
210151 GAGCCCATAG ATAATGGCAG TAGTTGAAAG TGCAGGAATA AGAAAGTAAT
210201 GAAAGGAGCA TTTTACATTA TCAAGAGCCT TGAAGTGACA CTTAATTGAT
210251 ATTAATCCAT ATATTGGCAT GTTTCATTGC TTTTGTAGAT ATTGTACCTG
210301 AAATAAGTAT TTTTGAGAAA AATGTCTGCT CTTTAATGAC TCAGTTTTAT
210351 TTTGCAGTGG ATTAAGGAAA TGAAACAAGC ATATTTTTAG CACCTATTAA
210401 GGGTCACGGG CCCTGTTGAT AGGTTTCACA GAAACTGTCT TTTAAAAATT
210451 CTAAACTAAA GCAATACATT ATTGTTATCT TCACAGAAAA CTAAGTCTAA
210501 TGAAAAATGG AGGGTTTGAG AGGTTCATTC ATTCAAAAAA TATTTATAAT
210551 ATACCAGGCC CTACTGGGGA TAAAGTAGTG TAGAAGAAAA GGATTTCCTT
210601 CCCTCCTTAA GTTTTATTAG TTGGTGGGTG TTTCATTGCC TAATGGCACC
210651 AGCTGGAAAG TGATCAGCTG GAAAGTGATG AGCTGGAATT AGAATCCAAA
210701 CCCATCTGAC TGTAAAACCC ATTTCCCTTT CACAGCACAT GCTGTTTTTG
210751 AAGTAATCAA CAAAGCTGGT AAATTATAAA CTATATCTAA GATCTCTCTG
210801 TTCATTGTTA CACTGATATT TTGTCATTAG GCTTCTGCTC AGCATGGGGA
210851 GGAAAGTAAT AACTTTGAAA GATTCTATTG TGATATGAAA TAATAACCAT
210901 TTTTATGAAT GCTTATCAAG TATTTCGTTT AAGTGGCCAT AGCATCAAGA
210951 ACACCTTATT TTAATGATGA ATTATAAAGC AATGTTTTTG TTTTCTGATT
211001 ATTACATGCA CATAATCTTT TACTTAGTAT TGAAAATGTA ATTTTATTTT
211051 CTGTTTTATT GTCTGTATGA GTTTAATTCA AAGGCAGGGA CAATAAACTT
211101 TAAGTGAATA TAAATTTTGA GATTTAGTTT AAAATGAGAA TTTTAATTTT
211151 GGAAAGTGTC TTAGAAAACA TGCAGAGCCC TTTATTTTTT AGGTGAGAAG
211201 ACCTAGGACC ATTTGGGTAA AAGGACTCAC AAGTTATAGT ACATGAGAAG
211251 TAAAGTTGGG GCTTGACTAT AGGCCTCCTG ACCCCCATTA CAGGCCTCGT
211301 TTAATAGGCT CCTGAGATGG CTAAAAAAAT AAAGAGAAGG GGAAACCAAC
211351 ATATCCCATG GCTTCCTAGC CAGGCCTAAC AATCAGAGTA TAGGGTTTAA
211401 TGCCCATCTT CCTAATATCT GGTTCTCTGT CCTAAGTTAG GGTTGTCTCA
211451 AGTTCTGTGC ATTTTCCACC TGGATGAAAA TGGAAGACAA TGGAATCTAC
211501 ATTAGTGACT TTTCCTAGAT TATGTTTGCT ACTGTTAAAC CACCCACTTT
211551 AGCTCCTTTG GCAAAAGAGG AAGCTAAAAT GTTAGGTAGG GTCTCAAGTG
211601 TCATTTGAAG CAAGATGAGC TCAAGAGCAA CTATTTTTCT GGGTTTAGGC
211651 TCAAAATAAT CTTATTAAAT ACAGTAATTA TACCTTCTAT TCATGTAAAA
211701 AAATATGGGC CCACTCTTCA ATATTGTTTC ATGAGAAATT GAGTGATGTG
211751 TTAACTCAGT GATGTGTTAA TATTACTAAT TAAAAATAGG AGTAAGTTAT
211801 TTGGTTAAAT GCCTTATCTT TTTAAGAGAA ATAGAGTTTA CTAATGCTTG
211851 GAAGTAAAAC ACCCTTGTGT TCAAGCAGGA AAGATCAATA CAAGATTGAT
211901 TCTGTGTGTG TGTGTGTGTA TCTCTGTGTG TGTTTGTGTG TGTTTTAATC
211951 ATAGATGTGC AGTTTTCCAA TAAGCCTAAG ATTAGTTTTT ATTTTCTCAT
212001 ACTTAGGGTG TAATAATCAT AAATACAACT TTGAGAAGTT CCCATACAAA
212051 TTACTCTTTT GATGATCTAT ACATATTCCC TTTCCTTTTT AAGACACAAC
212101 CATCTTTACT GTAAGCCTTT AACAAAACAC CTTGTCTGAT TTGGGGCAAC
212151 AACCATGAGT GGATAATAAC TTAGATGTTG ACCAAAATTT TGTGTAGACC
212201 CCCATAAATT TATTTGTATT AATGAATAAC ATTTTAAAAT TTGTCTGCAT
212251 ACATTAAAGC TTTATATGCC AAACAATAGT CTTTTGGCAG ATTCAAGGTA
212301 ACTTCCCTTT TTTACTATCA TCATGGACTA TGTATTTTTT CTGTTTTGGA
212351 ATTTTAATAG GTTCAGCTTA TTCCAACTGA TTATAATCAT TCCTTTTTAT
212401 CCATCAGTTA TCTACTTTAT AAAATATTTC TATAATTCGG GGACACTCTG
212451 CTATTTCAGA AAATTCTAAA TGCGTCATTA CTCTTCAAAA TCAGTAAGTC
212501 ATTGAGTCTG TCTTGCTTTA TCTACCTGAT GATCCAGCAC TAGTTATTCC
212551 CTAAGGGTAA ATGAATAAAA ATGCAAAGGA TATCAGCCTT GGGTCAGGAA
212601 TACATATTTA CACACTGACT ACTGGTGGTA GGCAGACAAC TGCAGAGAGA
212651 AAACTTCAAT CTAATGGGAA ATTTTCAAAA TCAGAAGTTA CACCGAGCTA
212701 TAAAATTCAA GCATAGCATC ACAAATTCCC TTTTTGTAAT TAAAGAGTTT
212751 TTAAACCCAA TCTTTTATCT ATCTGTTCCT TACCTGTGAG TTTCTCTCTT
212801 GTTTTAATAT ATTCTGTATC ATATTAAATA TATTGATTCA TTCACTAAAC
212851 AGCTTTTATG GGTTCCATAT TATGTTCTAC CACCGTACTA GGTAGTGTAG
212901 CTGTAGCAGT AAACAAGACA CAATAAATCT CTACCTTCCT GAAACTTGAC

FIGURE 3, page 60 of 87

212951 ACTAGACAAT CAGAAAATTA GACATTAGAA AATAAATCAG TAAACAAATT
213001 TGTGATTTTT GGTAGTGGTA AGTTTTACTA AGTGAAAAAT ATCAAGGATA
213051 GAAGAGAGGA AGAGTAGTGA GTGGGCTATT TGAGATGGAG GACTGAGGAA
213101 AGACCTCACT GAGAGGTTAT ATTTGCCCAG TGATATTAAT GAGGTACAGG
213151 ATTGAATAAG ATGAGGATGA GGATGAAAAG TGTTCCAGAG GAAGAACAGC
213201 AATTGCCAAC TTCTTATAGA GGAAAAAAAT TGTGGAGTTG GGGCAGAGCA
213251 GGGCATTTCT GTCACTTGAA CAGTGTGAGT TGGGGTAGAG AATTCACAGA
213301 TGAGGCGAGA GGCAGAGGTG GATCCTGAGA TTCTTAGGTG CCATTCTAGG
213351 AACTTTGGAG TTTAATTTTA ATGAGGAGCT TTTGGAGAAT TATGGAATAG
213401 GAACATTATA TGATTTACAG TTTTCAAAGA TTGCTGCTGA ATATGTTGAA
213451 TGTTGAAGTA AAGAGAAAAA TGAAGATAAA CTATTAGATT GTTTGTCTGA
213501 GTATCTGGGT GAGTGGTAGT GCCATTTACT TAGATGGGGC AGTCCAGGGA
213551 AGAGGTCAAT ATGGAGAACA TCCAGGAGTT CTGTTTGCAA CATGTTTGAA
213601 ATATCCAAGT GCCATTATGA AGGAAGTTAG ATAAATAAGT TTAAAGCTCA
213651 GGGAAAAGAT ACAGAGCTGA ATATATAATT TGGAGCCTCA CCACATCTTT
213701 GGTATTCAAT CAAGGGATGA GGATAAAGTC ATATCACTGG ACAACAGGGG
213751 GAGACGTTAA GAAGCTTACA GCTATGTCGT GGGCAATACC ACACATAGAC
213801 TTTGAGAAGT AGAAGAGCTA ATCAAGGACA AAGCAGAAGT CACTGGAAAT
213851 AGAAGGAAAA CCAGAAGAAG ATAGTGCCTT CAAAGCCAAG TGAATAAAGA
213901 TTTTCAAGTA GAAGGAGTTT ATTCCCTATG TCACATGCTG CTGACAAGTA
213951 AAGTAAGATG GGGCATACAA TTGATTAGTG TTTGGCAAGA AGGGAGGTCA
214001 TTGGTGACTT CACAGGAGTA GATTTTACAG AAAAAATAAT GGAGAAAAAT
214051 GAAGTCAGAT TAACAGAGTA TGATAGGCAA AAAAAAATGT AGAAAATGAG
214101 GAATGGCAAA TTTTGAGGAA TTTTGATAAG AAGTGGAGAG TAGACTTCAG
214151 TAATAGCTGA AGGAACAAGT GCAATCAAAA GAAGACTTTT TAAATCCCAG
214201 ACTGTATATT ACAGTGTATG TGTGTTCACA TGTATCTCTG ACTAACTTCA
214251 AATGTAAAGT CTCTGAATAG GCAGAAGGAG TGAAATCCAG TGCAGACGTG
214301 GAGGGATAGA GCTTGGAAAG GAGGAAAGAG GGAAGGCAGT TAAGGGAAAA
214351 TTTGAAGTCA GATGATAATG TAGCTCTCTT CTCAGTGTTT TTATTTTTGC
214401 TATGGAATGA GAAGCAAGTT TATTAGCTTC AAATAAAGAG GGGGAGGGCA
214451 TATCAGAGGT TTGTGAAGAG AGAACATGGT GAAAACATAC TTTAAAGAGT
214501 GGGAGACTGA ATTAACTAAA ACAAAAACAT TAGCTATCAG GAAATGAAAA
214551 GGATCCATTT GAGATTTGAT GTTATAAATT TAAGTGGAAC TAGTCAGCAT
214601 AGAATGGTGT TTTATTCAGC CATTTTCAGC TATTACACTG GGCATGTGAA
214651 GCTAGCAGAG TTTTGTTTAA TTCCAATTGT AATTTTCCCA GGAAAGTAAA
214701 ATAGAAACAG AAGGACCTGA TGGATATTGC TAGGAAGTGA TTACAGTGAC
214751 TGTGGACTCT AGCCTGAGCA TGTAGGGAAA TGAAGGCATA AGAGAGGTGA
214801 TGCACAGTGA AGATTTGATG AGGGTCAGAG AATTGTTGGA TTCAAAGTAC
214851 AAGAGTCAGT AAACTGGAAA GATAGGAGTC AGTTGTCAAA GAGAGGAATA
214901 TTGGCAGTTA TTGGTAATGA CAAAGTCTTA GGTGTTGCCA TGAAAGCCAA
214951 TGAGGTACGG TGGGGTAAAG TAAGGTGGGG GAAAAGATTA TTGGAATTAT
215001 AGAGATAAAG AAATACAGAG TCCAGGGAAC TGGATAGATC ATTTGCATGG
215051 AAGTTGGCCT CTCTGAGTAG TAGGGAAGAA GTCAGTTATC AAAGTGATAG
215101 CATCTTTAAG ATGTTCAGAG AAGTGACAGA GGTATTACCA GTTGTCTGTC
215151 TTAAAGAGGG GTAGCACGTG ATGGTATCTA ATGGAATGGG GCTTCAAAGG
215201 ATCTGTGGTT CTTCAGGAAG AAAAAAGGAG TAATAAATGC AACTACCCAA
215251 CTCCTACACC CTATCGTTAG TGAGACTATG GTAGAAAAAC AAACATGATA
215301 CCCAAGAGGG CTAAACTGTA GTAGTATTTC TCAGCAGGTC CAAGATTTCA
215351 CTTAGAGCTA GAAAGTTAAG AAAGCATTGA GGGTAGTTGT TGAGGATTTT
215401 CCTCAATGTA ATGGGTTGGC CTGGGGAAAC ACTAGAGAAG ATTTAGCACA
215451 TTTCAGATAG AAAGGATAGT GGAATTATAT TGCTAAATCG AACTATGCAT
215501 TGAATTGCAA TCCTCTCAAA GTTTTAAAAG TATCAATATT CTTAAATTAG
215551 TTTTTCCTAT TAAGTGTGCC TTGACACCAT AACCCAATAA CTGGTAACAA
215601 TCAAGGGGAG GGACACTGTA TCTACATTTT TAAGGCTTCT GAATTTTATT
215651 TATCTACTAA ATTTATTATT AGTAATTTTT ATATGCATTC AATTTAGAAT
215701 ACTAATAAAA AGTTTAATTT CTTTCATTTG AAAGAAAAGA GTTTTATAAC
215751 AGAACTCTTG AATGGCAATA ATATTTACCT ATTTAGTTTA TATTGTTTAA
215801 CCCTCCAAGT TAATTATTTA TGTTATTGTT CTATGTACTC AATTTTTAAA
215851 CCATTATCTT GGCCACTCTG ATCTTTCATC TGTGGTAAAT AGTTTTCTAC
215901 CTAAAGTACA TTGTCTACAA TTTCATTTAC TGAGGATGTG TTGAAAGCAT
215951 TATCCCTCAA TTTTTTTTAT TGTCTGAATA TGTTTTTAGT TTGCTACTCT
216001 TTATTTTTCT GGGTATGGAA TTCCAGTTGT TTTTCAGTTG ATGTTGATTG
216051 TCAGTCTAAT TGTCATTCCT ATGTAGAAGA TTTTTTTTTT CTGGTACTGT
216101 TAAGATGGTT CCTTTTTTGA TATTCTGTAT TTTCACAATG ATATGTCTAA
216151 ATATGGTTTA AAAATTTCTG CTTGAGATTT ACTGAAATTA TTTGATCTGA
216201 TGTTTGATGT CGTTGAATAA TTTTGATGAG CCTCAGCCAT TATCCCTTTA
216251 AATATTTCTT CATTTTCTCT ACTATTTTAG ACCCCCTCCG GATATCATCT
216301 ATGTCTCAAC TGCCATTTTA TATTTTCCAT AACTGTCTTC TTTGATCTAC
216351 ATTCTTGATA ATTTCTTCAA TACTATCATC CTTTTCACTA AAGTTCTCTT
216401 CTTCTTTATC TAATCTGCTC TTTAATACCT CAAGAGATTT TTAATTTTAG
216451 TTATTTTGTT CTGTTCCAGA AGGTCTATCT TGTTCTCTTT CAAACTTGCT

FIGURE 3, page 61 of 87

216501 TGGTTATTTA ATATTATTTA CCATTATTTA AATAATTATT TGCTCATATT
216551 TTAAAATATG TTTGATTTCT TGAAACACAT TAAACATTTC TATTTTATTT
216601 CAATATCTGG AATCTCAAAA TCTGACTACT GTGTATGTGT GTGTGTGTTT
216651 TCTTTTTCTT TTCTTTGCTG ACTTTCACTA TTGATATCTG ATTTGCTTGT
216701 GTGTTTAGCG ATTTTATCAG TGAGCTCATA TTCTTTGAAA CTTTAGCTGT
216751 GAGAAATTTA TGTGGTTTGT GTTGAAGTTG AGTTCCTCCA GCAAGTATTT
216801 TTATTTACTT CTAGTTGCTT AGGAGTAATA GCAGCTCAGG ACTACAGTTT
216851 TATTTTAAAT TCTGAAGTGG AGGTTTCTTC AGGGTACATA TAGATATCAT
216901 GGATTTAGTC AACATATGAT CATAGGAATA GGCTTATAAT TCCAAAACAG
216951 CATATTATTT ATTTCTTTTC TATCTCTCCA CCCAGAGGAG TGGCAACAGA
217001 GAAAGAAGGT TTCCTTTCTG TCCTCTCTGC ATGGTAGATT TATTTCTCAC
217051 TTCCCATTTC CTGAGAATGA ATGCATCACA TTGCACAAGA CCAGGAGTTA
217101 CCATTCACAT AGACTTCTAT GGTACATGCA GAAGAATCTG AAGTATCCCC
217151 TAGAATTTTT CAGTATAATA ACCCTGGTTA AAGTTGCATT CTTTGGGGGT
217201 TTCAGGTCTT TCTGCAGGGA TATCACTCAT CTTTCAGCGG GCCCCAGGGT
217251 TTTATAGTCT TTCTCTGACA CACTACACAT ATGTTACTAT ACAAATGCAA
217301 AGGCACCAGG ATTAACCAAT CTATGGCAAG GCAAAACTGG CTTTAGTATC
217351 AGCTTCCTTC TCAGGATTTC TGTCTTTGCA TTTTGTTTAC TTGTTTGTTT
217401 TTCTGTGACT TTTTTTGGCC AGTCACCACT GAATTCTAAC TTTCTTTTCA
217451 GCACCACAAC TTCTTAAAGA AAATTTATTT TAATGTTATA CAGAGTTTTA
217501 GTTATTTTAA GTAAGATATT CACTCAGTTT AGGGTATCTG TTCCAATATT
217551 TTACCGGAAT TAGAATCTTG TATATAGTTT TGTACTCAAA TATACATAGA
217601 AAACCATTTT ATGCATAATG TATTCAGTAT AAAAATGTTG TTAGATACAG
217651 AAAACTAGTG TTTTACTTAA TGATATCCCA TATTCTTGGG AGATGGTTTT
217701 GCTGCCAGGT CATAATATGC AACCTCACAT CCAGGAGGGG CTCCTTGCCT
217751 TGTCACAGAC CTTGCTGTCG ACCAAAACTA ACCTACTGAT CTTTTTTTCA
217801 TATTATTATT AATGAGAAGT AGAATCAAGT TTTAAATGTT TTAAAATTCT
217851 CTTTCTTGCA TCTGTGTGTT CTTCAGTGCA AGATATGTTC CTATAGTTCC
217901 AAGTATTTTA GTAAACGTAT CATCTTATAA CTGTTATTCT GTGGAATCAT
217951 AGTAGCATTT TCTTTTGAAT GAAAATTTTT CTTATACAGT TGTAAGAACT
218001 ATAATTTATT TATACTTTAC TTCATTCAGG ATATTTATTA CGATTACATT
218051 CTAGTGAAGG TTCAATTGTA AATAACCTAG TGCACTTCAG TGACAATTTC
218101 AGCAGAATAG ATTTTTAGAA TGGAATTGTT TTATGTATCT ATATTTTTGT
218151 TTCTTTCAGT GCCTGATAGT GCACCAGAAA ATATCACTTA CAAAAATATT
218201 TCTTCTGGAG AGATTGAGCT ATCATTCCTT CCCCCAAGTA GTCCCAATGG
218251 AATCATAAAA AAATATACAA TTTATCTCAA GAGAAGTAAT GGAAATGAGG
218301 AAAGAACTAT AAATACAACC TCTTTAACCC AAAACATTAA AGGTAAAAGA
218351 ACAAATCTAA TATTGGATAT TTGCATTTAT AATGACAGAG TAGCCACAAA
218401 TATTAGTTTA ATGTTAATAG TTTCAGATTA TTTTCATGCA GGGTATTACA
218451 ATTTTGTCTT TTTGGTTAAA TAAGCTAGGA GTTTATTGCA GGTCACATGA
218501 AAGAATACTA TAGATCCATC CTTTTCCACA TTATCCTATA TCATTTTGTC
218551 TTCATAAATA AGAGCTACTA TTGCCAAAGA ATGACATTTT CACTTAGTTT
218601 TTATTTTTGG AAGATTGTGT TGACAGCCAT TTCATAGTTT GCCTCTTGCA
218651 TATTATTAAA TGATATTTTG TAAGTTTCAA CTTACCTATT TGATTTCTCT
218701 TTAGTACTGA AGAAATATAC CCAATATATC ATTGAGGTGT CTGCTAGTAC
218751 ACTGAAAGGT GAAGGAGTTC GGAGTGCTCC CATAAGTATA CTGACGGAGG
218801 AAGATGGTAA ATATAATAGT GGATATTGAT ATACTTTGAT TCTATAACAT
218851 TCCAAGAAAC ACACGTATAG AATGAAACAA TGTAAAAACT CCTCTAGTCA
218901 TGGGTATCAG TTGTGTACCA TACCAGCGTT ATACAGAGAT TTCATTGTCA
218951 TGGTATAAAA GAAGCTAGCA ACATCAGATT TACATTCAGT GAAATCAGGC
219001 ATAAAATGTT TTTTATTTTC TGAAGTCATC AGTACTCTGT AAAAAACAGT
219051 CAGTCATGTT TTTCCATGGG GATTTTCAAG GCTTAAAATT TGGTTTGAAC
219101 GTTAACTGAT ATATGTCATG ACTGAGTTTT TCAACTTTTA CATTTTTAAG
219151 AATAGACATT AACATGAGCT TTGAAGCAGA TTATGTTTAT GTAAATGTTC
219201 AGCACTTTTT TACGATATTA ATGATTAACT TGATAATGAG ATCAGGCTAT
219251 TGTACAGGCT TCTGCATAAT TGGACAAGAT GCTATTCCCC AAAGTTAGTA
219301 GCTTTCATAC TGAATATTTA AACATACCTT TCCCTAACCC AAATAAAATC
219351 AACTTTACTA CTGAGGCCAC TTTACATTGA TACCTTACCA AGTTAGACAT
219401 ATATTATGCT AAGAATATAA CTTCTGAAAG ATATATTTGG GTTAGGATTT
219451 GCATTTTATG TTTTATACAT TGCATATTTA AAGAAAATTA TTATTTTTTT
219501 CTGTAAAAGG AATTCCTATT TCCAAGAAGG GTAGGCCTGG AAGTATCATA
219551 CGTGTTTGTG GAGTATCTTT TCTTTTTCAT CTTTCTTTCT TTCAAGTTTC
219601 CCCATCTTCA AGCTAGGCCA TAGCCTGTGA CTGTTAAGGG CAGAATGTGC
219651 TTAGACACTG CTAGGAAGGG AGACTTTTCC CTGCATTGCT CTCTTTCTTT
219701 TCAAAATAAT AAAGTCTTCA AATCCCTCTT CTCTTTTTGC AGGTCTCTCC
219751 ATGTTTTAAC CTCTACCAAA GCATCTTGGC TAGGGCTGTC TGTGTTGCCC
219801 CAGTTTCTAA GTGGGCTGCC TCTGTGGGTC AGTTTTCCCT AATCATTGCA
219851 TCTACTTACT AATGCTTGCT TTTCCATCAA AACTTACCTG CCCAAATTCC
219901 AATTTTTCTT CATAAATAGA TTCTCCTTGC TCTGAAAGTT AAAATTATCT
219951 TAATAAAAAA ACCTTCCAAA TGAGTCAATG GTTAAAAACT AGGGAAGAAA
220001 GTTAGTGCTC TTTTCTATCT TATGTAATAC CTAAGATTAT ATGTAGTAAA

FIGURE 3, page 62 of 87

220051 AATTTTACCA ATGCCTTTTT GAAAATAGTA CCCACTTCTT TATAACTAAT
220101 CTAATCAAAA GTTCCTAATG GTAAGAATTT GAGATCTTAT ATGATGGAAT
220151 GAGACCAGTA GTGAACATAT ATTTTGAGCA GGCAGACGTT TTACCACTCA
220201 AGTCAATAGT TCCAAAGTAT GTTGTGCATC TGAATTACCT GGGCTGTTAA
220251 AAATATGCTT CCTCAAGGTA AAGTTCCATC TAAATTCTTG GCCAAGTCAT
220301 ATGATTTCTA AGGAACAGGG TAAAGAACAA GACTCCCTTG TTGAAAAATT
220351 ACAGAAAATC GAGAATGGAT AAAGATCTGA GAACATTTGC CTCTTTGGGA
220401 ATTAGGAACT CCTTGCCCTC ATGAAGCTCA CGGTTAGAAC AAGAGACCTA
220451 AATTTGACAA ATGTGTGGAC AAATAATTTT TATGATTTTT AATTACTGGT
220501 ATAAATGTTC CCCCAAATTA TTCACCAGGA CAAAAGAAGG ACCTAAGTTA
220551 CTCTGGGGTG TGAGGTAAAG CGTAGCGGTG GAAGTTATGT CGAAGCTGTG
220601 ACATGAAAAT GAATAAAGAG GGAGGGTGAG AAATAGGAAA GATCATGCCA
220651 GGTAGAGGAG TGAGAGATTT GTGAAGTCCT CATGCCAGGT AGAGGAGTGA
220701 CAGATTGTGA AGTTTCTTCT CAGCTACCTT GAGATGCTCT GAGATGACAA
220751 ATTGAATGCA CTGCAAAAGT TCTAATTTTT CTAGTTTCAA TTTTGTTAGA
220801 TTGTATTTTA GAATACATGT GCCAAAATAT TTTAGAATAC ATATGCCAAA
220851 ATGATTAAAA CTTAGTCTGC TACAGTGGAT GTACAGTGAT TTTTTTAGAT
220901 AGACATGTTA ATTACGTTTA CTTAGCAATA AAATGTTTTA CATTAAGAAT
220951 AAAATATTCG GAGATCTACT GAAGGTTAGC TTTTAAAGAC ACCACGCTTT
221001 ATCTGGTATT CCACATAAGC ATCTTAAAGC ATATTATAGA GTAGAAATGG
221051 TTAGTTGCAA CATATTAGTT TCTAAGTTAC TGCTATTTTT AATTGAAGTC
221101 CTTTTTGTAA ACAATAAACA GATTTTACAA GGATGCTAGG AAAAATATTT
221151 ATAGGTATTT GCTTTGACAA ATGAAAGAGA ATTTTCAGAG ATAATTCTTA
221201 TCTTGGGAAA CAGACATCTC TAACTGATGT ATACATTCCT GTGATAATCA
221251 ATATTTGATA GCAACATTAT TATAGTGCCA GTGAAAATAA CAGAATGAAA
221301 ATACCAAATA CAGCTATCAC TATTATTCCT TATAACTTGT CTCATAAACT
221351 TTCTGCTGCT CAATAAAATT TTTTTGGAAA ATTATTGTTA GTTAAATAAT
221401 GAAAACATGC ACACATGGGA ACACATACAA CTACAGCTGA GATTATTCAG
221451 AGAAGTAAAA AAGAAAAAAT ATTGAAGTAA GTCAGGTAGC ATTCTGTCCA
221501 AATTATTGGA AATAGTGATC TGTATATGAA CTGTATTTCA ATTGACATTG
221551 TTTAAAGATG TAAACAAATT CTCAGAATTT CTGTTAGCTA CCTATGAATT
221601 CACATTCCCG TGCATAACTG TAACAATGAA CCAAATTTTA GTGTTTTCCT
221651 TTTTTACATG TAAAAAGTTG TATTCCATTA TTCTAAGACA TTACTGTGTT
221701 ATTACACAGC AGCTGAGAAA TGTCATTCTA AATGTTTTAC CTAAATGGAA
221751 ATATAAAGTT GGCTGACTAT TTTGCAGTAA TGTTTTTATT GCTTATTCAA
221801 TGCCAAATAG CAAATGTATT TATATTTTAC ACTATTACAG CAGAGTTACA
221851 AGTAGATTCT AAACTATTTT CTTATTTACG TGCTACATTG GCATTTCCTT
221901 TGTAAACCAT TCAATTTTGA AGACTGAGTG AACAGAGTTT GATATTATTT
221951 TACTTTTTAA TGACACAACA GAGATTGAGG AATGTAGTTT TCATCATTTG
222001 TGAGGTCAGT CATTTTAACT GCTTTCTCAA TGTTATGCTT ATCACTTTCC
222051 CAACTTCTTG GATGTGTGAT TTTTTTCCCA CCTCTTTTTT ATTGTCTAGG
222101 GATCTCTTTT ACTGTATATT TATTCACCCT CAATAAAATT TTTATTTTTA
222151 TTAGAGGATG ACAGTTGACC AAGATGTACT TGAACAGTAG GTGAGTCACT
222201 GTGACATACC CCTTGTTCTT CTTTCTCATG AAATATTTTT TTCCATTGAA
222251 TCACAGAAAC AGATGTTCTA ATACCACCAT GCAAAATCTT CCTTTATCAT
222301 CTCATTTTGA AAGTAAACAG TCTCTTGTGC TTCTGGAGAA AAGCACTGAA
222351 CCTAATTCCT TTACCAGAAA GTTTATAATA AAAATTGTGT GCATTTCCAT
222401 GTTAACTTTT TCTTATATAT GTTTAATAAA ACACATTATT CTATACCCTA
222451 ACTTTACAGC TCCTGATTCT CCCCCTCAAG ACTTCTCTGT AAAACAGTTG
222501 TCTGGTGTCA CGGTGAAGTT GTCATGGCAA CCACCCCTGG AGCCAAATGG
222551 AATTATCCTT TATTACACAG TTTATGTCTG GTAATAATTT TTTTTTTGGA
222601 AATAGTTCTG AGAACAGATA TTAATCTGTA ACATAATAGG AATGTAGCTT
222651 TTAGATTTCA GAATGTGGTG CTACATTAGG AACCTGATTA TTAATAGGCT
222701 AGTTAATATG TTTTGATTAA GAAACAAGTT TTTCCATATT ATGTAGTGGT
222751 TCAATCATGG TCAAATGAAA TAATTTTGCA ATTAAAACAA AAAATTATGT
222801 GTTACGCATA ATTATACTAA ATTCCTACTC TTAAAAGTCA TTGACAAGTC
222851 AATTTGTATG AATGTAAGCA TATACTTTTA CACTTCCTGA AGTTTTACAC
222901 AAGTANNNNN NNNNNNNNNN NNNNNNNNNN NNNNNNNNNN NNNNNNNNNN
222951 NNNNNNNNNN NNNNNNNNNN NNNNNNNNNN NNNNNNNNNN NNNNNNNNNT
223001 CATGAGAACT TGGTAGATTG AAATCTTTAC TTTGAATGTA ATGTAAATCC
223051 TCTTTAGATT CACCAATTAG GTAACACATT ACCTAGTGGA TTTCATATAT
223101 TTCAACTCAG AAAATACAAT TTACACAATA CTTCGTAAAA CATAGCCATT
223151 TCCTTTTATA TTTCTGAATT TGAAGGGCCA GCATTGAGGG AGATGCCATG
223201 ATGTTTTAAA GAAGTCTCCT CTTCTTCTCT TTCCTAAGTT AAGATTTTTC
223251 TTTCCCTAAT TCCCCTTTAA CCCCTTTACA TATTTCTCTT TAAGACTATA
223301 TTTTTTGTTT TCTTTGTTGC CTGATTCCTA GTGACTTTGC CTAGTCGTGA
223351 CGAAAGTGGG AGTGTCTTGA CTCCCAGTTA GCGAAAAGGA AGCAGGGAAG
223401 AAGGTTACCA TTCCTTTTCA TTACCCTATT TATTTATTCA CTCATTCATT
223451 CATTGAACAA TATTGATAGA ATACCTATAT ACTCATGAAG AAGACTCACA
223501 TAAGACCGTT GCCCTCAAGA GTGTTGTATC TCTTACACTC CCAAGAGATA
223551 ACTGGATTAT ATACCCATAA ACAAGCAAAC AAGGGAATGT TGGGGGGAAGG

FIGURE 3, page 63 of 87

223601 AGGTCTACTT TTGATGGGAT GCTTCAGGAA GTTCTCTTTG AAGAAGTGTC
223651 ATTGAGCTGT GATCCAGTTG ACAAGAAAGA GCTTCTTGCC ATGTAAAAAT
223701 CTACAGGGCA GAACTTTCAA GAAGGAGGGA ATACCAACTG CACAAGCTCT
223751 GTGGGGAAAC AAAACTTGTC ACTTTGAAGA CCAGAAAGGA GGTCAATGTT
223801 GCTGGGGATT AGAGAACCAG AGGAGGGTAA CAGTGGGGAC AGGAAATAAA
223851 GTTCAGGAGT CAAGCCATGG TAAGGATTTT GTTTTCATTT TAACTATAAA
223901 GGGAGTTCAT AGATAATTTA AATCACTTTA GATTCCTTAT AAAGAATGAA
223951 TTGTCAGGGA CAAAAGTGTT AGCAGGGATG CTAGGCTATT TTAGTAGTCT
224001 GGGAAAGAGA TGGTAGTGGC AACAGAGGGG AGAAGTAGGT GGCTTTGAGC
224051 TACATTTGGG AAGAAAAACT AACAGGACTT GGTGATGGAT GGCTGTGCAG
224101 ATAAGAAAAN NNNNNNNNNN NNNNNNNNNN NNNNNNNNNN NNNNNNNNNN
224151 NNNNNNNNNN NNNNNNNNNN NNNNNNNNNN NNNNNNNNNN NNNNNNNNNN
224201 NNNNNNNNNN NNNNNNNNNN NNNNNNNNNN NNNNNNNNNT GAATCAAGTG
224251 TGGTTACTAC TAGAATTTGA TGGCATTGAT TAAGTTAGAA AAAAATTTAA
224301 ATGAAACAGA TTAAGTGAGA ATCAAGATTT TTCTGGCTGG GATTTTCAGC
224351 CCTGCATTAT GAGAATAATT GTTTTCTTCT ATACAGTGAT CATGCTTCCC
224401 TTCCTAGAGC TTCCGTGTAT ATCTAGCATA ATGCATAACA CACCTAGACA
224451 GAAACACATG TGGTTGGATA GCATTTTAAG GGATGCCGTT CACCCAGTTT
224501 TTCTCTCTCT GGGTATGAAC TCCATGTCAA TGGGAGCCTC CTATTCTAGG
224551 AACTTAGCTA TAACTTTAGT TGTCTATTTA TNNNNNNNNN NNNNNNNNNN
224601 NNNNNNNNNN NNNNNNNNNN NNNNNNNNNN NNNNNNNNNN NNNNNNNNNN
224651 NNNNNNNNNN NNNNNNNNNN NNNNNNNNNN TACTACAGAA AGATGAGCTT
224701 ATAAAAAGCA GTGCTAAATT AGGCCACAGG AAAATGCTTC CAGTTAAGGG
224751 ATAAGTATGA CATTTCCAAG GGATAATAAA GGGTAAAGAT ATCTTCTGGA
224801 TCCTCCCTCA ATATAACATC AATATCTTCT TTGAACCTTG AAAATAATTA
224851 AATAGAGAGA AGAAAATATA TAAAACCTGT GTAAATATGT GATTTTATAT
224901 AAATGAGATG TTCTTCCTAG AGGATAAGAA ATATTGGAAG AGATTTTTGC
224951 CAGGAAGTTT TTTCTTACTG GAAGTGTGCC TATTTGCAGA ATTAAAGAAC
225001 ACGATCAGAA CTGGAAAGCA AATACTAATA GTGTGAGTCT TACAATGAGA
225051 AAAGAAAAAA AATTCTTACC TATGTAGAAG TCAAAATAAA AGATTTGTGA
225101 TGACTATTTC ATGAAGAAAA CATAGCTTAA AGAATAGGCA ACCTTTTTCT
225151 AACTGACATC TGAGTATTAT ATAATATAGG TATTTTCTGT CAATATGTAC
225201 ACATTCAGAT TAATTAACAT GTCAATATAT GCTATTGGGG ATAATTAAAA
225251 ATTTTTAATG TGCTGTAAGA AACTATTGCT GATAGGAAGG TGATTTAGTC
225301 AACCTAGTTC TGCTTAGATC TATTTTTATG GAGCTTGAAT TTTTATTCCT
225351 GTGAATTCTC TTATTTAAGG TCTATTGGGA AGCCCTTACT CTCCGTTTCA
225401 TCTCACACTT TATAAATCAT TCTTGTGACC TTTACTCTGT TCAAATAAAT
225451 GTTAGCCATT GCAGAATTCC AAAGGGTATT TGGCATGATA CATTTGATGT
225501 CTTCAGTGTA AGTAATGTTA TAGGAAAAAT CCTGTTAAGT ATTTTACATG
225551 TGCTATTTCA TTTAGTCCTC AGCACAATCC TATAACATAG ATACATTATT
225601 ATTCCCATTT TAAAGACAAG ATAAATGTTA CTTACAACAG TTAAGTAAAT
225651 TGCTCAAAGC TACTATCTGG GAATTGGTAG AACTACAGTT AAGCCAAGGT
225701 TATGATTCCA GTCATGGCAT TTGCAAAAGC TTGAGTCTTA TTCTCATTAA
225751 TGACATTTTC TTTTTCTATT CTAGTCTATT GGAAGATATT ATTCAAATCA
225801 AATTTTTTTA TCTTTAAAAT TCTGGAATTC TTAGTTTAAA TTATTAATTA
225851 AATGTACTTA TCTAATTTAT TTTTTTAAAA CAGTTTTTTG AGTATTTGTT
225901 TGCCTGATTA GATTGTGAAC TCTAAATTAA GGTACCATAT ACATGGTCTC
225951 TTGCATTTGT TACAGAAATA ATTGTAATGT CTTTTATGTA GTGGATATAT
226001 CAGAGAAAGA CTGAGCTTTC AAAATAAACC CAACTGCAAC TGGATTCTTG
226051 CTCTACCATT TATTCCTGTG TGACCTTGGG CAAAGGTATT TGACCTCTCT
226101 CAGCCAGTTT TCTCATCTAT ACAATTTTGA CAATAATACT TTATTTGTTG
226151 ATTGTATAGA TATCTTCATA TTTGCCTTCT TCCTTGAGAG TATTAAAAAA
226201 GTATCTTTGG CATTTATCTT ATGGATAAGT CAAAGTTTTG TTTTAAATTT
226251 TAGATTCTCT TTTTTCAGGG AGTAAAATGT TTGAACACAA TCCTTTTGGT
226301 CTGTTCTAGG TTGCTGCTGA AAACAGTGCT GGCATTGGAG TGTTTAGTGA
226351 TCCATTTCTC TTCCAAACTG CAGAAAGTGG TAATTTTCCT GTCATTTATT
226401 TTAAATTGAC TTAGTCATGA GTTTGTCGTT TAAAATAATA AAGAACATAA
226451 ATAAAAACTG ACACTAAAAT ACATATAATT CTCAGTAGCA TGGCCACTTA
226501 ATTAGTTTTA GAGTTCTTTC GGATAGCTAA TTTATTCCTT AAAATATATA
226551 TTATTCTTTC TGATTATAAG AACAGTAAAT GTTATCTTAC AAAACTTTGA
226601 AAAAACAAGA ATAAAAAATG AAAATTATCC ATAGACTTAT CATATAAAAA
226651 ATGCTTTTAT CATTTTGGTG CATTTCTGGC TTGTCTATTT CCCCCATTAA
226701 TATGTATCTA TATGACTATA CATTAATGAA AATAAGCTTG TGCTACATAT
226751 GCAAGTTTAT ATCCTGCCTT TTCTTTTTAA CATGAAGTCA TAAGCTTGTT
226801 ATAACATAAG ACTTTTGGAA ACACGGATTT TAATGGTTAT TATATTATTG
226851 GGTAACATGC AGTCATTACC AAACCAATTT AAGATACCTC CATTCTTCCA
226901 GGGGCATAGA GGAAAAATCT TGATGTCACC TGTGGCTCTT TTCTCTCACA
226951 GTACACATCT AATCTATCAG TAAATCTTAC CAGCACAATC ATCAAAGTGT
227001 ATTCTGAATC TCACACTCAT TGCTGACATC CTGTCCAACA TTATTCCCAA
227051 GAATTGTTGC ATTATATTTT ATTTTTATTA GAATGCAGCT GTCCTGAAGT
227101 CCCTTAATTC CTACCTTATA TCATTCATAT AGACCTCCTT CCAAAGATCT

FIGURE 3, page 64 of 87

227151 AACTTTCTTA TGTAATTTAT GTGGCTATTA CTTATAAATT ATATTTTAGC
227201 ATCCTTTTGT ACAATGTAAA CCTAAACTCT AGTTATTTGG CATCTTAATA
227251 CTAGGCATCT TTACTATCAC TTATTTTTTT TTTATCTCAG ACGTTTTGTT
227301 TCATTTTGAT TTCTTTCAAA AATGACTTGT CATGTTTGTT TTATATTCTG
227351 AAGGATCTTG GTGTTTTACT CTATCAGTTT TACACACTTT ACCATGAGGT
227401 TAATGGGAAT AATTTCCCCT AATTCTAGCT TCATATTGGT TTCAAGCCAA
227451 CTCAAATAGA ACTCAGATTA TTATTATTAT TACTCTATAT AATTAATAAT
227501 TGATAGAAAA GCATAATGAA ATTCTGAAGT AAGTTGATTT TGAAAATGTA
227551 AAATACAATA ATTACAACCA ATTGCAGGGT ATCCACTTGA TATTAGGCAC
227601 TAGACATTTA TAAACATTCC AGAAATCTGC TTTTTGGTGA AAATGGTTGT
227651 ATAATTGATT CAGTTTGCTA TGTTTTTCAT ATCTAATGAA ACTACATATT
227701 CCAAAATAGT TAAGGAAATA AGAAATTTAT CCCAACTTGT TTGTATATTC
227751 ACAACTATTG ATTGAATTTT TTTCATACTT ATTTGAAACG TTTCATCAAT
227801 GCATGTATTA GCCCAGTTAT CCTAAAGTAA AGTTGACTTG CCCCAACTCC
227851 AGTTTTTTAT TTTAGGCAAA GTTCAGTTAA ATACATTTAT AAAAATCTTA
227901 CACAAATAGA TTTTATGCAG TGTATTATAT ATTTAATTTC ATGTACCATG
227951 AAATTATATA AATGCAATTC TAAGTTTTAT AACAAAGTTT TTTCCTTCCC
228001 AATCTTTCTC TTCCCCAGCT CCAGGAAAAG TGGTGAATCT CACAGTTGAG
228051 GCCTACAACG CTTCAGCAGT TAAGCTGATT TGGTATTTAC CTCGGCAACC
228101 AAATGGCAAA ATTACCAGCT TCAAGATTAG TGTCAAGCAT GCCAGAAGTG
228151 GGATAGTAGT GAAAGATGTC TCAATCAGAG TAGAGGACAT TTTGACTGGG
228201 AAATTGCCAG AATGCAATGT AAGTATCACA GAACACTTTC TATGTCTTGA
228251 AAAATCTTAG ATAAATTTAA TTTTCATATT TCTAGCATCT AGATACTATA
228301 TTTTTACCAA AGTTTTATTA GTTATTTGAT TACTTATGGT ATCATGTTAT
228351 ACACAACGTT TTATTATTTG ATTACTTAGG GTATCATGTT ACACAATTGG
228401 CCTCATTCAG GTAGAATACA GGAATGGTTT GAGAATTCAA GAGTGAGGGA
228451 TTAAAATCAT TTAGGGAATT CGGAAAAGAC TTCATCAAAG GAGTAGCATT
228501 TGTGATACAC CATGGAGCAA GGACAGATAG AGATTTTGTG ATGGTGGCAT
228551 TCCCGGTGGA GGATACTTTA TAAAGCCCTG AGGTGGAAAA GTGTAAGATA
228601 TAATTGGAGA AAATATTTTA CTTCCATATG ACAGGAGGGA AGAGTACATG
228651 TAGGGTAATA GTTGAGGTTA AATTTGCAGA GGTAGACTGT CATTGTTGTG
228701 CATATCTTTG GTAAAGAATT TGTCGTTACT CTGGTCATTG ATGATAAACC
228751 TCATAATAGT AATGCTTTAT TATAGAATAA GCATCGTCAT TTTAATTATA
228801 TGATAAGCAT AATAATGCTT TTCCTAAAAT CATTTTGGTA ATCTCTGTGT
228851 TACTATTAAT GCAAACACAG TCAAACAGTT ATTTTTGCTG TAAATACTTT
228901 ATAAAAGTCT AAAAATCTTC TTTTTCAACT TATGATATAG TTCTAATACA
228951 CGCACACACC TAACGTGTGA GCTAGTGGCA TACTACTACT TTTTAGTACT
229001 TATGAGAAAA AAAAGTTCAT TAACAGTAAG AAAGCAGCAT TTGAACATAC
229051 ACAAGAGTAA AATTATTTCA GCTCTTTGGC TCTTGCACTG TTAACATGAA
229101 GCTTAAAAAT TCTTACAGAT GATTGTGCTG TAGTTTTACC TTTATTTTAA
229151 GCCACTTGAA ATTCTATTCG TAAAGGTTAA GGTATAAGGA ATACAATAAA
229201 TATGTCCTCT TCTAAAACTG CAGACATAAA TGGGTACAAT TAAAATCTAG
229251 CAAATTTGTC TATAACTTTT GCATGTTATG TGTGTATGTA TAAGCATAAA
229301 AGAAAAAGAA ATGAATTACA TGTTCTTATT CTTATGTTCA CCAAGAGATA
229351 CAACATTATT TCTCTATTGA TCTTATTTTA TTTACTAGGA GAATAGTGAA
229401 TCTTTTTTAT GGAGTACAGC CAGCCCTTCT CCAACCCTTG GTAGAGTTAC
229451 ACCTCCATCG CGTACCACAC ATTCATCAAG CACGTTGACA CAGAATGAGA
229501 TCAGCTCTGT GTGGAAAGAG CCTATCAGTT TTGTAGTGAC ACACTTGAGA
229551 CCTTATACAA CATATCTTTT TGAAGTTTCA GCTGTTACAA CTGAAGCAGG
229601 TTATATTGAT AGTACGATTG TCAGAACACC AGAATCAGGT ATGGTTCACT
229651 TTTTGTAGAT AAAAAGATTT AAATGATTAG AGAATAATGT TTAATTTATG
229701 TAGATATTTA ATTTTAATCT TCTTTACCTT TCAGTAACTT TTTTCCCCTA
229751 ATAATATACC ATAGGCATCC CATCAAGGGT TTCTTCGAAT TTCTATACTC
229801 TTTTATATTA TAGCACAAAA TAAGTATTTG AAAGGAGAAA GATTTGCAAA
229851 AAACAATTCT TGAGCCACTG ACCGTGATCC TCATATAGCT TTTATCATTT
229901 TATAATGTCA GCAATTTTTA GTAATCATCT TTGCCGTTCT AAATGATTTA
229951 TAATCATTTA CACCCTTCTC TCACTGTTAT TGCCATCATC AAAAGCAGAA
230001 ATACCTGCAC TAGCAGAACG AGCATGTGAT CAACATTTAG TTATCAGATA
230051 CAAGCAGTAG CTAAAATATA TACCTACTTA TATCCCATTT GCACTGCAGT
230101 TTCCTCATCT GAAAAATAGA GACAGTAATA GTACCTTCCT TAGGGTGCCA
230151 GTGTTAAAAT TAAATGAGAA TAATTAGATA TTATCATTAC TACTGAATTT
230201 TATGAGAACA TATTTTTGGT AAGGTATTCA TATATTTAAT TATGGTACTA
230251 TATCAGTATT CATGTAAATA CATGTATTTA TGTATTTCAT ATATTTATAA
230301 AATTTAAGGG ATATTGATAT AGTCCCACAT TACATAAGGT ATTTATTATA
230351 TATATAATAT ATATAGCTGA CAGATATATC ATAATATAGT ATCAGGCATT
230401 AGGTTGTAAT TGCTAATTTC TGAGGTATTG AAAATTATTG GTAGGGTAAT
230451 TTCACTAAAG CATGTTTTTT CTGATAAAAT AGCTGTTGGC TTCTATTATT
230501 TTTCATTTCA TATAAGTTTG AAGTTTTTTT GTTCATTTAA ATAACCATCT
230551 TTGAATTATA CCATTTTCTT CTTACATACT CCTTACTTTT TATACAATAA
230601 AAAAATGATT TCGGGGGGAG CCAAGATGGC CGAATAGGAA CAGCTCCGGT
230651 CTACAGCTCC CAGCATGAGC GATGCAGAAG ACGGGTGATT TCTGCATTTC

FIGURE 3, page 65 of 87

230701 CATCTGAGGT ACCGGGTTCA TCTCACTAGG GAGTGCCAGA CAGTGGGTGC
230751 AGGACAGTGG GTGCAGCGCA CCGTGCGTGA GCCGAAGCAG GGCGAGGCAT
230801 TGCCTCACTC GGGAAGCGCA AGGGGTCAGG GAGTTCCCTT TCCTAGTCAA
230851 AGAAAGGGGT GACAGATGGC ACCTGGAAAA TCCAGTCACT CCCACCCGAA
230901 TACTGCGCTT TTCCGACGGG CTTAAAAAAC GGCACACCAG GAGATTATAT
230951 CCTGCACATG GCTCAGGGGG TCCTACCCCC ACGGAGTCTG CCTGATTGCT
231001 AGCACAGCAG TCTGAGATCA AACTGCAAGG TGGCAGCGAG GCTGGGTGAG
231051 GGGCACCCGC CATTGCCCAG GCTTGCTTAG GTAAACAAAG CAGNNNNNNN
231101 NNNNNNNNNN NNNNNNNNNN NNNNNNNNNN NNNNNNNNNN NNNNNNNNNN
231151 NNNNNNNNNN NNNNNNNNNN NNNNNNNNNN NNNNNNNNNN NNNNNNNNNN
231201 NNNNNNNNNN NNNNNNNNNN NNNNNNNNNN NNNNNNNNNN NNNNNNNNNN
231251 NNNNNNNNNN NNNNNNNNNN NNNNNNNNNN NNNNNNNNNN NNNNNNNNNN
231301 NNNNNNNNNN NNNNNNNNNN NNNNNNNNNN NNNNNNNNNN NNNNNNNNNN
231351 NNNNNNNNNN NNNNNNNNNN NNNNNNNNNN NNNNNNNNNN NNNNNNNNNN
231401 NNNNNNNNNN NNNNNNNNNN NNNNNNNNNN NNNNNNNNNN NNNNNNNNNN
231451 NNNNNNNNNN NNNNNNNNNN NNNNNNNNNN NNNNNNNNNN NNNNNNNNNN
231501 NNNNNNNNNN NNNNNNNNNN NNNNNNNNNN NNNNNNNNNN NNNNNNNNNN
231551 NNNNNNNNNN NNNNNNNNNN NNNNNNNNNN NNNNNNNNNN NNNNNNNNNN
231601 NNNNNNNNNN NNNNNNNNNN NNNNNNNNNN NNNNNNNNNN NNNNNNNNNN
231651 NNNNNNNNNN NNNNNNNNNN NNNNNNNNNN NNNNNNNNNN NNNNNNNNNN
231701 NNNNNNNNNN NNNNNNNNNN NNNNNNNNNN NNNNNNNNNN NNNNNNNNNN
231751 NNNNNNNNNN NNNNNNNNNN NNNNNNNNNN NNNNNNNNNN NNNNNNNNNN
231801 NNNNNNNNNN NNNNNNNNNN NNNNNNNNNN NNNNNNNNNN NNNNNNNNNN
231851 NNNNNNNNNN NNNNNNNNNN NNNNNNNNNN NNNNNNNNNN NNNNNNNNNN
231901 NNNNNNNNNN NNNNNNNNNN NNNNNNNNNN NNNNNNNNNN NNNNNNNNNN
231951 NNNNNNNNNN NNNNNNNNNN NNNNNNNNNN NNNNNNNNNN NNNNNNNNNN
232001 NNNNNNNNNN NNNNNNNNNN NNNNNNNNNN NNNNNNNNNN NNNNNNNNNN
232051 NNNNNNNNNN NNNNNNNNNN NNNNNNNNNN NNNNNNNNNN NNNNNNNNNN
232101 NNNNNNNNNN NNNNNNNNNN NNNNNNNNNN NNNNNNNNNN NNNNNNNNNN
232151 NNNNNNNNNN NNNNNNNNNN NNNNNNNNNN NNNNNNNNNN NNNNNNNNNN
232201 NNNNNNNNNN NNNNNNNNNN NNNNNNNNNN NNNNNNNNNN NNNNNNNNNN
232251 NNNNNNNNNN NNNNNNNNNN NNNNNNNNNN NNNNNNNNNN NNNNNNNNNN
232301 NNNNNNNNNN NNNNNNNNNN NNNNNNNNNN NNNNNNNNNN NNNNNNNNNN
232351 NNNNNNNNNN NNNNNNNNNN NNNNNNNNNN NNNNNNNNNN NNNNNNNNNN
232401 NNNNNNNNNN NNNNNNNNNN NNNNNNNNNN NNNNNNNNNN NNNNNNNNNN
232451 NNNNNNNNNN NNNNNNNNNN NNNNNNNNNN NNNNNNNNNN NNNNNNNNNN
232501 NNNNNNNNNN NNNNNNNNNN NNNNNNNNNN NNNNNNNNNN NNNNNNNNNN
232551 NNNNNNNNNN NNNNNNNNNN NNNNNNNNNN NNNNNNNNNN NNNNNNNNNN
232601 NNNNNNNNNN NNNNNNNNNN NNNNNNNNNN NNNNNNNNNN NNNNNNNNNN
232651 NNNNNNNNNN NNNNNNNNNN NNNNNNNNNN NNNNNNNNNN NNNNNNNNNN
232701 NNNNNNNNNN NNNNNNNNNN NNNNNNNNNN NNNNNNNNNN NNNNNNNNNN
232751 NNNNNNNNNN NNNNNNNNNN NNNNNNNNNN NNNNNNNNNN NNNNNNNNNN
232801 NNNNNNNNNN NNNNNNNNNN NNNNNNNNNN NNNNNNNNNN NNNNNNNNNN
232851 NNNNNNNNNN NNNNNNNNNN NNNNNNNNNN NNNNNNNNNN NNNNNNNNNN
232901 NNNNNNNNNN NNNNNNNNNN NNNNNNNNNN NNNNNNNNNN NNNNNNNNNN
232951 NNNNNNNNNN NNNNNNNNNN NNNNNNNNNN NNNNNNNNNN NNNNNNNNNN
233001 NNNNNNNNNN NNNNNNNNNN NNNNNNNNNN NNNNNNNNNN NNNNNNNNNN
233051 NNNNNNNNNN NNNNNNNNNN NNNNNNNNNN NNNNNNNNNN NNNNNNNNNN
233101 NNNNNNNNNN NNNNNNNNNN NNNNNNNNNN NNNNNNNNNN NNNNNNNNNN
233151 NNNNNNNNNN NNNNNNNNNN NNNNNNNNNN NNNNNNNNNN NNNNNNNNNN
233201 NNNNNNNNNN NNNNNNNNNN NNNNNNNNNN NNNNNNNNNN NNNNNNNNNN
233251 NNNNNNNNNN NNNNNNNNNN NNNNNNNNNN NNNNNNNNNN NNNNNNNNNN
233301 NNNNNNNNNN NNNNNNNNNN NNNNNNNNNN NNNNNNNNNN NNNNNNNNNN
233351 NNNNNNNNNN NNNNNNNNNN NNNNNNNNNN NNNNNNNNNN NNNNNNNNNN
233401 NNNNNNNNNN NNNNNNNNNN NNNNNNNNNN NNNNNNNNNN NNNNNNNNNN
233451 NNNNNNNNNN NNNNNNNNNN NNNNNNNNNN NNNNNNNNNN NNNNNNNNNN
233501 NNNNNNNNNN NNNNNNNNNN NNNNNNNNNN NNNNNNNNNN NNNNNNNNNN
233551 NNNNNNNNNN NNNNNNNNNN NNNNNNNNNN NNNNNNNNNN NNNNNNNNNN
233601 NNNNNNNNNN NNNNNNNNNN NNNNNNNNNN NNNNNNNNNN NNNNNNNNNN
233651 NNNNNNNNNN NNNNNNNNNN NNNNNNNNNN NNNNNNNNNN NNNNNNNNNN
233701 NNNNNNNNNN NNNNNNNNNN NNNNNNNNNN NNNNNNNNNN NNNNNNNNNN
233751 NNNNNNNNNN NNNNNNNNNN NNNNNNNNNN NNNNNNNNNN NNNNNNNNNN
233801 NNNNNNNNNN NNNNNNNNNN NNNNNNNNNN NNNNNNNNNN NNNNNNNNNN
233851 NNNNNNNNNN NNNNNNNNNN NNNNNNNNNN NNNNNNNNNN NNNNNNNNNN
233901 NNNNNNNNNN NNNNNNNNNN NNNNNNNNNN NNNNNNNNNN NNNNNNNNNN
233951 NNNNNNNNNN NNNNNNNNNN NNNNNNNNNN NNNNNNNNNN NNNNNNNNNN
234001 NNNNNNNNNN NNNNNNNNNN NNNNNNNNNN NNNNNNNNNN NNNNNNNNNN
234051 NNNNNNNNNN NNNNNNNNNN NNNNNNNNNN NNNNNNNNNN NNNNNNNNNN
234101 NNNNNNNNNN NNNNNNNNNN NNNNNNNNNN NNNNNNNNNN NNNNNNNNNN
234151 NNNNNNNNNN NNNNNNNNNN NNNNNNNNNN NNNNNNNNNN NNNNNNNNNN
234201 NNNNNNNNNN NNNNNNNNNN NNNNNNNNNN NNNNNNNNNN NNNNNNNNNN

FIGURE 3, page 66 of 87

```
234251 NNNNNNNNNN NNNNNNNNNN NNNNNNNNNN NNNNNNNNNN NNNNNNNNNN
234301 NNNNNNNNNN NNNNNNNNNN NNNNNNNNNN NNNNNNNNNN NNNNNNNNNN
234351 NNNNNNNNNN NNNNNNNNNN NNNNNNNNNN NNNNNNNNNN NNNNNNNNNN
234401 NNNNNNNNNN NNNNNNNNNN NNNNNNNNNN NNNNNNNNNN NNNNNNNNNN
234451 NNNNNNNNNN NNNNNNNNNN NNNNNNNNNN NNNNNNNNNN NNNNNNNNNN
234501 NNNNNNNNNN NNNNNNNNNN NNNNNNNNNN NNNNNNNNNN NNNNNNNNNN
234551 NNNNNNNNNN NNNNNNNNNN NNNNNNNNNN NNNNNNNNNN NNNNNNNNNN
234601 NNNNNNNNNN NNNNNNNNNN NNNNNNNNNN NNNNNNNNNN NNNNNNNNNN
234651 NNNNNNNNNN NNNNNNNNNN NNNNNNNNNN NNNNNNNNNN NNNNNNNNNN
234701 NNNNNNNNNN NNNNNNNNNN NNNNNNNNNN NNNNNNNNNN NNNNNNNNNN
234751 NNNNNNNNNN NNNNNNNNNN NNNNNNNNNN NNNNNNNNNN NNNNNNNNNN
234801 NNNNNNNNNN NNNNNNNNNN NNNNNNNNNN NNNNNNNNNN NNNNNNNNNN
234851 NNNNNNNNNN NNNNNNNNNN NNNNNNNNNN NNNNNNNNNN NNNNNNNNNN
234901 NNNNNNNNNN NNNNNNNNNN NNNNNNNNNN NNNNNNNNNN NNNNNNNNNN
234951 NNNNNNNNNN NNNNNNNNNN NNNNNNNNNN NNNNNNNNNN NNNNNNNNNN
235001 NNNNNNNNNN NNNNNNNNNN NNNNNNNNNN NNNNNNNNNN NNNNNNNNNN
235051 NNNNNNNNNN NNNNNNNNNN NNNNNNNNNN NNNNNNNNNN NNNNNNNNNN
235101 NNNNNNNNNN NNNNNNNNNN NNNNNNNNNN NNNNNNNNNN NNNNNNNNNN
235151 NNNNNNNNNN NNNNNNNNNN NNNNNNNNNN NNNNNNNNNN NNNNNNNNNN
235201 NNNNNNNNNN NNNNNNNNNN NNNNNNNNNN NNNNNNNNNN NNNNNNNNNN
235251 NNNNNNNNNN NNNNNNNNNN NNNNNNNNNN NNNNNNNNNN NNNNNNNNNN
235301 NNNNNNNNNN NNNNNNNNNN NNNNNNNNNN NNNNNNNNNN NNNNNNNNNN
235351 NNNNNNNNNN NNNNNNNNNN NNNNNNNNNN NNNNNNNNNN NNNNNNNNNN
235401 NNNNNNNNNN NNNNNNNNNN NNNNNNNNNN NNNNNNNNNN NNNNNNNNNN
235451 NNNNNNNNNN NNNNNNNNNN NNNNNNNNNN NNNNNNNNNN NNNNNNNNNN
235501 NNNNNNNNNN NNNNNNNNNN NNNNNNNNNN NNNNNNNNNN NNNNNNNNNN
235551 NNNNNNNNNN NNNNNNNNNN NNNNNNNNNN NNNNNNNNNN NNNNNNNNNN
235601 NNNNNNNNNN NNNNNNNNNN NNNNNNNNNN NNNNNNNNNN NNNNNNNNNN
235651 NNNNNNNNNN NNNNNNNNNN NNNNNNNNNN NNNNNNNNNN NNNNNNNNNN
235701 NNNNNNNNNN NNNNNNNNNN NNNNNNNNNN NNNNNNNNNN NNNNNNNNNN
235751 NNNNNNNNNN NNNNNNNNNN NNNNNNNNNN NNNNNNNNNN NNNNNNNNNN
235801 NNNNNNNNNN NNNNNNNNNN NNNNNNNNNN NNNNNNNNNN NNNNNNNNNN
235851 NNNNNNNNNN NNNNNNNNNN NNNNNNNNNN NNNNNNNNNN NNNNNNNNNN
235901 NNNNNNNNNN NNNNNNNNNN NNNNNNNNNN NNNNNNNNNN NNNNNNNNNN
235951 NNNNNNNNNN NNNNNNNNNN NNNNNNNNNN NNNNNNNNNN NNNNNNNNNN
236001 NNNNNNNNNN NNAAAACCAA ACACCGCATA TTCTCACTCA TAGGTGGGAA
236051 TTGAACAATG AGAACACATG GACACAGGAA GGGGAACATC ACACTCTGGG
236101 GACTGTTGTG GGGTGGGGGC AGGGGGGAGG TATAGCTTTA GGAGTTATAC
236151 CTAATGCTAA ATGACGAGTT AATGGGTGCA GCAAACCAAC ATGGCACATG
236201 TATACATATG TAACTAACCT GCACGTTGTG CACATGTACC CTAAAACTTA
236251 AAGTGTAATA ATAATAAAAT TTTTAAAACA ATGATTTCAT AAGGGTCATA
236301 CAAGGTGAAA TTTGCTAGAC AATAATTTTG TTTTGAAAAA TATTTGGAAT
236351 TGTTTTATTT CAATTAAAAG AATAAACATC TAAGAAAAAT AGAGTAATTT
236401 AAAATGTCAT TATTATTTTC ATGTTATCAA TATTACATTT GAATCCTCCA
236451 AATGTAGATT ATAAATTTGT TCTTAGAATA AATACAAATA TTGATACAAA
236501 AAGTAAAAAT TATTTGCTCA TAATTTTGAG GGTCATTTTC TTGAAACTTC
236551 TACCTGTGTT AATAAGAGAG AAAATGTTTA TCAAGCCAGA TATCCAGACT
236601 TTGTTCATCC AGACTTTGTT GAATGCAGTA TATATATGCA GGTATAAATG
236651 TTTCAAGACA ATGTAACATT GGCAATAAAT GTATTACAAT GAATATTAGA
236701 ATGAAACTTG CGCAGTGCAA TAGTAAACAG TATTAAATAA AATCAGTAAT
236751 TGTTAAAAAT AAGTTTATCT GATGATCCAG CATGTGTTAT TCACAATTTT
236801 CAATTATATT CCATTTATTC TTTTTTAAGA TAAAAAAACT CTGCTTTTAA
236851 GCGCGATATT TTATTTTCCT TCTTTGCCTT TGTGTTTTAT TATGTGTATT
236901 TAATAGGGTG CGCTTTCATT TTAAATATAT GTTATGTATT TATTTTCTAT
236951 AATTATTTTA GTGCCTGAAG GACCACCACA AAACTGCGTA ACAGGCAACA
237001 TCACAGGAAA GTCCTTTTCA ATTTTATGGG ACCCACCAAC TATAGTAACA
237051 GGGAAATTTA GTTATAGAGT TGAATTATAT GGACCATCAG GTAAGCCTTA
237101 ATTGGTTTTG TGTTTGCCTT TTGGAGTGAG AATAATAAAA TATGTTACCA
237151 ATATCAAACT CTGTTTAAAA GTATCAGACT CTTTTTAAAA GACTTTAAGA
237201 TTGAAGCAAA CAATAGGAAA GTCATAAGGA AGGGGAGGTC CTTTGATTTT
237251 TTAATTCAAA ACCATAAATG AGTATAAGAA TGACAAAACT ATTCATGTTC
237301 CACATTTCAT GTGATGCATG TGAAAAACTA GAGATAACTC CTCAAGAAAA
237351 AAGTGTTAGT GGAGATATAC ATCTTCAAAT ATTTGAACAA GAAGTCCTTG
237401 GCTTACATTC ATGAAGAACA ATGGACTTTG ACTATATTAA ATTAGATTTC
237451 TATTCACTGC TAGGAGCCTA GTTTTTAATC ATTAGAAAGA GCTCTCTAAA
237501 AATAACATGG AAAATCTCTG TATCTTCTGC TCTATTTTGC TGTGGACCTA
237551 AAACTGCTTT AAAAAAGAAA ACCTATTAAA ATTTTTGGGC AGCTTTATAA
237601 AGTGGCAAGT TCTCCAACTT TGTAAGCAAG CAGGACCTGG GCATCCACTT
237651 GCCAGAGATA CTTTGAGAGG ATCAAGTATT ATATCATTAG GATCAAGTAT
237701 TATATCATTA GAAGTGAATT ATGTAAAGTC TAAAATTCTC TCCTGATTGA
237751 GAGCCTCTGA TTCTATGAAA TAAGTTTAAT TCTAACAATG ATGAGATAAA
```

FIGURE 3, page 67 of 87

237801 TAATAAAGCC ACATATTATC ATTTATTTGG GGGCATCAAA AAAGATACAG
237851 AGTTCCAACT CATTTTATTT TGCAATTTCT GTGGTATGAA TCACTCATCA
237901 CCATCATGAG TAACCTTTAT CTTTCATCCC TAAGTAACTT ATGCTCCTAA
237951 AATTCTGAAA TACTTTTACT TCCTAAAAAA AGATAATTCC CTCCACTCAC
238001 CCATCCGATA CACAGAAACA GACATGGATA CACAGCTACA TCTTTTCTGT
238051 CTGACATTAT TGTTCAATAC TTGGCTGAAG TACTCTTTCA TTTGTAAGGC
238101 TGGCTGATAA ATCAAGTGAG AGGCATGTAG CAATAATTGC ATTTAGCAAC
238151 ATGGGAGTGA TCACATGCTT TCAGTATGGT GGAACATGTG GGGTAAATAC
238201 ATGATTGAAT TAGTTTAAGA GTGAATGGGA GAAGATCATT GGAACAATGG
238251 GTGTAGAAAT TCTTTTGAGT TTAGCTGCAA AGCAAAGCAG TGAATAGAGA
238301 GTAAGGGTAG GGATAAGTGA AGTCAACAGG TCTCTTCAGT AAGAACATAT
238351 AAAGCATGTT TGTTTGCTGA TGGAAATGAG GAAAATAAGG AAAATGTTAA
238401 TGATATAAGA AAAACGAGAA TTACTGGAAA GGTGTCTGTG TGGGCAGAAG
238451 GTGAGATCTT TTGCTCAAAT GTAGCCATTG GTTTGAGATA AGAATACAGA
238501 TAATTTGTCC ATACTAACAG ATAATTTGTC CATAAGTTGT TCTTATAGGT
238551 TGTAAGGCAG AGTATATGGG TGTAGATGCT GGTAAATATA TAGTTGTGTT
238601 GGTGGGAGCC TGTGGCAAAT ATTTTCTAAC TGGTTTACCT TTTTCAGTGT
238651 AGTGGGAAGC AAGACTATTA GTTGGGAGTG AAGATAGGGC AGAAGGTATT
238701 AGAGGTCTGA GCAGAGAAGA GTAAGTGTAA AATAATCTTC TAGAAGAGTA
238751 GAGTGATTGG ACCATTGACT ATGTAAGTTG AGTAAGATTC CAGGCACCAT
238801 GTAGGGCTCA TTCAAGGTTT GGCTATGAAT AAAGTGACAT CAATTAATGG
238851 CTTTGTGCTG TAAATGAGCT GCCTTCAACA ACAGAAGGGC GAGGGAATTG
238901 GAGGCCTGTG TAAGGCAGTG ATTATAATTG AAACTGACAC TGAAGATGGG
238951 TAGAGTGGAA ATCAAGTGGT GAGGGGCCAA ATAAAATAAA ACAAAAATAA
239001 AATAGGTGAT TAAATCAATG GATTGTTGAT TTCAGTGGAT TTAAAGAATT
239051 ATCAGTTCAG AATTATAGAG GAAATGTAAA GGAAGTAAGC AAAAGTGGTT
239101 AGAAAAAAGT TGCATGAAAT TGAGATTCTT AATGATACGG AGTAATTGGT
239151 GATAGTAATG TCCAAGTTAT GATCTTGAGG GAGTGGCTGA AATTCTGAAA
239201 AACTAGATTA TTTAAGGAAA TATCTAAGTA ATTTAAGGAT TAAGTCTCAG
239251 GATATTAAAA TCAGCACAAA TTAAGATGGT AGCCTTGAAC CAAAGCTAGA
239301 CCATGAAAGT AAATGAGAGT AAATGACCCT CAGGTTAGTA GATTACGACA
239351 ACTGTGAGGG CTAGTGGATT TCACTGGTGA TACAGTATTT AAAGCTGTGG
239401 GCTTTTATAA GGAGGGAGAG AGAATAGTAA ATAAAGTGGA GCAATGAGGA
239451 GCAAGGACAA CACCTACCAC ACCTAAAGGC CTGGTTACTT GAGAGCTGTG
239501 GGGCAAAAAC AGACTGCCAC CATTTGGGGT GGCTGCAGGG GAACAAAAAC
239551 AGTGTTCTCA GGAAAGAGCC AGTTTGTAGT TAGAGCAAGA AGGTAAAGGA
239601 AACATTTAAA GCAAAGTCGA AGATTTAAAG TATTGTGCTG ACAGACTAAG
239651 GAATTTTGTT CAGAAGCTAA ACTAGAAATA TTTTCTAAAT ATATCCTCTT
239701 ATAGAAGATA ATGAAATTAT TTAGCATTTT TTTTTTTTTT TTTTTTTTTT
239751 TTTTGAGACG GAGTCTTGCT CTGTCGCCCA GGCTGGAGTG CAGTGGCGGG
239801 ATCTCGGCTC ACTGCAAGCT CCGCCTCCCG GGTTCACGCC ATTCTCCTGC
239851 CTCAGCCTCC CGAGTAGCTG GGACTACAGG CGCCCGCCAC TACGCCCGGC
239901 TAATTTTTTG TATTTTTAGT AGAGACGGGG TTTCACCGTT TTAGCCGGGA
239951 TGGTCTCGAT CTCCTGACCT CGTGATCCGC CCGCCTCGGC CTCCCAAAGT
240001 TATTTAGCAT TTTAATTGAA TAAATTTGAG TATAAAATCT GGTCACTTTT
240051 TGAACTGATA AAATTTGATG CTTCCCTTTT CAATATGTCA AAAATAACCT
240101 GGTAATTCAA AAAGGCTTTA TGATTTAATA AAAGTCATTT TAAGCACTGG
240151 AACATTTTCA TGTTCTTTCA TTTATTTTCA TTAAATTGAT ATCAGTGCAC
240201 TACTAAGCCA CATGTTTAAA ATATATGCAG TTTTGATATT ATAATAACAA
240251 ATTTTAGTGC ATAGGTTAAC ACTTGAATTG TTGTCTTTGG CTCTGTACTT
240301 AAATGTGAAC ATGATTGCAC GCTTGATAAA AAATAATCCA TAGCTATCTT
240351 CCACTTTTTG CAGGTCGCAT TTTGGATAAC AGCACAAAAG ACCTCAAGTT
240401 TGCATTCACT AACCTAACAC CATTTACAAT GTATGATGTC TATATTGCGG
240451 CTGAAACCAG TGCAGGGACT GGGCCCAAGT CAAATATTTC AGTATTCACT
240501 CCACCAGATG GTAAGAACAT AGGGAATGAG TGAGATATTT TTGGTATGCT
240551 TATGAACTTC ATGAATTGGT AAAACATGAT ATTAGAAGCA ATTTGTTTTA
240601 CATTTACTTA AATCATGTTA TTTCCTTATT AAATTACTAC CTAATTCATT
240651 CTGAACATGT GTTCTCCAGA ATGTTAAACT CATAGCATGC TTCATAATAA
240701 AAGGGACCCA AGATCAGGTA AGGTTAGGAA ATATCATATG TAGTATTGGC
240751 CTGTTAGAGA TTCACAATAA AATTTAGCAA AACCTCAAGA AGTCATAAGG
240801 TAAACAAACA CATTTAGTAT GGTTTAACTA CATTTTTAAA TGTGGAATCT
240851 ATTTTTTCTC ACAGAACTAG TATTTAGAAG AATTCCTATA CTCCCAATTC
240901 TTTCAACAAA ATATGTTTAT AATCAAAACG GGATTCTAAG CAAGTGAAGA
240951 TTCTGAGTGG ATGTATGATA TAGATTTACC AGCATTTACT GAAATTATGA
241001 AAACATTATT TTTCCTCAAG AAACTTCCTT ATAAGTATTC ATTAAACATC
241051 ATTGTTTTAG GTGAACTATA CTTTAAAAAG AATGTTTCCA TACTATTTCA
241101 CAACATATCT TTCAGGCCCA CACTGAACTT GCTAAATGTC TTAATTTCTA
241151 TTTAGGGATT GTAATTATGG ACAAAAATAA CAGTAAATTC TTATAACACA
241201 TTAACACTTG GAAAAGTTTC CAGACTTTGT TTGTGTGGAA GCTAACATAC
241251 AGTAACTTAT AAATGAAATG TAGACATGTA TACACACACA CACACTCACA
241301 CACACGCGCA CACACACACA CACACACACA CACAGGTCAT ACATTCATCG

FIGURE 3, page 68 of 87

241351 TTCAAGCGTT TGACCATTAG AGGGCAGTAA CTATTAGGAA ATTTTGTACT
241401 TCTACCCTTT AAAGAAACAA CCATTGATAT TTTTTTGAAA GAACATAAAA
241451 GTTACGTTTT ATCTATTTCA GATGAAAATC CTGACATATA TATAGTTTTA
241501 GAATACATAT AAGAAAGTTG TACATACTCA TAAGGAAAAT GTTCTTTTTT
241551 TGTATTAAAA TTTTACCTTT GTGTTTCTAT CAGAAGAATC CTAGCATTGT
241601 GTAGCTTCTT CCTTAAATCT TAAGTTTTCC TCCATCTCCA CCTAAAAACT
241651 GCTCTTAAGC ATGTCCTAGG AAACTAGACA GATTTATGGA CACTATCAAA
241701 TAAAGCAGAG CCCTTGATTT TGGTCTTAAT AGAGTTTTCT CAACCAACTC
241751 AATGTACCTA TTGATTTCTA TTCTTGTTAT ACAATTAAAT ACATCCTGAA
241801 CTATTGTCTT CTTTCAAGAC CAGCTGATTT TGGTGCTTCC AAATAGAATC
241851 CACAACTCAA TAAACATATT TTTATTGTCA TCATTCTTGG ACTACATCAT
241901 GTGACAAAAA TAGGGAAATA GATAATGCAT ATGCTGTGTA CAATGTCATG
241951 TTATTTGTCT TGGATTATTT TAAAATTTAC TTGCCTTAAT TTCTACATTT
242001 TTTATCCACA AAAGAAGTAG AATCTTCAGG TCATAGTTCA GTATATTTCA
242051 CAAGGCCTAT TTTTCACACC AAATCATTTT AAGTAGATGA CTCCATTTGC
242101 CCTCTATAAA AAGCAATTTG TCCTGTGTTT CATTCTGTTA TCTTCCTGAG
242151 TCACTCCTCC TATAGATCAC ACCCTGGTGG GTCTTAGAGG GGCCTCCTGG
242201 CAACTGGTGG GTTCCACCAA AGGCAGGGTT GGCATGGTTC TTATATCCTC
242251 ATGTCAGCCT TCATCCATGG AGTTCTCTTG GGATAGTTCA GCCACAGGAG
242301 CTGCCTCAAT GGAATACTCT GGCAAATGCA GTAAATGTAG CTTTCTACTT
242351 CTGACACCAC TAATTAATCC TGGTTTCAGT ATTTAAAACT TTGAAATAAA
242401 TGGATCTTTA AACTATATGA AAACAATGTG ATAACTCATT AGAACTATCT
242451 TTCAATTTAA AAATGATTTC TTAATTTTAT ATTATCCTTT TCATTAATAC
242501 AACAGGGTTT TTAGTATTCT AATTAAAGTT ACTTAATTTA ATTTCTTCTC
242551 CATATTTTAA ACCAGTCTAT CATCTATTTA AAAAATAATT AGGACTAGTT
242601 TGCTTCTTTT AAATTACCTT TTAAAACAAT TGGTGCTCTT ATAAATCTCC
242651 AGATACTCAT AGAAAAATGT TGCATTGACC TCTTATAGAG AATGTTATGT
242701 GCTATTACAT TACAGTGGAG TTGATTTCAT TACCCCTGGG GATGTTACGG
242751 TCCATAGTCT ACTTTGAAAG AAAATCAGCA TCCTATTATT TTAGCAGTTC
242801 TCTTATGTAT TTCCTAAGCC CTCTATATGT CTCTTAATAT TTTGATGAGT
242851 AGATTTCTGC ATAGGCATGA AAATAAATGA TTTTGGAAAA AAAAGATAAT
242901 AATCTCCAAA GCTATAAAAT GTCATAGAGT TGCCTATTCC AAAATCAGAT
242951 AATGCTGATG AATATAACAT AGGCAACAGC ATTCTTCTAA ATTGTGTGAG
243001 GGGTAAAAAA AATAAGCAGA CTGTGATGCT TCAATATTGT CTAACAACTT
243051 TTCTGTCAGG GTAGTTTAGC ATGACCATTT CTTAAAAGCA GACAAATTTC
243101 TGAGATTCTT GTTTACTCCC TCTTAAACAG ACTATGGCAG TGAAGACGTT
243151 TGTCCTCAGT GATTTAAACT TGTTACTTTC TGCAAATAGT AGTAAAATCT
243201 TTGCAGGAAA ATAACTGAGA GCCTGCCAAC TTTGTGTTTT CAGGATTTGC
243251 AATGGCTTTA ATTTTTACTA CTTGTTTTTC AAAATATACT TCTAAAGAAA
243301 CTTTAATTTG CTAGATAATG GCAAAAATGA TCTTAATGTA TTTTCTTTTA
243351 CCTCAATGCT GTTTGTCTCT ATTTCATTTC TTCTCATAGT TTTTCATTTG
243401 AACACTTCAA ATCATTTGGA ATATATTTTA ATAAATCATA TGCTATTGTG
243451 TTTCTAATGC ATTAGTAAAA TTTATAAATA TATTAACTCG AGAATAATTC
243501 TTAGGTAGTC CATGTATATA ACACCTTCAA AATTAAAATT ATTTTGCCAT
243551 TATCTAGAAA ATTCATCATC GAGCAGCATT AATTTTGAAG TTGGAGAAAA
243601 TGGCATTGGG GTAAAGAAAA TGTGAGATTT TTTTGGCCAA ATGTCTAACT
243651 TATTTCTCAT TTATTTGTAA AATTTGTAAA TGTATCGACT TGAGAATGAC
243701 TCTTAGGTAT TTCCTGTGGA CATCACCTTC AAAACTGATG CTGAACCATG
243751 AATAATTGAG TTGTGTGTTT GATTTTCTTT AGGTAATTTT GTATCAATAT
243801 TAAAGTCTTC TCTAGTTTCC CCATAAGAAT TTGTGGTCTA ACAGATCAAG
243851 TATCTTTTTA AAGACAAGAT ACAATGCTGT TGACTCCATT TCCTTTATCC
243901 CCTAAGCTTA AATAGGAAAA AAAAGATAAG TTTATAGTCA TTATTTTTAT
243951 GCAAGTTTGA GGTACATTTT AAGGTAATAT AGAACCACTT AATCTTTACC
244001 TGGATTGTAA TTTTTGGCAT TAAGTATCAT GGGGCAACAC TTACTAAGAA
244051 AGTAAGTATT GAATATATAG AATATATAGA AATATATATG CTAATTAAAA
244101 GATAAAAAAT AGTGTCTGCT ACTACTCTTG GTTTCACTAG CAAAATAAGA
244151 GACAGTAAAA TATATATAGT TTTCTGCTGT CCTGCATAAT ATTTGATATC
244201 TAACACATTA GTGTGTTGCG TTGACTTGAA CTGATCATTT CACTTATCTT
244251 TCAATAGGCA GGGTTTAGTT GCCTGATTAA TATGATCAAT GTAGTCATTA
244301 GCTGTTTTTT TTTTTTCAGT TGAGATTCTA CATCAGTTCA AAATAAATGG
244351 AAAAAGTGCC AGATCTCCTC TGACTTAAGT TATGCAATAC TGGCTATTGT
244401 TTTGTCTGCA TAAAAACTGC AAAATAAAAT TTTAAAAAGA GATGGAATAG
244451 GAGCTTTGCT ATTTAAATAG CCATGTTATT TTACACCACA CAATTAATTG
244501 GAAAGTTTCT CCACCCTTGA AAAATGCATA TTGGTAAATT GCATATTGGT
244551 AAATATGATG ATGCAAACAT GAGCTCTAGG TACAATATAT TTTAGTGAAA
244601 TAAAACTCAT ACTAGAGGTG ACCTGTGCAA AGGGCTTTAT CTGTCTTATT
244651 CCTTCCTCTG TCCTCAAGTG CCTAGAACAG TGATCATATG ATCAATGCTC
244701 AGTGTGTTGA ATGATGAATG AATGGCCCAA CGATTGTCAC AATATCTAGG
244751 GAGTCTTTAC CGGTTACTTC ATGAAGACAA AGGAAAAAAC TCAATCTATT
244801 GGATGAAAAC TTTGTATAGT CATAGTTACT ATAAAGCCAA CTTAAGCATA
244851 ATTATATTTG CTCATTATAA ATAACATATA TGGGAGTTAT AAAATTATTT

FIGURE 3, page 69 of 87

244901 TTCAATTCCT TTCTGTTGTC TTAAAAAGAA AGGGGGTCAT TTTTCCTTTG
244951 TTCCCTTTTA AGACTATATG CCTGTCTTCT AACTAGAATT TGCTAAACCT
245001 GTACCGCTGC CAGAGAGTTT AGGGAAATTA ACTGAAAGTG TAACAACAAT
245051 CTGATAATAA GGGATCATAA TTTTATGCCA TTTTCTCTTT CTTAAAAGTT
245101 TTAGAAATTT GAGAAATTTT CTTGAACTCT TTGTTCCTTA TAGTAACCTG
245151 TATAGTAATA GGAAAGCTAT AATGACACCC ATTTTATAGA TAAGGAAAGT
245201 AGAGGTTGGA GGGATGCATG AGCTATTCAT AATCACAAGT TGAACTGTAA
245251 ATAAAAATGA TCAAAAGCCC AGGGGATATT TGTTTTTTGC CCGTTACTCC
245301 TGTGAAACTG GGAAGTTCCC TAGATGTCAC TCTTAGTGAC TTTACAACTA
245351 GAACTTGCTT TAAGTTCTTG GTACTTTATT TTAAACCAAT TGTTAGTTTG
245401 TTCCTATTTT TATTTACTAT TGCAATGAGT GAGGGCACCT GAAATTTGAA
245451 AATAACATGA TTATTTTTAA AATATCAGAA AAAAATCAAT CAACTCTTCA
245501 AACAATTTCA TGTAATAAAT TAAAACGCAG TCTAATTTAA CTTACCAACT
245551 ATATTTAATT GCATTCAGAG TCTTCTGGAT ATTAATTTTC AATCTGTTGT
245601 TATAATTTTT ATGAAACCAT CAAGATTTCA ACTGGCATTA ATTATCACCA
245651 AATAGGCAGA TTCTCAAGAA AATTATTTTT ATTAATTAAT TTGTTTCAAA
245701 CAAATGTTAT GACTTTTATT TTGGAAAATT ATTCTGTTAT TCTGCTCCTT
245751 ACTTACATTT CGAGAACAAT GTTTAGAAAT TTAGGCAAGA TGGCCGAATA
245801 GGAACAGCTC CAGTCTACAG CTCCCAGCGT GAACGACGCA GAAGACGGGT
245851 GATTTCTGCA TTTCCATCTG AGGTACCGGG TTCATCTCAC TAGGGCCAGA
245901 CAGTGGGCGC AGGTCAGTGG GTGTGCGCAC CGTGTGCGAG CCGAAGCAGG
245951 GCGAGGCATT GCCTCACTCG GGAAGCGCAA GGGGTCAGGG AGTTCCCTTT
246001 CCCCTTGTCA AAGAAAGGGG TGATGGACGG CACCTGGAAA ATCGGGTCAC
246051 TCCGACCCGA ATACTGCGCT TTTCTGACGG GCTTAAAAAA CGGCGCACCA
246101 CGAGATTATA TCCCACACCT GGCTCAGAGG GTCCTACGCC CACGGAGTCT
246151 CGCTGATTGC TAGTACAGCA GTCTGAGATC AAACTGCAAG GCGGCAGCGA
246201 AGCTGGGTGA GGGGCGCCCG CCATTGCCCA GGCTTGCTTA GGTAAACAAA
246251 GCAGCCTGGA AGCTCCAACT GGGTGGAGCC CACAACAGCT ACAAGGAGGC
246301 CTGCTTGCTC TGTAGGNNNN NNNNNNNNNN NNNNNNNNNN NNNNNNNNNN
246351 NNNNNNNNNN NNNNNNNNNN NNNNNNNNNN NNNNNNNNNN NNNNNNNNNN
246401 NNNNNNNNNN NNNNNNNNNN NNNNNNNNNN NNNNNNNNNN NNNNNNNNNN
246451 NNNNNNNNNN NNNNNNNNNN NNNNNNNNNN NNNNNNNNNN NNNNNNNNNN
246501 NNNNNNNNNN NNNNNNNNNN NNNNNNNNNN NNNNNNNNNN NNNNNNNNNN
246551 NNNNNNNNNN NNNNNNNNNN NNNNNNNNNN NNNNNNNNNN NNNNNNNNNN
246601 NNNNNNNNNN NNNNNNNNNN NNNNNNNNNN NNNNNNNNNN NNNNNNNNNN
246651 NNNNNNNNNN NNNNNNNNNN NNNNNNNNNN NNNNNNNNNN NNNNNNNNNN
246701 NNNNNNNNNN NNNNNNNNNN NNNNNNNNNN NNNNNNNNNN NNNNNNNNNN
246751 NNNNNNNNNN NNNNNNNNNN NNNNNNNNNN NNNNNNNNNN NNNNNNNNNN
246801 NNNNNNNNNN NNNNNNNNNN NNNNNNNNNN NNNNNNNNNN NNNNNNNNNN
246851 NNNNNNNNNN NNNNNNNNNN NNNNNNNNNN NNNNNNNNNN NNNNNNNNNN
246901 NNNNNNNNNN NNNNNNNNNN NNNNNNNNNN NNNNNNNNNN NNNNNNNNNN
246951 NNNNNNNNNN NNNNNNNNNN NNNNNNNNNN NNNNNNNNNN NNNNNNNNNN
247001 NNNNNNNNNN NNNNNNNNNN NNNNNNNNNN NNNNNNNNNN NNNNNNNNNN
247051 NNNNNNNNNN NNNNNNNNNN NNNNNNNNNN NNNNNNNNNN NNNNNNNNNN
247101 NNNNNNNNNN NNNNNNNNNN NNNNNNNNNN NNNNNNNNNN NNNNNNNNNN
247151 NNNNNNNNNN NNNNNNNNNN NNNNNNNNNN NNNNNNNNNN NNNNNNNNNN
247201 NNNNNNNNNN NNNNNNNNNN NNNNNNNNNN NNNNNNNNNN NNNNNNNNNN
247251 NNNNNNNNNN NNNNNNNNNN NNNNNNNNNN NNNNNNNNNN NNNNNNNNNN
247301 NNNNNNNNNN NNNNNNNNNN NNNNNNNNNN NNNNNNNNNN NNNNNNNNNN
247351 NNNNNNNNNN NNNNNNNNNN NNNNNNNNNN NNNNNNNNNN NNNNNNNNNN
247401 NNNNNNNNNN NNNNNNNNNN NNNNNNNNNN NNNNNNNNNN NNNNNNNNNN
247451 NNNNNNNNNN NNNNNNNNNN NNNNNNNNNN NNNNNNNNNN NNNNNNNNNN
247501 NNNNNNNNNN NNNNNNNNNN NNNNNNNNNN NNNNNNNNNN NNNNNNNNNN
247551 NNNNNNNNNN NNNNNNNNNN NNNNNNNNNN NNNNNNNNNN NNNNNNNNNN
247601 NNNNNNNNNN NNNNNNNNNN NNNNNNNNNN NNNNNNNNNN NNNNNNNNNN
247651 NNNNNNNNNN NNNNNNNNNN NNNNNNNNNN NNNNNNNNNN NNNNNNNNNN
247701 NNNNNNNNNN NNNNNNNNNN NNNNNNNNNN NNNNNNNNNN NNNNNNNNNN
247751 NNNNNNNNNN NNNNNNNNNN NNNNNNNNNN NNNNNNNNNN NNNNNNNNNN
247801 NNNNNNNNNN NNNNNNNNNN NNNNNNNNNN NNNNNNNNNN NNNNNNNNNN
247851 NNNNNNNNNN NNNNNNNNNN NNNNNNNNNN NNNNNNNNNN NNNNNNNNNN
247901 NNNNNNNNNN NNNNNNNNNN NNNNNNNNNN NNNNNNNNNN NNNNNNNNNN
247951 NNNNNNNNNN NNNNNNNNNN NNNNNNNNNN NNNNNNNNNN NNNNNNNNNN
248001 NNNNNNNNNN NNNNNNNNNN NNNNNNNNNN NNNNNNNNNN NNNNNNNNNN
248051 NNNNNNNNNN NNNNNNNNNN NNNNNNNNNN NNNNNNNNNN NNNNNNNNNN
248101 NNNNNNNNNN NNNNNNNNNN NNNNNNNNNN NNNNNNNNNN NNNNNNNNNN
248151 NNNNNNNNNN NNNNNNNNNN NNNNNNNNNN NNNNNNNNNN NNNNNNNNNN
248201 NNNNNNNNNN NNNNNNNNNN NNNNNNNNNN NNNNNNNNNN NNNNNNNNNN
248251 NNNNNNNNNN NNNNNNNNNN NNNNNNNNNN NNNNNNNNNN NNNNNNNNNN
248301 NNNNNNNNNN NNNNNNNNNN NNNNNNNNNN NNNNNNNNNN NNNNNNNNNN
248351 NNNNNNNNNN NNNNNNNNNN NNNNNNNNNN NNNNNNNNNN NNNNNNNNNN
248401 NNNNNNNNNN NNNNNNNNNN NNNNNNNNNN NNNNNNNNNN NNNNNNNNNN

FIGURE 3, page 70 of 87

```
248451 NNNNNNNNNN NNNNNNNNNN NNNNNNNNNN NNNNNNNNNN NNNNNNNNNN
248501 NNNNNNNNNN NNNNNNNNNN NNNNNNNNNN NNNNNNNNNN NNNNNNNNNN
248551 NNNNNNNNNN NNNNNNNNNN NNNNNNNNNN NNNNNNNNNN NNNNNNNNNN
248601 NNNNNNNNNN NNNNNNNNNN NNNNNNNNNN NNNNNNNNNN NNNNNNNNNN
248651 NNNNNNNNNN NNNNNNNNNN NNNNNNNNNN NNNNNNNNNN NNNNNNNNNN
248701 NNNNNNNNNN NNNNNNNNNN NNNNNNNNNN NNNNNNNNNN NNNNNNNNNN
248751 NNNNNNNNNN NNNNNNNNNN NNNNNNNNNN NNNNNNNNNN NNNNNNNNNN
248801 NNNNNNNNNN NNNNNNNNNN NNNNNNNNNN NNNNNNNNNN NNNNNNNNNN
248851 NNNNNNNNNN NNNNNNNNNN NNNNNNNNNN NNNNNNNNNN NNNNNNNNNN
248901 NNNNNNNNNN NNNNNNNNNN NNNNNNNNNN NNNNNNNNNN NNNNNNNNNN
248951 NNNNNNNNNN NNNNNNNNNN NNNNNNNNNN NNNNNNNNNN NNNNNNNNNN
249001 NNNNNNNNNN NNNNNNNNNN NNNNNNNNNN NNNNNNNNNN NNNNNNNNNN
249051 NNNNNNNNNN NNNNNNNNNN NNNNNNNNNN NNNNNNNNNN NNNNNNNNNN
249101 NNNNNNNNNN NNNNNNNNNN NNNNNNNNNN NNNNNNNNNN NNNNNNNNNN
249151 NNNNNNNNNN NNNNNNNNNN NNNNNNNNNN NNNNNNNNNN NNNNNNNNNN
249201 NNNNNNNNNN NNNNNNNNNN NNNNNNNNNN NNNNNNNNNN NNNNNNNNNN
249251 NNNNNNNNNN NNNNNNNNNN NNNNNNNNNN NNNNNNNNNN NNNNNNNNNN
249301 NNNNNNNNNN NNNNNNNNNN NNNNNNNNNN NNNNNNNNNN NNNNNNNNNN
249351 NNNNNNNNNN NNNNNNNNNN NNNNNNNNNN NNNNNNNNNN NNNNNNNNNN
249401 NNNNNNNNNN NNNNNNNNNN NNNNNNNNNN NNNNNNNNNN NNNNNNNNNN
249451 NNNNNNNNNN NNNNNNNNNN NNNNNNNNNN NNNNNNNNNN NNNNNNNNNN
249501 NNNNNNNNNN NNNNNNNNNN NNNNNNNNNN NNNNNNNNNN NNNNNNNNNN
249551 NNNNNNNNNN NNNNNNNNNN NNNNNNNNNN NNNNNNNNNN NNNNNNNNNN
249601 NNNNNNNNNN NNNNNNNNNN NNNNNNNNNN NNNNNNNNNN NNNNNNNNNN
249651 NNNNNNNNNN NNNNNNNNNN NNNNNNNNNN NNNNNNNNNN NNNNNNNNNN
249701 NNNNNNNNNN NNNNNNNNNN NNNNNNNNNN NNNNNNNNNN NNNNNNNNNN
249751 NNNNNNNNNN NNNNNNNNNN NNNNNNNNNN NNNNNNNNNN NNNNNNNNNN
249801 NNNNNNNNNN NNNNNNNNNN NNNNNNNNNN NNNNNNNNNN NNNNNNNNNN
249851 NNNNNNNNNN NNNNNNNNNN NNNNNNNNNN NNNNNNNNNN NNNNNNNNNN
249901 NNNNNNNNNN NNNNNNNNNN NNNNNNNNNN NNNNNNNNNN NNNNNNNNNN
249951 NNNNNNNNNN NNNNNNNNNN NNNNNNNNNN NNNNNNNNNN NNNNNNNNNN
250001 NNNNNNNNNN NNNNNNNNNN NNNNNNNNNN NNNNNNNNNN NNNNNNNNNN
250051 NNNNNNNNNN NNNNNNNNNN NNNNNNNNNN NNNNNNNNNN NNNNNNNNNN
250101 NNNNNNNNNN NNNNNNNNNN NNNNNNNNNN NNNNNNNNNN NNNNNNNNNN
250151 NNNNNNNNNN NNNNNNNNNN NNNNNNNNNN NNNNNNNNNN NNNNNNNNNN
250201 NNNNNNNNNN NNNNNNNNNN NNNNNNNNNN NNNNNNNNNN NNNNNNNNNN
250251 NNNNNNNNNN NNNNNNNNNN NNNNNNNNNN NNNNNNNNNN NNNNNNNNNN
250301 NNNNNNNNNN NNNNNNNNNN NNNNNNNNNN NNNNNNNNNN NNNNNNNNNN
250351 NNNNNNNNNN NNNNNNNNNN NNNNNNNNNN NNNNNNNNNN NNNNNNNNNN
250401 NNNNNNNNNN NNNNNNNNNN NNNNNNNNNN NNNNNNNNNN NNNNNNNNNN
250451 NNNNNNNNNN NNNNNNNNNN NNNNNNNNNN NNNNNNNNNN NNNNNNNNNN
250501 NNNNNNNNNN NNNNNNNNNN NNNNNNNNNN NNNNNNNNNN NNNNNNNNNN
250551 NNNNNNNNNN NNNNNNNNNN NNNNNNNNNN NNNNNNNNNN NNNNNNNNNN
250601 NNNNNNNNNN NNNNNNNNNN NNNNNNNNNN NNNNNNNNNN NNNNNNNNNN
250651 NNNNNNNNNN NNNNNNNNNN NNNNNNNNNN NNNNNNNNNN NNNNNNNNNN
250701 NNNNNNNNNN NNNNNNNNNN NNNNNNNNNN NNNNNNNNNN NNNNNNNNNN
250751 NNNNNNNNNN NNNNNNNNNN NNNNNNNNNN NNNNNNNNNN NNNNNNNNNN
250801 NNNNNNNNNN NNNNNNNNNN NNNNNNNNNN NNNNNNNNNN NNNNNNNNNN
250851 NNNNNNNNNN NNNNNNNNNN NNNNNNNNNN NNNNNNNNNN NNNNNNNNNN
250901 NNNNNNNNNN NNNNNNNNNN NNNNNNNNNN NNNNNNNNNN NNNNNNNNNN
250951 NNNNNNNNNN NNNNNNNNNN NNNNNNNNNN NNNNNNNNNN NNNNNNNNNN
251001 NNNNNNNNNN NNNNNNNNNN NNNNNNNNNN NNNNNNNNNN NNNNNNNNNN
251051 NNNNNNNNNN NNNNNNNNNN NNNNNNNNNN NNNNNNNNNN NNNNNNNNNN
251101 NNNNNNNNNN NNNNNNNNNN NNNNNNNNNN NNNNNNNNNN NNNNNNNNNN
251151 NNNNNNNNNN NNNNNNNNNN NNNNNNNNNN NNNNNNNNNN NNNNNNNNNN
251201 NNNNNNNNNN NNNNNNNNNN NNNNNNNNNN NNNNNNNNNN NNNNNNNNNN
251251 NNNNNNNNNN NNNNNNNNNN NNNNNNNNNN NNNNNNNNNN NNNNNNNNNN
251301 NNNNNNNNNN NNNNNNNNNN NNNNNNNNNN NNNNNNNNNN NNNNNNNNNN
251351 NNNNNNNNNN NNNNNNNNNN NNNNNNNNNN NNNNNNNNNN NNNNNNNNNN
251401 NNNNNNNNNN NNNNNNNNNN NNNNNNNNNN NNNNNNNNNN NNNNNNNNNN
251451 NNNNNNNNNN NNNNNNNNNN NNNNNNNNNN NNNNNNNNNN NNNNNNNCAT
251501 GTATACATAT GTAACTAACC TGCACAATGT GCACATGTAC CCTAAAACTT
251551 AAAGTATAAT AATAAAAGGA AAAAAAGAAA TTTAGTATTA AATATCCATG
251601 TATTTAAAGA CATTTAATTT AACAAAAATT TATTATACTT TCAGTTCTGG
251651 GGTACATGTG CAGAACGTAT AGGTTTGTTA CATAGGTATA CATGTGTCAT
251701 GGTGGTTTAC TGCACCCATC AAAGTGTCAT CTACATTAGG TACTTCTCCT
251751 AATGCTATCC CTCCCCTAGC CCCCCACCCA CCGACAGGCC CCGGTGTATG
251801 ATGTTCCTCT CCCTGTGTCC ATGTGTTCTC ATTGTTCAGC TCCCTCTTAT
251851 GAGTGTGAAC ATGCGGTGTT TGGTTTTTTG TCCTTGTGAT AGTTTGCTGA
251901 GAATGATGGT TTCCAGCTTT ATCCATGTCC CTGCAAAGGA CATGACCTCA
251951 TCCTTTTTTT AAGACTTATT TAATTTTTAA CAAAATAAAT TGTTTTTGTC
```

FIGURE 3, page 71 of 87

252001 TATTTTCTTT CTTTCTTGTT TTTTGTTTGT TTGTTTGTTT GTTTGTTTGT
252051 TTTTTGATGG AGTCTCGCTC TTTCTTCCAG GCTGGAGTGC AGTGGTGTAA
252101 TCTCCACTCA CTGTAACCTC CGCCTCTTGG GTTCAAGCAA TTCTCCTGCC
252151 TCAGCCTCCT GAGTAGCTGG GATTACAGGC ACGCACCACC ATGCCTGGCT
252201 AATTTTTGTA TTTTTTAGTA GAGATGGGGT TTCACCATGT TGGTCAGGCT
252251 GGTCTCGAAC TCCTTACCTC AGGTGATTGG CCTCCCTTGG CCTCCCAAAG
252301 TGCTGGGATT ACAGCCATGA GCCACCGCAC CTAGCCTAGT CTGTTTTCTA
252351 ATAGAATTGT TTATATATCT TAAATTGTGA ACTAAGAATT TAGACACTTT
252401 TTTCACTTGA AAAAATATTT TTAAATTCCC CCTTTTTCCT TTTCTTTCTT
252451 TCTTTCTTTC TTAGTTCCAG GGGCAGTGTT TGATTTACAA CTTGCAGAGG
252501 TAGAATCCAC GCAAGTAAGA ATTACTTGGA AGAAACCACG ACAACCAAAT
252551 GGAATTATTA ACCAATACCG AGTGAAAGTG CTAGTTCCAG AGACAGGAAT
252601 AATTTTGGAA AATACTTTGC TCACTGGAAA TAATGAGGTA TTGCATTTTT
252651 ATTTCACTTA TTGGTGAACC CTTTCTGCTT GGTTCTGGCT CTGATAGCTT
252701 GGAAGATTTG CTAGCACCCA CACATGTAAT ATTTGACCAC TTACTAGTAC
252751 AAAGTAAAGT AAATTTGGGG CATGTTGATA ATCTAGCTAG ATCATATTTC
252801 ATTTTAGGTT ATATATTATT AGTTAAGTGC TATTATTCCT TTTCATCATA
252851 TGAAAAAATGT TAATTGTGCA ATTAAACAGG ACTAAAGGTA TTTTCATAAG
252901 TTAATATTAT TTTTCTAAAT TAGTTAATGA ATTGTTCGGA AACTCTTGTT
252951 ATGATTTAAG TGCTCCTTCA AAGGCTGTGC TTGCAATTTG GAACAGTTGC
253001 CAGTGAAAGG CACAGTAACT TTAGTAGCTG TTGTTGACAA ATGATTCTGT
253051 TCTATTTGGT CTTGGGAAGC TAAATTTCTC AAAGCTGCCT CTTTTTTTTT
253101 TTCAAAGTAC ATTTGATTAA GAGTCACATT ACTAAATAAA AGAAATTTAA
253151 GTCGTTTCAT AGATTTTAAA TAAGAGGACC AGGATCTTTA GGCAATGTGT
253201 TTGCTTCTAT TCACACTGGA AGTCTTATTT TTTTCCTTTT GTTTCTGTTA
253251 GGAAGTACAG GCAACACTGA TTTTTCTTTC CACTGTCTTT GTTCACCTCA
253301 CTTCATCAAC TGTTCACCTG TGAGACTCTT TCAGCCTCCA GGCTAGTCAT
253351 GTCCAGATAC TGGCTGCTCC CCGGGGCATT CAAAGAATAA ACTTCCTTAG
253401 GACCAGTGCA GCAATCACTG GGCCTTAAAG ACAAACACGA TAGTTATTCA
253451 GCACCTGGCG TCTGCTGTGT TGTTTCAGAA TTGCTGCTGC TTCTACCTGT
253501 GCTGTTATTT TCCCCCACAC ATGCTTTCAT TCTATTTCTA GTCCCAGCCT
253551 TCCTCTATTT CTGGCACTTA CCTGTATGTG ACAGTTGACC TCACCATGTG
253601 CTCAATGCAT TCTGGCCACC CAGGACTTAT CACTCCAAGT TGCTCACCAT
253651 CTTCAACCCA GGGTTAAATT TTAATCCTAT GTTGATTCCT TTCCTCTGTG
253701 CAAAAGATGT TGAATTATGC TTTCTGTGAT ACTCTGGTTG ACAACTCAGG
253751 CAAAGGGCAA AAGCTTAACC CTTTGCTCCT GCTGAGAAGG TCTTAAATTA
253801 GATACTGAGC TTTCCTAGTA CTAGATGACA GGTTTCCCAC TTCTGCTAAT
253851 GACATCTGTT GAATGGGTGG CCACACCTGT TTTTCCATGA AGCTAAGAGG
253901 TTCTAGAAAG GCTTTTTTTT TGTGATTCTG TCTCTATCTG GTCTGCAATT
253951 CTCGTCTCAT AGTAGAGAGC TCATGAGCTT TGGAGACGTA CAAATTTGGA
254001 TTTAAATTAT GATTTTGTCT CTCACTGTGC TATATAGCAA GTGGTTAAGA
254051 CTGTAAACCA GGTTTAAACT CTAGTTCTGC CATTACTAAC TGTTTAACCC
254101 TGGAAAAGTT GGCCTGAGCT CTCTGAACAT CAGTTTCTTC TTCTCTAAGA
254151 TAGTGATTAT AAGTCCCTAT AACAAAGGGT TAATAATGAG AATTTAATGG
254201 GTTCATGTGT GTAAAGAGCT TAGAACTGTA CCTGGCATAT AGTAAGTGCT
254251 GTGCTAAATA ATTGTGACCT ATTGTGATCA TTAATCTTGG CATAGGATCA
254301 TCCACCTTAG TTGCTACCCA ATATTACTTC CCTTATACTC TCTCAATGAA
254351 AGGAGACATT ATGCTT
(SEQ ID NO: 3)

FEATURES:

Exon: 1985-2162
Intron: 2163-2879
Exon: 2880-3025
Intron: 3026-7759
Exon: 7760-7928
Intron: 7929-9538
Exon: 9539-9829
Intron: 9830-10072
Exon: 10073-10348
Intron: 10349-10714
Exon: 10715-10866
Intron: 10867-14541
Exon: 14542-14683
Intron: 14684-17531
Exon: 17532-17801
Intron: 17802-25894
Exon: 25895-25913
Intron: 25914-32704
Exon: 32705-32751
Intron: 32752-38464

| | |
|---|---|
| Exon: | 38465-38537 |
| Intron: | 38538-50608 |
| Exon: | 50609-50647 |
| Intron: | 50648-52767 |
| Exon: | 52768-52863 |
| Intron: | 52864-65210 |
| Exon: | 65211-65257 |
| Intron: | 65258-71845 |
| Exon: | 71846-71967 |
| Intron: | 71968-74327 |
| Exon: | 74328-74331 |
| Intron: | 74332-77230 |
| Exon: | 77231-77413 |
| Intron: | 77414-80379 |
| Exon: | 80380-80624 |
| Intron: | 80625-82987 |
| Exon: | 82988-83054 |
| Intron: | 83055-86199 |
| Exon: | 86200-86358 |
| Intron: | 86359-86969 |
| Exon: | 86970-87192 |
| Intron: | 87193-88876 |
| Exon: | 88877-88950 |
| Intron: | 88951-98823 |
| Exon: | 98824-98923 |
| Intron: | 98924-101576 |
| Exon: | 101577-101705 |
| Intron: | 101706-116163 |
| Exon: | 116164-116245 |
| Intron: | 116246-119319 |
| Exon: | 119320-119410 |
| Intron: | 119411-120716 |
| Exon: | 120717-120722 |
| Intron: | 120723-124462 |
| Exon: | 124463-124539 |
| Intron: | 124540-135466 |
| Exon: | 135467-135601 |
| Intron: | 135602-135798 |
| Exon: | 135799-135924 |
| Intron: | 135925-136803 |
| Exon: | 136804-136953 |
| Intron: | 136954-139371 |
| Exon: | 139372-139507 |
| Intron: | 139508-145261 |
| Exon: | 145262-145385 |
| Intron: | 145386-145645 |
| Exon: | 145646-145679 |
| Intron: | 145680-228018 |
| Exon: | 228019-228019 |
| Intron: | 228020-228018 |
| Exon: | 228019-228019 |

SNPs:

| DNA Position | Major | Minor | Domain | Protein Position | Major | Minor |
|---|---|---|---|---|---|---|
| 36 | - | T | Beyond ORF(5') | | | |
| 1414 | A | C G | Beyond ORF(5') | | | |
| 1743 | T | C | Beyond ORF(5') | | | |
| 2766 | T | A | Intron | | | |
| 3155 | C | T | Intron | | | |
| 5816 | G | A | Intron | | | |
| 6074 | C | T | Intron | | | |
| 9550 | T | C | Exon | 169 | S | P |
| 9644 | A | G | Exon | 200 | E | G |
| 16630 | T | G | Intron | | | |
| 17957 | G | A | Intron | | | |
| 18299 | T | G | Intron | | | |
| 23521 | C | G | Intron | | | |

FIGURE 3, page 73 of 87

| | | | | | | |
|---|---|---|---|---|---|---|
| 28463 | C | A | Intron | | | |
| 35221 | C | T | Intron | | | |
| 41813 | A | G | Intron | | | |
| 41957 | C | T | Intron | | | |
| 42599 | G | T | Intron | | | |
| 47819 | G | A | Intron | | | |
| 51990 | - | A | Intron | | | |
| 51992 | - | T A | Intron | | | |
| 52788 | T | A | Exon | 608 | V | E |
| 59029 | A | C | Intron | | | |
| 60776 | C | T | Intron | | | |
| 61193 | A | G | Intron | | | |
| 62994 | C | T | Intron | | | |
| 63244 | T | C | Intron | | | |
| 65053 | A | T | Intron | | | |
| 68460 | C | A | Intron | | | |
| 69326 | A | G | Intron | | | |
| 73039 | C | G | Intron | | | |
| 73084 | A | G | Intron | | | |
| 75205 | G | A | Intron | | | |
| 75491 | A | C | Intron | | | |
| 75962 | A | T | Intron | | | |
| 82853 | T | A | Intron | | | |
| 82930 | T | C | Intron | | | |
| 88505 | T | C | Intron | | | |
| 95970 | - | A C | Intron | | | |
| 96524 | C | T | Intron | | | |
| 100868 | G | A | Intron | | | |
| 102246 | A | G | Intron | | | |
| 107335 | T | C | Intron | | | |
| 107921 | C | T | Intron | | | |
| 110413 | T | G | Intron | | | |
| 111600 | A | G | Intron | | | |
| 114518 | G | C | Intron | | | |
| 114614 | C | T | Intron | | | |
| 124669 | G | A | Intron | | | |
| 125409 | G | A | Intron | | | |
| 129447 | C | A | Intron | | | |
| 135139 | A | G | Intron | | | |
| 148111 | A | T | Intron | | | |
| 200822 | T | G | Intron | | | |
| 207967 | A | G | Intron | | | |
| 213624 | A | C | Intron | | | |
| 215753 | A | G | Intron | | | |
| 216081 | T | A | Intron | | | |
| 218692 | G | T | Intron | | | |
| 218705 | T | G | Intron | | | |
| 218754 | G | C | Intron | | | |
| 218852 | C | T | Intron | | | |
| 219261 | T | C | Intron | | | |
| 219359 | - | T | Intron | | | |
| 219362 | - | A T | Intron | | | |
| 220577 | G | T | Intron | | | |
| 220995 | C | T | Intron | | | |
| 225263 | C | T | Intron | | | |
| 226704 | G | A | Intron | | | |
| 228390 | T | A | Beyond ORF(3') | | | |
| 228472 | G | T | Beyond ORF(3') | | | |
| 229014 | A | C | Beyond ORF(3') | | | |
| 229585 | C | T | Beyond ORF(3') | | | |
| 237335 | T | G | Beyond ORF(3') | | | |
| 237771 | T | G | Beyond ORF(3') | | | |
| 239304 | T | C | Beyond ORF(3') | | | |
| 239767 | C | T | Beyond ORF(3') | | | |

Context:

DNA
Position

FIGURE 3, page 74 of 87

36 CATTATCTATGGAACATAATCTGAGGCTTTTTTT
[-,T]
ACAGTTGGTAGATACTTATGTACAAGATTTTGCTGTGAAAATCAGGGCAAGAAGGTAGTG
ATGCAAGGTAGCAGATAACATTGAAATACATTTTTGAAAATAATTTTTAAAATTGATGTA
ATGCAATTAGATTACTTGAGCTAATAGCATAGCTTTATTTTATTTTATTTATTTTTATTTT
ATTTATTTTTTTGAGACACAGTCTTGCTCTGTTGCCCAGGCTGGAGTGCAGTTGCCGATA
TTGGCTCACTTCAGCCTCCGCCTCCTGAGCTCAAGCAATTCTCGTGCCTCAGCCTCCTGA

1414 TCTTTAATAACTAACTTTATTATTCCTAAAATATAAATAAAAAATAATGCACATTTTTCA
GCATCACTATACACATGTTCATTTTTTGGTTTTAGATATTAATCTATACCCAGTTCAAAC
TGTGGAAACTGAACTAACATGACTGAAATAAAATAGTGTTATATTTTGTTCTTTAGACTC
TTTTTTCCCTTCCTGAGATTTTGATATGTATTTGGAGAGTTTTGAGTCAATATTTATTTG
ATTTGTTTTCTTTTCTGGAGTGATATTGTAAATACTTTAAAGATTTTGATTGAGTGAGAG
[A,C,G]
TGTGAGCTATATTTTCTTCTTTCCTGTATGATATACATACATTGTTTCCAATCTAATTTC
TATTAAATAACTATAGGAGAGCCCACAGCCTTGTTATTTTACATATCACTATTTAGATAT
TTGTTATTTATTTATTTGTGTTGGCCTGAAGTAAATGTTACTTTTGTACGATATTTGAAG
GATAGATTTATTTTATAAATTAATAGTTTAAATAAGATTTTGCCAGCATTTGAAATGAAC
AAATGTTTGGACAATGAAAACATCAGTATGAAAGGGAATACTGTAATTACTTTAGTACAT

1743 TGATATACATACATTGTTTCCAATCTAATTTCTATTAAATAACTATAGGAGAGCCCACAG
CCTTGTTATTTTACATATCACTATTTAGATATTTGTTATTTATTTATTTGTGTTGGCCTG
AAGTAAATGTTACTTTTGTACGATATTTGAAGGATAGATTTATTTTATAAATTAATAGTT
TAAATAAGATTTTGCCAGCATTTGAAATGAACAAATGTTTGGACAATGAAAACATCAGTA
TGAAAGGGAATACTGTAATTACTTTAGTACATAGTATTCCTTAATATCCATTAAAATTGG
[T,C]
CCAAGCAAACTCTAATTATGAACATCATATTAACATTTGATCTAATTACTGAATATAATT
AAAAGCAAAATAAGTTAATTTACTAAAGAATTCTGAAATTTACTATTTTCAGTATTTCAG
GATAACCAACATCTTTTTTCTATTAATCTAGAATAAATTTCCATATATTAATGTTGTTTA
CTTTTAATGTTAGTGTGCTCAAAAAGTATTGTTAACTTTTAAAATTCAATTCTACAGATA
ATATTCTTTTTATCTCAGGAATAGATCATCATTAAAAACTATTAATGTCACTGAAACATC

2766 ATTTTATGTGTTTATTAAACGAAACAACATAAAATGCATGAATCATTTGTCTATGACTTT
TATTATTCAATATAAAAATTCTAAGTTATATTAGAATTTCAAATTATGTATTTTGTATTG
GAAACCTGTTATAATATTGTTCTCATATCCAGAGCAGTGGACAGGTTTTAGAACGGAGAT
AGTATTTTATGGGTAAGAAATCTATCTGTCTTCAGCTTGAATATGCCTATAATAAAGTAT
TAGAGGGGTGACCCAATGTGTTTTATGGATTTCATTTCTGACATTTCTAATTCAAGCTTT
[T,A]
TTGAAAAACATTTTTTATCACTTTAATTTATAAACTGTAGGTAAAATTCAGGCCATTTCA
GACATTACTTGTAAACACAAATACAGTAATTTGTTCAATTATTTGTTTTATAGCACCAAG
CGATCCTCCCAAAGATGTTTATTATGCAAACCTCAGTTCTTCATCAATAATTCTTTTCTG
GACACCTCCTTCAAAACCTAATGGGATTATACAATATTACTCTGTTTATTACAGAAATAC
TTCAGGTACTTTTATGCAGGTAAGAACTGAATTTTCTTCTAGTTCTTTATTAACATCCTT

3155 ATTTGTTCAATTATTTGTTTTATAGCACCAAGCGATCCTCCCAAAGATGTTTATTATGCA
AACCTCAGTTCTTCATCAATAATTCTTTTCTGGACACCTCCTTCAAAACCTAATGGGATT
ATACAATATTACTCTGTTTATTACAGAAATACTTCAGGTACTTTTATGCAGGTAAGAACT
GAATTTTCTTCTAGTTCTTTATTAACATCCTTAAGTTTTATTAATAATACAGACTTGTCA
CAGTAAAAGAAATTGTTTACCTTACATTGATAATTAGGCACAGATGTATTTTATAAAACT
[C,T]
CCATTGACATAGAAAAATGCGGTGTAGAAATGTCAGATACATTTAATCTCTCTTTACAGA
CACACACACACACACATACAACTTCTATATAAGCTTCACATGTATTAAAAATAGTGAATC
TGCCACCTACTGAAAATTCTGTTTATAAAGATGGCCCTCAATTACACTTCCTCCAATAAG
TGTTCTCTAAAGTGCTGATGGTATCATTTATCCTCAAAGTTATTTATTAGCTAAATTTTT
TTTCATTTGTTTGTATATGATATAAATAGTTCTAGTGTTTGGATGTGTTTGTTTTTCTTT

5816 CTCAATACATATTTTAATTGAAAGATTTAAAAAATATTATAGTAGACCAACATCACTTTT
AGTACATAGTCATAATTTTGGAGCCCTTGAGTATGTAGCAAAGCCATCTTTCCTTTTTCT
TATCTTGGAGAATTTAACCTCTTTGCTACTACTTGGCAATCCATATTGTTCTTCCTTCAG
TTGTTGCACATTGTATTTTGTACAGCATATTAACTTTTCTACTTTTAAGTTTTACCCAC
TTATGTTTCCTTAGTGTGCCTGGCATAATGTCTTCTATTTTAAAAAGTGTTAAATGGGCC
[G,A]
GGTGTGGTGGCTCACGCCTGTAATCCCAGCACTTTGGGAGGCTGAAGCAGGTGGATCACG
AGGTCAGGAGATCGAGACCATCCTGGCTAACAAGGTGAAACCCTGTCTCTACTAAAAATA
CAAAAAATTAGCCGGGCATGGTGGCAGGCTCCTGTAGTCCCAGGTACTCAGGAGGCTGAG
GCAGGAGAATGGTGTGAACCTGGGAGGTGGAGGTTGCAGTGAGCCGAGATCGTGCCACTG
CCCTCTAGCCTGGGCAACAGAGTGAGACTCTGTTTTAAAGAAAAAAAAAGTGTTAAATGA

6074 CCTGGCATAATGTCTTCTATTTTAAAAAGTGTTAAATGGGCCGGGTGTGGTGGCTCACGC
CTGTAATCCCAGCACTTTGGGAGGCTGAAGCAGGTGGATCACGAGGTCAGGAGATCGAGA
CCATCCTGGCTAACAAGGTGAAACCCTGTCTCTACTAAAAATACAAAAAATTAGCCGGGC

ATGGTGGCAGGCTCCTGTAGTCCCAGGTACTCAGGAGGCTGAGGCAGGAGAATGGTGTGA
ACCTGGGAGGTGGAGGTTGCAGTGAGCCGAGATCGTGCCACTGCCCTCTAGCCTGGGCAA
[C,T]
AGAGTGAGACTCTGTTTTAAAGAAAAAAAAAGTGTTAAATGAATATTAGTTGGTTGGTCA
AATTTGAAAAAGTTTTACTAAATACCTTCTGACTATATTTATATAAACAAAAGAATAAGC
CTTACTTAGATAATTTGTGCCAAAAGACATTTTGTTTTTGCAAAAATAAACAGCTGAATA
AAATAATCATCTGGATAATTGATTTAATGTTACAAATTTGTTACATGCCTATGCACATTA
AGTCACACAGTCAGCAGGAATGACTTCTGGGTGATTCAGATAATTTGTTATGTATTAGCC

9550 CACACGCACACACACACAATCTCCACATAGTAGGAAAGAAGAGTCAAGAGAATATTATAG
AAACAATTCCCATACATATTAAAGATGACAGAGTTTATTTTGAATGATTTTTAAAATAAT
TATTTAGAAGATATTTTATAATAGGTGAATGTTTGCCACATCTGCATTTAAATAATTTAA
GAGCTGATGATGTAATAGTTGCCATTTCAACAATTATACTCAGTTTGTGAATTTAGATTC
TGTTTAGGGTAACTGTTGATTTTTGTATTTTGCCCATTACCTATCATAGTACCTGAAGGG
[T,C]
TTGTTGGAAACCTGACTTACGAATCCATTTCGTCAACTGCAATAAATGTAAGCTGGGTCC
CACCGGCTCAACCAAACGGTCTAGTCTTCTACTATGTTTCACTGATCTTACAGCAGACTC
CTCGCCATGTGAGACCACCTCTTGTTACATATGAGAGAAGCATATATTTTGATAATCTGG
AAAAATACACTGATTATATATTAAAAATTACTCCATCAACAGAAAAGGGATTCTCTGATA
CCTATACTGCCCAGCTATACATCAAGACTGAAGAAGATGGTAGGCTAGACCCTTTTATTG

9644 TTATTTTGAATGATTTTTAAAATAATTATTTAGAAGATATTTTATAATAGGTGAATGTTT
GCCACATCTGCATTTAAATAATTTAAGAGCTGATGATGTAATAGTTGCCATTTCAACAAT
TATACTCAGTTTGTGAATTTAGATTCTGTTTAGGGTAACTGTTGATTTTTGTATTTTGCC
CATTACCTATCATAGTACCTGAAGGGTTTGTTGGAAACCTGACTTACGAATCCATTTCGT
CAACTGCAATAAATGTAAGCTGGGTCCCACCGGCTCAACCAAACGGTCTAGTCTTCTACT
[A,G]
TGTTTCACTGATCTTACAGCAGACTCCTCGCCATGTGAGACCACCTCTTGTTACATATGA
GAGAAGCATATATTTTGATAATCTGGAAAAATACACTGATTATATATTAAAAATTACTCC
ATCAACAGAAAAGGGATTCTCTGATACCTATACTGCCCAGCTATACATCAAGACTGAAGA
AGATGGTAGGCTAGACCCTTTTATTGTCTGTTAAGCAGATTGTTGTTCTTTTCATTTACA
TTGCTTTCTGATAGGAAATAGTCTTCAATTATATTGATTCTGTTTGATCTCAAGTAATTA

16630 ATTTTATAAAAATGTTCTTATATGATTCTGAAAACAAGGAAGTGAATAGTTAATAGCATT
TAATTGCCAGATCCCTTGATCAGCCAGAAATTATCTTTAAAAAATTTTTTAATGCCACAT
ATTCCCTAAATATTCTCCTTTAGTACTGGTGTCTTTATCTTACAGAGGAAGAAAAGTTTA
TAACAGCTCAGTTTAGACCCAGGTAGAGCGGTGTAGGCAGATCAGGGATCACCTGAGTAT
TCTTTAAAGCACTATGTTTTGCATAATGGCAGCAAGTTATTTTCTTTCAATTTTCATTGT
[T,G]
TGTAATCCACAAATTGACTGTGTCCCAATTTTTCTTCTACCATTATCTTTTACTGTGACC
AGAAAAGTTATTCTACTAATGCCACCATTAGGGGACATTGGCTAATTGGACATTTCTGTG
GGAAGTAACCAGTTTCTCTAATGTGCAGTCACTTTGGTGGGCTAGGATATTGTTCTTTGA
CCAGGCCTACCAGATATAGAGGACCTCTGAGAAGCTGGGTTAGTTTCAAGTAAATTCAGA
GAAGCTCTAGAAAATAAGACTGAGACTCCTTAAATCTTCCTTCCAATGATGTCTACAAAA

17957 TCTACAAAAGTTTCTCCCCAAGATCACATGTACACTTTCATAAAGCTTCTTGCCAATACC
TCATATGTCTTTAAAGTAAGAGCTTCAACCTCAGCTGGTGAAGGTGATGAAAGCACATGC
CATGTCAGCACACTACCTGAAACAGGTAACTAACGTGAAACAGGTAACTAACATGAAACC
TTTAACTATTTGGGGATTGTGTCAATACCACCTGCAATCTTTATAGCATACTTATCTAAA
CATACAAAGCACATATTAAAAAAATACAACACAGGCTTTTTATCCCACGTGTTGCTTGAGT
[G,A]
CCAGCTGTGTACTACATTGACCCTTCTCCAAAACATTGGGAGATTGAAGGGAGGAAAAAA
AGAGAGATGATCCTCTTTACTGTATTTCCACAAATATAAAACCCCCACCTAATGAATTAT
GCTTTATTGTGATTTAAAAGAAGAAATAAACATGTAAACCTTTCATGTATATCTCTTTTT
AGTCTTACTTGTTTTTATGGAATTCTAGATGTTTTCCTGAACTATATGGTTGCAGTATCA
GACTCATTTTCATCTATTTTCTCCCCTTTATACCAGCCTTTATCTTTCATGTTATTTGAA

18299 GATTGAAGGGAGGAAAAAAAGAGAGATGATCCTCTTTACTGTATTTCCACAAATATAAAA
CCCCCACCTAATGAATTATGCTTTATTGTGATTTAAAAGAAGAAATAAACATGTAAACCT
TTCATGTATATCTCTTTTTAGTCTTACTTGTTTTTATGGAATTCTAGATGTTTTCCTGAA
CTATATGGTTGCAGTATCAGACTCATTTTCATCTATTTTCTCCCCTTTATACCAGCCTTT
ATCTTTCATGTTATTTGAATAAAATATCCGGGTCGTTAAGCTTTAGTCCACAAGACGAAA
[T,G]
TCTCACCTTCCCTAGCAGTGCTCTGTCCTGTATCATAATATCCTTCATCCTATTTTCTTC
CATATTCTACCTGCTTATATAAATTAAAACCTGTTTCTTTCCTGATAACACCACTTCACT
GTAGATATTGGCAATAATTGTTAACTTCTGGCACATCCAGACCCTTTATCTTGGAAACGT
CTTTCAAGCTGTCTTGAGGCTGTAAACCTAGAACATCAAGACATAGTCTGCCTTCTCTCT
GATTTCAGCATCTAACTCCACATCCTTTCCTTCTCATTCTTCCAGTGCAACATTTTTTCA

23521 ATGTGATCTACCTGCCTCGGCCTCCCAAAATGCTGGTATTACAGGCGTGAGCCACCGCTC
CCAGCCTGCCCAGCTAATTTTTTATTTATTTTTGTAGAGATAGTCTCACTATGTTGCCCA

GGCTGGTCTCAAACTCCTGGTTCAAGCAATCCTTCTGCTTCAGCCTCCCAAAGTGTTGGG
ATTACAGGCATGAGCCACACACCCAATCTAGCTTATTTGTTAAATACATTACTTATATAT
TTTATAAGAATTTATAAAATTCTTATATACCATTTAATAGATTGAATGTGGGCAGTAAAA
[C,G]
TGCTGCCCTTCTATGGCTACAAATTAGTGCACTAAATCAAAAGTTCACTTTTCCTTTGTA
TCCTACTTACATAGCTTTCCTCATCCATCTCCTGAATTAAGATTTGAAATAAAGGATGTA
GGAAAGTTGCATGATTCTGATTGCTCTCAAGCAAGTGAATAAAAACATTCAACTTACCGG
TGGGTAATCACTAGAAGCACAAAAGACATTATAGTTGCCTATCATAAATCAGAGGGAAAT
AACTATTAGTATATCTAATTGAAATTCAGGTGTTTTATACAGTATCTTTTATATAGACTT

28463 AAAATGTATCACTATAGGATACCCTGTTTATTGCATAAGATAAAAGAAAAATATGTTGTG
ATAACCAAAAAGTTTTAAGGGCTTTCAAGTTATGTAAAAATGGACCTATGGACATGGTTA
ATTGTCCTCAGGATGCAAAATTGGAGCTGAAATAGTATATCAAACAATTGCAAAAAGTGT
ACTGCAGCTATCTCTTGGGTCAAATCTGGTACCCAGAAATGGAGAAAAGCCTCAAGAAAC
ATTGCTGGTTGGCCCTCTGCCACTTGACTGTATGATCTGATCACATGTAAGTTTCACAAA
[C,A]
GATTCATATTTCTCTGCTAGTTTGACGTTGAGAATTTGCTCATAAACCTCCCTAATTTTA
TCTTCTTGGTCCTTTGAGAAACACATAGTATCCCAACTTGTCAGAGAGGAAATTTGAGCT
GGTCCTTCTTTATCCAGGAGAGACCTGAAAAATTAGGTGGTGTGAGTACTGCAGAGTGAG
GCTGATTTTCCAAAGCACTAACTTTGTTCTGATTAAGAACAATTTACAATGGTCTCCACT
GCTGGTAATGATTATCTTCTTTTACGTTCTGAAAAATCTGCTCTGGCTGGGAAGGTGCTG

35221 TTACAATATTCAAAACTTCAAGTGTCAATTATAAATGTATGTGAAAACAAAAAATTATTT
AGTATACTAATTTAAAACATTAGAAACATAGAGATTTTTTTGTATAAAAACTTATCAAGA
ATTTTTTTTCTCATTGTTCAGCTTATGTTACAGAGAGGGCCTCTTTTCTATGTTTCAGTT
AATTGTTATACACTTTCAAAGTTTAGATCAGTTTTCAATATTTTATCCTTTGCACTTTCA
ATATTGTCAAATATCAGCAAGAGTTCTCTTGGTGTGAAATTTTTGTTTTGCTGTTTTTTA
[C,T]
TTCCTTCAAGACATCATCCTTCATTGAATTCATCAGAACCACTTGCTTTAATTTCTGTCC
ATATTTGTCTTCAGTAAGTTGTCTTGGCTGCATATGTAAAGTTTCTTGAACAGCAGTGTT
AACATTCCCATGGTCAGCTCTTTGTTCTGAAACTCCGTTTATGTTATATTCAAATTTCAT
TTCCAGCACTCTCACTTTTGTTGCTCTGCTACCATCTTTGTTAGCCAATATGTGTCACAC
GAGTTCATTGCTGTGAGACAAGGAGGCAACATAACTACACAATTTTCTCCCTGTGCATAA

41813 TGTGAACAACCTATAATCAGGTCTTTAATCTTGTCTGACAACCTCTGACTTTTAAATGGA
GTATTTACTTCATTTAGATTTAAACTTAGTATTAATTTACTTGACTTTGGATGTACTATT
TTTTCTTTGTTTTCTATATGTCCTATCTCATTTTTAGTTCCTCTGTTCTTGCTTTCTTTC
TTGCCTTCTACTGGGTTAACTATATATTTTTAGCATTATATTTTAATTCTTCTATTTGAC
TTTTAGCTATGTTTCTTTGTATTATTATTTTTCGTGGCTTCTCAAGGGACTGCAATATGA
[A,G]
TACTTGACTTATATCTACTTAATTTATGTAACTGGAAATAAAATACATGAATTTTGCAGA
AGTATTCCCATGTACTTCCCTGTAGTTTCTGCTGTTATTGTTATATTTTTTGTACTTACT
TTTATAGATGTCAGGTTGTTATACGTGTCAGCTATATATATTAATATACGTGTGTATGTG
TGCATGCACACTCGGTTTTTCAGCTGTCTTTCTACTGAGCTCCTTGGATTCTCCGTCATG
TACATATAATTAAAATATTAGGCAAGGATTTAAGGGGAGTTTAGTCCCAAACTTTGGATC

41957 ATCTCATTTTTAGTTCCTCTGTTCTTGCTTTCTTTCTTGCCTTCTACTGGGTTAACTATA
TATTTTTAGCATTATATTTTAATTCTTCTATTTGACTTTTAGCTATGTTTCTTTGTATTA
TTATTTTTCGTGGCTTCTCAAGGGACTGCAATATGAATACTTGACTTATATCTACTTAAT
TTATGTAACTGGAAATAAAATACATGAATTTTGCAGAAGTATTCCCATGTACTTCCCTGT
AGTTTCTGCTGTTATTGTTATATTTTTTGTACTTACTTTTATAGATGTCAGGTTGTTATA
[C,T]
GTGTCAGCTATATATATTAATATACGTGTGTATGTGTGCATGCACACTCGGTTTTTCAGC
TGTCTTTCTACTGAGCTCCTTGGATTCTCCGTCATGTACATATAATTAAAATATTAGGCA
AGGATTTAAGGGGAGTTTAGTCCCAAACTTTGGATCTAACTCCTCTGTTTCCAACTACTT
TAGCAGCCTCATACTTTATTCTCTGACACCTCAAGCCAATAGCTGCGTTTTTTTTCCTTT
TCCAAGTTCATACATGTTATCTGCAGAATAGTTTGATATAAGTTATCACCAGATCAGAGT

42599 TTGCAAAATTTTTGCCCAAAATATGAATCTGAGCTCCTTTCAAGGTTTTTATTAAAATAT
CTAGTCACACTGAACACTTTAGTGTATAATAGCCTTAATGTCACTTGGTGATGGGTAGAT
AGAAGAGGAGTTTACATTGCAATAATATATATGGCTTTAAATTGATTATTAGACATTTTT
GTTCTAAAAATCTTTTGATCCAAGTGTGGTGGCTCACACCTGTAATCACAGAGCTTTGGA
AGGCTGAGGTGGGAGGATCTTTTGAGCCTAGGAGTTTGAGAACAGCCTTGGCAATGTAGC
[G,T]
AGATCCCGTTAGTACAAAAAAAAAAAATTAGCCTAGAGTGGTGGTGTGTGCCTGTAGTTCC
ACCTACTCAGGAGGCTGAGGTGGAGGATTGCTTAAGCCCAGATGTTTAAGGTTACACTGA
GCTATGAAGGTACCACTGCACTCCAGCCTGGGCAACAAAATGGCACCCCTCATCCCTGTAA
TCCCAGCACTTTGGGAGGCCAGGGTGGGCAGATCTCCAGGTCAGGATTTCGAGACCAGCC
TGGCCAACATGGTGAAACCCTGTCTCTACTAAAAATACAAAATTAGTCAGGTGTGGTGGC

47819 ATAGGGCAGTTGCCTTGAAATAGTCTAGTTCAGCACACAGTTCATCAAAGAGAAGATACT

FIGURE 3, page 77 of 87

GGATATAAATGAGGGTTACTGCTGGTCACTTATGAATACTTCTGAGGTAGCCTTGTTTAA
AAAATTGTCTACAAGTTATACCATATATTTCACCTCAGATCAGATTCATTTTTGGTTTAT
CTTTCTAAATACATTTGAGTGAAAATGTGGACTAGATTTTGTACCACATGAAAACAAAAG
GCTGTTTCAATGAACCATCATTTATTTCCACAGTCAACAAACACTTATGAGTGCCAGTAT
[G,A]
TTCCAGTGTCCCATCACTGTGCCTGTCACATAATAGGAGGCTGAAATTGTCATTATGTTT
CCTATAGCCAGGTTACAAATAACTCTTGCCTGGATTTAGTGGTTTTTCTTTTTAAGACCT
TTTCTTCTCTGAAAGCTTAATTGGAGAATACTAGAGTCTGTGAACGAATATTGATCTGCT
GAAAATTTTTACTGTGTAGCAAAATTTGCTAGTAACAAACACCAGCTATCCTAAAATCTG
AACATTGGAGGAAAAAATAGTTGATCATAGAGGCATGGCATCTAGTCATCCCTCCAGAT

51990 TACAATCAGTGAAATTCCATCTCATGTGCCATCTCTTCTCTAAAAACATTTTCTGAACAC
CCACGTCAATCAAATACATCTGATTTATATTAGAATATTTTGAAAATGTATCTTATGTTC
AGATGATCTGAGTTCAAATTTAGTGACTGAGGCATTTGAAAAAATTATGAAAATTCTAAA
ACTTCTTCCTCTATAAATTTACATTTTTTTTCCCTAAAGATAGTGTTTTCTCTAATTGCT
TTTCTTCATGATAGGTAAAGATAAAACAGAATGTGTTGTAAATAGTGTGCCAGTTTTGGT
[-,A]
AATATATATATATATATATAGTAAATAAGCAATAGATCTGTAAATAATTCGATAAAAATTTA
AGATGAAATCCAAAATTTTAACTGAAGTCCAGACCTCTCTCTACAGAATCCAGACTCAAG
CTTCTATCTAGTATTTGATTTCTCCTTCTGGGTGTCTGAGAGGAATTTCAAAGTTAACCT
ACTCAAAAGAAATTGTTAATCTTCCTCCCCAAAGCTTACCCCTCTTACGGTCACCCACAT
CTTGATTAATAGTGACTTCATCTTTTTATTTGCTCAATCCATAAACCTTAGGGCATTTTT

51992 CAATCAGTGAAATTCCATCTCATGTGCCATCTCTTCTCTAAAAACATTTTCTGAACACCC
ACGTCAATCAAATACATCTGATTTATATTAGAATATTTTGAAAATGTATCTTATGTTCAG
ATGATCTGAGTTCAAATTTAGTGACTGAGGCATTTGAAAAAATTATGAAAATTCTAAAAC
TTCTTCCTCTATAAATTTACATTTTTTTTCCCTAAAGATAGTGTTTTCTCTAATTGCTTT
TCTTCATGATAGGTAAAGATAAAACAGAATGTGTTGTAAATAGTGTGCCAGTTTTGGTAA
[-,T,A]
TATATATATATATATAGTAAATAAGCAATAGATCTGTAAATAATTCGATAAAAATTTAAG
ATGAAATCCAAAATTTTAACTGAAGTCCAGACCTCTCTCTACAGAATCCAGACTCAAGCT
TCTATCTAGTATTTGATTTCTCCTTCTGGGTGTCTGAGAGGAATTTCAAAGTTAACCTAC
TCAAAAGAAATTGTTAATCTTCCTCCCCAAAGCTTACCCCTCTTACGGTCACCCACATCT
TGATTAATAGTGACTTCATCTTTTTATTTGCTCAATCCATAAACCTTAGGGCATTTTTA

52788 CTCAACACAGTAGCTAGAGTGATTCTGTGAAAGAGAGAGCCTGCCACTTCTCTGCTCAAA
TGAAAGCCATGACAATGTCCTCTAGTGTCATGTACTGGTAGCTTGTACCAGTCACTCAGT
CCTTCTTGTTATTCTCCAAATATACCAGGCATGCCTCCAACTATACAGTTTCCTCTGCTT
CAAATTTCTCTTTCTGAAATATTGACATGGCTAGGTCCCCTACCTACATATGGAATTTAG
TATCTTCTTTTTCTTTTTTTTTTTATTATTATACTTTAAGTTTTAGGGTACATGTGCACA
[T,A]
TGTGCAGGTTAGTTACATATGTATACATGTGCCATGCTGGTGCGCTGCACCCACTAACTC
GTCATCTAGCATTAGGTATATCTCCCAATGCTATCCCTCCCCCCTCCCCCCACCCCACAA
CAGTCCCCAGAGTGTGATGTTCCCCTTCCTGTGTCCATGTGATCTCATTGTTCAATTCCC
ACCTATGAGTGAGAATATGTGGTGTTTGGTTTTTTTGTTCTTGCGATAGTTTACTGAGAA
TGATGATTTCCAATTTCACCCATGTCCCTACAAAGGACATGAACTCATCATTTTTTATGG

59029 AAAAGTTGGATTTCTAAATAATCCTACATTCTCAAGTCTTTCCACTTGAATATCATTCTT
TCCACCCTATTTCCTCCACTTCTTACCCCCTTTTAAGTTCTATGGCCATATTTTATTTCC
AGGAGACACAGGGGAAATGGTCTTTCTACCACTGTGATTAGGAGAGAAAGATGAAAAGAT
TTATATTTTTCAACTTCGTGATAACAAACATATGATTGCATTCTCAAAACTCATAGCTTT
TCAACTAAGTAGTCATAAGTGGTTGAGGATAATTCTTTAAATTTTGACGATGAGTTGGTT
[A,C]
CTCGTCTTTTAGTTTCAAGAATGGAGGAAATTTTTGCTTCCAATGGAATAGAAGACATTT
TTCTAATGATAAATATTGTACAATTGAATTTCCAAATTTCATAATTTATACATCAAAATA
AAAGTTCTATTTATTATATTAAGTCAGGAAGAGATAATTTGAGATTATATGGGGAACTGC
ATATATTATTGCAACATAATATATATGGTGAAATAACATAAGAATAAAAGAAATTATAAC
AGTTAAGTAACGGAAGTCTTGAAGAGCAATAATCCTTTTAATATTAAAAATAAGGCATTC

60776 GTGTGTATATATGTGGTGGTGATGTAAAGTCACAAGCTGTTAAATGTTTCTGTGGTGCAC
AATAGATACTTATGCTGAGGAAATGTACAACTTTAAAGGAGTGTGGGTGTGAAATTAGTA
TGAAATGGAATGGGACTCTCATAATGTGCGTCTCCTATAGACCACCAAGACTGGAAGACA
GCAAGAAAGGAAAATTCCTGGGGTAACACTTAGGTTGGGAAAACCACAGGATACCATACT
CATGAGGAATTTTAACTACCCAAACATCTGTTAGGTTAAAAAAAATTCAACAAAACATGC
[C,T]
TCATCAAAGAAGTTTCTAAGGAATGCAACTTTATGATCTAAAAAGAAGAAAACCAAATAG
AGGGCAAAGTACACTTTAACATTATTTAAAATTAAAATTGTCAATGTGTTACTAAATAT
CAGTTGTTTTCCTTAGTTTTTTCTAAACTGTGTAATACACTTATGTGATAAGTGTTATAG
TAACAGAGGTAGAAATTATCCTTTTTATAAAGAAGCAATTATATAATGGTAAGAAGTGAT
TTTAGCCATAAGTAAATAGGAGTCTATAATTCAAGACATTTAGAAGTTCATTTGGTGGCA

61193 ATATCAGTTGTTTTCCTTAGTTTTTTCTAAACTGTGTAATACACTTATGTGATAAGTGTT
ATAGTAACAGAGGTAGAAATTATCCTTTTTATAAAGAAGCAATTATATAATGGTAAGAAG
TGATTTTAGCCATAAGTAAATAGGAGTCTATAATTCAAGACATTTAGAAGTTCATTTGGT
GGCAGTGCAGTATTAGGATGGGCTCCATCTTGCTGCCACTAGAGAAAATAAATATCATTT
ATTCTAGACATGATGGTTGCACTTCTGCAAAATTAGTTAGATGCTGTTGAAAATCTTCTA
[A,G]
ATTAGTTACACAGGACTCCCTAATGGGTAATTCAAGACAACATTTCTGTCCTCTAGGCCC
GAATATTGAAGTTATTGGTATAACCACTTAGGTTCCCATAGACATCTCAAACTCCATATT
GCCACCTTCCCTTGCAAGTCTTTTCCTTTCTGTGTGTTCCGTGTCTCAGTTTACTGCACC
ACTATTCATCTAGTTGTTCAAACTAGTTATCTAGAAATCATTGTTAGTTCTTTTTACCTA
CTCTCATCCCCCACGAGGCAAAACCTGAGTCCTATTGTATTTACCTTCTAAATATCTCTT

62994 ATATAGAAAGGAAATAATTATTGCATTTAGAAATATTTCAAACAGTGAAGGAAAATAATA
AATGTCCATTTCAGAATAGATTGGAGAAGCATTAAAAATATCTAAATGATTAACTGAGAT
AATTAGCTGGTAATAAGTATGTATAGTGAGACAGAGTTATAATAGATTGATGGTCCATGA
AAGAACAAAGGGGAAGAACAATGTTTAAATTTAGAGTGCTAAGTGTGATTACAAAGAGGA
GATATATGGGTGAAATCATAATTTAAAGGAAATGATAGAAAGCATATAACATTAAAGTAT
[C,T]
TAATAAAGTATTCAACTATATATTTAATGTCAAAAGACCTTATGCTAGATTATGATGCAA
ATATTCTAGAATTTAAATAAAAATACTTGTTTTTGAAATCCTATTTACATAAGCAAGTAG
AAAGTTGTAGCAAAATCACTAAAAATCAAACAAAGAAAAGTGTAAAGATTATCACTGTTT
TTTTTTAAATCATCAATATTTTAGAAAGTCTGATTTTCATAAAGGAAAAAGGGGAGGAAA
TTTTCTCCCCATTAATAGCTTAGCTGTATTTTATCTTTTTAAACTTCAAATGAATTCTCC

63244 TGAAATCATAATTTAAAGGAAATGATAGAAAGCATATAACATTAAAGTATCTAATAAAGT
ATTCAACTATATATTTAATGTCAAAAGACCTTATGCTAGATTATGATGCAAATATTCTAG
AATTTAAATAAAAATACTTGTTTTTGAAATCCTATTTACATAAGCAAGTAGAAAGTTGTA
GCAAAATCACTAAAAATCAAACAAAGAAAAGTGTAAAGATTATCACTGTTTTTTTTTAAA
TCATCAATATTTTAGAAAGTCTGATTTTCATAAAGGAAAAAGGGGAGGAAATTTTCTCCC
[T,C]
ATTAATAGCTTAGCTGTATTTTATCTTTTTAAACTTCAAATGAATTCTCCTATTTTCTCT
GAGATCTCAGACTAAATTTCACATTGAATTGAATTAACTTTTACTCTTCTGAGAATCTTC
TTTCTGTCCATTCAACAAGAAGTGTAAAGTAGGTGTAATACATTGTGAATTTTTGTCTTT
AACCTCAGTTCTAAGTTCTAGCTCAGCATTAGGCCCTAGGTCAGCAAAATTTCAGCTCCT
ATTTCTTCTGCATTTACCAAGAAAGAATTCTGATTTAACTATGAAAATTCCAAACTATAG

65053 AGAGGTTTTCTTTCTATTTTGTATTTTTTTTCTAGCTTAAGCCAGTCTGAAATTAGTCAG
GAAATAACTCATTTAAGCATCAAATAAGATGATCATACAGTGAGGTCTAATACTATGAAC
ATCCATGAATCATTCTTAGTATTCATGAATCTAATCTGACAAATTCTTAGGCTTACTGTA
TTTGTAACACTATTGTGCTATACCCTCTGCAGCACCACCTTGCGGTTAGGAAATCTAATT
AGAAAACACACTTAACATCTCATAAAATGATAGGAAATATTTCCTACACTGACAGTGGTG
[A,T]
TGCGTTTTGGTCAGCGAAATCACTGGGCTCTAGGAAAACATCCAAACTACAAAAGGATAG
CCAGTTATCAAAGTGTTTTAACCAGTGGACAGGAATATGTCCTGAGATACTCTTGCTGTG
TGGAAATAAGATGAATCCAATTGCAGAGCTTCTTCAGGGCCCTTGATGCCCTGAATTGCT
TAAGACACAGGAATCCACCAGCGAGTTGGATTTCTTCTAGTCCTGAGAGACATCTAACAG
TCAGTGCTAATTTGTCCAGGTGTGCTGAGTCAAAGTCGACTTGTAGTCCTTGAAGTTGTT

68460 ACCTTGATCACCTGTATGAGCTTTTTGTCCTCTTAGTGCCTAGCACATAGTAAGCACTTA
ATAAATATTTATTCATTCAATGAATGCATAAATTTATTCTCAAGGCCAACTAAACATTTG
GTTATAATAAAGACAAGGGGACTCTAAAATATTTTCCTGTTTTATACCACTTGAAATGTG
TGGCCGATCAGAAAATTGTTTCTGTCCACACTGGTTCTTACAGAGCTGGAAGTCAAATTT
TTCAAATAACATTAATAATAAGGGAGCCTTAATACATTTATACAGAGGTCATATCCCATC
[C,A]
CCTTTTATAGAGTCAGAGGCAGAAGAGAGGCCATTGAAACCCACAAAGCATCTTATATTT
ATATTTTTCAAGGCAATTAATTATGCTGATGGCAGGAGACCTCTTATAGCTCTCATCTGT
TATGTATAATTACCTAAATGAATTAGGCTACAATTTGAGGCAGTTTTCCTAGGACCATAA
AGCTAGCAGTAAAAAGAATGAAAATGTCTGTTTATGCAGGGTATGTGTATGATTCCTTGA
TACCTTAGTTGTTGCAGAAACTGTGTACCCAATTCTGTCTTCATCATTAGCATCTCTTAG

69326 GATTGAGTTGTGCACCTAAATTCCATAGACATAATGTTATATGCCTAAGAAATATATTCT
AAATATCAATTACTTATTCACAGTTTAAAGATTGTCACCACTATTAATCTCTTAGTCTGT
TTTGTGTTGCTATAAGAAAGTATCAGAGACTTGGTAATTTGTAAGAATAGACATTTGTTT
TCTTATAGTTCTGGAAGCTGGGAGGTCCAAGATGAAGGTGCAGACAGATTTGCTTATCTG
GTGAGGGTTGCACCCTCTGGAGGGGAGGAACGCGTGTCCTCACACAGTGGAAAGCAGAAG
[A,G]
GCAAGCTATCCAAATGCTTAGTGAAGCCTGTCTTATAAGGACCTTAATCCCATTCACCAT
GGGAGGTATTCTCATGACGTAATCACCTCTTATAGGCCCCACCTCTTCATACCATCACAT
TGGCCATTGTATTTCAACATCTAAATTTTGGAGGGGACATGTTCAAATGATAGTAACATC
TTATAGCTCTCTAGTATTGAAATAAACCTTTTGACTCTCTTCAGAGCATGTGATTCACTT
GAACCAGATATACTGCCCATATTTATACCATCCCAACTTGCAAGAAATTATCTGCAATTT

FIGURE 3, page 79 of 87

73039 CTATAAAAGGGCAAGGAAAAAGAACAGAGGAAATGTAGCAAGAGAACGAATGAAAAATAA
TCTAAACCTATAGAATTTGGTGAAAAATCAACTAACTCATGATGGTGAGTGAGTAGGATA
ATTAAGGATGATTGTAAGTTATATGACAGAAGATTATGAGGAGGAACAGATCTGTAGAGG
AAAGGAATGAGTTCAGTATTAGACACACTGAGTTTGAAATATGTGGCAGTCCTCCAGGTC
AATACACCCATTGGCAGTATTAAATATGGATCTGGAGCTCAGGAGAGAAATTCTGGATTT
[C,G]
CAGATTTGGGTAATGTTAGTATTTAGAAGATAGTCAAAATTATAAGAGTGAATGAGATTC
ACTATGGAATGTGCAAAGTAAGATGACAACCTAAGGACAGCACCCTGGGGACTATCAACA
CTTAAATAAGAGGCCATTGAAGAGACTGAATGGGAGTAGATAGCCATTTGGATGGAAATC
CAGGTATGAAAGTCAAACCCTTCATATAAGATAGGATGCTCAATGATGTCAATAATGCAG
AACTGTTAGCCAGAATAAAGACTGGAAGTATTTCCTTTGCACCCTGCTTGGGTTTTGCTG

73084 ACGAATGAAAAATAATCTAAACCTATAGAATTTGGTGAAAAATCAACTAACTCATGATGG
TGAGTGAGTAGGATAATTAAGGATGATTGTAAGTTATATGACAGAAGATTATGAGGAGGA
ACAGATCTGTAGAGGAAAGGAATGAGTTCAGTATTAGACACACTGAGTTTGAAATATGTG
GCAGTCCTCCAGGTCAATACACCCATTGGCAGTATTAAATATGGATCTGGAGCTCAGGAG
AGAAATTCTGGATTTCCAGATTTGGGTAATGTTAGTATTTAGAAGATAGTCAAAATTATA
[A,G]
GAGTGAATGAGATTCACTATGGAATGTGCAAAGTAAGATGACAACCTAAGGACAGCACCC
TGGGGACTATCAACACTTAAATAAGAGGCCATTGAAGAGACTGAATGGGAGTAGATAGCC
ATTTGGATGGAAATCCAGGTATGAAAGTCAAACCCTTCATATAAGATAGGATGCTCAATG
ATGTCAATAATGCAGAACTGTTAGCCAGAATAAAGACTGGAAGTATTTCCTTTGCACCCT
GCTTGGGTTTTGCTGGGCCTGATGAACACAGTTTTCTAATAGCATCTTATGCATTAAATT

75205 ATGGGAAAGGGTGGAGGCGGGGTAGGAAGAGAAAAAAAATAGGAAGTGGGGCAGGAAGAG
GAGAACCAGAGTCTAATTGCTGATAATGAATATAAAGTAACACTTCAAAAATGATGAAAG
ACATTTTATAACAATAGATTATCAAGTACAATATGAGCAAACAAACTTGGAATTGATTGA
AGGAAAATGAGTCAGAAAGATGTGATTTCAGTCCTGGGTAAGTGGACAAGTAATAGCTAA
CAACAACAAAGGTGTAGTAGGTTTAATAAAGAAAGGTAATGATGATCTTTTGTACTGCCA
[G,A]
ATTTGAGGACCGAGAATTCCTTTCAAATTTTGTTAAATACTTTTAAAGATATAATATATG
CGTGCCATGTCATATTTTGCGACTTGATATTTGTTATCTATTGTTTTAATGGAAGGCATT
GGAAGAGTATAATTTATAAATTATACTTATAAATTATAAATTTATAATTTATAAATTATA
AATAGTTAAATTTATAAGATCAAACCCAGTGACCTTGTGGAAGTGTAGAATTCTATGGAC
TCTTGAAAGACCTGGGCTCAAATCCTTCCTCTGCTACTAAGTAACACTGAGGAAGTCACC

75491 CTTTTGTACTGCCAGATTTGAGGACCGAGAATTCCTTTCAAATTTTGTTAAATACTTTTA
AAGATATAATATATGCGTGCCATGTCATATTTTGCGACTTGATATTTGTTATCTATTGTT
TTAATGGAAGGCATTGGAAGAGTATAATTTATAAATTATACTTATAAATTATAAATTTAT
AATTTATAAATTATAAATAGTTAAATTTATAAGATCAAACCCAGTGACCTTGTGGAAGTG
TAGAATTCTATGGACTCTTGAAAGACCTGGGCTCAAATCCTTCCTCTGCTACTAAGTAAC
[A,C]
CTGAGGAAGTCACCTTACCTCTATAAAATCAGAATTCAAATAGCTATAAAAGACAAGTGA
CATGAACCAGTAGTCAAAGTGAAGCCAATTGAGTGGGGCTCCAATGAATGGGACCCAGGC
CCCTTTACAGAGGTCAATAGTTACCCATCTCTGCACCTCTCAATAATATTTTTTCAGCAT
GAAATTAAGCCTAGTCTTAAGGAAAATTACAAAAAGCATATTTTTATGTGATATTCAAAT
GTTAACAACTAGTTAAATACACATTTTCTGCCAGTGGCATATATTCCTGATCAATAGGAT

75962 TTTTCAGCATGAAATTAAGCCTAGTCTTAAGGAAAATTACAAAAAGCATATTTTTATGTG
ATATTCAAATGTTAACAACTAGTTAAATACACATTTTCTGCCAGTGGCATATATTCCTGA
TCAATAGGATTTCTACGCTGATTTGTTTTTCTTCCATTTTCGAGAAGTGGGGCATTTCTG
TCCACTGCTCTGTCTTAAGGTGGGAATGATCTATTTGACTGTATGCAACGATAGTATTAT
TTATATCATCCTTTTACTATGTTTCTTTTTTTTCTTTTTTTATAGCAACATCTTTTTTTT
[A,T]
AAAAAAAATTGAGTTAATTTTATTTACATTACCTCAGCAAACATCTCTATAAATGAGTTT
CCAGGACAACATTTACAATATAGTTATACCATATGCAAATCAATGTGTGTTTCGCCATAT
TATCAATAAAATATGTTCTTAGCAAAGAGCATTAAAAGAATACATTGAACCAACCAACCA
AACAAAAAATATTTCAAAGTTATAAGGGAAGGTCAAGTTGAAAATGGACTTAATAGTGTT
CACTGTGTATAAAACCTGGTTTTAAGTGTTTCAATTAAGATACCTGAAAGTAGTATGTAT

82853 TTACCTAGCTACAGAGAGAAGGAACAGATGTTAGAGTAGATGAAGGGAGAGCGTAGATAC
AGTGGCTGTAGTGCTCTGTTCTTCCTACATTCACATTAAAATCATGGTCAGTCCAGGTCT
CAGTGATAGGGCTGTTTAGATCACTCAGCCTTTGTTCTCAGCGTTTAGTACCAGAACATC
AATTTTTAGAAATACTTCATTGTTAATGTTCTTCCTACATATATTATATTCAAGTGCAAG
AAAATACAATTAATAGACTATATGCAGTTGTTTTTTAAAGAATTATTTAAAATTACATGT
[T,A]
ACCATAATCAGTTTTATATATATATATATAACTATATATATACATACATATATAGATACA
TGCATATATATATATATACACACACATACATAAGCAATCACTTGAAAATAGTAACAAATA
TTTGTTTGTTTTAGGTTTACGCAGTCAATAGTGCTGGTGCAGGTCCAAAGGTTCCGATGA
GAATAACCATGGATATCAAAGGTACATACATGAGCTACCTTCCTATGAAATGCTATTAAT

```
          CAGTGATTATAATTTAAATTCCATACTTGAAATAAGGATGTAGACAAGCCTTTAAGTGAT
82930     GTTCTTCCTACATTCACATTAAAATCATGGTCAGTCCAGGTCTCAGTGATAGGGCTGTTT
          AGATCACTCAGCCTTTGTTCTCAGCGTTTAGTACCAGAACATCAATTTTTAGAAATACTT
          CATTGTTAATGTTCTTCCTACATATATTATATTCAAGTGCAAGAAAATACAATTAATAGA
          CTATATGCAGTTGTTTTTTAAAGAATTATTTAAAATTACATGTTACCATAATCAGTTTTA
          TATATATATATATAACTATATATATACATACATATATAGATACATGCATATATATATATA
          [T,C]
          ACACACACATACATAAGCAATCACTTGAAAATAGTAACAAATATTTGTTTGTTTTAGGTT
          TACGCAGTCAATAGTGCTGGTGCAGGTCCAAAGGTTCCGATGAGAATAACCATGGATATC
          AAAGGTACATACATGAGCTACCTTCCTATGAAATGCTATTAATCAGTGATTATAATTTAA
          ATTCCATACTTGAAATAAGGATGTAGACAAGCCTTTAAGTGATAAATATGCATATATTAA
          GCACATACTAAGTAAAAATGTGTGGTTATTAAAGCTATAGTTAAAAACGTTTAAATGATG

88505     GAGGTTCAATCATGTATTGCAACGTATTGGTTTTATGTTTTTAAATGCCCTTGTGCCTTT
          ATTTTTAAATTAAGTAAATTTCAATTGTCTCTGAGGATCTTAGATTCTTTTTGTAATTTT
          TAAGCTTGATCTTCTTCTGTATCCTTTACTTCAAATGCTATGGAAGCAAAAAAGTATACA
          AATGCAACTGTGCACACACAGAAATAACAAACATTTTCTTAATGTGTTTATATGTGAACA
          AGACAAGTTCTATATCATCATTTTAATCTAATTCACTAGCATTTGCAAAAGTGATTGAGG
          [T,C]
          ATAACAGTTATGCCTTTTATTTATAAATTATGTTAGTGTAACACCCTTCACAGATATCAA
          ATCATTCCATCTAAACAAATCCTTGAAGGAGGTGAGCTGATTCAGTTGTTCAAACTGCTA
          ACTGCTCACGAGTTTACCAAATTTTTAGCCCCTGCCTCATCAAATTCAATGGGTCAAAGT
          ACGAGATAATTATTTGTCTCATATAAATATAGCATATATTTCTCCTGATGATGATTCCAT
          TCCAAATTTTCATCTTGTAAATTCATTTTCTTTTGAATTAAATAAATAGTTTTTATAATT

95970     AGAAAATGCAGGGAGTTGTGTCTTTCAATTTTAAATAGTGTGCTGTGTTAGTCTGCTCAG
          GCTGCCATCACAAAATATCATAGATGGGGTGTGTTAAACAATAGAAGTTTATTTCCTCAC
          AGTCCAGAAGGCTAGAAATCTAGGATCAAGTTTCCTGCCCATTTGGTATCAGGTGAGGGC
          TCTCTTTCTGGCTTACAGATGGTTGCCTTCTTGCAGTGTTCTTACATGGCCTTTCCTTGG
          TGCATGGATGGAGATAGAGAAAATATGGTGGGGGGAGGAGGAGGAGAAAGGAGTGAGTGG
          [-,A,C]
          ACACACACACACACACACACAGAGAGAGAGAAAGAGAGAGAGAGAGATGGAGAACAAGCT
          CTCTGTGTCTCTTCTTATAAGTCACTAATCCCATCAGATCGGGGCCTCACCCTATGGCCT
          CATTTAACTGTAATTCCTTTCTTACTCCAAATACAGCCACACTGGGGATTAGGGCTTCAA
          CATATTAATTTGGGGGAAACACATGTATTCAGCCCATAATATATGATCATTGAGAAGGTA
          TTTCAGCAAACCTTTAAAGGAAGTGAAGTGGCTACCCAGAAAGATATACAAGGCATACAC

96524     TTAAAGGAAGTGAAGTGGCTACCCAGAAAGATATACAAGGCATACACACCTTTGCAGGCA
          GAGGAAGAAGCTGCTGCAAAAGCCATGTGTCAACAATGGCCTTGTGTTATTCATCAATAA
          GGAGGCTAATCTGGCTCCCTAGGAGTGAGCAAGCAAGGTGGGGACTGGAAGGGAAATCAG
          AGGGGTAACAGGGGACCAGACAGTTAATGAGGGACCAGATCACACATGCCACTGGAAGGA
          TATGGGCTTTTCTCAGTGGGAGATGAGGAGGATTTTAAGCAGAGAAATAATGTTTTAAAA
          [C,T]
          GATTGTCCTTGCTTGTATGTTGAAAATAGGTGGAACAAGGACAAAGGTGGATACAGGCAG
          ACTTGCTAAGTTTTTAATTCATGCAAGACAGGATGGTGGCCTAGATCAGATTATCAGCAG
          CAAAGGTGGAGCAAAGTGAATGGAACATACATAAAACTAGAAAAAATGGTGTCATGAACC
          CCCAAATACCTACTAACTCAATTTAATAATAATTAACATTTGGCCACATTTGTTTTATTT
          AGACATTGTTCACTTATTTCTGAAGTAAAGTAAGTCACATAACGCATATTCCACTCCTAA

100868    AGATCTATTCTCACCTGAACATTCCTTGGGCTTTTATACATTCTGCTTTTGTTCAGTCAC
          CCTGAAATGTGCTTCCTCCTCCTTCTCATCCTGGGACATCCAAGTCAAATTCTACTTCTT
          TACCTCCTCTAAATAATAATAACTATTTATGTAACTAATCAGGCACTGTCTTATGTGTTG
          TAATTTGAATCTTTTTTTCTCTTTTCATGTTTTTTCTGCATTGAAATCTTGCCTCTCAAC
          TAAATTGTAATGTCTTTGAGGGTAGGGAACATGTTTTATACTTTCCATATCATCCTTGAT
          [G,A]
          TCCAACTCTTAATAAATACTAAATATTTGAAATGTGAAAGATAGAATAGCTAAACATTAC
          TTTGTAATATACCATACTGTGTCATGGAGAAATAAGCATTTAAAGGGTTTAAGATGAAAA
          GAATCTGATTTGATTCTCAGATTCATGTGGCTTTTATTTTTGAACCTAAGTTTTCTGATT
          GTAAAGATAATATCTACTCACAATATTTTTATAAAAATTCAATAAGATAATTTGAAAATA
          ATTTTTAAGTATTTTCATGCATGTAAAAATATTTCATATATGTGAACACAATGGGGCATT

102246    TTCCTGGGACAAATATTTTTCCACATTAAACCTTTGACATTATGTTTAATAATTCATTTC
          ATATGATAGATTTTTACATTAAACTTTTCTGGAAGTGTCCACATTTTCAATCACAGGTTT
          AAATTAATTAAATTTATAACTACTTGATATTATTTATATCCATTTTTATAAAAGCTTTTT
          AATAACTATTTCAGTATAAAAGTACATAAAAGTCTAAGTTGTATATGATATCATTTTTAC
          ATTTCTTTGTATTTAAAAATTAAATATAAAGTAAAAAGTTACCTTCAGAGGGAAAAGTAA
          [A,G]
          AACATGTGTACTAAATATGTTTCATTGGTACCTATTGGAAATAGTAAAGTACATAATTTT
          AAAGAAAAAATAATTATAAATCCTTTTAAAAGCATTATCAATTATTCAAAATGTTGGCAC
          ATTATAAAAACTTGTCTATTAAGATAATTCATCAAATTCTTAATGAAAACTACCATCAGG
```

FIGURE 3, page 81 of 87

CTATTTTAACGTTTGCATTTTTATAAGATTCAATAACATGTAATGCTTATAAGCACAAAG
TAGTTGTTACCAAGTATTTGCTCAGCTCTGTTAAAATTAAAAAAATTATTATTAATTTTG

107335 TCCGTTCTAAACTTAAGCTATCTTTGCAAACAATGGCAAAAATTTGTGAATTCGGAATAC
AAGAAATGTTCTATGCTTAGAATGAAATTGGAGATACTTAATGCTCATATTCTTGTAATA
ACAAATCAAAAATAATTCAGTGTGTTTGTATACTAAATAATGAATCTTTACTTGCAGATA
CTCTTCATTTTTCTTTAGACGCAAGGAGATTTTTGTCATCCAGTAAGTTACTGTGGTAAT
GCAGAACTCTGCTGTGATTATTTTAATCTTGTCAGGTGGTGTGCTCTATATTTTAAAATA
[T,C]
ATAATATTGAACATCTTGTTGTTTAATGCACTATTTTTTCCAAAGCTCCCCCCAAAAGCT
ATATTTCTATTTACAACATGTCCTTTATAATATTGCATGCTATTGATAATGGTCAAGTTA
ATCTTATCAAAATGCACATTGACTCATAATGTGCATGTCCTGAGAATTTGCTGTGTTCTC
ATGTTGTGTTAGATTTGATAGCAAATTAAGTTTGCACCTAGATTCCTGTACAGGCTTCTC
ATTCTGTTATCAACATGACGCAAGAGTTGAGCTCTACATCTGATGGGTGGAAACTATATT

107921 GGTGGAAACTATATTTACATTTCATACAAGCTCATTTTTGCAACTGTAGATGGTTAACCT
GTAAGGACCAAGACAATGACATTTCTTGTTCCCTGACTCTCTAGTGCATACACAGAATGG
CATATTTCATGGAAACGTTATTTCTCCACTGACCAATGGGTAGCCAACTGTGCACGCTTC
CAGGCACTCCCCTGATGCTCAGAAATGCCATTTGTATCCTGGCACAAACATTTTTTGTTA
CATTCTGAGAGTAGCATAGCAGAATATCAGCACTAGCAGGGACCCCAGTAACTGATTGAG
[C,T]
GTCCCAAACATAATAAATTTCTTCATGCAAAGAATGTAAATGAAGGAATATGAATGGAGG
CAGAGAATAAAAAGGCATTTGATTTCAAAATCACACGCCTTACTAAAGAAGAATCCGTCT
TCATGAGCTATAAGGCTGAATGGGGCCAAAGCTCCTGATAGTCTGGTTAACCATGAATAA
TACTCTGCATTATTAAAATCAAGGAAGCCCGGTCTATTTCTAATCTAATCACATTTAGCA
TTTGGGAATCATAAGTAACCTTGTTTTAACTTCAGATTAACTAGTTACCAAGTTCCCATT

110413 TTTTAAATTTATATTGAGCACCACGGAAACATCAATGATTTGGTAAAAGAATACAGAAGG
ATGTGACAGAATGCAGAAGGATGTGAAAGAATGCAGAAGGATGTGAAAGAACAAAATAAA
GAAAACTAATAGGAAATAACAAAAATTAAGGCACCTTTAAAAGTATTAAAATAGATGCTT
TGGATAAGCGATAGAATATTGTAGAAGTAGATGTAATTTATGTGTCATTAGTGACTTGAT
GAAATATATAAACTAAAAACTCACACTCAGTATCATACAAAACTTGGAAATATTAATATT
[T,G]
TACCAGAGAAATAGATTCTTCACAAATTTAATCTAAGTAGCAAGTACATGCTATGGGATA
CAAATACATATTTTTACACCAATTGACAAATTTGAGATTCTTTTATTTTTAACTTAACAT
CACTGGTTAAGTAGAAGAAAAGTTTCTCAGTTTGTCCCATACCACTGGTAATGCTGGTTG
AAGCTGCTCAGCTATAGGTTATCATCTGTGGCTCTCTATTAGGACTATATTTTAATTCCC
TATAGATTTCAACTAATTGACCTTGAGGGAAAGCTGAGTCTCTGTGACAATATGGTCTTC

111600 ATAAATCAGTCAAATTAATTTTTTTGTATATAAACATTAAAGCTTAAAACCTCAAAGAAA
AATACAATTTAGAATGTAGCCAACACCTAAGGGAGAAATACACCTATACAACATGAGGCT
AAGAACGAAAGCAATGATAAGTATACTACAGACAACAATGAGGAAGGAAATATCTAACTT
TTATTTGAAATAGTCAGGTAATGTACCTCAAAATGTCTTCTCAATTTGAGCATTCCTAAT
AGGTATTTGAAGATTTCAACTCACAAATGATTGTGACATAAGTACAGACTAGAAAATTAC
[A,G]
TAAAAACTGGACTACTAGAAGCTTTCTTATCTTATATAAACATAAATGTGAAGAACAGAT
TCTAAAAAGTGATTGGATTTAGATAAAAAAGAGTGATACAAAAGAAAATAAAGCCAAATC
AGATTCCACCTCTCTTTTTCTTAAAGTGTGTGCCTATTTGTTTATCACTTGAGTAGGCAA
GAGCAATTTTATTGTTCATTTATCTAACTTCCTAACAAAGTACACCTGTTAATTTATAAC
GTTAGGTTATCTGCTATGGCTTTTGCTTAGACTCACATGCTTTTTGTTGATAAATCTATT

114518 CCCAAATCAAAGATTCTTCTCATTTGGTAGCCCTTTCAGCCATCTCCATATCCATCTAGA
ATAAGGAATTCTTTCTTGCTTTCTTTAAATCACTCTAGGGTATTGTGGGGCACTCTTAAG
CTTATCCACCAAGACTCTTTGTTAGTCACTGCTACTTTGTCACTTAGATGCCCTGTTTGG
CAATGGAATAGTCTATCACTTTATGTTTACCCTGAGAAGCTGGAAGATACAACATCTCTT
TCTGCTTGGGGGGCACCCATCATTAACTGAGAATTCTAACATTCTACTTTGTAATACCTG
[G,C]
TCCAGCATCCCCATATTTTTCAACAATTCCTGTATTGTAATGAAATATACTTCCTTTTAA
ATCCTGTTTTCTTCATTGAATACACCTCTTTTTGACCATTTTCATATTTATTATGCTCTG
TTTTTCAAACCATTTTTTTTCTTTTATTCATTCTTTGCTTCAAAAAACATATCTTCTTAC
AAATATTCTTCAATTAAAGAATATAGTAAAATCCCTAATATTATTCTAGATTTAAAACTT
TGAAAAAGTCATATGTTCCTTAGTTCATTTCATTATATTTTGTGCCTTTTGTGTTTTTTG

114614 AGGGTATTGTGGGGCACTCTTAAGCTTATCCACCAAGACTCTTTGTTAGTCACTGCTACT
TTGTCACTTAGATGCCCTGTTTGGCAATGGAATAGTCTATCACTTTATGTTTACCCTGAG
AAGCTGGAAGATACAACATCTCTTTCTGCTTGGGGGGCACCCATCATTAACTGAGAATTC
TAACATTCTACTTTGTAATACCTGGTCCAGCATCCCCATATTTTTCAACAATTCCTGTAT
TGTAATGAAATATACTTCCTTTTAAATCCTGTTTTCTTCATTGAATACACCTCTTTTTGA
[C,T]
CATTTTCATATTTATTATGCTCTGTTTTTCAAACCATTTTTTTTCTTTTATTCATTCTTT
GCTTCAAAAAACATATCTTCTTACAAATATTCTTCAATTAAAGAATATAGTAAAATCCCT

```
          AATATTATTCTAGATTTAAAACTTTGAAAAAGTCATATGTTCCTTAGTTCATTTCATTAT
          ATTTTGTGCCTTTTGTGTTTTTTGCAGTGCTAATTTGTTGTGCATGACGTAAGTGTTATT
          AATGATACGCCCCTCTCTAAGTTTGTGTATGTTGTGTAGCCTATTTAGCTGTTAAAATTA

124669    TATATTATGAACTCCTTTGTATTACTTTTATAGTAAAAAAAGTAGTAACAATTTAAAAAG
          CCAATTAACATTGATTCCTTATATTTTCTTCTAGATAATAATAACAGAGTAAAGCTGATA
          GCTGACGCTAGTGTTCCAGGTTCGGATTATATTAATGCCAGCTATATTTCTGTAAGTTAC
          TATTTTATATATTTTATAATTGTATAAAACATAATTACTGAAATTGTATTATCTTTCCAA
          TTACTTAAAACAACAAATTTATTACAACTCCTATGGATCTTAATATGCTAGTTATTTACA
          [G,A]
          CCACATTGTGTACCCTTATTTTATAGATGTGGATATGGATATGCCTAACAGAGATACTAA
          CTTATCAAAAATTATTTCACCAGTGCGCGGCAGATGTTCAACTTCAGGCTACACATCCCT
          GATCTTTCCACTAATTCATATGCTTTGTTAATGTATTCTCCATATGCAATGAAGTTTGCC
          AATCTCTGTGAATTAAAAATTATCAAATGGACAGTTATGTCCATATAACATGAAAATTTA
          TTATGCAGCTCTTCCCTTCTAGATCTGCAGTCCTTCAAGCGGGTAATAATGCCATCACCA

125409    TTGATTCATCCACTTCTTCCTAAGACGGGATTCTATCTCTAAACAACTCTGCTTTACAGT
          TGTTGGGTTTTTTTTTAACCAAGTTATGTCTCTTTATATTCTTACCCACTGACTTAAATT
          CTAATGCATAGCAAGCTTAACCATCTTCATTATGGTGAATCTACAAATACATGAAGATTT
          CCTCTGCTGCCCACACTCTCCATAGGCTTTTTCTTATCCATAGGTCTTCTCATCCATGCC
          CTCTATTTCCTTCAGTTCTATTAAGGCTCTTGTTATATGACGTTCCACCCTTTCTCCAAC
          [G,A]
          TCAAACATACTTGTGCTGTGTCTCATTCCCTCCAAGCCTTTGTCATGGAGGAAAAAAACG
          AATTAGTTCTAAATCTGATATTGGTTGATAACTAATCTAAAATTACAATCATATATTGGG
          TCCTGTTGTCAAAGGAGTGAATAATGGGAGAATTTAAGACTTTAAGACTTTTTAACCAGA
          GAAGTGAAGGAAAGTTTAGAGAAGCTAAGGTATTCTTTAAATTTCATTCTATTTTAATGC
          TAGAACTTTAAATCTGTATTTAAAGAATTACATGAATTTACTATTATGGTAACATTTTAT

129447    CCAGAGGAAAATCTCTGAGCTAATTTAAGGACTGCAATGAAAAGTGGCATCCATGGGTAA
          AGGTCATAATGAAAGTTGACCTGTGGAATGAAACTTACACTTTGTTCCATGTATCACAGA
          GCTTTAAAAACCAGTAAACTCTATATTCCAATTAAAGGGCAAAAGTCCAGGCAAGAAGTT
          TCCTCTCAGAAAAACTCAAAAGTTTGCACACACATATTCAAAGGTAGAAGCAGAAATAGC
          AAACAGAATTGACATACTTTCTTCATTTTCATAAGATACAATGGAAATATCTCCAAAACA
          [C,A]
          CTTTGGGCAAACATTTTACCTGGTGCTTTACCATTTTCTGAAATAAATTAGCCATTACAG
          GAAGAAAACTTAAATGTGTCTTAGCTTCTTTACATGAGAATCAAGGGGGGAAATGTGACC
          ATATAAAGATATATTTAAATAACAGATAATACATAGATATATGTATTAAAAAGAAATATA
          AAATAATATTTCAAATCCTGGAAAACTGAGATCATATAATGTTAGTTTTGTAAATAAGTT
          GTAACAAGATTGTATAGGAATAATCCCAATTATTTATATATGTGTATGTATATAAAATAT

135139    TTACCATGTTTTTCTTGGGTCAGAACTCCAGACAGTAAATGCCACTAGACTAATGACTAA
          TGCCACAGTTTAAGTAGATAAGTAATTTCTTAGAGGAAGAGTGTACATATATCTGCACAA
          CCAATAAATACATGGCAGAAACATCATGGAGTGGGTTTAGAGAGCTGGTTCTGGGCTCAA
          CCTGCCTTACCAATTTTGAGATCTTGGCAAGTTACTTCACCTTTCTAAGCTTCAATATCT
          TCATCTATAAAATGAGCATAATATTAGTACTAATTCACAATGATTTTATAAGAATATTGA
          [A,G]
          TATAAGATGCTTAGCAAACTGCTACAAAGACTCAGACTTAAGACCTTTATTAAGTTCTGT
          TATTATTGTAAATATTATTATGTAGTCCTTAATGTTTTATTCAAAAGTTAGACATAAATT
          TTGAGAACCATTTGTTGTGTAGTATATCAGATTGTGAGGATAAATTTAGACGTTGGAAAT
          TTTGAGTATTTAAGATTATCTAGTATTTACGGTATTCTAAAATATTAGGTAATTTTACAA
          CCAGCATATGTTTCATGCATTGATCGAAAACTAAAACACTGTATCTGTGAACACAGTGAT

148111    TATCTTCATTAGTTTCTTGTCTAAGACTTCATAGATACTAGTTACTCTCTGGGGTCCCTG
          AAGCAATAGTATTAACCCTCACACAAATCAGTAAATGTGAGTAGTAGTTGGTTAGACGGA
          TCAGTCATGGTAGATTTTTGTGTATTTTAATGTAGCAGATAGGAGATTCAAGCTTTTTTT
          CTCTCAAGCTTGAGAATACAGAGGGCATAGGTCTGGCTTACCTTGTAAAAAATGCCAGCA
          GCTAACAATGAAATTCTACCCAACACAGGCTGGGTATTTCTCTGATTTTTTGCCTTGGGT
          [A,T]
          TACAGTATTCCTAGAGTTACCAGAAAACTATAGTGGACAATTAGCGGTGGATGCCAAGAG
          AATGCTTGGAACTTTGAGAATGTTGGGGTGGACATTAATCAATTGATATAAGCTTTGGGT
          ATGGAGGACAACGTTATGTTATAATCATTAGAAGAAATTTCAAAGGCGATAAAGAAAAAC
          TATTTCAGAAACGCTCTTCCCTGAAACACCAAGAAAGTGACCTATTATGTTAATATTTTT
          GTTATATGCAATGTGCCCTGTTAGTTTTGTTAGAAAATGTACATTTTATTATATCCATTT

200822    ATGGGAGAGACATGTTATTCCTTTTGCCTTATTCTATTGGTTAGATACAAATCATAGGTC
          CCAACTAACTAAAGAAGAGGAGATTTTACAAAGCAGGAACAACAGGAGGTGGGTATAGTG
          GGTATCTACCTGAGAGGCCATGCACTACACTCCCCCAGCCTACTATTTTATATTTCAAAC
          ACTTATTAGAATAATCCTTCCAGATTTAAGTATGTTATTTACATTATGAAAGTAACCTAA
          TAAGAATTGAGAACAGATGACGAAGGTATATATGTGTTTAAGTAACCTAACTCTTCACTA
          [T,G]
          CATTGCAGAAAATCAATAGATTCTAAAAATGAGTGTTAACAGAGCAGTATATGCATATTA
```

FIGURE 3, page 83 of 87

TTTAGTGTTTTAGGGGTAAACACCATAAGAACTGAAAACAGGAGTGGTTTAAAGTGTTGC
TTCTGGGAAGTAAGAGGTAGGGAGGGTATAAACAGGGAATTGTTATTTTCATTATAAACC
CTTCATCATCTTTTTTTGTAGCCATGTAGATATAACATGATGATTAAACTTAAAAATATA
ACCCTCCTATGCTAGGCATGATTTGATCTCATTACCCTTATTGAATTTTTTTCCAGTGAA

207967 CATACATAACTCGATTAAATGTGTTTTTCTTTTACTAGATTTACCCACAATGAAGTAAAA
AGCATCAGATCACAAGCTTCATAGAAATTTACTTAACTGAAGGAATACTGTATCTGGTAT
ATCAAAATAACTCATTATTGAAGACTAAAATGTACGAATGCAAAAATCAGCTGAAGTAAT
TCAGCTGACATGGTATTTGTGCCAAGTCAACTATACACCCTGCAGTGTGCCAAAAAGTTA
CTTTTGCAACTTTAAATTATTGCCTTAATATTTTAGGAGAGAACTTGAAGTCACCAACAT
[A,G]
GAAAGGCCTATAAGCCCAAGAATTTGAGGAGACTGCAATTATTTGGAAGCGATATAGATA
TCTAGTCCCCCGTATAAATTCTTCTTACTGGCCTTATATTAAATGGCACCAATCCCAAGA
GTATTATTTTAAGGACATTAAACAGTTTGTCTCTTGTCCTTATAGGGTTAAAGAAATACA
CAAAATACAAAATGAGAGTGGCAGCCTCAACCCACGATGGAGAAAGTTCTTTGTCTGAAG
AAAATGACATCTTTGTGAGAACTTCAGAAGATGGTAAGAATATCAATTGCAGCTTTAATT

213624 CCTGAGATTCTTAGGTGCCATTCTAGGAACTTTGGAGTTTAATTTTAATGAGGAGCTTTT
GGAGAATTATGGAATAGGAACATTATATGATTTACAGTTTTCAAAGATTGCTGCTGAATA
TGTTGAATGTTGAAGTAAAGAGAAAAATGAAGATAAACTATTAGATTGTTTGTCTGAGTA
TCTGGGTGAGTGGTAGTGCCATTTACTTAGATGGGGCAGTCCAGGGAAGAGGTCAATATG
GAGAACATCCAGGAGTTCTGTTTGCAACATGTTTGAAATATCCAAGTGCCATTATGAAGG
[A,C]
AGTTAGATAAATAAGTTTAAAGCTCAGGGAAAAGATACAGAGCTGAATATATAATTTGGA
GCCTCACCACATCTTTGGTATTCAATCAAGGGATGAGGATAAAGTCATATCACTGGACAA
CAGGGGGAGACGTTAAGAAGCTTACAGCTATGTCGTGGGCAATACCACACATAGACTTTG
AGAAGTAGAAGAGCTAATCAAGGACAAAGCAGAAGTCACTGGAAATAGAAGGAAAACCAG
AAGAAGATAGTGCCTTCAAAGCCAAGTGAATAAAGATTTTCAAGTAGAAGGAGTTTATTC

215753 TCAGATAGAAAGGATAGTGGAATTATATTGCTAAATCGAACTATGCATTGAATTGCAATC
CTCTCAAAGTTTTAAAAGTATCAATATTCTTAAATTAGTTTTTCCTATTAAGTGTGCCTT
GACACCATAACCCAATAACTGGTAACAATCAAGGGGAGGGACACTGTATCTACATTTTTA
AGGCTTCTGAATTTTATTTATCTACTAAATTTATTATTAGTAATTTTTATATGCATTCAA
TTTAGAATACTAATAAAAAGTTTAATTTCTTTCATTTGAAAGAAAAGAGTTTTATAACAG
[A,G]
ACTCTTGAATGGCAATAATATTTACCTATTTAGTTTATATTGTTTAACCCTCCAAGTTAA
TTATTTATGTTATTGTTCTATGTACTCAATTTTTAAACCATTATCTTGGCCACTCTGATC
TTTCATCTGTGGTAAATAGTTTTCTACCTAAAGTACATTGTCTACAATTTCATTTACTGA
GGATGTGTTGAAAGCATTATCCCTCAATTTTTTTTATTGTCTGAATATGTTTTTAGTTTG
CTACTCTTTATTTTTCTGGGTATGGAATTCCAGTTGTTTTTCAGTTGATGTTGATTGTCA

216081 ATTTAGTTTATATTGTTTAACCCTCCAAGTTAATTATTTATGTTATTGTTCTATGTACTC
AATTTTTAAACCATTATCTTGGCCACTCTGATCTTTCATCTGTGGTAAATAGTTTTCTAC
CTAAAGTACATTGTCTACAATTTCATTTACTGAGGATGTGTTGAAAGCATTATCCCTCAA
TTTTTTTTATTGTCTGAATATGTTTTTAGTTTGCTACTCTTTATTTTTCTGGGTATGGAA
TTCCAGTTGTTTTTCAGTTGATGTTGATTGTCAGTCTAATTGTCATTCCTATGTAGAAGA
[T,A]
TTTTTTTTTCTGGTACTGTTAAGATGGTTCCTTTTTTGATATTCTGTATTTTCACAATGA
TATGTCTAAATATGGTTTAAAAAATTTCTGCTTGAGATTTACTGAAATTATTTGATCTGAT
GTTTGATGTCGTTGAATAATTTTGATGAGCCTCAGCCATTATCCCTTTAAATATTTCTTC
ATTTCTCTCTACTATTTTAGACCCCCTCCGGATATCATCTATGTCTCAACTGCCATTTTAT
ATTTTCCATAACTGTCTTCTTTGATCTACATTCTTGATAATTTCTTCAATACTATCATCC

218692 AGCCACAAATATTAGTTTAATGTTAATAGTTTCAGATTATTTTCATGCAGGGTATTACAA
TTTTGTCTTTTTGGTTAAATAAGCTAGGAGTTTATTGCAGGTCACATGAAAGAATACTAT
AGATCCATCCTTTTCCACATTATCCTATATCATTTTGTCTTCATAAATAAGAGCTACTAT
TGCCAAAGAATGACATTTTCACTTAGTTTTTATTTTTGGAAGATTGTGTTGACAGCCATT
TCATAGTTTGCCTCTTGCATATTATTAAATGATATTTTGTAAGTTTCAACTTACCTATTT
[G,T]
ATTTCTCTTTAGTACTGAAGAAATATACCCAATATATCATTGAGGTGTCTGCTAGTACAC
TGAAAGGTGAAGGAGTTCGGAGTGCTCCCATAAGTATACTGACGGAGGAAGATGGTAAAT
ATAATAGTGGATATTGATATACTTTGATTCTATAACATTCCAAGAAACACACGTATAGAA
TGAAACAATGTAAAAACTCCTCTAGTCATGGGTATCAGTTGTGTACCATACCAGCGTTAT
ACAGAGATTTCATTGTCATGGTATAAAAGAAGCTAGCAACATCAGATTTACATTCAGTGA

218705 AGTTTAATGTTAATAGTTTCAGATTATTTTCATGCAGGGTATTACAATTTTGTCTTTTTG
GTTAAATAAGCTAGGAGTTTATTGCAGGTCACATGAAAGAATACTATAGATCCATCCTTT
TCCACATTATCCTATATCATTTTGTCTTCATAAATAAGAGCTACTATTGCCAAAGAATGA
CATTTTCACTTAGTTTTTATTTTTGGAAGATTGTGTTGACAGCCATTTCATAGTTTGCCT
CTTGCATATTATTAAATGATATTTTGTAAGTTTCAACTTACCTATTTGATTTCTCTTTAG
[T,G]

FIGURE 3, page 84 of 87

ACTGAAGAAATATACCCAATATATCATTGAGGTGTCTGCTAGTACACTGAAAGGTGAAGG
AGTTCGGAGTGCTCCCATAAGTATACTGACGGAGGAAGATGGTAAATATAATAGTGGATA
TTGATATACTTTGATTCTATAACATTCCAAGAAACACACGTATAGAATGAAACAATGTAA
AAACTCCTCTAGTCATGGGTATCAGTTGTGTACCATACCAGCGTTATACAGAGATTTCAT
TGTCATGGTATAAAAGAAGCTAGCAACATCAGATTTACATTCAGTGAAATCAGGCATAAA

218754 TTGTCTTTTTGGTTAAATAAGCTAGGAGTTTATTGCAGGTCACATGAAAGAATACTATAG
ATCCATCCTTTTCCACATTATCCTATATCATTTTGTCTTCATAAATAAGAGCTACTATTG
CCAAAGAATGACATTTTCACTTAGTTTTTATTTTTGGAAGATTGTGTTGACAGCCATTTC
ATAGTTTGCCTCTTGCATATTATTAAATGATATTTTGTAAGTTTCAACTTACCTATTTGA
TTTCTCTTTAGTACTGAAGAAATATACCCAATATATCATTGAGGTGTCTGCTAGTACACT
[G,C]
AAAGGTGAAGGAGTTCGGAGTGCTCCCATAAGTATACTGACGGAGGAAGATGGTAAATAT
AATAGTGGATATTGATATACTTTGATTCTATAACATTCCAAGAAACACACGTATAGAATG
AAACAATGTAAAAACTCCTCTAGTCATGGGTATCAGTTGTGTACCATACCAGCGTTATAC
AGAGATTTCATTGTCATGGTATAAAAGAAGCTAGCAACATCAGATTTACATTCAGTGAAA
TCAGGCATAAAATGTTTTTTATTTTCTGAAGTCATCAGTACTCTGTAAAAAACAGTCAGT

218852 TCATAAATAAGAGCTACTATTGCCAAAGAATGACATTTTCACTTAGTTTTTATTTTTGGA
AGATTGTGTTGACAGCCATTTCATAGTTTGCCTCTTGCATATTATTAAATGATATTTTGT
AAGTTTCAACTTACCTATTTGATTTCTCTTTAGTACTGAAGAAATATACCCAATATATCA
TTGAGGTGTCTGCTAGTACACTGAAAGGTGAAGGAGTTCGGAGTGCTCCCATAAGTATAC
TGACGGAGGAAGATGGTAAATATAATAGTGGATATTGATATACTTTGATTCTATAACATT
[C,T]
CAAGAAACACACGTATAGAATGAAACAATGTAAAAACTCCTCTAGTCATGGGTATCAGTT
GTGTACCATACCAGCGTTATACAGAGATTTCATTGTCATGGTATAAAAGAAGCTAGCAAC
ATCAGATTTACATTCAGTGAAATCAGGCATAAAATGTTTTTTATTTTCTGAAGTCATCAG
TACTCTGTAAAAAACAGTCAGTCATGTTTTTCCATGGGGATTTTCAAGGCTTAAAATTTG
GTTTGAACGTTAACTGATATATGTCATGACTGAGTTTTTCAACTTTTACATTTTTAAGAA

219261 GAAGCTAGCAACATCAGATTTACATTCAGTGAAATCAGGCATAAAATGTTTTTTATTTTC
TGAAGTCATCAGTACTCTGTAAAAAACAGTCAGTCATGTTTTTCCATGGGGATTTTCAAG
GCTTAAAATTTGGTTTGAACGTTAACTGATATATGTCATGACTGAGTTTTTCAACTTTTA
CATTTTTAAGAATAGACATTAACATGAGCTTTGAAGCAGATTATGTTTATGTAAATGTTC
AGCACTTTTTTACGATATTAATGATTAACTTGATAATGAGATCAGGCTATTGTACAGGCT
[T,C]
CTGCATAATTGGACAAGATGCTATTCCCCAAAGTTAGTAGCTTTCATACTGAATATTTAA
ACATACCTTTCCCTAACCCAAATAAAATCAACTTTACTACTGAGGCCACTTTACATTGAT
ACCTTACCAAGTTAGACATATATTATGCTAAGAATATAACTTCTGAAAGATATATTTGGG
TTAGGATTTGCATTTTATGTTTTATACATTGCATATTTAAAGAAAATTATTATTTTTTTC
TGTAAAAGGAATTCCTATTTCCAAGAAGGGTAGGCCTGGAAGTATCATACGTGTTTGTGG

219359 TTTTTCCATGGGGATTTTCAAGGCTTAAAATTTGGTTTGAACGTTAACTGATATATGTCA
TGACTGAGTTTTTCAACTTTTACATTTTTAAGAATAGACATTAACATGAGCTTTGAAGCA
GATTATGTTTATGTAAATGTTCAGCACTTTTTTACGATATTAATGATTAACTTGATAATG
AGATCAGGCTATTGTACAGGCTTCTGCATAATTGGACAAGATGCTATTCCCCAAAGTTAG
TAGCTTTCATACTGAATATTTAAACATACCTTTCCCTAACCCAAATAAAATCAACTTTAC
[-,T]
ACTGAGGCCACTTTACATTGATACCTTACCAAGTTAGACATATATTATGCTAAGAATATA
ACTTCTGAAAGATATATTTGGGTTAGGATTTGCATTTTATGTTTTATACATTGCATATTT
AAAGAAAATTATTATTTTTTTCTGTAAAAGGAATTCCTATTTCCAAGAAGGGTAGGCCTG
GAAGTATCATACGTGTTTGTGGAGTATCTTTTCTTTTTCATCTTTCTTTCTTTCAAGTTT
CCCCATCTTCAAGCTAGGCCATAGCCTGTGACTGTTAAGGGCAGAATGTGCTTAGACACT

219362 TTCCATGGGGATTTTCAAGGCTTAAAATTTGGTTTGAACGTTAACTGATATATGTCATGA
CTGAGTTTTTCAACTTTTACATTTTTAAGAATAGACATTAACATGAGCTTTGAAGCAGAT
TATGTTTATGTAAATGTTCAGCACTTTTTTACGATATTAATGATTAACTTGATAATGAGA
TCAGGCTATTGTACAGGCTTCTGCATAATTGGACAAGATGCTATTCCCCAAAGTTAGTAG
CTTTCATACTGAATATTTAAACATACCTTTCCCTAACCCAAATAAAATCAACTTTACTAC
[-,A,T]
GAGGCCACTTTACATTGATACCTTACCAAGTTAGACATATATTATGCTAAGAATATAACT
TCTGAAAGATATATTTGGGTTAGGATTTGCATTTTATGTTTTATACATTGCATATTTAAA
GAAAATTATTATTTTTTTCTGTAAAAGGAATTCCTATTTCCAAGAAGGGTAGGCCTGGAA
GTATCATACGTGTTTGTGGAGTATCTTTTCTTTTTCATCTTTCTTTCTTTCAAGTTTCCC
CATCTTCAAGCTAGGCCATAGCCTGTGACTGTTAAGGGCAGAATGTGCTTAGACACTGCT

220577 CATCTAAATTCTTGGCCAAGTCATATGATTTCTAAGGAACAGGGTAAAGAACAAGACTCC
CTTGTTGAAAAAATTACAGAAAATCGAGAATGGATAAAGATCTGAGAACATTTGCCTCTTT
GGGAATTAGGAACTCCTTGCCCTCATGAAGCTCACGGTTAGAACAAGAGACCTAAATTTG
ACAAATGTGTGGACAAATAATTTTTATGATTTTTAATTACTGGTATAAATGTTCCCCCAA
ATTATTCACCAGGACAAAAGAAGGACCTAAGTTACTCTGGGGTGTGAGGTAAAGCGTAGC

FIGURE 3, page 85 of 87

[G,T]
GTGGAAGTTATGTCGAAGCTGTGACATGAAAATGAATAAAGAGGGAGGGTGAGAAATAGG
AAAGATCATGCCAGGTAGAGGAGTGAGAGATTTGTGAAGTCCTCATGCCAGGTAGAGGAG
TGACAGATTGTGAAGTTTCTTCTCAGCTACCTTGAGATGCTCTGAGATGACAAATTGAAT
GCACTGCAAAAGTTCTAATTTTTCTAGTTTCAATTTTGTTAGATTGTATTTTAGAATACA
TGTGCCAAAATATTTTAGAATACATATGCCAAAATGATTAAAACTTAGTCTGCTACAGTG

220995 GAGTGACAGATTGTGAAGTTTCTTCTCAGCTACCTTGAGATGCTCTGAGATGACAAATTG
AATGCACTGCAAAAGTTCTAATTTTTCTAGTTTCAATTTTGTTAGATTGTATTTTAGAAT
ACATGTGCCAAAATATTTTAGAATACATATGCCAAAATGATTAAAACTTAGTCTGCTACA
GTGGATGTACAGTGATTTTTTTAGATAGACATGTTAATTACGTTTACTTAGCAATAAAAT
GTTTTACATTAAGAATAAAATATTCGGAGATCTACTGAAGGTTAGCTTTTAAAGACACCA
[C,T]
GCTTTATCTGGTATTCCACATAAGCATCTTAAAGCATATTATAGAGTAGAAATGGTTAGT
TGCAACATATTAGTTTCTAAGTTACTGCTATTTTTAATTGAAGTCCTTTTTGTAAACAAT
AAACAGATTTTACAAGGATGCTAGGAAAAATATTTATAGGTATTTGCTTTGACAAATGAA
AGAGAATTTTCAGAGATAATTCTTATCTTGGGAAACAGACATCTCTAACTGATGTATACA
TTCCTGTGATAATCAATATTTGATAGCAACATTATTATAGTGCCAGTGAAAATAACAGAA

225263 TCTTACTGGAAGTGTGCCTATTTGCAGAATTAAAGAACACGATCAGAACTGGAAAGCAAA
TACTAATAGTGTGAGTCTTACAATGAGAAAAGAAAAAAAATTCTTACCTATGTAGAAGTC
AAAATAAAAGATTTGTGATGACTATTTCATGAAGAAAACATAGCTTAAAGAATAGGCAAC
CTTTTTCTAACTGACATCTGAGTATTATATAATATAGGTATTTTCTGTCAATATGTACAC
ATTCAGATTAATTAACATGTCAATATATGCTATTGGGGATAATTAAAAATTTTTAATGTG
[C,T]
TGTAAGAAACTATTGCTGATAGGAAGGTGATTTAGTCAACCTAGTTCTGCTTAGATCTAT
TTTTATGGAGCTTGAATTTTTATTCCTGTGAATTCTCTTATTTAAGGTCTATTGGGAAGC
CCTTACTCTCCGTTTCATCTCACACTTTATAAATCATTCTTGTGACCTTTACTCTGTTCA
AATAAATGTTAGCCATTGCAGAATTCCAAAGGGTATTTGGCATGATACATTTGATGTCTT
CAGTGTAAGTAATGTTATAGGAAAAATCCTGTTAAGTATTTTACATGTGCTATTTCATTT

226704 AATTGACTTAGTCATGAGTTTGTCGTTTAAAATAATAAAGAACATAAATAAAAACTGACA
CTAAAATACATATAATTCTCAGTAGCATGGCCACTTAATTAGTTTTAGAGTTCTTTCGGA
TAGCTAATTTATTCCTTAAAATATATATTATTCTTTCTGATTATAAGAACAGTAAATGTT
ATCTTACAAAACTTTGAAAAAACAAGAATAAAAAATGAAAATTATCCATAGACTTATCAT
ATAAAAAATGCTTTTATCATTTTGGTGCATTTCTGGCTTGTCTATTTCCCCCATTAATAT
[G,A]
TATCTATATGACTATACATTAATGAAAATAAGCTTGTGCTACATATGCAAGTTTATATCC
TGCCTTTTCTTTTTAACATGAAGTCATAAGCTTGTTATAACATAAGACTTTTGGAAACAC
GGATTTTAATGGTTATTATATTATTGGGTAACATGCAGTCATTACCAAACCAATTTAAGA
TACCTCCATTCTTCCAGGGGCATAGAGGAAAAATCTTGATGTCACCTGTGGCTCTTTTCT
CTCACAGTACACATCTAATCTATCAGTAAATCTTACCAGCACAATCATCAAAGTGTATTC

228390 CCTCGGCAACCAAATGGCAAAATTACCAGCTTCAAGATTAGTGTCAAGCATGCCAGAAGT
GGGATAGTAGTGAAAGATGTCTCAATCAGAGTAGAGGACATTTTGACTGGGAAATTGCCA
GAATGCAATGTAAGTATCACAGAACACTTTCTATGTCTTGAAAAATCTTAGATAAATTTA
ATTTTCATATTTCTAGCATCTAGATACTATATTTTTACCAAAGTTTTATTAGTTATTTGA
TTACTTATGGTATCATGTTATACACAACGTTTTATTATTTGATTACTTAGGGTATCATGT
[T,A]
ACACAATTGGCCTCATTCAGGTAGAATACAGGAATGGTTTGAGAATTCAAGAGTGAGGGA
TTAAAATCATTTAGGGAATTCGGAAAAGACTTCATCAAAGGAGTAGCATTTGTGATACAC
CATGGAGCAAGGACAGATAGAGATTTTGTGATGGTGGCATTCCCGGTGGAGGATACTTTA
TAAAGCCCTGAGGTGGAAAAGTGTAAGATATAATTGGAGAAAATATTTTACTTCCATATG
ACAGGAGGGAAGAGTACATGTAGGGTAATAGTTGAGGTTAAATTTGCAGAGGTAGACTGT

228472 CAATCAGAGTAGAGGACATTTTGACTGGGAAATTGCCAGAATGCAATGTAAGTATCACAG
AACACTTTCTATGTCTTGAAAAATCTTAGATAAATTTAATTTTCATATTTCTAGCATCTA
GATACTATATTTTTACCAAAGTTTTATTAGTTATTTGATTACTTATGGTATCATGTTATA
CACAACGTTTTATTATTTGATTACTTAGGGTATCATGTTACACAATTGGCCTCATTCAGG
TAGAATACAGGAATGGTTTGAGAATTCAAGAGTGAGGGATTAAAATCATTTAGGGAATTC
[G,T]
GAAAAGACTTCATCAAAGGAGTAGCATTTGTGATACACCATGGAGCAAGGACAGATAGAG
ATTTTGTGATGGTGGCATTCCCGGTGGAGGATACTTTATAAAGCCCTGAGGTGGAAAAGT
GTAAGATATAATTGGAGAAAATATTTTACTTCCATATGACAGGAGGGAAGAGTACATGTA
GGGTAATAGTTGAGGTTAAATTTGCAGAGGTAGACTGTCATTGTTGTGCATATCTTTGGT
AAAGAATTTGTCGTTACTCTGGTCATTGATGATAAACCTCATAATAGTAATGCTTTATTA

229014 AAGAATTTGTCGTTACTCTGGTCATTGATGATAAACCTCATAATAGTAATGCTTTATTAT
AGAATAAGCATCGTCATTTTAATTATATGATAAGCATAATAATGCTTTTCCTAAAATCAT
TTTGGTAATCTCTGTGTTACTATTAATGCAAACACAGTCAAACAGTTATTTTTGCTGTAA
ATACTTTATAAAAGTCTAAAAATCTTCTTTTTCAACTTATGATATAGTTCTAATACACGC

ACACACCTAACGTGTGAGCTAGTGGCATACTACTACTTTTTAGTACTTATGAGAAAAAAA
[A,C]
GTTCATTAACAGTAAGAAAGCAGCATTTGAACATACACAAGAGTAAAATTATTTCAGCTC
TTTGGCTCTTGCACTGTTAACATGAAGCTTAAAAATTCTTACAGATGATTGTGCTGTAGT
TTTACCTTTATTTTAAGCCACTTGAAATTCTATTCGTAAAGGTTAAGGTATAAGGAATAC
AATAAATATGTCCTCTTCTAAAACTGCAGACATAAATGGGTACAATTAAAATCTAGCAAA
TTTGTCTATAACTTTTGCATGTTATGTGTGTATGTATAAGCATAAAAGAAAAAGAAATGA

229585 TATGTATAAGCATAAAAGAAAAAGAAATGAATTACATGTTCTTATTCTTATGTTCACCAA
GAGATACAACATTATTTCTCTATTGATCTTATTTTATTTACTAGGAGAATAGTGAATCTT
TTTTATGGAGTACAGCCAGCCCTTCTCCAACCCTTGGTAGAGTTACACCTCCATCGCGTA
CCACACATTCATCAAGCACGTTGACACAGAATGAGATCAGCTCTGTGTGGAAAGAGCCTA
TCAGTTTTGTAGTGACACACTTGAGACCTTATACAACATATCTTTTTGAAGTTTCAGCTG
[C,T]
TACAACTGAAGCAGGTTATATTGATAGTACGATTGTCAGAACACCAGAATCAGGTATGGT
TCACTTTTTGTAGATAAAAAGATTTAAATGATTAGAGAATAATGTTTAATTTATGTAGAT
ATTTAATTTTAATCTTCTTTACCTTTCAGTAACTTTTTTCCCCTAATAATATACCATAGG
CATCCCATCAAGGGTTTCTTCGAATTTCTATACTCTTTTATATTATAGCACAAAATAAGT
ATTTGAAAGGAGAAAGATTTGCAAAAAACAATTCTTGAGCCACTGACCGTGATCCTCATA

237335 ACCAACTATAGTAACAGGGAAATTTAGTTATAGAGTTGAATTATATGGACCATCAGGTAA
GCCTTAATTGGTTTTGTGTTTGCCTTTTGGAGTGAGAATAATAAAATATGTTACCAATAT
CAAACTCTGTTTAAAAGTATCAGACTCTTTTTAAAAGACTTTAAGATTGAAGCAAACAAT
AGGAAAGTCATAAGGAAGGGGAGGTCCTTTGATTTTTTAATTCAAAACCATAAATGAGTA
TAAGAATGACAAAACTATTCATGTTCCACATTTCATGTGATGCATGTGAAAAACTAGAGA
[T,G]
AACTCCTCAAGAAAAAAGTGTTAGTGGAGATATACATCTTCAAATATTTGAACAAGAAGT
CCTTGGCTTACATTCATGAAGAACAATGGACTTTGACTATATTAAATTAGATTTCTATTC
ACTGCTAGGAGCCTAGTTTTTAATCATTAGAAAGAGCTCTCTAAAAATAACATGGAAAAT
CTCTGTATCTTCTGCTCTATTTTGCTGTGGACCTAAAACTGCTTTAAAAAAGAAAACCTA
TTAAAATTTTTGGGCAGCTTTATAAAGTGGCAAGTTCTCCAACTTTGTAAGCAAGCAGGA

237771 GTTTTTAATCATTAGAAAGAGCTCTCTAAAAATAACATGGAAAATCTCTGTATCTTCTGC
TCTATTTTGCTGTGGACCTAAAACTGCTTTAAAAAAGAAAACCTATTAAAATTTTTGGGC
AGCTTTATAAAGTGGCAAGTTCTCCAACTTTGTAAGCAAGCAGGACCTGGGCATCCACTT
GCCAGAGATACTTTGAGAGGATCAAGTATTATATCATTAGGATCAAGTATTATATCATTA
GAAGTGAATTATGTAAAGTCTAAAATTCTCTCCTGATTGAGAGCCTCTGATTCTATGAAA
[T,G]
AAGTTTAATTCTAACAATGATGAGATAAATAATAAAGCCACATATTATCATTTATTTGGG
GGCATCAAAAAAGATACAGAGTTCCAACTCATTTTATTTTGCAATTTCTGTGGTATGAAT
CACTCATCACCATCATGAGTAACCTTTATCTTTCATCCCTAAGTAACTTATGCTCCTAAA
ATTCTGAAATACTTTTACTTCCTAAAAAAAGATAATTCCCTCCACTCACCCATCCGATAC
ACAGAAACAGACATGGATACACAGCTACATCTTTTCTGTCTGACATTATTGTTCAATACT

239304 AGGTGATTAAATCAATGGATTGTTGATTTCAGTGGATTTAAAGAATTATCAGTTCAGAAT
TATAGAGGAAATGTAAAGGAAGTAAGCAAAAGTGGTTAGAAAAAAGTTGCATGAAATTGA
GATTCTTAATGATACGGAGTAATTGGTGATAGTAATGTCCAAGTTATGATCTTGAGGGAG
TGGCTGAAATTCTGAAAAACTAGATTATTTAAGGAAATATCTAAGTAATTTAAGGATTAA
GTCTCAGGATATTAAAATCAGCACAAATTAAGATGGTAGCCTTGAACCAAAGCTAGACCA
[T,C]
GAAAGTAAATGAGAGTAAATGACCCTCAGGTTAGTAGATTACGACAACTGTGAGGGCTAG
TGGATTTCACTGGTGATACAGTATTTAAAGCTGTGGGCTTTTATAAGGAGGGAGAGAGAA
TAGTAAATAAAGTGGAGCAATGAGGAGCAAGGACAACACCTACCACACCTAAAGGCCTGG
TTACTTGAGAGCTGTGGGGCAAAAACAGACTGCCACCATTTGGGGTGGCTGCAGGGGAAC
AAAAACAGTGTTCTCAGGAAAGAGCCAGTTTGTAGTTAGAGCAAGAAGGTAAAGGAAACA

239767 CCACACCTAAAGGCCTGGTTACTTGAGAGCTGTGGGGCAAAAACAGACTGCCACCATTTG
GGGTGGCTGCAGGGGAACAAAAACAGTGTTCTCAGGAAAGAGCCAGTTTGTAGTTAGAGC
AAGAAGGTAAAGGAAACATTTAAAGCAAAGTCGAAGATTTAAAGTATTGTGCTGACAGAC
TAAGGAATTTTGTTCAGAAGCTAAACTAGAAATATTTTCTAAATATATCCTCTTATAGAA
GATAATGAAATTATTTAGCATTTTTTTTTTTTTTTTTTTTTTTTTTTTGAGACGGAGTCT
[C,T]
GCTCTGTCGCCCAGGCTGGAGTGCAGTGGCGGGATCTCGGCTCACTGCAAGCTCCGCCTC
CCGGGTTCACGCCATTCTCCTGCCTCAGCCTCCCGAGTAGCTGGGACTACAGGCGCCCGC
CACTACGCCCGGCTAATTTTTTGTATTTTTAGTAGAGACGGGGTTTCACCGTTTAGCCG
GGATGGTCTCGATCTCCTGACCTCGTGATCCGCCCGCCTCGGCCTCCCAAAGTTATTTAG
CATTTTAATTGAATAAATTTGAGTATAAAATCTGGTCACTTTTTGAACTGATAAAATTTG

Chromosome map:
Chromosome 12

FIGURE 3, page 87 of 87

SEQUENCE LISTING

```
<160> NUMBER OF SEQ ID NOS: 4

<210> SEQ ID NO 1
<211> LENGTH: 7108
<212> TYPE: DNA
<213> ORGANISM: Human

<400> SEQUENCE: 1

taattgtgta cttgccagaa ggatctgtct ttaaatcatt aatgcaggca acatttctct     60

ctagagccat caatgtgatt ctactggctg aaaaatgtaa taaagatgga ttttcttatc    120

atttttcttt tactttttat tgggacttca gagacacagg ttgatgtttc caatgtcgtt    180

cctggtacta ggtacgatat aaccatctct tcaatttcta caacatacac ctcacctgtt    240

actagaatag tgacaccaaa tgtaacaaaa ccagggcctc cagtcttcct agccggggaa    300

agagtcggat ctgctgggat tcttctgtct tggaatacac cacctaatcc aaatggaagg    360

attatatctt acattgtcaa atataaggaa gtttgtccgt ggatgcaaac agtatataca    420

caagtcagat caaagccaga cagtctggaa gttcttctta ctaatcttaa tcctggaaca    480

acatatgaaa ttaaggttgc tgctgaaaac agtgctggca ttggagtgtt tagtgatcca    540

tttctcttcc aaactgcaga aagtgctcca ggaaaagtgg tgaatctcac agttgaggcc    600

tacaacgctt cagcagttaa gctgatttgg tatttacctc ggcaaccaaa tggcaaaatt    660

accagcttca agattagtgt caaacatgcc agaagtggga tagtagtgaa agatgtctca    720
```

-continued

```
atcagagtag aggacatttt gactgggaaa ttgccagaat gcaatgagaa tagtgaatct    780
tttttatgga gtacagccag cccttctcca acccttggta gagttacacc tccatcgcgt    840
accacacatt catcaagcac gttgacacag aatgagatca gctctgtgtg gaaagagcct    900
atcagttttg tagtgacaca cttgagacct tatacaacat atctttttga agtttcagct    960
gctacaactg aagcaggtta tattgatagt acgattgtca gaacaccaga atcagtgcct   1020
gaaggaccac cacaaaactg cgtaacaggc aacatcacag gaaagtcctt ttcaatttta   1080
tgggacccac caactatagt aacagggaaa tttagttata gagttgaatt atatggacca   1140
tcaggtcgca ttttggataa cagcacaaaa gacctcaagt ttgcattcac taacctaaca   1200
ccatttacaa tgtatgatgt ctatattgcg gctgaaacca gtgcagggac tgggcccaag   1260
tcaaatattt cagtattcac tccaccagat gttccagggg cagtgtttga tttacaactt   1320
gcagaggtag aatccacgca agtaagaatt acttggaaga aaccacgaca accaaatgga   1380
attattaacc aataccgagt gaaagtgcta gttccagaga caggaataat tttggaaaat   1440
actttgctca ctggaaataa tgagtatata aatgacccca tggctccaga aattgtgaac   1500
atagtagagc caatggtagg attatatgag ggttcagcag agatgtcgtc tgaccttcac   1560
tcacttgcta catttatata taacagccat ccagataaaa actttcctgc aaggaataga   1620
gctgaagacc agacttcacc agttgtaact acaaggaatc agtatattac tgacattgca   1680
gctgaacagc tgtcttatgt tatcaggaga cttgtacctt tcactgagca catgattagt   1740
gtatctgctt tcaccatcat gggagaagga ccaccaacag ttctcagtgt taggacacgt   1800
cagcaagtgc caagctccat taaaattata aactataaaa atattagttc ttcatctatt   1860
ttgttatatt gggatcctcc agaatatccc aatggaaaaa taactcacta tacgatttat   1920
gcaatggaat tggatacaaa cagagcattc cagataacta ccatagataa cagctttctc   1980
ataacagggt taaagaaata cacaaaatac aaaatgagag tggcagcctc aacccacgat   2040
ggagaaagtt ctttgtctga agaaaatgac atctttgtga gaacttcaga agatgaaccg   2100
gaatcatcac ctcaagatgt cgaagtaatt gatgttaccg cagatgaaat aaggttgaag   2160
tggtcaccac ccgaaaagcc caatgggatc attattgctt atgaagtgct atataaaaat   2220
atagatactt tatatatgaa gaacacatca acaacagaca taatattaag gaacttaaga   2280
cctcacaccc tctataacat ttctgtaagg tcttacacca gatttggtca tggcaatcag   2340
gtatcttctt tactctctgt aaggacttcg gagactgtgc ctgatagtgc accagaaaat   2400
atcacttaca aaaatatttc ttctggagag attgagctat cattccttcc cccaagtagt   2460
cccaatggaa tcataaaaaa atatacaatt tatctcaaga gaagtaatgg aaatgaggaa   2520
agaactataa atacaacctc tttaacccaa aacattaaag tactgaagaa atatacccaa   2580
tatatcattg aggtgtctgc tagtacactg aaaggtgaag gagttcggag tgctcccata   2640
agtatactga cggaggaaga tgctcctgat tctcccccctc aagacttctc tgtaaaacag   2700
ttgtctggtg tcacggtgaa gttgtcatgg caaccacccc tggagccaaa tggaattatc   2760
ctttattaca cagtttatgt ctggaataga tcatcattaa aaactattaa tgtcactgaa   2820
acatcattgg agttatcaga tttggattat aatgttgaat acagtgctta tgtaacagct   2880
agcaccagat ttggtgatgg gaaaacagga agcaatatca ttagctttca aacaccagag   2940
ggagcaccaa gcgatcctcc caaagatgtt tattatgcaa acctcagttc ttcatcaata   3000
attcttttct ggacacctcc ttcaaaacct aatgggatta tacaatatta ctctgtttat   3060
tacagaaata cttcaggtac ttttatgcag aattttacac tccatgaact aaccaatgac   3120
```

-continued

```
tttgacaata tgactgtatc cacaattata gataaactga caatattcag ctactataca   3180
ttttggttaa cagcaagtac ttcagttgga aatgggaata aaagcagtga catcattgaa   3240
gtatacacag atcaagacat acctgaaggg tttgttggaa acctgactta cgaatccatt   3300
tcgtcaactg caataaatgt aagctgggtc ccaccggctc aaccaaacgg tctagtcttc   3360
tactatgttt cactgatctt acagcagact cctcgccatg tgagaccacc tcttgttaca   3420
tatgagagaa gcatatattt tgataatctg gaaaaataca ctgattatat attaaaaatt   3480
actccatcaa cagaaaaggg attctctgat acctatactg cccagctata catcaagact   3540
gaagaagatg tcccagaaac ttcaccaata atcaacactt ttaaaaacct ttcctctacc   3600
tcagttctct tatcatggga tcccccagta aagccaaatg gtgcaataat aagttatgat   3660
ttaactttac aaggaccaaa tgaaaattat tctttcatta cttctgataa ttacataata   3720
ttggaagagc tttcaccatt tacattatat agctttttg ctgccgcaag aactagaaaa   3780
ggacttggtc cttccagtat tcttttcttt tacacagatg agtcagtgcc gttagcacct   3840
ccacaaaatt tgactttaat caactgtact tcagactttg tatggctgaa atggagccca   3900
agtcctcttc caggtggtat tgttaaagta tatagtttta aaattcatga acatgaaact   3960
gacactatat attataagaa tatatcagga tttaaaactg aagccaaact tgttggactg   4020
gaaccagtca gcacctactc tatccgtgta tctgcgttca ccaaagttgg aaatggcaat   4080
caatttagta atgtagtaaa attcacaacc caagaatcag ttccagatgt cgtgcagaat   4140
atgcagtgca tggcaactag ctggcagtca gttttagtga aatgggatcc acccaaaaag   4200
gcaaatggaa taataacgca gtatatggta acagttgaaa ggaattctac aaaagtttct   4260
ccccaagatc acatgtacac tttcataaag cttcttgcca atacctcata tgtctttaaa   4320
gtaagagctt caacctcagc tggtgaaggt gatgaaagca catgccatgt cagcacacta   4380
cctgaaacag ttcccagtgt tcccacaaat attgcttttt ctgatgttca gtcaactagt   4440
gcaacattga catggataag acctgacact atccttggct actttcaaaa ttacaaaatt   4500
accactcaac ttcgtgctca aaaatgcaaa gaatgggaat ccgaagaatg tgttgaatat   4560
caaaaaattc aatacctcta tgaagctcac ttaactgaag agacagtata tggattaaag   4620
aaatttagat ggtatagatt ccaagtggct gccagcacca atgctggcta tggcaatgct   4680
tcaaactgga tttctacaaa aactctgcct ggccctccag atggtcctcc tgaaaatgtt   4740
catgtagtag caacatcacc ttttagcatc agcataagct ggagtgaacc tgctgtcatt   4800
actggaccaa catgttatct gattgatgtc aaatcggtag ataatgatga atttaatata   4860
tccttcatca agtcaaatga agaaaataaa accatagaaa ttaaagattt agaaatattc   4920
acaaggtatt ctgtagtgat cactgcattt actgggaaca ttagtgctgc atatgtagaa   4980
gggaagtcaa gtgctgaaat gattgttact actttagaat cagccccaaa ggacccacct   5040
aacaacatga catttcagaa gataccagat gaagttacaa aatttcaatt aacgttcctt   5100
cctccttctc aacctaatgg aaatatccaa gtatatcaag ctctggttta ccgagaagat   5160
gatcctactg ctgtccagat tcacaacctc agtattatac agaaaaccaa cacattcgtc   5220
attgcaatgc tagaaggact aaaaggtgga catacataca atatcagtgt ttacgcagtc   5280
aatagtgctg gtgcaggtcc aaaggttccg atgagaataa ccatggatat caaagctcca   5340
gcacgaccaa aaaccaaacc aacccctatt tatgatgcca caggaaaact gcttgtgact   5400
tcaacaacaa ttacaatcag aatgccaata tgttactaca gtgatgatca tggaccaata   5460
```

-continued

```
aaaaatgtac aagtgcttgc gacagaaaca ggagctcagc atgatggaaa tgtaacaaag   5520
tggtatgatg catattttaa taaagcaagg ccatatttta caaatgaagg ctttcctaac   5580
cctccatgta cagaaggaaa gacaaagttt agtggcaatg aagaaatcta catcataggt   5640
gctgataatg catgcatgat tcctggcaat gaagacaaaa tttgcaatgg accactgaaa   5700
ccaaaaaagc aatacttatt taaatttaga gctacaaata ttatgggaca atttactgac   5760
tctgattatt ctgaccctgt taagacttta ggggaaggac tttcagaaag aaccgtagag   5820
atcattcttt ccgtcacttt gtgtatcctt tcaataattc tccttggaac agctattttt   5880
gcatttgcaa gaattcgaca gaagcagaaa gaaggtggca catactctcc tcaggatgca   5940
gaaattattg acactaaatt gaagctggat cagctcatca cagtggcaga cctggaactg   6000
aaggacgaga gattaacgcg gccaataagc aagaaatcct tcctgcaaca tgttgaagag   6060
ctttgcacaa acaacaacct aaagtttcaa gaagaatttt cggaattacc aaaatttctt   6120
caggatcttt cttcaactga tgctgatctg ccttggaata gagcaaaaaa ccgtttccca   6180
aacataaaac catataataa taataacaga gtaaagctga tagctgacgc tagtgttcca   6240
ggttcggatt atattaatgc cagctatatt tctggttatt tatgtccaaa tgaatttatt   6300
gctactcaag gtccactacc aggaacagtt ggagattttt ggagaatggt gtgggaaacc   6360
agggcaaaaa cattagtaat gctaacacag tgttttgaaa aaggacggat cagatgccat   6420
cagtattggc cagaggacaa caagccagtt actgtctttg gagatatagt gattacaaag   6480
ctaatggagg atgttcaaat agattggact atcagggatc tgaaaattga aaggcatggg   6540
gattgcatga ctgttcgaca gtgtaacttt actgcctggc cagagcatgg ggttcctgag   6600
aacagcgccc ctctaattca ctttgtgaag ttggttcgag caagcagggc acatgacacc   6660
acacctatga ttgttcactg cagtgctgga gttggaagaa ctggagtttt tattgctctg   6720
gaccatttaa cacaacatat aaatgaccat gattttgtgg atatatatgg actagtagct   6780
gaactgagaa gtgaaagaat gtgcatggtg cagaatctgg cacagtatat ctttttacac   6840
cagtgcattc tggatctctt atcaaataag ggaagtaatc agcccatctg ttttgttaac   6900
tattcagcac ttcagaagat ggactctttg gacgccatgg aaggtgatgt tgagcttgaa   6960
tgggaagaaa ccactatgta aatattcaga ccaaaggata caattggaag agatttttaa   7020
atcccagggg ccaaagttac cccctcattc ttccgaattg aaatgtgcaa ccttaaagaa   7080
atatctatgc ttctctcact gtgccttt                                      7108
```

<210> SEQ ID NO 2
<211> LENGTH: 2291
<212> TYPE: PRT
<213> ORGANISM: Human

<400> SEQUENCE: 2

```
Met Asp Phe Leu Ile Ile Phe Leu Leu Leu Phe Ile Gly Thr Ser Glu
 1               5                  10                  15

Thr Gln Val Asp Val Ser Asn Val Val Pro Gly Thr Arg Tyr Asp Ile
            20                  25                  30

Thr Ile Ser Ser Ile Ser Thr Thr Tyr Thr Ser Pro Val Thr Arg Ile
        35                  40                  45

Val Thr Pro Asn Val Thr Lys Pro Gly Pro Pro Val Phe Leu Ala Gly
    50                  55                  60

Glu Arg Val Gly Ser Ala Gly Ile Leu Leu Ser Trp Asn Thr Pro Pro
65                  70                  75                  80
```

-continued

```
Asn Pro Asn Gly Arg Ile Ile Ser Tyr Ile Val Lys Tyr Lys Glu Val
                85                  90                  95

Cys Pro Trp Met Gln Thr Val Tyr Thr Gln Val Arg Ser Lys Pro Asp
            100                 105                 110

Ser Leu Glu Val Leu Leu Thr Asn Leu Asn Pro Gly Thr Thr Tyr Glu
        115                 120                 125

Ile Lys Val Ala Ala Glu Asn Ser Ala Gly Ile Gly Val Phe Ser Asp
    130                 135                 140

Pro Phe Leu Phe Gln Thr Ala Glu Ser Ala Pro Gly Lys Val Val Asn
145                 150                 155                 160

Leu Thr Val Glu Ala Tyr Asn Ala Ser Ala Val Lys Leu Ile Trp Tyr
                165                 170                 175

Leu Pro Arg Gln Pro Asn Gly Lys Ile Thr Ser Phe Lys Ile Ser Val
            180                 185                 190

Lys His Ala Arg Ser Gly Ile Val Val Lys Asp Val Ser Ile Arg Val
        195                 200                 205

Glu Asp Ile Leu Thr Gly Lys Leu Pro Glu Cys Asn Glu Asn Ser Glu
    210                 215                 220

Ser Phe Leu Trp Ser Thr Ala Ser Pro Ser Pro Thr Leu Gly Arg Val
225                 230                 235                 240

Thr Pro Pro Ser Arg Thr Thr His Ser Ser Ser Thr Leu Thr Gln Asn
                245                 250                 255

Glu Ile Ser Ser Val Trp Lys Glu Pro Ile Ser Phe Val Val Thr His
            260                 265                 270

Leu Arg Pro Tyr Thr Thr Tyr Leu Phe Glu Val Ser Ala Ala Thr Thr
        275                 280                 285

Glu Ala Gly Tyr Ile Asp Ser Thr Ile Val Arg Thr Pro Glu Ser Val
    290                 295                 300

Pro Glu Gly Pro Pro Gln Asn Cys Val Thr Gly Asn Ile Thr Gly Lys
305                 310                 315                 320

Ser Phe Ser Ile Leu Trp Asp Pro Pro Thr Ile Val Thr Gly Lys Phe
                325                 330                 335

Ser Tyr Arg Val Glu Leu Tyr Gly Pro Ser Gly Arg Ile Leu Asp Asn
            340                 345                 350

Ser Thr Lys Asp Leu Lys Phe Ala Phe Thr Asn Leu Thr Pro Phe Thr
        355                 360                 365

Met Tyr Asp Val Tyr Ile Ala Ala Glu Thr Ser Ala Gly Thr Gly Pro
    370                 375                 380

Lys Ser Asn Ile Ser Val Phe Thr Pro Pro Asp Val Pro Gly Ala Val
385                 390                 395                 400

Phe Asp Leu Gln Leu Ala Glu Val Glu Ser Thr Gln Val Arg Ile Thr
                405                 410                 415

Trp Lys Lys Pro Arg Gln Pro Asn Gly Ile Ile Asn Gln Tyr Arg Val
            420                 425                 430

Lys Val Leu Val Pro Glu Thr Gly Ile Ile Leu Glu Asn Thr Leu Leu
        435                 440                 445

Thr Gly Asn Asn Glu Tyr Ile Asn Asp Pro Met Ala Pro Glu Ile Val
    450                 455                 460

Asn Ile Val Glu Pro Met Val Gly Leu Tyr Glu Gly Ser Ala Glu Met
465                 470                 475                 480

Ser Ser Asp Leu His Ser Leu Ala Thr Phe Ile Tyr Asn Ser His Pro
                485                 490                 495

Asp Lys Asn Phe Pro Ala Arg Asn Arg Ala Glu Asp Gln Thr Ser Pro
```

-continued

```
            500                 505                 510

Val Val Thr Thr Arg Asn Gln Tyr Ile Thr Asp Ile Ala Ala Glu Gln
        515                 520                 525

Leu Ser Tyr Val Ile Arg Arg Leu Val Pro Phe Thr Glu His Met Ile
    530                 535                 540

Ser Val Ser Ala Phe Thr Ile Met Gly Glu Gly Pro Pro Thr Val Leu
545                 550                 555                 560

Ser Val Arg Thr Arg Gln Gln Val Pro Ser Ser Ile Lys Ile Ile Asn
                565                 570                 575

Tyr Lys Asn Ile Ser Ser Ser Ser Ile Leu Leu Tyr Trp Asp Pro Pro
            580                 585                 590

Glu Tyr Pro Asn Gly Lys Ile Thr His Tyr Thr Ile Tyr Ala Met Glu
        595                 600                 605

Leu Asp Thr Asn Arg Ala Phe Gln Ile Thr Thr Ile Asp Asn Ser Phe
    610                 615                 620

Leu Ile Thr Gly Leu Lys Lys Tyr Thr Lys Tyr Lys Met Arg Val Ala
625                 630                 635                 640

Ala Ser Thr His Asp Gly Glu Ser Ser Leu Ser Glu Glu Asn Asp Ile
                645                 650                 655

Phe Val Arg Thr Ser Glu Asp Glu Pro Glu Ser Ser Pro Gln Asp Val
            660                 665                 670

Glu Val Ile Asp Val Thr Ala Asp Glu Ile Arg Leu Lys Trp Ser Pro
        675                 680                 685

Pro Glu Lys Pro Asn Gly Ile Ile Ile Ala Tyr Glu Val Leu Tyr Lys
    690                 695                 700

Asn Ile Asp Thr Leu Tyr Met Lys Asn Thr Ser Thr Thr Asp Ile Ile
705                 710                 715                 720

Leu Arg Asn Leu Arg Pro His Thr Leu Tyr Asn Ile Ser Val Arg Ser
                725                 730                 735

Tyr Thr Arg Phe Gly His Gly Asn Gln Val Ser Ser Leu Leu Ser Val
            740                 745                 750

Arg Thr Ser Glu Thr Val Pro Asp Ser Ala Pro Glu Asn Ile Thr Tyr
        755                 760                 765

Lys Asn Ile Ser Ser Gly Glu Ile Glu Leu Ser Phe Leu Pro Pro Ser
    770                 775                 780

Ser Pro Asn Gly Ile Ile Lys Lys Tyr Thr Ile Tyr Leu Lys Arg Ser
785                 790                 795                 800

Asn Gly Asn Glu Glu Arg Thr Ile Asn Thr Thr Ser Leu Thr Gln Asn
                805                 810                 815

Ile Lys Val Leu Lys Lys Tyr Thr Gln Tyr Ile Ile Glu Val Ser Ala
            820                 825                 830

Ser Thr Leu Lys Gly Glu Gly Val Arg Ser Ala Pro Ile Ser Ile Leu
        835                 840                 845

Thr Glu Glu Asp Ala Pro Asp Ser Pro Pro Gln Asp Phe Ser Val Lys
    850                 855                 860

Gln Leu Ser Gly Val Thr Val Lys Leu Ser Trp Gln Pro Pro Leu Glu
865                 870                 875                 880

Pro Asn Gly Ile Ile Leu Tyr Tyr Thr Val Tyr Val Trp Asn Arg Ser
                885                 890                 895

Ser Leu Lys Thr Ile Asn Val Thr Glu Thr Ser Leu Glu Leu Ser Asp
            900                 905                 910

Leu Asp Tyr Asn Val Glu Tyr Ser Ala Tyr Val Thr Ala Ser Thr Arg
        915                 920                 925
```

-continued

```
Phe Gly Asp Gly Lys Thr Gly Ser Asn Ile Ile Ser Phe Gln Thr Pro
    930                 935                 940

Glu Gly Ala Pro Ser Asp Pro Pro Lys Asp Val Tyr Tyr Ala Asn Leu
945                 950                 955                 960

Ser Ser Ser Ser Ile Ile Leu Phe Trp Thr Pro Pro Ser Lys Pro Asn
                965                 970                 975

Gly Ile Ile Gln Tyr Tyr Ser Val Tyr Tyr Arg Asn Thr Ser Gly Thr
            980                 985                 990

Phe Met Gln Asn Phe Thr Leu His Glu Leu Thr Asn Asp Phe Asp Asn
        995                 1000                1005

Met Thr Val Ser Thr Ile Ile Asp Lys Leu Thr Ile Phe Ser Tyr Tyr
    1010                1015                1020

Thr Phe Trp Leu Thr Ala Ser Thr Ser Val Gly Asn Gly Asn Lys Ser
1025                1030                1035                1040

Ser Asp Ile Ile Glu Val Tyr Thr Asp Gln Asp Ile Pro Glu Gly Phe
                1045                1050                1055

Val Gly Asn Leu Thr Tyr Glu Ser Ile Ser Ser Thr Ala Ile Asn Val
            1060                1065                1070

Ser Trp Val Pro Pro Ala Gln Pro Asn Gly Leu Val Phe Tyr Tyr Val
        1075                1080                1085

Ser Leu Ile Leu Gln Gln Thr Pro Arg His Val Arg Pro Pro Leu Val
    1090                1095                1100

Thr Tyr Glu Arg Ser Ile Tyr Phe Asp Asn Leu Glu Lys Tyr Thr Asp
1105                1110                1115                1120

Tyr Ile Leu Lys Ile Thr Pro Ser Thr Glu Lys Gly Phe Ser Asp Thr
                1125                1130                1135

Tyr Thr Ala Gln Leu Tyr Ile Lys Thr Glu Glu Asp Val Pro Glu Thr
            1140                1145                1150

Ser Pro Ile Ile Asn Thr Phe Lys Asn Leu Ser Ser Thr Ser Val Leu
        1155                1160                1165

Leu Ser Trp Asp Pro Pro Val Lys Pro Asn Gly Ala Ile Ile Ser Tyr
    1170                1175                1180

Asp Leu Thr Leu Gln Gly Pro Asn Glu Asn Tyr Ser Phe Ile Thr Ser
1185                1190                1195                1200

Asp Asn Tyr Ile Ile Leu Glu Glu Leu Ser Pro Phe Thr Leu Tyr Ser
                1205                1210                1215

Phe Phe Ala Ala Ala Arg Thr Arg Lys Gly Leu Gly Pro Ser Ser Ile
            1220                1225                1230

Leu Phe Phe Tyr Thr Asp Glu Ser Val Pro Leu Ala Pro Pro Gln Asn
        1235                1240                1245

Leu Thr Leu Ile Asn Cys Thr Ser Asp Phe Val Trp Leu Lys Trp Ser
    1250                1255                1260

Pro Ser Pro Leu Pro Gly Gly Ile Val Lys Val Tyr Ser Phe Lys Ile
1265                1270                1275                1280

His Glu His Glu Thr Asp Thr Ile Tyr Tyr Lys Asn Ile Ser Gly Phe
                1285                1290                1295

Lys Thr Glu Ala Lys Leu Val Gly Leu Glu Pro Val Ser Thr Tyr Ser
            1300                1305                1310

Ile Arg Val Ser Ala Phe Thr Lys Val Gly Asn Gly Asn Gln Phe Ser
        1315                1320                1325

Asn Val Val Lys Phe Thr Thr Gln Glu Ser Val Pro Asp Val Val Gln
    1330                1335                1340
```

-continued

```
Asn Met Gln Cys Met Ala Thr Ser Trp Gln Ser Val Leu Val Lys Trp
1345                1350                1355                1360

Asp Pro Pro Lys Lys Ala Asn Gly Ile Ile Thr Gln Tyr Met Val Thr
                1365                1370                1375

Val Glu Arg Asn Ser Thr Lys Val Ser Pro Gln Asp His Met Tyr Thr
            1380                1385                1390

Phe Ile Lys Leu Leu Ala Asn Thr Ser Tyr Val Phe Lys Val Arg Ala
        1395                1400                1405

Ser Thr Ser Ala Gly Glu Gly Asp Glu Ser Thr Cys His Val Ser Thr
    1410                1415                1420

Leu Pro Glu Thr Val Pro Ser Val Pro Thr Asn Ile Ala Phe Ser Asp
1425                1430                1435                1440

Val Gln Ser Thr Ser Ala Thr Leu Thr Trp Ile Arg Pro Asp Thr Ile
                1445                1450                1455

Leu Gly Tyr Phe Gln Asn Tyr Lys Ile Thr Thr Gln Leu Arg Ala Gln
            1460                1465                1470

Lys Cys Lys Glu Trp Glu Ser Glu Glu Cys Val Glu Tyr Gln Lys Ile
        1475                1480                1485

Gln Tyr Leu Tyr Glu Ala His Leu Thr Glu Glu Thr Val Tyr Gly Leu
    1490                1495                1500

Lys Lys Phe Arg Trp Tyr Arg Phe Gln Val Ala Ala Ser Thr Asn Ala
1505                1510                1515                1520

Gly Tyr Gly Asn Ala Ser Asn Trp Ile Ser Thr Lys Thr Leu Pro Gly
                1525                1530                1535

Pro Pro Asp Gly Pro Pro Glu Asn Val His Val Val Ala Thr Ser Pro
            1540                1545                1550

Phe Ser Ile Ser Ile Ser Trp Ser Glu Pro Ala Val Ile Thr Gly Pro
        1555                1560                1565

Thr Cys Tyr Leu Ile Asp Val Lys Ser Val Asp Asn Asp Glu Phe Asn
    1570                1575                1580

Ile Ser Phe Ile Lys Ser Asn Glu Glu Asn Lys Thr Ile Glu Ile Lys
1585                1590                1595                1600

Asp Leu Glu Ile Phe Thr Arg Tyr Ser Val Val Ile Thr Ala Phe Thr
                1605                1610                1615

Gly Asn Ile Ser Ala Ala Tyr Val Glu Gly Lys Ser Ser Ala Glu Met
            1620                1625                1630

Ile Val Thr Thr Leu Glu Ser Ala Pro Lys Asp Pro Pro Asn Asn Met
        1635                1640                1645

Thr Phe Gln Lys Ile Pro Asp Glu Val Thr Lys Phe Gln Leu Thr Phe
    1650                1655                1660

Leu Pro Pro Ser Gln Pro Asn Gly Asn Ile Gln Val Tyr Gln Ala Leu
1665                1670                1675                1680

Val Tyr Arg Glu Asp Asp Pro Thr Ala Val Gln Ile His Asn Leu Ser
                1685                1690                1695

Ile Ile Gln Lys Thr Asn Thr Phe Val Ile Ala Met Leu Glu Gly Leu
            1700                1705                1710

Lys Gly Gly His Thr Tyr Asn Ile Ser Val Tyr Ala Val Asn Ser Ala
        1715                1720                1725

Gly Ala Gly Pro Lys Val Pro Met Arg Ile Thr Met Asp Ile Lys Ala
    1730                1735                1740

Pro Ala Arg Pro Lys Thr Lys Pro Thr Pro Ile Tyr Asp Ala Thr Gly
1745                1750                1755                1760

Lys Leu Leu Val Thr Ser Thr Thr Ile Thr Ile Arg Met Pro Ile Cys
```

-continued

```
            1765                1770                1775

Tyr Tyr Ser Asp Asp His Gly Pro Ile Lys Asn Val Gln Val Leu Ala
        1780                1785                1790

Thr Glu Thr Gly Ala Gln His Asp Gly Asn Val Thr Lys Trp Tyr Asp
    1795                1800                1805

Ala Tyr Phe Asn Lys Ala Arg Pro Tyr Phe Thr Asn Glu Gly Phe Pro
    1810                1815                1820

Asn Pro Pro Cys Thr Glu Gly Lys Thr Lys Phe Ser Gly Asn Glu Glu
1825                1830                1835                1840

Ile Tyr Ile Ile Gly Ala Asp Asn Ala Cys Met Ile Pro Gly Asn Glu
            1845                1850                1855

Asp Lys Ile Cys Asn Gly Pro Leu Lys Pro Lys Lys Gln Tyr Leu Phe
        1860                1865                1870

Lys Phe Arg Ala Thr Asn Ile Met Gly Gln Phe Thr Asp Ser Asp Tyr
    1875                1880                1885

Ser Asp Pro Val Lys Thr Leu Gly Glu Gly Leu Ser Glu Arg Thr Val
    1890                1895                1900

Glu Ile Ile Leu Ser Val Thr Leu Cys Ile Leu Ser Ile Ile Leu Leu
1905                1910                1915                1920

Gly Thr Ala Ile Phe Ala Phe Ala Arg Ile Arg Gln Lys Gln Lys Glu
            1925                1930                1935

Gly Gly Thr Tyr Ser Pro Gln Asp Ala Glu Ile Ile Asp Thr Lys Leu
        1940                1945                1950

Lys Leu Asp Gln Leu Ile Thr Val Ala Asp Leu Glu Leu Lys Asp Glu
    1955                1960                1965

Arg Leu Thr Arg Pro Ile Ser Lys Lys Ser Phe Leu Gln His Val Glu
    1970                1975                1980

Glu Leu Cys Thr Asn Asn Asn Leu Lys Phe Gln Glu Glu Phe Ser Glu
1985                1990                1995                2000

Leu Pro Lys Phe Leu Gln Asp Leu Ser Ser Thr Asp Ala Asp Leu Pro
            2005                2010                2015

Trp Asn Arg Ala Lys Asn Arg Phe Pro Asn Ile Lys Pro Tyr Asn Asn
        2020                2025                2030

Asn Asn Arg Val Lys Leu Ile Ala Asp Ala Ser Val Pro Gly Ser Asp
    2035                2040                2045

Tyr Ile Asn Ala Ser Tyr Ile Ser Gly Tyr Leu Cys Pro Asn Glu Phe
    2050                2055                2060

Ile Ala Thr Gln Gly Pro Leu Pro Gly Thr Val Gly Asp Phe Trp Arg
2065                2070                2075                2080

Met Val Trp Glu Thr Arg Ala Lys Thr Leu Val Met Leu Thr Gln Cys
            2085                2090                2095

Phe Glu Lys Gly Arg Ile Arg Cys His Gln Tyr Trp Pro Glu Asp Asn
        2100                2105                2110

Lys Pro Val Thr Val Phe Gly Asp Ile Val Ile Thr Lys Leu Met Glu
    2115                2120                2125

Asp Val Gln Ile Asp Trp Thr Ile Arg Asp Leu Lys Ile Glu Arg His
    2130                2135                2140

Gly Asp Cys Met Thr Val Arg Gln Cys Asn Phe Thr Ala Trp Pro Glu
2145                2150                2155                2160

His Gly Val Pro Glu Asn Ser Ala Pro Leu Ile His Phe Val Lys Leu
            2165                2170                2175

Val Arg Ala Ser Arg Ala His Asp Thr Thr Pro Met Ile Val His Cys
        2180                2185                2190
```

-continued

```
Ser Ala Gly Val Gly Arg Thr Gly Val Phe Ile Ala Leu Asp His Leu
        2195                2200                2205

Thr Gln His Ile Asn Asp His Asp Phe Val Asp Ile Tyr Gly Leu Val
    2210                2215                2220

Ala Glu Leu Arg Ser Glu Arg Met Cys Met Val Gln Asn Leu Ala Gln
2225                2230                2235                2240

Tyr Ile Phe Leu His Gln Cys Ile Leu Asp Leu Leu Ser Asn Lys Gly
                2245                2250                2255

Ser Asn Gln Pro Ile Cys Phe Val Asn Tyr Ser Ala Leu Gln Lys Met
            2260                2265                2270

Asp Ser Leu Asp Ala Met Glu Gly Asp Val Glu Leu Glu Trp Glu Glu
        2275                2280                2285

Thr Thr Met
    2290


<210> SEQ ID NO 3
<211> LENGTH: 254366
<212> TYPE: DNA
<213> ORGANISM: Human
<220> FEATURE:
<221> NAME/KEY: misc_feature
<222> LOCATION: (1)...(254366)
<223> OTHER INFORMATION: n = A,T,C or G

<400> SEQUENCE: 3

cattatctat ggaacataat ctgaggcttt ttttttacag ttggtagata cttatgtaca     60

agattttgct gtgaaaatca gggcaagaag gtagtgatgc aaggtagcag ataacattga    120

aatacatttt tgaaaataat ttttaaaatt gatgtaatgc aattagatta cttgagctaa    180

tagcatagct ttattttatt ttatttattt tattttattt attttttga gacacagtct      240

tgctctgttg cccaggctgg agtgcagttg ccgatattgg ctcacttcag cctccgcctc    300

ctgagctcaa gcaattctcg tgcctcagcc tcctgaaagc tgggaccaca ggtctgccca    360

ccacgcaggg ctaatttttt tatttttagt ggagacaggg ttttgccatg ttgcccaggc    420

tgaccttaaa ctcctggtct caagtgatcc aaccgccttg gtctcccgaa gtgccggcat    480

tacaggtgtg agccaccaca ctcgtcttaa ttgcatagtt ttagagatcc atgttggatt    540

agctcttctg tagtgtcctg atgacctgtg accaatgata agagtatgga attaggtagt    600

ttctatgaaa aggcatcttt tctggcgact aatagccaca gtatcaagag ttttaaaagc    660

ccctctcctc tggtctcaat ggagtcaaag aaaactctcc cgactgctcc tgaaaaagga    720

tgtcaaatga aactgtttca aattgctgaa tagcctggct aatcctgcct gtctccaatc    780

acatactccg aatccatatt tttctcactg tggtaagctt tccaactatt tttcagaaaa    840

caaaacttat atttggaata acttggtgct tctgtggcag taaaaccatg actgaaatgt    900

atctctgtgg aaacccttac ttcatttaaa atttattatt cctcctaatg attcaaggct    960

tcaaatattt caatggtaaa gaaagagctt tttctattca gagggaatat tcatttactt   1020

cttcagtgct ttgtgtgtct aaagtagaaa aatatgagat tacatgagac atatactttt   1080

tcagtgttac tgatcatatt cccttatcta aattctttaa taactaactt tattattcct   1140

aaaatataaa taaaaaataa tgcacatttt tcagcatcac tatacacatg ttcatttttt   1200

ggttttagat attaatctat acccagttca aactgtggaa actgaactaa catgactgaa   1260

ataaaatagt gttatatttt gttctttaga ctcttttttc ccttcctgag attttgatat   1320

gtatttggag agttttgagt caatatttat ttgatttgtt ttcttttctg gagtgatatt   1380
```

-continued

```
gtaaatactt taaagatttt gattgagtga gaggtgtgag ctatattttc ttctttcctg   1440
tatgatatac atacattgtt tccaatctaa tttctattaa ataactatag gagagcccac   1500
agccttgtta ttttacatat cactatttag atatttgtta tttatttatt tgtgttggcc   1560
tgaagtaaat gttacttttg tacgatattt gaaggataga tttattttat aaattaatag   1620
tttaaataag attttgccag catttgaaat gaacaaatgt ttggacaatg aaaacatcag   1680
tatgaaaggg aatactgtaa ttactttagt acatagtatt ccttaatatc cattaaaatt   1740
ggtccaagca aactctaatt atgaacatca tattaacatt tgatctaatt actgaatata   1800
attaaaagca aaataagtta atttactaaa gaattctgaa atttactatt ttcagtattt   1860
caggataacc aacatctttt ttctattaat ctagaataaa tttccatata ttaatgttgt   1920
ttacttttaa tgttagtgtg ctcaaaaagt attgttaact tttaaaattc aattctacag   1980
ataatattct ttttatctca ggaatagatc atcattaaaa actattaatg tcactgaaac   2040
atcattggag ttatcagatt tggattataa tgttgaatac agtgcttatg taacagctag   2100
caccagattt ggtgatggga aaacaagaag caatatcatt agctttcaaa caccagaggg   2160
aggtgagtta aggatgtatg ccaattaaaa gaatgttctt tttctttaaa aaaaaaatcc   2220
tgcccagaaa aatattcaaa tatcaaaatg tatgatgaag cctaatattc atcatcagtt   2280
tgatgaaaaa ttgcattttg atcacttttt agctgtgtga tgttgggaaa attaatctct   2340
gtgtgcctca atttcccatt ggtaatgtgg aaacagtatc attctacttc acagggttct   2400
tatgaagatt acataagttt atatttttaa aagcacttag tacagaagtt acttggacaa   2460
atagaatttt atgtgtttat taaacgaaac aacataaaat gcatgaatca tttgtctatg   2520
acttttatta ttcaatataa aaattctaag ttatattaga atttcaaatt atgtattttg   2580
tattggaaac ctgttataat attgttctca tatccagagc agtggacagg ttttagaacg   2640
gagatagtat tttatgggta agaaatctat ctgtcttcag cttgaatatg cctataataa   2700
agtattagag gggtgaccca atgtgtttta tggatttcat ttctgacatt tctaattcaa   2760
gctttttga aaaacatttt ttatcacttt aatttataaa ctgtaggtaa aattcaggcc   2820
atttcagaca ttacttgtaa acacaaatac agtaatttgt tcaattattt gttttatagc   2880
accaagcgat cctcccaaag atgtttatta tgcaaacctc agttcttcat caataattct   2940
tttctggaca cctccttcaa aacctaatgg gattatacaa tattactctg tttattacag   3000
aaatacttca ggtactttta tgcaggtaag aactgaattt tcttctagtt ctttattaac   3060
atccttaagt tttattaata atacagactt gtcacagtaa aagaaattgt ttaccttaca   3120
ttgataatta ggcacagatg tattttataa aactcccatt gacatagaaa aatgcggtgt   3180
agaaatgtca gatacattta atctctcttt acagacacac acacacacac atacaacttc   3240
tatataagct tcacatgtat taaaaatagt gaatctgcca cctactgaaa attctgttta   3300
taaagatggc cctcaattac acttcctcca ataagtgttc tctaaagtgc tgatggtatc   3360
atttatcctc aaagttattt attagctaaa tttttttca tttgtttgta tatgatataa    3420
atagttctag tgtttggatg tgtttgtttt tctttaatta aaaaaagttt ttgatagcag   3480
gaagggttat tataataata gtatattagt agttaatgtt taatgtcaga tgaaatgaag   3540
accactcgga atgtgtttaa ttaatttgtc atagataaga ttctaggctt gcacagtttg   3600
tagatgggca ctctctagga tgtgaatgat gatggctatg aaaatagcta acatgcattt   3660
actttgaaaa aatattttca attttcaaca gaattatatt atttcttcaa attagatgtt   3720
```

-continued

```
tcacagaact ctaacatata aaaaggataa ttggaatgat tatgattgaa tcaaagatgc   3780
agagagctgg aatataatta gaaaaacacg gccgggcgtg gtggctcacg cctgtaatcc   3840
cagcactttg ggaggccgag gcgggcggat cacaaggtca ggagatcgag atcatcctgg   3900
ctaacacggt gaaaccccgt ctctactaaa aatacaaaaa attagccagg cgtcgtggca   3960
ggcgcctgta gtcccagcta ctggggaggc tgaggcagga gaatggcgtc aacccgggag   4020
gcggagcttg cagtgagctg agatcccgcc actgcactcc agcctgggcg agagagcgag   4080
actccatctc aaaagaaaaa gaaaaacacg aatttagaag aaatgctgca atgtacagaa   4140
tacatccctt agtggtagaa attattgacc acatgtttgt gtcttaggtg attcttaatt   4200
atttctatcc ttttaagtaa aagaagaaga aagataagtc ttacaaattc tgagttacct   4260
aatcccattt gtgactgaca gcccaagttt agtcactagt tagctctact gagtaacagc   4320
ctctgtaatt aagactttag tgcagctata gtgcaatgta ggctaatgaa gagggcaaga   4380
gcagaacttg caagctatct caggactaac ctagcaggga gaaagacaaa gtccagaagg   4440
tggtttagtg tttatattct gttctataag agtagggttg tataagtctg tctatttaaa   4500
acttgatgca aagagaaaac tactttataa aagacatgta gatataatta tagctgtaat   4560
gaaagacatg tagatatagt tacagatgta atcgtaaatc aacatttttg aacaaatgcc   4620
ttaagagcag aaggagaaag gaaggtctag ttttctactc tctatgtcac gcagtttttg   4680
ctttttgttt tgttctctgt agggaagaga aatggggcct agagaggcaa tttatttttt   4740
aaccaaaatg ttgtttacaa ttgtaacaat atgtcattat acccatagaa gatatgcaaa   4800
ttggagattt tccttctttt atgcatttaa aaaacattgc acaattgttc cagtagttct   4860
aaattttagc aatcattttg tctctgtaca atttacttat ggcttctatg tgatttatat   4920
tttggttctc tttatccata tctaaataat atagcataag tatcaaacta tggttccaac   4980
gtgatcttct aaacctactt attcacacct gggtgtgtaa tatgatctaa tttgcaattc   5040
atctgcctta gaacatgtta tcttttatta aataatctta agaatgcttt taagtgtgac   5100
agctgcaaga gggcacaggc taatgatgtt aaaatatttc agaagtatag tctcatattg   5160
cttgaagttt atccgtgctt taacttattc ctaaagttaa tgttaaaaat agcatcaata   5220
ccttcactac ctaattttct attttgaatt agtggaagaa agcctcaaaa tgaaaattat   5280
gtagcagaat aagtgtatac ctttttattt gttccttatc atctttcccc ttcctacaga   5340
actttgtaga atatgtcatg cgtggcatat catgttctgc ctcctattac cgataactgt   5400
tgcttctctt agttccctta tgccatgaca agcatcttgt agaaaaagaa ttgtgtaata   5460
tttatttttt catctccaaa agtcttctgc aactatgtca gacataggtt taatgctcaa   5520
tacatatttt aattgaaaga tttaaaaaat attatagtag accaacatca cttttagtac   5580
atagtcataa ttttggagcc cttgagtatg tagcaaagcc atctttcctt tttcttatct   5640
tggagaattt aacctctttg ctactacttg gcaatccata ttgttcttcc ttcagttgtt   5700
gcacattgta ttttgtacag catattaact tttctacttt ttaagtttta cccacttatg   5760
tttccttagt gtgcctggca taatgtcttc tattttaaaa agtgttaaat gggccgggtg   5820
tggtggctca cgcctgtaat cccagcactt tgggaggctg aagcaggtgg atcacgaggt   5880
caggagatcg agaccatcct ggctaacaag gtgaaaccct gtctctacta aaaatacaaa   5940
aaattagccg ggcatggtgg caggctcctg tagtcccagg tactcaggag gctgaggcag   6000
gagaatggtg tgaacctggg aggtggaggt tgcagtgagc cgagatcgtg ccactgccct   6060
ctagcctggg caacagagtg agactctgtt ttaaagaaaa aaaaagtgtt aaatgaatat   6120
```

-continued

```
tagttggttg gtcaaatttg aaaaagtttt actaaatacc ttctgactat atttatataa   6180
acaaaagaat aagccttact tagataattt gtgccaaaag acattttgtt tttgcaaaaa   6240
taaacagctg aataaaataa tcatctggat aattgattta atgttacaaa tttgttacat   6300
gcctatgcac attaagtcac acagtcagca ggaatgactt ctgggtgatt cagataattt   6360
gttatgtatt agccatcaag gtcataggta atcagaataa attctataac aaaaattaaa   6420
atttacatca aaaagctatg ttaatacttt taagtggtgc tttatataag ccagttgttc   6480
catgtgtaaa gtagatgtat tggaaggtat taaagttcat ggatcatatt ttgtgtgaga   6540
ttgctatatt actttaactt gtctatttct atgtaaatca ccacaaaatt gtagtaaatc   6600
ttttattgca ctatattttt ccctgaatac tggcaaaaga accataaaat tttgctaatt   6660
taatttgttg ataaatttca gaaccattct tactataaat ttggtaaatt tgcttatcct   6720
atgttattca tttaaatgaa actaattact gttttttttt aattgtgtgc tagacatggt   6780
attaatggct ttttgtgctt catgtcatct aatcctcaca agttgtctgt gaagtggaga   6840
tgattatttc cattttacag ttgaaggaag aaaagctttg agattaaatg atttatccag   6900
gataccctga cagaatttga atgcaggtct ataggactta aatggcttca tgtggattgg   6960
aatgattcag gttactctgc agatggaaat tataaaatta ttcatactga ttagctatgt   7020
gtttaagtct ccttttattt tagaattaat tttatttggc tatatgtttt atttttaaaa   7080
tttgatagga aagaaaatga ttacatacat accctaatac ttttttttaa gccttgggga   7140
aaaatgcaac tgggagtcag tcaagagaat ttaaaacttt ctcttactct acacatcaga   7200
gagtacatca gtctgctatc cctttgctac aactgtgaga agtaaagtct gaaaagaaat   7260
gtgaaagtct gaaagcccac taaatgtgaa taataatagc gatttgagtt catagaaaca   7320
ggcaaacaca ttcgaaattc cttcatcaca aatggaaaga aacacaatta aaagttttct   7380
aatactccca aacttgttta aaattagctg atgctttgaa aattacttga atgtttttat   7440
aaggaaagtg atgctgatca gcacagttgt agcatttcca tttggccact tgacattctt   7500
cattgttggc ttggagtttt tattctttgc tattttttttg tattggcttt gcaataaaaa   7560
ccaccatcta tttctctttt agtacaaaca tatttccagt ttaattgttg caataaaaaa   7620
tgttctatgt cgattttcct aaaacaacat attaaaataa tgataaataa taaaatcgat   7680
ccattgataa caattagttt gaagtgttca tgcatactaa aaaaatacat tctgaacaat   7740
gaatgtgttt atttttcaga attttacact ccatgaagta accaatgact ttgacaatat   7800
gactgtatcc acaattatag ataaactgac aatattcagc tactatacat tttggttaac   7860
agcaagtact tcagttggaa atgggaataa aagcagtgac atcattgaag tatacacaga   7920
tcaagacagt atgtaaacaa aaaacactaa tctttaatat gattaattta aaacttatta   7980
ttttaggaaa ttttactatt tgtttgaatt tgtaataaca tcttttattt agacacgttc   8040
attataggag tttgaaaatg caattaatat acttacaaaa ctattgcagt aatagcctct   8100
tctgttcaag aaaactgcta acatccattc atgaaaattc tgttcttttt attgcttcaa   8160
aagatgtcgt ggccatccag ttatgggcac aaaaagtact gcatacatgg atgaattttc   8220
cagtagttaa tttatttatt cattttcctt aaggacttaa aaaatctcta gcaacttgtt   8280
ttcttttcag actttgaatc tacacaggac tctgcagcac atctcttctc actgtgtttg   8340
tgactaatat atccagagta ttttccttaa ctccagaagt ttctcgtatg catcttctga   8400
agaatcctat ttatcccgag tattcagaaa actataatga ttgaagatct tgatgttttt   8460
```

-continued

```
tatgtttcaa ttttcagaat acagtgataa gtggatcatt gcctattttt cttgtagttg   8520
tttctgtcat ccatttgctt attttcaaag attaatccct tattgagaag tggcagtgac   8580
ctaaacttct ggagtaaaac tccatgttta ttatctgaaa gccataaatt gacagattcc   8640
ttaagcatga gaagtgaatg cttgatttgt tgttggaaca gtcttttgaa ttgttgacaa   8700
gttggtcaac ataaaaataa atgataaatg tggggaaata tgtatttggg gagtctttag   8760
caaaaatgtt atattgtaat atatgatcaa taccatttca ggtattcttt aaatgcagat   8820
ctctcccagg atttttgcca acctatgaca ttttatcact tataatttcc acaccatgga   8880
taataagcac ttactatgca ctactccagg tggatgtcaa atttacgtta atagagttta   8940
atatcacaat acaacttata tctgagaatt ggaacttgtg tgtaagtaga gtaactttgt   9000
aatgtacaaa tgtgagttgg tagtctggtg actggagaga ttttgagact agatcttggg   9060
aaagctttta gtattgattc ttctggctac ccacatgacc ttggagaagt aacttaatgg   9120
ctgagcttta gtttcctcat atgtacaaca agggtaatat ttagaagaaa taagctaaaa   9180
agatggttta aataacataa attatcaaaa tatttaaata aggcagtata catacacata   9240
ttatgcacac acacgcacac acacacaatc tccacatagt aggaaagaag agtcaagaga   9300
atattataga aacaattccc atacatatta aagatgacag agtttatttt gaatgatttt   9360
taaaataatt atttagaaga tattttataa taggtgaatg tttgccacat ctgcatttaa   9420
ataatttaag agctgatgat gtaatagttg ccatttcaac aattatactc agtttgtgaa   9480
tttagattct gtttagggta actgttgatt tttgtatttt gcccattacc tatcatagta   9540
cctgaagggt ttgttggaaa cctgacttac gaatccattt cgtcaactgc aataaatgta   9600
agctgggtcc caccggctca accaaacggt ctagtcttct actatgtttc actgatctta   9660
cagcagactc ctcgccatgt gagaccacct cttgttacat atgagagaag catatatttt   9720
gataatctgg aaaaatacac tgattatata ttaaaaatta ctccatcaac agaaaaggga   9780
ttctctgata cctatactgc ccagctatac atcaagactg aagaagatgg taggctagac   9840
ccttttattg tctgttaagc agattgttgt tcttttcatt tacattgctt tctgatagga   9900
aatagtcttc aattatattg attctgtttg atctcaagta attagccttt caataaacac   9960
agtgtttctt aaaataatct gctaagaaaa tcaaatccca ttatgattga atcctctttt  10020
tttaatgctg attcactttt gtttcattta atattctctt tttcttttat agtcccagaa  10080
acttcaccaa taatcaacac ttttaaaaac ctttcctcta cctcagttct cttatcatgg  10140
gatcccccag taaagccaaa tggtgcaata ataagttatg atttaacttt acaaggacca  10200
aatgaaaatt attctttcat tacttctgat aattacataa tattggaaga gctttcacca  10260
tttacattat atagcttttt tgctgccgca agaactagaa aaggacttgg tccttccagt  10320
attcttttct tttacacaga tgagtcaggt aagccagaat ccacatttct tcaaacaatt  10380
tcactgttgc agcgcctgct ctctcttttt aaggaacagc atggaatatg aaaggatatc  10440
tgattgtcta tttgtaacag ccttaccatt atatttactt tgttgatttt ttttttgcaa  10500
tttgagcttc agaatttcct gttctgttta aagctacttt ggaactactc tgtccaaata  10560
caaattataa ttaattatga tatttgtttc tgaaatttaa atatgatcat tttataaatc  10620
tttttaaact agtgtcttca agaaagtaag tcacggtgct atttttatgt taaaagtttt  10680
atgaatgtaa gtttcttcat gtgttttcct acagtgccgt tagcacctcc acaaaatttg  10740
actttaatca actgtacttc agactttgta tggctgaaat ggagcccaag tcctcttcca  10800
ggtggtattg ttaaagtata tagttttaaa attcatgaac atgaaactga cactatatat  10860
```

-continued

```
tataaggtag gttgattata acagtatatg tttattttta aaaatcagaa attgaattaa  10920
aatcttttga catataggag gaaaatggac tactaaatta aacaatgact atttttttaa  10980
acttctttat ttcctacaat ttaaggatgc ttatggaaaa cacaagcaag cgtttgacag  11040
gtatataagc tgaatacttc atagagcaat gtacttagat ttgtaacttc cagatatcta  11100
caatttaaga aacagttgca tcattttgtt aatgctggaa agtgtatagt actttttttcc  11160
tgacttacaa atataaaatg tatttctatc tattgttaac agcagcacca agggaatctt  11220
tttaaccttt tagaaaggta ttcatcttta ttctggactt ctggtcatct ttccagatag  11280
catatgatcc tacactaatt ggtcttttac gatatatcct tatttttttt tttattttca  11340
agagtaattc atttgcaaca ctaaccacat tttccctcct ccatttttgg aattcagaat  11400
tagtgaaaaa tatccacaga actgatgcaa caaagagtct caaatatatg tctgtgattt  11460
ctagcattta attgccaaaa tgtaattaac aagcatttat ttaagaaaag tttcttattt  11520
ttttccccaa aggcaaatga agtcctggaa tgttcttatt tagtttacag caagaagagt  11580
gcaaaaaatc tgcagtaaat attttactca atattatgag tattacaatt tatgactatg  11640
gtaaatcatt gttatagcat atgtagttta caaattgaat agtaaaagtc aaaagcaggc  11700
attaacttta tgtcatcggg aacaatgact ttctttctgg aaaccaagat attactttaa  11760
aacttgatag tctgagtata atttgaatcc tattactcca taaatgtgaa atttgtttcc  11820
cagaggtgtg aaataacatt aaatgacatg aagcctcttg ccctttaata tctatccctg  11880
gtttaatctt aacattattc catttttat ttgctttgtc tgtatgggtc actgggagat  11940
agatatcaaa aggaaaaaag aatcattttc tcagagtaat cgcattccta ggataattgt  12000
gtacgtgtgt tagagtgtgg ttgtctatat atggatcttg tctcctcaga atggtgatct  12060
gtaacatagg ctctcttagc atagcggtga agcaagggct ctgactccaa attacctggc  12120
tcagattctg cctttgagac ttactgtgct tcagtaggga cattgcttac ctcttaatgc  12180
aaaatgggag ttacaaagat gtgtacattc gaaattgagg attaaaaagg aaagtctcca  12240
tagagcattt tgaacaattc caagcatgtg ataaatatgt tagctattgt tgctgtaatt  12300
gtacacagtt tttaaaagaa caaaaaaact gtccaacatt gtaatagcac taagcatgaa  12360
atgacaatat gccattatgt gaacatgaga ataacttgta ttctaagatt tgtaaacagg  12420
ttttctcaat agaagcacat ctttaatatt tcagaagtag caaaaatacc atctttatac  12480
cattaagtat tcaatacatc atttgggatg ggcagtagtt ttgtgtttta aaatctactg  12540
cgtcatgtta ctccttttta catctatttt ctctttcatc aattttcata atcttatttg  12600
ctttcaaatt cctttaaatg tactctcatg ccatcttttt ccctgtcttg gcatctagtt  12660
actatatctg ctttcctttt tctatttcgc tttctctcct agtgtgttct attttccttt  12720
ctctttcatc taccctgata tcctgacagt atcaatttat attattttct ctgtttttct  12780
attctttttc ttcttttaaa ttatgtgtgc atttgtggag gtagaataat gcttgaacca  12840
cttcaaatgt tactgctatc ccagtcaatc cactgtggtc cacagataat aaaatcaata  12900
ggtgacttag gtcactcaca catactgaaa gaaattattt atttagtaca aagttctatt  12960
aaaatatgtt tgtaagtatt catcactcat gtttctcttt ttgacaacat attcttgtgt  13020
aaatctgttc actatcccat aaactattct cttattatta tgccctcttg ggttcagttg  13080
tttctctggt ttttagccct tcctaaccaa aatcataatt tgcttgtttt gtgtttaatt  13140
ttttctcatt cagaaattgt agatttctct agttaatata aaaattcctt gatggcaggg  13200
```

-continued

```
accatgcctt acatgtgtct ataatctcca gattatctaa tggcatgttt tgtaaatagt  13260
aagcaggaaa gaatgactga aataaagaga ttcagtaagc ccctaaattc agtgaatttc  13320
tagagattat tttaaaatag gattctaatt gtaaattccc caagaattaa tattcttgtt  13380
aaaatttctg ttactgtgat gtttgataaa tgatcaacat ggtttatatt ttgtcagata  13440
taatgtaaga ttcctacatt tatatcacat aggagattat cttctctttc catgaggata  13500
gctgattaat cttagctgct ttcttggtta ggacaattat ctttgaatga aaactttgta  13560
cttaatgata atttttttct atgagaaagc atattcctcc ttgggcaact atgatactct  13620
tttgttcctt ttctcatatc tctaaaaaca gtgtcaaatt agaaatagag gaatcggctg  13680
ggaaaactcc caatttaagc ttcatggaag cagatatttt aaaattatta ttttaaaata  13740
ataataattt attattatta tatataataa tgttattatt atttattact gttttgccag  13800
tgtctacata cagtagctga agaataaata aatttacaca ggaatgctgt gggtattaaa  13860
aatgaattta gataagttca gaaaactcaa gtatctctga ccatgcacaa gttggattta  13920
aattgcagac tgtaattatg caaattaaaa aaaatgagta tataattcca agtgaaaatc  13980
atgaaaataa aacactctag ttttttaaaa aggcaattat acgccaggtg cagtggctca  14040
cgcctgtaat cccagcactt tgggaggccg aggtgggcag atcacctcag gtcaggagtt  14100
caagaccagc ctggccaaca tggctaaact ctgtctctac taaaaactac aaatattagc  14160
tgggtgtggt ggcacatgcc tgtaatccca gctacttggg aggctgaggc agggagaatg  14220
gcttgaacct gggagtccac ctcccactgc actccaacct gggcaacaaa atgagactct  14280
gtcaagaaaa aaaaaaagtc taaaaaaggc aattatgagg ttcttcaggg aaaagaaggt  14340
gcccaattca tccttgtatc ataaactgag cacactctat ggcacaaaat aaatgctaat  14400
atttgtttta ttataattta aaatatccat gcttattaaa ctataggtta aatataaaag  14460
gaataacttc aatgaaaata ttccattgat gaacaatttt ttgacagtgc attaactaat  14520
aacttttttt ctgtttttca gaatatatca ggatttaaaa ctgaagccaa acttgttgga  14580
ctggaaccag tcagcaccta ctctatccgt gtatctgcgt tcaccaaagt tggaaatggc  14640
aatcaattta gtaatgtagt aaaattcaca acccaagaat caggttagat acagtttttg  14700
agcctaaaat gtttcttttt atatttaaca cctttctttt ccttttctta gtttatatga  14760
taaagtatca ttacttaaga gtctactcaa agggaaattg catttcagtg ctttacgttt  14820
agtcttggtc ttgtgtgaaa tcatatgctg tatgtgtgtt tatacatata ttttcacaca  14880
tggtttttcc ttttgaacag aggaagttga aataaaatag tagtttggga acaaaatagc  14940
cttctagata tctgtgaaaa ttacctaatt cttagaactc tttgagacag ctggggaaaa  15000
agggggaaat gaactagcag tcacttttaa cgggctgatt tatattttta atgaaacaat  15060
atctataatt ttcttttaag aagattagtt gtgacatttg gagagcatga gtcattgcat  15120
aagcccccta tgttcccatc atcccatctt taccatgtgg cggacactga aatatcattg  15180
gtctaattca tcaacagctt acctgctgtg tcacacatgt agtatacatg acatatcttg  15240
cctttgtgtg cacactgaat agtttttatt taggacctat ttaatgatgg cttagaaatg  15300
tacttttcct tttctcaact gcaccatacc tttaaaagca cctcttctta attttttttt  15360
tgtttacttc tgtcaatgtt tattgaatga gcaaaagatc ccgttctagt catttcttct  15420
tatcagctct ggatgcactt cctggtatgt tagtgaatct ttaaatcgag attgtagacc  15480
actgactact aaattaatca tttctgcata aatttatggc tacctgacac tgtttttcgt  15540
gcatttctgt aacaaatgca aaataaatag catttataat ggataaaagt acatgctgtg  15600
```

-continued

```
aagtcatttt ctggatttga atttgagccc catgacctac tagttgtata atcttggcaa  15660
aggctcatga ctctgtgagc ctctgtaacc ttaactgaaa agaagcacat attagcagta  15720
gccatctcat aatgttgttg tcaaaaatat ttggaaagat ccacataaag cactttatag  15780
agtgttgtac acacagtaaa tgcccacttc atagagtgtt ggacacacag taaatgaccc  15840
ctgaatatta ctgttgcccc cattcccatg ttacagatga agaagccatg attgagctag  15900
attagatgaa aaggaccttg aaaaaattag tgaagaacct aactagaaca ttggccttct  15960
gacttctagt gaagagtgga catgactgca ggaaatgcat gttgtgaatg agtgatagaa  16020
tataaaaatg ttcaacccat aaataaaaaa atattttaat aatatttgta catgaggaca  16080
ataagaatca gggctaatct tgtagaaagt gctctgtaaa cccataaata ttttttatca  16140
gtaagataaa attgtacccc aacattctat actctgatta tttaaataaa taaaattttc  16200
acctttaagt gttttaatat caatggttaa tttttttttg aggttcaaaa aatcaggaaa  16260
atggatattc acaaaatctg gatttagaaa ctaaagttca gcaaattgtc aactatctta  16320
tgttaactta ttttataaaa atgttcttat atgattctga aaacaaggaa gtgaatagtt  16380
aatagcattt aattgccaga tcccttgatc agccagaaat tatctttaaa aaattttta  16440
atgccacata ttccctaaat attctccttt agtactggtg tctttatctt acagaggaag  16500
aaaagtttat aacagctcag tttagaccca ggtagagcgg tgtaggcaga tcagggatca  16560
cctgagtatt ctttaaagca ctatgttttg cataatggca gcaagttatt ttctttcaat  16620
tttcattgtt tgtaatccac aaattgactg tgtcccaatt tttcttctac cattatcttt  16680
tactgtgacc agaaaagtta ttctactaat gccaccatta ggggacattg gctaattgga  16740
catttctgtg ggaagtaacc agtttctcta atgtgcagtc actttggtgg gctaggatat  16800
tgttctttga ccaggcctac cagatataga ggacctctga gaagctgggt tagtttcaag  16860
taaattcaga gaagctctag aaaataagac tgagactcct taaatcttcc ttccaatgat  16920
gtctacaaaa ggtacttaaa aatgaaatcc tcaagattct tccaaagaag ccatcccggt  16980
aaaaaccagt acctttaaat tagttagggg tttccaagta ctgtgaagcc cagatttgtc  17040
acaacaggga ggcacctgca tactatgttt tgcataaaaa tgttccataa taaagtattg  17100
ctaagatttt tcctttccaa ttaagagagc agttatcaaa cactgcctgg gnnnnnnnnn  17160
nnnnnnnnnn nnnnnnnnnn nnnnnnnnnn nnnnnnnnnn ntaagagagc agttatcaaa  17220
cactgcctgg gcctgggctt gaggctacac atttgcttct gagcttttga ggatgtgatt  17280
ggtgcttcga actggaagat atttagtgac tggttcaata ctgtaatgat taatacaata  17340
gcataaaaag caagtcaaca gccttttgat tctgtctatg ttaatgactt tttaagcaca  17400
cattgaaaat ttgatatatt aaatattttt ctagttctaa acacagatgt atctagtgat  17460
cacgtaattc aatcaattat ctacttacat atgtatacac tttaactttg ggcatatgtt  17520
tatctcttaa gttccagatg tcgtgcagaa tatgcagtgc atggcaacta gctggcagtc  17580
agttttagtg aaatgggatc cacccaaaaa ggcaaatgga ataataacgc agtatatggt  17640
aacagttgaa aggaattcta caaaagtttc tccccaagat cacatgtaca ctttcataaa  17700
gcttcttgcc aatacctcat atgtctttaa agtaagagct tcaacctcag ctggtgaagg  17760
tgatgaaagc acatgccatg tcagcacact acctgaaaca ggtaactaac gtgaaacagg  17820
taactaacat gaaaccttta actatttggg gattgtgtca ataccacctg caatctttat  17880
agcatactta tctaaacata caaagcacat attaaaaaat acaacacagg ctttttatcc  17940
```

-continued

```
cacgtgttgc ttgagtgcca gctgtgtact acattgaccc ttctccaaaa cattgggaga  18000
ttgaagggag gaaaaaaaga gagatgatcc tctttactgt atttccacaa atataaaacc  18060
cccacctaat gaattatgct ttattgtgat ttaaaagaag aaataaacat gtaaaccttt  18120
catgtatatc tctttttagt cttacttgtt tttatggaat tctagatgtt ttcctgaact  18180
atatggttgc agtatcagac tcattttcat ctattttctc ccctttatac cagcctttat  18240
ctttcatgtt atttgaataa aatatccggg tcgttaagct ttagtccaca agacgaaatt  18300
ctcaccttcc ctagcagtgc tctgtcctgt atcataatat ccttcatcct attttcttcc  18360
atattctacc tgcttatata aattaaaacc tgtttctttc ctgataacac cacttcactg  18420
tagatattgg caataattgt taacttctgg cacatccaga ccctttatct tggaaacgtc  18480
tttcaagctg tcttgaggct gtaaacctag aacatcaaga catagtctgc cttctctctg  18540
atttcagcat ctaactccac atcctttcct tctcattctt ccagtgcaac atttttttcag  18600
actacggtgt ttccctttcc aggatggaat agttacattt caacaacacc atctctttgc  18660
tccttagatc tcataccatg tcattgtgac ttaccctcca ggaagcttcc tcactctgag  18720
aaggccccat tatttgtttt ttccaagatg ctgactggta aatatttcta ggaaaaaata  18780
gaaatgattc tactttgttt gtctataaat tcatcgtcct taattgtccc agctgctcca  18840
aaattttcta tgtatccctt gtttattctt cataggaaat atgttcatag gaatactctc  18900
tattccatat gaaaattgtt ctctttctga acctagtctg ttcccccatc atccatattt  18960
attgttattt tactaataat atcaaatata ttgataggcc ctccttccat caaaatttat  19020
ccatgtcttt atttatgccc tccagatatc ttctcttagg aagtccttgc cttcctcttt  19080
cagggatcta gctgttcatt ttcattttaa tcttatgtct tctctaggat attaccccat  19140
caatttattc taatatctcc tgcatttatc ctctttctct ttttcttgca cattcaccca  19200
aattgttgaa aaatcccaac tgaagaccta gttggagtat caactccaaa tatatatgaa  19260
atggaatttg tgttacatga aatcactgtc tttttcttag ttttctatgc ctgttcttga  19320
caatccattg gaccccaagc ctcatagttt tatacaattc cttactccat ctcttctaca  19380
tacaatcagg tcttatcaat tcaatttcca tcagggctct gcaatttgcc ccttctccac  19440
cttggccacc accattgtat attagaggga ccttgttgct tcctgtaata acatcttaac  19500
tagccttatc acccacacta ctttagccta cccataagtc tcatctttcc tcctactcac  19560
ttaattgaat tggttctaac atacaattag accatttata cattggcagg tgaaatgtaa  19620
tatctgaaca ataaagttta gacgtgtcaa gttgggtacc tgaagcacag aagtaataat  19680
gaaaggcacc atgtgtagga gatgggttaa aatactccaa atattttgct cattctcatt  19740
gtctagaaaa tatcccagaa tccatcgcta attagaattt ggcttctctc tagcttttta  19800
ttcttatatc cttttattgt atcttctcat atagctgatg tctccagcca aacttcattt  19860
atttagcatg ctatttcact atttcagtat tttaactcag aaaacattta ttaaacatct  19920
agtatgaact aataattgac tagattctct tctttaaaca tatccaacca tttttcatca  19980
tcagattgct ttgcttcctt taactgtatt attattttcc ctttctatga cacataaaat  20040
tttattcatt tttaaaagcc cagcttaaat gtgccttctt tattaaagcc tttaatggca  20100
tttctggact tcatcccaga cttgctgact catagcctca atgagtgaag cttaagaatc  20160
catgcactta agaatctctc taggtaattc cgatattctg tatgtattgg agagtactgg  20220
agtagattac caggaacttt tgaggacagg caaagagtgt cagaaaggtc catcaagggg  20280
tgacaggtgt tttcccagtg ggtggccagc acatcattgc tatgtggagt ctgtgggaag  20340
```

-continued

```
aaaaaatgtc aaaatgtcaa aatccaggta ggtggtctgc atcagggtgg tctagcacca  20400
ggtataatgg tcttgatcat tgggcaggag ctgagtcttt gagaactggc aaataaaatt  20460
acaggacaac atatctgaaa taaatgagag attcaggaac aaggcaggag atactaggtt  20520
ggtgcaaaag taactgnnnn nnnnnnnnnn nnnnnnnnnn nnnnnnnnnn nnnnnnnnnn  20580
nnnnnnnnnn nnnnnnnnnn nnnnnnnnnn nnnnnnnnnn nnnnnnnnnn nnnnnnnnnn  20640
nnnnnnnnnn nnnnnnnnnn nnnnnnnnnn nnnnnnnnnn nnnnnnnnnn nnnnnnnnnn  20700
nnnnnnnnnn nnnnnnnnnn nnnnnnnnnn nnnnnnnnnn nnnnnnnnnn nnnnnnnnnn  20760
nnnnnnnnnn nnnnnnnnnn nnnnnnnnnn nnnnnnnnnn nnnnnnnnnn nnnnnnnnnn  20820
nnnnnnnnnn nnnnnnnnnn nnnnnnnnnn nnnnnnnnnn nnnnnnnnnn nnnnnnnnnn  20880
nnnnnnnnnn nnnnnnnnnn nnnnnnnnnn nnnnnnnnnn nnnnnnnnnn nnnnnnnnnn  20940
nnnnnnnnnn nnnnnnnnnn nnnnnnnnnn nnnnnnnnnn nnnnnnnnnn nnnnnnnnnn  21000
nnnnnnnnnn nnnnnnnnnn nnnnnnnnnn nnnnnnnnnn nnnnnnnnnn nnnnnnnnnn  21060
nnnnnnnnnn nnnnnnnnnn nnnnnnnnnn nnnnnnnnnn nnnnnnnnnn nnnnnnnnnn  21120
nnnnnnnnnn nnnnnnnnnn nnnnnnnnnn nnnnnnnnnn nnnnnnnnnn nnnnnnnnnn  21180
nnnnnnnnnn nnnnnnnnnn nnnnnnnnnn nnnnnnnnnn nnnnnnnnnn nnnnnnnnnn  21240
nnnnnnnnnn nnnnnnnnnn nnnnnnnnnn nnnnnnnnnn nnnnnnnnnn nnnnnnnnnn  21300
nnnnnnnnnn nnnnnnnnnn nnnnnnnnnn nnnnnnnnnn nnnnnnnnnn nnnnnnnnnn  21360
nnnnnnnnnn nnnnnnnnnn nnnnnnnnnn nnnnnnnnnn nnnnnnnnnn nnnnnnnnnn  21420
nnnnnnnnnn nnnnnnnnnn nnnnnnnnnn nnnnnnnnnn nnnnnnnnnn nnnnnnnnnn  21480
nnnnnnnnnn nnnnnnnnnn nnnnnnnnnn nnnnnnnnnn nnnnnnnnnn nnnnnnnnnn  21540
nnnnnnnnnn nnnnnnnnnn nnnnnnnnnn nnnnnnnnnn nnnnnnnnnn nnnnnnnnnn  21600
nnnnnnnnnn nnnnnnnnnn nnnnnnnnnn nnnnnnnnnn nnnnnnnnnn nnnnnnnnnn  21660
nnnnnnnnnn nnnnnnnnnn nnnnnnnnnn nnnnnnnnnn nnnnnnnnnn nnnnnnnnnn  21720
nnnnnnnnnn nnnnnnnnnn nnnnnnnnnn nnnnnnnnnn nnnnnnnnnn nnnnnnnnnn  21780
nnnnnnnnnn nnnnnnnnnn nnnnnnnnnn nnnnnnnnnn nnnnnnnnnn nnnnnnnnnn  21840
nnnnnnnnnn nnnnnnnnnn nnnnnnnnnn nnnnnnnnnn nnnnnnnnnn nnnnnnnnnn  21900
nnnnnnnnnn nnnnnnnnnn nnnnnnnnnn nnnnnnnnnn nnnnnnnnnn nnnnnnnnnn  21960
nnnnnnnnnn nnnnnnnnnn nnnnnnnnnn nnnnnnnnnn nnnnnnnnnn nnnnnnnnnn  22020
nnnnnnnnnn nnnnnnnnnn nnnnnnnnnn nnnnnnnnnn nnnnnnnnnn nnnnnnnnnn  22080
nnnnnnnnnn nnnnnnnnnn nnnnnnnnnn nnnnnnnnnn nnnnnnnnnn nnnnnnnnnn  22140
nnnnnnnnnn nnnnnnnnnn nnnnnnnnnn nnnnnnnnnn nnnnnnnnnn nnnnnnnnnn  22200
nnnnnnnnnn nnnnnnnnnn nnnnnnnnnn nnnnnnnnnn nnnnnnnnnn nnnnnnnnnn  22260
nnnnnnnnnn nnnnnnnnnn nnnnnnnnnn nnnnnnnnnn nnnnnnnnnn nnnnnnnnnn  22320
nnnnnnnnnn nnnnnnnnnn nnnnnnnnnn nnnnnnnnnn nnnnnnnnnn nnnnnnnnnn  22380
nnnnnnnnnn nnnnnnnnnn nnnnnnnnnn nnnnnnnnnn nnnnnnnnnn nnnnnnnnnn  22440
nnnnnnnnnn nnnnnnnnnn nnnnnnnnnn nnnnnnnnnn nnnnnnnnna tttggtttta  22500
aaaacttggt cttttgtgga agataatttt ataatttggg tttatccaga gctcttccaa  22560
gctccataat ttagaatcaa aagagaaaaa taaggtactt ccctcagatg caaaaattta  22620
atttagggaa agtaaaatgt gtatttctgg tttttagggg tgttcttttc tgcagtgatt  22680
```

-continued

```
tctttattag ctttttgtcc agtggaagat atcaggcata tgcagtgatc cactggaaat  22740
ccactgagct tgcaaatata ttaatgctac aatatgattg acttggcatg tattcaattt  22800
aattatcatc atcatcatca tcatcatttt agagacaata tcgcactatg tcaccgaggc  22860
tggagtgcag tggctttatc tcagctcact gtagccttaa cctcctgggc tcaagtgatc  22920
cttctacctc agcctcctga gtagctagga ctacatgttt gcaccaccat gaccagctta  22980
ttttttgttt gtttgtttgt ttgagacagg gtctcattct cttgcccagg ctggagtgaa  23040
gtggcgctat cttgactcac tgcagcctcc acctctcagg ttcaagcaat tctcgtgcct  23100
caggactccc aagtagctga gatcataggt gtgcaccacc acacctggct aatttttgta  23160
tttttagtag agacagggtt tcaccatgtg ggccagtctg ggtatcgaac tcctgacttc  23220
atgtgatcta cctgcctcgg cctcccaaaa tgctggtatt acaggcgtga gccaccgctc  23280
ccagcctgcc cagctaattt tttatttatt tttgtagaga tagtctcact atgttgccca  23340
ggctggtctc aaactcctgg ttcaagcaat ccttctgctt cagcctccca aagtgttggg  23400
attacaggca tgagccacac acccaatcta gcttatttgt taaatacatt acttatatat  23460
tttataagaa tttataaaat tcttatatac catttaatag attgaatgtg ggcagtaaaa  23520
ctgctgccct tctatggcta caaattagtg cactaaatca aaagttcact tttcctttgt  23580
atcctactta catagctttc ctcatccatc tcctgaatta agatttgaaa taaaggatgt  23640
aggaaagttg catgattctg attgctctca agcaagtgaa taaaaacatt caacttaccg  23700
gtgggtaatc actagaagca caaaagacat tatagttgcc tatcataaat cagagggaaa  23760
taactattag tatatctaat tgaaattcag gtgttttata cagtatcttt tatatagact  23820
taattattaa atataatatt tttcttcagt gtgaacatca ggtgaggaat ctctttttac  23880
acttcttgta gtgcagtgga cagttgacca atatatactt atttactgct tgctatgttc  23940
aggttctagg tgtggggttc aagacccaag tttgagtgcc aggtggcatt ggggatcttt  24000
gccctgcaca tccaaataac tccattatta taataaaaac atatttaata tgtataaaac  24060
aaacacaaac ctacataata tgttggtcaa ttnnnnnnnn nnnnnnnnnn nnnnnnnnnn  24120
nnnnnnnnnn nnnnnnnnnn nnnnnnnnnn nnnnnnnnnn nnnnnnnnnn nnnnnnnnnn  24180
nnnnnnnnnn nnnnnnnnnn nnnnnnnnnn nnnnnnnnnn nnnnnnnnnn nnnnnnnnnn  24240
nnnnnnnnnn nnnnnnnnnn nnnnnnnnnn nnnnnnnnnn nnnnnnnnnn nnnnnnnnnn  24300
nnnnnnnnnn nnnnnnnnnn nnnnnnnnnn nnnnnnnnnn nnnnnnnnnn nnnnnnnnnn  24360
nnnnnnnnnn nnnnnnnnnn nnnnnnnnnn nnnnnnnnnn nnnnnnnnnn nnnnnnnnnn  24420
nnnnnnnnnn nnnnnnnnnn nnnnnnnnnn nnnnnnnnnn nnnnnnnnnn nnnnnnnnnn  24480
nnnnnnnnnn nnnnnnnnnn nnnnnnnnnn nnnnnnnnnn nnnnnnnnnn nnnnnnnnnn  24540
nnnnnnnnnn nnnnnnnnnn nnnnnnnnnn nnnnnnnnnn nnnnnnnnnn nnnnnnnnnn  24600
nnnnnnnnnt ttatcagtat gctatgagaa aaatggcaat tgtacatatc aaagaacatt  24660
tcctctttta ttggaaatat tcttggatgg ttaggttgag atcagaagag attatgggtt  24720
gactaaagca ctcatggtaa gctgccctcc gacaccctca ctattcatga aaatagtgag  24780
aatagtagtt agaggagaat aaataggaat ttcaagatac agcaagagaa aacacatagt  24840
ggagaaagga atgcagtaca aggggtcagg ctgagaccaa agcttgacta cagaggaggg  24900
tattttatta gaaggagtgt aagcaggaag gttgaataac tgaagtggac ccctacttac  24960
tctgctctta gtttgatgtg actgtcccag aagtttgaat ctgttataat agaaaatcag  25020
gaacttgtgc taaatttaga gaaggaaaca acataagtaa ttctaaaaac agtgattgtt  25080
```

-continued

```
tttggccatt ttcctgaaca ctgcagaaat ctctttagat ggaggatttg ttcattacat  25140
atttactgag cctcctaagt aatacagaat aaaatctcca gtcatttcaa tggcccataa  25200
agcccttctt ctcaatccag ttatctgtca cttcccttat cttgaaattt atgctcaaat  25260
gctacctctt caaaaaggat ttctgactaa tttgcccttg aacgtccttc ctcccagcta  25320
gaattttcca tactcctttc ctgctttact tttctctttt ggatatatta tatgtaccat  25380
tatctgtggg tctgttctca catgctgcat ggggacagag atttttcttg gttcaaacct  25440
atttccaatg tccagaaaag tatctggcat acgtgataat aagtatatta taaatgaatg  25500
aatcaatcaa tgcacaggcc aagaagagtg ataggcatag agcaaacacc aagtatgcat  25560
atgctgggtg tcttaagtag aaacttgcag tcacaaaaca atttttaaac agttatgtat  25620
taaaacatat gagaaaggca tgtcttgatg aatnnnnnnn nnnnnnnnnn nnnnnnnnnn  25680
nnnnnnnnnn nnnnnnnnnn nnnnnnnnnn nnnnnnnnnn nnnnnnnnnn nnnnnnnnnn  25740
nnngtttcac catgttggcc aggctggtct tgaactcctg agctcaggca atgtgcccac  25800
ctcggcctcc caagtgctgg gattacagac atgagccact gcacctggcc tttttttttt  25860
tttttttttt ctttttggta tggatgtacc acagttccct taaccattca ctagttgaag  25920
gacatgtgag ttgtgtccat tttgtggcta ttagaaataa agcttctata aacacacgtg  25980
cacaattttt gtaggaacat aaattttcct atgtctagga tatgcactga ggagcacatt  26040
gctgagtcat atggtagttg catgttaagt ttttttaaga aactgacaaa ctgttttcca  26100
aaggaattgt accccttaa attcacacca acaatgtatg agccatccag gttcacacat  26160
aggtgtataa tgatgtatca ttctggtttt gtgtttccct gatggctaac gttcaatagc  26220
taattgaata tattttttat gtacttatgt accatctgta tatcctcttc tatgaaatgg  26280
ctgttcatta cttttgccca tttcctcatt ggattgtttt gttttattgt tgagtttggg  26340
gacattttta atacattcta gctacttgtt tttgttagat atatggtttg caaatgattt  26400
ttgccaggct gtagcttgtc ttttcttttc tttcttttct ttttttgaga cggagtctcg  26460
ctctgtcgcc cggggtggag tgcagtggcg caatctcagc tcaccggaac ctccgcctcc  26520
cgggttcaag caattctcct gccccagcct cccgagtagc tgggactaca gacgcgtgcc  26580
accatgcccg gctaattttt tgtattttta gtagaggcag agcttcgcag tgttacccag  26640
gatggtctca atctcctgat ttcgtgatcc gcccacctcg gcctcccaaa gtgctgggat  26700
tacaggcgtc agccatcgcg cccggcctgt agtgtgcctt ttcatcctgt tagtagggtc  26760
ttttacaaag caaaactttt taattttgat gaagtcctat ttatcaattt tttcttttat  26820
ggattgtgtc tatggatgtc taattgctct agcaccactt gatgaaagag ctgtctctcc  26880
tccattgaat tgctttttct tttgaagctt agtatgttgc ttgaaactat gcttgttaat  26940
actgtatact gaaaacgtac aaagaataat gttccaattt aagttagatt taagttaatg  27000
atgttcatta ataaggactc ttcagatata aatattccag aatttctctt agctttctaa  27060
tcaaaacaac catcagtgaa tattacctta ctttggaagg tatagatata catttgaatt  27120
aaatttagtt tttccaaata acccctaatt tgagaaatat attctatctt gaaactaaaa  27180
taatttaata caactttatt ttcttccctc ccctcccctc tcctgtccac attttgtaaa  27240
atctggtcct gaataagtca caatataaaa ataaatgtac acttaacttc cacttcctcc  27300
aaccacaggc tactttctgt tcctcaacct tgggaacaag gtgaaaaaca gtaagcaatt  27360
tgggcagggc attgccaaaa caagattcaa gcagccacat gtggacacct cttaaaagaa  27420
```

-continued

```
tttggggaaa cgagaccaaa gaagtcaggt ttgattttta gtgacaataa caaacatgaa  27480
gtgactcttc ccaagtaaga gtgccactgg gatgtggcct ggccacatgc ttacctatgc  27540
tatacttccc aggaaaccct gatgctctgc tccaggagag acctttatcc tttggaggtt  27600
cagtgtcttg ggagctcttt gattttgtca aagagatgag cagagattcc ctgtgggtat  27660
tttaaggctt ggtgtcaagg tatttttctg acactgctga gcaaagtcca tgtatcaaat  27720
gatctgtttc tagtttgttt aaattcttca catcacttgt agacctaaca tggcaaagct  27780
tcattattta atcataataa cacctactac ccatactaac ttatgattta ttttctgtgc  27840
ctggaaatag tctctgtgtt taacaataat acctggatgc aaaacaatcc actgttatat  27900
ggccacaaaa tattaatgat cttctgaagg ccaagaaaac attttaacta tagttcttgc  27960
acagaaattc acacccagaa tccccaaaat taaaaaaaat ttggacaaca caaataatag  28020
tttaagatac acatacatac aacacagata ctcttacaca taacatcttt tacggaaatg  28080
tgtttagtga aactgttcat ttgttgacag ccacagaagt catattttgc taaatagctg  28140
ctccagctgt ttttttcttt ggaaaatgta tcactatagg ataccctgtt tattgcataa  28200
gataaaagaa aaatatgttg tgataaccaa aaagttttaa gggctttcaa gttatgtaaa  28260
aatggaccta tggacatggt taattgtcct caggatgcaa aattggagct gaaatagtat  28320
atcaaacaat tgcaaaaagt gtactgcagc tatctcttgg gtcaaatctg gtacccagaa  28380
atggagaaaa gcctcaagaa acattgctgg ttggccctct gccacttgac tgtatgatct  28440
gatcacatgt aagtttcaca aacgattcat atttctctgc tagtttgacg ttgagaattt  28500
gctcataaac ctccctaatt ttatcttctt ggtcctttga gaaacacata gtatcccaac  28560
ttgtcagaga ggaaatttga gctggtcctt ctttatccag gagagacctg aaaaattagg  28620
tggtgtgagt actgcagagt gaggctgatt ttccaaagca ctaactttgt tctgattaag  28680
aacaatttac aatggtctcc actgctggta atgattatct tcttttacgt tctgaaaaat  28740
ctgctctggc tgggaaggtg ctgctcactg ccaggtggga tgggntgcca tacctttgga  28800
aaaccatggc ttagcagtgc cacctccatc tccatggttc actccagggt cacccaccgg  28860
tcatgccatg ctgttgaggg gcagagacct ggagcagaca ctgatatgac tgcctgcaca  28920
gccactggct tctcggtggt attcaaacgc caagccattt tcccatactc tttgagtttg  28980
aggaactttt tggagattgc ttgagattct ctgcgtagaa aatcatgcca tttgtaaaaa  29040
gggtcagttt tgcttcttcc tttctcatct gtatgccttt tgttttttct gtcttactgc  29100
actgactaga aatttagctc tatgttgaat aagagcaatg aaagaggaca cccttgcctt  29160
gttcctgatc ttgagagaaa gcattcaatt cttttaccat tgtttgtgat gttagctgta  29220
ggttcctctt tatcgagttg aggaaattac cctttacttg tatttttctg agaattttta  29280
tcttaaatgg gggttaaatt ttgtcaaatg cttttttttg cattgattga tagtattctt  29340
gcaatttttc atctttgctt gttaataagg tggattatgt tgattgatct tctaatattg  29400
aaccagcctt gggattctta cactgcttgg ccatgatatg catattccta ccccacttgg  29460
cattgatgta tgtgtatata taactgattt ctatttgatg atattttgtt aaggattttt  29520
gcatctatat ttatgaaaaa tactggtcag tagtttgctt ttttgcactg cctttatcta  29580
gttactgtat aagagtaata ctagctgtgt gaaatgaatc tcttctaatt tctaaaacag  29640
attgtgtgga aatggtattc atttatcttt aaacaattgg gagagttctc cagtgaaact  29700
atctgaactt agagatgtct ttttggagaa ttttaaaatt acatttttat gctctcagga  29760
tgcaaagttt gagctgaaat atactatcaa acaagttaga aaaagcaaca cttctcgata  29820
```

-continued

```
attcatagat tgcaaaggaa atcttaagat aatttttaaa atacatcaaa ctgaatatgc  29880

taaaatatat tgaattgaaa tgaaaattca acatatcaaa atttgtgaga ctcagtgaaa  29940

agaaagaaat ttgtagcact aagtgaatat atttaaaaag agaaaataga ccaataatct  30000

aaattccctc cacaaaagaa agcctagaga tagaaaaggc agagaatcca aaccatgcag  30060

aaggcaggga ataataaaat gcagaaatca atgaaattga aaacagaaaa acagtaggaa  30120

aaatcaatga aatgaaaagc ttgttctttg aaaaaataaa taaaattgac aaatctctag  30180

caagcctgac aaagaaaaaa agagaaaatt caagaatgaa acaagtgcag acactgcaga  30240

cataaaaaaa aaataagaga atactacaaa cagctctcac agttaaattt tatatatgag  30300

atgaaatgta ctgattcttc aggaaacaca cctactacac tatactccct aatatgaaat  30360

aggtaatttg aatattttga acagttgaat aaaattaata ctataagtat taaagacatt  30420

aagtgtataa tggtttcttt gtttgggctg ctataatacc agaaactgga tgaccgataa  30480

acaacaaaac tttatttctt acagtctgga agctggaaag tccaacatca gggcaccagc  30540

agattcagtg cttggtgagg gcccattttc gtgttcatag atggttcctt cttgttgtgt  30600

cctcatatgg tgaaagggat gaggcagcac tctgcagcct aatcccactc gtgattactg  30660

ccctaatccc actcgtgagg gcagagccct catgagctaa tcccactcat aagggcccta  30720

atcccactcg tgagggcaga gccctcatga gctaatcacc tcccaaaggc cttatatcct  30780

aatgtcatca cactgctgtt taggtttcaa catatgaatt ttggggtgat gcaaatattc  30840

agaccaaagc agtttcttt tataccactc tagtagagaa agggaggagt acgtctgtta  30900

ttgccaggta ggggtagaaa tccgggtttc caacttgggc tttgttatac ccaaggagag  30960

gatttctcct tgctcctggg ttagcttggg atttttggct ccctactaag tctccactgg  31020

gatcaccctg gttgggagga gtagtgatac cttttcactg atgtccacat gttttccatt  31080

gacattatgg tggaagggtc ttattactan nnnnnnnnnn nnnnnnnnnn nnnnnnnnnn  31140

nnnnnnnnnn nnnnnnnnnn nnnnnnnnnn nnnnnnnnnn nnnnnnnnnn nnnnnnnnnn  31200

nnnnnnnnnn nnnnnnnnnn nnnnnnnnnn nnnnnnnnnn nnnnnnnnnn nnnnnnnnnn  31260

nnnnnnnnnn nnnnnnnnnn nnnnnnnnnn nnnnnnnnnn nnnnnnnnnn nnnnnnnnnn  31320

nnnnnnnnnn nnnnnnnnnn nnnnnnnnnn nnnnnnnnnn nnnnnnnnnn nnnnnnnnnn  31380

nnnnnnnnnn nnnnnnnnnn nnnnnnnnnn nnnnnnnnnn nnnnnnnnnn nnnnnnnnnn  31440

nnnnnnnnnn nnnnnnnnnn nnnnnnnnnn nnnnnnnnnn nnnnnnnnnn nnnnnnnnnn  31500

nnnnnnnnnn nnnnnnnnnn nnnnnnnnnn nnnnnnnnnn nnnnnnnnnn nnnnnnnnnn  31560

nnnnnnnnnn nnnnnnnnnn nnnnnnnnnn nnnnnnnnnn nnnnnnnnnn nnnnnnnnnn  31620

nnnnnnnnnn nnnnnnnnnn nnnnnnncat ccatgggtat attttgaata tcaagcaggg  31680

atacttttta tccatctatt caagatcaag ttattaaaca catattaagt gctgtggtag  31740

aaagtattgg gatgactgta atgaaatgaa tatatttctt gtgctattaa agtttagaat  31800

tatataattt tagatcttca ttgaatctca tagataactt catttagtca tttcattttg  31860

cagacatagg aaatgaagca cacaactgaa gtgtttgttg agttttctac aattaattat  31920

ttgcaaaact attactagtc cagaattctt tctactatat tgtctcccct accttagaaa  31980

ttcaatacat cattgtgttc attggaatta caggagtttt cttccattat ttcacaatgt  32040

ctaagtacag acattatgaa gtagggaaat ttactttcat tataaaactt tcttcattaa  32100

catgtataga tacatttata atgtgagtat atacatactt ttgtccaaag tggatttaaa  32160
```

-continued

```
attcaaaaaa aactaaattt ctatgatcaa atccatgctt agtctataaa actaaaaata  32220
ttgtgagtta acgtaataag atctgtaaaa tactgaggcc attatgggaa atgtttaaag  32280
ttcctacatt catatcacat tttttatctt ggatcagttc caaaagtgta atgtttgcta  32340
ttttgaaatt atcttaggta tcaaattcca acttataaat ttaaaagttc tttaaatgta  32400
attcctttta taaaaagtga atttgggtta ctctgcataa ttctccttga ccccactgat  32460
gctttaatat ctctcattaa gtggactcca ggcagccact ctttgcttta tccaagctcc  32520
agctaaggcc agctgttctt tgagcagtgt ttttattaac ttatttagga actggtgcat  32580
atcttattac cctattttcc attcctgtcc tatgcagctg tagttgatac ttttcataac  32640
agcctttaca tatcaacctc ctcccctatt ttttttctta ttctctttta cttccctttt  32700
taagtaaatt aagcatgtgt gtgcatgcaa aagccctctt ctttctttct ggtaaccata  32760
tgacgtgaaa gcttcaggaa tgtgcctgtt gtttgtctga gattataaac gtcatggaaa  32820
aacttttact aatgatgtaa acattcagaa atgtagaata catgaatttt aataatagca  32880
aaatttcttc aatgttgcat ttaagaaatt aatttagacc taatttaaaa tcaatgcaat  32940
gtaaatacaa agaaaaggat ttgaacagat agaagactgt acaaaatact actaacctca  33000
gcttactgaa tttcaaatat tacaagtttc atggcatatg aaaatacaag tttgaggagg  33060
gagctatttt ataaatgtaa gacacgcata agttgcagcc actatgagat taaacacatt  33120
caaaattcaa ataaggtaaa agtagcattt tttagtatat taataagtta tcattgcaat  33180
ttgaattttc actacctact cactacaacc ttgaataaat cacccattgc ttctatgtct  33240
agataccttt ttatgcagaa ttactatttt aaaagcaact tatattagaa atataataaa  33300
tattattcca tatgaattgc aataatgaaa tctatactta ttaaaagata cattaaaaat  33360
taatagccca agccaggcat ggtggctcat gcctgtaatc ccagcacttt ggggaggccg  33420
aggcaaggtg gatcacttga agtcaggagt tcgagatcag cctggccagc atggcaaaac  33480
cccgtctcta ctaaaaatac aaaagttann nnnnnnnnnn nnnnnnnnnn nnnnnnnnnn  33540
nnnnnnnnnn nnnnnnnnnn nnnnnnnnnn nnnnnnnnnn nnnnnnnnnn nnnnnnnnnn  33600
nnnnnnnnnn nnnnnnnnnn nnnnnnnnnn nnnnnnnnnn nnnnnnnnnn nnnnnnnnnn  33660
nnnnnnnnnn nnnnnnnnnn nnnnnnnnnn nnnnnnnnnn nnnnnnnnnn nnnnnnnnnn  33720
nnnnnnnnnn nnnnnnnnnn nnnnnnnnnn nnnnnnnnnn nnnnnnnnng atctcactct  33780
gtcacacagg ctggatatgc agtggcacca tcacagctca ctgcagcttt aacctttttgg  33840
gctcaagcga tcatcctgcc tcagtctccc gagtagctgg gactacaggc acatgccacc  33900
acacctggct aatttttaaa atttttattg agacaagatc tcactatgtt gcctaggctg  33960
gtctcaaacc actgaactca atcaatcctc ctgccttggc ctcacaaaat gctgcgatta  34020
caggcatgag acactgtgac tggcctactt taatattttt taaaaatcaa gatcacattt  34080
tgtaattttt aaacacacta cattaatgat atttgttgtg catgagaggt ctagcatttt  34140
taaactttgg acttgaaatt taaagcaaaa tttgtattta ggttgttatc aaagaaatgg  34200
ttaactgtgt aaaacatgtt aaaagttgtg tgtgcacctt aaaagctaaa taggatgcca  34260
tactcagaag cactattagg aactttgact gcagattaaa caggtaccaa acaatagttg  34320
aaagtagttg gtgacatact tgggctaatc attgctaagg cttcctttct aatatggatg  34380
tatgagaaat atagtaaagc ccatgattgt ttttctatta aaaatctaca tttacaaaat  34440
attatctaga aagtatgagt gtctagtact tttaatttct atatacatgc ataacctgtg  34500
acttgttttg agtattattt gtacattttt atgggaaagc tttttcatgc ttttaatatt  34560
```

-continued

```
ttctacttat gggaaatgta tatgcagtga catgtacaga acttgtgtac aattcaatga  34620
gttttgacaa gggcatacac ccatggaacc accattcatn nnnnnnnnnn nnnnnnnnnn  34680
nnnnnnnnnn nnnnnnnnnn nnnnnnnnna tatattttat tgtaacttta attcacattt  34740
ttctgatgat tcattatgtt ggatactttc atatgattat tggccattca tatacaggca  34800
gtctttgctt tacatagtag tataggacta aaaaatgatt atagaaactg aatttgtgca  34860
aagtaatcct aataatcaat gtagaaaatt atgattgttc tgtgaccttc aaaaattttg  34920
ttacaatatt caaaacttca agtgtcaatt ataaatgtat gtgaaaacaa aaaattattt  34980
agtatactaa tttaaaacat tagaaacata gagatttttt tgtataaaaa cttatcaaga  35040
attttttttc tcattgttca gcttatgtta cagagagggc ctcttttcta tgtttcagtt  35100
aattgttata cactttcaaa gtttagatca gttttcaata ttttatcctt tgcactttca  35160
atattgtcaa atatcagcaa gagttctctt ggtgtgaaat ttttgttttg ctgtttttta  35220
cttccttcaa gacatcatcc ttcattgaat tcatcagaac cacttgcttt aatttctgtc  35280
catatttgtc ttcagtaagt tgtcttggct gcatatgtaa agtttcttga acagcagtgt  35340
taacattccc atggtcagct ctttgttctg aaactccgtt tatgttatat tcaaatttca  35400
tttccagcac tctcactttt gttgctctgc taccatcttt gttagccaat atgtgtcaca  35460
cgagttcatt gctgtgagac aaggaggcaa cataactaca caattttctc cctgtgcata  35520
aactgaagaa caaatgcaca atgaccaatc aatgacagat tttgaacaaa gtgatgtcac  35580
tgattataat gtgcatctgt tatttatgta atgattttat ggatgaaaga gctagaagca  35640
aagttttcat attataaaat ttttcatacc caatatatga tagtaacaaa ttcaaactct  35700
gttttgagaa gacaggtgtt acttaactaa accatagtaa caaaaattca agcacattgg  35760
aatgtgcaaa ggactgactt atctccttta gggaagtttc tgttcaagtc attactgcat  35820
ttttctcctg aattgtctgt ctttttagta ctgagttata ggagttcttt atacattttg  35880
gatacaattn nnnnnnnnnn nnnnnnnnnn nnnnnnnnnn nnnnnnnnnn nnnnnnnnnn  35940
nnnnnnnnnn nnnnnnnnnn nnnnnnnnnn nnnnnnnnnn nnnnnnnnnn nnnnnnnnnn  36000
nnnnnnnnnn nnnnnnnnnn nnnnnnnnnn nnnnnnnnnn nnnnnnnnnn nnnnnnnnnn  36060
nnnnnnnnnn nnnnnnnnnn nnnnnnnnnn nnnnnnnnnn nnnnnnnnnn nnnnnnnnnn  36120
nnnnnnnnnn nnnnnnnnnn nnnnnnnnnn nnnnnnnnnn nnnnnnnnnn nnnnnnnnnn  36180
nnnnnnnnnn nnnnnnnnnn nnnnnnnnnn nnnnnnnnnn nnnnnnnnnn nnnnnnnnnn  36240
nnnnnnnnnn nnnnnnnnnn nnnnnnnnnn nnnnnnnnnn nnnnnnnnnn nnnnnnnnnn  36300
nnnnnnnnnn nnnnnnnnnn nnnnnnnnnn nnnnnnnnnn nnnnnnnnnn nnnnnnnnnn  36360
nnnnnnnnnn nnnnnnnnnn nnnnnnnnnn nnnnnnnnnn nnnnnnnnnn nnnnnnnnnn  36420
nnnnnnnnnn nnnnnnnnnn nnnnnnnnnn nnnnnnnnnn nnnnnnnnnn nnnnnnnnnn  36480
nnnnnnnnnn nnnnnnnnnn nnnnnnnnnn nnnnnnnnnn nnnnnnnnnn nnnnnnnnnn  36540
nnnnnnnnnn nnnnnnnnnn nnnnnnnnnn nnnnnnnnnn nnnnnnnnnn nnnnnnnnnn  36600
nnnnnnnnnn nnnnnnnnnn nnnnnnnnnn nnnnnnnnnn nnnnnnnnnn nnnnnnnnnn  36660
nnnnnnnnnn nnnnnnnnnn nnnnnnnnnn nnnnnnnnnn nnnnnnnnnn nnnnnnnnnn  36720
nnnnnnnnnn nnnnnnnnnn nnnnnnnnnn nnnnnnnnnn nnnnnnnnnn nnnnnnnnnn  36780
nnnnnnnnnn nnnnnnnnnn nnnnnnnnnn nnnnnnnnnn nnnnnnnnnn nnnnnnnnnn  36840
nnnnnnnnnn nnnnnnnnnn nnnnnnnnnn nnnnnnnnnn nnnnnnnnnn nnnnnnnnnn  36900
```

-continued

```
nnnnnnnnnn nnnnnnnnnn nnnnnnnnnn nnnnnnnnnn nnnnnnnnnn nnnnnnnnnn  36960
nnnnnnnnnn nnnnnnnnnn nnnnnnnnnn nnnnnnnnnn nnnnnnnnnn nnnnnnnnnn  37020
nnnnnnnnnn nnnnnnnnnn nnnnnnnnnn nnnnnnnnnn nnnnnnnnnn nnnnnnnnnn  37080
nnnnnnnnnn nnnnnnnnnn nnnnnnnnnn nnnnnnnnnn nnnnnnnnnn nnnnnnnnnn  37140
nnnnnnnnnn nnnnnnnnnn nnnnnnnnnn nnnnnnnnnn nnnnnnnnnn nnnnnnnnnn  37200
nnnnnnnnnn nnnnnnnnnn nnnnnnnnnn nnnnnnnnnn nnnnnnnnnn nnnnnnnnnn  37260
nnnnnnnnnn nnnnnnnnnn nnnnnnnnnn nnnnnnnnnn nnnnnnnnnn nnnnnnnnnn  37320
nnnnnnnnnn nnnnnnnnnn nnnnnnnnnn nnnnnnnnnn nnnnnnnnnn nnnnnnnnnn  37380
nnnnnnnnnn nnnnnnnnnn nnnnnnnnnn nnnnnnnnnn nnnnnnnnnn nnnnnnnnnn  37440
nnnnnnnnnn nnnnnnnnnn nnnnnnnnnn nnnnnnnnnn nnnnnnnnnn nnnnnnnnnn  37500
nnnnnnnnnn nnnnnnnnnn nnnnnnnnnn nnnnnnnnnn nnnnnnnnnn nnnnnnnnnn  37560
nnnnnnnnnn nnnnnnnnnn nnnnnnnnnn nnnnnnnnnn nnnnnnnnnn nnnnnnnnnn  37620
nnnnnnnnnn nnnnnnnnnn nnnnnnnnnn nnnnnnnnnn nnnnnnnnnn nnnnnnnnnn  37680
nnnnnnnnnn nnnnnnnnnn nnnnnnnnnn nnnnnnnnnn nnnnnnnnnn nnnnnnnnnn  37740
nnnnnnnnnn nnnnnnnnnn nnnnnnnnnn nnnnnnnnnn nnnnnnnnnn nnnnnnnnnn  37800
nnnnnnnnnn nnnnnnnnnn nnnnnnnnnn nnnnnnnnnn nnnnnnnnnn nnnnnnnnnn  37860
nnnnnnnnnn nnnnnnnnnn nnnnnnnnnn nnnnnnnnnn nnnnnnnnnn nnnnnnnnnn  37920
nnnnnnnnnn nnnnnnnnnn nnnnnnnnnt gtataaggtg taaggaaggg gtccagtttc  37980
agttttctgc atatggctag ccagttttcc caacaccatt tattaaatag ggaatcattt  38040
ccccattgct tgtttctgtc atttttgtca aagatcagat ggttttagat gtgtggcttt  38100
atttctgagg cctctgttct gttccattgg tctatatatc tgtttggtac cagtaccatg  38160
ctgttttggt tactgtagcc ttgtaatata gtttgaagcc aggtaccatg atgcctccag  38220
ctttgttctt tttgctaagg attgtctttg ctatgtgctc ttttttggtt ccatatgaaa  38280
tttaaagtgg tttttttcta attctgtgaa gaaagtcaat ggtagcttca agggggatag  38340
cactgaatct ataaattatg gagtctcact ctgtcaccca ggctggggtg caatggcatg  38400
atcttggctc actgcaacct ctgcctcccg ggttcaagtg attctcctgc ctcagcctcc  38460
tgagtagctg ggattacagg catgtgccac ctggctaatt tttatatttt tagtagagac  38520
agggtttcac cctgttggtc aggctggtct cgaactgctg acctcatgat ctaccagcct  38580
tggactccca aagtacctgg attacaggtg tgagccacca cacccagcct acaattcttt  38640
attagagata tgtataacaa atattatgtt ccagtcaata gcttgacttt ctgttttctt  38700
aatggcacct gtgcataatc agacgagttt aattttgatg aaatctaaat tagcaacttt  38760
taatctcatg tcagtacatt ttgtgtccta attaaatatt gtgaaaataa tatcctgggt  38820
tttattctag aaatgttata gttttaactt atacatttat atttttgatt catcttgaat  38880
tttgggtgtg tagtatgaga agtgattcaa agtttttttt tgtacattta tcaaaacatt  38940
taataactat tttaaagata cttttattta taataaataa acataggtca taataaattg  39000
atataggtca atcacttgac cctatgtgct tgaatttatt tctggaatat attttattcc  39060
attgatttat ttatctgtta ttgtaataaa accacactgt gttgataact gtagctttat  39120
tataagtctt gaaatcagtt tgtgtaagtt ctacaaatgt gttctttttt caaaattctt  39180
ctggctattt ttggtctttg catgtccata taaactttta aattataatg atcttattaa  39240
tttttacaaa aatgcccatg gcattttcat tgggattgca tcagatctat atacatgcat  39300
```

-continued

```
gtatacatct atacatgggg agaattgaca tctcagcaat gagttactaa tgaatatgtt  39360
attatttctc catttttaaa attatttatt tcagtaatgt tttgtggttt taagtaaatg  39420
gattttgcat atcttttgtt aaaattattt gcatgtattt aattttttaa tgttattcta  39480
aatagaattg attttagtca ttagtttgat gcaaaataca gaaacacaat caatttttat  39540
attgacattg tatcctatga cattgttaaa tttacttctt agttctggaa tgttaaaaaa  39600
atttaaataa tattctatat taaaattatt gtgtcttcta aaattaaaag tatttttctc  39660
tctttctttc tttcttaact ccatgacttt attgtttgtt tgttttgcct tatagcactg  39720
gcttgactct ccagtacagt gttaaacaga ggtgataaaa gccaatatcc ttgtgttgtt  39780
cccaatttca gggagaagga ttagtttttc atcattttat atgatattgg ctgtagactt  39840
tctgtagata ccccttatta aattgaagaa gattctttca tttatagttt gctatgagta  39900
tttattgtga atggatgtta aattttgcca cttgattctg aatttaaggc aataatttgc  39960
tttttctctt ttattctctt gctgtgataa gttacatggt ttatttttga atgttaaatt  40020
atatttacat tcctgggata aaacacactt gatcagatgt gttattctac tatatattgc  40080
tggatttgat ttagtaacat tttgcttaag attgttgtat ttttgttcag gataggtatt  40140
ggtctataat tttcttttat tataacattt tttctcagat atttacatca aagttatact  40200
accctaatat cagtagttgg ggaatgttct ttcctccttt attttcacag ttattatttc  40260
atcctaaact atttgataga attcactagt gaaaccatct gaacctggag ttttctattg  40320
tggcagattt tgtattactt tgacttcttt aataaatata gaactactca tactttcttt  40380
ttaaaaaatt ttactttagg gccgggcgcg gtggctcacg cctgtaatcc cagctctttg  40440
ggaggccaag gcaggcggat cacgaggtca gtagatcgag accttcctgg ctaacacagt  40500
gaaaccccgt ctctactaaa aatagaaaaa attagccggg catggtggcg ggcgcctgta  40560
gtcccagcta ctcgggaggc tgaggcagga gaatggcgtg aacccgggag gtggagcttg  40620
cagtgagccg agatcatgcc actgcactcc agcctgggcc acagagtgag actccgtctt  40680
aaaaaaaaaa aaaattattt taagttctgg gatacatgta cagaatgtgc aggtttgtta  40740
cacaggtata catgtgccat ggtggtttgc tgtacctatt aacccatcag aatttctata  40800
tcattttata tgttatgttt ccaagaaact tgaccatttt atttaaaatg ttgaaaatat  40860
tggctcaagg ttttttgtaa tctgcagtga tattcctgat tttattcatg atgtgaattg  40920
tgtttacttt ctttttatac atcttaataa gtgtttatga aatttataaa tttttccaaa  40980
taaccaactt ttatattaat taatgttctc tattgttttt gtgctttcca ttacatcgat  41040
ttctgatcat tatgattttc ttgcttctaa atattttgcc ataaggttct atgtattagt  41100
tccatgtggt taatagtgtt ttgcaaaatg tctgtatcat tatcactttt ccgcctaatc  41160
gttctaacag ttattgagaa ggaaatgata aaatatttaa ctacgattgt gggttttttt  41220
ctttcagttc tgtccaggtt tgcttcatgt agtttcagtt aaaaaaaaag tttttaccaa  41280
aaacatgcgt attgtgattg ttatattttc ctaattaact gatcctttga tcattataaa  41340
ctatcccttt tatctttggg gacacttctt gtattaaggc ttttttgtct gttattaata  41400
taacacatgt tcttttattc gtggtttgca tcatatatct ttttctattc ttacttgtga  41460
attatttgta ttgtatttaa actgtggctg gtggacaaca aagtacgtct cttgtgaaca  41520
acctataatc aggtctttaa tcttgtctga caacctctga cttttaaatg gagtatttac  41580
ttcatttaga tttaaactta gtattaattt acttgacttt ggatgtacta tttttctttt  41640
```

-continued

```
gttttctata tgtcctatct catttttagt tcctctgttc ttgctttctt tcttgccttc  41700
tactgggtta actatatatt tttagcatta tattttaatt cttctatttg acttttagct  41760
atgtttcttt gtattattat ttttcgtggc ttctcaaggg actgcaatat gaatacttga  41820
cttatatcta cttaatttat gtaactggaa ataaaataca tgaattttgc agaagtattc  41880
ccatgtactt ccctgtagtt tctgctgtta ttgttatatt ttttgtactt acttttatag  41940
atgtcaggtt gttatacgtg tcagctatat atattaatat acgtgtgtat gtgtgcatgc  42000
acactcggtt tttcagctgt ctttctactg agctccttgg attctccgtc atgtacatat  42060
aattaaaata ttaggcaagg atttaagggg agtttagtcc caaactttgg atctaactcc  42120
tctgtttcca actactttag cagcctcata ctttattctc tgacacctca agccaatagc  42180
tgcgtttttt ttccttttcc aagttcatac atgttatctg cagaatagtt tgatataagt  42240
tatcaccaga tcagagttcc tcaagttgga atattttgtt ttaaattctt agctgctttt  42300
gcaaaatttt tgcccaaaat atgaatctga gctcctttca aggtttttat taaaatatct  42360
agtcacactg aacactttag tgtataatag ccttaatgtc acttggtgat gggtagatag  42420
aagaggagtt tacattgcaa taatatatat ggctttaaat tgattattag acatttttgt  42480
tctaaaaatc ttttgatcca agtgtggtgg ctcacacctg taatcacaga gctttggaag  42540
gctgaggtgg gaggatcttt tgagcctagg agtttgagaa cagccttggc aatgtagcga  42600
gatcccgtta gtacaaaaaa aaaaattagc ctagagtggt ggtgtgtgcc tgtagttcca  42660
cctactcagg aggctgaggt ggaggattgc ttaagcccag atgtttaagg ttacactgag  42720
ctatgaaggt accactgcac tccagcctgg gcaacaaaat ggcaccctca tccctgtaat  42780
cccagcactt tgggaggcca gggtgggcag atctccaggt caggatttcg agaccagcct  42840
ggccaacatg gtgaaaccct gtctctacta aaaatacaaa attagtcagg tgtggtggca  42900
catgcctgta atcccagctg ctcaggaggg tgaggtggga caattggttg aaatcaggag  42960
gcagaggttg cagtgagcca agatcatgcc attgcactcc agcctgggca acaagagcga  43020
aaccccatct caaaaaaaaa aaaaaaaaag aaaaaagaaa aagaaaaaga aaagaaaatc  43080
ttttggcaat cagagagttt tctgttggtt gctttatacc actgaggccc atgtccccaa  43140
cctcacacca tcctttgagc ctttgttctc attgtttctc cttccatctc ttccttctct  43200
ctcgctttct catatgggct cctgaacaat cccaattctt tctttattct ttcttatgga  43260
tattttccca aagcttacag tcagaactcc ttgtgtatat tttaatcaat aaagtttnnn  43320
nnnnnnnnnn nnnnnnnnnn nnnnnnnnnn nnnnnnnnnn nnnnnnnnnn nnnnnnnnnn  43380
nnnnnnnnnn nnnnnnnnnn nnnnnnnnnn nnnnnnnnnn nnnnnnnnnn nnnnnnnnnn  43440
nnnnnnnnnn nnnnnnnnnn nnnnnnnnnn nnnnnnnnnn nnnnnnnnnn nnnnnnnnnn  43500
nnnnnnnnnn nnnnnnnnnn nntattttttg aaatctgtcc atccatccat tcatctatcc  43560
gtctgttgat ttgttcactg attcacattt ttgctaagca agtacttatt aaatatcaat  43620
gtgtgccagg cattatatgc ttatctgttt cttctgacct tttttttttt cctattctac  43680
ttcactgtac attaactatt gatatagact caattcttca tctctggtgt tttgataata  43740
tgagtactcc tttcaaatgt tcatttactc tcatgatttc aattacttat agatacagga  43800
attctcccaa attcctttac gtgacccatt atgctaacac aaacctctcc tgtgataact  43860
ctgtttatcc tgctaacaag atatgaagct aacattttat ttcctcatac tcattcttgg  43920
gtaaatctcc acaagccagt atgtctttct aatttcttcg tcactctcaa tggttcaatt  43980
tagtctccag gtgttatagg agtggtctca atagataatt aagttggctt tctaattagt  44040
```

-continued

```
cttctaagaa ctgtttcaga taaactatgt aaaatcaaag ttgtcatttt tgataaatat  44100
tctcatgaga tgacttactg catgcagctg tcaaaactaa tgaatttata aatcaagcca  44160
gctcattttg cctttgtatt agtctgttct cacactgcta tgaagaaata gctaagactg  44220
ggcaatttat aatggaaaga agtttaagtg actcacagtt cagcatgact ggggaggcct  44280
caggaaactt acagtcatgg caaaaaggga accaaacacc tccttcttca catggcagca  44340
gcaaggaaaa gtatgagtgc ccattgaagg ggcgagcccc ttataaaact atcagatctt  44400
gtgagaccta actcactatc atgagaacag gatgggggaa accacaccca tgattcaatt  44460
atctcttcct ggtccctccc atgacatatg gggattatgg gaactacaat tcaagatgag  44520
atttgggtgg ggacacagcc aaaccatatt ggcctccaaa cagaatatgt ataactatat  44580
gtataactag ctttccttgt aacgatccct aaaaaatgac tttttctttg gaagttttat  44640
tgagaaattt tttaaaggta agtgtttcac agtatgtaat tttaagacta aaattatagc  44700
catggtttat atttggggcc ccaattgtcc aactatacat gcatgggaac agatacaaaa  44760
caattttaaa atatcttact cctatttcat gcacattgaa tacatttata agactaattt  44820
ggcacattag tatgaatggg tcagtccata ttctcagctt tgtagtagca ctcaaaatcc  44880
tgtttgtgtt tcataacttg ataaatactc caaaatttct ctggattaag ccaggctacc  44940
agagagagtt gcacatgaac ggtatactta caatctctga agacatagtt ttaataaaac  45000
atatttgaga attattccac ctacgtactc agagtgacgt tgtaagaatg ggaaattttt  45060
ttttttggat ttttttaatt tttatttttt attatacttt aagttttagg gtacatgtgc  45120
acaacgtgca ggtttgttac atatgtatac atgtgccatg ttggtgtgct gcacccatta  45180
acttgtcatt tagcattagg tatatctcct aatgctatcc ctccccccctc cccccacccc  45240
acaacaggcc ccggtgtgtg acgttccgct tcctgtgtcc atgtgttctc attgttcagt  45300
tcccacctat gagtgagaac atgggggtgtt tggtttttaa aataaatttt ttttcccatc  45360
ccaaaaaatc agaatgggaa aaaattttta tttttattta tttatttatt ttttatgaga  45420
tggagtctca ctctgtcgcc cgggctggag tgcagtggcg cgatctgggc tcactgcaag  45480
ctccgcctcc cgggttcatg ccattctcct gcctcagcct cctgagtagc tggggctgca  45540
ggcgcctgcc actacgcccg gctaattttt tgttgtattt ttagtagaga cgaggttcca  45600
ccgtgttagc caggatggtc tggatctcgt gacctcgtga tccgcccgcc ttggcctccc  45660
aaagtgctgg gattacaggc ctgagccacc gcacccggcc aagaatggga aaaattaaac  45720
atacttagta tttactgtgt atggatgttg tcgaggacat tgcttattaa attatggtac  45780
cctctttatg ggtttttttca gaagaaatgt atctttggtt tcagtatcag agattattgt  45840
atttttgttc atttaattta tctttatttg cgataacaaa gatttactat cttgcttttc  45900
cctttatttt atttatttgt tataaagagc caaatttata atttacttct aggaagtcta  45960
cagtgtgtat tttgtcagtt aatctaattc ctgggttcat tccatttgtt ttacccctat  46020
tttctctgtg ctcaatatac catcacatcc tgtcaatatt tctttacatt tttctttagc  46080
tctactccta attattttta acctaccaga tcattgtaat ctatgttgtg ctttatatgt  46140
aaaatatcga acaagttttt atcaaacttg cctattccta ataacaagtg atatgaaggc  46200
tcagactttt aagtttatat gtcactaatt aatctctgtc tgttgtttct ctgtcaccta  46260
ctgtagtcac ctaaactgct ttcaaacttt cactgccttt caataacacc aaacctgata  46320
atcccccaca ctttttttctt atgactgcct tacactattt tccttcagcc taagattttt  46380
```

-continued

```
cccagccctt gacaaacatt ttgttgccac ttatgtatct ctccccgtac tcaacccact  46440
gaatcctttt tctttcacat ctttactaat cctcagttgt tccttcaaat tagagctccc  46500
agatcttctt ctctgtcctg ttgcatttac ctctttgtag ttatttctat taactaaaat  46560
atttttcatc tatgtatgaa aaggttctta tacattgact tgtatcctgc ccacatcatt  46620
caatgtgaat gttcaataaa tgctattgat taaattcaag ctagtgcaaa atttgtagct  46680
ggtatgctga aatatgcttt gaacttaact ttgaaggtat ttccattttt gtattgatcc  46740
atactatatt aatgttagca aattttactt tgtgtatgtt taaattatct atctgtatgt  46800
tgtgtttcta aaaggatagt agattattta aaatttctag agacaaaaat attcttaaac  46860
ttgggaagat tgggttgata attttgtatg ttttataaat ataattcaca aatataactt  46920
ttcagacatc tgttttgctt aaaagagagt acatctgttc ctgaaaaata aaaatatata  46980
gtcataaata aacaatttaa acttggtcat ccaacttagt gtacttatcc aggtcaatga  47040
gaagtcaata caaaactacc ttcacaatcc tatcaggaga gtttggcaat ttctaataac  47100
tgatattcag aagtttatag aataattaca ttttatacat gtattcatct tctaagtaga  47160
atttactggt cagtaaaaac tctcatgcat ttaaacctat aacaaattct tgcttattta  47220
gatctacaga ccctaatttc aaccatgatg aaagtatttt agtgataaga ataatttatg  47280
aataaaaatg taatttagtg aataccttgg cagttaatgt tgatcgcttc atcacagttc  47340
agtcatgttt agaaaatcta agcaagctgt gtgattactc caggaagcat ggaatgatgt  47400
gttcaaatta gtaccatctg tggatagaaa aagtttgagg tttttagtca ttcttaaaga  47460
atggaaatct gattctccat gctgaaatga gtgtaatcct ttttctatct gtaattcaat  47520
agggcagttg ccttgaaata gtctagttca gcacacagtt catcaaagag aagatactgg  47580
atataaatga gggttactgc tggtcactta tgaatacttc tgaggtagcc ttgtttaaaa  47640
aattgtctac aagttatacc atatatttca cctcagatca gattcatttt tggtttatct  47700
ttctaaatac atttgagtga aaatgtggac tagattttgt accacatgaa aacaaaaggc  47760
tgtttcaatg aaccatcatt tatttccaca gtcaacaaac acttatgagt gccagtatgt  47820
tccagtgtcc catcactgtg cctgtcacat aataggaggc tgaaattgtc attatgtttc  47880
ctatagccag gttacaaata actcttgcct ggatttagtg gtttttcttt ttaagacctt  47940
ttcttctctg aaagcttaat tggagaatac tagagtctgt gaacgaatat tgatctgctg  48000
aaaattttta ctgtgtagca aaatttgcta gtaacaaaca ccagctatcc taaaatctga  48060
acattggagg aaaaaatagt tgatcataga ggcatgggca tctagtcatc cctccagatg  48120
ggattagcaa agggcagcct cttctgcctt ctctagttca ttagctagtg aatatttccc  48180
tctcatttcc agtggtttag caaactctag ggagagaaaa ttgaaacatg ggaaaggtaa  48240
ctggtagtag atctaaaaaa gaataaataa aagaaggaaa gcatttgtac actgattctt  48300
atgaggaaag agtagagtgt aagattttaa tgaaaacaaa agtcaatata aaaattttca  48360
aggccaggtg ccatggcgca tgcttgtgat cctagcactt tgggaggctg aggtgggcag  48420
atcagttgag cccaggagtt caagaccagc ctgggtaaca tggcgcaact ccatctctac  48480
aaaaagtacg aaattagttg ggtgtgatgg cacacgcctg tgattccagc tacccgagag  48540
actgggttgg gagggtcata tgagcctggg aggttgaggc tgcaatgagc catgattgtg  48600
ccactgcatt ccagcctcag caacagagta agactctgtc tcaagaaaaa aaaagtaaaa  48660
atttccacat aataaaaacg atcatcagca aaataaaaag acaaataaca gatttggaaa  48720
atatatcttc atcaaggatc acaaaaaggt tatattaaag gcttaaataa ataaatagca  48780
```

-continued aagccataca cccaatagaa aaaaaagtag aaaaaataca aatgatagtt tatgaaaaag 48840
gaaattaaag agagagaagt gcaataagct tcacactgaa acagaatttt ttccctctga 48900
aacttttatt gcatactctg ttggcttggg gaacaggcat tctcatgcat gttgacagga 48960
gtaggtattg gtaaaacctt tctggagtgt gatttagcaa tgtctaccaa tgctacaaat 49020
atgcatatgt tttacctagc aacgattatc ctacagattt actcacacat atgtgtggaa 49080
tatgaaagca taggcttgta cattacagct tgtttactgc aaatattgga cacagcttaa 49140
tatcatttca tagaggctgg taaaatcaaa ttcgatatat ccatttcaat gtgcttactc 49200
catacaactc caaacactga agaaaaaggc aaaatatatc caaagcatat atatagtgac 49260
cctaaatccc agtttccagg gcagtctggg tttatgcttg ctgtgctggc atttcatcca 49320
atagacattg ccttttactc tcaaaagtga cctgtctgta taacaaataa tttgctgcaa 49380
tggagtgaat gtttatttcc cccctagaat catatgttgt agtcctaact ccctgtgtga 49440
tgctattaga aggtgaggcc tttcagaggt aattaggtca ttagggtaga accctccatg 49500
aatgggatta atgcccttat aaaaagaatg cagagagctc ttttgccctc tttctgctat 49560
acaaggacac aataagaagc cagcagtctg gaaccaggag gctggttctc accagaaacc 49620
tgccatgctg gcaccctcat ctgactttca gttccagaac gttgagaaat aaatttctgt 49680
tgtttgtaaa tcactcagtc tatagtaact tgctacagca gccaaactaa gacagtcact 49740
ctagatatat tctttggaag tgagagaagg gactgggagg aagaagagag tcggatatga 49800
ggttagatga aaagaaaggg aaggctgcac tccagcctgt gcaacagagt gagaccttgt 49860
caaaacaaaa caaaaacaaa aacaaaaaca aaacaaaaaa aacttttcaa gtatatcact 49920
gtgcttcaga taaagctaaa agtcatatat ttggtttaag gactcagttt aatgtgattc 49980
cacttacatt gcctacttcg ccccttccca ttcatctcct tgtagaccca gcagccttca 50040
ttaagtgttt tcaatgtgtg acactcttct tcttcagggt cttaacacct tcacacatcc 50100
tgatattttt tatctgtgaa gcttcttctt atccttcagg tctctaatta aattatcctt 50160
caccaggaaa gccaaataaa gtcccctgtt ataccctcga ttcatttgct cacacattca 50220
aaaaacattt attgaatcac cattttgttt cattcagtag tctagactct gagagagaaa 50280
atctgttatg tacattgaca ttttatgtgt ttataaccta caaataaaca tctatttttg 50340
agtgattttt ttcaatattt ttattgagat ggatgcggaa gcaaaatctt tttgaatctt 50400
ttatatataa tgttggggtg atgtggaggt gaaagtagat taggcctctt tggagtgggt 50460
tttcagtgca gagctgagat ttataggaaa gtaaatatca gttcaaaata atgcaggcta 50520
tacaaactaa tagagctatc tgaaaatgaa ttttaaaata aactaccctt gagatgttga 50580
gtttcccttg ctctatgtat gtaagcagag gctgggtaag tagtgattgc tcattttgta 50640
gggggaggtt tgtattggtc ttctattgct gtgtaacaaa ttatcacaaa cttagtggct 50700
taaaacaata cccatttatt agctcatagt tctataggtc agaagtccag gcgtgttgtg 50760
cctaggtttt ctacttattc tcacaagctg aagtcaactt gtcagtcaac attttcttgt 50820
gtaactcagg gtcctctttc aggttcacgt ggttgtggta gaatttagtt ccttgcagtc 50880
acaggattga gagccccttc cctggctggc ttttagctaa gggcttctct cagctcccaa 50940
agatgttctg tgttccttat catgcagctc cctccttctt gagagccaac aatagagaaa 51000
tttttgtacg ttgaatccat ctctttaaag ctttgacttc cttttctgaa aacggccaaa 51060
aatactatcc tccttttaga gggctcaggt tataaggtca ggtccactgg atagctctct 51120

-continued

```
attttaaagt aaactgatta agattcttag ttacagcagc aacatagctt tccatctgta  51180
cctagatcag tgtttggttg agtaagtgga agaatctgtt tttgtacagg gaccgggaat  51240
cttgagggat atctgcagac acaaaggtca gacaaagaga caagatgacc aagatgatct  51300
ctcaatttca aattctgaga ttacgtgatt tttctcattt atttgcctgt tcttatggat  51360
tcagtcgcca aaatatatct taaaaactga cttctgtact gttgctatca cctaatttcg  51420
tctttcctgg acaaatcaag tagtctctga atttctccct tttcctgttt tgcaattacc  51480
agactgtagt tgataaaatg tacctctgga catactgtga catttttat agctttcaat  51540
tgcctgacaa gctatctata gtttcctctg acacagtaag tccccaagct attgtgcagt  51600
cttgctgttt gttattgccg acatgaatta caagctgcaa ttaaacttgt cttagctcac  51660
atcaccctct cttccatgat ctccactttt acaatcagtg aaattccatc tcatgtgcca  51720
tctcttctct aaaaacattt tctgaacacc cacgtcaatc aaatacatct gatttatatt  51780
agaatatttt gaaaatgtat cttatgttca gatgatctga gttcaaattt agtgactgag  51840
gcatttgaaa aaattatgaa aattctaaaa cttcttcctc tataaattta catttttttt  51900
ccctaaagat agtgttttct ctaattgctt ttcttcatga taggtaaaga taaaacagaa  51960
tgtgttgtaa atagtgtgcc agttttggta aatatatata tatatatagt aaataagcaa  52020
tagatctgta aataattcga taaaaattta agatgaaatc caaaatttta actgaagtcc  52080
agacctctct ctacagaatc cagactcaag cttctatcta gtatttgatt tctccttctg  52140
ggtgtctgag aggaatttca aagttaacct actcaaaaga aattgttaat cttcctcccc  52200
aaagcttacc cctcttacgg tcacccacat cttgattaat agtgacttca tctttttatt  52260
tgctcaatcc ataaacctta gggcattttt tattcctctc tttctctgat atttcacata  52320
ccacacatca gcaaaccctg ccagctctcc ttcacattat attcaggagc tgaatgtttc  52380
tcttcacttc tgccactacc accttggacc aggccactgt gatctcttgt gttgacattg  52440
cagttgcctg ctaattactc tccagccttg ttacccttta gtctgttctc aacacagtag  52500
ctagagtgat tctgtgaaag agagagcctg ccacttctct gctcaaatga aagccatgac  52560
aatgtcctct agtgtcatgt actggtagct tgtaccagtc actcagtcct tcttgttatt  52620
ctccaaatat accaggcatg cctccaacta tacagtttcc tctgcttcaa atttctcttt  52680
ctgaaatatt gacatggcta ggtcccctac ctacatatgg aatttagtat cttctttttc  52740
tttttttttt tattattata ctttaagttt tagggtacat gtgcacattg tgcaggttag  52800
ttacatatgt atacatgtgc catgctggtg cgctgcaccc actaactcgt catctagcat  52860
taggtatatc tcccaatgct atccctcccc cctcccccca ccccacaaca gtccccagag  52920
tgtgatgttc cccttcctgt gtccatgtga tctcattgtt caattcccac ctatgagtga  52980
gaatatgtgg tgtttggttt ttttgttctt gcgatagttt actgagaatg atgatttcca  53040
atttcaccca tgtccctaca aaggacatga actcatcatt ttttatggat gcatagtatt  53100
ccatggtgta tatgtgccac attttcttaa tccagtctat cattgttgga catttgggtt  53160
ggttccaagt ctttgctatc gtgaataatg ccgcaataaa cacacaagaa aaaaacaaac  53220
aacccccatc aaaaagtggg cgaaggacat gaacagacac ttctcaaaag aagacattta  53280
tgcagccaaa agacacatga aaaaatgctc atcatcactg gccatcagag aaatgcaaat  53340
caaaaccaca atgagatacc atctcacacc agttagaatg gcaatcatta aaaagtcagg  53400
aaacaacagg tgctggagag gatgtggaga aataggaaca cttttacact gttggtggga  53460
ctgtaaacta gttcaaccat tgtggaagtc agtgtggcga ttcctcaggg atctagaact  53520
```

-continued ggaaatacca tttgacccag ccatcccatt actgggtata tacccaaagg actataaatc 53580
atgctgctat aaaggaattt agtatcttct aatcccttct ctgattacct aatttaaatt 53640
ttcaatatcc ctgaaactct ccttcttctc attcttcttt ttctccgcaa ctctgatcat 53700
catccaaaac actacagttg gccctccaaa tccatgtgtt ctgcatccgt ggattcaatc 53760
aactacagct ggaaaatata caaaaccaaa atgtgtctgt accccacatg cccagacttt 53820
tatttcttgg cattaatctc taaacagtac aacagctatt tatagagcat ttacattgtg 53880
ttaggtattg taaataacct agagattatt tgaattatat gagaagatgt gtgtagttta 53940
tatgcagata ctacaccatt ttatataagg aatttgaacg tcttctgatt ttgttctccg 54000
tggaaggtct gggagccagt accctgtgga tacaaaaggt gactatgtac aatacttatt 54060
gatactttta ttgtttacag ctcccctgaa tgtaaatttt caggggcagg aatttttgtc 54120
tgttttgttc attgtatttt cagcacctat aatcctacct gtacatatta gatgctctta 54180
gatatttatt gaatgttgaa ttaatatatc tttagagatc aatgagcttt ctaaatattt 54240
attaatttc ttattttaaa atgtgaatat taatatacag ttcgcattat gtaattttca 54300
catgtcatca ttttgattct ctttatctcc atcttcttaa caaaggccgt tgaagatata 54360
caaagaaagg catggttaag aagagttcca atatcactta attgattgct ctttcttatt 54420
tctaaccata acatgtgtat attacttgcc caataaactg tctcttgaaa acaggacatg 54480
agctttattg tatcctgaat ccctaacacc aggctcagag cctgacacat ggtatgcatt 54540
tggcaaacct gtagttagtg tggaagcaaa taaatgactc caagcaggac tacatgttaa 54600
ttctaaatat acatgagata aaataaaaaa aaatagatga attatataca ttaaaactgt 54660
cagtaatatt gtttatttaa aattgtttta taatcaacat ttannnnnnn nnnnnnnnnn 54720
nnnnnnnnnn nnnnnnnnnn nnnnnnnnnn nnntaatgcc cttgacccag gcccacattt 54780
ttccttcata tttagaggtt ctgttgcttt taagcccaac tttacaacct tttcagtgac 54840
ttcaaactta cacacacaca cgtgtgacca caataaccct gattgatctg tctgcaagtc 54900
gtttttcagc ttgtgttttt caactgcaca aaattctgag gcaaagaaat atcaagcatt 54960
caactcccag cttgagatgg gaagaagaaa atacagagaa gaaacacaaa tacttgaaat 55020
tgttttgcca tctatacatc tttcaggact ttaagtgctt ttccatacaa accactaaat 55080
gtataggtaa agattgctct tgcaacttag gttttatgtt tatagctaac tggttgccct 55140
gcttgcttgg agaatatcat taaccataat taagtaaaaa atgtatattc cttatcctga 55200
actctgttta catagaattg tgatggttac tatgcaacat aaataagttg caaatcaagt 55260
cctgcaagcc agagctctgg gaaatggctg cattctctga aatgccattt ctgccccagc 55320
cctccagagc aaatttcagg tttgccaggc cacccatccc atataaatcc ttcagatata 55380
ggccttatgt tatcatcttc ctatcttgac tgagactctt taaaggggat tcctttcaaa 55440
tccaaattac atattcttaa acatttttga tacttattag tatagtaaca tacctacaca 55500
cacacacata gattttcagt gacaaatacc atgttagtac ttatagatag tgaaatacac 55560
tttgatctag agggctttat tttctaggcc accaattgtg tctcctgtta caatttccca 55620
gagtatctgg cataatgtct gtaatagtaa atgttcaata aatgtttgtt aatataattt 55680
gacatttgag gtagaatcct gacaactcag actttgacac aattgtccaa ccttttctct 55740
ttctggcact ttgacacttg gtttctgtaa gatctaccct tctgtttttt ctcctacctt 55800
cctggtagct ccgtctccgt cctctttgct gaattattct cagcaaataa ttgtttttta 55860

-continued

```
actgtaagca ttggagagat gagagagctg tacttggccc ttttctcttc tttatcagca  55920
cacaaccnnn nnnnnnnnnn nnnnnnnnnn nnnnnnnnnn nnnnnnnnnn nnnnnnnnnn  55980
nnnnnnnnnn nnnnnnnnnn nnnnnnnnnn nnnnnnnnnn nnnnnnnnnn nnnnnnnnnn  56040
nnnnnnnnnn nnnnnnnnnn nnnnnnnnnn nnnnnnnnnn nnnnnnnnnn nnnnnnnnnn  56100
nnnnnnnnnn nnnnnnnnnn nnnnnnnnnn nnnnnnnnnn nnnnnnnnnn nnnnnnnnnn  56160
nnnnnnnnnn nnnnnnnnnn nnnnnnnnnn nnnnnnnnnn nnnnnnnnnn nnnnnnnnnn  56220
nnnnnnnnnn nnnnnnnnnn nnnnnnnnnn nnnnnnnnnn nnnnnnnnnn nnnnnnnnnn  56280
nnnnnnnnnn nnnnnnnnnn nnnnnnnnnn nnnnnnnnnn nnnnnnnnnn nnnnnnnnnn  56340
nnnnnnnnnn nnnnnnnnnn nnnnnnnnnn nnnnnnnnnn nnnnnnnnnn nnnnnnnnnn  56400
nnnnnnnnnn nnnnnnnnnn nnnnnnnnnn nnnnnnnnnn nnnnnnnnnn nnnnnnnnnn  56460
nnnnnnnnnn nnnnnnnnnn nnnnnnnnnn nnnnnnnnnn nnnnnnnnnn nnnnnnnnnn  56520
nnnnnnnnnn nnnnnnnnnn nnnnnnnnnn nnnnnnnnnn nnnnnnnnnn nnnnnnnnnn  56580
nnnnnnnnnn nnnnnnnnnn nnnnnnnnnn nnnnnnnnnn nnnnnnnnnn nnnnnnnnnn  56640
nnnnnnnnnn nnnnnnnnnn nnnnnnnnnn nnnnnnnnnn nnnnnnnnnn nnnnnnnnnn  56700
nnnnnnnnnn nnnnnnnnnn nnnnnnnnnn nnnnnnnnnn nnnnnnnnnn nnnnnnnnnn  56760
nnnnnnnnnn nnnnnnnnnn nnnnnnnnnn nnnnnnnnnn nnnnnnnnnn nnnnnnnnnn  56820
nnnnnnnnnn nnnnnnnnnn nnnnnnnnnn nnnnnnnnnn nnnnnnnnnn nnnnnnnnnn  56880
nnnnnnnnnn nnnnnnnnnn nnnnnnnnnn nnnnnnnnnn nnnnnnnnnn nnnnnnnnnn  56940
nnnnnnnnnn nnnnnnnnnn nnnnnnnnnn nnnnnnnnnn nnnnnnnnnn nnnnnnnnnn  57000
nnnnnnnnnn nnnnnnnnnn nnnnnnnnnn nnnnnnnnnn nnnnnnnnnn nnnnnnnnnn  57060
nnnnnnnnnn nnnnnnnnnn nnnnnnnnnn nnnnnnnnnn nnnnnnnnnn nnnnnnnnnn  57120
nnnnnnnnnn nnnnnnnnnn nnnnnnnnnn nnnnnnnnnn nnnnnnnnnn nnnnnnnnnn  57180
nnnnnnnnnn nnnnnnnnnn nnnnnnnnnn nnnnnnnnnn nnnnnnnnnn nnnnnnnnnn  57240
nnnnnnnnnn nnnnnnnnnn nnnnnnnnnn nnnnnnnnnn nnnnnnnnnn nnnnnnnnnn  57300
nnnnnnnnnn nnnnnnnnnn nnnnnnnnnn nnnnnnnnnn nnnnnnnnnn nnnnnnnnnn  57360
nnnnnnnnnn nnnnnnnnnn nnnnnnnnnn nnnnnnnnnn nnnnnnnnnn nnnnnnnnnn  57420
nnnnnnnnnn nnnnnnnnnn nnnnnnnnnn nnnnnnnnnn nnnnnnnnnn nnnnnnnnnn  57480
nnnnnnnnnn nnnnnnnnnn nnnnnnnnnn nnnnnnnnnn nnnnnnnnnn nnnnnnnnnn  57540
nnnnnnnnnn nnnnnnnnnn nnnnnnnnnn nnnnnnnnnn nnnnnnnnnn nnnnnnnnnn  57600
nnnnnnnnnn nnnnnnnnnn nnnnnnnnnn nnnnnnnnnn nnnnnnnnnn nnnnnnnnnn  57660
nnnnnnnnnn nnnnnnnnnn nnnnnnnnnn nnnnnnnnnn nnnnnnnnnn nnnnnnnnnn  57720
nnnnnnnnnn nnnnnnnnnn nnnnnnnnnn nnnnnnnnnn nnnnnnnnnn nnnnnnnnnn  57780
nnnnnnnnnn nnnnnnnnnn nnnnnnnnnn nnnnnnnnnn nnnnnnnnnn nnnnnnnnnn  57840
nnnnnnnnnn nnnnnnnnnn nnnnnnnnnn nnnnnnnnnn nnnnnnnnnn nnnnnnnnnn  57900
nnnnnnnnnn nnnnnnnnnn nnnnnnnnnn nnnnnnnnnn nnnnnnnnnn nnnnnnnnnn  57960
nnnnnnnnnn nnnnnnnnnn nnnnnnnnnn nnnnnnnnnn nnnnnnnnnn nnnnnnnnnn  58020
nnnnnnnnnn nnnnnnnnnn nnnnnnnnnn nnnnnnnnnn nnnnnnnnnn nnnnnnnnnn  58080
nnnnnnnnnn nnnnnnnnnn tgccgtggcc tcccacagtg ctgagatttc gggcatgagc  58140
taccatccca cgcatatttt cttattgtct agaatagttc ccagtaccag tagatactct  58200
ataaatattc cctgaatgac agaaatttga ttcattaagt tctagtgggt aggacaaaac  58260
```

-continued

```
agattgtttt ccagtgcagg tgatgataag gatgacgata ctataacaaa gatagcaaaa  58320
atatagaaaa aattcagttt actttggggt tagtcagtag gtatggttat tttgaacctg  58380
ctgattttgt caagaaatag ctattctaat ataactagaa aacagaaata aataaatgcc  58440
cagagaacaa aaccaaatac atcagtagcc tagatctggc ttgtggacag ctgatttgta  58500
acctttggtt aaattatgcc tgtgcctttg tgcctgctgc cactaagagt tcctattctg  58560
agtatctcac ttggggagta cctgcttcta attgccacac tgagccagga agtgaacttt  58620
ttaaatgcac agtctcttgc aagcacactt gacactatta tacaagatgt ttaattagca  58680
taaaacaaca tataacatga tcagttcaga agttggtaaa tgaaactgaa aagttggatt  58740
tctaaataat cctacattct caagtctttc cacttgaata tcattctttc caccctattt  58800
cctccacttc ttacccctt ttaagttcta tggccatatt ttatttccag gagacacagg  58860
ggaaatggtc tttctaccac tgtgattagg agagaaagat gaaaagattt atatttttca  58920
acttcgtgat aacaaacata tgattgcatt ctcaaaactc atagcttttc aactaagtag  58980
tcataagtgg ttgaggataa ttctttaaat tttgacgatg agttggttac tcgtctttta  59040
gtttcaagaa tggaggaaat ttttgcttcc aatggaatag aagacatttt tctaatgata  59100
aatattgtac aattgaattt ccaaatttca taatttatac atcaaaataa aagttctatt  59160
tattatatta agtcaggaag agataatttg agattatatg gggaactgca tatattattg  59220
caacataata tatatggtga aataacataa gaataaaaga aattataaca gttaagtaac  59280
ggaagtcttg aagagcaata atccttttaa tattaaaaat aaggcattca tagatgttgc  59340
ttctgcatac caaagatgaa aatataatgg ccatgttgca aactcaaaaa ataatttgga  59400
tgaagaatat taataagttt tgtattatgt ataattcact taaaaatgtg gcatgagtca  59460
tgtggtggct catgcctgta atcccagcac tttgggaggc tgatgcgggc ggatcatttg  59520
aggtcaggaa tttgaaatca gcctttccaa catggtgaaa ccctgtctct tctaaaaata  59580
caaaaaatta tccgaacatg gtggtgggca cctgtaatcc caactccttg ggaggctgag  59640
ggaggagaat tgcttggacc cgggaggtgg agcttgcaat gagccaagat tgtgccactg  59700
cactctagcc tgggttacaa agccagactc catctcaaaa ataaaataaa aatgcaatat  59760
gttgtttcat gatataaaat aaaataataa ctctttctct gaattagaga aaagactaaa  59820
caacaatata aaatagtaca aaataactat ctcagagaac tgcattttat cctaatgaca  59880
taaagttgta ctcaagcact tactaatata acatcttgtc aaaacctgga tcttctctat  59940
aaagagttat tgattaatgg gtagtttgaa atcaaattgt ttaaaatttg agtaactcca  60000
ataaaagacc acctagtttt aataataaat attataaaag tttctacaat ggattatata  60060
atcagaaaac atgttatcat taactatctg agcccataac aaagagcatc aaaattgaag  60120
atcaggaaga aaagtcagaa tgcaagctga gatttaaatt ggattaccct gtgaatctga  60180
gtgtacacct gtaaaacaga ataaataagg gaaacaatat tcaaccaact caagctaacc  60240
attctttctc tcacatgctc tcacctagat cattgaagcc aaattgcttt tgttctcaac  60300
taatccgtat aatagccata atcctactgc atgctgagag tgtatagata caaatataag  60360
cataaaaatt ttaaaaaatg gcagaaatat ttaccttgaa acattacagt catgcaaatt  60420
attttactca tctatttttc tgattatcct taaagtcaaa agcagtttga gtggtgtgtg  60480
tatatatgtg gtggtgatgt aaagtcacaa gctgttaaat gtttctgtgg tgcacaatag  60540
atacttatgc tgaggaaatg tacaacttta aaggagtgtg ggtgtgaaat tagtatgaaa  60600
```

-continued

```
tggaatggga ctctcataat gtgcgtctcc tatagaccac caagactgga agacagcaag  60660
aaaggaaaat tcctggggta acacttaggt tgggaaaacc acaggatacc atactcatga  60720
ggaattttaa ctacccaaac atctgttagg ttaaaaaaaa ttcaacaaaa catgcctcat  60780
caaagaagtt tctaaggaat gcaactttat gatctaaaaa gaagaaaacc aaatagaggg  60840
caaagtacac tttaacatta tttaaaatta aaaattgtca atgtgttact aaatatcagt  60900
tgttttcctt agttttttct aaactgtgta atacacttat gtgataagtg ttatagtaac  60960
agaggtagaa attatccttt ttataaagaa gcaattatat aatggtaaga agtgatttta  61020
gccataagta aataggagtc tataattcaa gacatttaga agttcatttg gtggcagtgc  61080
agtattagga tgggctccat cttgctgcca ctagagaaaa taaatatcat ttattctaga  61140
catgatggtt gcacttctgc aaaattagtt agatgctgtt gaaaatcttc taaattagtt  61200
acacaggact ccctaatggg taattcaaga caacatttct gtcctctagg cccgaatatt  61260
gaagttattg gtataaccac ttaggttccc atagacatct caaactccat attgccacct  61320
tcccttgcaa gtcttttcct ttctgtgtgt tccgtgtctc agtttactgc accactattc  61380
atctagttgt tcaaactagt tatctagaaa tcattgttag ttctttttac ctactctcat  61440
cccccacgag gcaaaacctg agtcctattg tatttacctt ctaaatatct cttgtatttg  61500
tttatttttc ttttcaagtg tctctaaatc cagactttta catttatctc ttagataatt  61560
acaaaagaga tctaaatggt ctttctgctc tcattttcta ccattcacct gaactcagca  61620
tttcaataca cctgcctgac catgaatttc ctctgctgaa aatctttgat cattttctac  61680
atgcctgcat gttaaaacta tgcccattag taagttctac aaggtcactt atgatttggt  61740
ttatatttct cacacatgca ctgttctttc tcctttatga tccagaatct ttgctattct  61800
ttcttattgt cctttctttc ctcctcttct ggtgaccagc tttgttttcg ctatgttttt  61860
aagtatctct tttgagaaac ctttcagaaa tccttatttc cagtcccacc tcccaaaatt  61920
tgtttctcaa caagtgagca tattacatca tagttatttc tctctctttc tttagtgggg  61980
ctttgagttc cttaaaagca taaatagcca gccgcgcatg tcttatgtac ctttctgtcc  62040
cctgtgccta cttttaatct aagatttgtt atgaatatgg aagaaaggca tttgacttta  62100
atgttaaagt gttacagtgt caaaattctc catattttaa aatagttcat gctgatattt  62160
tttaattttt ttggtctaat gcttgtcttt caaatgcttg cattgttatt gccaaaatta  62220
aaattctctt ggccagtagc ttttcatgtt tgatatattc agcttctttt atttcacaaa  62280
accagtatat atttattatt attattatac tttaagtttt agggtacatg tgcacaatgt  62340
gcaggttagt tacatatgta tacatgtgcc atgctggtgt gctgcaccca ttaactcatc  62400
attagcatta ggtatatnnn nnnnnnnnnn nnnnnnnnnn nnnnnnnnnn nnnnnnnnnn  62460
nnnnnnnccc ccatcccaca acagtcccca gagtgtgatg ttccccttcc tgtgtccatg  62520
tgttcgcatt gttcaattcc tacctatgag agagaatatg cggtgtttga aaaccagtat  62580
attttatatt gttgatcatt ttgtgatttt ccttttcatt aattaacata agaaatataa  62640
attattgcat ataggaaata tttgtattgc atgtaagaaa tatgaattat tgcatataga  62700
aaggaaataa ttattgcatt tagaaatatt tcaaacagtg aaggaaaata ataaatgtcc  62760
atttcagaat agattggaga agcattaaaa atatctaaat gattaactga gataattagc  62820
tggtaataag tatgtatagt gagacagagt tataatagat tgatggtcca tgaaagaaca  62880
aaggggaaga acaatgttta aatttagagt gctaagtgtg attacaaaga ggagatatat  62940
gggtgaaatc ataatttaaa ggaaatgata gaaagcatat aacattaaag tatctaataa  63000
```

-continued

```
agtattcaac tatatattta atgtcaaaag accttatgct agattatgat gcaaatattc  63060
tagaatttaa ataaaaatac ttgtttttga aatcctattt acataagcaa gtagaaagtt  63120
gtagcaaaat cactaaaaat caaacaaaga aaagtgtaaa gattatcact gttttttttt  63180
aaatcatcaa tattttagaa agtctgattt tcataaagga aaaaggggag gaaattttct  63240
ccccattaat agcttagctg tattttatct ttttaaactt caaatgaatt ctcctatttt  63300
ctctgagatc tcagactaaa tttcacattg aattgaatta acttttactc ttctgagaat  63360
cttctttctg tccattcaac aagaagtgta aagtaggtgt aatacattgt gaatttttgt  63420
ctttaacctc agttctaagt tctagctcag cattaggccc taggtcagca aaatttcagc  63480
tcctatttct tctgcattta ccaagaaaga attctgattt aactatgaaa attccaaact  63540
atagaaaaat cctgggatta ctatgtatgg tgtcttggtc actttttgtt catgcctagt  63600
aaatcaattg agatccatag gctgcacagt taagaatatt agcaatgact taccttactg  63660
tgtgtttgct atgtgctggt actattctaa gtacttaaaa cattgattca ttcataagtc  63720
tttatttcta gcacagagtc tacactctta gatcttgact aggacttgag caaagcctca  63780
gggtggtaga aaagtaccaa gagatggaga ggtactaact gatatgacat agagaagcta  63840
tccaactgtc caatcatctc ccaaaacaaa ttgagtgaga attttgacat gcacctcaaa  63900
attatacttt tgaggtttct gataccettg attttcattt ttctttaatg atatcctaga  63960
tattttttac cccaattatg cctgcataca aatgaacagg agaagaaaat agcaagattt  64020
atcctggccc taagactcca gtatgacgat ggccttacct gaattattcc agtttgttcc  64080
aatgcagagc ttcatggtag catgaaaatg gtgatatttt atgctctaat ggaacacgct  64140
gacctgttgt tctaaaaact ttgggaattg gaggaagtga gtagggagaa ccctcttcat  64200
agtttatcca gaattaaaat agaatgaaag ataggagacc agtctgtgga atatttgatg  64260
gcttgataca tgtttccatg ttgattacca gctcccaaac ttcctttaca tctacttccc  64320
tagtcttcac agaaggagta attcaatccc cttttccaat ccactcattt ctaagagttg  64380
taatcattgg tcatctaatc tgaagagcag tgtcactatt ttttcaaatg gcatgtcgac  64440
gttatagagc agtgattctt aaacttgaac tacagtcatt acaaccacct ggaggactgt  64500
taattactaa gccccacact cacggttttt gattcagtaa gtctggggta gtgcctcaga  64560
aactgctttt ctatggcttc cccagtgatg ttgatgctgc tggcctggag acacattttg  64620
aggaccactg ttgtagaaag ttgttttata aacatgatgc tattctcaga aaatatgtat  64680
tctctgattc caaagtaata gtagtaatta gaatattttc attcttacct ggcatgtcca  64740
gtattgaaac tgagaggttt tctttctatt ttgtattttt tttctagctt aagccagtct  64800
gaaattagtc aggaaataac tcatttaagc atcaaataag atgatcatac agtgaggtct  64860
aatactatga acatccatga atcattctta gtattcatga atctaatctg acaaattctt  64920
aggcttactg tatttgtaac actattgtgc tataccctct gcagcaccac cttgcggtta  64980
ggaaatctaa ttagaaaaca cacttaacat ctcataaaat gataggaaat atttcctaca  65040
ctgacagtgg tgatgcgttt tggtcagcga aatcactggg ctctaggaaa acatccaaac  65100
tacaaaagga tagccagtta tcaaagtgtt ttaaccagtg gacaggaata tgtcctgaga  65160
tactcttgct gtgtggaaat aagatgaatc caattgcaga gcttcttcag ggcccttgat  65220
gccctgaatt gcttaagaca caggaatcca ccagcgagtt ggatttcttc tagtcctgag  65280
agacatctaa cagtcagtgc taatttgtcc aggtgtgctg agtcaaagtc gacttgtagt  65340
```

-continued

```
ccttgaagtt gttaatattt gtatagctga gaaaggacag agcccttcac ttagtgatga  65400
cagtcactag aaatctggtg gcctagtgca ccaaattctg aaactaaaac accctgagtg  65460
gtaggccctt ttaataaact ttatactgaa cttaaattca aataattgtg cagacaattt  65520
aaattgaagg tatatagagc tgaagttttc tgttttgtaa gttgatgtta aaccatatat  65580
tcatttatgt ttattctttt aggaaagtga tcataacgag gtacactaaa aaccatagag  65640
tattttctag aatattttcc actattaagt tagacttaca gggatctgca gatggcaaag  65700
ttacaaataa gtctttgaat gtgcttattt taaaagtata gtatcaggca caacaaaact  65760
tgttgattct taaacaaagt ggcatggatg ggggcattca aatttttata tggactaggc  65820
aaaatgatgg tctatccaga ctcacctttg agctaacaca ctcagcatca agacacagat  65880
ggatgggaaa gatgaccctg acccacataa gacccacatt cctgtgcaag gatagaagca  65940
tgataatcag gaaatgatgg ttgttagtta cagaaaatgc attatggtga aaaccagggg  66000
gaaagtgctt atgagaggaa gtgattggat tatggggaat gagagaataa ggatagatca  66060
ttcctactga gtaaattgct gtgatttata agagaaaggg tatagtgata tcttggccca  66120
ttactgacta gattcatttc acaaacaatc ctaaatcaga atgtgacagt ttatggggag  66180
acaaacaaag ctcccaaaga tgcttataag ttactaagct tttaaactgg catattttca  66240
actcctcata cttttgccac catcagctcc atttattttt gtagctgaca ttcataaatg  66300
taattctgta gccaccctta tgtgacacta gtaatagttt actatatgct gtgataaaag  66360
ggaaaatgct ggatatattt tattatatgt tttgggattt tgttaaattt cataagaaag  66420
atacctaaaa taattttata tgtatttaag tatattataa tactctacaa tactaaaata  66480
attaagtgct gttttataat agatgggcat tttggtgttc taaatatttc tcttaaatta  66540
cctatgaatt aatcaaacag ttacctttca ttgctccaga caggtgaaac acatattgtt  66600
atatattata tattaatata tattcagtta tataagttta cttttatttt tcagtttgga  66660
tttaggagct ctaatccttc aagaatacaa gttgacaaaa tacattctga aggaaatttt  66720
tggcaaagga ttcaacacag aaaacttgtg taacaagaca ggcaatttta tcaagaactt  66780
tactgaaaat gcaaacattg tttacagtga ttgtttcttt taaaaaatga agaaagaagg  66840
gaaaacgatt tttggaaaag ttcaagaaat ggcattaaag catagctcag caaggggcta  66900
aataccttgc ttttttataa tgattgatca gtgcaaggaa attaaaatat ttagtagtat  66960
aggtgattat atgtgttgtc atgaatgatc tttgaatgtc atttttctct tacctctgct  67020
tggggtcaca cactccctga tgagagattt gattgctagt attaaaggaa tgattgcagg  67080
gttgacattt tattgtgaaa gaagagaagt tgaaagcaaa gcgctatatt tctttctgag  67140
ctggcataca gacacactca caagccagag ttttccttgg gaaaactttg cactttgtcc  67200
tcaaatgaga cccgaagaag ccattataga gcagagatac agaaattttt ccagatacaa  67260
gctaccgcag aaaaatctca caactttctt agccgcagaa aattctcaat acatttttca  67320
tgatgtctgg gcaacgataa tgtgccactc tacttgcttg ctagaatgag ttaggttgaa  67380
aagtatagtc ccaacagcat cgagtagtat atgttacaga ggtacatgaa tcaaatagat  67440
gttggagatg atctttcctt tttgacgtaa ttaattttag cccatctttc tggtatgagt  67500
tagataccaa ggatcacagt ctatcacagc cccttctact tcatggcgtt tgtctttttg  67560
ttcacaatag ccatcctaac aaaagaagac attaacgctg gtcttaacgg ccttacattt  67620
tctggccccc atttcctctc ggattctctc attccaactc aactgggctt cagcttcact  67680
gtggtccttg ttattcttag gacataccag gcgaaatcct gcctcagggt cttcacgctg  67740
```

-continued

```
gccattctcc tcctggacac tctttctcca aacagccaaa cagtattccc ttacctcctt  67800
caaatatttg tttaaatgtt atctgcttag tgaggcatga gctgaccact atatttaaaa  67860
tagtaacgcc ctaagcatct tcatgcccat gaccttgtct catttttcac catggtacat  67920
aatacttcct aacatggtat ataatttact tgtgtattat atattcattt atttatattt  67980
ttctaatata tattatttgt ctctctccat taaaatggaa gttccatggt ctttgtctct  68040
ttggttctct tctatatttc cagcacttcc aaagtgcctg gcatgccata ggtgttcagt  68100
aaactgttgc taaatgaaaa gggttaaaca gtagaagctt tatggatgga tccaaagcta  68160
ccttgatcac ctgtatgagc tttttgtcct cttagtgcct agcacatagt aagcacttaa  68220
taaatattta ttcattcaat gaatgcataa atttattctc aaggccaact aaacatttgg  68280
ttataataaa gacaagggga ctctaaaata ttttcctgtt ttataccact tgaaatgtgt  68340
ggccgatcag aaaattgttt ctgtccacac tggttcttac agagctggaa gtcaaatttt  68400
tcaaataaca ttaataataa gggagcctta atacatttat acagaggtca tatcccatcc  68460
ccttttatag agtcagaggc agaagagagg ccattgaaac ccacaaagca tcttatattt  68520
atatttttca aggcaattaa ttatgctgat ggcaggagac ctcttatagc tctcatctgt  68580
tatgtataat tacctaaatg aattaggcta caatttgagg cagttttcct aggaccataa  68640
agctagcagt aaaaagaatg aaaatgtctg tttatgcagg gtatgtgtat gattccttga  68700
taccttagtt gttgcagaaa ctgtgtaccc aattctgtct tcatcattag catctcttag  68760
ctcatcaaat cgaatcctgg agcattcttt ctttaccctc tcccctggat gttttcttgg  68820
caatgtaaaa ctggatcttt gagtacgggg tgtcaatgtt cagattattg tacagttttc  68880
agaagtacaa ataggaagag tatctttgtc actccaaagg tatttgttca ctgaaagttc  68940
ctgaaatgta ttttctagat tcctgtatag ttatattcaa gtactattat taaaatatgt  69000
caatgctatt attaaaatat ttttggattg agttgtgcac ctaaattcca tagacataat  69060
gttatatgcc taagaaatat attctaaata tcaattactt attcacagtt taaagattgt  69120
caccactatt aatctcttag tctgttttgt gttgctataa gaaagtatca gagacttggt  69180
aatttgtaag aatagacatt tgttttctta tagttctgga agctgggagg tccaagatga  69240
aggtgcagac agatttgctt atctggtgag ggttgcaccc tctggagggg aggaacgcgt  69300
gtcctcacac agtggaaagc agaagagcaa gctatccaaa tgcttagtga agcctgtctt  69360
ataaggacct taatcccatt caccatggga ggtattctca tgacgtaatc acctcttata  69420
ggccccacct cttcatacca tcacattggc cattgtattt caacatctaa attttggagg  69480
ggacatgttc aaatgatagt aacatcttat agctctctag tattgaaata aacctttttga  69540
ctctcttcag agcatgtgat tcacttgaac cagatatact gcccatattt ataccatccc  69600
aacttgcaag aaattatctg caatttaaaa acaaagacag aaactttctc cattctgatc  69660
ctatttgcct cattccaagc tcatctttcc atttgccaga taggcctctc agacttctgg  69720
aggttctcaa actcaatgaa tatgaatcca aatttgtcat ctcctaccat agtcttaccc  69780
caccaaaatc agtgtatgtt cctgaatgtg ctgttgtgaa ctgccaaaat tcactaatat  69840
taatgcatga gttagctttt actannnnnn nnnnnnnnnn nnnnnnnnnn nnnnnnnnnn  69900
nnnnnnnnnn nnnnaatttg cacccacatc aaattattcc gagttctttt tattaatctt  69960
tctatagtga ctctaggttt catctccttc tatctatccc ttctgtcact attcttattt  70020
aggatctcat gttttacttg gccttttgga aagagcttat ctacactcag tgtttttcaa  70080
```

-continued

```
ataacttaac tttttcatag ttacctgagt tgtcttccta aatcaatgga aaaataattc  70140
ttttctcaaa aacctcagcg gaatcccact atttaaagaa taaactccaa attctttaac  70200
gtaacaatca ggtactctct agcttaattc ctaaattact acttgggctt gtacattttt  70260
attcctccat aaatactggt ctctctgtga tagttctgtt tcttggattt agggattctg  70320
aatctttttt tgtaccatga atccctttgg aaatctggtg aagtttattg actccttcct  70380
agagtaattt atttttact tgtaaaataa taacattacc aagataagca attctacagc  70440
aatacaactc tatctgtctg tgggtcctgt tgtttatgtc tttgtggctt ttctatgatc  70500
ctccccttat cacagaagtg cccctaaccc tgctctatcc ttctcatcta tcaaagacta  70560
gtgcaattcc caccttcact gtgcatcttt accttgcaac cctgccccat ctgtatcatc  70620
actttgctct ctcattgtag attatatgtt atttatttct atttatccct tatctttatc  70680
ttttatgata ccttggtaat tgacaacaat gtggcaaata ctgaactagc cacttttaca  70740
tactttgttt tcataatttc ttttaaagca ctataaaata ttcatatgat ggggaaactg  70800
aggtccaaac attttggtgt ttcaccaaga tcatacaact tgtattcttg ctagattatg  70860
agttatttga ggaaaggaat atttcatctt cctgattata tcttctccgg atctgtggga  70920
tagtactttt tcaataatgt ttgcccatat gtatttaaaa attgaaaata ttgggaaata  70980
cttatctctc aatatttaat atcattagaa ttgactaggg gccccaggag gacagaggtg  71040
tgtgcagcag tgttcttagg ttaatgtctg tgtgaaatta actgtggcta aatctttccc  71100
tgcatactat tatctctcct aattcccagt ggcttcacaa attgaaattg tacacataag  71160
gattttaaac agaaacattt ttaagatatt gtctcttgtt ttgcgttact gaaaaaataa  71220
caaagtagga caaattaaga aagtagaaca aattaaagaa tttaattgga gtcataagga  71280
attcaagaaa tatttgaaga ttgcatttct aataatagat cagaacaatt gaataaccat  71340
ttcatattct ccaccctcag tgaaaacaat aaaatcaact caatttacat ttgtaaaaca  71400
atatatgtat actttcatta taccagtttt aattttcagc tgtgcttctc tatctctctg  71460
tagtcaaata ctacgtttct gcaagggttt tcttaaaaca gcattgctag gttaactgtt  71520
ttaaaataaa aatatttgct taaaaaggtt tactttagca atagtaatgc tttcctttca  71580
aaatattatt tcaagtttta aaataatgaa cttatgattt taattaatta agttttcatg  71640
tggaagttgt tcatctagag taactaattt taaagaattg gatcttttta tttggtaatg  71700
cctttagcac tctgtgaaat ataaattaat gtaaaattaa aattaattta ttatgactat  71760
ccatttttca tggtcttttc tattattgtg ctgtagcaag tactaattct aatgtagcta  71820
gataattaat tttctattgt catagctcca gatggtcctc ctgaaaatgt tcatgtagta  71880
gcaacatcac cttttagcat cagcataagc tggagtgaac ctgctgtcat tactggacca  71940
acatgttatc tgattgatgt caaatcggta aggcatgtct taccttctgt aaaaagccag  72000
tataaaatgg ttaataatac aagatttgga accagactat ttgaatttga attttggctc  72060
tgttagacag taggaaaatt actttacttg tttgtgtttc aatgtctaca tctgtaaaga  72120
ttaataatag taaacagggt atgaggactg aatcagttaa catgcataaa gaacttggaa  72180
cattccctga gatatggtaa atgctcaata aatataagat attagtaaca ttattataat  72240
atgttttatc agtgtataga atgtgtatat atatgtatgt atatatacac acatacaagt  72300
ggttaaattg gtagtaatac aaatatctgg tttacagtac ggtagaaagt aattcataat  72360
acaaaatgag aagagagaag gcattaggag aaatatcttc cagataaaat aacatcagag  72420
ctaagtcttg aaaaataagt gaagcagaac ataaaaggta aatgggaata ggggtgtaaa  72480
```

-continued

```
aaagtaagcc tcattcaaga aaaatcaagt cttttggcaa tcccaggcta tagcattaaa  72540
aaaaataagt tctaagagat gaggctagat ccagaggctg actatacaac aagttacaga  72600
gttagggttt tatgttaagg gcagtggggt gccagttggt gatacagatt tctactgtat  72660
aacataggca tggttgcagt gtagaggata gattgagagc agtatggggg gtgtaaaatc  72720
aggcaaggag acaggaaact ataaaagggc aaggaaaaag aacagaggaa atgtagcaag  72780
agaacgaatg aaaaataatc taaacctata gaatttggtg aaaaatcaac taactcatga  72840
tggtgagtga gtaggataat taaggatgat tgtaagttat atgacagaag attatgagga  72900
ggaacagatc tgtagaggaa aggaatgagt tcagtattag acacactgag tttgaaatat  72960
gtggcagtcc tccaggtcaa tacacccatt ggcagtatta aatatggatc tggagctcag  73020
gagagaaatt ctggatttcc agatttgggt aatgttagta tttagaagat agtcaaaatt  73080
ataagagtga atgagattca ctatggaatg tgcaaagtaa gatgacaacc taaggacagc  73140
accctgggga ctatcaacac ttaaataaga ggccattgaa gagactgaat gggagtagat  73200
agccatttgg atggaaatcc aggtatgaaa gtcaaaccct tcatataaga taggatgctc  73260
aatgatgtca ataatgcaga actgttagcc agaataaaga ctggaagtat ttcctttgca  73320
ccctgcttgg gttttgctgg gcctgatgaa cacagttttc taatagcatc ttatgcatta  73380
aattgtatag catagtgatt tctcctcctt tctctctgtc tcttgaccaa ctttataatt  73440
ttattatgtc tttgtagtat tccttaaatg gagatataat gcttctatct caaaagacct  73500
gtcatcatta aaataaaatt gaaagaattg ttgatgtatt tgttctccaa ttcagtctct  73560
attttctgtt ccttttgtag agcatatttg tgaagatttt agtatgtaat tagccaaaaa  73620
taattagcac gaatgatgaa tgccctggga atatgcatta aaaacaaatt ataaaatgat  73680
aaagctttac tctgtcaaat gaaaggcact ttattaatga aaatagttct cccttggaaa  73740
ttctgcttaa aggaacaaaa aaaataaaac atattaagaa gtgattttgt aatctcattc  73800
ttgtagcctt cttgctgagt ttcaaagtga gcaagggaaa gagggtagaa tgggaagata  73860
acaaatattt taattgctta ttttctacaa gttacatgtt catctcttcc tattcattat  73920
cttattatat gttatccagc aatattttca tataaacatt attaccttca ttttgcataa  73980
aagaaatcta aggaacagag acggtgaata acttctcaca gagctaagac ttggctaaaa  74040
ctaacagatc aacaatggtt tgacaggaga aagggaaggt cattaaataa caaataaaat  74100
tcgccaacat aaatatagcc tcaccaaaac tcctttagat caacaatagc aagaacagat  74160
tcagatagaa cctagtaatt cacagtttct ttaggattct tggaattaag tagaggtatt  74220
tccttccttc cttccttcct tccttccttc ctccctccca ccctccctcc ttcccttact  74280
tccttccttc cttcctcaca cattttaaaa tacttccaat gtaccagaac tgtgctaggt  74340
gctggatatg tagaagtgaa caactctgat aaagcacttc tgcagctcat ttcattaata  74400
tgtaattatc aacattcaag aatcactggt tcccagacta aggaagaata catagcattg  74460
cacttgggac ttattgtgca gcctgtcttc tacaaaatac tagccacacc gataaaactc  74520
ttaactttaa aagtgtaaac aaaaattgtc aatcttaata aaatgtaaat atcatcctag  74580
atgattctgc tggaaattaa tgcatttagg atcattttca ttgttccttt tactctttga  74640
ctgaacaaat tgttatgagt agcttctgtg catcaagaca aggatgaaaa acataaagct  74700
ctgctgtcag gtagctcaca ccctagtggt acacactgga atagaaacag ctaattatag  74760
agtttgaggt atgaagtttt gtggggaata taaggtaaca aaataattaa agttcctgtt  74820
```

-continued

```
atgggaggaa tagaagataa aggagacttc atagagcagg ttaaatatat tctaggactt  74880
gacgaatgaa taggggtaca caagatggga aagggtggag gcggggtagg aagagaaaaa  74940
aaataggaag tggggcagga agaggagaac cagagtctaa ttgctgataa tgaatataaa  75000
gtaacacttc aaaaatgatg aaagacattt tataacaata gattatcaag tacaatatga  75060
gcaaacaaac ttggaattga ttgaaggaaa atgagtcaga aagatgtgat ttcagtcctg  75120
ggtaagtgga caagtaatag ctaacaacaa caaaggtgta gtaggtttaa taaagaaagg  75180
taatgatgat cttttgtact gccagatttg aggaccgaga attcctttca aattttgtta  75240
aatactttta aagatataat atatgcgtgc catgtcatat tttgcgactt gatatttgtt  75300
atctattgtt ttaatggaag gcattggaag agtataattt ataaattata cttataaatt  75360
ataaatttat aatttataaa ttataaatag ttaaatttat aagatcaaac ccagtgacct  75420
tgtggaagtg tagaattcta tggactcttg aaagacctgg gctcaaatcc ttcctctgct  75480
actaagtaac actgaggaag tcaccttacc tctataaaat cagaattcaa atagctataa  75540
aagacaagtg acatgaacca gtagtcaaag tgaagccaat tgagtggggc tccaatgaat  75600
gggacccagg cccctttaca gaggtcaata gttacccatc tctgcacctc tcaataatat  75660
tttttcagca tgaaattaag cctagtctta aggaaaatta caaaaagcat atttttatgt  75720
gatattcaaa tgttaacaac tagttaaata cacattttct gccagtggca tatattcctg  75780
atcaatagga tttctacgct gatttgtttt tcttccattt tcgagaagtg gggcatttct  75840
gtccactgct ctgtcttaag gtgggaatga tctatttgac tgtatgcaac gatagtatta  75900
tttatatcat ccttttacta tgtttctttt ttttcttttt ttatagcaac atcttttttt  75960
taaaaaaaaa ttgagttaat tttatttaca ttacctcagc aaacatctct ataaatgagt  76020
ttccaggaca acatttacaa tatagttata ccatatgcaa atcaatgtgt gtttcgccat  76080
attatcaata aaatatgttc ttagcaaaga gcattaaaag aatacattga accaaccaac  76140
caaacaaaaa atatttcaaa gttataaggg aaggtcaagt tgaaaatgga cttaatagtg  76200
ttcactgtgt ataaaacctg gttttaagtg tttcaattaa gatacctgaa agtagtatgt  76260
atgataggat tttgaatttt ctcatggtta tcttgggaaa agcccttcta cttagtgcta  76320
gcaagtttag ttatgtttaa tatctggagt gaataggcca gaacctccat aaaggacaga  76380
ctatgtttga acaaatcata tagctacatt tcatatgcct aaagacactc atttatgcac  76440
attaataatt atgacatcca caattaatta ctatccagtg ctacacatag tactaaatca  76500
gagtttttca aactgcagcc atcatcagaa tttttaaatg aggtggaata aagttaaaaa  76560
gagcagaaaa tatcaaagtg tacttcagaa agatggtgta tttctgaaaa atgtgttaca  76620
gtcataagat acgtatatat tttatatcta tcagtcttat cttctgaatt atgttacaaa  76680
gagtgtttcc ttttgtgggt aatggtgaaa aaatattgaa atctatgtgc caactacttt  76740
agatttgtcc tttctaaatc tcagtgaaac actgtaaata gttgttatta gcccaatttt  76800
acatgcattg aaagactaga ctgtgtaggt ggtttctcaa atactacagg agctataagt  76860
ggccaatttg ggatttgagg cctgtgtgat taggtaccaa aacctctatg ctttcttcta  76920
caaaatattg gagtcaaaag tagagtttca ttgactgcaa agatgatttt tgcttattta  76980
tttaatgggt tggttaatca cggttggctg gtttgtcttt tttcttttac tttcaactat  77040
taaaataatt aataattagt aagctgttat aatagcactt tagatttccc agagcaatct  77100
gattgtaaaa taaataaata caaatttggc tagataaata catctcacgt agctttgtat  77160
tattatgttt tggtgactca gatttcaagt gctgcttcct taatttttac ttatattttc  77220
```

-continued ctataggtag ataatgatga atttaatata tccttcatca agtcaaatga agaaaataaa 77280
accatagaaa ttaaagattt agaaatattc acaaggtatt ctgtagtgat cactgcattt 77340
actgggaaca ttagtgctgc atatgtagaa gggaagtcaa gtgctgaaat gattgttact 77400
actttagaat caggtaagga gaatttctca accttgctaa aaattgactg agatttagct 77460
ggctttctta cagttcatca tactccacca aaaaaggata tgtgttatga gaagttttta 77520
aagcatataa acaaaaaaat tagtgactct ctgcaactga caaaaaggaa gatttctatt 77580
tatatttttg aggtaaagag gagttatgta gaatattcaa tccttgtaaa tacagcaaca 77640
attaaaggta tccgctgtat ttctttgcac ttatttaatc tgctagttgt ttcagaaatt 77700
aagtaagctt gcctaagaga taatatttcc aactgtctat atccaataac acttcaacta 77760
aaattctatt tcaattattt ctgtcccatt atttgaatga atattaaact tgtaatactc 77820
tgtgagtatt aaataatctg gaattcgaaa gtagaatcca gctcacattt atcacagctg 77880
ttgtcttccc ttagtcaagt aatatatgtc ttattatata actctttgat aaatgtcaga 77940
atacatacag atttcctcaa gttcttatga acagggtctg aatgaataat aagattgtaa 78000
ccaataagaa ataaatttgg aaatcaacat cccagaactt gcttgcccca tcctccttca 78060
gactcctgat gttctttgcc accagatata tcattggaaa aagcagatga agggatatgt 78120
tgctatagtt tatttgttgc tatctgtaag gtaagtatag gaagtaaaat ttttttacag 78180
ctagtttttt tcgttacatt atattctcta tgcattttgt ctgtaaagtt atggttctaa 78240
attaaaaggt aaattttatt atcagcatcc taaaattcca tttgttccta ttcgtctgcc 78300
aagtatcaca ggtatctatt ttctgattat gctttttact tctcaatccc tcctacctgt 78360
gaggaaagat atgatgaatg tactcacatt tataccataa agcattgttt gtcaaatctt 78420
aatgtgctat ctgtttcaag gatatcacaa tttaatacat ttttactaaa tctctaagag 78480
tagaatttta tgtgtataac caaaaatctg ggtactagga aattttttac aacattgaga 78540
gaattccttg gtttatctga cttaaaatca catcctaaat ttagagaaac atctcataag 78600
aaaatatatt tatgacacag cataaaaacg tgtagtaaca aatgcaaaaa tatctctctt 78660
gaaccaactt aacctttatt ttagctttgc atttttccat ttaaaatgaa atatttgaca 78720
caatagtacg tttatctgct tctctctctt ttattctttg ctgttaattt atttacattt 78780
tttgcaagat aatgaagctt gaatatctga actgttgaca gccaaatatt acatttcttc 78840
atggaaattc tttacttagt atggaaggat ataactattt caagttgaac aaaatagata 78900
tagtcattca atcagtcact tatataaaga acactaatta tgttatgcat caagaagtag 78960
ctcctttatt cataaaataa cttttatcct catacatatt ttaataatgt attggtgctt 79020
agcttgtcat atgttaagct gttatttatc taaaataaac taaaatattt atactatata 79080
aagaactctt aaaacccagc aatttaaaaa aatccaatta gaaaattggc agaagacatg 79140
aacagacatt tcaccacaaa ggagacattg ttggtaaaac aaacaaacaa acaaaaaatg 79200
acaacataag ttttcaatac cattagccat tcggaaaatg caaattaaag ccacaataag 79260
gtattattgt ctatgtacta gaacagataa gataataatt taaaatatgg cgatgatacc 79320
caatgctggc aagggatgca gaaagactgg acctctcata cattgctagt aggaatgtaa 79380
aatggaatag ccacaatgga aaataatttt gcagccactt ataaaactaa acatgaaatt 79440
actgtgtgac ccagtagtca cactcttggg cactgatcac agagaattga aaaattatgc 79500
tcacacaaac atctgtcacc aagattgatt gcagttttat tagtaataat gaaaactgga 79560

-continued

```
aacaacccaa atgtttttcc atgattaaac aaactctgct acatccacaa aatggaacac  79620
tactcggcaa taaaaagaag aatgtactat taatacatgt agtatccacc ttgatggacc  79680
tcaaggccat tgtgctattg tcattttcaa aatgacaaaa ctatacagag gaagagttat  79740
tagtgttgtg aagaagcata tactgcaaat aaaagaggat actaggagag agtttcttta  79800
gggtgatgta atagttttat atcttgttta cggtggtggt taaaggaatc tatacagaag  79860
acaaaattgc ataaaagtat aacaaaacat ggaaaggggt gaaattggga taaagtctgt  79920
agcattaaca gtattgtacc aatatcagtt tcctggtttc atataaactc cagttacata  79980
agatattacc aatggggaaa actgggagaa agttaaatgg tatgtcctgt ttttgccact  80040
tcttttgact ctaaattgtc atgccattgc actccagtca gggtgacaaa gggagaccct  80100
gtctcgaaaa caaacaaaag attaaaatgt catagaaaca cattctgtgt aaaaataagt  80160
gcatataaaa caaacaaact ggatcaccat tatggttgct gtgaattaca gatgtcaatg  80220
attctataat gcgtcagtca ttttgctagt ttttgcagtt tatatggttt aatttgtgga  80280
atactcttta aaaacagaag ttcaaagcaa ataaatttat gtggagataa aaaggaatac  80340
aatattttta aaaattaatt gttaaatatt ttattttagc cccaaaggac ccacctaaca  80400
acatgacatt tcagaagata ccagatgaag ttacaaaatt tcaattaacg ttccttcctc  80460
cttctcaacc taatggaaat atccaagtat atcaagctct ggtttaccga gaagatgatc  80520
ctactgctgt ccagattcac aacctcagta ttatacagaa aaccaacaca ttcgtcattg  80580
caatgctaga aggactaaaa ggtggacata catacaatat cagtgtaaga atccgtagct  80640
tcagttaatt acccaaatga caatgtcagt ttatgaactt ggcatttaaa aatattgcag  80700
tttgtgtaca catgacattt cccatatctt tttgtgagat tgtttgacat ctcaacaaaa  80760
ataaattttg agaactgaaa ttacctattt tctgctataa tacaagtact attaaattaa  80820
aatatgtaaa taaccaagaa gtttgcacaa taatagtaga aactcagaca taaaagagaa  80880
agaaaatgca cattaaaagt aaaagaacag tgatatataa agagataact ctgcctaaaa  80940
aaaagctata tgattatgaa tttaaaatgg aaaagcaaat tttaaggaca aaagacagaa  81000
ataattgttt acctgtttaa aattctcatg cattttaacc aagtattact aaaagctaat  81060
agcattttat gtcttaattc taaattccct atatttggac agaaatgtat gcatgagttc  81120
atatacatac acagagacat atacagacac aatttgtttt attccttgcc tacttttaga  81180
tcatcttgaa attttcaaat aaaattatat ggttcagaga aatcatcttc taagaaacag  81240
aatttactct aaatcttcaa gtagtttagt aatctgccta ccaactcttg attaatatca  81300
atgtaattat caggtcattg ataataattt gtatatgtat atgtgtataa aatgaatata  81360
tttactactt ctctcagtca ctttgacttt atatctttat aaaataaatc ttttggggat  81420
tctttttgca tgtcccatta agtggaccac cattgtgaaa gatcgattag agggaagacg  81480
gtgactaaga gaataaagta acctgggttc aaatactggc gtctgtgcca gggcagcttt  81540
atcaaatctg agcccagttt tcttatgtga aaaattggta ataggaataa taacttcttt  81600
ataggatatt tgtgaggatt aaatattcat agttatggta ggtagtgaat ggtacatata  81660
ttttggctat tggaagagag aaaataggaa ccaaaaatgt gcaactaatt aataattttt  81720
aaaaatcctg tttgcagact gcaatttgca gtatccttaa aaccttgaag tttgttagga  81780
tgtataactt tagcacctgt attgacctac tgaatcaaaa tctgcatatt tgcatttaac  81840
aaggtgtgcg aatgacttct ttgcacactg caatttcaga ggcagtgccc aaattttcac  81900
ttattatttc acttaaatgt tagattctac cataaagaaa taaaaataat ggaccatact  81960
```

-continued

```
ataacatacg ttttttattt ttaatacttt ttttttgaat ttacaaactc aaatattttc  82020
tctaggcatt ttcaagccac attttatggt cttggtttat ttatcatatc taccacatgt  82080
atattgtaat attaactcaa taaaaacatt ttaaaagtat ctagagtgtg ggagggtggg  82140
ccactaatat ataaaacaaa ttaagtaatt ccaataaaca tttcgtatac tgaattgggt  82200
ttatcgagta caatgaaata agccaagaat atagtctctg tttaatatag caagataaag  82260
tgaagaaaag aagattctct gtctacagct tccttagcac aaagttaatt gaaaggattc  82320
acgtttgtgt aaatcaccct ctgtgtatac aaacagaaat gttttatgtg tatatgctgc  82380
attatgcagg ttatagcgtc agatactttg gggcaggggt gaagaagggc ataaaggcca  82440
tctttcaggg gaatgattta atacaggaaa actgggaggc tgaaggaata ggatttcatc  82500
ttagagaggg aaaaaaagag gatcttgaat atggatttac agaaggccag agttacctag  82560
ctacagagag aaggaacaga tgttagagta gatgaaggga gagcgtagat acagtggctg  82620
tagtgctctg ttcttcctac attcacatta aaatcatggt cagtccaggt ctcagtgata  82680
gggctgttta gatcactcag cctttgttct cagcgtttag taccagaaca tcaattttta  82740
gaaatacttc attgttaatg ttcttcctac atatattata ttcaagtgca agaaaataca  82800
attaatagac tatatgcagt tgttttttaa agaattattt aaaattacat gttaccataa  82860
tcagttttat atatatatat ataactatat atatacatac atatatagat acatgcatat  82920
atatatatat acacacacat acataagcaa tcacttgaaa atagtaacaa atatttgttt  82980
gttttaggtt tacgcagtca atagtgctgg tgcaggtcca aaggttccga tgagaataac  83040
catggatatc aaaggtacat acatgagcta ccttcctatg aaatgctatt aatcagtgat  83100
tataatttaa attccatact tgaaataagg atgtagacaa gcctttaagt gataaatatg  83160
catatattaa gcacatacta agtaaaaatg tgtggttatt aaagctatag ttaaaaacgt  83220
ttaaatgatg atgtgaatta ccatgttaaa taaggagaat gtctttattt tatatttctt  83280
taatatattt tatatttcta agtttaaatt tttaaagaca aattttatag tccgttattt  83340
gatgtttctt taaatgttat cgaaaagaaa gtgtgtttaa attgcctatc attagacttt  83400
gactaggtct aattagatta ttagattgtt tgactgattt ttattttgga agtgagattc  83460
tttcagttaa ttaaatagtg ttttttgaac taccatgtag gttggtttat gattctgaca  83520
gtaaagtaaa tctatcaatt catgattctg gcaagtattt tttatagaaa atataactaa  83580
aatttgggtc atcctttcaa aataaaacaa acaaacaaac catggaaacc nnnnnnnnnn  83640
nnnnnnnnnn nnnnnnnnnn nnnnnnnnnn nnnnnnnnnn nnnnnnnnnn nnnnnnnnnn  83700
nnnnnnnnnn nnnnnnnnnn nnnnnnnnnn nnnnnnnnnn nnnnnnnnnn nnnnnnnnnn  83760
nnnnnnnnnn nnnnnnnnnn nnnnnnnnnn nnnnnnnnnn nnnnnnnnnn nnnnnnnnnn  83820
nnnnnnnnnn nnnnnnnnnn nnnnnnnnnn nnnnnnnnnn nnnnnnnnnn nnnnnnnnnn  83880
nnnnnnnnnn nnnntgatta aaggtgacag cattaggctg ggtttagggt caaactgctg  83940
gtattgaatc atggattagc cacttgatat ctatttgact ttgagaaagt ttcttaacct  84000
ctataggcct gaaaaatgga gataatacta gttcctatct caaagttact aactttgagg  84060
attaaaagag aatctgaaaa aacccttaag acccctgcct ggaaacatgt actattaaga  84120
ataaaaaata ttcactgtta gatgaaactg ataaatttta tctttttgtc aatggattat  84180
ttatataatt gtgatactct ttataagtgt ttgatttaaa ttgataaatt atttactttg  84240
ggaagtacaa atgcataagg tctttaaaaa catcaattat ttcacaaaat gacttcacaa  84300
```

-continued

```
agaatagtat gagtcatacc ttttaaattt atctttgtta ttcagtggca gacgtgtagg  84360
tgtacagata gcaatacatg catcactttt atgctttagt aaaacttccc atttcagatg  84420
ctattcccat ccccatgcca ggttggttaa tcttgacttt tactccttac ctaaggcagg  84480
cagacttacg acttctagtc tagagaagat atatgaacaa tgtcttagtg gtgggatcct  84540
agagaaatta tgttttctct actaatacac attattttat taatgatgtg gaatattcaa  84600
ttggtagtag tctcatgaaa tttgcatttg acagatatta tgaagttgga tagtaatgtc  84660
caatgctgga ttcctctaac tggaaatctt ttcctgggga ctcccaagtg gcctggctga  84720
gaatctcaga actacctgaa acctgagcct cttcctactg aatcctgcct ttcatcttcc  84780
cttttacagg tgtcatacct gtgatctgtg gcacttactc cttccctctg tcccttaatt  84840
cttcacagat aattccccca aaaaacctct tacacatcca gtctcatttt agcctttatt  84900
tctcttagta cccaaactga tacattgagt aagaaatttg catttgaatc tgatgctcaa  84960
aaaagagtga actacagaac cgagtcaaaa aaatgtgatt caaatgttga tagttatctt  85020
tgataactgt atgacataag ctcttttccc tatctacaaa ataaaaacaa tgttgataat  85080
cctgtgggat tattgagaag ctttttaaaa aagattctta aaaatatgga aattgaaatt  85140
tggttaagta acttactgat gctcaagcac tacattcaca cacacacaca cacacacaca  85200
cacacacaca cacacacaca gtgagctata agaccaaatg aaacaagcag agcttctata  85260
catatatttt ggagatattt gtatgcattg atgacaaatt atgaattatc atggctcttc  85320
tagaagttat tctgttaatc tgttaaggtt aaaagtacat atatcttttg ttctagaaat  85380
tctgctctta ggaatctatt tcatagagac aaaaagatca gtaaataaag ctcattgtaa  85440
aacaaagcta attattgtaa aacatgttta aaaactggag gaaaagtgaa ttcccatcac  85500
cagatgaacg gttgaataaa tatgatgcag ctgcaccatg atatataata tagtcattaa  85560
gaagaatgag ttagctctgt acctggtcac ttggaaacat ttaaccaagt tatatttaag  85620
caaaaaaagc aatatgaggg gtaattataa tacatactag agccccatta gaaaaagcaa  85680
acagtgagaa gagtgtgttg tgcatgacta tttatgtatt tttatatgat tatgtgaaca  85740
tggaaaaaaa tatgggatgc tatcatctag atgtttagca tggattaact gtgggagggg  85800
tgctagtatg actagaacag aaattagtaa accagctaaa agaagcaaaa gaaactacac  85860
taaaattata gtaaaaagta aatatgttta tgcatttata aaaaatatat atgagtgaga  85920
gcatgtataa attgaatttt taatatgcaa agaggagtca ggtgcctgaa aatcacacct  85980
gggctctatt atctcaggga agtctcaaat gtataattat gctttcagga gataataatt  86040
gctaaatgtc tgctgtctcc aagcacaatt ctctataatt tgttatttat gtttgtcatc  86100
actttatctg taaattaact gcatgaaagg agaaagattt tttcttttgt tgatgaaaca  86160
ataacatcaa ttgcagtgat atttcttctt tgtttatagc tccagcacga ccaaaaacca  86220
aaccaacccc tatttatgat gccacaggaa aactgcttgt gacttcaaca acaattacaa  86280
tcagaatgcc aatatgttac tacagtgatg atcatggacc aataaaaaat gtacaagtgc  86340
ttgtgacaga aacaggaggt atcatcacat gtcaatttat cttgttaaat tgtggagtgt  86400
agattactga gtgctaaaaa gaatttagtt caaattaaga ttgactccca gttatcacac  86460
acctcttgag attaatagat tgtcaatatt attattaatg ataccaatca tttctttgta  86520
aataaataaa ttatttattt attttatttg taaaactttt ataaatgtca tttatttata  86580
ccaattattt attctttttt acctatcaag aaaggcacag ttaaaatatg tgatttatta  86640
attccatata ctagtagata aacatgtttt gattttggta agatggaatc ttgatagctt  86700
```

-continued ctttggaggg gtgaacaagt gagttactct tgattgaggg atgctctttc tctacctgat 86760
aaatcatcct ttataacagt tcctgtagat tcacatgtaa cagagaagaa cagggttacc 86820
tgcctataca ggtggatcac ttgaattatc tctggtgact gatgttgcat cgagagtccc 86880
cttatacaat tataaaaaca ctatttataa ttgtaaaaat atattcatat gttacttgga 86940
attattgttc tctttgtttc tgaaaacagc tcagcatgat ggaaatgtaa caaagtggta 87000
tgatgcatat tttaataaag caaggccata ttttacaaat gaaggctttc ctaaccctcc 87060
atgtacagaa ggaaagacaa agtttagtgg caatgaagaa atctacatca taggtgctga 87120
taatgcatgc atgattcctg gcaatgaaga caaaatttgc aatggaccac tgaaaccaaa 87180
aaagcaatac ttgtaagtat aggttatatc taccatgcat tctgttagca agctagttag 87240
tatctttcat ccatccatct gcctgtcctt tcatctttcc aataagcact ggatgtccgc 87300
cacgtatagt gacctgattt ttctggcact aggaatagaa agataaactg aaaattattc 87360
ttacattcca taaacataca gtattatagg ggaagcaggc aaccctaaga gtaattatga 87420
tttgatataa gttacataaa gaccatatga aaaatgtgct attggagaac ataggtatat 87480
aggagaattt aattctttct gtagaggaca atgtgactaa tgtgtttttc acttattatt 87540
ttaccatcca tgctgatgta caggattttt gaaacactat cctatccttt gatttaacag 87600
tggcttccct ttatgtcact cataacaata actctctgct ttttatctca tgaatgagtg 87660
atagaaatat ttaataccac ctttaatatt tagctttttg tagcccctaa aaacccaaca 87720
ttttaaaatc aatttgatat tttggctgta ttaaattatt tgctaaattg attatcttcc 87780
ttttgaattg attatgttat ttttgtattg taagactaca atttttaaaa gaatcatctt 87840
atccttgtgt gattttcaaa atataatttt tactagtaat tttttaaatg caggtgcttt 87900
catttgtgcc tgttagttaa aacattatca aattctttac aaatatccta agccaagtta 87960
acattggaaa aattagagaa attaggcaaa taaaaataat gctttatcat ctctattaaa 88020
tgcaattact ttggttcaaa ttctaggtta ttgcctgaat agctatacac atatgatagt 88080
tataaaaatg atatactacc aagtatcatg tttattcata tttatagttt atttattttg 88140
catatttgtt cctgaaacag actcttcata taacaaataa aatcataaga attttataat 88200
ggtagaggtt caatcatgta ttgcaacgta ttggttttat gtttttaaat gcccttgtgc 88260
ctttattttt aaattaagta aatttcaatt gtctctgagg atcttagatt ctttttgtaa 88320
tttttaagct tgatcttctt ctgtatcctt tacttcaaat gctatggaag caaaaaagta 88380
tacaaatgca actgtgcaca cacagaaata acaaacattt tcttaatgtg tttatatgtg 88440
aacaagacaa gttctatatc atcattttaa tctaattcac tagcatttgc aaaagtgatt 88500
gaggtataac agttatgcct tttatttata aattatgtta gtgtaacacc cttcacagat 88560
atcaaatcat tccatctaaa caaatccttg aaggaggtga gctgattcag ttgttcaaac 88620
tgctaactgc tcacgagttt accaaatttt tagcccctgc ctcatcaaat tcaatgggtc 88680
aaagtacgag ataattattt gtctcatata aatatagcat atatttctcc tgatgatgat 88740
tccattccaa attttcatct tgtaaattca ttttcttttg aattaaataa atagttttta 88800
taattacttc ttgagttatt cataggaaaa atcacatgat atgcaaagtg ttgatttttc 88860
ttttttttatt ttatagattt aaatttagag ctacaaatat tatgggacaa tttactgact 88920
ctgattattc tgaccctgtt aagactttag gtaagacatt tttgtaattc atttataatc 88980
tcaacatatt tatcaaagtt ggaacattta ttagtaaatg tattaatcca tgtctagatg 89040

-continued

```
ttttaaaata taaactcatt taaatgttaa ttagcctctc tagtaatatt tgtgggtttt  89100
taaaattttt tcttttaggt ttaggagtac ctgtgaaggt ttgttacaca aacatctgtc  89160
atctcatctt aactatcctt taagttaggt cagtgcttct cagagggatt ttatacccca  89220
ggggatattt ggcaaagtct ggagccattt ttggctgcca taacaggatg gtagtggtgg  89280
tggtgcatgc tactggcatc tagtgggcaa agattaggaa tgctgctaaa tttccacaat  89340
gcacaaaaca gcccgtaatg tcagtggtcc tgaggatgag aaactctgac ttaagcccta  89400
atgttgactc cattttacag atgaggaaac caacacccag attctttcag tatttaagtg  89460
gctaggccag gattccaaca ttacagaaca ggatttcata acattacatt acaaatatgg  89520
gatttagacc tgggttcaaa tcttggctct gtcacttgag aaaataattt aatttctata  89580
aatctgagtt tcctttgttg ggaaaatatt gataagagta tcatccttga ggggttgttg  89640
aagttttgtg taaaacaaca tatataaata tattaatatt ttatagttag taaattttta  89700
aagtttaata gctttttttgg ataggttata ataaaatatt ttagaaacat ttttatttag  89760
gagaaattat ttctctagaa tttcactgag aggatcacaa cattctacat tgtttgtgcc  89820
aggccctcaa aagccccagt ttattcgtct taaagaattg catgaacagg gtatttctgg  89880
ggcaccactt gaaaatgtaa gacttcatgt gttgcccaga tcctggcgag ctgttgctca  89940
gtgtatcttg aactgctaat agacttcagt gagagttatg actggagaaa gacggattgt  90000
cccaccattt ttagccagaa attctcattg ggttatggaa atactaattg tataaaaagc  90060
cagcctccac agcctctaca tgtagtcaag gaaactttgc atcttgaaga aatagagggg  90120
gcatgtagtt tgctacatag atgtttgtag agaaataaca aatttctttg gctaaaatgt  90180
ttgtttaatt ttatacaaat cattggtttg attaatttta cccaataatt tcatcatttt  90240
aaagctagct gattagtttt gtggttttga aattgtatca agtgtttctt catttgatag  90300
gtgagtctat cacactctga tgccaccaca gtaaaataaa tgtcttcttg tcatcagcat  90360
aatttcctat aggttacagc attcataagc cattacttca gctaagtagt gatcctggtg  90420
catttgccaa tggaaggtaa aagacctaga caagatagat aacccatgtg tcttaggaga  90480
taatatttta taggagcagt gctgaaagga gctagccttg ctgtattgta tgatgttgtc  90540
tttcatcaac ttactggttt catacagatt attcatggga aggcaacatg ttccgtcagt  90600
tatctgagag gcaaagttga gacattcagg gtaatggaaa tgagaaagaa aagctataaa  90660
agggggggag cgccaagcat caggaaccac agtgcacagg agcatgattc cttagattct  90720
gctaaatggc ttctctctgc ccaatgatgg cctcatccag cactataagt aatctcaaag  90780
agctcctcag caatggtctt ctctttcttc tttccactca cagtcaaggt ggtggaatac  90840
aaccattaat cctggaatgt agcagaaata cacagtcagg tttttgattc cttctttgga  90900
agtataacca ctgccacccc aatcatctag gtatgaatct ttgtgtgctc tggaaacaga  90960
aggagtctac agtgagtaaa agatgtgtaa tgaaggacag agcacaggat cctgccaaga  91020
ctaaggaagg agggactggt gaaatgtaga ctggacacaa tatatagaaa ggcactgggc  91080
tgctgaggga tagtgacaag gaagggtcct atgtgtctat gatcaaatta ctcagagttc  91140
agtgtatttt ttgtagacca gtgacatgat gacagtcttt taggttgctc cttagagtga  91200
tcttccaggg actctctcct gagatacagc agctttgtta attggccttt gccctacagt  91260
gcttattctg gattgaccac atggagttct gctatttaga tagtcattta tagcgagtaa  91320
gacagtgaca agtggaatca aaggaacttg cttggtttgt aatcgttagt tgtagtgaaa  91380
tgagaatgca cccctggagc agaattcctc aatgactagc aaagcagccc agccatttct  91440
```

-continued ctggttaatg gatttaacac catcaattac tgttgtcata tttgctttct accagactat 91500
tgagtgtcgt ggttctatgg agattagagt cactttcata ggtcaagaaa caaacaacat 91560
cccctagaag tggtcctggt ccatttgaca ttgatagaac gctgtagatc aggggtgtcc 91620
aatctattgg cttttctagg ccacattgga ataagaagaa ttgtcttgga ctacatataa 91680
aatacatcaa cactaacaat agccgatgaa ccaaaaaaaa ttgtaaaacc atatcctaat 91740
gttttaagaa agtttacaaa tttctgttgg cccacgtcca aagttgtcct gggccacatg 91800
cagcccatga gctgcgagtt ggacaagctc gccacagatt caaaagagtt cttagtaaaa 91860
gaacattgcc agggaagaaa ctctagaaga actcaaaaag aaaacaaagt tgatcaattc 91920
tccaatggtt agtggcaaga atggtttcat ggttgtgaga atgaaggcag gcaaataata 91980
aagtgcattc atataatacc cctggtgtca tcagaagatg acaaagggtg attgagtcct 92040
ttttttctct caaatatgtc atgtgttggg atatatgaat catttgcagc aggctaggga 92100
ctcaaacatt cctggtaagc tgctgaagac atatgtgtgc atgtaatccc agactacaga 92160
gagaagtcta ggtcccatca aggtcatcca cccaccaggg gataagcatt cattcactgg 92220
tattttgcac accacaggca atgagcacta agccgagttg cctgtctgtt gaaactttgg 92280
gatttaagag cttttgcacg actctgtttc cacagaccat tgtagtggta attatgcctc 92340
tcagagacgt tattatttgg agtttaaaat taggggcaaa agaatcacca tagactgata 92400
atcttaaaaa tgtttaagtt tagtgaaagg gactaatgaa agtacaagtg agagatggcc 92460
aggtagaact tcactggatg gataagtatg agtctgtgga agagcagttt gcatttaggg 92520
aaacctttct ggcctgtagg gataaacagg gaagataacg tatgcattat tttaatccta 92580
aataaatact tgaaacttat ttgatttcgt ttttactcaa gattgagtat tggcattttt 92640
attatcaaaa ttcacaaaaa accctcttaa actttttgaa aaaatcttcc ctaggcacat 92700
cagtttatgg aaagtgcttg taggcaatgt tttgattaca aggtttaatt atagagggat 92760
cctgtgattt gaaaaccaga cacccgtttc tgtaccttac agggctctca ttaaagctga 92820
acatgatgaa atcttaaacc ccatggcaaa ggcactctgt gattgttttc ttttgtcata 92880
acacttctca tttaattact atgctaacaa tgaaaagttc caatgtgctc acttagattc 92940
agaaataggg agttgctatg tatcttttgc atccaaagga ttacttccct aaagtcacca 93000
gaggaacaga ggaagattgt attttgttaa cgagacagtg gtaatgtggt ggtgaacctc 93060
acatactctg tagtcaagac agacgtattt caggcaggct tggtatatat tgaatttatg 93120
agattgtggg ttagttactt aaaaaattat ttttaagttc tgaaatctta tttctaaaat 93180
gagaatacta atactccatt ttagaagcta actaggagat taaatcagat gaataaaatg 93240
gatgaataaa tatgaaatgt ttgttaataa agatacctgt cattgtttat gtaccaagtc 93300
tttaaggggt tttacatata aactcatgca tcttcactgc aactctgtaa caacacctcc 93360
tatttacata gcgccaattt ctaggtaaga agtttgaagc attgtgtttt ttactaactt 93420
gaccaagctt tttaaccatc ccaaaggtgg tggcagaacc tgctttcaga cccaggcagc 93480
gtgacctcag tcagtgctgt acttgtaacc actgcacaca ctacctgcaa atcactaagt 93540
ccccaagtag cccccagttc attactatgg gtgatgtttc tgctcccaca acctatcttt 93600
gctgtaccat tttctcttct tgatagtttt aattatttct agcagctctc ttttctcaca 93660
ctttgtcttg gcttttgagg ttagtgttca cagataagca tgtgttgctt ttgtgtttag 93720
agatatggtt tctttttatt tttttaacac cgaataatgt gacttttctc acaccctagc 93780

-continued

```
aaacacttta ttagctacct ttaaattttt tcctgtctgt atggatgaaa atgatgttca  93840
tcccaatggg gtgttttaat ctatatgttt aaaattttat tgaatattga caaattatac  93900
acgtatatat ttatggggaa cagagtgatg ccatgatata tgtataccat gtgcaattat  93960
tgaatcaagt taattaacaa atccatcacc tcaagcactt atcatttatt cctcctatct  94020
aactctattt cttgacttat ggaattgagt aacttttagt aaattatttg ctcagtgttt  94080
gaataccta ggtgactagc actgggccaa aagagaagat gaactcccta tactttagtc  94140
ctgttataag aactcaattt ttataataat aataataata ataataataa taataataaa  94200
gaaggaggaa gaggaggagg aggaggaagg ggaggaggag aagaaggaga gggagaaata  94260
aggaggaaaa gactttccat tttatatgca tctttatcag gagccaggca ttgtactatg  94320
agctttatat ctaattgaat tcaagtttct ccttagagaa taggcttaaa aacagactta  94380
aaaagttgga tacatatgct gaatttaaat aatgataact tcagtcagaa gataatactt  94440
atgaaaaatt agtgctttag aattatgatt tgccaaatta tagtagtaca atttattatg  94500
taaacagacc aatttaatgt gatttgtcac aggattttaa gtctagtcag aaatgacttg  94560
cacctactac aaaaagaaac atgtttatat ttttaagtaa aagaattcca ttttctatta  94620
aaggatttgg agaagtgaca tcattctcta ctgttaatgc tctgtgggtc catgcataac  94680
agtgaatcag aaagtgtact tgataatcag ggaacatttt gtcctctctt agtgacactt  94740
ttgtaattca tgtgcccaaa ggattacata ttgtttatta atatattata tgtcatttcc  94800
tcatttggcc agtgctttga aatggtaatc taatctaaaa aaaatttttt gtgtggtcta  94860
tgagaacatt tttttcccac tgagttctaa ggcccagtga ttcattatta cctaataaag  94920
aggattcttt attcatcttc atgcctcctt tcccaagcat atccaattag agtcaccatg  94980
tgaaaattca taaatcaaac cgttcgtatt ttaatgtata aaaaaatgta cctaaaatac  95040
tttaggtgat acatgctgct ttctcatttt ttaaatttag caggagattc tagcagacca  95100
tgaagtgctg ataactgttt taaattcagt atttattcaa atccaccatg caggatagcc  95160
acaggaactc ttttatattg gtaacattac ataagtacca atacaggaca aaaagatgaa  95220
gcattaatac gtgcctattt tacacattgg taacctattt tgtcacttga ctgtaatact  95280
ttgtgcagta aaattataaa ttatgtaact taaaattgat tacaattata attagtagtt  95340
gtgcttaata atttttatat tcttatttgg ttcaatgcct gatcttcaaa cacgaacatt  95400
tttaatcttt ttcaaaatca atatatttgt tcattagtaa atttagcaaa tatttattta  95460
atatttactc tgtgcccagt acatctctca gaccgtggaa tagttttgta taaaacaaaa  95520
acccctgtac tcaagggggc ttacattctg gaggaaagga cagagaataa atagtaagaa  95580
taataaataa gtgatttata tgttaaaata agataaagtt atggaggaaa aaagtagaac  95640
agagggaaga aggaggggga ggaggaggca gaaaatgcag ggagttgtgt ctttcaattt  95700
taaatagtgt gctgtgttag tctgctcagg ctgccatcac aaaatatcat agatggggtg  95760
tgttaaacaa tagaagttta tttcctcaca gtccagaagg ctagaaatct aggatcaagt  95820
ttcctgccca tttggtatca ggtgagggct ctctttctgg cttacagatg gttgccttct  95880
tgcagtgttc ttacatggcc tttccttggt gcatggatgg agatagagaa aatatggtgg  95940
ggggaggagg aggagaaagg agtgagtggc acacacacac acacacacac agagagagag  96000
aaagagagag agagagatgg agaacaagct ctctgtgtct cttcttataa gtcactaatc  96060
ccatcagatc ggggcctcac cctatggcct catttaactg taattccttt cttactccaa  96120
atacagccac actggggatt agggcttcaa catattaatt tgggggaaac acatgtattc  96180
```

-continued

```
agcccataat atatgatcat tgagaaggta tttcagcaaa cctttaaagg aagtgaagtg  96240
gctacccaga aagatataca aggcatacac acctttgcag gcagaggaag aagctgctgc  96300
aaaagccatg tgtcaacaat ggccttgtgt tattcatcaa taaggaggct aatctggctc  96360
cctaggagtg agcaagcaag gtggggactg gaagggaaat cagaggggta acaggggacc  96420
agacagttaa tgagggacca gatcacacat gccactggaa ggatatgggc ttttctcagt  96480
gggagatgag gaggatttta agcagagaaa taatgtttta aaacgattgt ccttgcttgt  96540
atgttgaaaa taggtggaac aaggacaaag gtggatacag gcagacttgc taagttttta  96600
attcatgcaa gacaggatgg tggcctagat cagattatca gcagcaaagg tggagcaaag  96660
tgaatggaac atacataaaa ctagaaaaaa tggtgtcatg aacccccaaa tacctactaa  96720
ctcaatttaa taataattaa catttggcca catttgtttt atttagacat tgttcactta  96780
tttctgaagt aaagtaagtc acataacgca tattccactc ctaaatactt tagtatgttt  96840
ctctaataag tacattttta ttatattgct gtgattaaac ttaacaataa attattgata  96900
ttatttaagc tacttgtata tacgttttca aatcagtctt tgattttttt ctttaaagtt  96960
aatttatttg aatcaggatc caaataggaa tttacacatt atctttgatt gttctgtttc  97020
ttctattatt tttttaaaga gccttctttt ctcctttcct tccccctat gtcatagact  97080
ccctgaagca atcagatagg ttgtcacgta ggaagtccca tattttggat ctgtctggtg  97140
gttttctctt gatgtccttt aatttttttt ctttccacca ctttcttata aattagaaat  97200
aagatctaaa gctttgagta ttcgcagtca acatttttgt cagaagtact ttataggtct  97260
tgctcactag atcaaaatac cttccatcag gaagtgtaga atatctgatt gttacacgtg  97320
atgctaaaat tgatcagtag gcttggtggc agcaacagca tgatccttca ttggaaagtt  97380
ggttttgacc acttataaca agcgtataat ctatacagcg atattttgtc atcctgtaaa  97440
tgtccaattc cccattaact ttcctcctaa tcattttaga atacatttat gtttgttacc  97500
tgaatcaact atttcgttag aaatactgat tattaatttt tttttatttt gagctggtgt  97560
tttgctcttg ttacccaggc tggagtgcag tggcacgatg tcggctcact gcaacctcca  97620
ccttccgatt tcaagctatt ctcctgcctc agcctaccga gtagctggga ttacaggcgc  97680
ctgccaccac gcccagctaa tttttgtatt tttagtagag acggggtttc accatgttgg  97740
ccaggttgtc tcgaactcct aaccttggga tctgcctgcc tcggcttccc aaagtgctgg  97800
gattataggc atgagccacc gtgcccagcc ctgtttatta atttctaatt ttgtcactcc  97860
tttaacattt atgcagcaaa attatcttct aataatgagc tttatctcct taactagggc  97920
tatttttaaa aagtcataaa atgtagttca gataagaaac cnnnnnnnnn nnnnnnnnnn  97980
nnnnnnnnnn nnnnnnnnnn nnnnnnnnnn natttttgtt atttgtattt cttttattaa  98040
ataatcttat tttttatttc tgatcaattt ccatttttat taaatataag gcttgaattc  98100
ttccctcttt ggccagtagg agccccttca ggaggatcat ttgttccttt tataccagta  98160
gccttttgtt agcttcctag atctctagca ccattatatg tcttgaattt gtttagttcc  98220
ttcctcccac tttgcaatta ccatctttcc aaagttacat agtttctttg gtgaaaatta  98280
caaatatgtt gaagatagag cctacaggat ttcctcacat gttttggatg tattctatga  98340
aagagagtca aagatgactc cagggttttg gccttagcaa ctacagtaat ggagtgtcca  98400
tcaactgaga ggtgggagga tacagttgaa aggagggaag tgtacatgtt cagttttgga  98460
catatcaatt taacatttta agtatacttc aaaataaaga cgtctggtag gcagttagat  98520
```

-continued

```
atataagtct gaagtctggt ggataaaaac taagtagtca tcatcatata gatgaaatta  98580
aaactgtgag gctagatggg ctcacactgg ggagtgagtt tagatagaaa aagcaagaag  98640
acccgggact gagccccaaa gttaaaaaat ctaggagaag aggaacaaac aagctgctac  98700
attttactag tattcttcag caaagaatat tttcttatgc caagataata ttttttggta  98760
gtttgggatt caaaataaga ttccataata atatttaatg atcctgttat ccctcttctc  98820
caggggaagg actttcagaa agaaccgtag agatcattct ttccgtcact ttgtgtatcc  98880
tttcaataat tctccttgga acagctattt ttgcatttgc aaggtaagat ttatttgcgc  98940
ttacattcca ggatgcttta tgggcattat atcagtcata gtccaatcag gagacagaag  99000
ccacaacagt tacttgaatg ggaaacattt ttatttttaa tagacagata aaaatgtatt  99060
tatcatgtac aatatgatac tttaaagtgt atatgcgttg tgtagtgact aaatctagcc  99120
ataaaaggaa agaaatcctg ccatttgaac agaaaacatt taatgtaaag aattgttaac  99180
tagcagaaat ggctaactac taaagagagt aaaagagaaa tctaagagtc cagaagtagc  99240
aagcaaaaca aagcagctac tctctttaac ttgaaggaga gaggacagta aacaactaag  99300
aactgaaaga agttgtctcc caagacttac atggaatcgc tacttctagc acatgcaacc  99360
tatcaccaaa cagtgagcaa agaaatatga cagagggaag gggttggagc tgttccgtag  99420
aagctacccg tcattattag atggtaggca ggctgaaatt ggtaatagaa gcatcccatt  99480
cttgctgaat ggtgtaggtg agctggtact acttgagact gttcacgaat ggcatgggca  99540
gaacgttcac ttcagaggca acaagagctc atccaagtga gctgctgggc tctcacaatg  99600
aataacaata atgcaggatt ggatcccaca agggcagtgt tttcctcttc ctactgcctc  99660
tcagggtcac tctagtgccc tctattgaca aagcctcact ttcggccggc tggcaaagga  99720
gaaatgcagg ttccagctcc aatatcaaag agcacagcaa aaaaaaggag gtttggagat  99780
gagagacaac aaggtgaaaa cacaaaagca gaagctttca ggccacctac atcttttaaa  99840
gtaatttgta actcttatag gtttaattta aaatatctca atcaggtcta aatattaaag  99900
tttatacaga aagagatctt ttttatagtt agaacaacac ttgtaaaata tccagcttcc  99960
ttatatggta gaccccccttc tcatgcttac tttctgaaca tgtctgtgct gaattttcca 100020
agtgtatctt tccattctca gcatcagcat cctacttccc ttattattta cagggcctcg 100080
ttggaaatct tacttctgac ctcaaaatct agcttcttaa ggcagattgc cgagttaaag 100140
ggaccttaca tttgtaaagt aaactttcta ccaatttcct aaatagttca atagactatt 100200
tttatttcaa ctgaagaatg tagttctgta ttctaaatgc catgcattat ggttcatctt 100260
gactctctta aagcataatt ttaatagata atttgaaagg ctcttgaaaa agatattttc 100320
tctataccac ataactattt gcagatttag ccagaagaca gtgagagagt tatcattcga 100380
ggcactttga atgctataat gtgtaaaata tgggcctttc cctaaggagt atggactggc 100440
cacatttatg taatttccct gctctaaaat cttttctgac ttctcatttc tctacaagat 100500
gaactccttg tgtgagtagg aaatggtcct ccttattccc cacaacttgc ctactcacta 100560
gctaaagaga tctattctca cctgaacatt ccttgggctt ttatacattc tgcttttgtt 100620
cagtcaccct gaaatgtgct tcctcctcct tctcatcctg ggacatccaa gtcaaattct 100680
acttctttac ctcctctaaa taataataac tatttatgta actaatcagg cactgtctta 100740
tgtgttgtaa tttgaatctt tttttctctt ttcatgtttt ttctgcattg aaatcttgcc 100800
tctcaactaa attgtaatgt ctttgagggt agggaacatg ttttatactt tccatatcat 100860
ccttgatgtc caactcttaa taaatactaa atatttgaaa tgtgaaagat agaatagcta 100920
```

-continued aacattactt tgtaatatac catactgtgt catggagaaa taagcattta aagggtttaa 100980
gatgaaaaga atctgatttg attctcagat tcatgtggct tttatttttg aacctaagtt 101040
ttctgattgt aaagataata tctactcaca atatttttat aaaaattcaa taagataatt 101100
tgaaaataat ttttaagtat tttcatgcat gtaaaaatat ttcatatatg tgaacacaat 101160
ggggcattat ctgttagcaa tactattgat agcattgaac tattttcact ttggcatagt 101220
tcctttatat gacaaatcaa tgacatagct agagagaaga gaaacaagat cacaacgtaa 101280
gtcttcttgg ctctatattt aaatgtacca atggctcagg ccttcgtcaa ctaattcttc 101340
ttaaatttag aacttcatcc caataactta ttagaaaaaa aagaaagtag aataggttct 101400
atggaattaa aacaagaaaa agaagtcgag tagctataaa tttgcaacat attcagagag 101460
gtgattttaa caaggaaatt atttgactaa atgtctttac ttaaaaagaa aactaaacct 101520
aattttatat actttgtgtg aaactccctt cttggacttt actccgcttg ttttagaatt 101580
cgacagaagc agaaagaagg tggcacatac tctcctcagg atgcagaaat tattgacact 101640
aaattgaagc tggatcagct catcacagtg gcagacctgg aactgaagga cgagagatta 101700
acgcggtgag cacactcctc tgggtgaact gtggtccaga gggcctggag ccatgaccct 101760
attctgacct atgcttgttg gaagtgtttg tggggctcta atttacacag gtcacagaga 101820
tcttctttca aagagtgacc tccgtcttct acacacttct cactgctgtt cagagaatca 101880
cttaatcttc ctaatatttt gagttaaata tgaactttgg actataatgt tcaatcagga 101940
ttattttcct gggacaaata tttttccaca ttaaaccttt gacattatgt ttaataattc 102000
atttcatatg atagattttt acattaaact tttctggaag tgtccacatt ttcaatcaca 102060
ggtttaaatt aattaaattt ataactactt gatattattt atatccattt ttataaaagc 102120
tttttaataa ctatttcagt ataaaagtac ataaaagtct aagttgtata tgatatcatt 102180
tttacatttc tttgtattta aaaattaaat ataaagtaaa aagttacctt cagagggaaa 102240
agtaaaaaca tgtgtactaa atatgtttca ttggtaccta ttggaaatag taaagtacat 102300
aattttaaag aaaaaataat tataaatcct tttaaaagca ttatcaatta ttcaaaatgt 102360
tggcacatta taaaaacttg tctattaaga taattcatca aattcttaat gaaaactacc 102420
atcaggctat tttaacgttt gcatttttat aagattcaat aacatgtaat gcttataagc 102480
acaaagtagt tgttaccaag tatttgctca gctctgttaa aattaaaaaa attattatta 102540
attttgaaaa tatggcatca aatgtcttgg actcaaaaag ttattcattt gtagttgtca 102600
cttgttaaag ttggtcttta tctaatagat ggactttgca agtatatttc cagcatatct 102660
aaaaatacct aatatgtgct atagagggaa gtgtcatctg ataagcaaag tccttccaaa 102720
tgctacaaaa tgaaggttat tcaatgttat cactaaattg cagggaaatg tgttttcttg 102780
gatatgacag ctgacttttt aaacattcag atgttgatct ttgtgttcta atacagtggt 102840
cctatccaca aatggatagt actccaaaga tttaagtgtc agatgattgt aagttatcca 102900
agacatagtt ttctatataa gaaatattat gtacaaaata tcaaatatgt aaaaagaatc 102960
aataaaagat tcccagggta actcatctaa gtaaaaccat atcataggaa cacaagcact 103020
gctactacta gactgtgtct cagcccttaa ggaatcattc tgcatcatca aagaaagttt 103080
ttcctccttt tcccctatgg gccaaatgaa ttttagtggt atcctcctag cctccttcct 103140
gcactccatc gtcagttcct tttgcccctc ctcaggcctg tgtggcccat ccctttattc 103200
tacaactgaa aatgcacaag ggaaaaaatt caaatctctc aatgcaatta attttagcta 103260

-continued tttgaacaat atagttgaat ctgttcatac taaaatgtaa acttctaaga ccgaccccct 103320
ccccaacact ggtaggcatt ttcattttgt taaaagaata cttagtagcc cgtgaaaaat 103380
cctgaataag tatatcttca gcaaatgtaa taacgtgaaa aagcactctt tttgtttatt 103440
atgtcatgtt tttaaacagt caatattgga gaaagtatta tttatcgaag aggttacatt 103500
cgaggcagac tgtggtgaga ttcaatcccc taagcactat atattttcac agcttgcccc 103560
tttctctact tctgaacact aaatacatca tcataaaaaa attagaaaag gtcgggtgtg 103620
gtgactcatg cctgtaatcc cagcactttg ggaggctgtg gagggtgaat aacctgaggt 103680
caggagtttg aaaccagcct ggctagcatg gtgaaacccc atctctatta aaaatttaaa 103740
attagcccag catggtggca tgtgcctgta gtcccagcta ctccagcctg ggtgacagag 103800
cgagactcca tgtcaaacaa aaagagtaga tttttttttt ttaagaatga ctgtcatggc 103860
agctacagaa aagtttcaga tcatgaaaaa ggtgggcaag gaatgtatag attgtttact 103920
attggttatt tataattcag ggtctacttt atttgacctt cactcttcat tatttatttt 103980
tccacttctg tgtttattta catattgcat tatttgtaaa agggtttaaa agtgaaataa 104040
tatttcagat aatttttatt ttgttacaca cagagaatta gtatatatta cccatgataa 104100
tagcaaaatt ggaaatatta gtttccatgc ttttcacttt ttcacttgtt tgttgtgatt 104160
ctggtattca caattgtttg taattccaat ggcacataat aacatgcttt gctggactta 104220
ttacagaaat gcattaaaat aacaattaag tgatttgggc attaattctt cagtacagag 104280
atctgtgtcc agctttacta tttatgcaat atttttatgt taataaagtc actaaaacat 104340
tagacaataa gactggaaaa aataacaaat ataattagct gcatgtacat atgcgtggat 104400
cctgtcattt ggtgaagctc taaaactctt catctgtttt gaggtgtttg aagatctaaa 104460
tctgttcaaa gtcaatcaga gactgatggt agattctagg agtgagaatc aagaagtctg 104520
atttagctcc ctaaattgtt ggcagacttc caccatatgt ctttgttatc tgcaggaaag 104580
aacttccata atttctctta aatctaccca gctaataggc tgggcatagt ggctcatgcc 104640
tgtaatctca gcactttggg aggcctaggt gggtggatca cctgaggtca ggattttgag 104700
accagccggc ccaacatggt gaaaccccat ctctactaaa aatacaaaaa ttagccaggc 104760
atggtggcgc atgcctgtaa tcccagctac tcaggaggct gaggcaggag aatcacttga 104820
acccaggagg ctgaaagtgg cagtgagcca agatcacacc attgcactcc agcctgggca 104880
acaagagtga aactccgtta aaaaaaaaaa aaaaaaatct acccagctaa catacgctct 104940
ctctacttga ttcttaggca tgtccttttt attccaacct gctaaatttt tcatgcaaaa 105000
ttgagctcat aacttttctg agtcctgtat gttttcccat gtccaaaaga taaatgataa 105060
aagaagaatc tctaatcaat aattaaaata ttaattttag gaagttacca actaggcaaa 105120
aataaaacaa aaaacaaaca tggtgcttgg tactaagtcc tttcaatgat ttgtggtttc 105180
atattttaga aattatttaa ctattttata ctctctgcct gtatatttac actttaaaac 105240
ccattctgta atttttgtta tttgtaaact cattatttaa ttatgctcca ctttgtttca 105300
caaaactttt gaaaatgcct tctctcactc tatcattcta tactatttct tcccaaatga 105360
gagcaggagt caaataaaga tgtagtactc tttaattcta tgaaaacatt caaggatata 105420
ctaaaataac gttttaaatt ctcaatttga atgataatta tattatgtac aaagattatt 105480
cacattttat gtttaagttt agataacaca aactataatt cttaggaaga atatgtaaca 105540
ttttgggctc atctgtttca cacttaccga attaggaaat gatccttggg ttttgttatc 105600
taataaacat acagaacaac attttgtgat ggctcctgca aaacaccacc acttagccca 105660

-continued

```
ctgaagttag aaaggtttct tagagctctt attggcaaga tcagcagaca cagacacgca 105720
cagtaagaca cagacctgta tcactgagac tgactcacct tgtggattgc ctttaactac 105780
tttaactgta caacgattac cttcccatga gagtcacatc acttataatt aaataaccca 105840
acagaatttt cgtaagctaa aaatgctatt tgctaaataa gcttattttt tactatcttc 105900
tttccgcatt taagtcacgg aagttttgtt tcttatgccg actaaatcag aaaagaatag 105960
taaaacaaca ttaatcaatg tcactaatat tcttacttga cagaaactca gtttctttta 106020
gtcctcaatt ttttttcaaa aattttatgc accacttcat attaattacc ctgcctattt 106080
tagttgagtg aatgtaatgg cacattattt taagcctcaa agcccaatcc aataatcacg 106140
aatagaatta aaattcacaa gataaagtaa acaatctaat gagttggaaa aatttctatt 106200
ttaagagaag tcttcttcaa taattttctt tcttcagtaa cttcagaagt gtacatgttg 106260
aatttttgtt aaatacacag ttatgtcttc aggaagatta ctgcttaaaa aaattctaca 106320
tatgtacttt gtaaactgta aaccagaata cctttggtat tgttactatt gtgatttata 106380
tttgtaatat tgaatactac cccggtctac tttcatatat agagtttgct aacaaaataa 106440
tagctactgt ttatgagcaa ctcctgtgtt aaactctgca tgtagtgatt tcacttaact 106500
ctttcaaacc ttagtggtag gtacacctat ccccatttta cagatggatt aaaaaatgat 106560
gataggacag gtttatgtaa atgtctaagg tcatacagct aataagcagg agagctacaa 106620
gctagcccag gtctttctct gaggtatgaa gatacacgtg tgtgtgtgtg tgtgtgtgtg 106680
tgtgtgtgtg tgtgtgtgtg tttaacttcg aagcatacta gagaagatta atgtaaactt 106740
ttcttaaata gacaaagacc catggaattc ttcctcagca gcattttcta tgatgagaat 106800
gagtctaaag aaagaggttc ctctttggat ttctttgttg tctcatgata tgaagcaaag 106860
aagtgatggc atttaatgtt gactcaaact tgcaggaact ggaaaacttt tagtagtgta 106920
atttttattt tggcttcaat aataactcat aatttttgac tgatatatga aattctaata 106980
gttcacattt taagtgtcat cattctttga caaattctgt tcatatattt tacttccgtt 107040
ctaaacttaa gctatctttg caaacaatgg caaaaatttg tgaattcgga atacaagaaa 107100
tgttctatgc ttagaatgaa attggagata cttaatgctc atattcttgt aataacaaat 107160
caaaaataat tcagtgtgtt tgtatactaa ataatgaatc tttacttgca gatactcttc 107220
atttttcttt agacgcaagg agatttttgt catccagtaa gttactgtgg taatgcagaa 107280
ctctgctgtg attattttaa tcttgtcagg tggtgtgctc tatattttaa aatacataat 107340
attgaacatc ttgttgttta atgcactatt ttttccaaag ctccccccaa aagctatatt 107400
tctatttaca acatgtcctt tataatattg catgctattg ataatggtca agttaatctt 107460
atcaaaatgc acattgactc ataatgtgca tgtcctgaga atttgctgtg ttctcatgtt 107520
gtgttagatt tgatagcaaa ttaagtttgc acctagattc ctgtacaggc ttctcattct 107580
gttatcaaca tgacgcaaga gttgagctct acatctgatg ggtggaaact atatttacat 107640
ttcatacaag ctcatttttg caactgtaga tggttaacct gtaaggacca agacaatgac 107700
atttcttgtt ccctgactct ctagtgcata cacagaatgg catatttcat ggaaacgtta 107760
tttctccact gaccaatggg tagccaactg tgcacgcttc caggcactcc cctgatgctc 107820
agaaatgcca tttgtatcct ggcacaaaca ttttttgtta cattctgaga gtagcatagc 107880
agaatatcag cactagcagg gaccccagta actgattgag cgtcccaaac ataataaatt 107940
tcttcatgca aagaatgtaa atgaaggaat atgaatggag gcagagaata aaaaggcatt 108000
```

-continued

```
tgatttcaaa atcacacgcc ttactaaaga agaatccgtc ttcatgagct ataaggctga 108060
atggggccaa agctcctgat agtctggtta accatgaata atactctgca ttattaaaat 108120
caaggaagcc cggtctattt ctaatctaat cacatttagc atttgggaat cataagtaac 108180
cttgttttaa cttcagatta actagttacc aagttcccat tgacagaatt aaaatacttt 108240
aatgaaaata catttccttc agaggacctg cttgatgggg ttcaaacatt tgtcaaagta 108300
agacactgtt aaactgaaga tttaattgat cacattacac ataaaatatc aattttcaac 108360
cagcactcaa agttaacctc tgggccattc cagactcaga ggcggtttgg ttgagcaact 108420
ctgctgaatg tctttcttca tcatcataaa atagaatcct tttcctattc tttttctcct 108480
tctctctttc tctctctctc actctctctc tctctctctt gctctctctc tctcgctctc 108540
tctctttctc tccctccttc cnnnnnnnnn nnnnnnnnnn nnnnnnnnnn nnnnnnnnnn 108600
nnnnnnnnnn nnnnnnnnnn nnnnnnnnnn nnnnnnnnnn nnnnnnnnnn nnnnnnnnnn 108660
nnnnnnnnnn nnnnnnnnnn nnnnnnnnnn nnnnnnnnnn nnnnnnnnnn nnnnnnnnnn 108720
nnnnnnnnnn nnnnnnnnnn nnnnnnnnnn nnnnnnnnnn nnnnnnnnnn nnnnnnnnnn 108780
nnnnnnnnnn nnnnnnnnnn nnnnnnnnnn nnnnnnnnnn nnnnnnnnnn nnnnnnnnnn 108840
nnnnnnnnnn nnnnnnnnnn nnnnnnnnnn nntattcatt gagtcccttg ctcagggccc 108900
catccatctc ttcacataac tttgatcagt ctctttctcc tctctatcta caaattctac 108960
cctgttgccc cggatgtagc taaacaatgc ccatggtttt catttagaat acatggttga 109020
caaaagaaga cttctggcaa gaatatttct tcaaatgtgc taatgtggaa aggcttagta 109080
ataaggaaaa ttcaacttct gccacactgg ggatcatacc tctgagcttt ttgacatcag 109140
caagaatatt gcattcactt ctcatctaaa aggccatttc atcttgttta aataaaaata 109200
aataacaatt gagggccggg cgcggtggct cacgcctgta atcccagcac tttgggaggc 109260
cgaggcgggc ggatcacgag gtcaggagat cgagaccatc ccggctaaaa cggtgaaacc 109320
ccgtctctac taaaaataca aaaaattagc cgggcgtagt ggcgggcgcc tgtagtccca 109380
gctactcggg aggctgaggc aggagaatgg cgtgaacccg ggaggcggag cttgcagtga 109440
gccgagatcc cgccactgca ctccagcctg ggcgacagag cgagactccg tcttaaaaaa 109500
aaaaaaaaaa aaaaaaaaaa ccaattgagt atctctcaag tgctaggcac tgttttaggc 109560
actgggaata gtgtgatgag aaaggaagaa acattgcctc caaagagcta tccttcaaat 109620
ttaatgcttc ttttaaactg atttgtccta cacatatgag aagatatgtt gagaaggtaa 109680
tacatatcat ttactattaa ttgttttcct gatttaaaaa agtattacat ggccaggcgc 109740
ggtggctcat gcctgtaatc ccagcacttt gggaggtcga ggcgggtaga tcccctgagg 109800
tcaggagttc gagaccagcc tggccaacat ggcaaaatcc cgtctctact aaaagtacaa 109860
aaattagcca ggcatagtgg cagacacctg taatcccagc tactcaggag gctgaggcag 109920
gagaatcgct tgaacccagg aggcagaggt tgcaatgagc cgagtttgca ccattgcact 109980
ccagcctggg caacaatcgt gaaatcccat ctcaaaaaaa aaaaaaagga agtattctat 110040
tactcactta tggtatattt ctcttataaa attttagaat cagctgtata ggaccaacca 110100
tgggttagga tattttaaat ttatattgag caccacggaa acatcaatga tttggtaaaa 110160
gaatacagaa ggatgtgaca gaatgcagaa ggatgtgaaa gaatgcagaa ggatgtgaaa 110220
gaacaaaata aagaaaacta ataggaaata acaaaaatta aggcaccttt aaaagtatta 110280
aaatagatgc tttggataag cgatagaata ttgtagaagt agatgtaatt tatgtgtcat 110340
tagtgacttg atgaaatata taaactaaaa actcacactc agtatcatac aaaacttgga 110400
```

-continued aatattaata ttgtaccaga gaaatagatt cttcacaaat ttaatctaag tagcaagtac 110460
atgctatggg atacaaatac atatttttac accaattgac aaatttgaga ttcttttatt 110520
tttaacttaa catcactggt taagtagaag aaaagtttct cagtttgtcc cataccactg 110580
gtaatgctgg ttgaagctgc tcagctatag gttatcatct gtggctctct attaggacta 110640
tattttaatt ccctatagat ttcaactaat tgaccttgag ggaaagctga gtctctgtga 110700
caatatggtc ttcaatcacc actgccaaca taaataaatg cttcctttct agatccatca 110760
agagtaatct gagtggaatt taagtttttg ataggcttta aagaaatgag tccagacgtg 110820
aaataagaca cttttcaacc aaaaggatat agaatttaag acagttaaga ttcgtgtaat 110880
aaaaagtgtt tagccctttc tattggaaat tagtcagtta tcttattgaa atctggacag 110940
ttcccaaatt gatttatcca gtaatgaact gattatagtc tgacagtaac cttcactatc 111000
ataaatgaat atcctaccag tctaaaaatg ctttccattt aacagttttt ttttaagttt 111060
ttaaaatgtt aataaaaagt tttctatttg agtatgtttg agtatctcct tggatcactt 111120
cattcgaaac tagcactcct gaaatagcat tgttgatttt catgcacatc aatttctgtg 111180
agtttctagt gcttatttaa gcaaacagtt tttcctatta ggaatttaat tatacctctc 111240
agtgataagt tagtgcattt tccttatagt atgtcccatt ttcttttcta attctctcta 111300
taaatcagtc aaattaattt ttttgtatat aaacattaaa gcttaaaacc tcaaagaaaa 111360
atacaattta gaatgtagcc aacacctaag ggagaaatac acctatacaa catgaggcta 111420
agaacgaaag caatgataag tatactacag acaacaatga ggaaggaaat atctaacttt 111480
tatttgaaat agtcaggtaa tgtacctcaa aatgtcttct caatttgagc attcctaata 111540
ggtatttgaa gatttcaact cacaaatgat tgtgacataa gtacagacta gaaaattaca 111600
taaaaactgg actactagaa gctttcttat cttatataaa cataaatgtg aagaacagat 111660
tctaaaaagt gattggattt agataaaaaa gagtgataca aaagaaaata aagccaaatc 111720
agattccacc tctcttttc ttaaagtgtg tgcctatttg tttatcactt gagtaggcaa 111780
gagcaatttt attgttcatt tatctaactt cctaacaaag tacacctgtt aatttataac 111840
gttaggttat ctgctatggc ttttgcttag actcacatgc tttttgttga taaatctatt 111900
gattatacgt atttaaagct ttgagttagg acctcttgag aattctcagt ttcttaataa 111960
tttagtgtga aaatgtattc aattcagata ttccctcaca ataaagccag aatattcata 112020
ttttgctttc tgtgtatctt aatctgaatt catccacaat tttatatttg atatgtttta 112080
tttaatgttt actgtgaata atgttatgag ggacatctag taagccaagt gttaatcctg 112140
ccccagccct gaagtatata tgagcccaaa cacttgtatc cttaatgcag ggacttaaat 112200
agccataata caacatagaa gatgatttgt ccttggaaat ttgattttac aggcaaagga 112260
aattattttc tttttagtag aacagagtaa gatcgatagg gttgttaaca tttgaatcag 112320
gtattaaaga ataagtaaaa tttccgttgt acgaagaatg cctggaatgg tataaaattg 112380
agagggaggg atatatagag aatatctgga gtgcaaacag gatgcatgaa gaggagttac 112440
aaggaataat gtcagaaatg tgggcatggt tagaaatgtt ttacatgatt atatgaaaac 112500
tgaattatta tggtcattgt attagagatt tgtttgggat ctcgaattga gagctagaaa 112560
tccagacttg gatttgaaag ctagatattc gtgactacta tattttagca caatatagtc 112620
tatccatctt tgagtaaaat taagagaata ttcttttgga aataatggaa aaaatccctt 112680
ccttatatca gtatcaattg tagaacagta tggataggag cagcttgaga tgaacaaact 112740

-continued aaattagcaa tagtaattat catactattg atagtaacca atacttatgt attgcttact 112800
aaaggcagag acctttaaat atatgaactt aatttaatac atttcccaaa ctaggaaact 112860
gaggcacaga aaaattaagt attgcacatg ataatataac tagtaattgt tcaagcaggt 112920
atttgaaacc aataaaggca tcatattttc taataaggca ataattcaca aatatccacc 112980
caaacccatt atagccagtt atggtttaaa atatctttag gcggacatca tgaaatgcac 113040
atctttatta tccccttga ggggtgaggg agctggggta tttatccacc aactctggtt 113100
agtcattggt tgatggatgt ttcttggaat atttaccctc cgatgcttct agcctggatg 113160
caggagacac tcgaggagag tggcaggtcc ttgtagtagg aaactatctc cttgcatgcg 113220
aatgttgagt gcccaggcga tgtgggttag gcaccaatga catctgcaca aacttttaaa 113280
aatctgaatt tcacagcact taataaattt acgatgatgt atttctgcga aaaaaaaaat 113340
ctttagggag agattttaaa tgcaaaatga attaagaata gtgaaacagc aacttttggt 113400
agagtttttc actgaaaaga catgaactta aaacaaaaaa atgtatattt attcaattaa 113460
tcataacttc tgaaatgaag aatagagatg attaaagaag agcaataata tgaataatat 113520
tttgctttag ctatttcttg ctcacttttc tttaatatga ttattcacat ttaatgtctc 113580
ttagggattt cacaaatgta tactgatgct tcaaatggtt tattgacatt ttcccagaaa 113640
ccaacatcta ctttagattc tagttatctc agtaaaaata cttttgcagt accggctcaa 113700
atgatcctct aggaaaaagg aatctctctg cgatgggtgg cagtctcact gtccttatat 113760
aggtggacta ctagcctgtc actaaatcat atatattgtg cttaaatttt gccaatcaca 113820
atggaataat atttgctgtt attataaaag ttatttccac aaagttcaag agtttctatg 113880
tccatgtggt agcagggaaa tagaccttgg taatcaaagc atctcagtca tttatatctt 113940
aagttcagtt gatcagaatt tacccaacac aaccttctat tctttcctat ttctgaagaa 114000
caaggtatca taggggcact gggcaacaag ttatcttaag ggagctaggt agtatgtgtg 114060
gatgtagcct gtagtttatc tttctttctt gctggtcttc gctgaggggt aattattttt 114120
aacaaagatt gattgtggct tcagtcccca ctgcaactgt tactatgtca gagatatttc 114180
cagggcctcc aatattcaga cattctattt tcccttcccc aaatcaaaga ttcttctcat 114240
ttggtagccc tttcagccat ctccatatcc atctagaata aggaattctt tcttgctttc 114300
tttaaatcac tctagggtat tgtggggcac tcttaagctt atccaccaag actctttgtt 114360
agtcactgct actttgtcac ttagatgccc tgtttggcaa tggaatagtc tatcacttta 114420
tgtttaccct gagaagctgg aagatacaac atctctttct gcttgggggg cacccatcat 114480
taactgagaa ttctaacatt ctactttgta atacctggtc cagcatcccc atatttttca 114540
acaattcctg tattgtaatg aaatatactt ccttttaaat cctgttttct tcattgaata 114600
cacctctttt tgaccatttt catatttatt atgctctgtt tttcaaacca tttttttttct 114660
tttattcatt ctttgcttca aaaaacatat cttcttacaa atattcttca attaaagaat 114720
atagtaaaat ccctaatatt attctagatt taaaactttg aaaaagtcat atgttcctta 114780
gttcatttca ttatattttg tgccttttgt gttttttgca gtgctaattt gttgtgcatg 114840
acgtaagtgt tattaatgat acgcccctct ctaagtttgt gtatgttgtg tagcctattt 114900
agctgttaaa attatttttg tttacagagt ataagtaatt tggccaatga tctgtcacaa 114960
aagataggtc taaaataatg gaaatagtta taatttgttg ttgctgtgta tttatccaaa 115020
ctcactcatg aaacaatact taaccaatgt gatgtcatgt ttcatggatt cattctgtct 115080
ggttcaacac tttctatata tagaggaaat atttttaaaa tccacattag ctcttttaga 115140

-continued ccactaaata ccatgcaata tattaaaaag tgatctattt ttaatgtagt atcctaaatg 115200
cctaacattt ttaagcattt ataatgacat ttataataac aacaacatct tttcagctcg 115260
agaaagaatg taaattattt gccatgtttg agtccaaata atgtaatttc aaaaaaataa 115320
ataaaattta aaataatgat catatattag ttaaaggcat agcacatttt acattattga 115380
tttattataa ttttctgact ttaatctaca cttctttcag aattagctgt ccactctgac 115440
tcacaatgca tttaacacaa tctctattgc aggttactta gttatagaaa atccatcaag 115500
taagtttgtt aaatattttc tttcttcttt ttgaatatca aagttagatg cactgactca 115560
gtagaacctt aatgtgtgat tcactttttg tatgtttgtt ggaaaaacct ccaagctgga 115620
tataaatcat aaaagcatga ctaattgcat ggtaactgga gaaatgcttt ctctctctct 115680
ggggtgaagc ctgcatgtct gtattttagc ttgggaagta atacggggat atttaaactc 115740
cttggggttt gaaaaccatg tcattatgag aatgaggtca ctgcaatatt tttatatcttc 115800 taaaaccttg taatgtataa aatgttttct gtctgacaaa gaggtattat gtgctttagg 115860
agtcaatgat aacttcatgc ccttacattt acttgaaaaa ttttcttcat taaaatgcta 115920
aatcctttat ttaatgtcac taaaaaattg aaggaatttt gtgccatgaa tacaaagaaa 115980
gtgagcttaa agaagaaaag ttaattttat aagtataaca gagtgacttt aaaaagctgt 116040
gttgtttgtg attttgggga tgtccattgt tctttaactt gttaaaagtg aagccagtgc 116100
caatgctaac gcgaacaaat acaatctaac atgaccctat tttatacctt tctttacttg 116160
gaggccaata agcaagaaat ccttcctgca acatgttgaa gagctttgca caaacaacaa 116220
cctaaagttt caagaagaat tttcggtatg ttactagcag ttgtcacaac attgcaagac 116280
ctccagtcgt ttcatgtgtc acatttcatg tccattttaa gcaagcaagg ccatgaagga 116340
ctctggcctt gataatcaat acccaattac caggttgatt gttttgatag taatgttaca 116400
ctgggccgcc tctggtgcaa cctgatcaga attattcacc tactgtgtca ggaaaaggtg 116460
gtcttcttca gacctcccct gtattggcag catgaccttg tctattctct gctctttcat 116520
ccagatgtag gtgcaaatgt agaatgccat attcattagt ttgttttgta ttcaaggttt 116580
aggtcatact ataagtgtag ttttatattt aagtaattat tttacatttg gacactaaat 116640
tatttcattt tacgtttacc tacttggttt acattagtga tatagatgaa tgtgagatca 116700
aaacttgaag cttccagaaa ctataagaaa attatttcta gaactgtcta aaaataaaaa 116760
aaaagataag taatgtccac gttttacagg gggccttttt aaagttacta tggaataaat 116820
gctgtatcat ataatgaaaa tgtataaaat taagaatttg tcactttaaa tctacttaaa 116880
agttgggaat agtttttttt ttaacatttt gtatatctat aaaattgaaa ttatttaaaa 116940
acataaggta gatatcaaat cttcaagcta ctttaagagt tataagcatc ttttctaact 117000
tagatgatta ttttgttatt aagaaagaca gatttctaca tgtcaccaaa aacattattt 117060
ctattttatt tttttccatg aaatttccag tgtgtgaact cctgaaacaa agaataaaac 117120
aattgggtta aataattcag aattataata tttcagtctc ttagggaata ataacaaaaa 117180
tgagagaaga ttaatggtat ttcctgcagc cttttggtta tgcttcttaa gaaatattgg 117240
tctggactta acaaaatcaa tagtgccata aaattcttcc tagcatttag acagcaagaa 117300
ttctcaattt ttcaggagca aaagtgtaat ttccctagaa taagagtgaa tgtaattaca 117360
ttatgcatga ccaagtagat aaaaagtttt attagcaata acattttcac atatatgaga 117420
aagtttctag tttaagtttt ttgaagacca tagtttgaag aactttttaa aaatttcatt 117480

-continued ttgtctaatg ctttgttaag aatttctaaa gcaaattatt aaattatgtt ttaataaata 117540
catttttggt gcatatattt gataaacctt ttaactcagg acatattcac tcatatctta 117600
aatatttata agttcctact atgtgatagg cattgtattt ggcacataca atcagcactt 117660
accagctaag tgactttggg caaatttctt aaactctctt tgcctcaata tcttcatttg 117720
taaaattata atatctactt tattaaatta tgaatataaa atgattgaat ataagcaata 117780
ctaagaacag tagctggcac aagtattagc tattacgatg ataaattcta ccataaagaa 117840
gctcatatta tggtaagaac tgcagatgtg taaaaattgc aaatttactg tatcttgatg 117900
gagatatgca tgaagattga ggatcaaatc tgtttgtata tcaaccagaa aagagtttat 117960
aaaaaaggtg tctttcagga tgaactttag gatgagcaga agtctaatga gaaggtaaag 118020
gaaaaaaggt gttccagaga caggaaaagg ataggaatgc aaaaacggtc taactcatct 118080
gtggtcccac tgaaaagaga gaaagcaata ggagaaagag ctaaataggg agaattgtgg 118140
ccttgtgcac cctgataagg ataacactgc ccagtgtaac attaccatct aaacaatcaa 118200
cctagtgttt gagcattgct taccaaagcc agagctgctt aagtctagaa atggaaactt 118260
ttatgtgaaa taattataaa atataagtgc tctttcagtc tatttaaact cacctttttt 118320
ctcccttctt tatgtatttc caaaactttg acacaaggaa gctgttctag gactccttat 118380
tgggttaaaa aaattttgta agcctttggt gccaacacat cagaattcag atcttacacc 118440
attcctgtcc cttaatacat acccatatgt aaacaattgt ccagatttta attttgagaa 118500
aaaaaaataa gaaagggaaa cttatccaat taaaagaaat aatttatatt gatgttgaaa 118560
aattgttaaa acacatattt ttagtgcttt ttatggaatt tggcaagttg agatttctaa 118620
aatggaaaac tataaatttc acacatgtaa attttcagct caacaaaata atgaacatat 118680
tttcttatgc cagacttttt aatgatgctt gctttgccaa gagcaaggta gatagataat 118740
atcataaatt ttcatcaaat gtcaataata gatcttcttg acccttcatc tatatctgat 118800
aattcttaat tgcacctttg cattccatta ttgatttagc aatgcttatt aagagcagga 118860
attgacctct ggcatcttct caaactgacc aatgttgtac caattaatag gcatgaaatc 118920
acactgcctg aggagagaaa acaaaaaata aatcattgaa atccctttc ctactaagta 118980 gacattaaaa tattaaacaa tagtgtgtac ctgatgaaac cattagtaac atatgtaaaa 119040
tggtcactaa catggttgcc acatcttaag gcttcccaaa gtgcaaagaa attatctccg 119100
aaagagcaaa acccagctga ccaactttat tcaggatatt tttggtgaaa gcctaggtaa 119160
actcattact gttaacttga ccttgtttcc acagttatga taggtgtttt taatttaaaa 119220
attaaaaaaa aagtttagga caaataactg tcttttaata agtgaaattt cttgtttacc 119280
tctgataaat gtaaactttg taatgacttt attttacagg aattaccaaa atttcttcag 119340
gatctttctt caactgatgc tgatctgcct tggaatagag caaaaaaccg cttcccaaac 119400
ataaaaccat gtatgtgcat ttgttggttt tggtttagct aggaaatatt tttaaatgcc 119460
taccatctta actttttgt ttccttaata tattttattt tatattgttt gaattataat 119520
aatgtatttt attggcagtg actaccaaat tatatatctt ttgctttgtt catatttaac 119580
taaagttagt atacgtggtt ttcagtttgt tcacacaagt tcacttatgc aggtgcaaga 119640
aactgtagac ctaatagttt cttagctttg taattaaacc caagtaatga acctgtttaa 119700
catcttccta cagacctagc atcaaatgca aagggaatat tctcacttag ctttgtgcat 119760
tagtttccct tcacagcata gcagtgtttt cctatggaac ataaaaaaaa tgcattgtaa 119820
aatattcatt gaagaccaga gtaaatgcgc acttacatga attcatttta catatgaggc 119880

-continued

```
agaatgagct tcaccatagt acatacagct tcatttttca atcaataaga aaataaacag 119940
tgttattgct taaagaatta acagtgatgt gaaaggaaaa taggacattt ctctgttact 120000
aataactata tgtttgctat tatatttttg aacagatatc cctattttca atattctgat 120060
tcaatacatt ttacactatg aaattaaaaa gtgacattgt gatgtcctga aacgtttcaa 120120
agtctagagt tttgaaatgt tcccaatttt aaagataata tacatctgtg tgtgtatata 120180
tatatttttg tctatgcttt ttcaaatgta tattgggga atagctacac ttcttaaaaa 120240
ttgaattctt ctttctagaa agacgtagac ctagagaagg atgtgatcat agaatgtcga 120300
attgtaaagg acatgcatag gaagaaacag accaaattct gatattctag aactagggaa 120360
taacttatga agttcacgaa ggaaacaaat gtaaggaaac atgatatagg aagtagtaat 120420
ctactagaac ctgttaattt ctaagaagta gaataggatg aaaatacaaa tagctttaac 120480
cacctaaatc ctttctgcaa caaaacaaat cataagtaaa tgattttaag agcaagataa 120540
caagactcag tcagaggaaa taaacattca taatttcttt ttctttcttt cttttttct 120600
ttctttcttt tttttcttc tttcttttct ttctttctct ctttcttatc tctcttcctt 120660
tcttttcttt tctcttttct tttctttctt tttggacttt tgatcttgtt gtccaggctg 120720
gagtgcggta gtgcaacctt ggctcactgc aacttctgcc tcctgggttc aagcaatctc 120780
ctgcctcagc ctcccaagta gctgggatta caggcatgtg ccgccatgcc cagctaattt 120840
tgtattttaa gtggagatgg tttttcacca tgtttgtcag gctggttaaa tttctaagac 120900
caggacattt ttcaacgcat ccttttattc tttcttttag agagttaacc taggttggat 120960
gcaatgtaag tataaaagtt atggacattc ccatgtcttt atatttatct gcacctaaat 121020
ttcatccaga ctgtttgctt catgcttatt tggtgatatt ctgtgaaaat aaatactgta 121080
atctgattaa gggacagtaa ctgtggaata attagtattt tttcaattgt atagaattaa 121140
tggcctggcg cggtggctca cgcctgtaat cccagcacgt tgggaggctg aggcgggcag 121200
atcacttgag gtcagaagtt caagactagc ctggcaaatg tggtgaaacc ccatctgtac 121260
taaaaatcca aaaaaaaaaa aaaaaattag ccgggcgtga tggcaggtgc ctgtaatccc 121320
agctactcga gaggctgagg caggagactt gcttgaacct gggaggcaga ggttgcagtg 121380
agcccgagat cgcaccattg cattccatcc tgggtgacag agcgagactc tatctcaaaa 121440
aataataata ataattaatt tataatatat cagtatatat aaagtaagta attcaaatat 121500
gtctaactta cttccaaggg agtgtctaat ttgaaatatg taaaatttga tagatcagaa 121560
agttttttg ctgtgtgact tttnnnnnnn nnnnnnnnnn nnnnnnnnnn nnnnnnnnnn 121620
nnnnnnnnnn nnnnnnnnnn nnnnnnnnnn nnnnnnnnnn nnnnnnnnnn nnnnnnnnnn 121680
nnnnnnnnnn nnnnnnnnnn nnnnnnnnnn nnnnnnnnnn nnnnnnnnnn nnnnnnnnnn 121740
nnnnnnnnnn nnnnnnnnnn nnnnnnnnnn nnnnnnnnnn nnnnnnnnnn nnnnnnnnnn 121800
nnnnnnnnnn nnnnnnnnnn nnnnnnnnnn nnnnnnnnnn nnnnnnnnnn nnnnnnnnnn 121860
nnnnnnnnnn nnnnnnnnnn nnnnnnnnnn nnnnnnnnnn nnnnnnnnnn nnnnnnnnnn 121920
nnnnnnnnnn nnnnnnnnnn nnnnnnnnnn nnnnnnnnnn nnnnnnnnnn nnnnnnnnnn 121980
nnnnnnnnnn nnnnnnnnnn nnnnnnnnnn nnnnnnnnnn nnnnnnnnnn nnnnnnnnnn 122040
nnnnnnnnnn nnnnnnnnnn nnnnnnnnnn nnnnnnnnnn nnnnnnnnnn nnnnnnnnnn 122100
nnnnnnnnnn nnnnnnnnnn nnnnnnnnnn nnnnnnnnnn nnnnnnnnnn nnnnnnnnnn 122160
nnnnnnnnnn nnnnnnnnnn nnnnnnnnnn nnnnnnnnnn nnnnnnnnnn nnnnnnnnnn 122220
```

-continued

```
nnnnnnnnnn nnnnnnnnnn nnnnnnnnnn nnnnnnnnnn nnnnnnnnnn nnnnnnnnnn 122280
nnnncagaga ttgatttcat tttaatagaa tttgaatttt agctaataga atttgaattt 122340
tagcttgagc cagctaaatg aagtccattg tttctctccc cctgagtaat gtaagaagca 122400
gaatgccaaa tatcacagca tgttttagaa gacattagct taaaacactt taagatgcta 122460
gaattagcag caaatacttg cagaagagat ttccaaatct ccgtttgaca gacgacctat 122520
gaccttcaga aatattccaa caccacaaag aaaagtttag cttgtagttg actcagatag 122580
ttataaggag gtgtatctag tgaatagaaa cataatgatt ctcttcctta gtaacaggac 122640
tagttacaat gtcattaaac tagatcatat aaaattctat atttgggaca taaatcattt 122700
gcagaaatgt gtttaatcat tcccatttct aaacataacc acattgggca agtaattgtg 122760
attactaaca atacaactaa ttcattttaa catattatgt gcttaagttt taagaatgta 122820
agaacatgta ttgagtgcct attataagct ttcatgtaaa ttttcttcaa gaggattata 122880
caaaatctgt gttataatga catcttgtag ctgaggtaac caaggagcag agaagcttag 122940
caatttaccc aagcccatat gtatggtagg cagatcatct agaattcaga cccaatcctg 123000
tttacccatt tttcctcctt gaaaacaaac aacccatcaa aacaattaag tagtggatat 123060
ttcatgttta gttaaaaatc attactggat gtttcaatta taatatcaac ttggtaaaat 123120
ttctcaggaa aaatagtttc tgacattttt ctctgaagaa aagtaatgag tacagggtat 123180
ctagttttac tagctcttaa aatattctaa aaagtagtaa ttagaaattt gaaagaaaga 123240
ataggcagat gaattaatgg aaaagaatga atggtctaga aatagaccta actacctaga 123300
aaacaaagtg gtgttccaaa tcagggacaa aagatggaaa tgttaaaaaa ttgatactat 123360
ttgttgttcc aacgacannn nnnnnnnnnn nnnnnnnnnn nnnnnnnnnn nnnnnnnnnn 123420
nnnnnnnnnn nnnnnnnnnn nnnnnnnnnn nnnnnnnnnn nnnnnnnnnn nnnnnnnnnn 123480
nnnnnnnnnn nnnnnnnnnn nnnnnnnnnn nnnnnnnnnn nnnnnnnnnn nnnnnnnnnn 123540
nnnnnnnnnn nnnnnnnnnn nnnnnnnnnn nnnnnnnnnn nnnnnnnnnn nnnnnnnnnn 123600
nnnnnnnnnn nnnnnnnnnn nnnnnnnnnn nnnnnnnnnn nnnnnnnnnn nnnnnnnnnn 123660
nnnnnnnnnn nnnnnnnnnn nnnnnnnnnn nnnnnnnnnn nnnnnnnnnn nnnnnnnnnn 123720
nnnnnnnnnc agtttcactt gtatttaagg aaatcaaaat aaatattatg agacatcaat 123780
ttgtatttgt acaaagaaca taaagtgttt aataatacct tgtgataatg aaagtaagag 123840
aaaacagaat ttttcaaaca ctttggttca gagtatgaat tgttagagaa caattgagaa 123900
atgtttttca aaatttggaa tgcatatata taaaatctaa aaattttact gctggtagta 123960
tattctacaa gtacactcct atatatatgc aatatgcaaa aatttcaatt atatctattc 124020
aacattttat aattacaaag tgaatcattt aaataataat aaaaggttaa ataactacat 124080
tattatatat tcaaacagtg aaatactgta tagcttttaa aaataattaa ctacatatct 124140
ttgtttatgc tgatacggaa agacataggt aaatgaaaaa aacgatttgc agaacagatt 124200
gtatatcact ccatttgtag ctaaagaaaa ttagaatata aagaatatgt atagaaaatt 124260
ctggaaatat atacaaggac atattaatag tcattgtctc tgggtggtag aaatatggga 124320
gaagaaataa ctttttaaaa tttaccgcca tctgtgaaat tggaatgtta tattatgaac 124380
tcctttgtat tacttttata gtaaaaaaag tagtaacaat ttaaaaagcc aattaacatt 124440
gattccttat attttcttct agataataat aacagagtaa agctgatagc tgacgctagt 124500
gttccaggtt cggattatat taatgccagc tatatttctg taagttacta ttttatatat 124560
tttataattg tataaaacat aattactgaa attgtattat ctttccaatt acttaaaaca 124620
```

-continued acaaatttat tacaactcct atggatctta atatgctagt tatttacagc cacattgtgt 124680
acccttattt tatagatgtg gatatggata tgcctaacag agatactaac ttatcaaaaa 124740
ttatttcacc agtgcgcggc agatgttcaa cttcaggcta cacatccctg atctttccac 124800
taattcatat gctttgttaa tgtattctcc atatgcaatg aagtttgcca atctctgtga 124860
attaaaaatt atcaaatgga cagttatgtc catataacat gaaaatttat tatgcagctc 124920
ttcccttcta gatctgcagt ccttcaagcg ggtaataatg ccatcaccat cataggtaca 124980
ttgaaacctt atatgcactc aagatctcca cttggtttgc aaattcatgg aatcttaaag 125040
aaggaagtgc cttgaatttg accattcacc ttgaaactct aaaaaattcc tgtcagcctc 125100
ttttggcatt gattcatcca cttcttccta agacgggatt ctatctctaa acaactctgc 125160
tttacagttg ttgggttttt ttttaaccaa gttatgtctc tttatattct tacccactga 125220
cttaaattct aatgcatagc aagcttaacc atcttcatta tggtgaatct acaaatacat 125280
gaagatttcc tctgctgccc acactctcca taggcttttt cttatccata ggtcttctca 125340
tccatgccct ctatttcctt cagttctatt aaggctcttg ttatatgacg ttccaccctt 125400
tctccaacgt caaacatact tgtgctgtgt ctcattccct ccaagccttt gtcatggagg 125460
aaaaaaacga attagttcta aatctgatat tggttgataa ctaatctaaa attacaatca 125520
tatattgggt cctgttgtca aaggagtgaa taatgggaga atttaagact ttaagacttt 125580
ttaaccagag aagtgaagga aagtttagag aagctaaggt attctttaaa tttcattcta 125640
ttttaatgct agaactttaa atctgtattt aaagaattac atgaatttac tattatggta 125700
acattttatt catttatcaa atgattgatt ccctctaaaa tgtaattcaa aatgtaaaca 125760
ttttggtgaa atcttatgct tacaatttcc attaaaatct aaactctaca gcatgttaaa 125820
gttttacttg gatttacaaa atgatgcata tatgcattta gatatttaca tttcatcact 125880
actctgataa tcaaatgcca tcaagcagga caaggacaac tggttgtatc agtgacctat 125940
tgatttgtat catttttttat tcaccaataa gtagatacaa atcaacagct catattgtct 126000
aatgttccat aaggcatgac agtacaggat atgaatataa ttaagaagaa aaacagacaa 126060
ttttagtagg tgtagctgaa ccacacagat tatgtaagca aagtaatttt cgcaaacccc 126120
cagtgtcccc ttgaaatatg gtaggttgtc agcatacaac tatgagcaaa tgataacgtg 126180
gtatgagcaa taaactagga agcctgaaga tatatattct gctgtaatca agtgatgttg 126240
taatataata aatcttacaa caacgtcact atgacccaat gtaatgatat gcataatcat 126300
tgctgagctg catggtaagc aggctcagat ggaaggcact ttacaagaag gcggatttct 126360
atattggggc tggcagtgta ctgtagcact cagagaaatc tcctttgctc aggatgtcaa 126420
gaacagatgg gaacagatgt agcaatgata ctgcagtggc cctcactttc cacctacgta 126480
ttcctacaat cttcacctta gaaagaatgt ctggtatatc aatttccgcc tacccccaaa 126540
ttttattcga aagcacttcc aattgaaagt ttatgaacac ttgtcccagg agcaaaagac 126600
agaggtcatc tatgaatgga ttccgggttt caatttcttt ggaagctatg gcaaaggaa 126660 gagaactata gagggaggta ggaaagaaag caaaataact agtgttcaga tagaaacatg 126720
aaaaactgaa gtctggggaa gagacagagg aggaccagca tatggtctga gggatgtatg 126780
ttaagactgg gaccctccag cccagggttt ataactaggt taacatgcca atgtgtgttt 126840
tcctctgccg ttggccattc tcgagaatgg tgctcccaga gttaggactt ggaaaggctg 126900
gaagattttg atgaaggata gactgtgaaa gaggtaggaa gaagtgatat tgcagcccca 126960

-continued taatctgcca ccaactgtac aaatgagttt agaaaggttt tcaagagagt caaaaatgaa 127020
aatactgtga ttttaggtat aagaggaagg cttataatta attttgagga aggctcgtca 127080
aaattatctc tcctgtcaat ttcagatgcc tgcaattact ttaatttgat gacagctttt 127140
aacacaacta gagattaaag gctatcatgc aaatggttgc agtaacatta gaaacatcag 127200
aatttgttcc tatgttgaca gagcattata atannnnnnn nnnnnnnnnn nnnnnnnnnn 127260
nnnnnnnnnn nnnnnnnnnn nnnaatttat taatattgat cgtcctctct tctttgatcc 127320
ctccaaactt tgtatattta gcatagcctt tgtcagattc taactcacag tgatctcatt 127380
tattaactgc cttctctgtg tgaggaagag cataaggtac tgggcactac atgaggataa 127440
gcatgtatat ttcctcttat cttagtacca cgtaaggatg gagattcagt cttcatgatc 127500
ttactatcaa tccttcaata tgaattgagg accoctaaaa cacatacata tgaaaacaca 127560
aacacacatg catgtttata tacatcattt acaaggattt gctagacagt ttgggggata 127620
ttaagatgaa gaatctctgc ttttaatgac atcataatca tacaaaagga aaaaatatat 127680
atatataaac acatatatgt gtgtatacat aaatatattt gtatatgtgt atatacagtt 127740
atattttata tgtctatatt ttatatatgt atatatataa tataaacata tatacatttt 127800
gtatgtatgt atctagatat gtatatgcat gtatataaat tctcccacta ttcactcctt 127860
tagcaatagg acccaatata tatattgtaa ttttggaata attatcaaac aatatagaat 127920
atggtgatat atttttatat gccgatatgt atacatttgt atataaacat atacatatat 127980
gtgtatatgt acacacatat atgtacacat acacacatat acttataggc atatacaaat 128040
atatcaccat caatgcccaa cacattttct ttagcataat aaagcaattg agggtgtttg 128100
caggagtaaa tataaactgc acattttaca ttttttttcc ctagagctta tatgggtaaa 128160
taaagaaaac ctgttcaagg acattgatag gcactaaaat gtcattattt cctgtataat 128220
atggataaac tttaacataa aaaaatctgc aatttttgga aacctttaca tttatagagc 128280
acttcaaaat tttcaaagca atttcacatt ccttatttta caaatagtat tcaaaatgac 128340
tctctgaggt gtgcaagaaa ataatgatta tctctaattt ataattagga aactgaagat 128400
tagcttattt aagtagcctg ctctacaggg tacactatta gaaaggacta aagtcaaaac 128460
cagtgttcta gtctctaggc ctatacattg ttttcattat tcaaacttac tgccttcttc 128520
tatacaaatt taatgaaata ccttatcttc actaaactta atgctagaat tattgagaaa 128580
gtatgcagat aattaggttt gcaccattca acattcacaa tagttaaatc tcaaaggatg 128640
aaaagaagga ttggtctgac cttctccatc tcatatgcta ttctaaaact aattgtatct 128700
gcatatacaa attcactgga tataactgaa taactgctgt atgagattag aataaagcat 128760
aaaaatattg atttggaagc aatatttaaa ttactttttt agcatgtagt tccacaatac 128820
ctgagatgta gtaggcattt aataattgag ttcataaaaa ggaggattat atttagatgg 128880
gtaaatacat atgcttcaga gttcaaatgg acctgagttc aaattccttc tctgcatttt 128940
tgtagctgta tgacctgaaa ctttctgagt gaagtttcta cactgataaa gtaggaataa 129000
taatcaaccc tactttattc attgctgcta aatcatattt caattattca ctgaattaca 129060
cattggaagc atttaataaa tacatgttat ttttattgct gttgatgttt catggtagta 129120
gattctacat tttcctggct gataatccag aggaaaatct ctgagctaat ttaaggactg 129180
caatgaaaag tggcatccat gggtaaaggt cataatgaaa gttgacctgt ggaatgaaac 129240
ttacactttg ttccatgtat cacagagctt taaaaaccag taaactctat attccaatta 129300
aagggcaaaa gtccaggcaa gaagtttcct ctcagaaaaa ctcaaaagtt tgcacacaca 129360

-continued

```
tattcaaagg tagaagcaga aatagcaaac agaattgaca tactttcttc attttcataa 129420
gatacaatgg aaatatctcc aaaacacctt tgggcaaaca ttttacctgg tgctttacca 129480
ttttctgaaa taaattagcc attacaggaa gaaaacttaa atgtgtctta gcttctttac 129540
atgagaatca agggggggaaa tgtgaccata taaagatata tttaaataac agataataca 129600
tagatatatg tattaaaaag aaatataaaa taatatttca aatcctggaa aactgagatc 129660
atataatgtt agttttgtaa ataagttgta acaagattgt ataggaataa tcccaattat 129720
ttatatatgt gtatgtatat aaaatataca gtataatatt tagtatacaa tatgtgatat 129780
attgtctata ttactctgtg tggaacctac tcctccctta caggtactgg ctttctggcc 129840
ttgctcacca gtgggtctgc ataccctccc gtacgtactc agcatagaga agggtcaagt 129900
tgcctcaatc ctcagtgcca cctccacatc attctctatc cctctgccct aaaattgcca 129960
gcttgaattc atgctatcaa gcataggaca caccattgct ctttttggaa gttaattacc 130020
atcccctaag tcactttctc ttgtttctta aagatttcac tccgggatca ctgcttctct 130080
ctcatcactc ttctgtcata attattgatg atgtcaaaat tcatataaaa tattgaccca 130140
tagccctgct catcactttc tggacctctt ctcttgcagt gacttgcctt ccacatgacc 130200
tcatcacttt ctgccatgtt cacaacctag accttttcac caccaagaat tgtagcctct 130260
ccataatctt gattgcagat gtctcactat ctgtccaaat ccttctttcc agatcactgg 130320
actctgataa ttcttcaacc ctgctctgcc ctacagctct ttgattctat cgaattttcc 130380
atttctccta acccaatcaa gacttcattt tttctcttgc tcagcttgaa ctgcatgcct 130440
atttgtttcc tttcctctat tgtatatatc ctcaactctc aaatttatct cttatagtct 130500
cgacctttttg ataaatcccc aaactttgct aaataaaacc ctccatggat tcttctctgt 130560
gttactagaa gtgtattgga gaaaaattca tgatcacgcc aaaatatctc actttaaact 130620
catggccact aacctcaaaa acacagcctc ctaatctatt caatctccct ttcttctagg 130680
agattctttc tccttcttct ttcttctctg gcctctaaca ctatattcct catttcacc 130740
tacatctgat agccttgttt atatttcact gataaaacaa aagcaattaa aagagaacat 130800
tcacaaggtc ccctacttgt ctgcatctgt gtccatatac tcagtctttc tcctgtggct 130860
gcatatgaac tgtcctagtc cctgataaca gccaaccctc tcacttggac actacatgac 130920
ctctcccttt gcctctcaag aacatgggtt gaggaattct cccttctgca tcatcatttt 130980
ttctctttta gcagctaaac aaatctattg taatttctta catcataaaa atatcttgat 131040
attataggtt tctctctact tctttattgt tctttttatt tacattatag ccccttgaag 131100
aattgtcaac acttactatc ttcaattccc ttctcttatt tcttcagcac cctcaaataa 131160
gacttggata ctaagcaagc acaacactga atcagctatt ttcaaggtca tcaattaact 131220
actcagaaaa ttagccttaa gtctcagtct ccaatttatt tgacttttca gcagctctga 131280
ctctttcatc ttagtctcat aggttctatc tcatcttcta gacctgcaaa caaaataatt 131340
tagagctcag tacttgaatt tactatctct ttctaaactc tttttcttgg tgattgtaag 131400
agtcagggtt ctctagaggg acagaactaa caggatagat gtatatatga aggggcgttt 131460
attaaggagt gttgactcac acaatcacaa ggtgaagccc caaaataggc catctgcaag 131520
ctgaggagca aggaagccag tctaagtccc aaaatctcaa aagtagggaa gctgatagtg 131580
cagccttcag tctatgacca aagggccatg gcaaattact ggtgcaagtc ccagagtcca 131640
aaagctgaag tacgtggagt ccgatgttct agggcaggaa gcatccagca tttcccagtc 131700
```

-continued

```
cactgactca aatgttaatc tcctttggca ataccctcac agacacaccc agaaacaata 131760
ctttgtgttc ttcaatccaa tcaagatgac actcaatatt gaccatcgca gtgatgtcat 131820
ccaattttca tgactttaag taagagatat gagctgatta ctttcaaatt tatgtctcta 131880
gtttggactt cttactgaat tctaaagtca tatatctaat tgccttcgtg gcattcctac 131940
ctgaatatct aatagtgatt tcaaacataa tatgtccaat gtgagttttt tattttccct 132000
gcaaatctgt tcatactaaa acctcaaaaa cacaggcagt aaaagcaaaa atatacaaat 132060
gggattatat caaagtaaaa atcatatgca cacaaaggaa acaatcaaca gaatgaatag 132120
acaatctgca aaatgggaga aaatatttgc aaactattca tccaacaagg gattaatatc 132180
caaaatatac caggaactca actcaatagc agaaaaaaaa tccaatttaa aaatgggcaa 132240
atgagctgaa tgaacatctc tcaaaagaag acatacaaat ggccaacagg catatgaaag 132300
attgctcaac atcactaatc atcaaggaaa tacaaatcaa aaccacaatg aaacaccatc 132360
tctccccatt tagaatggtt attatcaaaa agacaaaaaa ataacaaatg ccagcaagaa 132420
tgcagagaaa gtggaattat tatacactat tatacactat ttagttttcc tcagaaaact 132480
aaaatacaac catcattatg acccagcaat accactactg ggtatatatc caaagggaag 132540
aaaatcagta tgtcaaaggc atatctatgc ttacgcagta agtgctgcag cactattcac 132600
aatagatgag ataaagaatc agcctaagta ttcatcaaca gatgaatgaa taaagaaaat 132660
atgctgtata tacgcaatgg aatactattt agccatgtaa aagaataaag tcctgtcatt 132720
tgtggcaata tggatgagct tggagaacat tatgataatt gaaataatcc aggaacagaa 132780
aaataaatac cacatgttct cacttatgca gaggctgaaa aagttgatct cgtgaaagta 132840
gagagtagaa tagtggttaa aagctgggaa ggggaagagg tgagagtaag agattggtta 132900
acgaatgcaa aattacagct agataggaga aataaatact ggtgtctata gctctgtagt 132960
gtgactataa caaaccacaa tttattgtat attttcaaat agctagaaga gcagaatttg 133020
atgttcccaa cataaagaaa ttataaatgt ttaaggagat ggatgtgctc attaccctga 133080
cttgagtatt acacattgca tacatgtatg aaaattttca cactgtattc cataaaaatg 133140
tgcaattatt atgtgtcaaa ataataagaa aagattatta aaaactgctc atctggagtc 133200
ttccccatct tcctttggag tcgttattga tttctctgtt tctctcatac ctcatatcaa 133260
atctattagc aaattcagtt ggttttgcct tcaaaatgta tccatatctg atcacttctc 133320
accatctcca ttgatatcac ccatgccacc aatatttctt ggctgaattg ttacaataac 133380
cctctaacta ttctccctcc tttcaccttt taaactccca taggttggtc tatggaagcc 133440
cacgtgaaac tgttaaacca cacactatgt ttgaaacctt tcagtgactt tctgtgtcat 133500
tcagagtaaa aagcaaagtc ttataattac tttttaggac ctaaagcacc acttatactc 133560
cctgcttttt ctagccatta tctgttactc ttccccctca tttactctac tccaggcacc 133620
tgctgttcct agaacattcc tgacaccctt ctcctttaag gtcgttggac ttgattttcc 133680
ttctacccac aattcttttc ccccgaatcc tgcaggcctc acttctttcc ttcttcaaaa 133740
ctgtcttcac attatcacca gtgatatgtg aagtttggag atgggctgga gaacactatg 133800
ataagtgaaa taagccagga acagaaaaat aaataccgca tattctcatg aagtatttat 133860
tttttctgaa taacctattt ctgaacagcc tattttctga aaagcctatt ttctgaaaac 133920
tttctctcat agcccttatc acttttataa attctatgta atttgcatac ataatataca 133980
ttaatagaca atgtctattt ctcctaatga taaaataaac gagggtagga atttcagtgt 134040
ctttggtcag tgatgaaccc ccagctccta aaatagtgcc tggaatgtaa tagtcactca 134100
```

-continued caaatattga ttcagtggag aatgtgcata tttaaaaaat ctgtaaagaa atcaaccaaa 134160
atgttaatgg tccttcactc tggatagtgg gattacaggt gaattctact ttctattatg 134220
tatttttcta aattttcaaa atattctaca ttaacatata ttatttttaa taagaaaaga 134280
tccctcacac tttaactaca tatttaggtc tttcggttga gactggaaag acagaaaagc 134340
tgcagtatac tgtgtattta agagaatcaa gattttctac aagcaaatgt tcctggcttg 134400
cactgtaatt tgggaaaatc acctaaagtg cctcctcatt gttccttaaa gtaaaataaa 134460
cttgctggat tacattttag agtccctgga aaatttaaat atatgttatt ttttgtatat 134520
tactattctc tgactactga gacaatttca atgtaaaaaa gtaaatgtta ccttttattc 134580
catattcctt aaagcatctt cctgtttgaa atagatgtca ttccattact actttttaac 134640
ttatacatta cctttcttta aaagaaatcc acagatactg ttcacaatta tataaactca 134700
agtgtcatgc ttttatgttc caggtaaata gaccaaattt cagagaaatt tgataaatat 134760
acacaaggat gtcataatag atttaagaca gatctcatgt cctatgagtt tactgtatta 134820
gcaaaatgaa acttcatatt accatgtttt tcttgggtca gaactccaga cagtaaatgc 134880
cactagacta atgactaatg ccacagttta agtagataag taatttctta gaggaagagt 134940
gtacatatat ctgcacaacc aataaataca tggcagaaac atcatggagt gggtttagag 135000
agctggttct gggctcaacc tgccttacca attttgagat cttggcaagt tacttcacct 135060
ttctaagctt caatatcttc atctataaaa tgagcataat attagtacta attcacaatg 135120
attttataag aatattgaat ataagatgct tagcaaactg ctacaaagac tcagacttaa 135180
gacctttatt aagttctgtt attattgtaa atattattat gtagtcctta atgttttatt 135240
caaaagttag acataaattt tgagaaccat ttgttgtgta gtatatcaga ttgtgaggat 135300
aaatttagac gttggaaatt ttgagtattt aagattatct agtatttacg gtattctaaa 135360
atattaggta attttacaac cagcatatgt ttcatgcatt gatcgaaaac taaaacactg 135420
tatctgtgaa cacagtgatg cagtgtttgt aattatatcc ttctagggtt atttatgtcc 135480
aaatgaattt attgctactc aaggtccact accaggaaca gttggagatt tttggagaat 135540
ggtgtgggaa accagagcaa aaacattagt aatgctaaca cagtgttttg aaaaaggacg 135600
ggtaagttat ttgaaaatgt tttacaaatg ttgttttacg attgtgttaa catatgtgtg 135660
aatatttcat ctaatactgt gagtcatcaa taacctggac atctataaag taattttaac 135720
ttagtcgtaa taactgtggt atacatatat atcaatataa caatgacgct tatgactgat 135780
gattttctct gaatgcagat cagatgccat cagtattggc cagaggacaa caagccagtt 135840
actgtctttg gagatatagt gattacaaag ctaatggagg atgttcaaat agattggact 135900
atcagggatc tgaaaattga aagggtaaaa aaaaaagggg gggacgagag aacatgatat 135960
aaaatatgat tgatctaaat gtctaaaata aaattaattt ctagaactat ccctttcaag 136020
gatacctgta tattcaacaa tgcttttgta ttgtcttctg aacagaattt tgaatcgata 136080
tccaacttta gtatcaatgt cactgtattt gttccagatc actctagtta aagtctgtat 136140
taaccaatta gcatcacatt cttaggttga caagagcaga aaaaggagag aaaatgatga 136200
gatcactagc tttattttat ctaatgaaga aactgtaata tctgacttga gacagcaatt 136260
tcccaagtca ctcatctcct gaatcctaat aatttgattt tctatttaat ctgcagccag 136320
atagaaaagg tagtatggga tctcacttta tgagatcttt atgggatcac tttatgggat 136380
ctcagtttat ataaatgcct atacacacag aagatgatat aaggatcttt atacttttca 136440

-continued cataacagat gctcaatacc tgtgtatgga ataatttgtg aatgtgttca tttaagtttt 136500
gggtcaaaag tgtttcaata cctattattc tgagtgctac aaaatggcat actatatttg 136560
aatattaatg tcctatatta acatttattt ccaagctttc ttatgttttc attcatattg 136620
aaaggcaatt ctctttattg taacaataaa aatctctctt ataggaaata atgaaaacat 136680
tttatttggt ttggtaaata gtcattttta aaagatcacc ttcaaaaact gggactattg 136740
ccttcaacct tcattgtgga acttaaataa ttttgtcatt cattaatccg tccctttgtc 136800
tagcatgggg attgcatgac tgttcgacag tgtaacttta ctgcctggcc agagcatggg 136860
gttccctgag aacagcgccc ctctaattca ctttgtgaag ttggttcgag caagcagggc 136920
acatgacacc acacctatga ttgttcactg caggtgagaa agtgatcaga aatggccttt 136980
gaacccattg gtctttttat tattaaaatt ccattggtta ttttttataa aatgttcatg 137040
taaatttctt ccagcttgcc gtcttcagag atttcacatt tagcatttct agacacattg 137100
gtatgattta tgttttctga catgatagat ctaaaccagt cttgactcga gtctttttca 137160
cagttgaagt ttggagatta gaggaaaatg tagtatgaat tctacttaaa tgagatactc 137220
agaataggta aataaataga aacagaaagt agagttgtgg ttattagtga ggagggagat 137280
gaaaaattat tatctaatgg gtacagacct tctatttggg atgatgaaaa gttctggaaa 137340
tatactgtgt tgatatttgc acaacattga gaatatactt aatgccactg aattgtacat 137400
gtaaaatggt caaaatggta gattctctgt tattcatctt tcaccacaat aaaaagattt 137460
ttttaaagta acaataactt ttaatatttt taacaggagt gtactataat taatgtggtt 137520
aaatactgta cataagaaaa gataaattca ttcagttttt aaacttttat tttaaaaaac 137580
tcaatatgta atttaaatga ttatacattt tccataaatt tctggatttt taaaattata 137640
agactaatac gtaaatgctt gctcattata aaatatatga acaatgctta tatttataaa 137700
acatgtagaa caaaaagtaa aagcctcatt tttaccttct caattttaaa tccctccata 137760
taggtataaa gcttaatata atagtatata ctaaaaacag tataacaatt tgcttctaca 137820
gtcaatgatt gattttatgc tggcatcact gatgattaaa acctttgatg gacagtagct 137880
gtcttcaatt tctctgtatc atgcaaatac actgccatgg gcactaaaag aaaagtactt 137940
tctccttttt agcctcaaaa agaatagagt ctcctccttt gtgatttaaa taagagataa 138000
gaagaaagtt gttcatatta ttgaccatnn nnnnnnnnnn nnnnnnnnnn nnnnnnnnnn 138060
nnnnnnnnnn nnnnnnnnnn nnnnnnnnnn nnnnnnnnnn nnnnnnnnnn nnnnnnnnnn 138120
nnnnnnnnnn nnnnnnnnnn nnnnnnnnnn nnnnnnnnnn nnnnnnnnnn nnnnnnnnnn 138180
nnnnnnnnnn nnnnnnnnnn nnnnnnnnnn nnnnnnnnnn nnnnnnnnnn nnnnnnnnnn 138240
nnnnnnnnnn nnnnnnnnnn nnnnnnnnnn nnnnnnnnnn nnnnnnnnnn nnnnnnnnnn 138300
nnnnnnnnnn nnnnnnnnnn nnnnnnnnnn nnnnnnnnnn nnnnnnnnnn nnnnnnnnnn 138360
nnnnnnnnnn nnnnnnnnnn nnnnnnnnnn nnnnnnnnnn nnnnnnnnnn nnnnnnnnnn 138420
nnnnnnnnnn nnnnnnnnnn nnnnnnnnnn nnnnnnnnnn nnnnnnnnnn nnnnnnnnnn 138480
nnnnnnnnnn nnnnnnnnnn nnnnnnnnnn nnnnnnnnnn nnnnnnnnnn nnnnnnnnnn 138540
nnnnnnnnnn nnnnnnnnnn nnnnnnnnnn nnnnnnnnnn nnnnnnnnnn nnnnnnnnnn 138600
nnnnnnnnnn nnnnnnnnnn nnnnnnnnnn nnnnnnnnnn nnnnnnnnnn nnnnnnnnnn 138660
nnnnnnnnnn nnnnnnnnnn nnnnnnnnnn nnnnnnnnnn nnnnnnnnnn nnnnnnnnnn 138720
nnnnnnnnnn nnnnnnnnnn nnnnnnnnnn nnnnnnnnnn nnnnnnnnnn nnnnnnnnnn 138780
nnnnnnnnnn nnnnnnnnnn nnnnnnnnnn nnnnnnnnca tatacctgtc tttgagtatt 138840

-continued gatgtaattt tttaaatgaa aatagttttt caattttatt atctatagga ggcaaaataa 138900
attctagaga aagaaagtga aaaggacaat tgcaacacta tttttcaaaa tgaaacaaag 138960
aaaatgctat ataagctaaa tattctacat ttgtaacatt tagcatttct gctggtaact 139020
gaatatttgg tcaatacaga gtctctggta ttaagaattt tcaatgattt taaaaaaatc 139080
tctatacttc aacaacacac cctaaaatat taagaaataa gaggttaagt tccactgatt 139140
aaagaaagac aaactcaaat atttgatagc atattaatga taatcatctt gccttgttta 139200
aacacaatct tggtaaccat aaaaaatcca aagacactcc aaagaaaatc tgcctccaaa 139260
taagagaaga aactattaga atttattgct atcatagctc attatcttta tccccatcaa 139320
aatgaacaac cctttgctga ataattttca tgtaatttac ccttcctgta gtgctggagt 139380
tggaagaact ggagttttta ttgctctgga ccatttaaca caacatataa atgaccatga 139440
ttttgtggat atatatggac tagtagctga actgagaagt gaaagaatgt gcatggtgca 139500
gaatctggta agatctctaa acctgcactg cattctaaag ttctagaatt tccacatggg 139560
agatccttag tggcagcaat ctggatggac atgagcttga agctgtggac accttctttt 139620
cctacattat aagccttttg gggaggattc gggagggcag ctgatagaga ttataggaga 139680
actaatgccc acatgccata gtcaccctgc agcattgtta ctgatggctc atcttaactt 139740
gttatactga taggcatgta ggcagtaaca taaaattgat ttatctttat cgtttagcaa 139800
ctttgggata tctggaaatg aactcaaatc aatatctttt gaatatcatt atcttttgaa 139860
aagttataaa tgggaaaaca gtttaaaata ttgactgtaa taaagttcta tgggttttac 139920
ttctccatat ttatccctat tgcataccag tactaataat gattattgta gcacgctatc 139980
aactattaac tgtgaggttt ttgtttgttg ttttggctta taggcaaaaa atatttacaa 140040
aatatataca attnnnnnnn nnnnnnnnnn nnnnnnnnnn nnnnnnnnnn nnnnnnnnnn 140100
nnnnnnnnnn nnnnnnnnnn nnnnnnnnnn nnnnnnnnnn nnnnnnnnnn nnnnnnnnnn 140160
nnnnnnnnnn nnnnnnnnnn nnnnnnnnnn nnnnnnnnnn nnnnnnnnnn nnnnnnnnnn 140220
nnnnnnnnnn nnnnnnnnnn nnnnnnnnnn nnnnnnnnnn nnnnnnnnnn nnnnnnnnnn 140280
nnnnnnnnnn nnnnnnnnnn nnnnnnnnnn nnnnnnnnnn nnnnnnnnnn nnnnnnnnnn 140340
nnnnnnnnnn nnnnnnnnnn nnnnnnnnnn nnnnnnnnnn nnnnnnnnnn nnnnnnnnnn 140400
nnnnnnnnnn nnnnnnnnnn nnnnnnnnnn nnnnnnnnnn nnnnnnnnnn nnnnnnnnnn 140460
nnnnnnnnnn nnnnnnnnnn nnnnnnnnnn nnnnnnnnnn nnnnnnnnnn nnnnnnnnnn 140520
nnnnnnnnnn nnnnnnnnnn nnnnnnnnnn nnnnnnnnnn nnnnnnnnnn nnnnnnnnnn 140580
nnnnnnnnnn nnnnnnnnnn nnnnnnnnnn nnnnnnnnnn nnnnnnnnnn nnnnnnnnnn 140640
nnnnnnnnnn nnnnnnnnnn nnnnnnnnnn nnnnnnnnnn nnnnnnnnnn nnnnnnnnnn 140700
nnnnnnnnnn nnnnnnnnnn nnnnnnnnnn nnnnnnnnnn nnnnnnnnnn nnnnnnnnnn 140760
nnnnnnnnnn nnnnnnnnnn nnnnnnnnnn nnnnnnnnnn nnnnnnnnnn nnnnnnnnnn 140820
nnnnnnnnnn nnnnnnnnnn nnnnnnnnnn nnnnnnnnnn nnnnnnnnnn nnnnnnnnnn 140880
nnnnnnnnnn nnnnnnnnnn nnnnnnnnnn nnnnnnnnnn nnnnnnnnnn nnnnnnnnnn 140940
nnnnnnnnnn nnnnnnnnnn nnnnnnnnnn nnnnnnnnnn nnnnnnnnnn nnnnnnnnnn 141000
nnnnnnnnnn nnnnnnnnnn nnnnnnnnnn nnnnnnnnnn nnnnnnnnnn nnnnnnnnnn 141060
nnnnnnnnnn nnnnnnnnnn nnnnnnnnnn nnnnnnnnnn nnnnnnnnnn nnnnnnnnnn 141120
nnnnnnnnnn nnnnnnnnnn nnnnnnnnnn nnnnnnnnnn nnnnnnnnnn nnnnnnnnnn 141180

-continued nnnnnnnnnn nnnnnnnnnn nnnnnnnnnn nnnnnnnnnn nnnnnnnnnn nnnnnnnnnn 141240
nnnnnnnnnn nnnnnnnnnn nnnnnnnnnn nnnnnnnnnn nnnnnnnnnn nnnnnnnnnn 141300
nnnnnnnnnn nnnnnnnnnn nnnnnnnnnn nnnnnnnnnn nnnnnnnnnn nnnnnnnnnn 141360
nnnnnnnnnn nnnnnnnnnn nnnnnnnnnn nnnnnnnnnn nnnnnnnnnn nnnnnnnnnn 141420
nnnnnnnnnn nnnnnnnnnn nnnnnnnnnn nnnnnnnnnn nnnnnnnnnn nnnnnnnnnn 141480
nnnnnnnnnn nnnnnnnnnn nnnnnnnnnn nnnnnnnnnn nnnnnnnnnn nnnnnnnnnn 141540
nnnnnnnnnn nnnnnnnnnn nnnnnnnnnn nnnnnnnnnn nnnnnnnnnn nnnnnnnnnn 141600
nnnnnnnnnn nnnnnnnnnn nnnnnnnnnn nnnnnnnnnn nnnnnnnnnn nnnnnnnnnn 141660
nnnnnnnnnn nnnnnnnnnn nnnnnnnnnn nnnnnnnnnn nnnnnnnnnn nnnnnnnnnn 141720
nnnnnnnnnn nnnnnnnnnn nnnnnnnnnn nnnnnnnnnn nnnnnnnnnn nnnnnnnnnn 141780
nnnnnnnnnn nnnnnnnnnn nnnnnnnnnn nnnnnnnnnn nnnnnnnnnn nnnnnnnnnn 141840
nnnnnnnnnn nnnnnnnnnn nnnnnnnnnn nnnnnnnnnn nnnnnnnnnn nnnnnnnnnn 141900
nnnnnnnnnn nnnnnnnnnn nnnnnnnnnn nnnnnnnnnn nnnnnnnnnn nnnnnnnnnn 141960
nnnnnnnnnn nnnnnnnnnn nnnnnnnnnn nnnnnnnnnn nnnnnnnnnn nnnnnnnnnn 142020
nnnnnnnnnn nnnnnnnnnn nnnnnnnnnn nnnnnnnnnn nnnnnnnnnn nnnnnnnnnn 142080
nnnnnnnnnn nnnnnnnnnn nnnnnnnnnn nnnnnnnnnn nnnnnnnnnn nnnnnnnnnn 142140
nnnnnnnnnn nnnnnnnnnn nnnnnnnnnn nnnnnnnnnn nnnnnnnnnn nnnnnnnnnn 142200
nnnnnnnnnn nnnnnnnnnn nnnnnnnnnn nnnnnnnnnn nnnnnnnnnn nnnnnnnnnn 142260
nnnnnnnnnn nnnnnnnnnn nnnnnnnnnn nnnnnnnnnn nnnnnnnnnn nnnnnnnnnn 142320
nnnnnnnnnn nnnnnnnnnn nnnnnnnnnn nnnnnnnnnn nnnnnnnnnn nnnnnnnnnn 142380
nnnnnnnnnn nnnnnnnnnn nnnnnnnnnn nnnnnnnnnn nnnnnnnnnn nnnnnnnnnn 142440
nnnnnnnnnn nnnnnnnnnn nnnnnnnnnn nnnnnnnnnn nnnnnnnnnn nnnnnnnnnn 142500
nnnnnnnnnn nnnnnnnnnn nnnnnnnnnn nnnnnnnnnn nnnnnnnnnn nnnnnnnnnn 142560
nnnnnnnnnn nnnnnnnnnn nnnnnnnnnn nnnnnnnnnn nnnnnnnnnn nnnnnnnnnn 142620
nnnnnnnnnn nnnnnnnnnn nnnnnnnnnn nnnnnnnnnn nnnnnnnnnn nnnnnnnnnn 142680
nnnnnnnnnn nnnnnnnnnn nnnnnnnnnn nnnnnnnnnn nnnnnnnnnn nnnnnnnnnn 142740
nnnnnnnnnn nnnnnnnnnn nnnnnnnnnn nnnnnnnnnn nnnnnnnnnn nnnnnnnnnn 142800
nnnnnnnnnn nnnnnnnnnn nnnnnnnnnn nnnnnnnnnn nnnnnnnnnn nnnnnnnnnn 142860
nnnnnnnnnn nnnnnnnnnn nnnnnnnnnn nnnnnnnnnn nnnnnnnnnn nnnnnnnnnn 142920
nnnnnnnnnn nnnnnnnnnn nnnnnnnnnn nnnnnnnnnn nnnnnnnnnn nnnnnnnnnn 142980
nnnnnnnnnn nnnnnnnnnn nnnnnnnnnn nnnnnnnnnn nnnnnnnnnn nnnnnnnnnn 143040
nnnnnnnnnn nnnnnnnnnn nnnnnnnnnn nnnnnnnnnn nnnnnnnnnn nnnnnnnnnn 143100
nnnnnnnnnn nnnnnnnnnn nnnnnnnnnn nnnnnnnnnn nnnnnnnnnn nnnnnnnnnn 143160
nnnnnnnnnn nnnnnnnnnn nnnnnnnnnn nnnnnnnnnn nnnnnnnnnn nnnnnnnnnn 143220
nnnnnnnnnn nnnnnnnnnn nnnnnnnnnn nnnnnnnnnn nnnnnnnnnn nnnnnnnnnn 143280
nnnnnnnnnn nnnnnnnnnn nnnnnnnnac aacaacaaaa ccaacaacaa cacattgtag 143340
ccccaggaaa tttgaaaggc ctttatgaga gaactctcct gtagtgagct aatatcctaa 143400
gatactttta gtgcctcaag gaagtggaaa tttactggtg tgaactcata taggggaaga 143460
aaaagaaaaa aagtcaacat attttggatg tccagttttt tgtcgggcat tttatgtatg 143520
ttaaatcctt taaatcttac aatacaggat ttatgacaca cactcccacc cccagatgag 143580

-continued gaaattgtgc atcagaagag tttaattctt aaggtaatat ggctctctag ggcagaaact 143640
ggaattaaac ttttttcaca acagtatgct gctttcttgg caataacaca taacggcaga 143700
aggaccttgg aacctgtagg actgtctcac agagttcagc ctgctctgct ggcaaagttt 143760
acacctatca ttctttccag tggagaagat gaaatcagga cagtcagaag tttcacatat 143820
caaatgtgac ttcacatatt tttttaaata ctagaactca taaatttaaa tgatttccaa 143880
aaagattata ttgtgtcaac atatttctgt caataatgta attcactgtg tcatgtatgt 143940
ttgaaaacac actcttggaa ttacctcgag aagtaactta ctagcaattt cagtagaaat 144000
tttattgctt tataacaaca cttcaattct taccaaaatt gaattctata aactagatca 144060
tccacctcat ttacaaaact taacacctaa tgacatttga attttcttta aattacatct 144120
gcccttaaat ggtaaaggtt gactagctgt gagaattaaa tgagactaag tcaacaaaca 144180
cttattatac aactactatg tgcccggcac tattataggt aatcagaata tagcagtgaa 144240
tatgacagag ttctgccttt ataaaactga cgttccagta atgagatgtt cttggaaaca 144300
ttttgtaatc cacaaagaaa tagatattcc taataatgac aaacaatttc tgaagacaat 144360
ttcaatagag gagttccaaa aggttttgag gtacagtagc aatagatacg aatataacct 144420
ctgaggctga tcacttttga gaatgttcta tttaaatcat tgtcaatttg aatatatgtc 144480
ttaaacattt gatgatattc ctttaaagtc agatatgttt gttatgtgca aatgagggtg 144540
atttgaaata tacttttttt tttagcttta actacttttg ataaggtcca aactcagaga 144600
tgctagtagg ttattgaatt atattgaaaa catttaaagg atccaaatgg tactgaattt 144660
agcccaaaca ttcagatgca atggtaggag tccttgtcca gcacctggat gtttgggtac 144720
ttcaatgacc cactgccttg tatttacaaa tcaggaccag atacttgatc ttaagcaggc 144780
cacatatcca ggtgactaac agatttattg gttaaacata ttttaaatgc gctgatgatg 144840
tatagatatg ctgactcaca gatttcaaaa gtaaatttag catttgtatt ccaacagtca 144900
ttctaacaag aaaactgtaa gagaatttac caattaggtc taacaggaaa aaaactcata 144960
aacaaattta tgtaatataa ttttctactt cttatgataa cagcaagaaa gaatatatta 145020
atacttggtg tttagtgaca agtgttagaa aaaaacttga agcttcaaga gaccacagga 145080
atttagaaag cctcctattt gaaatggtag aaaatcatat ctatactatg ataaattctg 145140
tgtctgtaac ttagctattt atttgatgaa ttcagtactg cttttagctt taacaatata 145200
actcccttta tgaaactctt catcaatata tttgtttaac cactctgtct ttggtgtcta 145260
ggcacagtat atctttttac accagtgcat tctggatctc ttatcaaata agggaagtaa 145320
tcagcccatc tgttttgtta actattcagc acttcagaag atggactctt tggacgccat 145380
ggaaggtaaa cagaaacaac agtatatgcc cagcttacta gtttaccacc tacggtaaga 145440
acataaattt cagaataacc atatgttaaa aatgtttaag aagctggatt agtgcacaga 145500
tcaggttttt tttctttaac ttttctctaa tccaagttgg gctaataata ccctttctgt 145560
ctacattata tttttatcat gaaacatttc aattttgaac tgttaacttc aacactctct 145620
tgtaacatgt tactttctgt tataggtgat gttgagcttg aatgggaaga aaccactatg 145680
taaatattca gaccaaagga tacaattgga agagattttt aaatcccagg ggccaaagtt 145740
accccctcat tcttccgaat tgaaatgtgc aaccttaaag aaatatctat gcttctctca 145800
ctgtgccttt ccaaacggat tgaacatttt aagnnnnnnn nnnnnnnnnn nnnnnnnnnn 145860
nnnnnnnnnn nnnnnnnnnn nnnnnnnnnn nnnnnnnnnn nnnnnnnnnn nnnnnnnnnn 145920

-continued nnnnnnnnnn nnnnnnnnnn nnnnnnnnnn nnnnnnnnnn nnnnnnnnnn nnnnnnnnnn 145980
nnnnnnnnnn nnnnnnnnnn nnnnnnnnnn nnnnnnnnnn nnnnnnnnnn nnnnnnnnnn 146040
nnnnnnnnnn nnnnnnnnnn nnnnnnnnnn nnnnnnnnnn nnnnnnnnnn nnnnnnnnnn 146100
nnnnnnnnnn nnnnnnnnnn nnnnnnnnnn nnnnnnnnnn nnnnnnnnnn nnnnnnnnnn 146160
nnnnnnnnnn nnnnnnnnnn nnnnnnnnnn nnnnnnnnnn nnnnnnnnnn nnnnnnnnnn 146220
nnnnnnnnnn nnnnnnnnnn nnnnnnnnnn nnnnnnnnnn nnnnnnnnnn nnnnnnnnnn 146280
nnnnnnnnnn nnnnnnnnnn nnnnnnnnnn nnnnnnnnnn nnnnnnnnnn nnnnnnnnnn 146340
nnnnnnnnnn nnnnnnnnnn nnnnnnnnnn nnnnnnnnnn nnnnnnnnnn nnnnnnnnnn 146400
nnnnnnnnnn nnnnnnnnnn nnnnnnnnnn nnnnnnnnnn nnnnnnnnnn nnnnnnnnnn 146460
nnnnnnnnnn nnnnnnnnnn nnnnnnnnnn nnnnnnnnnn nnnnnnnnnn nnnnnnnnnn 146520
nnnnnnnnnn nnnnnnnnnn nnnnnnnnnn nnnnnnnnnn nnnnnnnnnn nnnnnnnnnn 146580
nnnnnnnnnn nnnnnnnnnn nnnnnnnnnn nnnnnnnnnn nnnnnnnnnn nnnnnnnnnn 146640
nnnnnnnnnn nnnnnnnnnn nnnnnnnnnn nnnnnnnnnn nnnnnnnnnn nnnnnnnnnn 146700
nnnnnnnnnn nnnnnnnnnn nnnnnnnnnn nnnnnnnnnn nnnnnnnnnn nnnnnnnnnn 146760
nnnnnnnnnn nnnnnnnnnn nnnnnnnnnn nnnnnnnnnn nnnnnnnnnn nnnnnnnnnn 146820
nnnnnnnnnn nnnnnnnnnn nnnnnnnnnn nnnnnnnnnn nnnnnnnnnn nnnnnnnnnn 146880
nnnnnnnnnn nnnnnnnnnn nnnnnnnnnn nnnnnnnnnn nnnnnnnnnn nnnnnnnnnn 146940
nnnnnnnnnn nnnnnnnnnn nnnnnnnnnn nnnnnnnnnn nnnnnnnnnn nnnnnnnnnn 147000
nnnnnnnnnn nnnnnnnnnn nnnnnnnnnn nnnnnnnnnn nnnnnnnnnn nnnnnnnnnn 147060
nnnnnnnnnn nnnnnnnnnn nnnnnnnnnn nnnnnnnnnn nnnnnnnnnn nnnnnnnnnn 147120
nnnnnnnnnn nnnnnnnnnn nnnnnnnnnn nnnnnnnnnn nnnnnnnnnn nnnnnnnnnn 147180
nnnnnnnnnn nnnnnnnnnn nnnnnnnnnn nnnnnnnnnn nnnnnnnnnn nnnnnnnnnn 147240
nnnnnnnnnn nnnnnnnnnn nnnnnnnnnn nnnnnnnnnn nnnnnnnnnn nnnnnnnnnn 147300
nnnnnnnnnn nnnnnnnnnn nnnnnnnnnn nnnnnnnnnn nnnnnnnnnn nnnnnnnnnn 147360
nnnnnnnnnn nnnnnnnnnn nnnnnnnnnn nnnnnnnnnn nnnnnnnnnn nnnnnnnnnn 147420
nnnnnnnnnn nnnnnnnnnn nnnnnnnnnn nnnnnnnnnn nnnnnnnnnn nnnnnnnnnn 147480
nnnnnnnnnn nnnnnnnnnn nnnnnnnnnn nnnnnnnnnn nnnnnnnnnn nnnnnnnnnn 147540
nnnnnnnnnn nnnnnnnnnn nnnnnnnnnn nnnnnnnnnn nnnnnnnnnn nnnnnnnnnn 147600
nnnnnnnnnn nnnnnnnnnn nnnnnnnnnn nnnnnnnnnn nnnnnnnnnn nnnnnnnnnn 147660
nnnnnnnnnn nnnnnnnnnn nnnnnnnnnn nnnnnnnnnn nnnnnnnnnn nnnnnnnnnn 147720
nnnnnnnnnn nnnnnnnnnn nnnnnnnnnn nnnnnnnnnn nnnnnnnnnn nnnnnnnnnn 147780
nnnnnnnnnn nnnnnnnnnn nnnnnnnnnn tatcttcatt agtttcttgt ctaagacttc 147840
atagatacta gttactctct ggggtccctg aagcaatagt attaaccctc acacaaatca 147900
gtaaatgtga gtagtagttg gttagacgga tcagtcatgg tagatttttg tgtattttaa 147960
tgtagcagat aggagattca agcttttttt ctctcaagct tgagaataca gagggcatag 148020
gtctggctta ccttgtaaaa aatgccagca gctaacaatg aaattctacc caacacaggc 148080
tgggtatttc tctgattttt tgccttgggt ttacagtatt cctagagtta ccagaaaact 148140
atagtggaca attagcggtg gatgccaaga gaatgcttgg aactttgaga atgttggggt 148200
ggacattaat caattgatat aagctttggg tatggaggac aacgttatgt tataatcatt 148260
agaagaaatt tcaaaggcga taaagaaaaa ctatttcaga aacgctcttc cctgaaacac 148320

-continued caagaaagtg acctattatg ttaatatttt tgttatatgc aatgtgccct gttagttttg 148380
ttagaaaatg tacattttat tatatccatt ttcaaatcgt ttctggtagt ggggttttaa 148440
aatgataaat gaggttcaaa attaattcca gcctcctttc ttttagaaac agtgttagat 148500
tgaatctgca tcaggcgtgt tttcacatgc ttggcttcat aatctctctt cctcccccta 148560
tattgtttgc ctggaatctg cactaaagat aaggcagagt gcaaacctga ctcattggca 148620
accaatcaga agaactttat gtggaaaact cccttcgagg aggtacaggc agcatgaaca 148680
aaatttttga aaaagtggaa gcaaaggtag aaaaatatgg ttgaaatggc taaaacaatt 148740
ggtacttgtt ttaaaactat atttcatttc tgatatgaaa ccttatcttt tcttttaaag 148800
aaacacctaa caaaatattt atcagatcag caccacagta aagggaaaaa gacattaaaa 148860
attaaaaaag ataaaataac aaatatttat cagaaatgct caccettcaa aaaatctgga 148920
agattttgat tatatatttt tccaattatc ttctgtttgg taaatttcca agtaattgga 148980
taaatagttt atatttactt tgttttaaaa tgactcaaat tttcaattag agcataagct 149040
ttcaaaaaca atctggtcaa ctagcagact tttagcaaat aagacatatt tcagaaacag 149100
aaaattaatt gttatattat ttatgatagt tatacctaaa acctaggtgt tgttaaatat 149160
ttacatgttt aacacccaag tatacttaga gatcatttat tgtactcagt gatttctaac 149220
aacatgatta ttttggaact tgaacctata ctatttgttt tcattttttt gaaactttag 149280
gagaataact ttattttaaa cctctatttt tcaatatcag aaccagaaca acctgagaaa 149340
cttagagcct tcaatatttc cacacattcc ttttctctgc actggagcct accctctggt 149400
catgtggaaa ggtatcaagt ggatcttgtt cctgacagtg gctttgttac tatcagagat 149460
cttggaggtg gagaatatca ggtatagttt tcattattgt acttgccgag cctacttgta 149520
tttatatttt gctcctaata ggaaagttct ttattttatg aaacccatct accacaaaaa 149580
cttactcctt gttgggtttt tgaaagcata agttgaagac aaaaacgttg atgtcaaact 149640
gatgagtgtt aagtttcagc attggtggac tgttacctta gcaacatcta tgctgctttt 149700
tttttttttt tttttttttt aagttcaccc tgaacctaca gccagtcatc caagggttca 149760
tgaatagttt aacaaagaaa aggcagagct attgagtaat acgggctcat taattgtgta 149820
cttgccagaa ggatctgtct ttaaatcatt aatgcaggca acatttctct ctagagccat 149880
caatgtgatt ctactggctg aaaaatgtaa taaagatgga ttttcttatc atttttcttt 149940
tactttttat tgggacttca gagacacagg tatttcgtat acactcttta aaaacaaggg 150000
ctaagtcatg ggctgtagat ttctcaagac ttgaatagtt gttccttgtg acagtgaact 150060
aggatagata gaaatgctga cttaggctgt gataacgcag tacgttttgt aagtttttat 150120
tttaaagtca tttggtaaaa agttatataa catatttgta tcttacaata atatggaact 150180
tattgtgatg ttataaacag tgcagagtta tatagtgaag agttaatttt tgttatagtg 150240
atagatttat tttagcttgc ttgctttcca gaaagaattt taatgcaact atttgtttgt 150300
gnnnnnnnnn nnnnnnnnnn nnnnnnnnnn nnnnnnnnnn nnnnnnnnnn nnnnnnnnnn 150360
nnnnnnnnnn nnnnnnnnnn nnnnnnnnnn nnnnnnnnnn nnnnnnnnnn nnnnnnnnnn 150420
nnnnnnnnnn nnnnnnnnnn nnnnnnnnnn nnnnnnnnnn nnnnnnnnnn nnnnnnnnnn 150480
nnnnnnnnnn nnnnnnnnnn nnnnnnnnnn nnnnnnnnnn nnnnnnnnnn nnnnnnnnnn 150540
nnnnnnnnnn nnnnnnnnnn nnnnnnnnnn nnnnnnnnnn nnnnnnnnnn nnnnnnnnnn 150600
nnnnnnnnnn nnnnnnnnnn nnnnnnnnnn nnnnnnnnnn nnnnnnnnnn nnnnnnnnnn 150660

-continued nnnnnnnnnn nnnnnnnnnn nnnnnnnnnn nnnnnnnnnn nnnnnnnnnn nnnnnnnnnn 150720
nnnnnnnnnn nnnnnnnnnn nnnnnnnnnn nnnnnnnnnn nnnnnnnnnn nnnnnnnnnn 150780
nnnnnnnnnn nnnnnnnnnn nnnnnnnnnn nnnnnnnnnn nnnnnnnnnn nnnnnnnnnn 150840
nnnnnnnnnn nnnnnnnnnn nnnnnnnnnn nnnnnnnnnn nnnnnnnnnn nnnnnnnnnn 150900
nnnnnnnnnn nnnnnnnnnn nnnnnnnnnn nnnnnnnnnn nnnnnnnnnn nnnnnnnnnn 150960
nnnnnnnnnn nnnnnnnnnn nnnnnnnnnn nnnnnnnnnn nnnnnnnnnn nnnnnnnnnn 151020
nnnnnnnnnn nnnnnnnnnn nnnnnnnnnn nnnnnnnnnn nnnnnnnnnn nnnnnnnnnn 151080
nnnnnnnnnn nnnnnnnnnn nnnnnnnnnn nnnnnnnnnn nnnnnnnnnn nnnnnnnnnn 151140
nnnnnnnnnn nnnnnnnnnn nnnnnnnnnn nnnnnnnnnn nnnnnnnnnn nnnnnnnnnn 151200
nnnnnnnnnn nnnnnnnnnn nnnnnnnnnn nnnnnnnnnn nnnnnnnnnn nnnnnnnnnn 151260
nnnnnnnnnn nnnnnnnnnn nnnnnnnnnn nnnnnnnnnn nnnnnnnnnn nnnnnnnnnn 151320
nnnnnnnnnn nnnnnnnnnn nnnnnnnnnn nnnnnnnnnn nnnnnnnnnn nnnnnnnnnn 151380
nnnnnnnnnn nnnnnnnnnn nnnnnnnnnn nnnnnnnnnn nnnnnnnnnn nnnnnnnnnn 151440
nnnnnnnnnn nnnnnnnnnn nnnnnnnnnn nnnnnnnnnn nnnnnnnnnn nnnnnnnnnn 151500
nnnnnnnnnn nnnnnnnnnn nnnnnnnnnn nnnnnnnnnn nnnnnnnnnn nnnnnnnnnn 151560
nnnnnnnnnn nnnnnnnnnn nnnnnnnnnn nnnnnnnnnn nnnnnnnnnn nnnnnnnnnn 151620
nnnnnnnnnn nnnnnnnnnn nnnnnnnnnn nnnnnnnnnn nnnnnnnnnn nnnnnnnnnn 151680
nnnnnnnnnn nnnnnnnnnn nnnnnnnnnn nnnnnnnnnn nnnnnnnnnn nnnnnnnnnn 151740
nnnnnnnnnn nnnnnnnnnn nnnnnnnnnn nnnnnnnnnn nnnnnnnnnn nnnnnnnnnn 151800
nnnnnnnnnn nnnnnnnnnn nnnnnnnnnn nnnnnnnnnn nnnnnnnnnn nnnnnnnnnn 151860
nnnnnnnnnn nnnnnnnnnn nnnnnnnnnn nnnnnnnnnn nnnnnnnnnn nnnnnnnnnn 151920
nnnnnnnnnn nnnnnnnnnn nnnnnnnnnn nnnnnnnnnn nnnnnnnnnn nnnnnnnnnn 151980
nnnnnnnnnn nnnnnnnnnn nnnnnnnnnn nnnnnnnnnn nnnnnnnnnn nnnnnnnnnn 152040
nnnnnnnnnn nnnnnnnnnn nnnnnnnnnn nnnnnnnnnn nnnnnnnnnn nnnnnnnnnn 152100
nnnnnnnnnn nnnnnnnnnn nnnnnnnnnn nnnnnnnnnn nnnnnnnnnn nnnnnnnnnn 152160
nnnnnnnnnn nnnnnnnnnn nnnnnnnnnn nnnnnnnnnn nnnnnnnnnn nnnnnnnnnn 152220
nnnnnnnnnn nnnnnnnnnn nnnnnnnnnn nnnnnnnnnn nnnnnnnnnn nnnnnnnnnn 152280
nnnnnnnnnn nnnnnnnnnn nnnnnnnnnn nnnnnnnnnn nnnnnnnnnn nnnnnnnnnn 152340
nnnnnnnnnn nnnnnnnnnn nnnnnnnnnn nnnnnnnnnn nnnnnnnnnn nnnnnnnnnn 152400
nnnnnnnnnn nnnnnnnnnn nnnnnnnnnn nnnnnnnnnn nnnnnnnnnn nnnnnnnnnn 152460
nnnnnnnnnn nnnnnnnnnn nnnnnnnnnn nnnnnnnnnn nnnnnnnnnn nnnnnnnnnn 152520
nnnnnnnnnn nnnnnnnnnn nnnnnnnnnn nnnnnnnnnn nnnnnnnnnn nnnnnnnnnn 152580
nnnnnnnnnn nnnnnnnnnn nnnnnnnnnn nnnnnnnnnn nnnnnnnnnn nnnnnnnnnn 152640
nnnnnnnnnn nnnnnnnnnn nnnnnnnnnn nnnnnnnnnn nnnnnnnnnn nnnnnnnnnn 152700
nnnnnnnnnn nnnnnnnnnn nnnnnnnnnn nnnnnnnnnn nnnnnnnnnn nnnnnnnnnn 152760
nnnnnnnnnn nnnnnnnnnn nnnnnnnnnn nnnnnnnnnn nnnnnnnnnn nnnnnnnnnn 152820
nnnnnnnnnn nnnnnnnnnn nnnnnnnnnn nnnnnnnnnn nnnnnnnnnn nnnnnnnnnn 152880
nnnnnnnnnn nnnnnnnnnn nnnnnnnnnn nnnnnnnnnn nnnnnnnnnn nnnnnnnnnn 152940
nnnnnnnnnn nnnnnnnnnn nnnnnnnnnn nnnnnnnnnn nnnnnnnnnn nnnnnnnnnn 153000
nnnnnnnnnn nnnnnnnnnn nnnnnnnnnn nnnnnnnnnn nnnnnnnnnn nnnnnnnnnn 153060

-continued nnnnnnnnnn nnnnnnnnnn nnnnnnnnnn nnnnnnnnnn nnnnnnnnnn nnnnnnnnnn 153120
nnnnnnnnnn nnnnnnnnnn nnnnnnnnnn nnnnnnnnnn nnnnnnnnnn nnnnnnnnnn 153180
nnnnnnnnnn nnnnnnnnnn nnnnnnnnnn nnnnnnnnnn nnnnnnnnnn nnnnnnnnnn 153240
nnnnnnnnnn nnnnnnnnnn nnnnnnnnnn nnnnnnnnnn nnnnnnnnnn nnnnnnnnnn 153300
nnnnnnnnnn nnnnnnnnnn nnnnnnnnnn nnnnnnnnnn nnnnnnnnnn nnnnnnnnnn 153360
nnnnnnnnnn nnnnnnnnnn nnnnnnnnnn nnnnnnnnnn nnnnnnnnnn nnnnnnnnnn 153420
nnnnnnnnnn nnnnnnnnnn nnnnnnnnnn nnnnnnnnnn nnnnnnnnnn nnnnnnnnnn 153480
nnnnnnnnnn nnnnnnnnnn nnnnnnnnnn nnnnnnnnnn nnnnnnnnnn nnnnnnnnnn 153540
nnnnnnnnnn nnnnnnnnnn nnnnnnnnnn nnnnnnnnnn nnnnnnnnnn nnnnnnnnnn 153600
nnnnnnnnnn nnnnnnnnnn nnnnnnnnnn nnnnnnnnnn nnnnnnnnnn nnnnnnnnnn 153660
nnnnnnnnnn nnnnnnnnnn nnnnnnnnnn nnnnnnnnnn nnnnnnnnnn nnnnnnnnnn 153720
nnnnnnnnnn nnnnnnnnnn nnnnnnnnnn nnnnnnnnnn nnnnnnnnnn nnnnnnnnnn 153780
nnnnnnnnnn nnnnnnnnnn nnnnnnnnnn nnnnnnnnnn nnnnnnnnnn nnnnnnnnnn 153840
nnnnnnnnnn nnnnnnnnnn nnnnnnnnnn nnnnnnnnnn nnnnnnnnnn nnnnnnnnnn 153900
nnnnnnnnnn nnnnnnnnnn nnnnnnnnnn nnnnnnnnnn nnnnnnnnnn nnnnnnnnnn 153960
nnnnnnnnnn nnnnnnnnnn nnnnnnnnnn nnnnnnnnnn nnnnnnnnnn nnnnnnnnnn 154020
nnnnnnnnnn nnnnnnnnnn nnnnnnnnnn nnnnnnnnnn nnnnnnnnnn nnnnnnnnnn 154080
nnnnnnnnnn nnnnnnnnnn nnnnnnnnnn nnnnnnnnnn nnnnnnnnnn nnnnnnnnnn 154140
nnnnnnnnnn nnnnnnnnnn nnnnnnnnnn nnnnnnnnnn nnnnnnnnnn nnnnnnnnnn 154200
nnnnnnnnnn nnnnnnnnnn nnnnnnnnnn nnnnnnnnnn nnnnnnnnnn nnnnnnnnnn 154260
nnnnnnnnnn nnnnnnnnnn nnnnnnnnnn nnnnnnnnnn nnnnnnnnnn nnnnnnnnnn 154320
nnnnnnnnnn nnnnnnnnnn nnnnnnnnnn nnnnnnnnnn nnnnnnnnnn nnnnnnnnnn 154380
nnnnnnnnnn nnnnnnnnnn nnnnnnnnnn nnnnnnnnnn nnnnnnnnnn nnnnnnnnnn 154440
nnnnnnnnnn nnnnnnnnnn nnnnnnnnnn nnnnnnnnnn nnnnnnnnnn nnnnnnnnnn 154500
nnnnnnnnnn nnnnnnnnnn nnnnnnnnnn nnnnnnnnnn nnnnnnnnnn nnnnnnnnnn 154560
nnnnnnnnnn nnnnnnnnnn nnnnnnnnnn nnnnnnnnnn nnnnnnnnnn nnnnnnnnnn 154620
nnnnnnnnnn nnnnnnnnnn nnnnnnnnnn nnnnnnnnnn nnnnnnnnnn nnnnnnnnnn 154680
nnnnnnnnnn nnnnnnnnnn nnnnnnnnnn nnnnnnnnnn nnnnnnnnnn nnnnnnnnnn 154740
nnnnnnnnnn nnnnnnnnnn nnnnnnnnnn nnnnnnnnnn nnnnnnnnnn nnnnnnnnnn 154800
nnnnnnnnnn nnnnnnnnnn nnnnnnnnnn nnnnnnnnnn nnnnnnnnnn nnnnnnnnnn 154860
nnnnnnnnnn nnnnnnnnnn nnnnnnnnnn nnnnnnnnnn nnnnnnnnnn nnnnnnnnnn 154920
nnnnnnnnnn nnnnnnnnnn nnnnnnnnnn nnnnnnnnnn nnnnnnnnnn nnnnnnnnnn 154980
nnnnnnnnnn nnnnnnnnnn nnnnnnnnnn nnnnnnnnnn nnnnnnnnnn nnnnnnnnnn 155040
nnnnnnnnnn nnnnnnnnnn nnnnnnnnnn nnnnnnnnnn nnnnnnnnnn nnnnnnnnnn 155100
nnnnnnnnnn nnnnnnnnnn nnnnnnnnnn nnnnnnnnnn nnnnnnnnnn nnnnnnnnnn 155160
nnnnnnnnnn nnnnnnnnnn nnnnnnnnnn nnnnnnnnnn nnnnnnnnnn nnnnnnnnnn 155220
nnnnnnnnnn nnnnnnnnnn nnnnnnnnnn nnnnnnnnnn nnnnnnnnnn nnnnnnnnnn 155280
nnnnnnnnnn nnnnnnnnnn nnnnnnnnnn nnnnnnnnnn nnnnnnnnnn nnnnnnnnnn 155340
nnnnnnnnnn nnnnnnnnnn nnnnnnnnnn nnnnnnnnnn nnnnnnnnnn nnnnnnnnnn 155400

-continued

```
nnnnnnnnnn nnnnnnnnnn nnnnnnnnnn nnnnnnnnnn nnnnnnnnnn nnnnnnnnnn 155460
nnnnnnnnnn nnnnnnnnnn nnnnnnnnnn nnnnnnnnnn nnnnnnnnnn nnnnnnnnnn 155520
nnnnnnnnnn nnnnnnnnnn nnnnnnnnnn nnnnnnnnnn nnnnnnnnnn nnnnnnnnnn 155580
nnnnnnnnnn nnnnnnnnnn nnnnnnnnnn nnnnnnnnnn nnnnnnnnnn nnnnnnnnnn 155640
nnnnnnnnnn nnnnnnnnnn nnnnnnnnnn nnnnnnnnnn nnnnnnnnnn nnnnnnnnnn 155700
nnnnnnnnnn nnnnnnnnnn nnnnnnnnnn nnnnnnnnnn nnnnnnnnnn nnnnnnnnnn 155760
nnnnnnnnnn nnnnnnnnnn nnnnnnnnnn nnnnnnnnnn nnnnnnnnnn nnnnnnnnnn 155820
nnnnnnnnnn nnnnnnnnnn nnnnnnnnnn nnnnnnnnnn nnnnnnnnnn nnnnnnnnnn 155880
nnnnnnnnnn nnnnnnnnnn nnnnnnnnnn nnnnnnnnnn nnnnnnnnnn nnnnnnnnnn 155940
nnnnnnnnnn nnnnnnnnnn nnnnnnnnnn nnnnnnnnnn nnnnnnnnnn nnnnnnnnnn 156000
nnnnnnnnnn nnnnnnnnnn nnnnnnnnnn nnnnnnnnnn nnnnnnnnnn nnnnnnnnnn 156060
nnnnnnnnnn nnnnnnnnnn nnnnnnnnnn nnnnnnnnnn nnnnnnnnnn nnnnnnnnnn 156120
nnnnnnnnnn nnnnnnnnnn nnnnnnnnnn nnnnnnnnnn nnnnnnnnnn nnnnnnnnnn 156180
nnnnnnnnnn nnnnnnnnnn nnnnnnnnnn nnnnnnnnnn nnnnnnnnnn nnnnnnnnnn 156240
nnnnnnnnnn nnnnnnnnnn nnnnnnnnnn nnnnnnnnnn nnnnnnnnnn nnnnnnnnnn 156300
nnnnnnnnnn nnnnnnnnnn nnnnnnnnnn nnnnnnnnnn nnnnnnnnnn nnnnnnnnnn 156360
nnnnnnnnnn nnnnnnnnnn nnnnnnnnnn nnnnnnnnnn nnnnnnnnnn nnnnnnnnnn 156420
nnnnnnnnnn nnnnnnnnnn nnnnnnnnnn nnnnnnnnnn nnnnnnnnnn nnnnnnnnnn 156480
nnnnnnnnnn nnnnnnnnnn nnnnnnnnnn nnnnnnnnnn nnnnnnnnnn nnnnnnnnnn 156540
nnnnnnnnnn nnnnnnnnnn nnnnnnnnnn nnnnnnnnnn nnnnnnnnnn nnnnnnnnnn 156600
nnnnnnnnnn nnnnnnnnnn nnnnnnnnnn nnnnnnnnnn nnnnnnnnnn nnnnnnnnnn 156660
nnnnnnnnnn nnnnnnnnnn nnnnnnnnnn nnnnnnnnnn nnnnnnnnnn nnnnnnnnnn 156720
nnnnnnnnnn nnnnnnnnnn nnnnnnnnnn nnnnnnnnnn nnnnnnnnnn nnnnnnnnnn 156780
nnnnnnnnnn nnnnnnnnnn nnnnnnnnnn nnnnnnnnnn nnnnnnnnnn nnnnnnnnnn 156840
nnnnnnnnnn nnnnnnnnnn nnnnnnnnnn nnnnnnnnnn nnnnnnnnnn nnnnnnnnnn 156900
nnnnnnnnnn nnnnnnnnnn nnnnnnnnnn nnnnnnnnnn nnnnnnnnnn nnnnnnnnnn 156960
nnnnnnnnnn nnnnnnnnnn nnnnnnnnnn nnnnnnnnnn nnnnnnnnnn nnnnnnnnnn 157020
nnnnnnnnnn nnnnnnnnnn nnnnnnnnnn nnnnnnnnnn nnnnnnnnnn nnnnnnnnnn 157080
nnnnnnnnnn nnnnnnnnnn nnnnnnnnnn nnnnnnnnnn nnnnnnnnnn nnnnnnnnnn 157140
nnnnnnnnnn nnnnnnnnnn nnnnnnnnnn nnnnnnnnnn nnnnnnnnnn nnnnnnnnnn 157200
nnnnnnnnnn nnnnnnnnnn nnnnnnnnnn nnnnnnnnnn nnnnnnnnnn nnnnnnnnnn 157260
nnnnnnnnnn nnnnnnnnnn nnnnnnnnnn nnnnnnnnnn nnnnnnnnnn nnnnnnnnnn 157320
nnnnnnnnnn nnnnnnnnnn nnnnnnnnnn nnnnnnnnnn nnnnnnnnnn nnnnnnnnnn 157380
nnnnnnnnnn nnnnnnnnnn nnnnnnnnnn nnnnnnnnnn nnnnnnnnnn nnnnnnnnnn 157440
nnnnnnnnnn nnnnnnnnnn nnnnnnnnnn nnnnnnnnnn nnnnnnnnnn nnnnnnnnnn 157500
nnnnnnnnnn nnnnnnnnnn nnnnnnnnnn nnnnnnnnnn nnnnnnnnnn nnnnnnnnnn 157560
nnnnnnnnnn nnnnnnnnnn nnnnnnnnnn nnnnnnnnnn nnnnnnnnnn nnnnnnnnnn 157620
nnnnnnnnnn nnnnnnnnnn nnnnnnnnnn nnnnnnnnnn nnnnnnnnnn nnnnnnnnnn 157680
nnnnnnnnnn nnnnnnnnnn nnnnnnnnnn nnnnnnnnnn nnnnnnnnnn nnnnnnnnnn 157740
nnnnnnnnnn nnnnnnnnnn nnnnnnnnnn nnnnnnnnnn nnnnnnnnnn nnnnnnnnnn 157800
```

-continued nnnnnnnnnn nnnnnnnnnn nnnnnnnnnn nnnnnnnnnn nnnnnnnnnn nnnnnnnnnn 157860
nnnnnnnnnn nnnnnnnnnn nnnnnnnnnn nnnnnnnnnn nnnnnnnnnn nnnnnnnnnn 157920
nnnnnnnnnn nnnnnnnnnn nnnnnnnnnn nnnnnnnnnn nnnnnnnnnn nnnnnnnnnn 157980
nnnnnnnnnn nnnnnnnnnn nnnnnnnnnn nnnnnnnnnn nnnnnnnnnn nnnnnnnnnn 158040
nnnnnnnnnn nnnnnnnnnn nnnnnnnnnn nnnnnnnnnn nnnnnnnnnn nnnnnnnnnn 158100
nnnnnnnnnn nnnnnnnnnn nnnnnnnnnn nnnnnnnnnn nnnnnnnnnn nnnnnnnnnn 158160
nnnnnnnnnn nnnnnnnnnn nnnnnnnnnn nnnnnnnnnn nnnnnnnnnn nnnnnnnnnn 158220
nnnnnnnnnn nnnnnnnnnn nnnnnnnnnn nnnnnnnnnn nnnnnnnnnn nnnnnnnnnn 158280
nnnnnnnnnn nnnnnnnnnn nnnnnnnnnn nnnnnnnnnn nnnnnnnnnn nnnnnnnnnn 158340
nnnnnnnnnn nnnnnnnnnn nnnnnnnnnn nnnnnnnnnn nnnnnnnnnn nnnnnnnnnn 158400
nnnnnnnnnn nnnnnnnnnn nnnnnnnnnn nnnnnnnnnn nnnnnnnnnn nnnnnnnnnn 158460
nnnnnnnnnn nnnnnnnnnn nnnnnnnnnn nnnnnnnnnn nnnnnnnnnn nnnnnnnnnn 158520
nnnnnnnnnn nnnnnnnnnn nnnnnnnnnn nnnnnnnnnn nnnnnnnnnn nnnnnnnnnn 158580
nnnnnnnnnn nnnnnnnnnn nnnnnnnnnn nnnnnnnnnn nnnnnnnnnn nnnnnnnnnn 158640
nnnnnnnnnn nnnnnnnnnn nnnnnnnnnn nnnnnnnnnn nnnnnnnnnn nnnnnnnnnn 158700
nnnnnnnnnn nnnnnnnnnn nnnnnnnnnn nnnnnnnnnn nnnnnnnnnn nnnnnnnnnn 158760
nnnnnnnnnn nnnnnnnnnn nnnnnnnnnn nnnnnnnnnn nnnnnnnnnn nnnnnnnnnn 158820
nnnnnnnnnn nnnnnnnnnn nnnnnnnnnn nnnnnnnnnn nnnnnnnnnn nnnnnnnnnn 158880
nnnnnnnnnn nnnnnnnnnn nnnnnnnnnn nnnnnnnnnn nnnnnnnnnn nnnnnnnnnn 158940
nnnnnnnnnn nnnnnnnnnn nnnnnnnnnn nnnnnnnnnn nnnnnnnnnn nnnnnnnnnn 159000
nnnnnnnnnn nnnnnnnnnn nnnnnnnnnn nnnnnnnnnn nnnnnnnnnn nnnnnnnnnn 159060
nnnnnnnnnn nnnnnnnnnn nnnnnnnnnn nnnnnnnnnn nnnnnnnnnn nnnnnnnnnn 159120
nnnnnnnnnn nnnnnnnnnn nnnnnnnnnn nnnnnnnnnn nnnnnnnnnn nnnnnnnnnn 159180
nnnnnnnnnn nnnnnnnnnn nnnnnnnnnn nnnnnnnnnn nnnnnnnnnn nnnnnnnnnn 159240
nnnnnnnnnn nnnnnnnnnn nnnnnnnnnn nnnnnnnnnn nnnnnnnnnn nnnnnnnnnn 159300
nnnnnnnnnn nnnnnnnnnn nnnnnnnnnn nnnnnnnnnn nnnnnnnnnn nnnnnnnnnn 159360
nnnnnnnnnn nnnnnnnnnn nnnnnnnnnn nnnnnnnnnn nnnnnnnnnn nnnnnnnnnn 159420
nnnnnnnnnn nnnnnnnnnn nnnnnnnnnn nnnnnnnnnn nnnnnnnnnn nnnnnnnnnn 159480
nnnnnnnnnn nnnnnnnnnn nnnnnnnnnn nnnnnnnnnn nnnnnnnnnn nnnnnnnnnn 159540
nnnnnnnnnn nnnnnnnnnn nnnnnnnnnn nnnnnnnnnn nnnnnnnnnn nnnnnnnnnn 159600
nnnnnnnnnn nnnnnnnnnn nnnnnnnnnn nnnnnnnnnn nnnnnnnnnn nnnnnnnnnn 159660
nnnnnnnnnn nnnnnnnnnn nnnnnnnnnn nnnnnnnnnn nnnnnnnnnn nnnnnnnnnn 159720
nnnnnnnnnn nnnnnnnnnn nnnnnnnnnn nnnnnnnnnn nnnnnnnnnn nnnnnnnnnn 159780
nnnnnnnnnn nnnnnnnnnn nnnnnnnnnn nnnnnnnnnn nnnnnnnnnn nnnnnnnnnn 159840
nnnnnnnnnn nnnnnnnnnn nnnnnnnnnn nnnnnnnnnn nnnnnnnnnn nnnnnnnnnn 159900
nnnnnnnnnn nnnnnnnnnn nnnnnnnnnn nnnnnnnnnn nnnnnnnnnn nnnnnnnnnn 159960
nnnnnnnnnn nnnnnnnnnn nnnnnnnnnn nnnnnnnnnn nnnnnnnnnn nnnnnnnnnn 160020
nnnnnnnnnn nnnnnnnnnn nnnnnnnnnn nnnnnnnnnn nnnnnnnnnn nnnnnnnnnn 160080
nnnnnnnnnn nnnnnnnnnn nnnnnnnnnn nnnnnnnnnn nnnnnnnnnn nnnnnnnnnn 160140

-continued nnnnnnnnnn nnnnnnnnnn nnnnnnnnnn nnnnnnnnnn nnnnnnnnnn nnnnnnnnnn 160200
nnnnnnnnnn nnnnnnnnnn nnnnnnnnnn nnnnnnnnnn nnnnnnnnnn nnnnnnnnnn 160260
nnnnnnnnnn nnnnnnnnnn nnnnnnnnnn nnnnnnnnnn nnnnnnnnnn nnnnnnnnnn 160320
nnnnnnnnnn nnnnnnnnnn nnnnnnnnnn nnnnnnnnnn nnnnnnnnnn nnnnnnnnnn 160380
nnnnnnnnnn nnnnnnnnnn nnnnnnnnnn nnnnnnnnnn nnnnnnnnnn nnnnnnnnnn 160440
nnnnnnnnnn nnnnnnnnnn nnnnnnnnnn nnnnnnnnnn nnnnnnnnnn nnnnnnnnnn 160500
nnnnnnnnnn nnnnnnnnnn nnnnnnnnnn nnnnnnnnnn nnnnnnnnnn nnnnnnnnnn 160560
nnnnnnnnnn nnnnnnnnnn nnnnnnnnnn nnnnnnnnnn nnnnnnnnnn nnnnnnnnnn 160620
nnnnnnnnnn nnnnnnnnnn nnnnnnnnnn nnnnnnnnnn nnnnnnnnnn nnnnnnnnnn 160680
nnnnnnnnnn nnnnnnnnnn nnnnnnnnnn nnnnnnnnnn nnnnnnnnnn nnnnnnnnnn 160740
nnnnnnnnnn nnnnnnnnnn nnnnnnnnnn nnnnnnnnnn nnnnnnnnnn nnnnnnnnnn 160800
nnnnnnnnnn nnnnnnnnnn nnnnnnnnnn nnnnnnnnnn nnnnnnnnnn nnnnnnnnnn 160860
nnnnnnnnnn nnnnnnnnnn nnnnnnnnnn nnnnnnnnnn nnnnnnnnnn nnnnnnnnnn 160920
nnnnnnnnnn nnnnnnnnnn nnnnnnnnnn nnnnnnnnnn nnnnnnnnnn nnnnnnnnnn 160980
nnnnnnnnnn nnnnnnnnnn nnnnnnnnnn nnnnnnnnnn nnnnnnnnnn nnnnnnnnnn 161040
nnnnnnnnnn nnnnnnnnnn nnnnnnnnnn nnnnnnnnnn nnnnnnnnnn nnnnnnnnnn 161100
nnnnnnnnnn nnnnnnnnnn nnnnnnnnnn nnnnnnnnnn nnnnnnnnnn nnnnnnnnnn 161160
nnnnnnnnnn nnnnnnnnnn nnnnnnnnnn nnnnnnnnnn nnnnnnnnnn nnnnnnnnnn 161220
nnnnnnnnnn nnnnnnnnnn nnnnnnnnnn nnnnnnnnnn nnnnnnnnnn nnnnnnnnnn 161280
nnnnnnnnnn nnnnnnnnnn nnnnnnnnnn nnnnnnnnnn nnnnnnnnnn nnnnnnnnnn 161340
nnnnnnnnnn nnnnnnnnnn nnnnnnnnnn nnnnnnnnnn nnnnnnnnnn nnnnnnnnnn 161400
nnnnnnnnnn nnnnnnnnnn nnnnnnnnnn nnnnnnnnnn nnnnnnnnnn nnnnnnnnnn 161460
nnnnnnnnnn nnnnnnnnnn nnnnnnnnnn nnnnnnnnnn nnnnnnnnnn nnnnnnnnnn 161520
nnnnnnnnnn nnnnnnnnnn nnnnnnnnnn nnnnnnnnnn nnnnnnnnnn nnnnnnnnnn 161580
nnnnnnnnnn nnnnnnnnnn nnnnnnnnnn nnnnnnnnnn nnnnnnnnnn nnnnnnnnnn 161640
nnnnnnnnnn nnnnnnnnnn nnnnnnnnnn nnnnnnnnnn nnnnnnnnnn nnnnnnnnnn 161700
nnnnnnnnnn nnnnnnnnnn nnnnnnnnnn nnnnnnnnnn nnnnnnnnnn nnnnnnnnnn 161760
nnnnnnnnnn nnnnnnnnnn nnnnnnnnnn nnnnnnnnnn nnnnnnnnnn nnnnnnnnnn 161820
nnnnnnnnnn nnnnnnnnnn nnnnnnnnnn nnnnnnnnnn nnnnnnnnnn nnnnnnnnnn 161880
nnnnnnnnnn nnnnnnnnnn nnnnnnnnnn nnnnnnnnnn nnnnnnnnnn nnnnnnnnnn 161940
nnnnnnnnnn nnnnnnnnnn nnnnnnnnnn nnnnnnnnnn nnnnnnnnnn nnnnnnnnnn 162000
nnnnnnnnnn nnnnnnnnnn nnnnnnnnnn nnnnnnnnnn nnnnnnnnnn nnnnnnnnnn 162060
nnnnnnnnnn nnnnnnnnnn nnnnnnnnnn nnnnnnnnnn nnnnnnnnnn nnnnnnnnnn 162120
nnnnnnnnnn nnnnnnnnnn nnnnnnnnnn nnnnnnnnnn nnnnnnnnnn nnnnnnnnnn 162180
nnnnnnnnnn nnnnnnnnnn nnnnnnnnnn nnnnnnnnnn nnnnnnnnnn nnnnnnnnnn 162240
nnnnnnnnnn nnnnnnnnnn nnnnnnnnnn nnnnnnnnnn nnnnnnnnnn nnnnnnnnnn 162300
nnnnnnnnnn nnnnnnnnnn nnnnnnnnnn nnnnnnnnnn nnnnnnnnnn nnnnnnnnnn 162360
nnnnnnnnnn nnnnnnnnnn nnnnnnnnnn nnnnnnnnnn nnnnnnnnnn nnnnnnnnnn 162420
nnnnnnnnnn nnnnnnnnnn nnnnnnnnnn nnnnnnnnnn nnnnnnnnnn nnnnnnnnnn 162480
nnnnnnnnnn nnnnnnnnnn nnnnnnnnnn nnnnnnnnnn nnnnnnnnnn nnnnnnnnnn 162540

-continued nnnnnnnnnn nnnnnnnnnn nnnnnnnnnn nnnnnnnnnn nnnnnnnnnn nnnnnnnnnn 162600
nnnnnnnnnn nnnnnnnnnn nnnnnnnnnn nnnnnnnnnn nnnnnnnnnn nnnnnnnnnn 162660
nnnnnnnnnn nnnnnnnnnn nnnnnnnnnn nnnnnnnnnn nnnnnnnnnn nnnnnnnnnn 162720
nnnnnnnnnn nnnnnnnnnn nnnnnnnnnn nnnnnnnnnn nnnnnnnnnn nnnnnnnnnn 162780
nnnnnnnnnn nnnnnnnnnn nnnnnnnnnn nnnnnnnnnn nnnnnnnnnn nnnnnnnnnn 162840
nnnnnnnnnn nnnnnnnnnn nnnnnnnnnn nnnnnnnnnn nnnnnnnnnn nnnnnnnnnn 162900
nnnnnnnnnn nnnnnnnnnn nnnnnnnnnn nnnnnnnnnn nnnnnnnnnn nnnnnnnnnn 162960
nnnnnnnnnn nnnnnnnnnn nnnnnnnnnn nnnnnnnnnn nnnnnnnnnn nnnnnnnnnn 163020
nnnnnnnnnn nnnnnnnnnn nnnnnnnnnn nnnnnnnnnn nnnnnnnnnn nnnnnnnnnn 163080
nnnnnnnnnn nnnnnnnnnn nnnnnnnnnn nnnnnnnnnn nnnnnnnnnn nnnnnnnnnn 163140
nnnnnnnnnn nnnnnnnnnn nnnnnnnnnn nnnnnnnnnn nnnnnnnnnn nnnnnnnnnn 163200
nnnnnnnnnn nnnnnnnnnn nnnnnnnnnn nnnnnnnnnn nnnnnnnnnn nnnnnnnnnn 163260
nnnnnnnnnn nnnnnnnnnn nnnnnnnnnn nnnnnnnnnn nnnnnnnnnn nnnnnnnnnn 163320
nnnnnnnnnn nnnnnnnnnn nnnnnnnnnn nnnnnnnnnn nnnnnnnnnn nnnnnnnnnn 163380
nnnnnnnnnn nnnnnnnnnn nnnnnnnnnn nnnnnnnnnn nnnnnnnnnn nnnnnnnnnn 163440
nnnnnnnnnn nnnnnnnnnn nnnnnnnnnn nnnnnnnnnn nnnnnnnnnn nnnnnnnnnn 163500
nnnnnnnnnn nnnnnnnnnn nnnnnnnnnn nnnnnnnnnn nnnnnnnnnn nnnnnnnnnn 163560
nnnnnnnnnn nnnnnnnnnn nnnnnnnnnn nnnnnnnnnn nnnnnnnnnn nnnnnnnnnn 163620
nnnnnnnnnn nnnnnnnnnn nnnnnnnnnn nnnnnnnnnn nnnnnnnnnn nnnnnnnnnn 163680
nnnnnnnnnn nnnnnnnnnn nnnnnnnnnn nnnnnnnnnn nnnnnnnnnn nnnnnnnnnn 163740
nnnnnnnnnn nnnnnnnnnn nnnnnnnnnn nnnnnnnnnn nnnnnnnnnn nnnnnnnnnn 163800
nnnnnnnnnn nnnnnnnnnn nnnnnnnnnn nnnnnnnnnn nnnnnnnnnn nnnnnnnnnn 163860
nnnnnnnnnn nnnnnnnnnn nnnnnnnnnn nnnnnnnnnn nnnnnnnnnn nnnnnnnnnn 163920
nnnnnnnnnn nnnnnnnnnn nnnnnnnnnn nnnnnnnnnn nnnnnnnnnn nnnnnnnnnn 163980
nnnnnnnnnn nnnnnnnnnn nnnnnnnnnn nnnnnnnnnn nnnnnnnnnn nnnnnnnnnn 164040
nnnnnnnnnn nnnnnnnnnn nnnnnnnnnn nnnnnnnnnn nnnnnnnnnn nnnnnnnnnn 164100
nnnnnnnnnn nnnnnnnnnn nnnnnnnnnn nnnnnnnnnn nnnnnnnnnn nnnnnnnnnn 164160
nnnnnnnnnn nnnnnnnnnn nnnnnnnnnn nnnnnnnnnn nnnnnnnnnn nnnnnnnnnn 164220
nnnnnnnnnn nnnnnnnnnn nnnnnnnnnn nnnnnnnnnn nnnnnnnnnn nnnnnnnnnn 164280
nnnnnnnnnn nnnnnnnnnn nnnnnnnnnn nnnnnnnnnn nnnnnnnnnn nnnnnnnnnn 164340
nnnnnnnnnn nnnnnnnnnn nnnnnnnnnn nnnnnnnnnn nnnnnnnnnn nnnnnnnnnn 164400
nnnnnnnnnn nnnnnnnnnn nnnnnnnnnn nnnnnnnnnn nnnnnnnnnn nnnnnnnnnn 164460
nnnnnnnnnn nnnnnnnnnn nnnnnnnnnn nnnnnnnnnn nnnnnnnnnn nnnnnnnnnn 164520
nnnnnnnnnn nnnnnnnnnn nnnnnnnnnn nnnnnnnnnn nnnnnnnnnn nnnnnnnnnn 164580
nnnnnnnnnn nnnnnnnnnn nnnnnnnnnn nnnnnnnnnn nnnnnnnnnn nnnnnnnnnn 164640
nnnnnnnnnn nnnnnnnnnn nnnnnnnnnn nnnnnnnnnn nnnnnnnnnn nnnnnnnnnn 164700
nnnnnnnnnn nnnnnnnnnn nnnnnnnnnn nnnnnnnnnn nnnnnnnnnn nnnnnnnnnn 164760
nnnnnnnnnn nnnnnnnnnn nnnnnnnnnn nnnnnnnnnn nnnnnnnnnn nnnnnnnnnn 164820
nnnnnnnnnn nnnnnnnnnn nnnnnnnnnn nnnnnnnnnn nnnnnnnnnn nnnnnnnnnn 164880

-continued nnnnnnnnnn nnnnnnnnnn nnnnnnnnnn nnnnnnnnnn nnnnnnnnnn nnnnnnnnnn 164940
nnnnnnnnnn nnnnnnnnnn nnnnnnnnnn nnnnnnnnnn nnnnnnnnnn nnnnnnnnnn 165000
nnnnnnnnnn nnnnnnnnnn nnnnnnnnnn nnnnnnnnnn nnnnnnnnnn nnnnnnnnnn 165060
nnnnnnnnnn nnnnnnnnnn nnnnnnnnnn nnnnnnnnnn nnnnnnnnnn nnnnnnnnnn 165120
nnnnnnnnnn nnnnnnnnnn nnnnnnnnnn nnnnnnnnnn nnnnnnnnnn nnnnnnnnnn 165180
nnnnnnnnnn nnnnnnnnnn nnnnnnnnnn nnnnnnnnnn nnnnnnnnnn nnnnnnnnnn 165240
nnnnnnnnnn nnnnnnnnnn nnnnnnnnnn nnnnnnnnnn nnnnnnnnnn nnnnnnnnnn 165300
nnnnnnnnnn nnnnnnnnnn nnnnnnnnnn nnnnnnnnnn nnnnnnnnnn nnnnnnnnnn 165360
nnnnnnnnnn nnnnnnnnnn nnnnnnnnnn nnnnnnnnnn nnnnnnnnnn nnnnnnnnnn 165420
nnnnnnnnnn nnnnnnnnnn nnnnnnnnnn nnnnnnnnnn nnnnnnnnnn nnnnnnnnnn 165480
nnnnnnnnnn nnnnnnnnnn nnnnnnnnnn nnnnnnnnnn nnnnnnnnnn nnnnnnnnnn 165540
nnnnnnnnnn nnnnnnnnnn nnnnnnnnnn nnnnnnnnnn nnnnnnnnnn nnnnnnnnnn 165600
nnnnnnnnnn nnnnnnnnnn nnnnnnnnnn nnnnnnnnnn nnnnnnnnnn nnnnnnnnnn 165660
nnnnnnnnnn nnnnnnnnnn nnnnnnnnnn nnnnnnnnnn nnnnnnnnnn nnnnnnnnnn 165720
nnnnnnnnnn nnnnnnnnnn nnnnnnnnnn nnnnnnnnnn nnnnnnnnnn nnnnnnnnnn 165780
nnnnnnnnnn nnnnnnnnnn nnnnnnnnnn nnnnnnnnnn nnnnnnnnnn nnnnnnnnnn 165840
nnnnnnnnnn nnnnnnnnnn nnnnnnnnnn nnnnnnnnnn nnnnnnnnnn nnnnnnnnnn 165900
nnnnnnnnnn nnnnnnnnnn nnnnnnnnnn nnnnnnnnnn nnnnnnnnnn nnnnnnnnnn 165960
nnnnnnnnnn nnnnnnnnnn nnnnnnnnnn nnnnnnnnnn nnnnnnnnnn nnnnnnnnnn 166020
nnnnnnnnnn nnnnnnnnnn nnnnnnnnnn nnnnnnnnnn nnnnnnnnnn nnnnnnnnnn 166080
nnnnnnnnnn nnnnnnnnnn nnnnnnnnnn nnnnnnnnnn nnnnnnnnnn nnnnnnnnnn 166140
nnnnnnnnnn nnnnnnnnnn nnnnnnnnnn nnnnnnnnnn nnnnnnnnnn nnnnnnnnnn 166200
nnnnnnnnnn nnnnnnnnnn nnnnnnnnnn nnnnnnnnnn nnnnnnnnnn nnnnnnnnnn 166260
nnnnnnnnnn nnnnnnnnnn nnnnnnnnnn nnnnnnnnnn nnnnnnnnnn nnnnnnnnnn 166320
nnnnnnnnnn nnnnnnnnnn nnnnnnnnnn nnnnnnnnnn nnnnnnnnnn nnnnnnnnnn 166380
nnnnnnnnnn nnnnnnnnnn nnnnnnnnnn nnnnnnnnnn nnnnnnnnnn nnnnnnnnnn 166440
nnnnnnnnnn nnnnnnnnnn nnnnnnnnnn nnnnnnnnnn nnnnnnnnnn nnnnnnnnnn 166500
nnnnnnnnnn nnnnnnnnnn nnnnnnnnnn nnnnnnnnnn nnnnnnnnnn nnnnnnnnnn 166560
nnnnnnnnnn nnnnnnnnnn nnnnnnnnnn nnnnnnnnnn nnnnnnnnnn nnnnnnnnnn 166620
nnnnnnnnnn nnnnnnnnnn nnnnnnnnnn nnnnnnnnnn nnnnnnnnnn nnnnnnnnnn 166680
nnnnnnnnnn nnnnnnnnnn nnnnnnnnnn nnnnnnnnnn nnnnnnnnnn nnnnnnnnnn 166740
nnnnnnnnnn nnnnnnnnnn nnnnnnnnnn nnnnnnnnnn nnnnnnnnnn nnnnnnnnnn 166800
nnnnnnnnnn nnnnnnnnnn nnnnnnnnnn nnnnnnnnnn nnnnnnnnnn nnnnnnnnnn 166860
nnnnnnnnnn nnnnnnnnnn nnnnnnnnnn nnnnnnnnnn nnnnnnnnnn nnnnnnnnnn 166920
nnnnnnnnnn nnnnnnnnnn nnnnnnnnnn nnnnnnnnnn nnnnnnnnnn nnnnnnnnnn 166980
nnnnnnnnnn nnnnnnnnnn nnnnnnnnnn nnnnnnnnnn nnnnnnnnnn nnnnnnnnnn 167040
nnnnnnnnnn nnnnnnnnnn nnnnnnnnnn nnnnnnnnnn nnnnnnnnnn nnnnnnnnnn 167100
nnnnnnnnnn nnnnnnnnnn nnnnnnnnnn nnnnnnnnnn nnnnnnnnnn nnnnnnnnnn 167160
nnnnnnnnnn nnnnnnnnnn nnnnnnnnnn nnnnnnnnnn nnnnnnnnnn nnnnnnnnnn 167220
nnnnnnnnnn nnnnnnnnnn nnnnnnnnnn nnnnnnnnnn nnnnnnnnnn nnnnnnnnnn 167280

-continued nnnnnnnnnn nnnnnnnnnn nnnnnnnnnn nnnnnnnnnn nnnnnnnnnn nnnnnnnnnn 167340
nnnnnnnnnn nnnnnnnnnn nnnnnnnnnn nnnnnnnnnn nnnnnnnnnn nnnnnnnnnn 167400
nnnnnnnnnn nnnnnnnnnn nnnnnnnnnn nnnnnnnnnn nnnnnnnnnn nnnnnnnnnn 167460
nnnnnnnnnn nnnnnnnnnn nnnnnnnnnn nnnnnnnnnn nnnnnnnnnn nnnnnnnnnn 167520
nnnnnnnnnn nnnnnnnnnn nnnnnnnnnn nnnnnnnnnn nnnnnnnnnn nnnnnnnnnn 167580
nnnnnnnnnn nnnnnnnnnn nnnnnnnnnn nnnnnnnnnn nnnnnnnnnn nnnnnnnnnn 167640
nnnnnnnnnn nnnnnnnnnn nnnnnnnnnn nnnnnnnnnn nnnnnnnnnn nnnnnnnnnn 167700
nnnnnnnnnn nnnnnnnnnn nnnnnnnnnn nnnnnnnnnn nnnnnnnnnn nnnnnnnnnn 167760
nnnnnnnnnn nnnnnnnnnn nnnnnnnnnn nnnnnnnnnn nnnnnnnnnn nnnnnnnnnn 167820
nnnnnnnnnn nnnnnnnnnn nnnnnnnnnn nnnnnnnnnn nnnnnnnnnn nnnnnnnnnn 167880
nnnnnnnnnn nnnnnnnnnn nnnnnnnnnn nnnnnnnnnn nnnnnnnnnn nnnnnnnnnn 167940
nnnnnnnnnn nnnnnnnnnn nnnnnnnnnn nnnnnnnnnn nnnnnnnnnn nnnnnnnnnn 168000
nnnnnnnnnn nnnnnnnnnn nnnnnnnnnn nnnnnnnnnn nnnnnnnnnn nnnnnnnnnn 168060
nnnnnnnnnn nnnnnnnnnn nnnnnnnnnn nnnnnnnnnn nnnnnnnnnn nnnnnnnnnn 168120
nnnnnnnnnn nnnnnnnnnn nnnnnnnnnn nnnnnnnnnn nnnnnnnnnn nnnnnnnnnn 168180
nnnnnnnnnn nnnnnnnnnn nnnnnnnnnn nnnnnnnnnn nnnnnnnnnn nnnnnnnnnn 168240
nnnnnnnnnn nnnnnnnnnn nnnnnnnnnn nnnnnnnnnn nnnnnnnnnn nnnnnnnnnn 168300
nnnnnnnnnn nnnnnnnnnn nnnnnnnnnn nnnnnnnnnn nnnnnnnnnn nnnnnnnnnn 168360
nnnnnnnnnn nnnnnnnnnn nnnnnnnnnn nnnnnnnnnn nnnnnnnnnn nnnnnnnnnn 168420
nnnnnnnnnn nnnnnnnnnn nnnnnnnnnn nnnnnnnnnn nnnnnnnnnn nnnnnnnnnn 168480
nnnnnnnnnn nnnnnnnnnn nnnnnnnnnn nnnnnnnnnn nnnnnnnnnn nnnnnnnnnn 168540
nnnnnnnnnn nnnnnnnnnn nnnnnnnnnn nnnnnnnnnn nnnnnnnnnn nnnnnnnnnn 168600
nnnnnnnnnn nnnnnnnnnn nnnnnnnnnn nnnnnnnnnn nnnnnnnnnn nnnnnnnnnn 168660
nnnnnnnnnn nnnnnnnnnn nnnnnnnnnn nnnnnnnnnn nnnnnnnnnn nnnnnnnnnn 168720
nnnnnnnnnn nnnnnnnnnn nnnnnnnnnn nnnnnnnnnn nnnnnnnnnn nnnnnnnnnn 168780
nnnnnnnnnn nnnnnnnnnn nnnnnnnnnn nnnnnnnnnn nnnnnnnnnn nnnnnnnnnn 168840
nnnnnnnnnn nnnnnnnnnn nnnnnnnnnn nnnnnnnnnn nnnnnnnnnn nnnnnnnnnn 168900
nnnnnnnnnn nnnnnnnnnn nnnnnnnnnn nnnnnnnnnn nnnnnnnnnn nnnnnnnnnn 168960
nnnnnnnnnn nnnnnnnnnn nnnnnnnnnn nnnnnnnnnn nnnnnnnnnn nnnnnnnnnn 169020
nnnnnnnnnn nnnnnnnnnn nnnnnnnnnn nnnnnnnnnn nnnnnnnnnn nnnnnnnnnn 169080
nnnnnnnnnn nnnnnnnnnn nnnnnnnnnn nnnnnnnnnn nnnnnnnnnn nnnnnnnnnn 169140
nnnnnnnnnn nnnnnnnnnn nnnnnnnnnn nnnnnnnnnn nnnnnnnnnn nnnnnnnnnn 169200
nnnnnnnnnn nnnnnnnnnn nnnnnnnnnn nnnnnnnnnn nnnnnnnnnn nnnnnnnnnn 169260
nnnnnnnnnn nnnnnnnnnn nnnnnnnnnn nnnnnnnnnn nnnnnnnnnn nnnnnnnnnn 169320
nnnnnnnnnn nnnnnnnnnn nnnnnnnnnn nnnnnnnnnn nnnnnnnnnn nnnnnnnnnn 169380
nnnnnnnnnn nnnnnnnnnn nnnnnnnnnn nnnnnnnnnn nnnnnnnnnn nnnnnnnnnn 169440
nnnnnnnnnn nnnnnnnnnn nnnnnnnnnn nnnnnnnnnn nnnnnnnnnn nnnnnnnnnn 169500
nnnnnnnnnn nnnnnnnnnn nnnnnnnnnn nnnnnnnnnn nnnnnnnnnn nnnnnnnnnn 169560
nnnnnnnnnn nnnnnnnnnn nnnnnnnnnn nnnnnnnnnn nnnnnnnnnn nnnnnnnnnn 169620

-continued nnnnnnnnnn nnnnnnnnnn nnnnnnnnnn nnnnnnnnnn nnnnnnnnnn nnnnnnnnnn 169680
nnnnnnnnnn nnnnnnnnnn nnnnnnnnnn nnnnnnnnnn nnnnnnnnnn nnnnnnnnnn 169740
nnnnnnnnnn nnnnnnnnnn nnnnnnnnnn nnnnnnnnnn nnnnnnnnnn nnnnnnnnnn 169800
nnnnnnnnnn nnnnnnnnnn nnnnnnnnnn nnnnnnnnnn nnnnnnnnnn nnnnnnnnnn 169860
nnnnnnnnnn nnnnnnnnnn nnnnnnnnnn nnnnnnnnnn nnnnnnnnnn nnnnnnnnnn 169920
nnnnnnnnnn nnnnnnnnnn nnnnnnnnnn nnnnnnnnnn nnnnnnnnnn nnnnnnnnnn 169980
nnnnnnnnnn nnnnnnnnnn nnnnnnnnnn nnnnnnnnnn nnnnnnnnnn nnnnnnnnnn 170040
nnnnnnnnnn nnnnnnnnnn nnnnnnnnnn nnnnnnnnnn nnnnnnnnnn nnnnnnnnnn 170100
nnnnnnnnnn nnnnnnnnnn nnnnnnnnnn nnnnnnnnnn nnnnnnnnnn nnnnnnnnnn 170160
nnnnnnnnnn nnnnnnnnnn nnnnnnnnnn nnnnnnnnnn nnnnnnnnnn nnnnnnnnnn 170220
nnnnnnnnnn nnnnnnnnnn nnnnnnnnnn nnnnnnnnnn nnnnnnnnnn nnnnnnnnnn 170280
nnnnnnnnnn nnnnnnnnnn nnnnnnnnnn nnnnnnnnnn nnnnnnnnnn nnnnnnnnnn 170340
nnnnnnnnnn nnnnnnnnnn nnnnnnnnnn nnnnnnnnnn nnnnnnnnnn nnnnnnnnnn 170400
nnnnnnnnnn nnnnnnnnnn nnnnnnnnnn nnnnnnnnnn nnnnnnnnnn nnnnnnnnnn 170460
nnnnnnnnnn nnnnnnnnnn nnnnnnnnnn nnnnnnnnnn nnnnnnnnnn nnnnnnnnnn 170520
nnnnnnnnnn nnnnnnnnnn nnnnnnnnnn nnnnnnnnnn nnnnnnnnnn nnnnnnnnnn 170580
nnnnnnnnnn nnnnnnnnnn nnnnnnnnnn nnnnnnnnnn nnnnnnnnnn nnnnnnnnnn 170640
nnnnnnnnnn nnnnnnnnnn nnnnnnnnnn nnnnnnnnnn nnnnnnnnnn nnnnnnnnnn 170700
nnnnnnnnnn nnnnnnnnnn nnnnnnnnnn nnnnnnnnnn nnnnnnnnnn nnnnnnnnnn 170760
nnnnnnnnnn nnnnnnnnnn nnnnnnnnnn nnnnnnnnnn nnnnnnnnnn nnnnnnnnnn 170820
nnnnnnnnnn nnnnnnnnnn nnnnnnnnnn nnnnnnnnnn nnnnnnnnnn nnnnnnnnnn 170880
nnnnnnnnnn nnnnnnnnnn nnnnnnnnnn nnnnnnnnnn nnnnnnnnnn nnnnnnnnnn 170940
nnnnnnnnnn nnnnnnnnnn nnnnnnnnnn nnnnnnnnnn nnnnnnnnnn nnnnnnnnnn 171000
nnnnnnnnnn nnnnnnnnnn nnnnnnnnnn nnnnnnnnnn nnnnnnnnnn nnnnnnnnnn 171060
nnnnnnnnnn nnnnnnnnnn nnnnnnnnnn nnnnnnnnnn nnnnnnnnnn nnnnnnnnnn 171120
nnnnnnnnnn nnnnnnnnnn nnnnnnnnnn nnnnnnnnnn nnnnnnnnnn nnnnnnnnnn 171180
nnnnnnnnnn nnnnnnnnnn nnnnnnnnnn nnnnnnnnnn nnnnnnnnnn nnnnnnnnnn 171240
nnnnnnnnnn nnnnnnnnnn nnnnnnnnnn nnnnnnnnnn nnnnnnnnnn nnnnnnnnnn 171300
nnnnnnnnnn nnnnnnnnnn nnnnnnnnnn nnnnnnnnnn nnnnnnnnnn nnnnnnnnnn 171360
nnnnnnnnnn nnnnnnnnnn nnnnnnnnnn nnnnnnnnnn nnnnnnnnnn nnnnnnnnnn 171420
nnnnnnnnnn nnnnnnnnnn nnnnnnnnnn nnnnnnnnnn nnnnnnnnnn nnnnnnnnnn 171480
nnnnnnnnnn nnnnnnnnnn nnnnnnnnnn nnnnnnnnnn nnnnnnnnnn nnnnnnnnnn 171540
nnnnnnnnnn nnnnnnnnnn nnnnnnnnnn nnnnnnnnnn nnnnnnnnnn nnnnnnnnnn 171600
nnnnnnnnnn nnnnnnnnnn nnnnnnnnnn nnnnnnnnnn nnnnnnnnnn nnnnnnnnnn 171660
nnnnnnnnnn nnnnnnnnnn nnnnnnnnnn nnnnnnnnnn nnnnnnnnnn nnnnnnnnnn 171720
nnnnnnnnnn nnnnnnnnnn nnnnnnnnnn nnnnnnnnnn nnnnnnnnnn nnnnnnnnnn 171780
nnnnnnnnnn nnnnnnnnnn nnnnnnnnnn nnnnnnnnnn nnnnnnnnnn nnnnnnnnnn 171840
nnnnnnnnnn nnnnnnnnnn nnnnnnnnnn nnnnnnnnnn nnnnnnnnnn nnnnnnnnnn 171900
nnnnnnnnnn nnnnnnnnnn nnnnnnnnnn nnnnnnnnnn nnnnnnnnnn nnnnnnnnnn 171960
nnnnnnnnnn nnnnnnnnnn nnnnnnnnnn nnnnnnnnnn nnnnnnnnnn nnnnnnnnnn 172020

-continued nnnnnnnnnn nnnnnnnnnn nnnnnnnnnn nnnnnnnnnn nnnnnnnnnn nnnnnnnnnn 172080
nnnnnnnnnn nnnnnnnnnn nnnnnnnnnn nnnnnnnnnn nnnnnnnnnn nnnnnnnnnn 172140
nnnnnnnnnn nnnnnnnnnn nnnnnnnnnn nnnnnnnnnn nnnnnnnnnn nnnnnnnnnn 172200
nnnnnnnnnn nnnnnnnnnn nnnnnnnnnn nnnnnnnnnn nnnnnnnnnn nnnnnnnnnn 172260
nnnnnnnnnn nnnnnnnnnn nnnnnnnnnn nnnnnnnnnn nnnnnnnnnn nnnnnnnnnn 172320
nnnnnnnnnn nnnnnnnnnn nnnnnnnnnn nnnnnnnnnn nnnnnnnnnn nnnnnnnnnn 172380
nnnnnnnnnn nnnnnnnnnn nnnnnnnnnn nnnnnnnnnn nnnnnnnnnn nnnnnnnnnn 172440
nnnnnnnnnn nnnnnnnnnn nnnnnnnnnn nnnnnnnnnn nnnnnnnnnn nnnnnnnnnn 172500
nnnnnnnnnn nnnnnnnnnn nnnnnnnnnn nnnnnnnnnn nnnnnnnnnn nnnnnnnnnn 172560
nnnnnnnnnn nnnnnnnnnn nnnnnnnnnn nnnnnnnnnn nnnnnnnnnn nnnnnnnnnn 172620
nnnnnnnnnn nnnnnnnnnn nnnnnnnnnn nnnnnnnnnn nnnnnnnnnn nnnnnnnnnn 172680
nnnnnnnnnn nnnnnnnnnn nnnnnnnnnn nnnnnnnnnn nnnnnnnnnn nnnnnnnnnn 172740
nnnnnnnnnn nnnnnnnnnn nnnnnnnnnn nnnnnnnnnn nnnnnnnnnn nnnnnnnnnn 172800
nnnnnnnnnn nnnnnnnnnn nnnnnnnnnn nnnnnnnnnn nnnnnnnnnn nnnnnnnnnn 172860
nnnnnnnnnn nnnnnnnnnn nnnnnnnnnn nnnnnnnnnn nnnnnnnnnn nnnnnnnnnn 172920
nnnnnnnnnn nnnnnnnnnn nnnnnnnnnn nnnnnnnnnn nnnnnnnnnn nnnnnnnnnn 172980
nnnnnnnnnn nnnnnnnnnn nnnnnnnnnn nnnnnnnnnn nnnnnnnnnn nnnnnnnnnn 173040
nnnnnnnnnn nnnnnnnnnn nnnnnnnnnn nnnnnnnnnn nnnnnnnnnn nnnnnnnnnn 173100
nnnnnnnnnn nnnnnnnnnn nnnnnnnnnn nnnnnnnnnn nnnnnnnnnn nnnnnnnnnn 173160
nnnnnnnnnn nnnnnnnnnn nnnnnnnnnn nnnnnnnnnn nnnnnnnnnn nnnnnnnnnn 173220
nnnnnnnnnn nnnnnnnnnn nnnnnnnnnn nnnnnnnnnn nnnnnnnnnn nnnnnnnnnn 173280
nnnnnnnnnn nnnnnnnnnn nnnnnnnnnn nnnnnnnnnn nnnnnnnnnn nnnnnnnnnn 173340
nnnnnnnnnn nnnnnnnnnn nnnnnnnnnn nnnnnnnnnn nnnnnnnnnn nnnnnnnnnn 173400
nnnnnnnnnn nnnnnnnnnn nnnnnnnnnn nnnnnnnnnn nnnnnnnnnn nnnnnnnnnn 173460
nnnnnnnnnn nnnnnnnnnn nnnnnnnnnn nnnnnnnnnn nnnnnnnnnn nnnnnnnnnn 173520
nnnnnnnnnn nnnnnnnnnn nnnnnnnnnn nnnnnnnnnn nnnnnnnnnn nnnnnnnnnn 173580
nnnnnnnnnn nnnnnnnnnn nnnnnnnnnn nnnnnnnnnn nnnnnnnnnn nnnnnnnnnn 173640
nnnnnnnnnn nnnnnnnnnn nnnnnnnnnn nnnnnnnnnn nnnnnnnnnn nnnnnnnnnn 173700
nnnnnnnnnn nnnnnnnnnn nnnnnnnnnn nnnnnnnnnn nnnnnnnnnn nnnnnnnnnn 173760
nnnnnnnnnn nnnnnnnnnn nnnnnnnnnn nnnnnnnnnn nnnnnnnnnn nnnnnnnnnn 173820
nnnnnnnnnn nnnnnnnnnn nnnnnnnnnn nnnnnnnnnn nnnnnnnnnn nnnnnnnnnn 173880
nnnnnnnnnn nnnnnnnnnn nnnnnnnnnn nnnnnnnnnn nnnnnnnnnn nnnnnnnnnn 173940
nnnnnnnnnn nnnnnnnnnn nnnnnnnnnn nnnnnnnnnn nnnnnnnnnn nnnnnnnnnn 174000
nnnnnnnnnn nnnnnnnnnn nnnnnnnnnn nnnnnnnnnn nnnnnnnnnn nnnnnnnnnn 174060
nnnnnnnnnn nnnnnnnnnn nnnnnnnnnn nnnnnnnnnn nnnnnnnnnn nnnnnnnnnn 174120
nnnnnnnnnn nnnnnnnnnn nnnnnnnnnn nnnnnnnnnn nnnnnnnnnn nnnnnnnnnn 174180
nnnnnnnnnn nnnnnnnnnn nnnnnnnnnn nnnnnnnnnn nnnnnnnnnn nnnnnnnnnn 174240
nnnnnnnnnn nnnnnnnnnn nnnnnnnnnn nnnnnnnnnn nnnnnnnnnn nnnnnnnnnn 174300
nnnnnnnnnn nnnnnnnnnn nnnnnnnnnn nnnnnnnnnn nnnnnnnnnn nnnnnnnnnn 174360

-continued nnnnnnnnnn nnnnnnnnnn nnnnnnnnnn nnnnnnnnnn nnnnnnnnnn nnnnnnnnnn 174420
nnnnnnnnnn nnnnnnnnnn nnnnnnnnnn nnnnnnnnnn nnnnnnnnnn nnnnnnnnnn 174480
nnnnnnnnnn nnnnnnnnnn nnnnnnnnnn nnnnnnnnnn nnnnnnnnnn nnnnnnnnnn 174540
nnnnnnnnnn nnnnnnnnnn nnnnnnnnnn nnnnnnnnnn nnnnnnnnnn nnnnnnnnnn 174600
nnnnnnnnnn nnnnnnnnnn nnnnnnnnnn nnnnnnnnnn nnnnnnnnnn nnnnnnnnnn 174660
nnnnnnnnnn nnnnnnnnnn nnnnnnnnnn nnnnnnnnnn nnnnnnnnnn nnnnnnnnnn 174720
nnnnnnnnnn nnnnnnnnnn nnnnnnnnnn nnnnnnnnnn nnnnnnnnnn nnnnnnnnnn 174780
nnnnnnnnnn nnnnnnnnnn nnnnnnnnnn nnnnnnnnnn nnnnnnnnnn nnnnnnnnnn 174840
nnnnnnnnnn nnnnnnnnnn nnnnnnnnnn nnnnnnnnnn nnnnnnnnnn nnnnnnnnnn 174900
nnnnnnnnnn nnnnnnnnnn nnnnnnnnnn nnnnnnnnnn nnnnnnnnnn nnnnnnnnnn 174960
nnnnnnnnnn nnnnnnnnnn nnnnnnnnnn nnnnnnnnnn nnnnnnnnnn nnnnnnnnnn 175020
nnnnnnnnnn nnnnnnnnnn nnnnnnnnnn nnnnnnnnnn nnnnnnnnnn nnnnnnnnnn 175080
nnnnnnnnnn nnnnnnnnnn nnnnnnnnnn nnnnnnnnnn nnnnnnnnnn nnnnnnnnnn 175140
nnnnnnnnnn nnnnnnnnnn nnnnnnnnnn nnnnnnnnnn nnnnnnnnnn nnnnnnnnnn 175200
nnnnnnnnnn nnnnnnnnnn nnnnnnnnnn nnnnnnnnnn nnnnnnnnnn nnnnnnnnnn 175260
nnnnnnnnnn nnnnnnnnnn nnnnnnnnnn nnnnnnnnnn nnnnnnnnnn nnnnnnnnnn 175320
nnnnnnnnnn nnnnnnnnnn nnnnnnnnnn nnnnnnnnnn nnnnnnnnnn nnnnnnnnnn 175380
nnnnnnnnnn nnnnnnnnnn nnnnnnnnnn nnnnnnnnnn nnnnnnnnnn nnnnnnnnnn 175440
nnnnnnnnnn nnnnnnnnnn nnnnnnnnnn nnnnnnnnnn nnnnnnnnnn nnnnnnnnnn 175500
nnnnnnnnnn nnnnnnnnnn nnnnnnnnnn nnnnnnnnnn nnnnnnnnnn nnnnnnnnnn 175560
nnnnnnnnnn nnnnnnnnnn nnnnnnnnnn nnnnnnnnnn nnnnnnnnnn nnnnnnnnnn 175620
nnnnnnnnnn nnnnnnnnnn nnnnnnnnnn nnnnnnnnnn nnnnnnnnnn nnnnnnnnnn 175680
nnnnnnnnnn nnnnnnnnnn nnnnnnnnnn nnnnnnnnnn nnnnnnnnnn nnnnnnnnnn 175740
nnnnnnnnnn nnnnnnnnnn nnnnnnnnnn nnnnnnnnnn nnnnnnnnnn nnnnnnnnnn 175800
nnnnnnnnnn nnnnnnnnnn nnnnnnnnnn nnnnnnnnnn nnnnnnnnnn nnnnnnnnnn 175860
nnnnnnnnnn nnnnnnnnnn nnnnnnnnnn nnnnnnnnnn nnnnnnnnnn nnnnnnnnnn 175920
nnnnnnnnnn nnnnnnnnnn nnnnnnnnnn nnnnnnnnnn nnnnnnnnnn nnnnnnnnnn 175980
nnnnnnnnnn nnnnnnnnnn nnnnnnnnnn nnnnnnnnnn nnnnnnnnnn nnnnnnnnnn 176040
nnnnnnnnnn nnnnnnnnnn nnnnnnnnnn nnnnnnnnnn nnnnnnnnnn nnnnnnnnnn 176100
nnnnnnnnnn nnnnnnnnnn nnnnnnnnnn nnnnnnnnnn nnnnnnnnnn nnnnnnnnnn 176160
nnnnnnnnnn nnnnnnnnnn nnnnnnnnnn nnnnnnnnnn nnnnnnnnnn nnnnnnnnnn 176220
nnnnnnnnnn nnnnnnnnnn nnnnnnnnnn nnnnnnnnnn nnnnnnnnnn nnnnnnnnnn 176280
nnnnnnnnnn nnnnnnnnnn nnnnnnnnnn nnnnnnnnnn nnnnnnnnnn nnnnnnnnnn 176340
nnnnnnnnnn nnnnnnnnnn nnnnnnnnnn nnnnnnnnnn nnnnnnnnnn nnnnnnnnnn 176400
nnnnnnnnnn nnnnnnnnnn nnnnnnnnnn nnnnnnnnnn nnnnnnnnnn nnnnnnnnnn 176460
nnnnnnnnnn nnnnnnnnnn nnnnnnnnnn nnnnnnnnnn nnnnnnnnnn nnnnnnnnnn 176520
nnnnnnnnnn nnnnnnnnnn nnnnnnnnnn nnnnnnnnnn nnnnnnnnnn nnnnnnnnnn 176580
nnnnnnnnnn nnnnnnnnnn nnnnnnnnnn nnnnnnnnnn nnnnnnnnnn nnnnnnnnnn 176640
nnnnnnnnnn nnnnnnnnnn nnnnnnnnnn nnnnnnnnnn nnnnnnnnnn nnnnnnnnnn 176700
nnnnnnnnnn nnnnnnnnnn nnnnnnnnnn nnnnnnnnnn nnnnnnnnnn nnnnnnnnnn 176760

-continued nnnnnnnnnn nnnnnnnnnn nnnnnnnnnn nnnnnnnnnn nnnnnnnnnn nnnnnnnnnn 176820
nnnnnnnnnn nnnnnnnnnn nnnnnnnnnn nnnnnnnnnn nnnnnnnnnn nnnnnnnnnn 176880
nnnnnnnnnn nnnnnnnnnn nnnnnnnnnn nnnnnnnnnn nnnnnnnnnn nnnnnnnnnn 176940
nnnnnnnnnn nnnnnnnnnn nnnnnnnnnn nnnnnnnnnn nnnnnnnnnn nnnnnnnnnn 177000
nnnnnnnnnn nnnnnnnnnn nnnnnnnnnn nnnnnnnnnn nnnnnnnnnn nnnnnnnnnn 177060
nnnnnnnnnn nnnnnnnnnn nnnnnnnnnn nnnnnnnnnn nnnnnnnnnn nnnnnnnnnn 177120
nnnnnnnnnn nnnnnnnnnn nnnnnnnnnn nnnnnnnnnn nnnnnnnnnn nnnnnnnnnn 177180
nnnnnnnnnn nnnnnnnnnn nnnnnnnnnn nnnnnnnnnn nnnnnnnnnn nnnnnnnnnn 177240
nnnnnnnnnn nnnnnnnnnn nnnnnnnnnn nnnnnnnnnn nnnnnnnnnn nnnnnnnnnn 177300
nnnnnnnnnn nnnnnnnnnn nnnnnnnnnn nnnnnnnnnn nnnnnnnnnn nnnnnnnnnn 177360
nnnnnnnnnn nnnnnnnnnn nnnnnnnnnn nnnnnnnnnn nnnnnnnnnn nnnnnnnnnn 177420
nnnnnnnnnn nnnnnnnnnn nnnnnnnnnn nnnnnnnnnn nnnnnnnnnn nnnnnnnnnn 177480
nnnnnnnnnn nnnnnnnnnn nnnnnnnnnn nnnnnnnnnn nnnnnnnnnn nnnnnnnnnn 177540
nnnnnnnnnn nnnnnnnnnn nnnnnnnnnn nnnnnnnnnn nnnnnnnnnn nnnnnnnnnn 177600
nnnnnnnnnn nnnnnnnnnn nnnnnnnnnn nnnnnnnnnn nnnnnnnnnn nnnnnnnnnn 177660
nnnnnnnnnn nnnnnnnnnn nnnnnnnnnn nnnnnnnnnn nnnnnnnnnn nnnnnnnnnn 177720
nnnnnnnnnn nnnnnnnnnn nnnnnnnnnn nnnnnnnnnn nnnnnnnnnn nnnnnnnnnn 177780
nnnnnnnnnn nnnnnnnnnn nnnnnnnnnn nnnnnnnnnn nnnnnnnnnn nnnnnnnnnn 177840
nnnnnnnnnn nnnnnnnnnn nnnnnnnnnn nnnnnnnnnn nnnnnnnnnn nnnnnnnnnn 177900
nnnnnnnnnn nnnnnnnnnn nnnnnnnnnn nnnnnnnnnn nnnnnnnnnn nnnnnnnnnn 177960
nnnnnnnnnn nnnnnnnnnn nnnnnnnnnn nnnnnnnnnn nnnnnnnnnn nnnnnnnnnn 178020
nnnnnnnnnn nnnnnnnnnn nnnnnnnnnn nnnnnnnnnn nnnnnnnnnn nnnnnnnnnn 178080
nnnnnnnnnn nnnnnnnnnn nnnnnnnnnn nnnnnnnnnn nnnnnnnnnn nnnnnnnnnn 178140
nnnnnnnnnn nnnnnnnnnn nnnnnnnnnn nnnnnnnnnn nnnnnnnnnn nnnnnnnnnn 178200
nnnnnnnnnn nnnnnnnnnn nnnnnnnnnn nnnnnnnnnn nnnnnnnnnn nnnnnnnnnn 178260
nnnnnnnnnn nnnnnnnnnn nnnnnnnnnn nnnnnnnnnn nnnnnnnnnn nnnnnnnnnn 178320
nnnnnnnnnn nnnnnnnnnn nnnnnnnnnn nnnnnnnnnn nnnnnnnnnn nnnnnnnnnn 178380
nnnnnnnnnn nnnnnnnnnn nnnnnnnnnn nnnnnnnnnn nnnnnnnnnn nnnnnnnnnn 178440
nnnnnnnnnn nnnnnnnnnn nnnnnnnnnn nnnnnnnnnn nnnnnnnnnn nnnnnnnnnn 178500
nnnnnnnnnn nnnnnnnnnn nnnnnnnnnn nnnnnnnnnn nnnnnnnnnn nnnnnnnnnn 178560
nnnnnnnnnn nnnnnnnnnn nnnnnnnnnn nnnnnnnnnn nnnnnnnnnn nnnnnnnnnn 178620
nnnnnnnnnn nnnnnnnnnn nnnnnnnnnn nnnnnnnnnn nnnnnnnnnn nnnnnnnnnn 178680
nnnnnnnnnn nnnnnnnnnn nnnnnnnnnn nnnnnnnnnn nnnnnnnnnn nnnnnnnnnn 178740
nnnnnnnnnn nnnnnnnnnn nnnnnnnnnn nnnnnnnnnn nnnnnnnnnn nnnnnnnnnn 178800
nnnnnnnnnn nnnnnnnnnn nnnnnnnnnn nnnnnnnnnn nnnnnnnnnn nnnnnnnnnn 178860
nnnnnnnnnn nnnnnnnnnn nnnnnnnnnn nnnnnnnnnn nnnnnnnnnn nnnnnnnnnn 178920
nnnnnnnnnn nnnnnnnnnn nnnnnnnnnn nnnnnnnnnn nnnnnnnnnn nnnnnnnnnn 178980
nnnnnnnnnn nnnnnnnnnn nnnnnnnnnn nnnnnnnnnn nnnnnnnnnn nnnnnnnnnn 179040
nnnnnnnnnn nnnnnnnnnn nnnnnnnnnn nnnnnnnnnn nnnnnnnnnn nnnnnnnnnn 179100

-continued nnnnnnnnnn nnnnnnnnnn nnnnnnnnnn nnnnnnnnnn nnnnnnnnnn nnnnnnnnnn 179160
nnnnnnnnnn nnnnnnnnnn nnnnnnnnnn nnnnnnnnnn nnnnnnnnnn nnnnnnnnnn 179220
nnnnnnnnnn nnnnnnnnnn nnnnnnnnnn nnnnnnnnnn nnnnnnnnnn nnnnnnnnnn 179280
nnnnnnnnnn nnnnnnnnnn nnnnnnnnnn nnnnnnnnnn nnnnnnnnnn nnnnnnnnnn 179340
nnnnnnnnnn nnnnnnnnnn nnnnnnnnnn nnnnnnnnnn nnnnnnnnnn nnnnnnnnnn 179400
nnnnnnnnnn nnnnnnnnnn nnnnnnnnnn nnnnnnnnnn nnnnnnnnnn nnnnnnnnnn 179460
nnnnnnnnnn nnnnnnnnnn nnnnnnnnnn nnnnnnnnnn nnnnnnnnnn nnnnnnnnnn 179520
nnnnnnnnnn nnnnnnnnnn nnnnnnnnnn nnnnnnnnnn nnnnnnnnnn nnnnnnnnnn 179580
nnnnnnnnnn nnnnnnnnnn nnnnnnnnnn nnnnnnnnnn nnnnnnnnnn nnnnnnnnnn 179640
nnnnnnnnnn nnnnnnnnnn nnnnnnnnnn nnnnnnnnnn nnnnnnnnnn nnnnnnnnnn 179700
nnnnnnnnnn nnnnnnnnnn nnnnnnnnnn nnnnnnnnnn nnnnnnnnnn nnnnnnnnnn 179760
nnnnnnnnnn nnnnnnnnnn nnnnnnnnnn nnnnnnnnnn nnnnnnnnnn nnnnnnnnnn 179820
nnnnnnnnnn nnnnnnnnnn nnnnnnnnnn nnnnnnnnnn nnnnnnnnnn nnnnnnnnnn 179880
nnnnnnnnnn nnnnnnnnnn nnnnnnnnnn nnnnnnnnnn nnnnnnnnnn nnnnnnnnnn 179940
nnnnnnnnnn nnnnnnnnnn nnnnnnnnnn nnnnnnnnnn nnnnnnnnnn nnnnnnnnnn 180000
nnnnnnnnnn nnnnnnnnnn nnnnnnnnnn nnnnnnnnnn nnnnnnnnnn nnnnnnnnnn 180060
nnnnnnnnnn nnnnnnnnnn nnnnnnnnnn nnnnnnnnnn nnnnnnnnnn nnnnnnnnnn 180120
nnnnnnnnnn nnnnnnnnnn nnnnnnnnnn nnnnnnnnnn nnnnnnnnnn nnnnnnnnnn 180180
nnnnnnnnnn nnnnnnnnnn nnnnnnnnnn nnnnnnnnnn nnnnnnnnnn nnnnnnnnnn 180240
nnnnnnnnnn nnnnnnnnnn nnnnnnnnnn nnnnnnnnnn nnnnnnnnnn nnnnnnnnnn 180300
nnnnnnnnnn nnnnnnnnnn nnnnnnnnnn nnnnnnnnnn nnnnnnnnnn nnnnnnnnnn 180360
nnnnnnnnnn nnnnnnnnnn nnnnnnnnnn nnnnnnnnnn nnnnnnnnnn nnnnnnnnnn 180420
nnnnnnnnnn nnnnnnnnnn nnnnnnnnnn nnnnnnnnnn nnnnnnnnnn nnnnnnnnnn 180480
nnnnnnnnnn nnnnnnnnnn nnnnnnnnnn nnnnnnnnnn nnnnnnnnnn nnnnnnnnnn 180540
nnnnnnnnnn nnnnnnnnnn nnnnnnnnnn nnnnnnnnnn nnnnnnnnnn nnnnnnnnnn 180600
nnnnnnnnnn nnnnnnnnnn nnnnnnnnnn nnnnnnnnnn nnnnnnnnnn nnnnnnnnnn 180660
nnnnnnnnnn nnnnnnnnnn nnnnnnnnnn nnnnnnnnnn nnnnnnnnnn nnnnnnnnnn 180720
nnnnnnnnnn nnnnnnnnnn nnnnnnnnnn nnnnnnnnnn nnnnnnnnnn nnnnnnnnnn 180780
nnnnnnnnnn nnnnnnnnnn nnnnnnnnnn nnnnnnnnnn nnnnnnnnnn nnnnnnnnnn 180840
nnnnnnnnnn nnnnnnnnnn nnnnnnnnnn nnnnnnnnnn nnnnnnnnnn nnnnnnnnnn 180900
nnnnnnnnnn nnnnnnnnnn nnnnnnnnnn nnnnnnnnnn nnnnnnnnnn nnnnnnnnnn 180960
nnnnnnnnnn nnnnnnnnnn nnnnnnnnnn nnnnnnnnnn nnnnnnnnnn nnnnnnnnnn 181020
nnnnnnnnnn nnnnnnnnnn nnnnnnnnnn nnnnnnnnnn nnnnnnnnnn nnnnnnnnnn 181080
nnnnnnnnnn nnnnnnnnnn nnnnnnnnnn nnnnnnnnnn nnnnnnnnnn nnnnnnnnnn 181140
nnnnnnnnnn nnnnnnnnnn nnnnnnnnnn nnnnnnnnnn nnnnnnnnnn nnnnnnnnnn 181200
nnnnnnnnnn nnnnnnnnnn nnnnnnnnnn nnnnnnnnnn nnnnnnnnnn nnnnnnnnnn 181260
nnnnnnnnnn nnnnnnnnnn nnnnnnnnnn nnnnnnnnnn nnnnnnnnnn nnnnnnnnnn 181320
nnnnnnnnnn nnnnnnnnnn nnnnnnnnnn nnnnnnnnnn nnnnnnnnnn nnnnnnnnnn 181380
nnnnnnnnnn nnnnnnnnnn nnnnnnnnnn nnnnnnnnnn nnnnnnnnnn nnnnnnnnnn 181440
nnnnnnnnnn nnnnnnnnnn nnnnnnnnnn nnnnnnnnnn nnnnnnnnnn nnnnnnnnnn 181500

-continued nnnnnnnnnn nnnnnnnnnn nnnnnnnnnn nnnnnnnnnn nnnnnnnnnn nnnnnnnnnn 181560
nnnnnnnnnn nnnnnnnnnn nnnnnnnnnn nnnnnnnnnn nnnnnnnnnn nnnnnnnnnn 181620
nnnnnnnnnn nnnnnnnnnn nnnnnnnnnn nnnnnnnnnn nnnnnnnnnn nnnnnnnnnn 181680
nnnnnnnnnn nnnnnnnnnn nnnnnnnnnn nnnnnnnnnn nnnnnnnnnn nnnnnnnnnn 181740
nnnnnnnnnn nnnnnnnnnn nnnnnnnnnn nnnnnnnnnn nnnnnnnnnn nnnnnnnnnn 181800
nnnnnnnnnn nnnnnnnnnn nnnnnnnnnn nnnnnnnnnn nnnnnnnnnn nnnnnnnnnn 181860
nnnnnnnnnn nnnnnnnnnn nnnnnnnnnn nnnnnnnnnn nnnnnnnnnn nnnnnnnnnn 181920
nnnnnnnnnn nnnnnnnnnn nnnnnnnnnn nnnnnnnnnn nnnnnnnnnn nnnnnnnnnn 181980
nnnnnnnnnn nnnnnnnnnn nnnnnnnnnn nnnnnnnnnn nnnnnnnnnn nnnnnnnnnn 182040
nnnnnnnnnn nnnnnnnnnn nnnnnnnnnn nnnnnnnnnn nnnnnnnnnn nnnnnnnnnn 182100
nnnnnnnnnn nnnnnnnnnn nnnnnnnnnn nnnnnnnnnn nnnnnnnnnn nnnnnnnnnn 182160
nnnnnnnnnn nnnnnnnnnn nnnnnnnnnn nnnnnnnnnn nnnnnnnnnn nnnnnnnnnn 182220
nnnnnnnnnn nnnnnnnnnn nnnnnnnnnn nnnnnnnnnn nnnnnnnnnn nnnnnnnnnn 182280
nnnnnnnnnn nnnnnnnnnn nnnnnnnnnn nnnnnnnnnn nnnnnnnnnn nnnnnnnnnn 182340
nnnnnnnnnn nnnnnnnnnn nnnnnnnnnn nnnnnnnnnn nnnnnnnnnn nnnnnnnnnn 182400
nnnnnnnnnn nnnnnnnnnn nnnnnnnnnn nnnnnnnnnn nnnnnnnnnn nnnnnnnnnn 182460
nnnnnnnnnn nnnnnnnnnn nnnnnnnnnn nnnnnnnnnn nnnnnnnnnn nnnnnnnnnn 182520
nnnnnnnnnn nnnnnnnnnn nnnnnnnnnn nnnnnnnnnn nnnnnnnnnn nnnnnnnnnn 182580
nnnnnnnnnn nnnnnnnnnn nnnnnnnnnn nnnnnnnnnn nnnnnnnnnn nnnnnnnnnn 182640
nnnnnnnnnn nnnnnnnnnn nnnnnnnnnn nnnnnnnnnn nnnnnnnnnn nnnnnnnnnn 182700
nnnnnnnnnn nnnnnnnnnn nnnnnnnnnn nnnnnnnnnn nnnnnnnnnn nnnnnnnnnn 182760
nnnnnnnnnn nnnnnnnnnn nnnnnnnnnn nnnnnnnnnn nnnnnnnnnn nnnnnnnnnn 182820
nnnnnnnnnn nnnnnnnnnn nnnnnnnnnn nnnnnnnnnn nnnnnnnnnn nnnnnnnnnn 182880
nnnnnnnnnn nnnnnnnnnn nnnnnnnnnn nnnnnnnnnn nnnnnnnnnn nnnnnnnnnn 182940
nnnnnnnnnn nnnnnnnnnn nnnnnnnnnn nnnnnnnnnn nnnnnnnnnn nnnnnnnnnn 183000
nnnnnnnnnn nnnnnnnnnn nnnnnnnnnn nnnnnnnnnn nnnnnnnnnn nnnnnnnnnn 183060
nnnnnnnnnn nnnnnnnnnn nnnnnnnnnn nnnnnnnnnn nnnnnnnnnn nnnnnnnnnn 183120
nnnnnnnnnn nnnnnnnnnn nnnnnnnnnn nnnnnnnnnn nnnnnnnnnn nnnnnnnnnn 183180
nnnnnnnnnn nnnnnnnnnn nnnnnnnnnn nnnnnnnnnn nnnnnnnnnn nnnnnnnnnn 183240
nnnnnnnnnn nnnnnnnnnn nnnnnnnnnn nnnnnnnnnn nnnnnnnnnn nnnnnnnnnn 183300
nnnnnnnnnn nnnnnnnnnn nnnnnnnnnn nnnnnnnnnn nnnnnnnnnn nnnnnnnnnn 183360
nnnnnnnnnn nnnnnnnnnn nnnnnnnnnn nnnnnnnnnn nnnnnnnnnn nnnnnnnnnn 183420
nnnnnnnnnn nnnnnnnnnn nnnnnnnnnn nnnnnnnnnn nnnnnnnnnn nnnnnnnnnn 183480
nnnnnnnnnn nnnnnnnnnn nnnnnnnnnn nnnnnnnnnn nnnnnnnnnn nnnnnnnnnn 183540
nnnnnnnnnn nnnnnnnnnn nnnnnnnnnn nnnnnnnnnn nnnnnnnnnn nnnnnnnnnn 183600
nnnnnnnnnn nnnnnnnnnn nnnnnnnnnn nnnnnnnnnn nnnnnnnnnn nnnnnnnnnn 183660
nnnnnnnnnn nnnnnnnnnn nnnnnnnnnn nnnnnnnnnn nnnnnnnnnn nnnnnnnnnn 183720
nnnnnnnnnn nnnnnnnnnn nnnnnnnnnn nnnnnnnnnn nnnnnnnnnn nnnnnnnnnn 183780
nnnnnnnnnn nnnnnnnnnn nnnnnnnnnn nnnnnnnnnn nnnnnnnnnn nnnnnnnnnn 183840

-continued nnnnnnnnnn nnnnnnnnnn nnnnnnnnnn nnnnnnnnnn nnnnnnnnnn nnnnnnnnnn 183900
nnnnnnnnnn nnnnnnnnnn nnnnnnnnnn nnnnnnnnnn nnnnnnnnnn nnnnnnnnnn 183960
nnnnnnnnnn nnnnnnnnnn nnnnnnnnnn nnnnnnnnnn nnnnnnnnnn nnnnnnnnnn 184020
nnnnnnnnnn nnnnnnnnnn nnnnnnnnnn nnnnnnnnnn nnnnnnnnnn nnnnnnnnnn 184080
nnnnnnnnnn nnnnnnnnnn nnnnnnnnnn nnnnnnnnnn nnnnnnnnnn nnnnnnnnnn 184140
nnnnnnnnnn nnnnnnnnnn nnnnnnnnnn nnnnnnnnnn nnnnnnnnnn nnnnnnnnnn 184200
nnnnnnnnnn nnnnnnnnnn nnnnnnnnnn nnnnnnnnnn nnnnnnnnnn nnnnnnnnnn 184260
nnnnnnnnnn nnnnnnnnnn nnnnnnnnnn nnnnnnnnnn nnnnnnnnnn nnnnnnnnnn 184320
nnnnnnnnnn nnnnnnnnnn nnnnnnnnnn nnnnnnnnnn nnnnnnnnnn nnnnnnnnnn 184380
nnnnnnnnnn nnnnnnnnnn nnnnnnnnnn nnnnnnnnnn nnnnnnnnnn nnnnnnnnnn 184440
nnnnnnnnnn nnnnnnnnnn nnnnnnnnnn nnnnnnnnnn nnnnnnnnnn nnnnnnnnnn 184500
nnnnnnnnnn nnnnnnnnnn nnnnnnnnnn nnnnnnnnnn nnnnnnnnnn nnnnnnnnnn 184560
nnnnnnnnnn nnnnnnnnnn nnnnnnnnnn nnnnnnnnnn nnnnnnnnnn nnnnnnnnnn 184620
nnnnnnnnnn nnnnnnnnnn nnnnnnnnnn nnnnnnnnnn nnnnnnnnnn nnnnnnnnnn 184680
nnnnnnnnnn nnnnnnnnnn nnnnnnnnnn nnnnnnnnnn nnnnnnnnnn nnnnnnnnnn 184740
nnnnnnnnnn nnnnnnnnnn nnnnnnnnnn nnnnnnnnnn nnnnnnnnnn nnnnnnnnnn 184800
nnnnnnnnnn nnnnnnnnnn nnnnnnnnnn nnnnnnnnnn nnnnnnnnnn nnnnnnnnnn 184860
nnnnnnnnnn nnnnnnnnnn nnnnnnnnnn nnnnnnnnnn nnnnnnnnnn nnnnnnnnnn 184920
nnnnnnnnnn nnnnnnnnnn nnnnnnnnnn nnnnnnnnnn nnnnnnnnnn nnnnnnnnnn 184980
nnnnnnnnnn nnnnnnnnnn nnnnnnnnnn nnnnnnnnnn nnnnnnnnnn nnnnnnnnnn 185040
nnnnnnnnnn nnnnnnnnnn nnnnnnnnnn nnnnnnnnnn nnnnnnnnnn nnnnnnnnnn 185100
nnnnnnnnnn nnnnnnnnnn nnnnnnnnnn nnnnnnnnnn nnnnnnnnnn nnnnnnnnnn 185160
nnnnnnnnnn nnnnnnnnnn nnnnnnnnnn nnnnnnnnnn nnnnnnnnnn nnnnnnnnnn 185220
nnnnnnnnnn nnnnnnnnnn nnnnnnnnnn nnnnnnnnnn nnnnnnnnnn nnnnnnnnnn 185280
nnnnnnnnnn nnnnnnnnnn nnnnnnnnnn nnnnnnnnnn nnnnnnnnnn nnnnnnnnnn 185340
nnnnnnnnnn nnnnnnnnnn nnnnnnnnnn nnnnnnnnnn nnnnnnnnnn nnnnnnnnnn 185400
nnnnnnnnnn nnnnnnnnnn nnnnnnnnnn nnnnnnnnnn nnnnnnnnnn nnnnnnnnnn 185460
nnnnnnnnnn nnnnnnnnnn nnnnnnnnnn nnnnnnnnnn nnnnnnnnnn nnnnnnnnnn 185520
nnnnnnnnnn nnnnnnnnnn nnnnnnnnnn nnnnnnnnnn nnnnnnnnnn nnnnnnnnnn 185580
nnnnnnnnnn nnnnnnnnnn nnnnnnnnnn nnnnnnnnnn nnnnnnnnnn nnnnnnnnnn 185640
nnnnnnnnnn nnnnnnnnnn nnnnnnnnnn nnnnnnnnnn nnnnnnnnnn nnnnnnnnnn 185700
nnnnnnnnnn nnnnnnnnnn nnnnnnnnnn nnnnnnnnnn nnnnnnnnnn nnnnnnnnnn 185760
nnnnnnnnnn nnnnnnnnnn nnnnnnnnnn nnnnnnnnnn nnnnnnnnnn nnnnnnnnnn 185820
nnnnnnnnnn nnnnnnnnnn nnnnnnnnnn nnnnnnnnnn nnnnnnnnnn nnnnnnnnnn 185880
nnnnnnnnnn nnnnnnnnnn nnnnnnnnnn nnnnnnnnnn nnnnnnnnnn nnnnnnnnnn 185940
nnnnnnnnnn nnnnnnnnnn nnnnnnnnnn nnnnnnnnnn nnnnnnnnnn nnnnnnnnnn 186000
nnnnnnnnnn nnnnnnnnnn nnnnnnnnnn nnnnnnnnnn nnnnnnnnnn nnnnnnnnnn 186060
nnnnnnnnnn nnnnnnnnnn nnnnnnnnnn nnnnnnnnnn nnnnnnnnnn nnnnnnnnnn 186120
nnnnnnnnnn nnnnnnnnnn nnnnnnnnnn nnnnnnnnnn nnnnnnnnnn nnnnnnnnnn 186180
nnnnnnnnnn nnnnnnnnnn nnnnnnnnnn nnnnnnnnnn nnnnnnnnnn nnnnnnnnnn 186240

-continued nnnnnnnnnn nnnnnnnnnn nnnnnnnnnn nnnnnnnnnn nnnnnnnnnn nnnnnnnnnn 186300
nnnnnnnnnn nnnnnnnnnn nnnnnnnnnn nnnnnnnnnn nnnnnnnnnn nnnnnnnnnn 186360
nnnnnnnnnn nnnnnnnnnn nnnnnnnnnn nnnnnnnnnn nnnnnnnnnn nnnnnnnnnn 186420
nnnnnnnnnn nnnnnnnnnn nnnnnnnnnn nnnnnnnnnn nnnnnnnnnn nnnnnnnnnn 186480
nnnnnnnnnn nnnnnnnnnn nnnnnnnnnn nnnnnnnnnn nnnnnnnnnn nnnnnnnnnn 186540
nnnnnnnnnn nnnnnnnnnn nnnnnnnnnn nnnnnnnnnn nnnnnnnnnn nnnnnnnnnn 186600
nnnnnnnnnn nnnnnnnnnn nnnnnnnnnn nnnnnnnnnn nnnnnnnnnn nnnnnnnnnn 186660
nnnnnnnnnn nnnnnnnnnn nnnnnnnnnn nnnnnnnnnn nnnnnnnnnn nnnnnnnnnn 186720
nnnnnnnnnn nnnnnnnnnn nnnnnnnnnn nnnnnnnnnn nnnnnnnnnn nnnnnnnnnn 186780
nnnnnnnnnn nnnnnnnnnn nnnnnnnnnn nnnnnnnnnn nnnnnnnnnn nnnnnnnnnn 186840
nnnnnnnnnn nnnnnnnnnn nnnnnnnnnn nnnnnnnnnn nnnnnnnnnn nnnnnnnnnn 186900
nnnnnnnnnn nnnnnnnnnn nnnnnnnnnn nnnnnnnnnn nnnnnnnnnn nnnnnnnnnn 186960
nnnnnnnnnn nnnnnnnnnn nnnnnnnnnn nnnnnnnnnn nnnnnnnnnn nnnnnnnnnn 187020
nnnnnnnnnn nnnnnnnnnn nnnnnnnnnn nnnnnnnnnn nnnnnnnnnn nnnnnnnnnn 187080
nnnnnnnnnn nnnnnnnnnn nnnnnnnnnn nnnnnnnnnn nnnnnnnnnn nnnnnnnnnn 187140
nnnnnnnnnn nnnnnnnnnn nnnnnnnnnn nnnnnnnnnn nnnnnnnnnn nnnnnnnnnn 187200
nnnnnnnnnn nnnnnnnnnn nnnnnnnnnn nnnnnnnnnn nnnnnnnnnn nnnnnnnnnn 187260
nnnnnnnnnn nnnnnnnnnn nnnnnnnnnn nnnnnnnnnn nnnnnnnnnn nnnnnnnnnn 187320
nnnnnnnnnn nnnnnnnnnn nnnnnnnnnn nnnnnnnnnn nnnnnnnnnn nnnnnnnnnn 187380
nnnnnnnnnn nnnnnnnnnn nnnnnnnnnn nnnnnnnnnn nnnnnnnnnn nnnnnnnnnn 187440
nnnnnnnnnn nnnnnnnnnn nnnnnnnnnn nnnnnnnnnn nnnnnnnnnn nnnnnnnnnn 187500
nnnnnnnnnn nnnnnnnnnn nnnnnnnnnn nnnnnnnnnn nnnnnnnnnn nnnnnnnnnn 187560
nnnnnnnnnn nnnnnnnnnn nnnnnnnnnn nnnnnnnnnn nnnnnnnnnn nnnnnnnnnn 187620
nnnnnnnnnn nnnnnnnnnn nnnnnnnnnn nnnnnnnnnn nnnnnnnnnn nnnnnnnnnn 187680
nnnnnnnnnn nnnnnnnnnn nnnnnnnnnn nnnnnnnnnn nnnnnnnnnn nnnnnnnnnn 187740
nnnnnnnnnn nnnnnnnnnn nnnnnnnnnn nnnnnnnnnn nnnnnnnnnn nnnnnnnnnn 187800
nnnnnnnnnn nnnnnnnnnn nnnnnnnnnn nnnnnnnnnn nnnnnnnnnn nnnnnnnnnn 187860
nnnnnnnnnn nnnnnnnnnn nnnnnnnnnn nnnnnnnnnn nnnnnnnnnn nnnnnnnnnn 187920
nnnnnnnnnn nnnnnnnnnn nnnnnnnnnn nnnnnnnnnn nnnnnnnnnn nnnnnnnnnn 187980
nnnnnnnnnn nnnnnnnnnn nnnnnnnnnn nnnnnnnnnn nnnnnnnnnn nnnnnnnnnn 188040
nnnnnnnnnn nnnnnnnnnn nnnnnnnnnn nnnnnnnnnn nnnnnnnnnn nnnnnnnnnn 188100
nnnnnnnnnn nnnnnnnnnn nnnnnnnnnn nnnnnnnnnn nnnnnnnnnn nnnnnnnnnn 188160
nnnnnnnnnn nnnnnnnnnn nnnnnnnnnn nnnnnnnnnn nnnnnnnnnn nnnnnnnnnn 188220
nnnnnnnnnn nnnnnnnnnn nnnnnnnnnn nnnnnnnnnn nnnnnnnnnn nnnnnnnnnn 188280
nnnnnnnnnn nnnnnnnnnn nnnnnnnnnn nnnnnnnnnn nnnnnnnnnn nnnnnnnnnn 188340
nnnnnnnnnn nnnnnnnnnn nnnnnnnnnn nnnnnnnnnn nnnnnnnnnn nnnnnnnnnn 188400
nnnnnnnnnn nnnnnnnnnn nnnnnnnnnn nnnnnnnnnn nnnnnnnnnn nnnnnnnnnn 188460
nnnnnnnnnn nnnnnnnnnn nnnnnnnnnn nnnnnnnnnn nnnnnnnnnn nnnnnnnnnn 188520
nnnnnnnnnn nnnnnnnnnn nnnnnnnnnn nnnnnnnnnn nnnnnnnnnn nnnnnnnnnn 188580

-continued nnnnnnnnnn nnnnnnnnnn nnnnnnnnnn nnnnnnnnnn nnnnnnnnnn nnnnnnnnnn 188640
nnnnnnnnnn nnnnnnnnnn nnnnnnnnnn nnnnnnnnnn nnnnnnnnnn nnnnnnnnnn 188700
nnnnnnnnnn nnnnnnnnnn nnnnnnnnnn nnnnnnnnnn nnnnnnnnnn nnnnnnnnnn 188760
nnnnnnnnnn nnnnnnnnnn nnnnnnnnnn nnnnnnnnnn nnnnnnnnnn nnnnnnnnnn 188820
nnnnnnnnnn nnnnnnnnnn nnnnnnnnnn nnnnnnnnnn nnnnnnnnnn nnnnnnnnnn 188880
nnnnnnnnnn nnnnnnnnnn nnnnnnnnnn nnnnnnnnnn nnnnnnnnnn nnnnnnnnnn 188940
nnnnnnnnnn nnnnnnnnnn nnnnnnnnnn nnnnnnnnnn nnnnnnnnnn nnnnnnnnnn 189000
nnnnnnnnnn nnnnnnnnnn nnnnnnnnnn nnnnnnnnnn nnnnnnnnnn nnnnnnnnnn 189060
nnnnnnnnnn nnnnnnnnnn nnnnnnnnnn nnnnnnnnnn nnnnnnnnnn nnnnnnnnnn 189120
nnnnnnnnnn nnnnnnnnnn nnnnnnnnnn nnnnnnnnnn nnnnnnnnnn nnnnnnnnnn 189180
nnnnnnnnnn nnnnnnnnnn nnnnnnnnnn nnnnnnnnnn nnnnnnnnnn nnnnnnnnnn 189240
nnnnnnnnnn nnnnnnnnnn nnnnnnnnnn nnnnnnnnnn nnnnnnnnnn nnnnnnnnnn 189300
nnnnnnnnnn nnnnnnnnnn nnnnnnnnnn nnnnnnnnnn nnnnnnnnnn nnnnnnnnnn 189360
nnnnnnnnnn nnnnnnnnnn nnnnnnnnnn nnnnnnnnnn nnnnnnnnnn nnnnnnnnnn 189420
nnnnnnnnnn nnnnnnnnnn nnnnnnnnnn nnnnnnnnnn nnnnnnnnnn nnnnnnnnnn 189480
nnnnnnnnnn nnnnnnnnnn nnnnnnnnnn nnnnnnnnnn nnnnnnnnnn nnnnnnnnnn 189540
nnnnnnnnnn nnnnnnnnnn nnnnnnnnnn nnnnnnnnnn nnnnnnnnnn nnnnnnnnnn 189600
nnnnnnnnnn nnnnnnnnnn nnnnnnnnnn nnnnnnnnnn nnnnnnnnnn nnnnnnnnnn 189660
nnnnnnnnnn nnnnnnnnnn nnnnnnnnnn nnnnnnnnnn nnnnnnnnnn nnnnnnnnnn 189720
nnnnnnnnnn nnnnnnnnnn nnnnnnnnnn nnnnnnnnnn nnnnnnnnnn nnnnnnnnnn 189780
nnnnnnnnnn nnnnnnnnnn nnnnnnnnnn nnnnnnnnnn nnnnnnnnnn nnnnnnnnnn 189840
nnnnnnnnnn nnnnnnnnnn nnnnnnnnnn nnnnnnnnnn nnnnnnnnnn nnnnnnnnnn 189900
nnnnnnnnnn nnnnnnnnnn nnnnnnnnnn nnnnnnnnnn nnnnnnnnnn nnnnnnnnnn 189960
nnnnnnnnnn nnnnnnnnnn nnnnnnnnnn nnnnnnnnnn nnnnnnnnnn nnnnnnnnnn 190020
nnnnnnnnnn nnnnnnnnnn nnnnnnnnnn nnnnnnnnnn nnnnnnnnnn nnnnnnnnnn 190080
nnnnnnnnnn nnnnnnnnnn nnnnnnnnnn nnnnnnnnnn nnnnnnnnnn nnnnnnnnnn 190140
nnnnnnnnnn nnnnnnnnnn nnnnnnnnnn nnnnnnnnnn nnnnnnnnnn nnnnnnnnnn 190200
nnnnnnnnnn nnnnnnnnnn nnnnnnnnnn nnnnnnnnnn nnnnnnnnnn nnnnnnnnnn 190260
nnnnnnnnnn nnnnnnnnnn nnnnnnnnnn nnnnnnnnnn nnnnnnnnnn nnnnnnnnnn 190320
nnnnnnnnnn nnnnnnnnnn nnnnnnnnnn nnnnnnnnnn nnnnnnnnnn nnnnnnnnnn 190380
nnnnnnnnnn nnnnnnnnnn nnnnnnnnnn nnnnnnnnnn nnnnnnnnnn nnnnnnnnnn 190440
nnnnnnnnnn nnnnnnnnnn nnnnnnnnnn nnnnnnnnnn nnnnnnnnnn nnnnnnnnnn 190500
nnnnnnnnnn nnnnnnnnnn nnnnnnnnnn nnnnnnnnnn nnnnnnnnnn nnnnnnnnnn 190560
nnnnnnnnnn nnnnnnnnnn nnnnnnnnnn nnnnnnnnnn nnnnnnnnnn nnnnnnnnnn 190620
nnnnnnnnnn nnnnnnnnnn nnnnnnnnnn nnnnnnnnnn nnnnnnnnnn nnnnnnnnnn 190680
nnnnnnnnnn nnnnnnnnnn nnnnnnnnnn nnnnnnnnnn nnnnnnnnnn nnnnnnnnnn 190740
nnnnnnnnnn nnnnnnnnnn nnnnnnnnnn nnnnnnnnnn nnnnnnnnnn nnnnnnnnnn 190800
nnnnnnnnnn nnnnnnnnnn nnnnnnnnnn nnnnnnnnnn nnnnnnnnnn nnnnnnnnnn 190860
nnnnnnnnnn nnnnnnnnnn nnnnnnnnnn nnnnnnnnnn nnnnnnnnnn nnnnnnnnnn 190920
nnnnnnnnnn nnnnnnnnnn nnnnnnnnnn nnnnnnnnnn nnnnnnnnnn nnnnnnnnnn 190980

-continued nnnnnnnnnn nnnnnnnnnn nnnnnnnnnn nnnnnnnnnn nnnnnnnnnn nnnnnnnnnn 191040
nnnnnnnnnn nnnnnnnnnn nnnnnnnnnn nnnnnnnnnn nnnnnnnnnn nnnnnnnnnn 191100
nnnnnnnnnn nnnnnnnnnn nnnnnnnnnn nnnnnnnnnn nnnnnnnnnn nnnnnnnnnn 191160
nnnnnnnnnn nnnnnnnnnn nnnnnnnnnn nnnnnnnnnn nnnnnnnnnn nnnnnnnnnn 191220
nnnnnnnnnn nnnnnnnnnn nnnnnnnnnn nnnnnnnnnn nnnnnnnnnn nnnnnnnnnn 191280
nnnnnnnnnn nnnnnnnnnn nnnnnnnnnn nnnnnnnnnn nnnnnnnnnn nnnnnnnnnn 191340
nnnnnnnnnn nnnnnnnnnn nnnnnnnnnn nnnnnnnnnn nnnnnnnnnn nnnnnnnnnn 191400
nnnnnnnnnn nnnnnnnnnn nnnnnnnnnn nnnnnnnnnn nnnnnnnnnn nnnnnnnnnn 191460
nnnnnnnnnn nnnnnnnnnn nnnnnnnnnn nnnnnnnnnn nnnnnnnnnn nnnnnnnnnn 191520
nnnnnnnnnn nnnnnnnnnn nnnnnnnnnn nnnnnnnnnn nnnnnnnnnn nnnnnnnnnn 191580
nnnnnnnnnn nnnnnnnnnn nnnnnnnnnn nnnnnnnnnn nnnnnnnnnn nnnnnnnnnn 191640
nnnnnnnnnn nnnnnnnnnn nnnnnnnnnn nnnnnnnnnn nnnnnnnnnn nnnnnnnnnn 191700
nnnnnnnnnn nnnnnnnnnn nnnnnnnnnn nnnnnnnnnn nnnnnnnnnn nnnnnnnnnn 191760
nnnnnnnnnn nnnnnnnnnn nnnnnnnnnn nnnnnnnnnn nnnnnnnnnn nnnnnnnnnn 191820
nnnnnnnnnn nnnnnnnnnn nnnnnnnnnn nnnnnnnnnn nnnnnnnnnn nnnnnnnnnn 191880
nnnnnnnnnn nnnnnnnnnn nnnnnnnnnn nnnnnnnnnn nnnnnnnnnn nnnnnnnnnn 191940
nnnnnnnnnn nnnnnnnnnn nnnnnnnnnn nnnnnnnnnn nnnnnnnnnn nnnnnnnnnn 192000
nnnnnnnnnn nnnnnnnnnn nnnnnnnnnn nnnnnnnnnn nnnnnnnnnn nnnnnnnnnn 192060
nnnnnnnnnn nnnnnnnnnn nnnnnnnnnn nnnnnnnnnn nnnnnnnnnn nnnnnnnnnn 192120
nnnnnnnnnn nnnnnnnnnn nnnnnnnnnn nnnnnnnnnn nnnnnnnnnn nnnnnnnnnn 192180
nnnnnnnnnn nnnnnnnnnn nnnnnnnnnn nnnnnnnnnn nnnnnnnnnn nnnnnnnnnn 192240
nnnnnnnnnn nnnnnnnnnn nnnnnnnnnn nnnnnnnnnn nnnnnnnnnn nnnnnnnnnn 192300
nnnnnnnnnn nnnnnnnnnn nnnnnnnnnn nnnnnnnnnn nnnnnnnnnn nnnnnnnnnn 192360
nnnnnnnnnn nnnnnnnnnn nnnnnnnnnn nnnnnnnnnn nnnnnnnnnn nnnnnnnnnn 192420
nnnnnnnnnn nnnnnnnnnn nnnnnnnnnn nnnnnnnnnn nnnnnnnnnn nnnnnnnnnn 192480
nnnnnnnnnn nnnnnnnnnn nnnnnnnnnn nnnnnnnnnn nnnnnnnnnn nnnnnnnnnn 192540
nnnnnnnnnn nnnnnnnnnn nnnnnnnnnn nnnnnnnnnn nnnnnnnnnn nnnnnnnnnn 192600
nnnnnnnnnn nnnnnnnnnn nnnnnnnnnn nnnnnnnnnn nnnnnnnnnn nnnnnnnnnn 192660
nnnnnnnnnn nnnnnnnnnn nnnnnnnnnn nnnnnnnnnn nnnnnnnnnn nnnnnnnnnn 192720
nnnnnnnnnn nnnnnnnnnn nnnnnnnnnn nnnnnnnnnn nnnnnnnnnn nnnnnnnnnn 192780
nnnnnnnnnn nnnnnnnnnn nnnnnnnnnn nnnnnnnnnn nnnnnnnnnn nnnnnnnnnn 192840
nnnnnnnnnn nnnnnnnnnn nnnnnnnnnn nnnnnnnnnn nnnnnnnnnn nnnnnnnnnn 192900
nnnnnnnnnn nnnnnnnnnn nnnnnnnnnn nnnnnnnnnn nnnnnnnnnn nnnnnnnnnn 192960
nnnnnnnnnn nnnnnnnnnn nnnnnnnnnn nnnnnnnnnn nnnnnnnnnn nnnnnnnnnn 193020
nnnnnnnnnn nnnnnnnnnn nnnnnnnnnn nnnnnnnnnn nnnnnnnnnn nnnnnnnnnn 193080
nnnnnnnnnn nnnnnnnnnn nnnnnnnnnn nnnnnnnnnn nnnnnnnnnn nnnnnnnnnn 193140
nnnnnnnnnn nnnnnnnnnn nnnnnnnnnn nnnnnnnnnn nnnnnnnnnn nnnnnnnnnn 193200
nnnnnnnnnn nnnnnnnnnn nnnnnnnnnn nnnnnnnnnn nnnnnnnnnn nnnnnnnnnn 193260
nnnnnnnnnn nnnnnnnnnn nnnnnnnnnn nnnnnnnnnn nnnnnnnnnn nnnnnnnnnn 193320

-continued nnnnnnnnnn nnnnnnnnnn nnnnnnnnnn nnnnnnnnnn nnnnnnnnnn nnnnnnnnnn 193380
nnnnnnnnnn nnnnnnnnnn nnnnnnnnnn nnnnnnnnnn nnnnnnnnnn nnnnnnnnnn 193440
nnnnnnnnnn nnnnnnnnnn nnnnnnnnnn nnnnnnnnnn nnnnnnnnnn nnnnnnnnnn 193500
nnnnnnnnnn nnnnnnnnnn nnnnnnnnnn nnnnnnnnnn nnnnnnnnnn nnnnnnnnnn 193560
nnnnnnnnnn nnnnnnnnnn nnnnnnnnnn nnnnnnnnnn nnnnnnnnnn nnnnnnnnnn 193620
nnnnnnnnnn nnnnnnnnnn nnnnnnnnnn nnnnnnnnnn nnnnnnnnnn nnnnnnnnnn 193680
nnnnnnnnnn nnnnnnnnnn nnnnnnnnnn nnnnnnnnnn nnnnnnnnnn nnnnnnnnnn 193740
nnnnnnnnnn nnnnnnnnnn nnnnnnnnnn nnnnnnnnnn nnnnnnnnnn nnnnnnnnnn 193800
nnnnnnnnnn nnnnnnnnnn nnnnnnnnnn nnnnnnnnnn nnnnnnnnnn nnnnnnnnnn 193860
nnnnnnnnnn nnnnnnnnnn nnnnnnnnnn nnnnnnnnnn nnnnnnnnnn nnnnnnnnnn 193920
nnnnnnnnnn nnnnnnnnnn nnnnnnnnnn nnnnnnnnnn nnnnnnnnnn nnnnnnnnnn 193980
nnnnnnnnnn nnnnnnnnnn nnnnnnnnnn nnnnnnnnnn nnnnnnnnnn nnnnnnnnnn 194040
nnnnnnnnnn nnnnnnnnnn nnnnnnnnnn nnnnnnnnnn nnnnnnnnnn nnnnnnnnnn 194100
nnnnnnnnnn nnnnnnnnnn nnnnnnnnnn nnnnnnnnnn nnnnnnnnnn nnnnnnnnnn 194160
nnnnnnnnnn nnnnnnnnnn nnnnnnnnnn nnnnnnnnnn nnnnnnnnnn nnnnnnnnnn 194220
nnnnnnnnnn nnnnnnnnnn nnnnnnnnnn nnnnnnnnnn nnnnnnnnnn nnnnnnnnnn 194280
nnnnnnnnnn nnnnnnnnnn nnnnnnnnnn nnnnnnnnnn nnnnnnnnnn nnnnnnnnnn 194340
nnnnnnnnnn nnnnnnnnnn nnnnnnnnnn nnnnnnnnnn nnnnnnnnnn nnnnnnnnnn 194400
nnnnnnnnnn nnnnnnnnnn nnnnnnnnnn nnnnnnnnnn nnnnnnnnnn nnnnnnnnnn 194460
nnnnnnnnnn nnnnnnnnnn nnnnnnnnnn nnnnnnnnnn nnnnnnnnnn nnnnnnnnnn 194520
nnnnnnnnnn nnnnnnnnnn nnnnnnnnnn nnnnnnnnnn nnnnnnnnnn nnnnnnnnnn 194580
nnnnnnnnnn nnnnnnnnnn nnnnnnnnnn nnnnnnnnnn nnnnnnnnnn nnnnnnnnnn 194640
nnnnnnnnnn nnnnnnnnnn nnnnnnnnnn nnnnnnnnnn nnnnnnnnnn nnnnnnnnnn 194700
nnnnnnnnnn nnnnnnnnnn nnnnnnnnnn nnnnnnnnnn nnnnnnnnnn nnnnnnnnnn 194760
nnnnnnnnnn nnnnnnnnnn nnnnnnnnnn nnnnnnnnnn nnnnnnnnnn nnnnnnnnnn 194820
nnnnnnnnnn nnnnnnnnnn nnnnnnnnnn nnnnnnnnnn nnnnnnnnnn nnnnnnnnnn 194880
nnnnnnnnnn nnnnnnnnnn nnnnnnnnnn nnnnnnnnnn nnnnnnnnnn nnnnnnnnnn 194940
nnnnnnnnnn nnnnnnnnnn nnnnnnnnnn nnnnnnnnnn nnnnnnnnnn nnnnnnnnnn 195000
nnnnnnnnnn nnnnnnnnnn nnnnnnnnnn nnnnnnnnnn nnnnnnnnnn nnnnnnnnnn 195060
nnnnnnnnnn nnnnnnnnnn nnnnnnnnnn nnnnnnnnnn nnnnnnnnnn nnnnnnnnnn 195120
nnnnnnnnnn nnnnnnnnnn nnnnnnnnnn nnnnnnnnnn nnnnnnnnnn nnnnnnnnnn 195180
nnnnnnnnnn nnnnnnnnnn nnnnnnnnnn nnnnnnnnnn nnnnnnnnnn nnnnnnnnnn 195240
nnnnnnnnnn nnnnnnnnnn nnnnnnnnnn nnnnnnnnnn nnnnnnnnnn nnnnnnnnnn 195300
nnnnnnnnnn nnnnnnnnnn nnnnnnnnnn nnnnnnnnnn nnnnnnnnnn nnnnnnnnnn 195360
nnnnnnnnnn nnnnnnnnnn nnnnnnnnnn nnnnnnnnnn nnnnnnnnnn nnnnnnnnnn 195420
nnnnnnnnnn nnnnnnnnnn nnnnnnnnnn nnnnnnnnnn nnnnnnnnnn nnnnnnnnnn 195480
nnnnnnnnnn nnnnnnnnnn nnnnnnnnnn nnnnnnnnnn nnnnnnnnnn nnnnnnnnnn 195540
nnnnnnnnnn nnnnnnnnnn nnnnnnnnnn nnnnnnnnnn nnnnnnnnnn nnnnnnnnnn 195600
nnnnnnnnnn nnnnnnnnnn nnnnnnnnnn nnnnnnnnnn nnnnnnnnnn nnnnnnnnnn 195660
nnnnnnnnnn nnnnnnnnnn nnnnnnnnnn nnnnnnnnnn nnnnnnnnnn nnnnnnnnnn 195720

-continued nnnnnnnnnn nnnnnnnnnn nnnnnnnnnn nnnnnnnnnn nnnnnnnnnn nnnnnnnnnn 195780
nnnnnnnnnn nnnnnnnnnn nnnnnnnnnn nnnnnnnnnn nnnnnnnnnn nnnnnnnnnn 195840
nnnnnnnnnn nnnnnnnnnn nnnnnnnnnn nnnnnnnnnn nnnnnnnnnn nnnnnnnnnn 195900
nnnnnnnnnn nnnnnnnnnn nnnnnnnnnn nnnnnnnnnn nnnnnnnnnn nnnnnnnnnn 195960
nnnnnnnnnn nnnnnnnnnn nnnnnnnnnn nnnnnnnnnn nnnnnnnnnn nnnnnnnnnn 196020
nnnnnnnnnn nnnnnnnnnn nnnnnnnnnn nnnnnnnnnn nnnnnnnnnn nnnnnnnnnn 196080
nnnnnnnnnn nnnnnnnnnn nnnnnnnnnn nnnnnnnnnn nnnnnnnnnn nnnnnnnnnn 196140
nnnnnnnnnn nnnnnnnnnn nnnnnnnnnn nnnnnnnnnn nnnnnnnnnn nnnnnnnnnn 196200
nnnnnnnnnn nnnnnnnnnn nnnnnnnnnn nnnnnnnnnn nnnnnnnnnn nnnnnnnnnn 196260
nnnnnnnnnn nnnnnnnnnn nnnnnnnnnn nnnnnnnnnn nnnnnnnnnn nnnnnnnnnn 196320
nnnnnnnnnn nnnnnnnnnn nnnnnnnnnn nnnnnnnnnn nnnnnnnnnn nnnnnnnnnn 196380
nnnnnnnnnn nnnnnnnnnn nnnnnnnnnn nnnnnnnnnn nnnnnnnnnn nnnnnnnnnn 196440
nnnnnnnnnn nnnnnnnnnn nnnnnnnnnn nnnnnnnnnn nnnnnnnnnn nnnnnnnnnn 196500
nnnnnnnnnn nnnnnnnnnn nnnnnnnnnn nnnnnnnnnn nnnnnnnnnn nnnnnnnnnn 196560
nnnnnnnnnn nnnnnnnnnn nnnnnnnnnn nnnnnnnnnn nnnnnnnnnn nnnnnnnnnn 196620
nnnnnnnnnn nnnnnnnnnn nnnnnnnnnn nnnnnnnnnn nnnnnnnnnn nnnnnnnnnn 196680
nnnnnnnnnn nnnnnnnnnn nnnnnnnnnn nnnnnnnnnn nnnnnnnnnn nnnnnnnnnn 196740
nnnnnnnnnn nnnnnnnnnn nnnnnnnnnn nnnnnnnnnn nnnnnnnnnn nnnnnnnnnn 196800
nnnnnnnnnn nnnnnnnnnn nnnnnnnnnn nnnnnnnnnn nnnnnnnnnn nnnnnnnnnn 196860
nnnnnnnnnn nnnnnnnnnn nnnnnnnnnn nnnnnnnnnn nnnnnnnnnn nnnnnnnnnn 196920
nnnnnnnnnn nnnnnnnnnn nnnnnnnnnn nnnnnnnnnn nnnnnnnnnn nnnnnnnnnn 196980
nnnnnnnnnn nnnnnnnnnn nnnnnnnnnn nnnnnnnnnn nnnnnnnnnn nnnnnnnnnn 197040
nnnnnnnnnn nnnnnnnnnn nnnnnnnnnn nnnnnnnnnn nnnnnnnnnn nnnnnnnnnn 197100
nnnnnnnnnn nnnnnnnnnn nnnnnnnnnn nnnnnnnnnn nnnnnnnnnn nnnnnnnnnn 197160
nnnnnnnnnn nnnnnnnnnn nnnnnnnnnn nnnnnnnnnn nnnnnnnnnn nnnnnnnnnn 197220
nnnnnnnnnn nnnnnnnnnn nnnnnnnnnn nnnnnnnnnn nnnnnnnnnn nnnnnnnnnn 197280
nnnnnnnnnn nnnnnnnnnn nnnnnnnnnn nnnnnnnnnn nnnnnnnnnn nnnnnnnnnn 197340
nnnnnnnnnn nnnnnnnnnn nnnnnnnnnn nnnnnnnnnn nnnnnnnnnn nnnnnnnnnn 197400
nnnnnnnnnn nnnnnnnnnn nnnnnnnnnn nnnnnnnnnn nnnnnnnnnn nnnnnnnnnn 197460
nnnnnnnnnn nnnnnnnnnn nnnnnnnnnn nnnnnnnnnn nnnnnnnnnn nnnnnnnnnn 197520
nnnnnnnnnn nnnnnnnnnn nnnnnnnnnn nnnnnnnnnn nnnnnnnnnn nnnnnnnnnn 197580
nnnnnnnnnn nnnnnnnnnn nnnnnnnnnn nnnnnnnnnn nnnnnnnnnn nnnnnnnnnn 197640
nnnnnnnnnn nnnnnnnnnn nnnnnnnnnn nnnnnnnnnn nnnnnnnnnn nnnnnnnnnn 197700
nnnnnnnnnn nnnnnnnnnn nnnnnnnnnn nnnnnnnnnn nnnnnnnnnn nnnnnnnnnn 197760
nnnnnnnnnn nnnnnnnnnn nnnnnnnnnn nnnnnnnnnn nnnnnnnnnn nnnnnnnnnn 197820
nnnnnnnnnn nnnnnnnnnn nnnnnnnnnn nnnnnnnnnn nnnnnnnnnn nnnnnnnnnn 197880
nnnnnnnnnn nnnnnnnnnn nnnnnnnnnn nnnnnnnnnn nnnnnnnnnn nnnnnnnnnn 197940
nnnnnnnnnn nnnnnnnnnn nnnnnnnnnn nnnnnnnnnn nnnnnnnnnn nnnnnnnnnn 198000
nnnnnnnnnn nnnnnnnnnn nnnnnnnnnn nnnnnnnnnn nnnnnnnnnn nnnnnnnnnn 198060

-continued nnnnnnnnnn nnnnnnnnnn nnnnnnnnnn nnnnnnnnnn nnnnnnnnnn nnnnnnnnnn 198120
nnnnnnnnnn nnnnnnnnnn nnnnnnnnnn nnnnnnnnnn nnnnnnnnnn nnnnnnnnnn 198180
nnnnnnnnnn nnnnnnnnnn nnnnnnnnnn nnnnnnnnnn nnnnnnnnnn nnnnnnnnnn 198240
nnnnnnnnnn nnnnnnnnnn nnnnnnnnnn nnnnnnnnnn nnnnnnnnnn nnnnnnnnnn 198300
nnnnnnnnnn nnnnnnnnnn nnnnnnnnnn nnnnnnnnnn nnnnnnnnnn nnnnnnnnnn 198360
nnnnnnnnnn nnnnnnnnnn nnnnnnnnnn nnnnnnnnnn nnnnnnnnnn nnnnnnnnnn 198420
nnnnnnnnnn nnnnnnnnnn nnnnnnnnnn nnnnnnnnnn nnnnnnnnnn nnnnnnnnnn 198480
nnnnnnnnnn nnnnnnnnnn nnnnnnnnnn nnnnnnnnnn nnnnnnnnnn nnnnnnnnnn 198540
nnnnnnnnnn nnnnnnnnnn nnnnnnnnnn nnnnnnnnnn nnnnnnnnnn nnnnnnnnnn 198600
nnnnnnnnnn nnnnnnnnnn nnnnnnnnnn nnnnnnnnnn nnnnnnnnnn nnnnnnnnnn 198660
nnnnnnnnnn nnnnnnnnnn nnnnnnnnnn nnnnnnnnnn nnnnnnnnnn nnnnnnnnnn 198720
nnnnnnnnnn nnnnnnnnnn nnnnnnnnnn nnnnnnnnnn nnnnnnnnnn nnnnnnnnnn 198780
nnnnnnnnnn nnnnnnnnnn nnnnnnnnnn nnnnnnnnnn nnnnnnnnnn nnnnnnnnnn 198840
nnnnnnnnnn nnnnnnnnnn nnnnnnnnnn nnnnnnnnnn nnnnnnnnnn nnnnnnnnnn 198900
nnnnnnnnnn nnnnnnnnnn nnnnnnnnnn nnnnnnnnnn nnnnnnnnnn nnnnnnnnnn 198960
nnnnnnnnnn nnnnnnnnnn nnnnnnnnnn nnnnnntttc tttgaccttg gtacctctct 199020
cagggatgag gactctcttc ccatttctat tgatcttctg aaaaagtagc ctcattcccc 199080
aactcaagga actctttaaa tgcttgaaat cttattagaa gtcaccagtg acctccccag 199140
tgtgcaacac aagtaattaa atatttttaa ccacccttgt gttcttatct ccttcaaaat 199200
ccatccctct gtccccccac ttttcagctt ttgaaactat ttgttcctta atactttctg 199260
caattttatg tactgtgaca ttgcaattct ttggccttgc acaattaaaa atgaaagttc 199320
aaaaagctaa ctctctctat tttctaactt tttagtgaag atgttccaca gagctttggt 199380
ttcagccatc tcataacatt ttcttttgaa gacctaacag tttcaatcac tgcttcctat 199440
ttgtctgact cttttgcctt actttctact ctgatccttc tctctgacgc tctggattcc 199500
taattgcagc catttgtggg aagagtccac cagggctcat tacatctaaa taaatttctc 199560
cccataaaac aaaacagaaa tcttctctga gataataggg gcttcatgat gggagggaag 199620
atgtgacatt ggaatgagga cagagatctt gggacagtga tagtgacctg tgcaggttcc 199680
cacagggcac ccataaggtc tgtccaggca attaatagtg tcagtgtgtc aagaataagg 199740
cctaaagagc ggctgacttg aagtcttggt acctgggttt agaattttct aatccctctg 199800
actggacata acacaaatct ctgacctcaa ggtcatttgt ctannnnnnn nnnnnnnnnn 199860
nnnnnnnnnn nnnnnnnnnn nnnnnnnnnn nnnnnnnnnn nnnnnnnnnn nnnnnnnnnn 199920
nnnnnnnnnn nnnnnnnnnn nnnnnnnnnn nnnnnnnnnn nnnnnnnnnn nnnnnnnnnn 199980
nnnnnnnnnn nnnnnnnnnn nnnnnnnnnn nnnnnnnnnn nnnnnnnnnn nnnnnnnnnn 200040
nnnnnnnnnn nnnnnnnnnn nnnnnnnnnn nnnnnnnnnn nnnnnnnnnn nnnnnnnnnn 200100
nnnnnnnnnn nnnnnnnnnn nnnnnnnnnn nnnnnnnnnn nnnnnnnnnn nnnnnnnnnn 200160
nnnnnnnnnn nnnnnnnnnn nnnnnnnnnn nnnnnnnnnn nnnnnnnnnn nnnnnnnnnn 200220
nnnnnnnnnn nnnnnnnnnn nnnnnnnnnn nnnnnnnnnn nnnnnnnnnn nnnnnnnnnn 200280
nnnnnnnnnn nnnnnnnnnn nnnnnnnnnn nnnnnnnnnn nnnnnnnnnn nnnnnnnnnn 200340
nnnnnnnnnn nnnnnnnnnn nnnnnnnnnn nnnnnnnnnn nnnnnnnnnn nnnnnnnnnn 200400
nnnnnnnnnn nnnnnnnnnn nnnnnnnnnn nnnnnnnnnn nnnnnnnnnn nnnnnnnnnn 200460

-continued nnnnnnnnnn nnnnnnnnnn nnnntcatca agctagtaag aagggtctat ataatgtgat 200520
catgggagag acatgttatt ccttttgcct tattctattg gttagataca aatcataggt 200580
cccaactaac taaagaagag gagattttac aaagcaggaa caacaggagg tgggtatagt 200640
gggtatctac ctgagaggcc atgcactaca ctcccccagc ctactatttt atatttcaaa 200700
cacttattag aataatcctt ccagatttaa gtatgttatt tacattatga aagtaaccta 200760
ataagaattg agaacagatg acgaaggtat atatgtgttt aagtaaccta actcttcact 200820
atcattgcag aaaatcaata gattctaaaa atgagtgtta acagagcagt atatgcatat 200880
tatttagtgt tttaggggta aacaccataa gaactgaaaa caggagtggt ttaaagtgtt 200940
gcttctggga agtaagaggt agggagggta taaacaggga attgttattt tcattataaa 201000
cccttcatca tctttttttg tagccatgta gatataacat gatgattaaa cttaaaaata 201060
taaccctcct atgctaggca tgatttgatc tcattaccct tattgaattt ttttccagtg 201120
aatcccatga tctatttgtt tctgaataaa tatggattat ttaaacaagc tgaaatatgt 201180
ataagatttt actgttaata tttaaacaaa tatttgaaaa ttacattagc aaaatgagtc 201240
tcagggtttg agatctttta tttcaacttc cacacttata tatgtatctg atctataaca 201300
ttcctaataa atgaggtgaa tccagcctct gctaaaatat ttgatcaact gttataggat 201360
atctaccact gcaaaagtag ctcctatcct ataagctttg aagtattctt tgttatggtc 201420
ccataagcat ctatttctta agtaatcatg aggttttagg cactctgtta ggtacagaaa 201480
cccatagatg aataagaaac tacggtgttc tttactttga actgaaatac ctgtctttta 201540
attttcatca gttcgtccta agtctcctct ctagaccaac acagtagatt ccagtggtta 201600
tgaacatgaa ctttggagcc aggaaaaatg ttccaatcct acctctgctg tcactagttt 201660
tgtgaacttg aacagatgac tgtaaaatgg agataaaaat catctatctc tttgggggac 201720
aataaagcaa gatcacatga gtaaaagtat ttaacactct gtaacacaca gtagcttaaa 201780
atgttagcct ttgcagtaac aacaataata aacaatgatt taactctttc tcattgaaga 201840
taatggtcag agttttccga agacttaata tccttagttt ttattagtca tggcttctag 201900
gtccttcata tcatggatta tattcctgtg catattttcc agtttgtcaa ggatcctctt 201960
actcaccctg aacacaatat tctgtatgga gtttgaatgg agccaaattg agcataatta 202020
ttttctcctt cgaagtaaat ttcttccttc tttcaaaaca gtgaaataaa aaaaaatcat 202080
ttcattggga gcctcattcc actgagactg aagtctaaaa aaccctgaag tcatttccgt 202140
ggactgctct ttgcttgaac ttcacagtca gatcccatcc agtacttgtt caattagaaa 202200
cctgagacat ttttctccaa cagacatatt gctgcctagt attacagact tctgagattg 202260
atatagatgc atctttttca tccaacatat tccttgagaa tatcaacgtt tgtcactggt 202320
gaatgtaagt cttgtgctaa gtcttgtgcc aagtcttgtg ctaagggctt ggctggttgc 202380
taggaatgag gctgaggaca gaacccaaga gtagtttagg aatgtcttga gataggttta 202440
ttttattcag cattaggaac ataaacggag tcaagactta aagatttgtt cacctgaata 202500
atgtgttgaa tgatacggta tcctttagaa aatttcccag catatgctaa ttaaaaaaat 202560
ttttcttttt accacttctt gataacagca caaatcatgt tttagtctac attaaaatat 202620
agaagcattt cttaagaata agtcaaacat ttcattaatt caattcagca gacctccagt 202680
gaccccaaac tgatagatgt gatagggttt tttagaaaat acaattacat tcactataat 202740
gaagattact acatgtaaaa tcaagttggt ttattcaggt ggattaggaa tttatctctg 202800

-continued aagactccta attctttcac ataaattcca agaattcctg ggcagcatag gcaaggcctt 202860
tcatgttgac aaattgtgac attccctaac tcaatggtgc tcaaccagcg gcagttttgc 202920
tctccaagaa acatgtgtta atctttgaag acatgttcat tgtcacaact gaggtagctg 202980
ggggccaggg aagctgctaa acatcctaca atgtacagga cagcctccgc aacagaaaaa 203040
tatctaattc agaatgtcag tagtgctgag gttgggaacc ctgtattaaa tcagtgagtt 203100
gcaaattttt aggtgttgca atggactttt ttccctccta tttctctcat ttctactgct 203160
gcttctctct gccccttccc actactctct taagtccaaa ttctttccca acatttttgc 203220
ttttaatatt attacttttt ttctcattat gaaaacttaa ctannnnnnn nnnnnnnnnn 203280
nnnnnnnnnn nnnnnnnnnn nnnnnnnnnn nnnnnnnnnn nnnnnnnnnn nnnnnnnnnn 203340
nnnnnnnnnn nnnnnnnnnn nnnnnnnnnn nnnnnnnnnn nnnnnnnnnn nnnnnnnnnn 203400
nnnnnnnnnn nnnnnnnnnn nnnnnnnnnn nnnnnnnnnn nnnnnnnnnn nnnnnnnnnn 203460
nnnnnnnnnn nnnnnnnnnn nnnnnnnnnn nnnnnnnnnn nnnnnnnnnn nnnnnnnnnn 203520
nnnnnnnnnn nnnnnnnnnn nnnnnnnnnn nnnnnnnnnn nnnnnnnnnn nnnnnnnnnn 203580
nnnnnnnnnn nnnnnnnnnn nnnnnnnnnn nnnnnnnnnn nnncatatag agttccctat 203640
ccatagttct ttatcacaac ttttaaaaag tagcttttat gggaaacctg ttgcttttca 203700
tgacagcact tttctgggta gagttgtaac aagatttaga caattgcatt ttgtaaatat 203760
ttggaggact gaagattttt tgactcattt ctccattctt ttatctttca gaagaattaa 203820
tatttaagta acttgccatt gtagatagtt aactgaaatg ccataaaatt tcttgcttta 203880
ctgaactttt tcctgagcac ctactttctt ttttggaaag tattaagtgc tttgatattc 203940
ctaaggccta gaaaacctgt ttttggctct ctgagtgaag acaactccaa aacatgtaag 204000
ataattaaaa gacagatata ccaaaactta taaacaactg aaacctatat tatgaattaa 204060
tataaactct gagggtaaaa gagcatggaa ttgataagga atagaatttt tttaaaaaaa 204120
ggggttttgg aggtaagttt tgaagcagaa cttgaaaaaa attagtaaaa gagagtagat 204180
ttttcagcat attctttttt caaaactgtt tgattttgga aaattttgaa caggtttaaa 204240
agtacagaaa agagtctaat aagcctccat atacctgcca cctggattca gtaatcatca 204300
ataggctgcc attcttgcct ccggttttta aataaattcc agacttaaca tcattttgtt 204360
cctatatgcc taagcacgaa tttctaaaaa ccatggacat ttccacccat aaaataatgc 204420
catgaccaca atgaacaaaa ttactaatac catcctggta tcatttaata cctagaacac 204480
attcagattt ccttgattat cttcacatcc tatgttgatt aggtatgttc taattagact 204540
ccaaacaaag caacattttc tttgattaat gtgtagtctt atttccaaag tcaacattct 204600
acacaaatat ccaatattat ttggccataa caccttttcc ccattttgtt tcaatcaatt 204660
atgctagtgg ggatgaagaa atgagaatca tctagttagc tcaatgaaaa cctctactgt 204720
attcatccat aatctgttcc tgatgttttc acctcagtgt ttgccatttt ggtgaacttg 204780
acatgtgtga attacattat aggatctagg aacaattgca gttactttaa atattcctta 204840
tgtccagagt cttgacaggt atgccatgaa tcctgtgtga aaactattaa tattaccatg 204900
tagttttatt ctggtatgta acttcactct attataaact attatcatta atgtatatca 204960
agcaggcata tagacctctc atgtatggta tacaaatgag gacaggtaat tagagaagca 205020
aaacacattc taatacatca gtatgcctag aacacttacc atttgggggt gatcagttac 205080
aatatctcag tcatgaaacc tttgcatgag gacgtcttat cttaccataa agaaactaac 205140
tcaagtcaga acaaaatctg tttcttccca aaatacagta ttgttctctt aggaaataca 205200

-continued atgatcacaa tgtgttacaa tgattcaggg tattagtagc cggagaatga aattttggaa 205260
tctaaagaag acagtggtca tggaaatatg ttatctttta taacagcatg attccaaagt 205320
tataggtttt ttagaactaa tacttgattt aagtcatgaa gtgtaactgt cacagtcttt 205380
taaaatatct acttttaatt acagtatata aatgacccca tggctccaga aattgtgaac 205440
atagtagagc caatggtagg attatatgag ggttcagcag agatgtcgtc tgaccttcac 205500
tcacttgcta catttatata taacagccat ccagataaaa actttcctgc aaggaataga 205560
gctgaagacc agacttcacc agttggtagg tagaattttg attttctata aagttcattt 205620
aaaccaccag tgctagctag cacagaaatg aacctaagct tagagttcag ccatattatt 205680
aatggtcttt gggctggagt cggatttttt tttagctgtc ggaaaacctc atgcaacaaa 205740
tggaaatgcc acacaggcag aagctggccc ctcctaaccc atttgacctt cttcctggag 205800
aaagtagcac cctagagtct ctggccaagc tgcatagaca atcagttatt acagttgcca 205860
aagcaggtgt gatgggaagg gattaacata tcttcaaatc atttacaggc ctcacattct 205920
ctacagcttt tgactaatag gttttcaagt gtcactaaag gtaaataggt cagaaagtta 205980
caaatctagt gcatggtgtg ataaacaggt gtaggtgacc ccaacgatgt ggtgatgtca 206040
ttagtgtata cacttgctct tcagtgtcag tggctcttac agtttctaaa aggagaatgt 206100
catacgtggc aaattaaaaa tactcacctg acacatatta tctctctagt ttttctaaaa 206160
tgttaaatga gaaaaacatt ttattacctt ttctctaatt tggtacttgt cccattcaaa 206220
attaaaagtg ttattctatt tatggtagaa ttagtaaaaa aaaatcacat tacattcaat 206280
agatgtttat atttcactta ctgatccatt tttcttgtgc aaagaagact ggagggcaac 206340
actgaaaatt aagagtccca tgatttctga tgcagacatt cccttaaata tttcaagttt 206400
ggcctaattg ctacttaaga gttttagaag cacaaattct aaataaagcg aaaatctaac 206460
atttgaaatt cttctgggat atttatttgt cagttatcca agcatgcttg ctttcaagaa 206520
ttattttggt ttactgaatg tatgaacata tggtgaaatt tgagtccaaa taaaactctt 206580
tatttattta actcttttac taaaacctgg tattgattta taatatctca attatatatt 206640
tctttaactc ttctactaaa tcctggtatt gatttataat atttcattta tatattattg 206700
cctactcttt cttttcagaa aacattccta accagcctct ttaagaaagt tgttttctta 206760
aaaacactaa tgtcatgttt cagagtaatg tgtaaaaact aacaaaatta tattatgaac 206820
acaaaatgtt tgtggttatt attgggaggt actcagaaat tcatagtaat attcaatacg 206880
atctctaaaa ttaatatttt tatgtttact attattacac atctaacttt aatagaggtg 206940
tgcatggaga gattaatgaa tacggagaaa tcaggtttaa gattttatag tctaagaaaa 207000
aaataatttt gattgtgaag ccaaacacct ttcttttttt ctctttttac tgaattcaaa 207060
cagtaactac aaggaatcag tatattactg acattgcagc tgaacagctg tcttatgtta 207120
tcaggagact tgtacctttc actgagcaca tgattagtgt atctgctttc accatcatgg 207180
gagaaggacc accaacagtt ctcagtgtta ggacacgtca gcaaggtaag gatgtatttc 207240
ctttgaaaca attaactgca aatattgctg ttgtacactg tgatactttt ttttcattca 207300
tatgttcatt cttcttttta agtgccaagc tccattaaaa ttataaacta taaaaatatt 207360
agttcttcat ctattttgtt atattgggat cctccagaat atcccaatgg aaaaataact 207420
cactatacga tttatgcaat ggaattggat acaaacagag cattccagat aactaccata 207480
gataacagct ttctcataac aggtagaaaa caatgttttg ttgttgttgt tgttgttgtt 207540

-continued cattttacat ttctattctg gtggaaaata tgcccatctc cctgtgcctt atatactaca 207600
gaacacatgc tatgtcactt catattttgt tgttttgtgt caccatgaat ctttttaaaa 207660
tacctgcata cataactcga ttaaatgtgt ttttctttta ctagatttac ccacaatgaa 207720
gtaaaaagca tcagatcaca agcttcatag aaatttactt aactgaagga atactgtatc 207780
tggtatatca aaataactca ttattgaaga ctaaaatgta cgaatgcaaa aatcagctga 207840
agtaattcag ctgacatggt atttgtgcca agtcaactat acaccctgca gtgtgccaaa 207900
aagttacttt tgcaacttta aattattgcc ttaatatttt aggagagaac ttgaagtcac 207960
caacatagaa aggcctataa gcccaagaat ttgaggagac tgcaattatt tggaagcgat 208020
atagatatct agtcccccgt ataaattctt cttactggcc ttatattaaa tggcaccaat 208080
cccaagagta ttattttaag gacattaaac agtttgtctc ttgtccttat agggttaaag 208140
aaatacacaa aatacaaaat gagagtggca gcctcaaccc acgatggaga aagttctttg 208200
tctgaagaaa atgacatctt tgtgagaact tcagaagatg gtaagaatat caattgcagc 208260
tttaattttt ttaaaaaagt ggttgtaaat gctcactgcc ttcacttcat gctacctcta 208320
gggtctaaag caacaaacat caataaaaat ataggtacta caaatgttct tttcttcccc 208380
tagaaccgga atcatcacct caagatgtcg aagtaattga tgttaccgca gatgaaataa 208440
ggttgaagtg gtcaccaccc gaaaagccca atgggatcat tattgcttat gaagtgctat 208500
ataaaaatat agatacttta tatatgaaga acacatcaac aacagacata atattaagga 208560
acttaagacc tcacaccctc tataacattt ctgtaaggtc ttacaccaga tttggtcatg 208620
gcaatcaggt atcttcttta ctctctgtaa ggacttcgga gactggtgag cttttgtttt 208680
gctttgtttg tttaataata cacagtgata tagtaagcaa agctgataat cgccatgttg 208740
tttacatttt acataaccta aaatccctca ttattttgtt ttgtataatc cagaaattaa 208800
ttttcttttt caggcaaaag tgcaggaaaa ggtttattgt acaaattttt aagtctgatt 208860
tatataaggg aacttctaat caaaatctgt gaattttcaa atgaaaagac cttgagaaac 208920
caaggattct ttcaatgtac ctataaattt tagattgaat ggctacttgc tttcgagtta 208980
ggtaaaactg agacatactc ataggaatag attctgagat tctaatgagg tatgtgtata 209040
gatagtggtg cagagtggga gcacgaaaat ggcatgcctg gagaagactt atggaggaga 209100
cagcatttgg cctggatctt aatgaggagg ttggaatggg cagaaggatg ttatagagca 209160
ggggtcccca acctttttgg cactggggac cagtttcatg gaagaaaatt tttcccctcc 209220
ctccggacta gggaggggag tgaggttggt ttctggatga ttcaagcacg ttacgtttgt 209280
tgtgcacttt atttctatta ttattacatt gtaacatata atgaaataat tatacaactc 209340
accataatgc agaatcaatg ggagccctga gcttgttttc ctgcaactag atggtcctat 209400
ctgggggggta atgggagaca atgacagatc atcaggcatt aaattctcat aagaagcaca 209460
caacatagat cccttgcatg ggcaattcac aatagagttt gcgctcctat gaaaatctaa 209520
tgtcgacact gatctgacag gaggcagagc tcaggcagta attcaggcga tagggagtgg 209580
ctgtaaatac agaagcttta tgatgctcac ctgctgtgtg gcccagttcc taacaggcca 209640
tcagctggta ctagtccgtg gcgctgggat tggggacccc tgttatagag gttgctggat 209700
gggttgggag aggatatccc atctaaagga agtaaaacaa gcaaggaatt acttgtgttt 209760
tagtttcggt gaaactagag taagacagtt tgtctgttaa tcttattttg ttgtttatat 209820
tgtgttataa ttatatattg gtggcataac tattaggcca attctacaat gtattttgag 209880
aattaataac taaatataaa gttactattt taattgtacg tttaaaacaa taaatattta 209940

-continued

```
ctgactagat actggtggaa ccacatgaaa taatttttat aggtcacaaa tggccaaata 210000
tcagcaattt catatagttc agccagatac tatatacgaa tttctgtctt gaccttgagg 210060
atctagaaat ctagtaaagt agcttacttt tgtagaaaag tatcctgttg agactattca 210120
cagaaatgaa tacaatgaga tgatacaaaa gagcccatag ataatggcag tagttgaaag 210180
tgcaggaata agaaagtaat gaaaggagca ttttacatta tcaagagcct tgaagtgaca 210240
cttaattgat attaatccat atattggcat gtttcattgc ttttgtagat attgtacctg 210300
aaataagtat ttttgagaaa aatgtctgct ctttaatgac tcagttttat tttgcagtgg 210360
attaaggaaa tgaaacaagc atatttttag cacctattaa gggtcacggg ccctgttgat 210420
aggtttcaca gaaactgtct tttaaaaatt ctaaactaaa gcaatacatt attgttatct 210480
tcacagaaaa ctaagtctaa tgaaaaatgg agggtttgag aggttcattc attcaaaaaa 210540
tatttataat ataccaggcc ctactgggga taaagtagtg tagaagaaaa ggatttcctt 210600
ccctccttaa gttttattag ttggtgggtg tttcattgcc taatggcacc agctggaaag 210660
tgatcagctg gaaagtgatg agctggaatt agaatccaaa cccatctgac tgtaaaaccc 210720
atttcccttt cacagcacat gctgtttttg aagtaatcaa caaagctggt aaattataaa 210780
ctatatctaa gatctctctg ttcattgtta cactgatatt ttgtcattag gcttctgctc 210840
agcatgggga ggaaagtaat aactttgaaa gattctattg tgatatgaaa taataaccat 210900
ttttatgaat gcttatcaag tatttcgttt aagtggccat agcatcaaga acaccttatt 210960
ttaatgatga attataaagc aatgtttttg ttttctgatt attacatgca cataatcttt 211020
tacttagtat tgaaaatgta attttatttt ctgttttatt gtctgtatga gtttaattca 211080
aaggcaggga caataaactt taagtgaata taaattttga gatttagttt aaaatgagaa 211140
ttttaatttt ggaaagtgtc ttagaaaaca tgcagagccc tttatttttt aggtgagaag 211200
acctaggacc atttgggtaa aaggactcac aagttatagt acatgagaag taaagttggg 211260
gcttgactat aggcctcctg acccccatta caggcctcgt ttaataggct cctgagatgg 211320
ctaaaaaaat aaagagaagg ggaaaccaac atatcccatg gcttcctagc caggcctaac 211380
aatcagagta tagggtttaa tgcccatctt cctaatatct ggttctctgt cctaagttag 211440
ggttgtctca agttctgtgc attttccacc tggatgaaaa tggaagacaa tggaatctac 211500
attagtgact tttcctagat tatgtttgct actgttaaac cacccacttt agctcctttg 211560
gcaaaagagg aagctaaaat gttaggtagg gtctcaagtg tcatttgaag caagatgagc 211620
tcaagagcaa ctatttttct gggtttaggc tcaaaataat cttattaaat acagtaatta 211680
taccttctat tcatgtaaaa aaatatgggc ccactcttca atattgtttc atgagaaatt 211740
gagtgatgtg ttaactcagt gatgtgttaa tattactaat taaaaatagg agtaagttat 211800
ttggttaaat gccttatctt tttaagagaa atagagttta ctaatgcttg gaagtaaaac 211860
acccttgtgt tcaagcagga aagatcaata caagattgat tctgtgtgtg tgtgtgtgta 211920
tctctgtgtg tgtttgtgtg tgttttaatc atagatgtgc agttttccaa taagcctaag 211980
attagttttt attttctcat acttagggtg taataatcat aaatacaact ttgagaagtt 212040
cccatacaaa ttactctttt gatgatctat acatattccc tttccttttt aagacacaac 212100
catctttact gtaagccttt aacaaaacac cttgtctgat ttggggcaac aaccatgagt 212160
ggataataac ttagatgttg accaaaattt tgtgtagacc cccataaatt tatttgtatt 212220
aatgaataac attttaaaat ttgtctgcat acattaaagc tttatatgcc aaacaatagt 212280
```

-continued

```
cttttggcag attcaaggta acttcccttt tttactatca tcatggacta tgtatttttt 212340
ctgttttgga attttaatag gttcagctta ttccaactga ttataatcat tcctttttat 212400
ccatcagtta tctactttat aaaatatttc tataattcgg ggacactctg ctatttcaga 212460
aaattctaaa tgcgtcatta ctcttcaaaa tcagtaagtc attgagtctg tcttgcttta 212520
tctacctgat gatccagcac tagttattcc ctaagggtaa atgaataaaa atgcaaagga 212580
tatcagcctt gggtcaggaa tacatattta cacactgact actggtggta ggcagacaac 212640
tgcagagaga aaacttcaat ctaatgggaa attttcaaaa tcagaagtta caccgagcta 212700
taaaattcaa gcatagcatc acaaattccc tttttgtaat taaagagttt ttaaacccaa 212760
tcttttatct atctgttcct tacctgtgag tttctctctt gttttaatat attctgtatc 212820
atattaaata tattgattca ttcactaaac agcttttatg ggttccatat tatgttctac 212880
caccgtacta ggtagtgtag ctgtagcagt aaacaagaca caataaatct ctaccttcct 212940
gaaacttgac actagacaat cagaaaatta gacattagaa aataaatcag taaacaaatt 213000
tgtgattttt ggtagtggta agttttacta agtgaaaaat atcaaggata gaagagagga 213060
agagtagtga gtgggctatt tgagatggag gactgaggaa agacctcact gagaggttat 213120
atttgcccag tgatattaat gaggtacagg attgaataag atgaggatga ggatgaaaag 213180
tgttccagag gaagaacagc aattgccaac ttcttataga ggaaaaaaat tgtggagttg 213240
gggcagagca gggcatttct gtcacttgaa cagtgtgagt tggggtagag aattcacaga 213300
tgaggcgaga ggcagaggtg gatcctgaga ttcttaggtg ccattctagg aactttggag 213360
tttaatttta atgaggagct tttggagaat tatggaatag gaacattata tgatttacag 213420
ttttcaaaga ttgctgctga atatgttgaa tgttgaagta aagagaaaaa tgaagataaa 213480
ctattagatt gtttgtctga gtatctgggt gagtggtagt gccatttact tagatggggc 213540
agtccaggga agaggtcaat atggagaaca tccaggagtt ctgtttgcaa catgtttgaa 213600
atatccaagt gccattatga aggaagttag ataaataagt ttaaagctca gggaaaagat 213660
acagagctga atatataatt tggagcctca ccacatcttt ggtattcaat caagggatga 213720
ggataaagtc atatcactgg acaacagggg gagacgttaa gaagcttaca gctatgtcgt 213780
gggcaatacc acacatagac tttgagaagt agaagagcta atcaaggaca aagcagaagt 213840
cactggaaat agaaggaaaa ccagaagaag atagtgcctt caaagccaag tgaataaaga 213900
ttttcaagta gaaggagttt attccctatg tcacatgctg ctgacaagta aagtaagatg 213960
gggcatacaa ttgattagtg tttggcaaga agggaggtca ttggtgactt cacaggagta 214020
gattttacag aaaaaataat ggagaaaaat gaagtcagat taacagagta tgataggcaa 214080
aaaaaaatgt agaaaatgag gaatggcaaa ttttgaggaa ttttgataag aagtggagag 214140
tagacttcag taatagctga aggaacaagt gcaatcaaaa gaagactttt taaatcccag 214200
actgtatatt acagtgtatg tgtgttcaca tgtatctctg actaacttca aatgtaaagt 214260
ctctgaatag gcagaaggag tgaaatccag tgcagacgtg gagggataga gcttggaaag 214320
gaggaaagag ggaaggcagt taagggaaaa tttgaagtca gatgataatg tagctctctt 214380
ctcagtgttt ttatttttgc tatggaatga gaagcaagtt tattagcttc aaataaagag 214440
ggggagggca tatcagaggt ttgtgaagag agaacatggt gaaaacatac tttaaagagt 214500
gggagactga attaactaaa acaaaaacat tagctatcag gaaatgaaaa ggatccattt 214560
gagatttgat gttataaatt taagtggaac tagtcagcat agaatggtgt tttattcagc 214620
cattttcagc tattacactg ggcatgtgaa gctagcagag ttttgtttaa ttccaattgt 214680
```

-continued

```
aattttccca ggaaagtaaa atagaaacag aaggacctga tggatattgc taggaagtga 214740
ttacagtgac tgtggactct agcctgagca tgtagggaaa tgaaggcata agagaggtga 214800
tgcacagtga agatttgatg agggtcagag aattgttgga ttcaaagtac aagagtcagt 214860
aaactggaaa gataggagtc agttgtcaaa gagaggaata ttggcagtta ttggtaatga 214920
caaagtctta ggtgttgcca tgaaagccaa tgaggtacgg tggggtaaag taaggtgggg 214980
gaaaagatta ttggaattat agagataaag aaatacagag tccagggaac tggatagatc 215040
atttgcatgg aagttggcct ctctgagtag tagggaagaa gtcagttatc aaagtgatag 215100
catctttaag atgttcagag aagtgacaga ggtattacca gttgtctgtc ttaaagaggg 215160
gtagcacgtg atggtatcta atggaatggg gcttcaaagg atctgtggtt cttcaggaag 215220
aaaaaaggag taataaatgc aactacccaa ctcctacacc ctatcgttag tgagactatg 215280
gtagaaaaac aaacatgata cccaagaggg ctaaactgta gtagtatttc tcagcaggtc 215340
caagatttca cttagagcta gaaagttaag aaagcattga gggtagttgt tgaggatttt 215400
cctcaatgta atgggttggc ctggggaaac actagagaag atttagcaca tttcagatag 215460
aaaggatagt ggaattatat tgctaaatcg aactatgcat tgaattgcaa tcctctcaaa 215520
gttttaaaag tatcaatatt cttaaattag tttttcctat taagtgtgcc ttgacaccat 215580
aacccaataa ctggtaacaa tcaaggggag ggacactgta tctacatttt taaggcttct 215640
gaattttatt tatctactaa atttattatt agtaattttt atatgcattc aatttagaat 215700
actaataaaa agtttaattt ctttcatttg aaagaaaaga gttttataac agaactcttg 215760
aatggcaata atatttacct atttagttta tattgtttaa ccctccaagt taattattta 215820
tgttattgtt ctatgtactc aatttttaaa ccattatctt ggccactctg atctttcatc 215880
tgtggtaaat agttttctac ctaaagtaca ttgtctacaa tttcatttac tgaggatgtg 215940
ttgaaagcat tatccctcaa ttttttttat tgtctgaata tgtttttagt ttgctactct 216000
ttatttttct gggtatggaa ttccagttgt ttttcagttg atgttgattg tcagtctaat 216060
tgtcattcct atgtagaaga tttttttttt ctggtactgt taagatggtt cctttttttga 216120
tattctgtat tttcacaatg atatgtctaa atatggttta aaaatttctg cttgagattt 216180
actgaaatta tttgatctga tgtttgatgt cgttgaataa ttttgatgag cctcagccat 216240
tatcccttta aatatttctt cattttctct actattttag accccctccg gatatcatct 216300
atgtctcaac tgccatttta tattttccat aactgtcttc tttgatctac attcttgata 216360
atttcttcaa tactatcatc cttttcacta aagttctctt cttctttatc taatctgctc 216420
tttaatacct caagagattt ttaattttag ttattttgtt ctgttccaga aggtctatct 216480
tgttctcttt caaacttgct tggttattta atattattta ccattattta aataattatt 216540
tgctcatatt ttaaaatatg tttgatttct tgaaacacat taaacatttc tattttattt 216600
caatatctgg aatctcaaaa tctgactact gtgtatgtgt gtgtgtgttt tctttttctt 216660
ttctttgctg actttcacta ttgatatctg atttgcttgt gtgtttagcg attttatcag 216720
tgagctcata ttctttgaaa ctttagctgt gagaaattta tgtggtttgt gttgaagttg 216780
agttcctcca gcaagtattt ttatttactt ctagttgctt aggagtaata gcagctcagg 216840
actacagttt tattttaaat tctgaagtgg aggtttcttc agggtacata tagatatcat 216900
ggatttagtc aacatatgat cataggaata ggcttataat tccaaaacag catattattt 216960
atttcttttc tatctctcca cccagaggag tggcaacaga gaaagaaggt ttcctttctg 217020
```

-continued

```
tcctctctgc atggtagatt tatttctcac ttcccatttc ctgagaatga atgcatcaca 217080
ttgcacaaga ccaggagtta ccattcacat agacttctat ggtacatgca gaagaatctg 217140
aagtatcccc tagaattttt cagtataata accctggtta aagttgcatt ctttgggggt 217200
ttcaggtctt tctgcaggga tatcactcat ctttcagcgg gccccagggt tttatagtct 217260
ttctctgaca cactacacat atgttactat acaaatgcaa aggcaccagg attaaccaat 217320
ctatggcaag gcaaaactgg ctttagtatc agcttccttc tcaggatttc tgtctttgca 217380
ttttgtttac ttgtttgttt ttctgtgact ttttttggcc agtcaccact gaattctaac 217440
tttcttttca gcaccacaac ttcttaaaga aaatttattt taatgttata cagagtttta 217500
gttattttaa gtaagatatt cactcagttt agggtatctg ttccaatatt ttaccggaat 217560
tagaatcttg tatatagttt tgtactcaaa tatacataga aaaccatttt atgcataatg 217620
tattcagtat aaaaatgttg ttagatacag aaaactagtg ttttacttaa tgatatccca 217680
tattcttggg agatggtttt gctgccaggt cataaatatgc aacctcacat ccaggagggg 217740
ctccttgcct tgtcacagac cttgctgtcg accaaaacta acctactgat cttttttttca 217800
tattattatt aatgagaagt agaatcaagt tttaaatgtt ttaaaattct ctttcttgca 217860
tctgtgtgtt cttcagtgca agatatgttc ctatagttcc aagtatttta gtaaacgtat 217920
catcttataa ctgttattct gtggaatcat agtagcattt tcttttgaat gaaaattttt 217980
cttatacagt tgtaagaact ataatttatt tatactttac ttcattcagg atatttatta 218040
cgattacatt ctagtgaagg ttcaattgta aataacctag tgcacttcag tgacaatttc 218100
agcagaatag atttttagaa tggaattgtt ttatgtatct atatttttgt ttctttcagt 218160
gcctgatagt gcaccagaaa atatcactta caaaaatatt tcttctggag agattgagct 218220
atcattcctt cccccaagta gtcccaatgg aatcataaaa aaatatacaa tttatctcaa 218280
gagaagtaat ggaaatgagg aaagaactat aaatacaacc tctttaaccc aaaacattaa 218340
aggtaaaaga acaaatctaa tattggatat ttgcatttat aatgacagag tagccacaaa 218400
tattagttta atgttaatag tttcagatta ttttcatgca gggtattaca attttgtctt 218460
tttggttaaa taagctagga gtttattgca ggtcacatga aagaatacta tagatccatc 218520
cttttccaca ttatcctata tcattttgtc ttcataaata agagctacta ttgccaaaga 218580
atgacatttt cacttagttt ttatttttgg aagattgtgt tgacagccat ttcatagttt 218640
gcctcttgca tattattaaa tgatattttg taagtttcaa cttacctatt tgatttctct 218700
ttagtactga agaaatatac ccaatatatc attgaggtgt ctgctagtac actgaaaggt 218760
gaaggagttc ggagtgctcc cataagtata ctgacggagg aagatggtaa atataatagt 218820
ggatattgat atactttgat tctataacat tccaagaaac acacgtatag aatgaaacaa 218880
tgtaaaaact cctctagtca tgggtatcag ttgtgtacca taccagcgtt atacagagat 218940
ttcattgtca tggtataaaa gaagctagca acatcagatt tacattcagt gaaatcaggc 219000
ataaaatgtt ttttattttc tgaagtcatc agtactctgt aaaaaacagt cagtcatgtt 219060
tttccatggg gattttcaag gcttaaaatt tggtttgaac gttaactgat atatgtcatg 219120
actgagtttt tcaactttta catttttaag aatagacatt aacatgagct ttgaagcaga 219180
ttatgtttat gtaaatgttc agcacttttt tacgatatta atgattaact tgataatgag 219240
atcaggctat tgtacaggct tctgcataat tggacaagat gctattcccc aaagttagta 219300
gctttcatac tgaatattta aacatacctt tccctaaccc aaataaaatc aactttacta 219360
ctgaggccac tttacattga taccttacca agttagacat atattatgct aagaatataa 219420
```

-continued cttctgaaag atatatttgg gttaggattt gcattttatg ttttatacat tgcatattta 219480
aagaaaatta ttattttttt ctgtaaaagg aattcctatt tccaagaagg gtaggcctgg 219540
aagtatcata cgtgtttgtg gagtatcttt tctttttcat ctttctttct ttcaagtttc 219600
cccatcttca agctaggcca tagcctgtga ctgttaaggg cagaatgtgc ttagacactg 219660
ctaggaaggg agacttttcc ctgcattgct ctctttcttt tcaaaataat aaagtcttca 219720
aatccctctt ctctttttgc aggtctctcc atgttttaac ctctaccaaa gcatcttggc 219780
tagggctgtc tgtgttgccc cagtttctaa gtgggctgcc tctgtgggtc agttttccct 219840
aatcattgca tctacttact aatgcttgct tttccatcaa aacttacctg cccaaattcc 219900
aatttttctt cataaataga ttctccttgc tctgaaagtt aaaattatct taataaaaaa 219960
accttccaaa tgagtcaatg gttaaaaact agggaagaaa gttagtgctc ttttctatct 220020
tatgtaatac ctaagattat atgtagtaaa aattttacca atgccttttt gaaaatagta 220080
cccacttctt tataactaat ctaatcaaaa gttcctaatg gtaagaattt gagatcttat 220140
atgatggaat gagaccagta gtgaacatat attttgagca ggcagacgtt ttaccactca 220200
agtcaatagt tccaaagtat gttgtgcatc tgaattacct gggctgttaa aaatatgctt 220260
cctcaaggta aagttccatc taaattcttg gccaagtcat atgatttcta aggaacaggg 220320
taaagaacaa gactcccttg ttgaaaaatt acagaaaatc gagaatggat aaagatctga 220380
gaacatttgc ctctttggga attaggaact ccttgccctc atgaagctca cggttagaac 220440
aagagaccta aatttgacaa atgtgtggac aaataatttt tatgattttt aattactggt 220500
ataaatgttc ccccaaatta ttcaccagga caaaagaagg acctaagtta ctctggggtg 220560
tgaggtaaag cgtagcggtg gaagttatgt cgaagctgtg acatgaaaat gaataaagag 220620
ggagggtgag aaataggaaa gatcatgcca ggtagaggag tgagagattt gtgaagtcct 220680
catgccaggt agaggagtga cagattgtga agtttcttct cagctacctt gagatgctct 220740
gagatgacaa attgaatgca ctgcaaaagt tctaattttt ctagtttcaa ttttgttaga 220800
ttgtatttta gaatacatgt gccaaaatat tttagaatac atatgccaaa atgattaaaa 220860
cttagtctgc tacagtggat gtacagtgat ttttttagat agacatgtta attacgttta 220920
cttagcaata aaatgtttta cattaagaat aaaatattcg gagatctact gaaggttagc 220980
ttttaaagac accacgcttt atctggtatt ccacataagc atcttaaagc atattataga 221040
gtagaaatgg ttagttgcaa catattagtt tctaagttac tgctattttt aattgaagtc 221100
ctttttgtaa acaataaaca gattttacaa ggatgctagg aaaaatattt ataggtattt 221160
gctttgacaa atgaaagaga attttcagag ataattctta tcttgggaaa cagacatctc 221220
taactgatgt atacattcct gtgataatca atatttgata gcaacattat tatagtgcca 221280
gtgaaaataa cagaatgaaa ataccaaata cagctatcac tattattcct tataacttgt 221340
ctcataaact ttctgctgct caataaaatt tttttggaaa attattgtta gttaaataat 221400
gaaaacatgc acacatggga acacatacaa ctacagctga gattattcag agaagtaaaa 221460
aagaaaaaat attgaagtaa gtcaggtagc attctgtcca aattattgga aatagtgatc 221520
tgtatatgaa ctgtatttca attgacattg tttaaagatg taaacaaatt ctcagaattt 221580
ctgttagcta cctatgaatt cacattcccg tgcataactg taacaatgaa ccaaatttta 221640
gtgttttcct tttttacatg taaaaagttg tattccatta ttctaagaca ttactgtgtt 221700
attacacagc agctgagaaa tgtcattcta aatgttttac ctaaatggaa atataaagtt 221760

-continued

```
ggctgactat tttgcagtaa tgtttttatt gcttattcaa tgccaaatag caaatgtatt 221820
tatattttac actattacag cagagttaca agtagattct aaactatttt cttatttacg 221880
tgctacattg gcatttcctt tgtaaaccat tcaattttga agactgagtg aacagagttt 221940
gatattattt tactttttaa tgacacaaca gagattgagg aatgtagttt tcatcatttg 222000
tgaggtcagt cattttaact gctttctcaa tgttatgctt atcactttcc caacttcttg 222060
gatgtgtgat ttttttccca cctctttttt attgtctagg gatctctttt actgtatatt 222120
tattcaccct caataaaatt tttattttta ttagaggatg acagttgacc aagatgtact 222180
tgaacagtag gtgagtcact gtgacatacc ccttgttctt ctttctcatg aaatattttt 222240
ttccattgaa tcacagaaac agatgttcta ataccaccat gcaaaatctt cctttatcat 222300
ctcattttga aagtaaacag tctcttgtgc ttctggagaa aagcactgaa cctaattcct 222360
ttaccagaaa gtttataata aaaattgtgt gcatttccat gttaactttt tcttatatat 222420
gtttaataaa acacattatt ctataccota actttacagc tcctgattct ccccctcaag 222480
acttctctgt aaaacagttg tctggtgtca cggtgaagtt gtcatggcaa ccacccctgg 222540
agccaaatgg aattatcctt tattacacag tttatgtctg gtaataattt ttttttggga 222600
aatagttctg agaacagata ttaatctgta acataatagg aatgtagctt ttagatttca 222660
gaatgtggtg ctacattagg aacctgatta ttaataggct agttaatatg ttttgattaa 222720
gaaacaagtt tttccatatt atgtagtggt tcaatcatgg tcaaatgaaa taattttgca 222780
attaaaacaa aaaattatgt gttacgcata attatactaa attcctactc ttaaaagtca 222840
ttgacaagtc aatttgtatg aatgtaagca tatactttta cacttcctga agttttacac 222900
aagtannnnn nnnnnnnnnn nnnnnnnnnn nnnnnnnnnn nnnnnnnnnn nnnnnnnnnn 222960
nnnnnnnnnn nnnnnnnnnn nnnnnnnnnn nnnnnnnnnt catgagaact tggtagattg 223020
aaatctttac tttgaatgta atgtaaatcc tctttagatt caccaattag gtaacacatt 223080
acctagtgga tttcatatat ttcaactcag aaaatacaat ttacacaata cttcgtaaaa 223140
catagccatt tccttttata tttctgaatt tgaagggcca gcattgaggg agatgccatg 223200
atgttttaaa gaagtctcct cttcttctct ttcctaagtt aagatttttc tttccctaat 223260
tcccctttaa cccctttaca tatttctctt taagactata ttttttgttt tctttgttgc 223320
ctgattccta gtgactttgc ctagtcgtga cgaaagtggg agtgtcttga ctcccagtta 223380
gcgaaaagga agcagggaag aaggttacca ttccttttca ttaccctatt tatttattca 223440
ctcattcatt cattgaacaa tattgataga atacctatat actcatgaag aagactcaca 223500
taagaccgtt gccctcaaga gtgttgtatc tcttacactc ccaagagata actggattat 223560
atacccataa acaagcaaac aagggaatgt tgggggaagg aggtctactt ttgatgggat 223620
gcttcaggaa gttctctttg aagaagtgtc attgagctgt gatccagttg acaagaaaga 223680
gcttcttgcc atgtaaaaat ctacagggca gaactttcaa gaaggaggga ataccaactg 223740
cacaagctct gtggggaaac aaaacttgtc actttgaaga ccagaaagga ggtcaatgtt 223800
gctggggatt agagaaccag aggagggtaa cagtggggac aggaaataaa gttcaggagt 223860
caagccatgg taaggatttt gttttcattt taactataaa gggagttcat agataattta 223920
aatcacttta gattccttat aaagaatgaa ttgtcaggga caaaagtgtt agcagggatg 223980
ctaggctatt ttagtagtct gggaaagaga tggtagtggc aacagagggg agaagtaggt 224040
ggctttgagc tacatttggg aagaaaaact aacaggactt ggtgatggat ggctgtgcag 224100
ataagaaaan nnnnnnnnnn nnnnnnnnnn nnnnnnnnnn nnnnnnnnnn nnnnnnnnnn 224160
```

-continued

```
nnnnnnnnnn nnnnnnnnnn nnnnnnnnnn nnnnnnnnnn nnnnnnnnnn nnnnnnnnnn 224220
nnnnnnnnnn nnnnnnnnnt gaatcaagtg tggttactac tagaatttga tggcattgat 224280
taagttagaa aaaaatttaa atgaaacaga ttaagtgaga atcaagattt ttctggctgg 224340
gattttcagc cctgcattat gagaataatt gttttcttct atacagtgat catgcttccc 224400
ttcctagagc ttccgtgtat atctagcata atgcataaca cacctagaca gaaacacatg 224460
tggttggata gcattttaag ggatgccgtt cacccagttt ttctctctct gggtatgaac 224520
tccatgtcaa tgggagcctc ctattctagg aacttagcta taactttagt tgtctattta 224580
tnnnnnnnnn nnnnnnnnnn nnnnnnnnnn nnnnnnnnnn nnnnnnnnnn nnnnnnnnnn 224640
nnnnnnnnnn nnnnnnnnnn nnnnnnnnnn nnnnnnnnnn tactacagaa agatgagctt 224700
ataaaaagca gtgctaaatt aggccacagg aaaatgcttc cagttaaggg ataagtatga 224760
catttccaag ggataataaa gggtaaagat atcttctgga tcctccctca atataacatc 224820
aatatcttct ttgaaccttg aaaataatta aatagagaga agaaaatata taaaacctgt 224880
gtaaatatgt gattttatat aaatgagatg ttcttcctag aggataagaa atattggaag 224940
agatttttgc caggaagttt tttcttactg gaagtgtgcc tatttgcaga attaaagaac 225000
acgatcagaa ctggaaagca aatactaata gtgtgagtct tacaatgaga aaagaaaaaa 225060
aattcttacc tatgtagaag tcaaaataaa agatttgtga tgactatttc atgaagaaaa 225120
catagcttaa agaataggca accttttttct aactgacatc tgagtattat ataatatagg 225180
tattttctgt caatatgtac acattcagat taattaacat gtcaatatat gctattgggg 225240
ataattaaaa atttttaatg tgctgtaaga aactattgct gataggaagg tgatttagtc 225300
aacctagttc tgcttagatc tattttttatg gagcttgaat ttttattcct gtgaattctc 225360
ttatttaagg tctattggga agcccttact ctccgtttca tctcacactt tataaatcat 225420
tcttgtgacc tttactctgt tcaaataaat gttagccatt gcagaattcc aaagggtatt 225480
tggcatgata catttgatgt cttcagtgta agtaatgtta taggaaaaat cctgttaagt 225540
attttacatg tgctatttca tttagtcctc agcacaatcc tataacatag atacattatt 225600
attcccattt taaagacaag ataaatgtta cttacaacag ttaagtaaat tgctcaaagc 225660
tactatctgg gaattggtag aactacagtt aagccaaggt tatgattcca gtcatggcat 225720
ttgcaaaagc ttgagtctta ttctcattaa tgacattttc tttttctatt ctagtctatt 225780
ggaagatatt attcaaatca aattttttta tctttaaaat tctggaattc ttagtttaaa 225840
ttattaatta aatgtactta tctaatttat tttttaaaa cagttttttg agtatttgtt 225900
tgcctgatta gattgtgaac tctaaattaa ggtaccatat acatggtctc ttgcatttgt 225960
tacagaaata attgtaatgt cttttatgta gtggatatat cagagaaaga ctgagctttc 226020
aaaataaacc caactgcaac tggattcttg ctctaccatt tattcctgtg tgaccttggg 226080
caaaggtatt tgacctctct cagccagttt tctcatctat acaattttga caataatact 226140
ttatttgttg attgtataga tatcttcata tttgccttct tccttgagag tattaaaaaa 226200
gtatctttgg catttatctt atggataagt caaagttttg ttttaaattt tagattctct 226260
tttttcaggg agtaaaatgt ttgaacacaa tccttttggt ctgttctagg ttgctgctga 226320
aaacagtgct ggcattggag tgtttagtga tccatttctc ttccaaactg cagaaagtgg 226380
taattttcct gtcatttatt ttaaattgac ttagtcatga gtttgtcgtt taaaataata 226440
aagaacataa ataaaaactg acactaaaat acatataatt ctcagtagca tggccactta 226500
```

-continued attagtttta gagttctttc ggatagctaa tttattcctt aaaatatata ttattctttc 226560
tgattataag aacagtaaat gttatcttac aaaactttga aaaaacaaga ataaaaaatg 226620
aaaattatcc atagacttat catataaaaa atgcttttat cattttggtg catttctggc 226680
ttgtctattt cccccattaa tatgtatcta tatgactata cattaatgaa aataagcttg 226740
tgctacatat gcaagtttat atcctgcctt ttctttttaa catgaagtca taagcttgtt 226800
ataacataag acttttggaa acacggattt taatggttat tatattattg ggtaacatgc 226860
agtcattacc aaaccaattt aagatacctc cattcttcca ggggcataga ggaaaaatct 226920
tgatgtcacc tgtggctctt ttctctcaca gtacacatct aatctatcag taaatcttac 226980
cagcacaatc atcaaagtgt attctgaatc tcacactcat tgctgacatc ctgtccaaca 227040
ttattcccaa gaattgttgc attatatttt atttttatta gaatgcagct gtcctgaagt 227100
cccttaattc ctaccttata tcattcatat agacctcctt ccaaagatct aactttctta 227160
tgtaatttat gtggctatta cttataaatt atattttagc atccttttgt acaatgtaaa 227220
cctaaactct agttatttgg catcttaata ctaggcatct ttactatcac ttattttttt 227280
tttatctcag acgttttgtt tcattttgat ttctttcaaa aatgacttgt catgtttgtt 227340
ttatattctg aaggatcttg gtgttttact ctatcagttt tacacacttt accatgaggt 227400
taatgggaat aatttcccct aattctagct tcatattggt ttcaagccaa ctcaaataga 227460
actcagatta ttattattat tactctatat aattaataat tgatagaaaa gcataatgaa 227520
attctgaagt aagttgattt tgaaaatgta aaatacaata attacaacca attgcagggt 227580
atccacttga tattaggcac tagacattta taaacattcc agaaatctgc tttttggtga 227640
aaatggttgt ataattgatt cagtttgcta tgtttttcat atctaatgaa actacatatt 227700
ccaaaatagt taaggaaata agaaatttat cccaacttgt ttgtatattc acaactattg 227760
attgaatttt tttcatactt atttgaaacg tttcatcaat gcatgtatta gcccagttat 227820
cctaaagtaa agttgacttg ccccaactcc agttttttat tttaggcaaa gttcagttaa 227880
atacatttat aaaaatctta cacaaataga ttttatgcag tgtattatat atttaatttc 227940
atgtaccatg aaattatata aatgcaattc taagttttat aacaaagttt tttccttccc 228000
aatctttctc ttccccagct ccaggaaaag tggtgaatct cacagttgag gcctacaacg 228060
cttcagcagt taagctgatt tggtatttac ctcggcaacc aaatggcaaa attaccagct 228120
tcaagattag tgtcaagcat gccagaagtg ggatagtagt gaaagatgtc tcaatcagag 228180
tagaggacat tttgactggg aaattgccag aatgcaatgt aagtatcaca gaacactttc 228240
tatgtcttga aaaatcttag ataaatttaa ttttcatatt tctagcatct agatactata 228300
tttttaccaa agttttatta gttatttgat tacttatggt atcatgttat acacaacgtt 228360
ttattatttg attacttagg gtatcatgtt acacaattgg cctcattcag gtagaataca 228420
ggaatggttt gagaattcaa gagtgaggga ttaaaatcat ttagggaatt cggaaaagac 228480
ttcatcaaag gagtagcatt tgtgatacac catggagcaa ggacagatag agattttgtg 228540
atggtggcat tcccggtgga ggatacttta taaagccctg aggtggaaaa gtgtaagata 228600
taattggaga aaatatttta cttccatatg acaggaggga agagtacatg tagggtaata 228660
gttgaggtta aatttgcaga ggtagactgt cattgttgtg catatctttg gtaaagaatt 228720
tgtcgttact ctggtcattg atgataaacc tcataatagt aatgctttat tatagaataa 228780
gcatcgtcat tttaattata tgataagcat aataatgctt ttcctaaaat cattttggta 228840
atctctgtgt tactattaat gcaaacacag tcaaacagtt atttttgctg taaatacttt 228900

-continued ataaaagtct aaaaatcttc tttttcaact tatgatatag ttctaataca cgcacacacc 228960
taacgtgtga gctagtggca tactactact ttttagtact tatgagaaaa aaaagttcat 229020
taacagtaag aaagcagcat ttgaacatac acaagagtaa aattatttca gctctttggc 229080
tcttgcactg ttaacatgaa gcttaaaaat tcttacagat gattgtgctg tagttttacc 229140
tttattttaa gccacttgaa attctattcg taaaggttaa ggtataagga atacaataaa 229200
tatgtcctct tctaaaactg cagacataaa tgggtacaat taaaatctag caaatttgtc 229260
tataactttt gcatgttatg tgtgtatgta taagcataaa agaaaaagaa atgaattaca 229320
tgttcttatt cttatgttca ccaagagata caacattatt tctctattga tcttatttta 229380
tttactagga gaatagtgaa tcttttttat ggagtacagc cagcccttct ccaacccttg 229440
gtagagttac acctccatcg cgtaccacac attcatcaag cacgttgaca cagaatgaga 229500
tcagctctgt gtggaaagag cctatcagtt ttgtagtgac acacttgaga ccttatacaa 229560
catatctttt tgaagtttca gctgttacaa ctgaagcagg ttatattgat agtacgattg 229620
tcagaacacc agaatcaggt atggttcact ttttgtagat aaaaagattt aaatgattag 229680
agaataatgt ttaatttatg tagatattta attttaatct tctttacctt tcagtaactt 229740
ttttccccta ataatatacc ataggcatcc catcaagggt ttcttcgaat ttctatactc 229800
ttttatatta tagcacaaaa taagtatttg aaaggagaaa gatttgcaaa aaacaattct 229860
tgagccactg accgtgatcc tcatatagct tttatcattt tataatgtca gcaattttta 229920
gtaatcatct ttgccgttct aaatgattta taatcattta caccccttctc tcactgttat 229980
tgccatcatc aaaagcagaa atacctgcac tagcagaacg agcatgtgat caacatttag 230040
ttatcagata caagcagtag ctaaaatata tacctactta tatcccattt gcactgcagt 230100
ttcctcatct gaaaaataga gacagtaata gtaccttcct tagggtgcca gtgttaaaat 230160
taaatgagaa taattagata ttatcattac tactgaattt tatgagaaca tatttttggt 230220
aaggtattca tatatttaat tatggtacta tatcagtatt catgtaaata catgtattta 230280
tgtatttcat atatttataa aatttaaggg atattgatat agtcccacat tacataaggt 230340
atttattata tatataaatat atatagctga cagatatatc ataatatagt atcaggcatt 230400
aggttgtaat tgctaatttc tgaggtattg aaaattattg gtagggtaat ttcactaaag 230460
catgtttttt ctgataaaat agctgttggc ttctattatt tttcatttca tataagtttg 230520
aagtttttt gttcatttaa ataaccatct ttgaattata ccattttctt cttacatact 230580
ccttactttt tatacaataa aaaaatgatt tcggggggag ccaagatggc cgaataggaa 230640
cagctccggt ctacagctcc cagcatgagc gatgcagaag acgggtgatt tctgcatttc 230700
catctgaggt accgggttca tctcactagg gagtgccaga cagtgggtgc aggacagtgg 230760
gtgcagcgca ccgtgcgtga gccgaagcag ggcgaggcat tgcctcactc gggaagcgca 230820
aggggtcagg gagttccctt tcctagtcaa agaaaggggt gacagatggc acctggaaaa 230880
tccagtcact cccacccgaa tactgcgctt ttccgacggg cttaaaaaac ggcacaccag 230940
gagattatat cctgcacatg gctcaggggg tcctaccccc acggagtctg cctgattgct 231000
agcacagcag tctgagatca aactgcaagg tggcagcgag gctgggtgag ggcacccgc 231060
cattgcccag gcttgcttag gtaaacaaag cagnnnnnnn nnnnnnnnnn nnnnnnnnnn 231120
nnnnnnnnnn nnnnnnnnnn nnnnnnnnnn nnnnnnnnnn nnnnnnnnnn nnnnnnnnnn 231180
nnnnnnnnnn nnnnnnnnnn nnnnnnnnnn nnnnnnnnnn nnnnnnnnnn nnnnnnnnnn 231240

-continued nnnnnnnnnn nnnnnnnnnn nnnnnnnnnn nnnnnnnnnn nnnnnnnnnn nnnnnnnnnn 231300
nnnnnnnnnn nnnnnnnnnn nnnnnnnnnn nnnnnnnnnn nnnnnnnnnn nnnnnnnnnn 231360
nnnnnnnnnn nnnnnnnnnn nnnnnnnnnn nnnnnnnnnn nnnnnnnnnn nnnnnnnnnn 231420
nnnnnnnnnn nnnnnnnnnn nnnnnnnnnn nnnnnnnnnn nnnnnnnnnn nnnnnnnnnn 231480
nnnnnnnnnn nnnnnnnnnn nnnnnnnnnn nnnnnnnnnn nnnnnnnnnn nnnnnnnnnn 231540
nnnnnnnnnn nnnnnnnnnn nnnnnnnnnn nnnnnnnnnn nnnnnnnnnn nnnnnnnnnn 231600
nnnnnnnnnn nnnnnnnnnn nnnnnnnnnn nnnnnnnnnn nnnnnnnnnn nnnnnnnnnn 231660
nnnnnnnnnn nnnnnnnnnn nnnnnnnnnn nnnnnnnnnn nnnnnnnnnn nnnnnnnnnn 231720
nnnnnnnnnn nnnnnnnnnn nnnnnnnnnn nnnnnnnnnn nnnnnnnnnn nnnnnnnnnn 231780
nnnnnnnnnn nnnnnnnnnn nnnnnnnnnn nnnnnnnnnn nnnnnnnnnn nnnnnnnnnn 231840
nnnnnnnnnn nnnnnnnnnn nnnnnnnnnn nnnnnnnnnn nnnnnnnnnn nnnnnnnnnn 231900
nnnnnnnnnn nnnnnnnnnn nnnnnnnnnn nnnnnnnnnn nnnnnnnnnn nnnnnnnnnn 231960
nnnnnnnnnn nnnnnnnnnn nnnnnnnnnn nnnnnnnnnn nnnnnnnnnn nnnnnnnnnn 232020
nnnnnnnnnn nnnnnnnnnn nnnnnnnnnn nnnnnnnnnn nnnnnnnnnn nnnnnnnnnn 232080
nnnnnnnnnn nnnnnnnnnn nnnnnnnnnn nnnnnnnnnn nnnnnnnnnn nnnnnnnnnn 232140
nnnnnnnnnn nnnnnnnnnn nnnnnnnnnn nnnnnnnnnn nnnnnnnnnn nnnnnnnnnn 232200
nnnnnnnnnn nnnnnnnnnn nnnnnnnnnn nnnnnnnnnn nnnnnnnnnn nnnnnnnnnn 232260
nnnnnnnnnn nnnnnnnnnn nnnnnnnnnn nnnnnnnnnn nnnnnnnnnn nnnnnnnnnn 232320
nnnnnnnnnn nnnnnnnnnn nnnnnnnnnn nnnnnnnnnn nnnnnnnnnn nnnnnnnnnn 232380
nnnnnnnnnn nnnnnnnnnn nnnnnnnnnn nnnnnnnnnn nnnnnnnnnn nnnnnnnnnn 232440
nnnnnnnnnn nnnnnnnnnn nnnnnnnnnn nnnnnnnnnn nnnnnnnnnn nnnnnnnnnn 232500
nnnnnnnnnn nnnnnnnnnn nnnnnnnnnn nnnnnnnnnn nnnnnnnnnn nnnnnnnnnn 232560
nnnnnnnnnn nnnnnnnnnn nnnnnnnnnn nnnnnnnnnn nnnnnnnnnn nnnnnnnnnn 232620
nnnnnnnnnn nnnnnnnnnn nnnnnnnnnn nnnnnnnnnn nnnnnnnnnn nnnnnnnnnn 232680
nnnnnnnnnn nnnnnnnnnn nnnnnnnnnn nnnnnnnnnn nnnnnnnnnn nnnnnnnnnn 232740
nnnnnnnnnn nnnnnnnnnn nnnnnnnnnn nnnnnnnnnn nnnnnnnnnn nnnnnnnnnn 232800
nnnnnnnnnn nnnnnnnnnn nnnnnnnnnn nnnnnnnnnn nnnnnnnnnn nnnnnnnnnn 232860
nnnnnnnnnn nnnnnnnnnn nnnnnnnnnn nnnnnnnnnn nnnnnnnnnn nnnnnnnnnn 232920
nnnnnnnnnn nnnnnnnnnn nnnnnnnnnn nnnnnnnnnn nnnnnnnnnn nnnnnnnnnn 232980
nnnnnnnnnn nnnnnnnnnn nnnnnnnnnn nnnnnnnnnn nnnnnnnnnn nnnnnnnnnn 233040
nnnnnnnnnn nnnnnnnnnn nnnnnnnnnn nnnnnnnnnn nnnnnnnnnn nnnnnnnnnn 233100
nnnnnnnnnn nnnnnnnnnn nnnnnnnnnn nnnnnnnnnn nnnnnnnnnn nnnnnnnnnn 233160
nnnnnnnnnn nnnnnnnnnn nnnnnnnnnn nnnnnnnnnn nnnnnnnnnn nnnnnnnnnn 233220
nnnnnnnnnn nnnnnnnnnn nnnnnnnnnn nnnnnnnnnn nnnnnnnnnn nnnnnnnnnn 233280
nnnnnnnnnn nnnnnnnnnn nnnnnnnnnn nnnnnnnnnn nnnnnnnnnn nnnnnnnnnn 233340
nnnnnnnnnn nnnnnnnnnn nnnnnnnnnn nnnnnnnnnn nnnnnnnnnn nnnnnnnnnn 233400
nnnnnnnnnn nnnnnnnnnn nnnnnnnnnn nnnnnnnnnn nnnnnnnnnn nnnnnnnnnn 233460
nnnnnnnnnn nnnnnnnnnn nnnnnnnnnn nnnnnnnnnn nnnnnnnnnn nnnnnnnnnn 233520
nnnnnnnnnn nnnnnnnnnn nnnnnnnnnn nnnnnnnnnn nnnnnnnnnn nnnnnnnnnn 233580
nnnnnnnnnn nnnnnnnnnn nnnnnnnnnn nnnnnnnnnn nnnnnnnnnn nnnnnnnnnn 233640

-continued nnnnnnnnnn nnnnnnnnnn nnnnnnnnnn nnnnnnnnnn nnnnnnnnnn nnnnnnnnnn 233700
nnnnnnnnnn nnnnnnnnnn nnnnnnnnnn nnnnnnnnnn nnnnnnnnnn nnnnnnnnnn 233760
nnnnnnnnnn nnnnnnnnnn nnnnnnnnnn nnnnnnnnnn nnnnnnnnnn nnnnnnnnnn 233820
nnnnnnnnnn nnnnnnnnnn nnnnnnnnnn nnnnnnnnnn nnnnnnnnnn nnnnnnnnnn 233880
nnnnnnnnnn nnnnnnnnnn nnnnnnnnnn nnnnnnnnnn nnnnnnnnnn nnnnnnnnnn 233940
nnnnnnnnnn nnnnnnnnnn nnnnnnnnnn nnnnnnnnnn nnnnnnnnnn nnnnnnnnnn 234000
nnnnnnnnnn nnnnnnnnnn nnnnnnnnnn nnnnnnnnnn nnnnnnnnnn nnnnnnnnnn 234060
nnnnnnnnnn nnnnnnnnnn nnnnnnnnnn nnnnnnnnnn nnnnnnnnnn nnnnnnnnnn 234120
nnnnnnnnnn nnnnnnnnnn nnnnnnnnnn nnnnnnnnnn nnnnnnnnnn nnnnnnnnnn 234180
nnnnnnnnnn nnnnnnnnnn nnnnnnnnnn nnnnnnnnnn nnnnnnnnnn nnnnnnnnnn 234240
nnnnnnnnnn nnnnnnnnnn nnnnnnnnnn nnnnnnnnnn nnnnnnnnnn nnnnnnnnnn 234300
nnnnnnnnnn nnnnnnnnnn nnnnnnnnnn nnnnnnnnnn nnnnnnnnnn nnnnnnnnnn 234360
nnnnnnnnnn nnnnnnnnnn nnnnnnnnnn nnnnnnnnnn nnnnnnnnnn nnnnnnnnnn 234420
nnnnnnnnnn nnnnnnnnnn nnnnnnnnnn nnnnnnnnnn nnnnnnnnnn nnnnnnnnnn 234480
nnnnnnnnnn nnnnnnnnnn nnnnnnnnnn nnnnnnnnnn nnnnnnnnnn nnnnnnnnnn 234540
nnnnnnnnnn nnnnnnnnnn nnnnnnnnnn nnnnnnnnnn nnnnnnnnnn nnnnnnnnnn 234600
nnnnnnnnnn nnnnnnnnnn nnnnnnnnnn nnnnnnnnnn nnnnnnnnnn nnnnnnnnnn 234660
nnnnnnnnnn nnnnnnnnnn nnnnnnnnnn nnnnnnnnnn nnnnnnnnnn nnnnnnnnnn 234720
nnnnnnnnnn nnnnnnnnnn nnnnnnnnnn nnnnnnnnnn nnnnnnnnnn nnnnnnnnnn 234780
nnnnnnnnnn nnnnnnnnnn nnnnnnnnnn nnnnnnnnnn nnnnnnnnnn nnnnnnnnnn 234840
nnnnnnnnnn nnnnnnnnnn nnnnnnnnnn nnnnnnnnnn nnnnnnnnnn nnnnnnnnnn 234900
nnnnnnnnnn nnnnnnnnnn nnnnnnnnnn nnnnnnnnnn nnnnnnnnnn nnnnnnnnnn 234960
nnnnnnnnnn nnnnnnnnnn nnnnnnnnnn nnnnnnnnnn nnnnnnnnnn nnnnnnnnnn 235020
nnnnnnnnnn nnnnnnnnnn nnnnnnnnnn nnnnnnnnnn nnnnnnnnnn nnnnnnnnnn 235080
nnnnnnnnnn nnnnnnnnnn nnnnnnnnnn nnnnnnnnnn nnnnnnnnnn nnnnnnnnnn 235140
nnnnnnnnnn nnnnnnnnnn nnnnnnnnnn nnnnnnnnnn nnnnnnnnnn nnnnnnnnnn 235200
nnnnnnnnnn nnnnnnnnnn nnnnnnnnnn nnnnnnnnnn nnnnnnnnnn nnnnnnnnnn 235260
nnnnnnnnnn nnnnnnnnnn nnnnnnnnnn nnnnnnnnnn nnnnnnnnnn nnnnnnnnnn 235320
nnnnnnnnnn nnnnnnnnnn nnnnnnnnnn nnnnnnnnnn nnnnnnnnnn nnnnnnnnnn 235380
nnnnnnnnnn nnnnnnnnnn nnnnnnnnnn nnnnnnnnnn nnnnnnnnnn nnnnnnnnnn 235440
nnnnnnnnnn nnnnnnnnnn nnnnnnnnnn nnnnnnnnnn nnnnnnnnnn nnnnnnnnnn 235500
nnnnnnnnnn nnnnnnnnnn nnnnnnnnnn nnnnnnnnnn nnnnnnnnnn nnnnnnnnnn 235560
nnnnnnnnnn nnnnnnnnnn nnnnnnnnnn nnnnnnnnnn nnnnnnnnnn nnnnnnnnnn 235620
nnnnnnnnnn nnnnnnnnnn nnnnnnnnnn nnnnnnnnnn nnnnnnnnnn nnnnnnnnnn 235680
nnnnnnnnnn nnnnnnnnnn nnnnnnnnnn nnnnnnnnnn nnnnnnnnnn nnnnnnnnnn 235740
nnnnnnnnnn nnnnnnnnnn nnnnnnnnnn nnnnnnnnnn nnnnnnnnnn nnnnnnnnnn 235800
nnnnnnnnnn nnnnnnnnnn nnnnnnnnnn nnnnnnnnnn nnnnnnnnnn nnnnnnnnnn 235860
nnnnnnnnnn nnnnnnnnnn nnnnnnnnnn nnnnnnnnnn nnnnnnnnnn nnnnnnnnnn 235920
nnnnnnnnnn nnnnnnnnnn nnnnnnnnnn nnnnnnnnnn nnnnnnnnnn nnnnnnnnnn 235980

-continued nnnnnnnnnn nnnnnnnnnn nnnnnnnnnn nnaaaaccaa acaccgcata ttctcactca 236040
taggtgggaa ttgaacaatg agaacacatg gacacaggaa ggggaacatc acactctggg 236100
gactgttgtg gggtgggggc aggggggagg tatagcttta ggagttatac ctaatgctaa 236160
atgacgagtt aatgggtgca gcaaaccaac atggcacatg tatacatatg taactaacct 236220
gcacgttgtg cacatgtacc ctaaaactta aagtgtaata ataataaaat ttttaaaaca 236280
atgatttcat aagggtcata caaggtgaaa tttgctagac aataattttg ttttgaaaaa 236340
tatttggaat tgttttattt caattaaaag aataaacatc taagaaaaat agagtaattt 236400
aaaatgtcat tattattttc atgttatcaa tattacattt gaatcctcca aatgtagatt 236460
ataaatttgt tcttagaata aatacaaata ttgatacaaa aagtaaaaat tatttgctca 236520
taattttgag ggtcattttc ttgaaacttc tacctgtgtt aataagagag aaaatgttta 236580
tcaagccaga tatccagact ttgttcatcc agactttgtt gaatgcagta tatatatgca 236640
ggtataaatg tttcaagaca atgtaacatt ggcaataaat gtattacaat gaatattaga 236700
atgaaacttg cgcagtgcaa tagtaaacag tattaaataa aatcagtaat tgttaaaaat 236760
aagtttatct gatgatccag catgtgttat tcacaatttt caattatatt ccatttattc 236820
ttttttaaga taaaaaaact ctgcttttaa gcgcgatatt ttattttcct tctttgcctt 236880
tgtgttttat tatgtgtatt taatagggtg cgctttcatt ttaaatatat gttatgtatt 236940
tattttctat aattatttta gtgcctgaag gaccaccaca aaactgcgta acaggcaaca 237000
tcacaggaaa gtccttttca attttatggg acccaccaac tatagtaaca gggaaattta 237060
gttatagagt tgaattatat ggaccatcag gtaagcctta attggttttg tgtttgcctt 237120
ttggagtgag aataataaaa tatgttacca atatcaaact ctgtttaaaa gtatcagact 237180
ctttttaaaa gactttaaga ttgaagcaaa caataggaaa gtcataagga aggggaggtc 237240
ctttgatttt ttaattcaaa accataaatg agtataagaa tgacaaaact attcatgttc 237300
cacatttcat gtgatgcatg tgaaaaacta gagataactc ctcaagaaaa aagtgttagt 237360
ggagatatac atcttcaaat atttgaacaa gaagtccttg gcttacattc atgaagaaca 237420
atggactttg actatattaa attagatttc tattcactgc taggagccta gtttttaatc 237480
attagaaaga gctctctaaa aataacatgg aaaatctctg tatcttctgc tctattttgc 237540
tgtggaccta aaactgcttt aaaaaagaaa acctattaaa atttttgggc agctttataa 237600
agtggcaagt tctccaactt tgtaagcaag caggacctgg gcatccactt gccagagata 237660
ctttgagagg atcaagtatt atatcattag gatcaagtat tatatcatta gaagtgaatt 237720
atgtaaagtc taaaattctc tcctgattga gagcctctga ttctatgaaa taagtttaat 237780
tctaacaatg atgagataaa taataaagcc acatattatc atttatttgg gggcatcaaa 237840
aaagatacag agttccaact cattttattt tgcaatttct gtggtatgaa tcactcatca 237900
ccatcatgag taacctttat ctttcatccc taagtaactt atgctcctaa aattctgaaa 237960
tacttttact tcctaaaaaa agataattcc ctccactcac ccatccgata cacagaaaca 238020
gacatggata cacagctaca tcttttctgt ctgacattat tgttcaatac ttggctgaag 238080
tactctttca tttgtaaggc tggctgataa atcaagtgag aggcatgtag caataattgc 238140
atttagcaac atgggagtga tcacatgctt tcagtatggt ggaacatgtg gggtaaatac 238200
atgattgaat tagtttaaga gtgaatggga gaagatcatt ggaacaatgg gtgtagaaat 238260
tcttttgagt ttagctgcaa agcaaagcag tgaatagaga gtaagggtag ggataagtga 238320
agtcaacagg tctcttcagt aagaacatat aaagcatgtt tgtttgctga tggaaatgag 238380

-continued gaaaataagg aaaatgttaa tgatataaga aaaacgagaa ttactggaaa ggtgtctgtg 238440
tgggcagaag gtgagatctt ttgctcaaat gtagccattg gtttgagata agaatacaga 238500
taatttgtcc atactaacag ataatttgtc cataagttgt tcttataggt tgtaaggcag 238560
agtatatggg tgtagatgct ggtaaatata tagttgtgtt ggtgggagcc tgtggcaaat 238620
attttctaac tggtttacct ttttcagtgt agtgggaagc aagactatta gttgggagtg 238680
aagatagggc agaaggtatt agaggtctga gcagagaaga gtaagtgtaa aataatcttc 238740
tagaagagta gagtgattgg accattgact atgtaagttg agtaagattc caggcaccat 238800
gtagggctca ttcaaggttt ggctatgaat aaagtgacat caattaatgg ctttgtgctg 238860
taaatgagct gccttcaaca acagaagggc gagggaattg gaggcctgtg taaggcagtg 238920
attataattg aaactgacac tgaagatggg tagagtggaa atcaagtggt gaggggccaa 238980
ataaaataaa acaaaaataa aataggtgat taaatcaatg gattgttgat ttcagtggat 239040
ttaaagaatt atcagttcag aattatagag gaaatgtaaa ggaagtaagc aaaagtggtt 239100
agaaaaaagt tgcatgaaat tgagattctt aatgatacgg agtaattggt gatagtaatg 239160
tccaagttat gatcttgagg gagtggctga aattctgaaa aactagatta tttaaggaaa 239220
tatctaagta atttaaggat taagtctcag gatattaaaa tcagcacaaa ttaagatggt 239280
agccttgaac caaagctaga ccatgaaagt aaatgagagt aaatgaccct caggttagta 239340
gattacgaca actgtgaggg ctagtggatt tcactggtga tacagtattt aaagctgtgg 239400
gcttttataa ggagggagag agaatagtaa ataaagtgga gcaatgagga gcaaggacaa 239460
cacctaccac acctaaaggc ctggttactt gagagctgtg gggcaaaaac agactgccac 239520
catttggggt ggctgcaggg gaacaaaaac agtgttctca ggaaagagcc agtttgtagt 239580
tagagcaaga aggtaaagga aacatttaaa gcaaagtcga agatttaaag tattgtgctg 239640
acagactaag gaattttgtt cagaagctaa actagaaata ttttctaaat atatcctctt 239700
atagaagata atgaaattat ttagcatttt tttttttttt tttttttttt ttttgagacg 239760
gagtcttgct ctgtcgccca ggctggagtg cagtggcggg atctcggctc actgcaagct 239820
ccgcctcccg ggttcacgcc attctcctgc ctcagcctcc cgagtagctg ggactacagg 239880
cgcccgccac tacgcccggc taattttttg tatttttagt agagacgggg tttcaccgtt 239940
ttagccggga tggtctcgat ctcctgacct cgtgatccgc ccgcctcggc ctcccaaagt 240000
tatttagcat tttaattgaa taaatttgag tataaaatct ggtcactttt tgaactgata 240060
aaatttgatg cttccctttt caatatgtca aaaataacct ggtaattcaa aaaggcttta 240120
tgatttaata aaagtcattt taagcactgg aacattttca tgttctttca tttattttca 240180
ttaaattgat atcagtgcac tactaagcca catgtttaaa atatatgcag ttttgatatt 240240
ataataacaa attttagtgc ataggttaac acttgaattg ttgtctttgg ctctgtactt 240300
aaatgtgaac atgattgcac gcttgataaa aaataatcca tagctatctt ccactttttg 240360
caggtcgcat tttggataac agcacaaaag acctcaagtt tgcattcact aacctaacac 240420
catttacaat gtatgatgtc tatattgcgg ctgaaaccag tgcagggact gggcccaagt 240480
caaatatttc agtattcact ccaccagatg gtaagaacat agggaatgag tgagatattt 240540
ttggtatgct tatgaacttc atgaattggt aaaacatgat attagaagca atttgtttta 240600
catttactta aatcatgtta tttccttatt aaattactac ctaattcatt ctgaacatgt 240660
gttctccaga atgttaaact catagcatgc ttcataataa aagggaccca agatcaggta 240720

-continued aggttaggaa atatcatatg tagtattggc ctgttagaga ttcacaataa aatttagcaa 240780
aacctcaaga agtcataagg taaacaaaca catttagtat ggtttaacta catttttaaa 240840
tgtggaatct attttttctc acagaactag tatttagaag aattcctata ctcccaattc 240900
tttcaacaaa atatgtttat aatcaaaacg ggattctaag caagtgaaga ttctgagtgg 240960
atgtatgata tagatttacc agcatttact gaaattatga aaacattatt tttcctcaag 241020
aaacttcctt ataagtattc attaaacatc attgttttag gtgaactata ctttaaaaag 241080
aatgtttcca tactatttca caacatatct ttcaggccca cactgaactt gctaaatgtc 241140
ttaatttcta tttagggatt gtaattatgg acaaaaataa cagtaaattc ttataacaca 241200
ttaacacttg gaaaagtttc cagactttgt ttgtgtggaa gctaacatac agtaacttat 241260
aaatgaaatg tagacatgta tacacacaca cacactcaca cacacgcgca cacacacaca 241320
cacacacaca cacaggtcat acattcatcg ttcaagcgtt tgaccattag agggcagtaa 241380
ctattaggaa attttgtact tctacccttt aaagaaacaa ccattgatat ttttttgaaa 241440
gaacataaaa gttacgtttt atctatttca gatgaaaatc ctgacatata tatagtttta 241500
gaatacatat aagaaagttg tacatactca taaggaaaat gttctttttt tgtattaaaa 241560
ttttaccttt gtgtttctat cagaagaatc ctagcattgt gtagcttctt ccttaaatct 241620
taagttttcc tccatctcca cctaaaaact gctcttaagc atgtcctagg aaactagaca 241680
gatttatgga cactatcaaa taaagcagag cccttgattt tggtcttaat agagttttct 241740
caaccaactc aatgtaccta ttgatttcta ttcttgttat acaattaaat acatcctgaa 241800
ctattgtctt ctttcaagac cagctgattt tggtgcttcc aaatagaatc cacaactcaa 241860
taaacatatt tttattgtca tcattcttgg actacatcat gtgacaaaaa tagggaaata 241920
gataatgcat atgctgtgta caatgtcatg ttatttgtct tggattattt taaaatttac 241980
ttgccttaat ttctacattt tttatccaca aaagaagtag aatcttcagg tcatagttca 242040
gtatatttca caaggcctat ttttcacacc aaatcatttt aagtagatga ctccatttgc 242100
cctctataaa aagcaatttg tcctgtgttt cattctgtta tcttcctgag tcactcctcc 242160
tatagatcac accctggtgg gtcttagagg ggcctcctgg caactggtgg gttccaccaa 242220
aggcagggtt ggcatggttc ttatatcctc atgtcagcct tcatccatgg agttctcttg 242280
ggatagttca gccacaggag ctgcctcaat ggaatactct ggcaaatgca gtaaatgtag 242340
ctttctactt ctgacaccac taattaatcc tggtttcagt atttaaaact ttgaaataaa 242400
tggatcttta aactatatga aaacaatgtg ataactcatt agaactatct ttcaatttaa 242460
aaatgatttc ttaattttat attatccttt tcattaatac aacagggttt ttagtattct 242520
aattaaagtt acttaattta atttcttctc catattttaa accagtctat catctattta 242580
aaaaataatt aggactagtt tgcttctttt aaattacctt ttaaaacaat tggtgctctt 242640
ataaatctcc agatactcat agaaaaatgt tgcattgacc tcttatagag aatgttatgt 242700
gctattacat tacagtggag ttgatttcat taccccctggg gatgttacgg tccatagtct 242760
actttgaaag aaaatcagca tcctattatt ttagcagttc tcttatgtat ttcctaagcc 242820
ctctatatgt ctcttaatat tttgatgagt agatttctgc ataggcatga aaataaatga 242880
ttttggaaaa aaaagataat aatctccaaa gctataaaat gtcatagagt tgcctattcc 242940
aaaatcagat aatgctgatg aatataacat aggcaacagc attcttctaa attgtgtgag 243000
gggtaaaaaa aataagcaga ctgtgatgct tcaatattgt ctaacaactt ttctgtcagg 243060
gtagtttagc atgaccattt cttaaaagca gacaaatttc tgagattctt gtttactccc 243120

-continued

```
tcttaaacag actatggcag tgaagacgtt tgtcctcagt gatttaaact tgttactttc 243180
tgcaaatagt agtaaaatct ttgcaggaaa ataactgaga gcctgccaac tttgtgtttt 243240
caggatttgc aatggcttta atttttacta cttgtttttc aaaatatact tctaaagaaa 243300
ctttaatttg ctagataatg gcaaaaatga tcttaatgta ttttctttta cctcaatgct 243360
gtttgtctct atttcatttc ttctcatagt ttttcatttg aacacttcaa atcatttgga 243420
atatatttta ataaatcata tgctattgtg tttctaatgc attagtaaaa tttataaata 243480
tattaactcg agaataattc ttaggtagtc catgtatata acaccttcaa aattaaaatt 243540
attttgccat tatctagaaa attcatcatc gagcagcatt aattttgaag ttggagaaaa 243600
tggcattggg gtaaagaaaa tgtgagattt ttttggccaa atgtctaact tatttctcat 243660
ttatttgtaa aatttgtaaa tgtatcgact tgagaatgac tcttaggtat ttcctgtgga 243720
catcaccttc aaaactgatg ctgaaccatg aataattgag ttgtgtgttt gattttcttt 243780
aggtaatttt gtatcaatat taaagtcttc tctagtttcc ccataagaat ttgtggtcta 243840
acagatcaag tatcttttta aagacaagat acaatgctgt tgactccatt tcctttatcc 243900
cctaagctta aataggaaaa aaaagataag tttatagtca ttatttttat gcaagtttga 243960
ggtacatttt aaggtaatat agaaccactt aatctttacc tggattgtaa tttttggcat 244020
taagtatcat ggggcaacac ttactaagaa agtaagtatt gaatatatag aatatataga 244080
aatatatatg ctaattaaaa gataaaaaat agtgtctgct actactcttg gtttcactag 244140
caaaataaga gacagtaaaa tatatatagt tttctgctgt cctgcataat atttgatatc 244200
taacacatta gtgtgttgcg ttgacttgaa ctgatcattt cacttatctt tcaataggca 244260
gggtttagtt gcctgattaa tatgatcaat gtagtcatta gctgtttttt ttttttcagt 244320
tgagattcta catcagttca aaataaatgg aaaaagtgcc agatctcctc tgacttaagt 244380
tatgcaatac tggctattgt tttgtctgca taaaaactgc aaaataaaat tttaaaaaga 244440
gatggaatag gagctttgct atttaaatag ccatgttatt ttacaccaca caattaattg 244500
gaaagtttct ccacccttga aaaatgcata ttggtaaatt gcatattggt aaatatgatg 244560
atgcaaacat gagctctagg tacaatatat tttagtgaaa taaaactcat actagaggtg 244620
acctgtgcaa agggctttat ctgtcttatt ccttcctctg tcctcaagtg cctagaacag 244680
tgatcatatg atcaatgctc agtgtgttga atgatgaatg aatggcccaa cgattgtcac 244740
aatatctagg gagtctttac cggttacttc atgaagacaa aggaaaaaac tcaatctatt 244800
ggatgaaaac tttgtatagt catagttact ataaagccaa cttaagcata attatatttg 244860
ctcattataa ataacatata tgggagttat aaaattattt ttcaattcct ttctgttgtc 244920
ttaaaaagaa agggggtcat ttttcctttg ttccctttta agactatatg cctgtcttct 244980
aactagaatt tgctaaacct gtaccgctgc cagagagttt agggaaatta actgaaagtg 245040
taacaacaat ctgataataa gggatcataa ttttatgcca ttttctcttt cttaaaagtt 245100
ttagaaattt gagaaatttt cttgaactct ttgttcctta tagtaacctg tatagtaata 245160
ggaaagctat aatgacaccc attttataga taaggaaagt agaggttgga gggatgcatg 245220
agctattcat aatcacaagt tgaactgtaa ataaaaatga tcaaaagccc aggggatatt 245280
tgttttttgc ccgttactcc tgtgaaactg ggaagttccc tagatgtcac tcttagtgac 245340
tttacaacta gaacttgctt taagttcttg gtactttatt ttaaaccaat tgttagtttg 245400
ttcctatttt tatttactat tgcaatgagt gagggcacct gaaatttgaa aataacatga 245460
```

-continued ttatttttaa aatatcagaa aaaaatcaat caactcttca aacaatttca tgtaataaat 245520
taaaacgcag tctaatttaa cttaccaact atatttaatt gcattcagag tcttctggat 245580
attaattttc aatctgttgt tataattttt atgaaaccat caagatttca actggcatta 245640
attatcacca aataggcaga ttctcaagaa aattattttt attaattaat ttgtttcaaa 245700
caaatgttat gacttttatt ttggaaaatt attctgttat tctgctcctt acttacattt 245760
cgagaacaat gtttagaaat ttaggcaaga tggccgaata ggaacagctc cagtctacag 245820
ctcccagcgt gaacgacgca gaagacgggt gatttctgca tttccatctg aggtaccggg 245880
ttcatctcac tagggccaga cagtgggcgc aggtcagtgg gtgtgcgcac cgtgtgcgag 245940
ccgaagcagg gcgaggcatt gcctcactcg ggaagcgcaa ggggtcaggg agttcccttt 246000
ccccttgtca aagaaagggg tgatggacgg cacctggaaa atcgggtcac tccgacccga 246060
atactgcgct tttctgacgg gcttaaaaaa cggcgcacca cgagattata tcccacacct 246120
ggctcagagg gtcctacgcc cacggagtct cgctgattgc tagtacagca gtctgagatc 246180
aaactgcaag gcggcagcga agctgggtga ggggcgcccg ccattgccca ggcttgctta 246240
ggtaaacaaa gcagcctgga agctccaact gggtggagcc cacaacagct acaaggaggc 246300
ctgcttgctc tgtaggnnnn nnnnnnnnnn nnnnnnnnnn nnnnnnnnnn nnnnnnnnnn 246360
nnnnnnnnnn nnnnnnnnnn nnnnnnnnnn nnnnnnnnnn nnnnnnnnnn nnnnnnnnnn 246420
nnnnnnnnnn nnnnnnnnnn nnnnnnnnnn nnnnnnnnnn nnnnnnnnnn nnnnnnnnnn 246480
nnnnnnnnnn nnnnnnnnnn nnnnnnnnnn nnnnnnnnnn nnnnnnnnnn nnnnnnnnnn 246540
nnnnnnnnnn nnnnnnnnnn nnnnnnnnnn nnnnnnnnnn nnnnnnnnnn nnnnnnnnnn 246600
nnnnnnnnnn nnnnnnnnnn nnnnnnnnnn nnnnnnnnnn nnnnnnnnnn nnnnnnnnnn 246660
nnnnnnnnnn nnnnnnnnnn nnnnnnnnnn nnnnnnnnnn nnnnnnnnnn nnnnnnnnnn 246720
nnnnnnnnnn nnnnnnnnnn nnnnnnnnnn nnnnnnnnnn nnnnnnnnnn nnnnnnnnnn 246780
nnnnnnnnnn nnnnnnnnnn nnnnnnnnnn nnnnnnnnnn nnnnnnnnnn nnnnnnnnnn 246840
nnnnnnnnnn nnnnnnnnnn nnnnnnnnnn nnnnnnnnnn nnnnnnnnnn nnnnnnnnnn 246900
nnnnnnnnnn nnnnnnnnnn nnnnnnnnnn nnnnnnnnnn nnnnnnnnnn nnnnnnnnnn 246960
nnnnnnnnnn nnnnnnnnnn nnnnnnnnnn nnnnnnnnnn nnnnnnnnnn nnnnnnnnnn 247020
nnnnnnnnnn nnnnnnnnnn nnnnnnnnnn nnnnnnnnnn nnnnnnnnnn nnnnnnnnnn 247080
nnnnnnnnnn nnnnnnnnnn nnnnnnnnnn nnnnnnnnnn nnnnnnnnnn nnnnnnnnnn 247140
nnnnnnnnnn nnnnnnnnnn nnnnnnnnnn nnnnnnnnnn nnnnnnnnnn nnnnnnnnnn 247200
nnnnnnnnnn nnnnnnnnnn nnnnnnnnnn nnnnnnnnnn nnnnnnnnnn nnnnnnnnnn 247260
nnnnnnnnnn nnnnnnnnnn nnnnnnnnnn nnnnnnnnnn nnnnnnnnnn nnnnnnnnnn 247320
nnnnnnnnnn nnnnnnnnnn nnnnnnnnnn nnnnnnnnnn nnnnnnnnnn nnnnnnnnnn 247380
nnnnnnnnnn nnnnnnnnnn nnnnnnnnnn nnnnnnnnnn nnnnnnnnnn nnnnnnnnnn 247440
nnnnnnnnnn nnnnnnnnnn nnnnnnnnnn nnnnnnnnnn nnnnnnnnnn nnnnnnnnnn 247500
nnnnnnnnnn nnnnnnnnnn nnnnnnnnnn nnnnnnnnnn nnnnnnnnnn nnnnnnnnnn 247560
nnnnnnnnnn nnnnnnnnnn nnnnnnnnnn nnnnnnnnnn nnnnnnnnnn nnnnnnnnnn 247620
nnnnnnnnnn nnnnnnnnnn nnnnnnnnnn nnnnnnnnnn nnnnnnnnnn nnnnnnnnnn 247680
nnnnnnnnnn nnnnnnnnnn nnnnnnnnnn nnnnnnnnnn nnnnnnnnnn nnnnnnnnnn 247740
nnnnnnnnnn nnnnnnnnnn nnnnnnnnnn nnnnnnnnnn nnnnnnnnnn nnnnnnnnnn 247800
nnnnnnnnnn nnnnnnnnnn nnnnnnnnnn nnnnnnnnnn nnnnnnnnnn nnnnnnnnnn 247860

-continued nnnnnnnnnn nnnnnnnnnn nnnnnnnnnn nnnnnnnnnn nnnnnnnnnn nnnnnnnnnn 247920
nnnnnnnnnn nnnnnnnnnn nnnnnnnnnn nnnnnnnnnn nnnnnnnnnn nnnnnnnnnn 247980
nnnnnnnnnn nnnnnnnnnn nnnnnnnnnn nnnnnnnnnn nnnnnnnnnn nnnnnnnnnn 248040
nnnnnnnnnn nnnnnnnnnn nnnnnnnnnn nnnnnnnnnn nnnnnnnnnn nnnnnnnnnn 248100
nnnnnnnnnn nnnnnnnnnn nnnnnnnnnn nnnnnnnnnn nnnnnnnnnn nnnnnnnnnn 248160
nnnnnnnnnn nnnnnnnnnn nnnnnnnnnn nnnnnnnnnn nnnnnnnnnn nnnnnnnnnn 248220
nnnnnnnnnn nnnnnnnnnn nnnnnnnnnn nnnnnnnnnn nnnnnnnnnn nnnnnnnnnn 248280
nnnnnnnnnn nnnnnnnnnn nnnnnnnnnn nnnnnnnnnn nnnnnnnnnn nnnnnnnnnn 248340
nnnnnnnnnn nnnnnnnnnn nnnnnnnnnn nnnnnnnnnn nnnnnnnnnn nnnnnnnnnn 248400
nnnnnnnnnn nnnnnnnnnn nnnnnnnnnn nnnnnnnnnn nnnnnnnnnn nnnnnnnnnn 248460
nnnnnnnnnn nnnnnnnnnn nnnnnnnnnn nnnnnnnnnn nnnnnnnnnn nnnnnnnnnn 248520
nnnnnnnnnn nnnnnnnnnn nnnnnnnnnn nnnnnnnnnn nnnnnnnnnn nnnnnnnnnn 248580
nnnnnnnnnn nnnnnnnnnn nnnnnnnnnn nnnnnnnnnn nnnnnnnnnn nnnnnnnnnn 248640
nnnnnnnnnn nnnnnnnnnn nnnnnnnnnn nnnnnnnnnn nnnnnnnnnn nnnnnnnnnn 248700
nnnnnnnnnn nnnnnnnnnn nnnnnnnnnn nnnnnnnnnn nnnnnnnnnn nnnnnnnnnn 248760
nnnnnnnnnn nnnnnnnnnn nnnnnnnnnn nnnnnnnnnn nnnnnnnnnn nnnnnnnnnn 248820
nnnnnnnnnn nnnnnnnnnn nnnnnnnnnn nnnnnnnnnn nnnnnnnnnn nnnnnnnnnn 248880
nnnnnnnnnn nnnnnnnnnn nnnnnnnnnn nnnnnnnnnn nnnnnnnnnn nnnnnnnnnn 248940
nnnnnnnnnn nnnnnnnnnn nnnnnnnnnn nnnnnnnnnn nnnnnnnnnn nnnnnnnnnn 249000
nnnnnnnnnn nnnnnnnnnn nnnnnnnnnn nnnnnnnnnn nnnnnnnnnn nnnnnnnnnn 249060
nnnnnnnnnn nnnnnnnnnn nnnnnnnnnn nnnnnnnnnn nnnnnnnnnn nnnnnnnnnn 249120
nnnnnnnnnn nnnnnnnnnn nnnnnnnnnn nnnnnnnnnn nnnnnnnnnn nnnnnnnnnn 249180
nnnnnnnnnn nnnnnnnnnn nnnnnnnnnn nnnnnnnnnn nnnnnnnnnn nnnnnnnnnn 249240
nnnnnnnnnn nnnnnnnnnn nnnnnnnnnn nnnnnnnnnn nnnnnnnnnn nnnnnnnnnn 249300
nnnnnnnnnn nnnnnnnnnn nnnnnnnnnn nnnnnnnnnn nnnnnnnnnn nnnnnnnnnn 249360
nnnnnnnnnn nnnnnnnnnn nnnnnnnnnn nnnnnnnnnn nnnnnnnnnn nnnnnnnnnn 249420
nnnnnnnnnn nnnnnnnnnn nnnnnnnnnn nnnnnnnnnn nnnnnnnnnn nnnnnnnnnn 249480
nnnnnnnnnn nnnnnnnnnn nnnnnnnnnn nnnnnnnnnn nnnnnnnnnn nnnnnnnnnn 249540
nnnnnnnnnn nnnnnnnnnn nnnnnnnnnn nnnnnnnnnn nnnnnnnnnn nnnnnnnnnn 249600
nnnnnnnnnn nnnnnnnnnn nnnnnnnnnn nnnnnnnnnn nnnnnnnnnn nnnnnnnnnn 249660
nnnnnnnnnn nnnnnnnnnn nnnnnnnnnn nnnnnnnnnn nnnnnnnnnn nnnnnnnnnn 249720
nnnnnnnnnn nnnnnnnnnn nnnnnnnnnn nnnnnnnnnn nnnnnnnnnn nnnnnnnnnn 249780
nnnnnnnnnn nnnnnnnnnn nnnnnnnnnn nnnnnnnnnn nnnnnnnnnn nnnnnnnnnn 249840
nnnnnnnnnn nnnnnnnnnn nnnnnnnnnn nnnnnnnnnn nnnnnnnnnn nnnnnnnnnn 249900
nnnnnnnnnn nnnnnnnnnn nnnnnnnnnn nnnnnnnnnn nnnnnnnnnn nnnnnnnnnn 249960
nnnnnnnnnn nnnnnnnnnn nnnnnnnnnn nnnnnnnnnn nnnnnnnnnn nnnnnnnnnn 250020
nnnnnnnnnn nnnnnnnnnn nnnnnnnnnn nnnnnnnnnn nnnnnnnnnn nnnnnnnnnn 250080
nnnnnnnnnn nnnnnnnnnn nnnnnnnnnn nnnnnnnnnn nnnnnnnnnn nnnnnnnnnn 250140
nnnnnnnnnn nnnnnnnnnn nnnnnnnnnn nnnnnnnnnn nnnnnnnnnn nnnnnnnnnn 250200

-continued

```
nnnnnnnnnn nnnnnnnnnn nnnnnnnnnn nnnnnnnnnn nnnnnnnnnn nnnnnnnnnn 250260
nnnnnnnnnn nnnnnnnnnn nnnnnnnnnn nnnnnnnnnn nnnnnnnnnn nnnnnnnnnn 250320
nnnnnnnnnn nnnnnnnnnn nnnnnnnnnn nnnnnnnnnn nnnnnnnnnn nnnnnnnnnn 250380
nnnnnnnnnn nnnnnnnnnn nnnnnnnnnn nnnnnnnnnn nnnnnnnnnn nnnnnnnnnn 250440
nnnnnnnnnn nnnnnnnnnn nnnnnnnnnn nnnnnnnnnn nnnnnnnnnn nnnnnnnnnn 250500
nnnnnnnnnn nnnnnnnnnn nnnnnnnnnn nnnnnnnnnn nnnnnnnnnn nnnnnnnnnn 250560
nnnnnnnnnn nnnnnnnnnn nnnnnnnnnn nnnnnnnnnn nnnnnnnnnn nnnnnnnnnn 250620
nnnnnnnnnn nnnnnnnnnn nnnnnnnnnn nnnnnnnnnn nnnnnnnnnn nnnnnnnnnn 250680
nnnnnnnnnn nnnnnnnnnn nnnnnnnnnn nnnnnnnnnn nnnnnnnnnn nnnnnnnnnn 250740
nnnnnnnnnn nnnnnnnnnn nnnnnnnnnn nnnnnnnnnn nnnnnnnnnn nnnnnnnnnn 250800
nnnnnnnnnn nnnnnnnnnn nnnnnnnnnn nnnnnnnnnn nnnnnnnnnn nnnnnnnnnn 250860
nnnnnnnnnn nnnnnnnnnn nnnnnnnnnn nnnnnnnnnn nnnnnnnnnn nnnnnnnnnn 250920
nnnnnnnnnn nnnnnnnnnn nnnnnnnnnn nnnnnnnnnn nnnnnnnnnn nnnnnnnnnn 250980
nnnnnnnnnn nnnnnnnnnn nnnnnnnnnn nnnnnnnnnn nnnnnnnnnn nnnnnnnnnn 251040
nnnnnnnnnn nnnnnnnnnn nnnnnnnnnn nnnnnnnnnn nnnnnnnnnn nnnnnnnnnn 251100
nnnnnnnnnn nnnnnnnnnn nnnnnnnnnn nnnnnnnnnn nnnnnnnnnn nnnnnnnnnn 251160
nnnnnnnnnn nnnnnnnnnn nnnnnnnnnn nnnnnnnnnn nnnnnnnnnn nnnnnnnnnn 251220
nnnnnnnnnn nnnnnnnnnn nnnnnnnnnn nnnnnnnnnn nnnnnnnnnn nnnnnnnnnn 251280
nnnnnnnnnn nnnnnnnnnn nnnnnnnnnn nnnnnnnnnn nnnnnnnnnn nnnnnnnnnn 251340
nnnnnnnnnn nnnnnnnnnn nnnnnnnnnn nnnnnnnnnn nnnnnnnnnn nnnnnnnnnn 251400
nnnnnnnnnn nnnnnnnnnn nnnnnnnnnn nnnnnnnnnn nnnnnnnnnn nnnnnnnnnn 251460
nnnnnnnnnn nnnnnnnnnn nnnnnnnnnn nnnnnnncat gtatacatat gtaactaacc 251520
tgcacaatgt gcacatgtac cctaaaactt aaagtataat aataaaagga aaaaaagaaa 251580
tttagtatta aatatccatg tatttaaaga catttaattt aacaaaaatt tattatactt 251640
tcagttctgg ggtacatgtg cagaacgtat aggtttgtta cataggtata catgtgtcat 251700
ggtggtttac tgcacccatc aaagtgtcat ctacattagg tacttctcct aatgctatcc 251760
ctcccctagc cccccaccca ccgacaggcc ccggtgtatg atgttcctct ccctgtgtcc 251820
atgtgttctc attgttcagc tccctcttat gagtgtgaac atgcggtgtt tggtttttg 251880
tccttgtgat agtttgctga gaatgatggt ttccagcttt atccatgtcc ctgcaaagga 251940
catgacctca tcctttttt aagacttatt taatttttaa caaaataaat tgtttttgtc 252000
tattttcttt ctttcttgtt ttttgtttgt ttgtttgttt gtttgtttgt tttttgatgg 252060
agtctcgctc tttcttccag gctggagtgc agtggtgtaa tctccactca ctgtaacctc 252120
cgcctcttgg gttcaagcaa ttctcctgcc tcagcctcct gagtagctgg gattacaggc 252180
acgcaccacc atgcctggct aatttttgta ttttttagta gagatggggt ttcaccatgt 252240
tggtcaggct ggtctcgaac tccttacctc aggtgattgg cctcccttgg cctcccaaag 252300
tgctgggatt acagccatga gccaccgcac ctagcctagt ctgttttcta atagaattgt 252360
ttatatatct taaattgtga actaagaatt tagacacttt tttcacttga aaaaatattt 252420
ttaaattccc ccttttttcct tttctttctt tctttctttc ttagttccag gggcagtgtt 252480
tgatttacaa cttgcagagg tagaatccac gcaagtaaga attacttgga agaaaccacg 252540
acaaccaaat ggaattatta accaataccg agtgaaagtg ctagttccag agacaggaat 252600
```

-continued

```
aattttggaa aatactttgc tcactggaaa taatgaggta ttgcattttt atttcactta 252660
ttggtgaacc ctttctgctt ggttctggct ctgatagctt ggaagatttg ctagcaccca 252720
cacatgtaat atttgaccac ttactagtac aaagtaaagt aaatttgggg catgttgata 252780
atctagctag atcatatttc attttaggtt atatattatt agttaagtgc tattattcct 252840
tttcatcata tgaaaaatgt taattgtgca attaaacagg actaaaggta ttttcataag 252900
ttaatattat ttttctaaat tagttaatga attgttcgga aactcttgtt atgatttaag 252960
tgctccttca aaggctgtgc ttgcaatttg gaacagttgc cagtgaaagg cacagtaact 253020
ttagtagctg ttgttgacaa atgattctgt tctatttggt cttgggaagc taaatttctc 253080
aaagctgcct cttttttttt ttcaaagtac atttgattaa gagtcacatt actaaataaa 253140
agaaatttaa gtcgtttcat agattttaaa taagaggacc aggatcttta ggcaatgtgt 253200
ttgcttctat tcacactgga agtcttattt ttttcctttt gtttctgtta ggaagtacag 253260
gcaacactga tttttctttc cactgtcttt gttcacctca cttcatcaac tgttcacctg 253320
tgagactctt tcagcctcca ggctagtcat gtccagatac tggctgctcc ccggggcatt 253380
caaagaataa acttccttag gaccagtgca gcaatcactg ggccttaaag acaaacacga 253440
tagttattca gcacctggcg tctgctgtgt tgtttcagaa ttgctgctgc ttctacctgt 253500
gctgttattt tcccccacac atgctttcat tctatttcta gtcccagcct tcctctattt 253560
ctggcactta cctgtatgtg acagttgacc tcaccatgtg ctcaatgcat tctggccacc 253620
caggacttat cactccaagt tgctcaccat cttcaaccca gggttaaatt ttaatcctat 253680
gttgattcct ttcctctgtg caaaagatgt tgaattatgc tttctgtgat actctggttg 253740
acaactcagg caaagggcaa aagcttaacc ctttgctcct gctgagaagg tcttaaatta 253800
gatactgagc tttcctagta ctagatgaca ggtttcccac ttctgctaat gacatctgtt 253860
gaatgggtgg ccacacctgt ttttccatga agctaagagg ttctagaaag gctttttttt 253920
tgtgattctg tctctatctg gtctgcaatt ctcgtctcat agtagagagc tcatgagctt 253980
tggagacgta caaatttgga tttaaattat gattttgtct ctcactgtgc tatatagcaa 254040
gtggttaaga ctgtaaacca ggtttaaact ctagttctgc cattactaac tgtttaaccc 254100
tggaaaagtt ggcctgagct ctctgaacat cagtttcttc ttctctaaga tagtgattat 254160
aagtccctat aacaaagggt taataatgag aatttaatgg gttcatgtgt gtaaagagct 254220
tagaactgta cctggcatat agtaagtgct gtgctaaata attgtgacct attgtgatca 254280
ttaatcttgg cataggatca tccaccttag ttgctaccca atattacttc ccttatactc 254340
tctcaatgaa aggagacatt atgctt                                      254366
```

<210> SEQ ID NO 4
<211> LENGTH: 2301
<212> TYPE: PRT
<213> ORGANISM: Rat

<400> SEQUENCE: 4

```
Met Asp Phe His Phe Ser Phe Leu Phe Leu Leu Ile Gly Thr Ser Glu
 1               5                  10                  15

Ser Gln Val Asp Val Ser Ser Ser Phe Asp Gly Thr Gly Tyr Asp Ile
            20                  25                  30

Thr Leu Ser Ser Val Ser Ala Thr Thr Tyr Ser Ser Pro Val Ser Arg
        35                  40                  45

Thr Leu Ala Thr Asn Val Thr Lys Pro Gly Pro Pro Val Phe Leu Ala
```

-continued

```
    50                  55                  60

Gly Glu Arg Val Gly Ser Ala Gly Ile Leu Leu Ser Trp Asn Thr Pro
65                  70                  75                  80

Pro Asn Pro Asn Gly Arg Ile Ile Ser Tyr Val Val Lys Tyr Lys Glu
                85                  90                  95

Val Cys Pro Trp Met Gln Thr Ala Tyr Thr Arg Ala Arg Ala Lys Pro
            100                 105                 110

Asp Ser Leu Glu Val Leu Leu Thr Asn Leu Asn Pro Gly Thr Thr Tyr
        115                 120                 125

Glu Ile Lys Val Ala Ala Glu Asn Asn Ala Gly Ile Gly Val Phe Ser
    130                 135                 140

Asp Pro Phe Leu Phe Gln Thr Ala Glu Ser Ala Pro Gly Lys Val Val
145                 150                 155                 160

Asn Leu Thr Val Glu Ala Leu Asn Tyr Ser Ala Val Asn Leu Ile Trp
                165                 170                 175

Tyr Leu Pro Arg Gln Pro Asn Gly Lys Ile Thr Ser Phe Lys Ile Ser
            180                 185                 190

Val Lys His Ala Arg Ser Gly Ile Val Val Lys Asp Val Ser Leu Arg
        195                 200                 205

Val Glu Asp Ile Leu Ser Gly Lys Leu Pro Glu Cys Asn Glu Asn Ser
    210                 215                 220

Glu Ser Phe Leu Trp Ser Thr Thr Ser Pro Ser Pro Thr Leu Gly Arg
225                 230                 235                 240

Val Thr Pro Thr Val Arg Thr Thr Gln Ser Ser Ser Thr Ala Ala Arg
                245                 250                 255

Ser Lys Ile Ser Ser Val Trp Lys Glu Pro Ile Ser Phe Val Val Thr
            260                 265                 270

His Leu Arg Pro Tyr Thr Thr Tyr Leu Phe Glu Val Ser Ala Val Thr
        275                 280                 285

Thr Glu Ala Gly Tyr Ile Asp Ser Thr Ile Val Arg Thr Pro Glu Ser
    290                 295                 300

Val Pro Glu Gly Pro Pro Gln Asn Cys Ile Met Gly Asn Val Thr Gly
305                 310                 315                 320

Lys Ala Phe Ser Ile Ser Trp Asp Pro Pro Thr Ile Val Thr Gly Lys
                325                 330                 335

Phe Ser Tyr Arg Val Glu Leu Tyr Gly Pro Ser Gly Arg Ile Leu Asp
            340                 345                 350

Asn Ser Thr Lys Asp Leu Arg Phe Ala Phe Thr His Leu Thr Pro Phe
        355                 360                 365

Thr Met Tyr Asp Val Tyr Val Ala Ala Glu Thr Ser Ala Gly Val Gly
    370                 375                 380

Pro Lys Ser Asn Leu Ser Val Phe Thr Pro Pro Asp Val Pro Gly Ala
385                 390                 395                 400

Val Phe Asp Leu Gln Ile Ala Glu Val Glu Ala Thr Glu Ile Arg Ile
                405                 410                 415

Thr Trp Arg Lys Pro Arg Gln Pro Asn Gly Ile Ile Ser Gln Tyr Arg
            420                 425                 430

Val Lys Val Ser Val Leu Glu Thr Gly Val Val Leu Glu Asn Thr Leu
        435                 440                 445

Leu Thr Gly Gln Asp Glu Ser Ile Ser Asn Pro Met Ser Pro Glu Ile
    450                 455                 460

Met Asn Leu Val Asp Pro Met Ile Gly Phe Tyr Glu Gly Ser Gly Glu
465                 470                 475                 480
```

-continued

```
Met Ser Ser Asp Leu His Ser Pro Ala Ser Phe Ile Tyr Asn Ser His
                485                 490                 495

Pro His Asn Asp Phe Pro Ala Ser Thr Arg Ala Glu Glu Gln Ser Ser
            500                 505                 510

Pro Val Val Thr Thr Arg Asn Gln Tyr Met Thr Asp Ile Thr Ala Glu
        515                 520                 525

Gln Leu Ser Tyr Val Val Arg Arg Leu Val Pro Phe Thr Glu His Thr
    530                 535                 540

Ile Ser Val Ser Ala Phe Thr Ile Met Gly Glu Gly Pro Pro Thr Val
545                 550                 555                 560

Leu Thr Val Arg Thr Arg Glu Gln Val Pro Ser Ser Ile Gln Ile Ile
                565                 570                 575

Asn Tyr Lys Asn Ile Ser Ser Ser Ser Ile Leu Leu Tyr Trp Asp Pro
            580                 585                 590

Pro Glu Tyr Pro Asn Gly Lys Ile Thr His Tyr Thr Ile Tyr Ala Thr
        595                 600                 605

Glu Leu Asp Thr Asn Arg Ala Phe Gln Met Thr Thr Val Asp Asn Ser
    610                 615                 620

Phe Leu Ile Thr Gly Leu Lys Lys Tyr Thr Arg Tyr Lys Met Arg Val
625                 630                 635                 640

Ala Ala Ser Thr His Val Gly Glu Ser Ser Leu Ser Glu Glu Asn Asp
                645                 650                 655

Ile Phe Val Arg Thr Pro Glu Asp Glu Pro Glu Ser Ser Pro Gln Asp
            660                 665                 670

Val Gln Val Thr Gly Val Ser Pro Ser Glu Leu Arg Leu Lys Trp Ser
        675                 680                 685

Pro Pro Glu Lys Pro Asn Gly Ile Ile Ile Ala Tyr Glu Val Leu Tyr
    690                 695                 700

Gln Asn Ala Asp Thr Leu Phe Val Lys Asn Thr Ser Thr Thr Asp Ile
705                 710                 715                 720

Ile Ile Ser Asp Leu Lys Pro Tyr Thr Leu Tyr Asn Ile Ser Ile Arg
                725                 730                 735

Ser Tyr Thr Arg Leu Gly His Gly Asn Gln Ser Ser Ser Leu Leu Ser
            740                 745                 750

Val Arg Thr Ser Glu Thr Val Pro Asp Ser Ala Pro Glu Asn Ile Thr
        755                 760                 765

Tyr Lys Asn Ile Ser Ser Gly Glu Ile Glu Ile Ser Phe Leu Pro Pro
    770                 775                 780

Arg Ser Pro Asn Gly Ile Ile Gln Lys Tyr Thr Ile Tyr Leu Lys Arg
785                 790                 795                 800

Ser Asn Ser His Glu Ala Arg Thr Ile Asn Thr Thr Ser Leu Thr Gln
                805                 810                 815

Thr Ile Gly Gly Leu Lys Lys Tyr Thr His Tyr Val Ile Glu Val Ser
            820                 825                 830

Ala Ser Thr Leu Lys Gly Glu Gly Ile Arg Ser Arg Pro Ile Ser Ile
        835                 840                 845

Leu Thr Glu Glu Asp Ala Pro Asp Ser Pro Pro Gln Asn Phe Ser Val
    850                 855                 860

Lys Gln Leu Ser Gly Val Thr Val Met Leu Ser Trp Gln Pro Pro Leu
865                 870                 875                 880

Glu Pro Asn Gly Ile Ile Leu Tyr Tyr Thr Val Tyr Val Trp Asp Lys
                885                 890                 895
```

-continued

```
Ser Ser Leu Arg Ala Ile Asn Ala Thr Glu Ala Ser Leu Val Leu Ser
            900                 905                 910

Asp Leu Asp Tyr Asn Val Asp Tyr Gly Ala Cys Val Thr Ala Ser Thr
        915                 920                 925

Arg Phe Gly Asp Gly Asn Ala Arg Ser Ser Ile Ile Asn Phe Arg Thr
    930                 935                 940

Pro Glu Gly Glu Pro Ser Asp Pro Pro Asn Asp Val His Tyr Val Asn
945                 950                 955                 960

Leu Ser Ser Ser Ser Ile Ile Leu Phe Trp Thr Pro Pro Val Lys Pro
                965                 970                 975

Asn Gly Ile Ile Gln Tyr Tyr Ser Val Tyr Tyr Gln Asn Thr Ser Gly
            980                 985                 990

Thr Phe Val Gln Asn Phe Thr Leu Leu Gln Val Thr Lys Glu Ser Asp
        995                 1000                1005

Asn Val Thr Val Ser Ala Arg Ile Tyr Arg Leu Ala Ile Phe Ser Tyr
    1010                1015                1020

Tyr Thr Phe Trp Leu Thr Ala Ser Thr Ser Val Gly Asn Gly Asn Lys
1025                1030                1035                1040

Ser Ser Asp Ile Ile His Val Tyr Thr Asp Gln Asp Ile Pro Glu Gly
                1045                1050                1055

Pro Val Gly Asn Leu Thr Phe Glu Ser Ile Ser Ser Thr Ala Ile His
            1060                1065                1070

Val Ser Trp Glu Pro Pro Ser Gln Pro Asn Gly Leu Val Phe Tyr Tyr
        1075                1080                1085

Leu Ser Leu Asn Leu Gln Gln Ser Pro Pro Arg His Met Ile Pro Pro
    1090                1095                1100

Leu Val Thr Tyr Glu Asn Ser Ile Asp Phe Asp Asp Leu Glu Lys Tyr
1105                1110                1115                1120

Thr Asp Tyr Ile Phe Lys Ile Thr Pro Ser Thr Glu Lys Gly Phe Ser
                1125                1130                1135

Glu Thr Tyr Thr Thr Gln Leu His Ile Lys Thr Glu Glu Asp Val Pro
            1140                1145                1150

Asp Thr Pro Pro Ile Ile Asn Thr Phe Lys Asn Leu Ser Ser Thr Ser
        1155                1160                1165

Ile Leu Leu Ser Trp Asp Pro Pro Leu Lys Pro Asn Gly Ala Ile Leu
    1170                1175                1180

Gly Tyr His Leu Thr Leu Gln Gly Pro His Ala Asn His Thr Phe Val
1185                1190                1195                1200

Thr Ser Gly Asn His Ile Val Leu Glu Glu Leu Ser Pro Phe Thr Leu
                1205                1210                1215

Tyr Ser Phe Phe Ala Ala Ala Arg Thr Met Lys Gly Leu Gly Pro Ser
            1220                1225                1230

Ser Ile Leu Phe Phe Tyr Thr Asp Glu Ser Ala Pro Leu Ala Pro Pro
        1235                1240                1245

Gln Asn Leu Thr Leu Ile Asn Tyr Thr Ser Asp Phe Val Trp Leu Thr
    1250                1255                1260

Trp Ser Pro Ser Pro Leu Pro Gly Gly Ile Val Lys Val Tyr Ser Phe
1265                1270                1275                1280

Lys Ile His Glu His Glu Thr Asp Thr Val Phe Tyr Lys Asn Ile Ser
                1285                1290                1295

Gly Leu Gln Thr Asp Ala Lys Leu Glu Gly Leu Glu Pro Val Ser Thr
            1300                1305                1310

Tyr Ser Val Ser Val Ser Ala Phe Thr Lys Val Gly Asn Gly Asn Gln
```

-continued

```
        1315                1320                1325

Tyr Ser Asn Val Val Glu Phe Thr Thr Gln Glu Ser Val Pro Glu Ala
    1330                1335                1340

Val Arg Asn Ile Glu Cys Val Ala Arg Asp Trp Gln Ser Val Ser Val
1345                1350                1355                1360

Arg Trp Asp Pro Pro Arg Lys Thr Asn Gly Ile Ile Ile His Tyr Met
                1365                1370                1375

Ile Thr Val Gly Gly Asn Ser Thr Lys Val Ser Pro Arg Asp Pro Thr
            1380                1385                1390

Tyr Thr Phe Thr Lys Leu Leu Pro Asn Thr Ser Tyr Val Phe Glu Val
        1395                1400                1405

Arg Ala Ser Thr Ser Ala Gly Glu Gly Asn Glu Ser Arg Cys Asp Ile
    1410                1415                1420

Ser Thr Leu Pro Glu Thr Val Pro Ser Ala Pro Thr Asn Val Ala Phe
1425                1430                1435                1440

Ser Asn Val Gln Ser Thr Ser Ala Thr Leu Thr Trp Thr Lys Pro Asp
                1445                1450                1455

Thr Ile Phe Gly Tyr Phe Gln Asn Tyr Lys Ile Thr Thr Gln Leu Arg
            1460                1465                1470

Ala Gln Lys Cys Arg Glu Trp Glu Pro Glu Glu Cys Ile Glu His Gln
        1475                1480                1485

Lys Asp Gln Tyr Leu Tyr Glu Ala Asn Gln Thr Glu Glu Thr Val His
    1490                1495                1500

Gly Leu Lys Lys Phe Arg Trp Tyr Arg Phe Gln Val Ala Ala Ser Thr
1505                1510                1515                1520

Asn Val Gly Tyr Ser Asn Ala Ser Glu Trp Ile Ser Thr Gln Thr Leu
                1525                1530                1535

Pro Gly Pro Pro Asp Gly Pro Pro Glu Asn Val His Val Val Ala Thr
            1540                1545                1550

Ser Pro Phe Gly Ile Asn Ile Ser Trp Ser Glu Pro Ala Val Ile Thr
        1555                1560                1565

Gly Pro Thr Phe Tyr Leu Ile Asp Val Lys Ser Val Asp Asp Asp Asp
    1570                1575                1580

Phe Asn Ile Ser Phe Leu Lys Ser Asn Glu Glu Asn Lys Thr Thr Glu
1585                1590                1595                1600

Ile Asn Asn Leu Glu Val Phe Thr Arg Tyr Ser Val Val Ile Thr Ala
                1605                1610                1615

Phe Val Gly Asn Val Ser Arg Ala Tyr Thr Asp Gly Lys Ser Ser Ala
            1620                1625                1630

Glu Val Ile Ile Thr Thr Leu Glu Ser Val Pro Lys Asp Pro Pro Asn
        1635                1640                1645

Asn Met Thr Phe Gln Lys Ile Pro Asp Glu Val Thr Lys Phe Gln Leu
    1650                1655                1660

Thr Phe Leu Pro Pro Ser Gln Pro Asn Gly Asn Ile Arg Val Tyr Gln
1665                1670                1675                1680

Ala Leu Val Tyr Arg Glu Asp Asp Pro Thr Ala Val Gln Ile His Asn
                1685                1690                1695

Phe Ser Ile Ile Gln Lys Thr Asp Thr Ser Ile Ile Ala Met Leu Glu
            1700                1705                1710

Gly Leu Lys Gly Gly His Thr Tyr Asn Ile Ser Val Tyr Ala Ile Asn
        1715                1720                1725

Ser Ala Gly Ala Gly Pro Lys Val Gln Met Arg Ile Thr Met Asp Ile
    1730                1735                1740
```

-continued

```
Lys Ala Pro Ala Arg Pro Lys Ser Lys Pro Ile Pro Ile Arg Asp Ala
1745                1750                1755                1760

Thr Gly Lys Leu Leu Val Thr Ser Thr Thr Ile Thr Ile Arg Met Pro
                1765                1770                1775

Ile Cys Tyr Tyr Asn Asp Asp His Gly Pro Ile Arg Asn Val Gln Val
            1780                1785                1790

Leu Val Ala Glu Thr Gly Ala Gln Gln Asp Gly Asn Val Thr Lys Trp
        1795                1800                1805

Tyr Asp Ala Tyr Phe Asn Lys Ala Arg Pro Tyr Phe Thr Asn Glu Gly
    1810                1815                1820

Phe Pro Asn Pro Pro Cys Ile Glu Gly Lys Thr Lys Phe Ser Gly Asn
1825                1830                1835                1840

Glu Glu Ile Tyr Val Ile Gly Ala Asp Asn Ala Cys Met Ile Pro Gly
                1845                1850                1855

Asn Glu Glu Lys Ile Cys Asn Gly Pro Leu Lys Pro Lys Lys Gln Tyr
            1860                1865                1870

Leu Phe Lys Phe Arg Ala Thr Asn Val Met Gly Gln Phe Thr Asp Ser
        1875                1880                1885

Glu Tyr Ser Asp Pro Ile Lys Thr Leu Gly Glu Gly Leu Ser Glu Arg
    1890                1895                1900

Thr Val Glu Ile Ile Leu Ser Val Thr Leu Cys Ile Leu Ser Ile Ile
1905                1910                1915                1920

Leu Leu Gly Thr Ala Ile Phe Ala Phe Val Arg Ile Arg Gln Lys Gln
                1925                1930                1935

Lys Glu Gly Gly Thr Tyr Ser Pro Arg Asp Ala Glu Ile Ile Asp Thr
            1940                1945                1950

Lys Phe Lys Leu Asp Gln Leu Ile Thr Val Ala Asp Leu Glu Leu Lys
        1955                1960                1965

Asp Glu Arg Leu Thr Arg Leu Leu Ser Tyr Arg Lys Ser Ile Lys Pro
    1970                1975                1980

Ile Ser Lys Lys Ser Phe Leu Gln His Val Glu Glu Leu Cys Thr Asn
1985                1990                1995                2000

Ser Asn Leu Lys Phe Gln Glu Glu Phe Ser Glu Leu Pro Lys Phe Leu
                2005                2010                2015

Gln Asp Leu Ser Ser Thr Asp Ala Asp Leu Pro Trp Asn Arg Ala Lys
            2020                2025                2030

Asn Arg Phe Pro Asn Ile Lys Pro Tyr Asn Asn Asn Arg Val Lys Leu
        2035                2040                2045

Ile Ala Asp Val Ser Leu Pro Gly Ser Asp Tyr Ile Asn Ala Ser Tyr
    2050                2055                2060

Val Ser Gly Tyr Leu Cys Pro Asn Glu Phe Ile Ala Thr Gln Gly Pro
2065                2070                2075                2080

Leu Pro Gly Thr Val Gly Asp Phe Trp Arg Met Val Trp Glu Thr Arg
                2085                2090                2095

Thr Lys Thr Leu Val Met Leu Thr Gln Cys Phe Glu Lys Gly Arg Ile
            2100                2105                2110

Arg Cys His Gln Tyr Trp Pro Glu Asp Asn Lys Pro Val Thr Val Phe
        2115                2120                2125

Gly Asp Ile Val Ile Thr Lys Leu Met Glu Asp Ile Gln Ile Asp Trp
    2130                2135                2140

Thr Ile Arg Asp Leu Lys Ile Glu Arg His Gly Asp Cys Met Thr Val
2145                2150                2155                2160
```

-continued

```
Arg Gln Cys Asn Phe Thr Gly Trp Pro Glu His Gly Val Pro Glu Asn
            2165                2170                2175

Thr Thr Pro Leu Ile His Phe Val Lys Leu Val Arg Thr Ser Arg Ala
        2180                2185                2190

His Asp Thr Thr Pro Met Val Val His Cys Ser Ala Gly Val Gly Arg
    2195                2200                2205

Thr Gly Val Phe Ile Ala Leu Asp His Leu Thr Gln His Ile Asn Asn
    2210                2215                2220

His Asp Phe Val Asp Ile Tyr Gly Leu Val Ala Glu Leu Arg Ser Glu
2225                2230                2235                2240

Arg Met Cys Met Val Gln Asn Leu Ala Gln Tyr Ile Phe Leu His Gln
            2245                2250                2255

Cys Ile Leu Asp Leu Leu Ser Asn Lys Gly Gly His Gln Pro Val Cys
        2260                2265                2270

Phe Val Asn Tyr Ser Thr Leu Gln Lys Met Asp Ser Leu Asp Ala Met
    2275                2280                2285

Glu Gly Asp Val Glu Leu Glu Trp Glu Glu Thr Thr Met
    2290                2295                2300
```

ISOLATED HUMAN PHOSPHATASE PROTEINS, NUCLEIC ACID MOLECULES ENCODING HUMAN PHOSPHATASE PROTEINS, AND USES THEREOF

FIELD OF THE INVENTION

The present invention is in the field of phosphatase proteins that are related to the protein tyrosine phosphatase subfamily, recombinant DNA molecules and protein production. The present invention specifically provides novel phosphatase peptides and proteins and nucleic acid molecules encoding such peptide and protein molecules, all of which are useful in the development of human therapeutics and diagnostic compositions and methods.

BACKGROUND OF THE INVENTION

Phosphatase proteins, particularly members of the protein tyrosine phosphatase subfamily, are a major target for drug action and development. Accordingly, it is valuable to the field of pharmaceutical development to identify and characterize previously unknown members of this subfamily of phosphatase proteins. The present invention advances the state of the art by providing a previously unidentified human phosphatase proteins that have homology to members of the protein tyrosine phosphatase subfamily.

Protein Phosphatase

Cellular signal transduction is a fundamental mechanism whereby external stimuli that regulate diverse cellular processes are relayed to the interior of cells. The biochemical pathways through which signals are transmitted within cells comprise a circuitry of directly or functionally connected interactive proteins. One of the key biochemical mechanisms of signal transduction involves the reversible phosphorylation of certain residues on proteins. The phosphorylation state of a protein may affect its conformation and/or enzymic activity as well as its cellular location. The phosphorylation state of a protein is modified through the reciprocal actions of protein phosphatases (PKs) and protein phosphatases (PPs) at various specific amino acid residues.

Protein phosphorylation is the ubiquitous strategy used to control the activities of eukaryotic cells. It is estimated that 10% of the proteins active in a typical mammalian cell are phosphorylated. The high-energy phosphate that confers activation and is transferred from adenosine triphosphate molecules to protein-by-protein phosphatases is subsequently removed from the protein-by-protein phosphatases. In this way, the phosphatases control most cellular signaling events that regulate cell growth and differentiation, cell-to-cell contacts, the cell cycle, and oncogenesis.

The protein phosphorylation/dephosphorylation cycle is one of the major regulatory mechanisms employed by eukaryotic cells to control cellular activities. It is estimated that more than 10% of the active proteins in a typical mammalian cell are phosphorylated. During protein phosphorylation/dephosphorylation, phosphate groups are transferred from adenosine triphosphate molecules to protein-by-protein phosphatases and are removed from the protein-by-protein phosphatases.

Protein phosphatases function in cellular signaling events that regulate cell growth and differentiation, cell-to-cell contacts, the cell cycle, and oncogenesis. Three protein phosphatase families have been identified as evolutionarily distinct. These include the serine/threonine phosphatases, the protein tyrosine phosphatases, and the acid/alkaline phosphatases (Carbonneau H. and Tonks N. K. (1992) Annu. Rev. Cell Biol. 8:463–93).

The serine/threonine phosphatases are either cytosolic or associated with a receptor. On the basis of their sensitivity to two thermostable proteins, inhibitors 1 and 2, and their divalent cation requirements, the serine/threonine phosphatases can be separated into four distinct groups, PP-I, PP-IIA, PP-IIB, and PP-IIC.

PP-I dephosphorylates many of the proteins phosphorylated by cylic AMP-dependent protein phosphatase and is therefore an important regulator of many cyclic AMP mediated, hormone responses in cells. PP-IIA has broad specificity for control of cell cycle, growth and proliferation, and DNA replication and is the main phosphatase responsible for reversing the phosphorylations of serine/threonine phosphatases. PP-IIB, or calcineurin (Cn), is a Ca.sup.+2-activated phosphatase; it is involved in the regulation of such diverse cellular functions as ion channel regulation, neuronal transmission, gene transcription, muscle glycogen metabolism, and lymphocyte activation.

PP-IIC is a Mg.sup.++-dependent phosphatase which participates in a wide variety of functions including regulating cyclic AMP-activated protein-phosphatase activity, Ca.sup.++-dependent signal transduction, tRNA splicing, and signal transmission related to heat shock responses. PP-IIC is a monomeric protein with a molecular mass of about 40–45 kDa. One .alpha. and several .beta. isoforms of PP-IIC have been identified (Wenk, J. et al. (1992) FEBS Lett. 297: 135–138; Terasawa, T. et al. (1993) Arch. Biochem. Biophys. 307: 342–349; and Kato, S. et al. (1995) Arch. Biochem. Biophys. 318: 387–393).

The levels of protein phosphorylation required for normal cell growth and differentiation at any time are achieved through the coordinated action of PKs and PPS. Depending on the cellular context, these two types of enzymes may either antagonize or cooperate with each other during signal transduction. An imbalance between these enzymes may impair normal cell functions leading to metabolic disorders and cellular transformation.

For example, insulin binding to the insulin receptor, which is a PTK, triggers a variety of metabolic and growth promoting effects such as glucose transport, biosynthesis of glycogen and fats, DNA synthesis, cell division and differentiation. Diabetes mellitus, which is characterized by insufficient or a lack of insulin signal transduction, can be caused by any abnormality at any step along the insulin signaling pathway. (Olefsky, 1988, in "Cecil Textbook of Medicine," 18th Ed., 2:1360–81).

It is also well known, for example, that the overexpression of PTKs, such as HER2, can play a decisive role in the development of cancer (Slamon et al., 1987, Science 235:77–82) and that antibodies capable of blocking the activity of this enzyme can abrogate tumor growth (Drebin et al., 1988, Oncogene 2:387–394). Blocking the signal transduction capability of tyrosine phosphatases such as Flk-1 and the PDGF receptor have been shown to block tumor growth in animal models (Millauer et al., 1994, Nature 367:577; Ueno et al., Science, 252:844–848).

Relatively less is known with respect to the direct role of phosphatases in signal transduction; PPs may play a role in human diseases. For example, ectopic expression of RPTP.alpha. produces a transformed phenotype in embryonic fibroblasts (Zheng et al., Nature 359:336–339), and overexpression of RPTP.alpha. in embryonal carcinoma cells causes the cells to differentiate into a cell type with neuronal phenotype (den Hertog et al., EMBO J 12:3789–3798). The gene for human RPTP.gamma. has been localized to chromosome 3p21 which is a segment frequently altered in renal and small lung carcinoma. Mutations may occur in the extracellular segment of RPTP.gamma. which renders a RPTP that no longer respond to external signals (LaForgia et al., Wary et al., 1993, Cancer Res 52:478–482). Mutations in the gene encoding PTP1C (also known as HCP, SHP) are the cause of the moth-eaten phenotype in mice that suffer severe immunodeficiency, and systemic autoimmune disease accompanied by hyperproliferation of macrophages (Schultz et al., 1993, Cell 73:1445–1454). PTP1D (also known as Syp or PTP2C) has been shown to bind through SH2 domains to sites of phosphorylation in PDGFR, EGFR and insulin receptor substrate 1 (IRS-1). Reducing the activity of PTP1D by microinjection of anti-PTP1D antibody has been shown to block insulin or EGF-induced mitogenesis (Xiao et al., 1994, J Biol Chem 269:21244–21248).

The present invention has substantial similarity to protein tyrosine phosphatase (receptor type, Q). It is well established that protein tyrosine phosphorylation plays a key role in regulating structure proteins in migrating cells. Migrating cells interact with the extracellular matrix via focal adhesions (FA), which are contact points that link actin stress fibers to the membrane cytoskeleton and to transmembrane integrins. Engagement of integrins by the extracellular matrix in migrating cells induces tyrosine phosphorylation of several FA components including pp125FAK and paxillin. Specific PTPases have been linked to FA phosphorylation. For example LAR, a broadly expressed receptor PTPase, localizes to FAs in migrating cells but seems to be excluded from developing FAs at extending lamellopodia. This is consistent with a role of this receptor PTPase in FA disassembly by serving to dephosphorylate components that were activated initially by phosphorylation.

The potential importance of PTPases in the glomerulus has been underscored by the recent identification of GLEPP1, a type III receptor-like PTPase (rPTPase), which is localized to the specialized foot processes of the podocyte. GLEPP1 has been proposed to play a role in the regulation of podocyte foot process structure and function. In support of this hypothesis, GLEPP1 protein levels are reduced in several types of human glomerular disease and in several animal models of glomerulonephritis.

Glomerular disease is initiated by a variety of factors, including immunologic, infectious, and toxic agents, as well as hemodynamic processes. A central pathological feature of many types of acute and progressive glomerular disease is injury of mesangial cells, which respond by proliferating as well as by secreting growth factors and extracellular matrix proteins. This contributes to resolution of glomerular damage but may also lead to fibrosis, which occurs in many chronic disease processes. The glomerular mesangial cell is a mesenchymally derived cell that shares properties with fibroblasts and smooth muscle cells and provides structural support to the glomerular tuft.

PTPases play as potential mediators of the mesangial cell response in glomerular disease, because PTPases expressed in the rat anti-Thy 1 model, wherein a new receptor rPTP-GMC1, expressed by glomerular mesangial cells. rPTP-GMC1 is highly restricted to the mesangial cell and that expression is acutely up-regulated in actively proliferating and migrating mesangial cells in the anti-Thy 1 model. rPTP-GMC1 is similar in structure to GLEPP1 and may sense or regulate cell-cell or cell-matrix interactions to mediate glomerular repair. For a review, see Wright et al., J Biol Chem 1998 Sep 11;273(37):23929–37.

The discovery of a new human protein phosphatase and the polynucleotides encoding it satisfies a need in the art by providing new compositions that are useful in the diagnosis, prevention and treatment of biological processes associated with abnormal or unwanted protein phosphorylation.

SUMMARY OF THE INVENTION

The present invention is based in part on the identification of amino acid sequences of human phosphatase peptides and proteins that are related to the protein tyrosine phosphatase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate phosphatase activity in cells and tissues that express the phosphatase. Experimental data as provided in FIG. 1 indicates expression in colon adenocarcinoma and placenta.

DESCRIPTION OF THE FIGURE SHEETS

FIG. 1 provides the nucleotide sequence of a cDNA molecule or transcript sequence that encodes the phosphatase protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in colon adenocarcinoma and placenta.

FIG. 2 provides the predicted amino acid sequence of the phosphatase of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the phosphatase protein of the present invention. (SEQ ID NO:3) In addition structure and functional information, such as intron/exon structure, promoter location, etc., is provided where available, allowing one to readily determine specific uses of inventions based on this molecular sequence. 82 SNPs, including 6 indels, have been identified in the gene encoding the phosphatase protein provided by the present invention and are given in FIG. 3.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a phosphatase protein or part of a phosphatase protein and are related to the protein tyrosine phosphatase subfamily. Utilizing these sequences, additional genomic sequences were assembled and transcript and/or cDNA sequences were isolated and characterized. Based on this analysis, the present invention provides amino acid sequences of human phosphatase peptides and proteins that are related to the protein tyrosine phosphatase subfamily, nucleic acid sequences in the form of transcript sequences, cDNA sequences and/or genomic sequences that encode these phosphatase peptides and proteins, nucleic acid variation (allelic information), tissue distribution of expression, and information about the closest art known protein/peptide/domain that has structural or sequence homology to the phosphatase of the present invention.

In addition to being previously unknown, the peptides that are provided in the present invention are selected based on their ability to be used for the development of commercially important products and services. Specifically, the present peptides are selected based on homology and/or structural relatedness to known phosphatase proteins of the protein tyrosine phosphatase subfamily and the expression pattern observed. Experimental data as provided in FIG. 1 indicates expression in colon adenocarcinoma and placenta. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known protein tyrosine phosphatase family or subfamily of phosphatase proteins.

Specific Embodiments

Peptide Molecules

The present invention provides nucleic acid sequences that encode protein molecules that have been identified as being members of the phosphatase family of proteins and are related to the protein tyrosine phosphatase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the phosphatase peptides of the present invention, phosphatase peptides, or peptides/proteins of the present invention.

The present invention provides isolated peptide and protein molecules that consist of, consist essentially of, or comprise the amino acid sequences of the phosphatase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the phosphatase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated phosphatase peptide can be purified from cells that naturally express it, purified from cells that have been altered to express it (recombinant), or synthesized using known protein synthesis methods. Experimental data as provided in FIG. 1 indicates expression in colon adenocarcinoma and placenta. For example, a nucleic acid molecule encoding the phosphatase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the phosphatase peptides of the present invention are the naturally occurring mature proteins. A brief description of how various types of these proteins can be made/isolated is provided below.

The phosphatase peptides of the present invention can be attached to heterologous sequences to form chimeric or fusion proteins. Such chimeric and fusion proteins comprise a phosphatase peptide operatively linked to a heterologous protein having an amino acid sequence not substantially homologous to the phosphatase peptide. "Operatively linked" indicates that the phosphatase peptide and the heterologous protein are fused in-frame. The heterologous protein can be fused to the N-terminus or C-terminus of the phosphatase peptide.

In some uses, the fusion protein does not affect the activity of the phosphatase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant phosphatase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology,* 1992). Moreover, many expression vectors are commercially available that already encode a fusion moiety (e.g., a GST protein). A phosphatase peptide-encoding nucleic acid can be cloned into such an expression vector such that the fusion moiety is linked in-frame to the phosphatase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the phosphatase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology,* Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology,* von Heinje, G., Academic Press, 1987; and *Sequence Analysis Primer,* Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the phosphatase peptides of the present invention as well as being encoded by the same genetic locus as the phosphatase peptide provided herein. As indicated by the data presented in FIG. 3, the map position was determined to be on chromosome 12 by ePCR.

Allelic variants of a phosphatase peptide can readily be identified as being a human protein having a high degree (significant) of sequence homology/identity to at least a portion of the phosphatase peptide as well as being encoded by the same genetic locus as the phosphatase peptide provided herein. Genetic locus can readily be determined based on the genomic information provided in FIG. 3, such as the genomic sequence mapped to the reference human. As indicated by the data presented in FIG. 3, the map position was determined to be on chromosome 12 by ePCR. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a phosphatase peptide encoding nucleic acid molecule under stringent conditions as more fully described below.

FIG. 3 provides information on SNPs that have been identified in a gene encoding the phosphatase protein of the present invention. 82 SNP variants were found, including 6 indels (indicated by a "-") and 3 SNPs in exons, of which 3 of these cause changes in the amino acid sequence (i.e., nonsynonymous SNPs). SNPs, identified at different nucleotide positions in introns and regions 5' and 3' of the ORF, may affect control/regulatory elements.

Paralogs of a phosphatase peptide can readily be identified as having some degree of significant sequence homology/identity to at least a portion of the phosphatase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a phosphatase peptide encoding nucleic acid molecule under moderate to stringent conditions as more fully described below.

Orthologs of a phosphatase peptide can readily be identified as having some degree of significant sequence homology/identity to at least a portion of the phosphatase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a phosphatase peptide encoding nucleic acid molecule under moderate to stringent conditions, as more fully described below, depending on the degree of relatedness of the two organisms yielding the proteins.

Non-naturally occurring variants of the phosphatase peptides of the present invention can readily be generated using recombinant techniques. Such variants include, but are not limited to deletions, additions and substitutions in the amino acid sequence of the phosphatase peptide. For example, one class of substitutions are conserved amino acid substitution. Such substitutions are those that substitute a given amino acid in a phosphatase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant phosphatase peptides can be fully functional or can lack function in one or more activities, e.g. ability to bind substrate, ability to dephosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as phosphatase activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the phosphatase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a phosphatase peptide. Such fragments can be chosen based on the ability to retain one or more of the biological activities of the phosphatase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the phosphatase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in phosphatase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the phosphatase peptides of the present invention also encompass derivatives or analogs in which a substituted amino acid residue is not one encoded by the genetic code, in which a substituent group is included, in which the mature phosphatase peptide is fused with another compound, such as a compound to increase the half-life of the phosphatase peptide, or in which the additional amino acids are fused to the mature phosphatase peptide, such as a leader or secretory sequence or a sequence for purification of the mature phosphatase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a phosphatase-effector protein interaction or phosphatase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, phosphatases isolated from humans and their human/mammalian orthologs serve as targets for identifying agents for use in mammalian therapeutic applications, e.g. a human drug, particularly in modulating a biological or pathological response in a cell or tissue that expresses the phosphatase. Experimental data as provided in FIG. 1 indicates that phosphatase proteins of the present invention are expressed in the colon adenocarcinoma detected by a virtual northern blot. In addition, PCR-based tissue screening panel indicates expression in and placenta. A large percentage of pharmaceutical agents are being developed that modulate the activity of phosphatase proteins, particularly members of the protein tyrosine phosphatase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in colon adenocarcinoma and placenta. Such uses can readily be determined using the information provided herein, that which is known in the art, and routine experimentation.

The proteins of the present invention (including variants and fragments that may have been disclosed prior to the present invention) are useful for biological assays related to phosphatases that are related to members of the protein tyrosine phosphatase subfamily. Such assays involve any of the known phosphatase functions or activities or properties useful for diagnosis and treatment of phosphatase-related conditions that are specific for the subfamily of phosphatases that the one of the present invention belongs to, particularly in cells and tissues that express the phosphatase. Experimental data as provided in FIG. 1 indicates that phosphatase proteins of the present invention are expressed in the colon adenocarcinoma detected by a virtual northern blot. In addition, PCR-based tissue screening panel indicates expression in and placenta.

The proteins of the present invention are also useful in drug screening assays, in cell-based or cell-free systems. Cell-based systems can be native, i.e., cells that normally express the phosphatase, as a biopsy or expanded in cell culture. Experimental data as provided in FIG. 1 indicates expression in colon adenocarcinoma and placenta. In an alternate embodiment, cell-based assays involve recombinant host cells expressing the phosphatase protein.

The polypeptides can be used to identify compounds that modulate phosphatase activity of the protein in its natural state or an altered form that causes a specific disease or pathology associated with the phosphatase. Both the phosphatases of the present invention and appropriate variants and fragments can be used in high-throughput screens to assay candidate compounds for the ability to bind to the phosphatase. These compounds can be further screened against a functional phosphatase to determine the effect of the compound on the phosphatase activity. Further, these compounds can be tested in animal or invertebrate systems to determine activity/effectiveness. Compounds can be identified that activate (agonist) or inactivate (antagonist) the phosphatase to a desired degree.

Further, the proteins of the present invention can be used to screen a compound for the ability to stimulate or inhibit interaction between the phosphatase protein and a molecule that normally interacts with the phosphatase protein, e.g. a substrate or a component of the signal pathway that the phosphatase protein normally interacts (for example, another phosphatase). Such assays typically include the steps of combining the phosphatase protein with a candidate compound under conditions that allow the phosphatase protein, or fragment, to interact with the target molecule, and to detect the formation of a complex between the protein and the target or to detect the biochemical consequence of the interaction with the phosphatase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant phosphatases or appropriate fragments containing mutations that affect phosphatase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) phosphatase activity. The assays typically involve an assay of events in the signal transduction pathway that indicate phosphatase activity. Thus, the dephosphorylation of a substrate, activation of a protein, a change in the expression of genes that are up- or down-regulated in response to the phosphatase protein dependent signal cascade can be assayed.

Any of the biological or biochemical functions mediated by the phosphatase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the phosphatase can be assayed. Experimental data as provided in FIG. 1 indicates that phosphatase proteins of the present invention are expressed in the colon adenocarcinoma detected by a virtual northern blot. In addition, PCR-based tissue screening panel indicates expression in and placenta.

Binding and/or activating compounds can also be screened by using chimeric phosphatase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native phosphatase. Accordingly, a different set of signal transduction components is available as an end-point assay for activation. This allows for assays to be performed in other than the specific host cell from which the phosphatase is derived.

The proteins of the present invention are also useful in competition binding assays in methods designed to discover compounds that interact with the phosphatase (e.g. binding partners and/or ligands). Thus, a compound is exposed to a phosphatase polypeptide under conditions that allow the compound to bind or to otherwise interact with the polypeptide. Soluble phosphatase polypeptide is also added to the mixture. If the test compound interacts with the soluble phosphatase polypeptide, it decreases the amount of complex formed or activity from the phosphatase target. This type of assay is particularly useful in cases in which compounds are sought that interact with specific regions of the phosphatase. Thus, the soluble polypeptide that competes with the target phosphatase region is designed to contain peptide sequences corresponding to the region of interest.

To perform cell free drug screening assays, it is sometimes desirable to immobilize either the phosphatase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}S$-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of phosphatase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a phosphatase-binding protein and a candidate compound are incubated in the phosphatase protein-presenting wells and the amount of complex trapped in the well can be quantitated. Methods for detecting such complexes, in addition to those described above for the GST-immobilized complexes, include immunodetection of complexes using antibodies reactive with the phosphatase protein target molecule, or which are reactive with phosphatase protein and compete with the target molecule, as well as enzyme-linked assays which rely on detecting an enzymatic activity associated with the target molecule.

Agents that modulate one of the phosphatases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of phosphatase protein activity identified according to these drug screening assays can be used to treat a subject with a disorder mediated by the kinase pathway, by treating cells or tissues that express the phosphatase. Experimental data as provided in FIG. 1 indicates expression in colon adenocarcinoma and placenta. These methods of treatment include the steps of administering a modulator of phosphatase activity in a pharmaceutical composition to a subject in need of such treatment, the modulator being identified as described herein.

In yet another aspect of the invention, the phosphatase proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the phosphatase and are involved in phosphatase activity. Such phosphatase-binding proteins are also likely to be involved in the propagation of signals by the phosphatase proteins or phosphatase targets as, for example, downstream elements of a kinase-mediated signaling pathway. Alternatively, such phosphatase-binding proteins are likely to be phosphatase inhibitors.

The two-hybrid system is based on the modular nature of most transcription factors, which consist of separable DNA-binding and activation domains. Briefly, the assay utilizes two different DNA constructs. In one construct, the gene that codes for a phosphatase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a phosphatase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the phosphatase protein.

This invention further pertains to novel agents identified by the above-described screening assays. Accordingly, it is within the scope of this invention to further use an agent identified as described herein in an appropriate animal model. For example, an agent identified as described herein (e.g., a phosphatase-modulating agent, an antisense phosphatase nucleic acid molecule, a phosphatase-specific antibody, or a phosphatase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The phosphatase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in colon adenocarcinoma and placenta. The method involves contacting a biological sample with a compound capable of interacting with the phosphatase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered phosphatase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the phosphatase protein in which one or more of the phosphatase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and phosphatase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in colon adenocarcinoma and placenta. Accordingly, methods for treatment include the use of the phosphatase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or $F(ab')_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the phosphatase proteins. Antibodies can be prepared from any region of the peptide as described herein. However, preferred regions will include those involved in function/activity and/or phosphatase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that phosphatase proteins of the present invention are expressed in the colon adenocarcinoma detected by a virtual northern blot. In addition, PCR-based tissue screening panel indicates expression in and placenta. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in colon adenocarcinoma and placenta. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in colon adenocarcinoma and placenta. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in colon adenocarcinoma and placenta. Thus, where a specific protein has been correlated with expression in a specific tissue, antibodies that are specific for this protein can be used to identify a tissue type.

The antibodies are also useful for inhibiting protein function, for example, blocking the binding of the phosphatase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a phosphatase peptide or protein of the present invention (cDNA, transcript and genomic sequence). Such nucleic acid molecules will consist of, consist essentially of, or comprise a nucleotide sequence that encodes one of the phosphatase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5KB, 4KB, 3KB, 2KB, or 1KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the phosphatase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the phosphatase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. As indicated by the data presented in FIG. 3, the map position was determined to be on chromosome 12 by ePCR.

FIG. 3 provides information on SNPs that have been identified in a gene encoding the phosphatase protein of the present invention. 82 SNP variants were found, including 6 indels (indicated by a "-") and 3 SNPs in exons, of which 3 of these cause changes in the amino acid sequence (i.e., nonsynonymous SNPs). SNPs, identified at different nucleotide positions in introns and regions 5' and 3' of the ORF, may affect control/regulatory elements.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6×sodium chloride/sodium citrate (SSC) at about 45C, followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. 82 SNPs, including 6 indels, have been identified in the gene encoding the phosphatase protein provided by the present invention and are given in FIG. 3.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the map position was determined to be on chromosome 12 by ePCR.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that phosphatase proteins of the present invention are expressed in the colon adenocarcinoma detected by a virtual northern blot. In addition, PCR-based tissue screening panel indicates expression in and placenta. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in phosphatase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a phosphatase protein, such as by measuring a level of a phosphatase-encoding nucleic acid in a sample of cells from a subject e.g., mRNA or genomic DNA, or determining if a phosphatase gene has been mutated. Experimental data as provided in FIG. 1 indicates that phosphatase proteins of the present invention are expressed in the colon adenocarcinoma detected by a virtual northern blot. In addition, PCR-based tissue screening panel indicates expression in and placenta.

Nucleic acid expression assays are useful for drug screening to identify compounds that modulate phosphatase nucleic acid expression.

The invention thus provides a method for identifying a compound that can be used to treat a disorder associated with nucleic acid expression of the phosphatase gene, particularly biological and pathological processes that are mediated by the phosphatase in cells and tissues that express it. Experimental data as provided in FIG. 1 indicates expression in colon adenocarcinoma and placenta. The method typically includes assaying the ability of the compound to modulate the expression of the phosphatase nucleic acid and thus identifying a compound that can be used to treat a disorder characterized by undesired phosphatase nucleic acid expression. The assays can be performed in cell-based and cell-free systems. Cell-based assays include cells naturally expressing the phosphatase nucleic acid or recombinant cells genetically engineered to express specific nucleic acid sequences.

The assay for phosphatase nucleic acid expression can involve direct assay of nucleic acid levels, such as mRNA levels, or on collateral compounds involved in the signal pathway. Further, the expression of genes that are up- or down-regulated in response to the phosphatase protein signal pathway can also be assayed. In this embodiment the regulatory regions of these genes can be operably linked to a reporter gene such as luciferase.

Thus, modulators of phosphatase gene expression can be identified in a method wherein a cell is contacted with a candidate compound and the expression of mRNA determined. The level of expression of phosphatase mRNA in the presence of the candidate compound is compared to the level of expression of phosphatase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate phosphatase nucleic acid expression in cells and tissues that express the phosphatase. Experimental data as provided in FIG. 1 indicates that phosphatase proteins of the present invention are expressed in the colon adenocarcinoma detected by a virtual northern blot. In addition, PCR-based tissue screening panel indicates expression in and placenta. Modulation includes both up-regulation (i.e. activation or agonization) or down-regulation (suppression or antagonization) or nucleic acid expression.

Alternatively, a modulator for phosphatase nucleic acid expression can be a small molecule or drug identified using the screening assays described herein as long as the drug or small molecule inhibits the phosphatase nucleic acid expression in the cells and tissues that express the protein. Experimental data as provided in FIG. 1 indicates expression in colon adenocarcinoma and placenta.

The nucleic acid molecules are also useful for monitoring the effectiveness of modulating compounds on the expression or activity of the phosphatase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in phosphatase nucleic acid expression, and particularly in qualitative changes that lead to pathology. The nucleic acid molecules can be used to detect mutations in phosphatase genes and gene expression products such as mRNA. The nucleic acid molecules can be used as hybridization probes to detect naturally occurring genetic mutations in the phosphatase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the phosphatase gene associated with a dysfunction provides a diagnostic tool for an active disease or susceptibility to disease when the disease results from overexpression, underexpression, or altered expression of a phosphatase protein.

Individuals carrying mutations in the phosphatase gene can be detected at the nucleic acid level by a variety of techniques. FIG. 3 provides information on SNPs that have been identified in a gene encoding the phosphatase protein of the present invention. 82 SNP variants were found, including 6 indels (indicated by a "-") and 3 SNPs in exons, of which 3 of these cause changes in the amino acid sequence (i.e., nonsynonymous SNPs). SNPs, identified at different nucleotide positions in introns and regions 5' and 3' of the ORF, may affect control/regulatory elements. As indicated by the data presented in FIG. 3, the map position was determined to be on chromosome 12 by ePCR. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a phosphatase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant phosphatase gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO94/16101; Cohen et al, *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the phosphatase gene in an individual in order to select an appropriate compound or dosage regimen for treatment. FIG. 3 provides information on SNPs that have been identified in a gene encoding the phosphatase protein of the present invention. 82 SNP variants were found, including 6 indels (indicated by a "-") and 3 SNPs in exons, of which 3 of these cause changes in the amino acid sequence (i.e., nonsynonymous SNPs). SNPs, identified at different nucleotide positions in introns and regions 5' and 3' of the ORF, may affect control/regulatory elements.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control phosphatase gene expression in cells, tissues, and organisms. A DNA antisense nucleic acid molecule is designed to be complementary to a region of the gene involved in transcription, preventing transcription and hence production of phosphatase protein. An antisense RNA or DNA nucleic acid molecule would hybridize to the mRNA and thus block translation of mRNA into phosphatase protein.

Alternatively, a class of antisense molecules can be used to inactivate mRNA in order to decrease expression of phosphatase nucleic acid. Accordingly, these molecules can treat a disorder characterized by abnormal or undesired phosphatase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the phosphatase protein, such as substrate binding.

The nucleic acid molecules also provide vectors for gene therapy in patients containing cells that are aberrant in phosphatase gene expression. Thus, recombinant cells, which include the patient's cells that have been engineered ex vivo and returned to the patient, are introduced into an individual where the cells produce the desired phosphatase protein to treat the individual.

The invention also encompasses kits for detecting the presence of a phosphatase nucleic acid in a biological sample. Experimental data as provided in FIG. 1 indicates that phosphatase proteins of the present invention are expressed in the colon adenocarcinoma detected by a virtual northern blot. In addition, PCR-based tissue screening panel indicates expression in and placenta. For example, the kit can comprise reagents such as a labeled or labelable nucleic acid or agent capable of detecting phosphatase nucleic acid in a biological sample; means for determining the amount of phosphatase nucleic acid in the sample; and means for comparing the amount of phosphatase nucleic acid in the sample with a standard. The compound or agent can be packaged in a suitable container. The kit can further comprise instructions for using the kit to detect phosphatase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the phosphatase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the phosphatase gene of the present invention. FIG. 3 provides information on SNPs that have been identified in a gene encoding the phosphatase protein of the present invention. 82 SNP variants were found, including 6 indels (indicated by a "-") and 3 SNPs in exons, of which 3 of these cause changes in the amino acid sequence (i.e., nonsynonymous SNPs). SNPs, identified at different nucleotide positions in introns and regions 5' and 3' of the ORF, may affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1 982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified phosphatase gene of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual. 2nd. ed.,* Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd. ed.,* Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterophosphatase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli.* (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982) pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as phosphatases, appropriate secretion signals are incorporated into the vector. The signal sequence can be endogenous to the peptides or heterologous to these peptides.

Where the peptide is not secreted into the medium, which is typically the case with phosphatases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a phosphatase protein or peptide that can be further purified to produce desired amounts of phosphatase protein or fragments. Thus, host cells containing expression vectors are useful for peptide production.

Host cells are also useful for conducting cell-based assays involving the phosphatase protein or phosphatase protein fragments, such as those described above as well as other formats known in the art. Thus, a recombinant host cell expressing a native phosphatase protein is useful for assaying compounds that stimulate or inhibit phosphatase protein function.

Host cells are also useful for identifying phosphatase protein mutants in which these functions are affected. If the mutants naturally occur and give rise to a pathology, host cells containing the mutations are useful to assay compounds that have a desired effect on the mutant phosphatase protein (for example, stimulating or inhibiting function) which may not be indicated by their effect on the native phosphatase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a phosphatase protein and identifying and evaluating modulators of phosphatase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the phosphatase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the phosphatase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, kinase protein activation, and signal transduction, may not be evident from in vitro cell-free or cell-based assays. Accordingly, it is useful to provide non-human transgenic animals to assay in vivo phosphatase protein function, including substrate interaction, the effect of specific mutant phosphatase proteins on phosphatase protein function and substrate interaction, and the effect of chimeric phosphatase proteins. It is also possible to assess the effect of null mutations, that is mutations that substantially or completely eliminate one or more phosphatase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule consisting of a nucleotide sequence selected from the group consisting of:

(a) a nucleotide sequence that encodes a protein comprising the amino acid sequence of SEQ ID NO:2;

(b) a nucleotide sequence consisting of SEQ ID NO:1; and (c) a nucleotide sequence consisting of SEQ ID NO:3.

2. A nucleic acid vector comprising a nucleic acid molecule of claim 1.

3. A host cell containing the vector of claim 2.

4. A process for producing a polypeptide comprising amino acid sequence SEQ ID NO: 2 comprising culturing the host cell of claim 3 under conditions sufficient for the production of said polypeptide, and recovering the polypeptide from the host cell culture.

5. An isolated polynucleotide consisting of a nucleotide sequence set forth in SEQ ID NO:1.

6. An isolated polynucleotide consisting of a nucleotide sequence set forth in SEQ ID NO:3.

7. A vector according to claim 2, wherein said vector is selected from the group consisting of a plasmid, virus, and bacteriophage.

8. A vector according to claim 2, wherein said isolated nucleic acid molecule is inserted into said vector in proper orientation and correct reading frame such that the protein of SEQ ID NO:2 may be expressed by a cell transformed with said vector.

9. A vector according to claim 8, wherein said isolated nucleic acid molecule is operatively linked to a promoter sequence.

10. An isolated nucleic acid molecule consisting of a nucleotide sequence that is completely complementary to a nucleotide sequence of claim 1.

11. An isolated nucleic acid molecule comprising a nucleotide sequence selected from the group consisting of:

(a) a nucleotide sequence that encodes a protein comprising the amino acid sequence of SEQ ID NO:2; and (b) a nucleotide sequence consisting of SEQ ID NO:1.

12. A nucleic acid vector comprising a nucleic molecule of claim 11.

13. A host cell containing the vector of claim 12.

14. A process for producing a polypeptide comprising amino acid sequence SEQ ID NO:2 comprising culturing the host cell of claim 13 under conditions sufficient for the production of said polypeptide, and recovering the polypeptide from the host cell culture.

15. A vector according to claim 12, wherein said vector is selected from the group consisting of a plasmid, virus, and bacteriophage.

16. A vector according to claim 12, wherein said isolated nucleic acid molecule is inserted into said vector in proper orientation and connect reading frame such that the protein of SEQ ID NO:2 may be expressed by a cell transformed with said vector.

17. A vector according to claim 12, wherein said isolated nucleic acid molecule is operatively linked to a promoter sequence.

18. An isolated polynucleotide comprising a nucleotide sequence set forth in SEQ ID NO:1.

19. An isolated nucleic acid molecule comprising a nucleotide sequence that is completely complementary to a nucleotide sequence of claim 11.

* * * * *